US009765371B2

(12) United States Patent
Han et al.

(10) Patent No.: US 9,765,371 B2
(45) Date of Patent: Sep. 19, 2017

(54) **THERMOSTABLE *C. BESCII* ENZYMES**

(75) Inventors: Yejun Han, Urbana, IL (US); Xiaoyun Su, Urbana, IL (US); Dylan Dodd, Champaign, IL (US); Roderick I. Mackie, Urbana, IL (US); Isaac K. O. Cann, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 63 days.

(21) Appl. No.: 13/997,170

(22) PCT Filed: Dec. 20, 2011

(86) PCT No.: PCT/US2011/066272

§ 371 (c)(1), (2), (4) Date: Feb. 28, 2014

(87) PCT Pub. No.: WO2012/088165

PCT Pub. Date: Jun. 28, 2012

(65) Prior Publication Data

US 2015/0093790 A1 Apr. 2, 2015

Related U.S. Application Data

(60) Provisional application No. 61/425,623, filed on Dec. 21, 2010, provisional application No. 61/532,060, filed on Sep. 7, 2011.

(51) Int. Cl.

| | |
|---|---|
| ***C12P 19/14*** | (2006.01) |
| ***C12P 7/04*** | (2006.01) |
| ***C12P 7/16*** | (2006.01) |
| ***C12N 9/18*** | (2006.01) |
| ***C12N 9/26*** | (2006.01) |
| ***C12N 9/42*** | (2006.01) |
| ***C12N 1/20*** | (2006.01) |
| ***C12P 21/06*** | (2006.01) |
| ***C12P 19/34*** | (2006.01) |
| ***C12N 9/24*** | (2006.01) |
| ***C12P 7/14*** | (2006.01) |
| ***C12P 19/02*** | (2006.01) |

(52) U.S. Cl.

CPC ................ *C12P 19/14* (2013.01); *C12N 9/18* (2013.01); *C12N 9/2402* (2013.01); *C12N 9/2405* (2013.01); *C12N 9/248* (2013.01); *C12N 9/2434* (2013.01); *C12N 9/2482* (2013.01); *C12P 7/04* (2013.01); *C12P 7/14* (2013.01); *C12P 7/16* (2013.01); *C12P 19/02* (2013.01); *C12Y 301/01072* (2013.01); *C12Y 302/01008* (2013.01); *C12Y 302/01055* (2013.01); *C12Y 302/01072* (2013.01); *C12Y 302/01139* (2013.01)

(58) Field of Classification Search

CPC .. C12N 9/2405; C12N 9/2434; C12N 9/2482; C12N 9/248; C12N 9/2402; C12N 9/18; C12P 19/14; C12P 19/02; C12P 7/16; C12P 7/04; C12P 7/14; C12Y 302/01072; C12Y 302/01055; C12Y 302/01008; C12Y 301/01072; C12Y 302/01139

USPC ...... 435/99, 157, 160, 197, 201, 209, 252.8, 435/69.1, 91.1; 536/23.1, 23.2; 530/350

See application file for complete search history.

(56) References Cited

U.S. PATENT DOCUMENTS 8,323,952 B2 * 12/2012 Abbas .................... C07K 14/39 435/254.2
2009/0325240 A1 * 12/2009 Daniell .............. C12N 15/8214 435/101

FOREIGN PATENT DOCUMENTS

| | | |
|---|---|---|
| WO | 2006/056819 A1 | 6/2006 |
| WO | 2010/027857 A2 | 3/2010 |
| WO | 2010/075529 A2 | 7/2010 |

OTHER PUBLICATIONS

Francis et al., Strategies to optimize protein expression in *E. coli.* Current Protocols in Protein Scinece, 2010: pp. 5.24.1-5.24.29.*
UniProtKB-B9MMA3: 7 (seven) pages downloaded from http://www.uniprot.org/ on Nov. 7, 2016.*
UniProtKB-B9MN93: 7 (seven) pages downloaded from http://www.uniprot.org/ on Nov. 7, 2016.*
UniProtKB-B9MPF9: 7 (seven) pages downloaded from http://www.uniprot.org/ on Nov. 7, 2016.*
UniProtKB-B9MNR1: 6 (six) pages downloaded from http://www.uniprot.org/ on Nov. 7, 2016.*
ModBase:B9MMA3: 2 (two) pages downloaded from https://modbase.compbio.ucsf.edu/ on Nov. 7, 12016.*
ModBase:B9MN93: 2 (two) pages downloaded from https://modbase.compbio.ucsf.edu/ on Nov. 7, 12016.*
International Preliminary Report on Patentability received for PCT Patent Application No. PCT/US2011/066272, mailed on Jul. 4, 2013, 13 pages.

(Continued)

*Primary Examiner* — Ganapathirama Raghu

(74) *Attorney, Agent, or Firm* — Morrison & Foerster LLP

(57) ABSTRACT

The disclosure provides thermostable enzymes isolated from *Caldicellulosiruptor bescii* and fragments thereof useful for the degradation of cellulose and/or hemicellulose, including thermostable cellulases and hemicellulases. The disclosure further provides nucleic acids encoding the thermostable enzymes of the disclosure. The disclosure also provides methods for the conversion of cellulose and hemicellulose into fermentable sugars using thermostable enzymes of the disclosure. The disclosure also provides enzyme cocktails containing multiple enzymes disclosed herein. The enzymes can be used to release sugars present in cellulose or hemicellulose for subsequent fermentation to produce value-added products.

6 Claims, 93 Drawing Sheets

(56) References Cited

OTHER PUBLICATIONS

International Search Report and Written Opinion received for PCT Patent Application No. PCT/US2011/066272, mailed on Apr. 13, 2012, 20 pages.
Blumer-Schuette et al., "Extremely Thermophilic Microorganisms for Biomass Conversion: Status and Prospects", Current Opinion in Biotechnology, vol. 19, 2008, pp. 210-217.
Blumer-Schuette et al., "Phylogenetic, Microbiological, and Glycoside Hydrolase Diversities within the Extremely Thermophilic, Plant Biomass-Degrading", Applied and Environmental Microbiology, vol. 76, No. 24, Dec. 2010, pp. 8084-8092.
Dam et al., "Insights into Plant Biomass Conversion from the Genome of the Anaerobic Thermophilic Bacterium Caldicellulosiruptor Bescii DSM 6725", Nucleic Acids Research, vol. 39, No. 8, 2011, pp. 3240-3254.
Kataeva et al., "Genome Sequence of the Anaerobic, Thermophilic, and Cellulolytic Bacterium "Anaerocellum Thermophilum" DSM 6725 V", Journal of Bacteriology, vol. 191, No. 11, Jun. 2009, pp. 3760-3761.
Vanfossen et al., "Glycoside Hydrolase Inventory Drives Plant Polysaccharide Deconstruction by the Extremely Thermophilic Bacterium Caldicellulosiruptor Saccharolyticus", Biotechnology and Bioengineering, vol. 108, No. 2, Jul. 2011, pp. 1559-1569.
Wackett, Lawrence P., "Engineering Microbes to Produce Biofuels", Current Opinion in Biotechnology, vol. 22, 2011, pp. 388-393.
"SubName: Full=Glycoside hydrolase Family 9; Flags: Precursor", UniProt Accession No. B9MKU5, Mar. 24, 2009, 2 pages.
"SubName: Full=Mannan endo-1,4-beta-mannosidase., Cellulase;", UniProt Accession No. B9MKU6, Mar. 24, 2009, 2 pages.
"SubName: Full=Glycoside Hydrolase Family 48; Flags: Precursor", UniProt Accession No. B9MKU7, Mar. 24, 2009, 1 page.
"SubName: Full=Glycoside Hydrolase Family 5; Flags: Precursor", UniProt Accession No. B9MKT9, Mar. 24, 2009, 1 page.
SubName: Full=Cellulase; EC=3.2.1.4; UniProt Accession No. B9MPF9, Mar. 24, 2009, 1 page.
"SubName: Full=Beta-galactosidase; EC=3.2.1.21", UniProt Accession No. B9MNR1, Mar. 24, 2009, 1 page.
"SubName: Full=Heat Shock Protein Hsp20", UniProt Accession No. B9MJU9, Mar. 24, 2009, 1 page.
Yang et al., "Classification of 'Anaerocellum Thermophilum' Strain DSM 6725 as *Caldicellulosiruptor bescii* Sp. *Nov*.", International Journal of Systematic and Evolutionary Microbiology, vol. 60, 2010, pp. 2011-2015.
Yang, , "Efficient Degradation of Lignocellulosic Plant Biomass, without Pretreatment, by the Thermophilic Anaerobe "Anaerocellum thermophilum" DSM 6725", Applied and Environmental Microbiology, vol. 75, No. 14, Jul. 2009, pp. 4762-4769.
Gibbs et al., "Multidomain and Multifunctional Glycosyl Hydrolases from the Extreme Thermophile Caldicellulosiruptor Isolate Tok7B.1", Curr. Microbiol., vol. 40, 2000, pp. 333-340.
Jindou et al., "Novel Architecture of Family-9 Glycoside Hydrolases Identified in Cellulosomal Enzymes of Acetivibrio Cellulolyticus and Clostridium Thermocellum.", FEMS Microbiol. Lett., vol. 254, No. 2, 2006, pp. 308-316.
Li et al., "Increased Crystalline Cellulose Activity Via Combinations of Amino Acid Changes in the Family 9 Catalytic Domain and Family 3C Cellulose Binding Module of Thermobifida Fusca Cel9A.", Appl. Environ. Microbiol., vol. 76, No. 8, 2010, pp. 2582-2588.
Lochner et al., "Use of Label-Free Quantitative Proteomics to Distinguish the Secreted Cellulolytic Systems of Caldicellulosiruptor Bescii and Caldicellulosiruptor Obsidiansis", Appl. Environ. Microbiol., vol. 77, No. 12, Jun. 2011, pp. 4042-4054.
Saul et al., "CelB, A Gene Coding for a Bifunctional Cellulase from the Extreme Thermophile "Caldocellum Saccharolyticum"", Appl. Environ. Microbiol., vol. 56, No. 10, Oct. 1990, pp. 3117-3124.
Office Action received for Chinese Patent Application No. 201180068057.X, mailed on Jun. 12, 2015, 8 pages (4 pages of English Translation & 4 pages of Official Copy).
Lucas et al., "Complete Sequence of Chromosome of Caldicellulosiruptor Becscii DSM 6725, Complete Genome", Accession No. CP001393, Available at <http://www.ncbi.nlm.nih.gov/nuccore/CP001393.1>, Jan. 26, 2009, 662 pages.

* cited by examiner

1:pNP-α-L-ARABINOPYRANOSIDE
2:pNP-β-D-FUCOPYRANOSIDE
3:pNP-β-D-GALACTOPYRANOSIDE
4:pNP-β-D-GLUCOPYRANOSIDE
5:pNP-β-D-XYLOPYRANOSIDE
6:pNP-β-D-CELLOBIOSE

```
                                 *    *                                                     *   ▼
   Cb1952       112 YVYYYQVGDPIEDHNFWGPAEVMQ                         200 AATGFYTS-GGFIDDLG
ClloceCel9G     111 GVYYYQVGDGGKDHSWWGPAEVMQ                         199 AASGYYSS-SSFYDDLS
ThefuCel9A      112 NVLYVQVGDGDADHKWWGPAEVMP                         201 PAGAFYNSWSGYQDELV
                                +1   +2                                   -2   -3

                                  *    ***                                            ▼ *    **
   Cb1952       241 YAGGTNT------WTQCWDDVRYGA                    286 NITYTPKGLAWITGWGSLRYATT
CloceCel9G      240 WGKEQQTDIIAYKWGQCWDDVHYGA                    296 RVSYTPKGLAWLFQWGSLRHATT
ThefuCel9A      243 LSTEQQTDLRSYRWTIAWDDKSYGT                    299 RVPYSPGGMAVLDTWGALRYAAN
                                -3   -2-4-4                                    -3-2  -2-2
                                -4                                                     -3

                                  * *           *
   Cb1952       348-SFLVGFGQNYPQHPHHRNAHSSWANSMRIPE
CloceCel9G      358-SFVVGYGVNPPQHPHHRTAHGSWTDQMTSPT
ThefuCel9A      362SSYVVGFGNNPPRNPHHRTAHGSWTDSIASPA
                                 +1+1          +2
```

FIG. 79

| | | | | | | |
|---|---|---|---|---|---|---|
| Cb1952 | 447 | EIFVESKFGNSQGTNYTEIISYI | 500 | GPDVVKVETYYSEG | 542 | PGGEVEHKKQAQFKI |
| ADQ45731 | 484 | EIFVESKFGNSQGTNYTEIISYI | 537 | GPDVVKVETYYSEG | 579 | PGGEVEHKKQAQFKI |
| ABP66693 | 484 | EIFVESKFGNSQGANYTEIISYI | 537 | GPDIVKVETYYSEG | 579 | PGGEVEHKKQAQFKI |
| ADL42950 | 484 | EIFVESKFGNSQGANYTEIISYI | 537 | SADVVKVDTYYAEG | 579 | PGGEVEHKKQAQFKI |
| AAK06394 | 482 | EIFVESKFGNSQGPNYTEVISYI | 535 | SPDVVKVDTYYIEG | 577 | PGGEVEHKKQAQFKI |
| AAA73868 | 493 | EVIIKAGL-NSTGPNYTEIKAVV | 545 | DPLSLVTSSNYSEG | 589 | PGGQSACRREVQFRI |
| AAC38572 | 494 | EFFVEAGV-NCTGPNFVEIKALV | 546 | SADDLKVTVGYNTG | 588 | PGGQSDYKKEIQFRI |
| CAA39010 | 485 | EFFVMAGI-NASGQNFIEIKALL | 537 | SASDVTITTNYNAG | 579 | PGGQSAYRKEVQFRI |
| ABX43720 | 484 | ELFIQAGI-NASGPSFIEVKALV | 536 | TKNDFTVSTNYNNG | 578 | PGGQSAYKKEVQFRI |
| ABN51860 | 532 | DEIFVEAGVN-ASGNNFIEIKAI | 585 | SASDLQVSSSYNQG | 625 | PGGQSAYKKEVQFRI |
| CAB38941 | 503 | DEYFVEAAV-RSSGSNYTEIRAL | 556 | TVSDVQVTVSSSEG | 598 | PGGEGNYRKEVQFRI |
| BAB33148 | 471 | DEFFVEAAIN-QASDHFTEIKAL | 524 | SVDDIKVTIGYCES | 568 | PIGQEQYAAELQFRI |
| AAA23086 | 495 | DQLFVEAMLNQPPSGTFTEVKAM | 544 | AASDVTLSANYSEC | 585 | PGGQSQHRREIQFRL |
| AAW62376 | 511 | DEIFVEAQLNQAPGSTFTEVKAM | 560 | AASDVTLAANYSEC | 601 | PGGQSQHRREIQFRL |
| AAB42155 | 462 | EIFVEAQI-NTPGTTFTEIKAMI | 510 | DPADITVSSAYNQC | 550 | PGGQSEHRREVQFRI |

FIG. 82

THERMOSTABLE *C. BESCII* ENZYMES

CROSS-REFERENCE TO RELATED APPLICATIONS

This is a U.S. National Phase patent application of PCT/US2011/066272, filed Dec. 20, 2011, which claims the benefit of U.S. Provisional Application No. 61/425,623, filed Dec. 21, 2010, and U.S. Provisional Application No. 61/532,060, filed Sep. 7, 2011, both of which are hereby incorporated by reference in their entirety.

FIELD

The present disclosure relates to compositions and methods for the degradation of cellulose, hemicellulose, and cellulose and/or hemicellulose-containing materials. In particular, the disclosure provides thermostable enzymes for the degradation of cellulose, nucleic acids encoding the enzymes, and methods of use thereof. The disclosure also provides thermostable enzymes for the degradation of hemicellulose, nucleic acids encoding the enzymes, and methods of use thereof. The disclosure further provides thermostable enzymes that enhance the activity of thermostable cellulase and/or hemicellulases, nucleic acids encoding the enzymes, and methods of use thereof.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 335032000700SubSeqListing.txt, date recorded: Feb. 25, 2016, size: 524 KB).

BACKGROUND

Microorganisms that are currently being used to ferment sugars to biofuels such as ethanol usually cannot utilize complex polysaccharides such as cellulose and hemicellulose. As a result, a significant bottleneck occurs in the conversion of lignocellulosic materials to biofuels.

Cellulose, a major component of plants and one of the most abundant organic compounds on earth, is a polysaccharide composed on long chains of β(1-4) linked D-glucose molecules. Due to its sugar-based composition, cellulose is a rich potential source material for the production of biofuels. For example, sugars from cellulose may be fermented into biofuels such as ethanol. In order for the sugars within cellulose to be used for the production of biofuels or other commodity chemicals, the cellulose must be broken down into smaller molecules.

Cellulose may be enzymatically hydrolyzed by the action of cellulases. Cellulases include endoglucanases, exoglucanases, and beta-glucosidases. The actions of cellulases cleave the 1-4 β-D-glycosidic linkages in cellulose, and result in the ultimate release of β-D-glucose molecules. During the breakdown of cellulose into individual sugar molecules, glucose polymers of various lengths may be formed as intermediate breakdown products. Glucose polymers of approximately 2-6 molecules in length derived from the hydrolysis of cellulose are referred to as "cellodextrins" or "cellooligosaccharides."

Hemicellulose constitutes the second largest component of polysaccharides in many plants, such as the perennial grasses switchgrass and *Miscanthus*. Hemicellulose is a complex polysaccharide that has a xylose-linked backbone, with side chains of arabinose, glucuronyl, and acetyl groups. A structural model of a hemicellulose illustrates the xylose backbone residues joined together in beta-1,4-linkages (FIG. 1). Several functional groups decorate the backbone, including esters of acetyl (Ac) groups, arabinose, glucuronic acids, and esters of feroryl groups. The feroryl groups link the entire structure to lignin. Enzyme cocktails that hydrolyze hemicellulose into its major component sugars such as xylose (a 5-carbon sugar) and arabinose (a 5-carbon sugar) will significantly increase the fermentable sugars for biofuel production from lignocellulose-based feedstock. Enzymatic removal of hemicellulose by hemicellulases will also increase accessibility of cellulases to the cellulose component of plant cell walls or lignocellulosic feedstocks. Thus, the degradation of hemicellulose is a critical step in the utilization of lignocellulose feedstock for biofuel production.

Thermostable enzymes are particularly desirable for the efficient degradation of cellulose and hemicellulose, because thermostable enzymes are more compatible than non-thermostable enzymes with other processes involved in converting lignocellulose-based materials into biofuels. For example, treatments of lignocellulose-based materials to decrease the crystallinity of cellulose may require high temperatures that inactivate non-thermostable enzymes.

In addition, thermostable enzymes are desirable for the degradation of cellulose and/or hemicellulose because they may have a higher specific activity as compared to their mesophilic counterparts, and because they can operate at high temperatures that reduce or eliminate the risk of microbial contamination.

Accordingly, there is a need for thermostable enzymes and enzyme cocktails capable of degrading cellulose and/or hemicellulose.

BRIEF SUMMARY

This disclosure provides enzymes and enzyme cocktails which satisfy the need for thermostable enzymes capable of degrading cellulose and/or hemicellulose. In some aspects, the disclosure provides enzymes having cellulase activity. In some aspects, the disclosure provides truncated enzymes having cellulase activity. In some aspects, the disclosure provides improved enzyme mixtures for the degradation of cellulose-containing materials. In some aspects, the disclosure provides enzymes having hemicellulase activity. In some aspects, the disclosure provides improved enzyme mixtures for the degradation of hemicellulose-containing materials. The disclosure further provides enzyme cocktails containing one or more cellulases and one or more hemicellulases with improved activity on materials containing both cellulose and hemicellulose, wherein cellulase and hemicellulase mixtures have synergistic activity. The disclosure further provides polypeptides that enhance the activity of enzymes having cellulase or hemicellulase activity, and/or mixtures thereof. The disclosure further provides nucleotide sequences encoding the polypeptides disclosed herein. The polypeptides disclosed herein can be utilized alone, in combination, or with other enzymes.

In one embodiment, the disclosure provides a host cell, comprising two or more recombinant nucleic acids selected from the group consisting of the nucleotide sequences of SEQ ID NOs: 4, 8, 14, 20, 28, 34, and 38. In another embodiment, a host cell comprising three recombinant nucleic acids selected from the group consisting of the nucleotide sequences of SEQ ID NOs: 4, 8, 14, 20, 28, 34, and 38 is provided. In another embodiment, a host cell comprising four recombinant nucleic acids selected from the group consisting of the nucleotide sequences of SEQ ID NOs: 4, 8, 14, 20, 28, 34, and 38 is provided. In another embodiment, a host cell comprising five recombinant nucleic acids selected from the group consisting of the nucleotide sequences of SEQ ID NOs: 4, 8, 14, 20, 28, 34, and 38. In another embodiment, a host cell comprising six recombinant nucleic acids selected from the group consisting of the nucleotide sequences of SEQ ID NOs: 4, 8, 14, 20, 28, 34, and 38 is provided.

In another embodiment, the disclosure provides a host cell, comprising two or more recombinant nucleic acids selected from the group consisting of: a) a nucleic acid encoding the polypeptide of SEQ ID NO: 3 [*Caldicellulosiruptor bescii* endoxylanase (Cb193)], b) a nucleic acid encoding the polypeptide of SEQ ID NO: 7 [*Caldicellulosiruptor bescii* endoxylanase (Cb195)], c) a nucleic acid encoding the polypeptide of SEQ ID NO: 13 [*Caldicellulosiruptor bescii* α-arabinofuranosidase (Cb1172)], d) a nucleic acid encoding the polypeptide of SEQ ID NO: 19 [*Caldicellulosiruptor bescii* α-glucuronidase (Cb909)], e) a nucleic acid encoding the polypeptide of SEQ ID NO: 27 [*Caldicellulosiruptor bescii* β-xylosidase (Cb2487)], f) a nucleic acid encoding the polypeptide of SEQ ID NO: 33 [*Caldicellulosiruptor bescii* acetyl xylan esterase (Cb162)], g) a nucleic acid encoding the polypeptide of SEQ ID NO: 37 [*Caldicellulosiruptor bescii* endoxylanase (Cb193) lacking signal peptide].

In another embodiment, the disclosure provides a host cell, comprising two or more recombinant nucleic acids selected from the group consisting of: a) a nucleic acid encoding the polypeptide of SEQ ID NO: 3 [*Caldicellulosiruptor bescii* endoxylanase (Cb193)], b) a nucleic acid encoding the polypeptide of SEQ ID NO: 7 [*Caldicellulosiruptor bescii* endoxylanase (Cb195)], c) a nucleic acid encoding the polypeptide of SEQ ID NO: 13 [*Caldicellulosiruptor bescii* α-arabinofuranosidase (Cb1172)], d) a nucleic acid encoding the polypeptide of SEQ ID NO: 19 [*Caldicellulosiruptor bescii* α-glucuronidase (Cb909)], e) a nucleic acid encoding the polypeptide of SEQ ID NO: 27 [*Caldicellulosiruptor bescii* β-xylosidase (Cb2487)], f) a nucleic acid encoding the polypeptide of SEQ ID NO: 33 [*Caldicellulosiruptor bescii* acetyl xylan esterase (Cb162)], g) a nucleic acid encoding the polypeptide of SEQ ID NO: 37 [*Caldicellulosiruptor bescii* endoxylanase (Cb193) lacking signal peptide], wherein the host cell further comprises one or more recombinant nucleic acids encoding one or more cellulases.

In another embodiment, the disclosure provides a host cell comprising two or more recombinant nucleic acids selected from the group consisting of: a) a nucleic acid encoding the polypeptide of SEQ ID NO: 3 [*Caldicellulosiruptor bescii* endoxylanase (Cb193)], b) a nucleic acid encoding the polypeptide of SEQ ID NO: 7 [*Caldicellulosiruptor bescii* endoxylanase (Cb195)], c) a nucleic acid encoding the polypeptide of SEQ ID NO: 13 [*Caldicellulosiruptor bescii* α-arabinofuranosidase (Cb1172)], d) a nucleic acid encoding the polypeptide of SEQ ID NO: 19 [*Caldicellulosiruptor bescii* α-glucuronidase (Cb909)], e) a nucleic acid encoding the polypeptide of SEQ ID NO: 27 [*Caldicellulosiruptor bescii* β-xylosidase (Cb2487)], f) a nucleic acid encoding the polypeptide of SEQ ID NO: 33 [*Caldicellulosiruptor bescii* acetyl xylan esterase (Cb162)], g) a nucleic acid encoding the polypeptide of SEQ ID NO: 37 [*Caldicellulosiruptor bescii* endoxylanase (Cb193) lacking signal peptide], wherein the host cell is selected from the group consisting of *Escherichia* spp., *Pseudomonas* spp., *Proteus* spp., *Ralstonia* spp., *Streptomyces* spp., *Staphylococcus* spp., *Lactococcus* spp., *Bacillus* spp., *Saccharomyces cerevisiae, Schizosaccharomyces pombe, Yarrowia lipolytica, Hansenula polymorpha, Kluyveromyces lactis, Pichia pastoris, Aspergillus* spp., *Chrysosporium lucknowense*, or *Trichoderma reesei.*

In another embodiment, the disclosure provides a method for producing at least two of the enzymes selected from the group consisting of endoxylanase, α-arabinofuranosidase, α-glucuronidase, β-xylosidase, and acetyl xylan esterase, comprising: culturing a host cell comprising two or more recombinant nucleic acids selected from the group consisting of: a) a nucleic acid encoding the polypeptide of SEQ ID NO: 3 [*Caldicellulosiruptor bescii* endoxylanase (Cb193)], b) a nucleic acid encoding the polypeptide of SEQ ID NO: 7 [*Caldicellulosiruptor bescii* endoxylanase (Cb195)], c) a nucleic acid encoding the polypeptide of SEQ ID NO: 13 [*Caldicellulosiruptor bescii* α-arabinofuranosidase (Cb1172)], d) a nucleic acid encoding the polypeptide of SEQ ID NO: 19 [*Caldicellulosiruptor bescii* α-glucuronidase (Cb909)], e) a nucleic acid encoding the polypeptide of SEQ ID NO: 27 [*Caldicellulosiruptor bescii* β-xylosidase (Cb2487)], f) a nucleic acid encoding the polypeptide of SEQ ID NO: 33 [*Caldicellulosiruptor bescii* acetyl xylan esterase (Cb162)], g) a nucleic acid encoding the polypeptide of SEQ ID NO: 37 [*Caldicellulosiruptor bescii* endoxylanase (Cb193) lacking signal peptide] in a culture medium, under suitable conditions to produce the endoxylanase, α-arabinofuranosidase, α-glucuronidase, β-xylosidase, and acetyl xylan esterase.

In another embodiment, the disclosure provides a host cell, comprising two or more recombinant nucleic acids selected from the group consisting of: a) a nucleic acid encoding the polypeptide of SEQ ID NO: 3 [*Caldicellulosiruptor bescii* endoxylanase (Cb193)], b) a nucleic acid encoding the polypeptide of SEQ ID NO: 7 [*Caldicellulosiruptor bescii* endoxylanase (Cb195)], c) a nucleic acid encoding the polypeptide of SEQ ID NO: 13 [*Caldicellulosiruptor bescii* α-arabinofuranosidase (Cb1172)], d) a nucleic acid encoding the polypeptide of SEQ ID NO: 19 [*Caldicellulosiruptor bescii* α-glucuronidase (Cb909)], e) a nucleic acid encoding the polypeptide of SEQ ID NO: 27 [*Caldicellulosiruptor bescii* β-xylosidase (Cb2487)], f) a nucleic acid encoding the polypeptide of SEQ ID NO: 33 [*Caldicellulosiruptor bescii* acetyl xylan esterase (Cb162)], g) a nucleic acid encoding the polypeptide of SEQ ID NO: 37 [*Caldicellulosiruptor bescii* endoxylanase (Cb193) lacking signal peptide] and culture medium.

In another embodiment, the disclosure provides a composition comprising two or more recombinant proteins, the recombinant proteins selected from the group consisting of the polypeptide sequences of SEQ ID NOs: 3, 7, 13, 19, 27, 33 and 37.

In another embodiment, the disclosure provides a composition comprising six recombinant proteins, the recombinant proteins selected from the group consisting of the polypeptides of SEQ ID NOs: 3, 7, 13, 19, 27, 33 and 37.

In another embodiment, the disclosure provides a composition comprising two or more recombinant proteins, the recombinant proteins selected from the group consisting of the polypeptide sequences of SEQ ID NOs: 3, 7, 13, 19, 27, 33 and 37, wherein the composition further comprises one or more recombinant cellulases.

In yet another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fermentation product.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fermentation product, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fermentation product, wherein the biomass comprises a plant material.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fermentation product, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fuel.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fuel, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fuel, wherein the biomass comprises a plant material.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution; and culturing the sugar solution with a fermentative microorganism under conditions sufficient to produce a fuel, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution, wherein the biomass comprises a plant material.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, and wherein the composition may further comprise one or more recombinant cellulases, to yield a sugar solution, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In yet another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said one or more functional groups are selected from the group consisting of arabinose, glucuronyl, and acetyl.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said treating is conducted at a temperature between 40 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said treating is conducted at a temperature between 60 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said one or more functional groups are selected from the group consisting of arabinose, glucuronyl, and acetyl.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said treating is conducted at a temperature between 40 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein said treating cleaves said one or more functional groups from said xylose backbone to form cleaved hemicellulose, wherein said treating is conducted at a temperature between 60 and 80° C.

In another embodiment, the disclosure provides a host cell, comprising two or more recombinant nucleic acids selected from the group consisting of the nucleotide sequences of SEQ ID NOs: 4, 8, 14, 20, 28, 34, and 38, wherein at least one of the two or more recombinant nucleic acids is selected from the group consisting of the nucleotide sequences of SEQ ID NOs: 8, 14, 20, 28, and 34. In another embodiment, a host cell comprising three recombinant nucleic acids selected from the group consisting of the nucleotide sequences of SEQ ID NOs: 4, 8, 14, 20, 28, 34, and 38, wherein at least two of the three recombinant nucleic acids are selected from the group consisting of the nucleotide sequences of SEQ ID NOs: 8, 14, 20, 28, and 34, is provided. In another embodiment, a host cell comprising four recombinant nucleic acids selected from the group consisting of the nucleotide sequences of SEQ ID NOs: 4, 8, 14, 20, 28, 34, and 38, wherein at least three of the four recombinant nucleic acids are selected from the group consisting of the nucleotide sequences of SEQ ID NOs: 8, 14, 20, 28, and 34, is provided. In another embodiment, a host cell comprising five recombinant nucleic acids selected from the group consisting of the nucleotide sequences of SEQ ID NOs: 4, 8, 14, 20, 28, 34, and 38, wherein at least four of the five recombinant nucleic acids are selected from the group consisting of the nucleotide sequences of SEQ ID NOs: 8, 14, 20, 28, and 34, is provided In another embodiment, a host cell comprising six recombinant nucleic acids selected from the group consisting of the nucleotide sequences of SEQ ID NOs: 4, 8, 14, 20, 28, 34, and 38, wherein at least five of the six recombinant nucleic acids are selected from the group consisting of the nucleotide sequences of SEQ ID NOs: 8, 14, 20, 28, and 34, is provided.

In another embodiment, the disclosure provides a host cell, comprising two or more recombinant nucleic acids selected from the group consisting of: a) a nucleic acid encoding the polypeptide of SEQ ID NO: 3 *[Caldicellulosiruptor bescii* endoxylanase (Cb193)], b) a nucleic acid encoding the polypeptide of SEQ ID NO: 7 *[Caldicellulosiruptor bescii* endoxylanase (Cb195)], c) a nucleic acid encoding the polypeptide of SEQ ID NO: 13 *[Caldicellulosiruptor bescii* α-arabinofuranosidase (Cb1172)], d) a nucleic acid encoding the polypeptide of SEQ ID NO: 19 *[Caldicellulosiruptor bescii* α-glucuronidase (Cb909)], e) a nucleic acid encoding the polypeptide of SEQ ID NO: 27 *[Caldicellulosiruptor bescii* β-xylosidase (Cb2487)], f) a nucleic acid encoding the polypeptide of SEQ ID NO: 33 *[Caldicellulosiruptor bescii* acetyl xylan esterase (Cb162)], g) a nucleic acid encoding the polypeptide of SEQ ID NO: 37 *[Caldicellulosiruptor bescii* endoxylanase (Cb193) lacking signal peptide], wherein at least one of the two or more recombinant nucleic acids is selected from the group consisting of: a nucleic acid encoding the polypeptide of SEQ ID NO: 7 *[Caldicellulosiruptor bescii* endoxylanase (Cb195)], a nucleic acid encoding the polypeptide of SEQ ID NO: 13 [*Caldicellulosiruptor bescii* α-arabinofuranosidase (Cb1172)], a nucleic acid encoding the polypeptide of SEQ ID NO: 19 *[Caldicellulosiruptor bescii* α-glucuronidase (Cb909)], a nucleic acid encoding the polypeptide of SEQ ID NO: 27 *[Caldicellulosiruptor bescii* β-xylosidase (Cb2487)], and a nucleic acid encoding the polypeptide of SEQ ID NO: 33 *[Caldicellulosiruptor bescii* acetyl xylan esterase (Cb162)].

In another embodiment, the disclosure provides a host cell, comprising two or more recombinant nucleic acids selected from the group consisting of: a) a nucleic acid encoding the polypeptide of SEQ ID NO: 3 *[Caldicellulosiruptor bescii* endoxylanase (Cb193)], b) a nucleic acid encoding the polypeptide of SEQ ID NO: 7 *[Caldicellulosiruptor bescii* endoxylanase (Cb195)], c) a nucleic acid encoding the polypeptide of SEQ ID NO: 13 *[Caldicellulosiruptor bescii* α-arabinofuranosidase (Cb1172)], d) a nucleic acid encoding the polypeptide of SEQ ID NO: 19 *[Caldicellulosiruptor bescii* α-glucuronidase (Cb909)], e) a nucleic acid encoding the polypeptide of SEQ ID NO: 27 *[Caldicellulosiruptor bescii* β-xylosidase (Cb2487)], f) a nucleic acid encoding the polypeptide of SEQ ID NO: 33 *[Caldicellulosiruptor bescii* acetyl xylan esterase (Cb162)], g) a nucleic acid encoding the polypeptide of SEQ ID NO: 37 *[Caldicellulosiruptor bescii* endoxylanase (Cb193) lacking signal peptide], wherein at least one of the two or more recombinant nucleic acids is selected from the group consisting of: a nucleic acid encoding the polypeptide of SEQ ID NO: 7 *[Caldicellulosiruptor bescii* endoxylanase (Cb195)], a nucleic acid encoding the polypeptide of SEQ ID NO: 13 *[Caldicellulosiruptor bescii* α-arabinofuranosidase (Cb1172)], a nucleic acid encoding the polypeptide of SEQ ID NO: 19 *[Caldicellulosiruptor bescii* α-glucuronidase (Cb909)], a nucleic acid encoding the polypeptide of SEQ ID NO: 27 *[Caldicellulosiruptor bescii* β-xylosidase (Cb2487)], and a nucleic acid encoding the polypeptide of SEQ ID NO: 33 *[Caldicellulosiruptor bescii* acetyl xylan esterase (Cb162)], and wherein the host cell further comprises one or more recombinant nucleic acids encoding one or more cellulases.

In another embodiment, the disclosure provides a host cell comprising two or more recombinant nucleic acids selected from the group consisting of: a) a nucleic acid encoding the polypeptide of SEQ ID NO: 3 *[Caldicellulosiruptor bescii* endoxylanase (Cb193)], b) a nucleic acid encoding the polypeptide of SEQ ID NO: 7 *[Caldicellulosiruptor bescii* endoxylanase (Cb195)], c) a nucleic acid encoding the polypeptide of SEQ ID NO: 13 *[Caldicellulosiruptor bescii* α-arabinofuranosidase (Cb1172)], d) a nucleic acid encoding the polypeptide of SEQ ID NO: 19 *[Caldicellulosiruptor bescii* α-glucuronidase (Cb909)], e) a nucleic acid encoding the polypeptide of SEQ ID NO: 27 *[Caldicellulosiruptor bescii* β-xylosidase (Cb2487)], f) a nucleic acid encoding the polypeptide of SEQ ID NO: 33 *[Caldicellulosiruptor bescii* acetyl xylan esterase (Cb162)], g) a nucleic acid encoding the polypeptide of SEQ ID NO: 37 *[Caldicellulosiruptor bescii* endoxylanase (Cb193) lacking signal peptide], wherein at least one of the two or more recombinant nucleic acids is selected from the group consisting of: a nucleic acid encoding the polypeptide of SEQ ID NO: 7 *[Caldicellulosiruptor bescii* endoxylanase (Cb195)], a nucleic acid encoding the polypeptide of SEQ ID NO: 13 *[Caldicellulosiruptor bescii* α-arabinofuranosidase (Cb1172)], a nucleic acid encoding the polypeptide of SEQ ID NO: 19 *[Caldicellulosiruptor bescii* α-glucuronidase (Cb909)], a nucleic acid encoding the polypeptide of SEQ ID NO: 27 *[Caldicellulosiruptor bescii* β-xylosidase (Cb2487)], and a nucleic acid encoding the polypeptide of SEQ ID NO: 33 *[Caldicellulosiruptor bescii* acetyl xylan esterase (Cb162)], and wherein the host cell is selected from the group consisting of *Escherichia* spp., *Pseudomonas* spp., *Proteus* spp., *Ralstonia* spp., *Streptomyces* spp., *Staphylococcus* spp., *Lactococcus* spp., *Bacillus* spp., *Saccharomyces cerevisiae, Schizosaccharomyces pombe, Yarrowia lipolytica, Hansenula polymorpha, Kluyveromyces lactis, Pichia pastoris, Aspergillus* spp., *Chrysosporium lucknowense*, or *Trichoderma reesei.*

In another embodiment, the disclosure provides a method for producing at least two of the enzymes selected from the group consisting of endoxylanase, α-arabinofuranosidase, α-glucuronidase, β-xylosidase, and acetyl xylan esterase, comprising: culturing a host cell comprising two or more recombinant nucleic acids selected from the group consisting of: a) a nucleic acid encoding the polypeptide of SEQ ID NO: 3 *[Caldicellulosiruptor bescii* endoxylanase (Cb193)], b) a nucleic acid encoding the polypeptide of SEQ ID NO: 7 *[Caldicellulosiruptor bescii* endoxylanase (Cb195)], c) a nucleic acid encoding the polypeptide of SEQ ID NO: 13 *[Caldicellulosiruptor bescii* α-arabinofuranosidase (Cb1172)], d) a nucleic acid encoding the polypeptide of SEQ ID NO: 19 *[Caldicellulosiruptor bescii* α-glucuronidase (Cb909)], e) a nucleic acid encoding the polypeptide of SEQ ID NO: 27 *[Caldicellulosiruptor bescii* β-xylosidase (Cb2487)], f) a nucleic acid encoding the polypeptide of SEQ ID NO: 33 *[Caldicellulosiruptor bescii* acetyl xylan esterase (Cb162)], g) a nucleic acid encoding the polypeptide of SEQ ID NO: 37 *[Caldicellulosiruptor bescii* endoxylanase (Cb193) lacking signal peptide], wherein at least one of the two or more recombinant nucleic acids is selected from the group consisting of: a nucleic acid encoding the polypeptide of SEQ ID NO: 7 *[Caldicellulosiruptor bescii* endoxylanase (Cb195)], a nucleic acid encoding the polypeptide of SEQ ID NO: 13 *[Caldicellulosiruptor bescii* α-arabinofuranosidase (Cb1172)], a nucleic acid encoding the polypeptide of SEQ ID NO: 19 *[Caldicellulosiruptor bescii* α-glucuronidase (Cb909)], a nucleic acid encoding the polypeptide of SEQ ID NO: 27 *[Caldicellulosiruptor bescii* β-xylosidase (Cb2487)], and a nucleic acid encoding the polypeptide of SEQ ID NO: 33 *[Caldicellulosiruptor bescii* acetyl xylan esterase (Cb162)] in a culture medium, under suitable conditions to produce the endoxylanase, α-arabinofuranosidase, α-glucuronidase, β-xylosidase, and acetyl xylan esterase.

In another embodiment, the disclosure provides a host cell, comprising two or more recombinant nucleic acids selected from the group consisting of: a) a nucleic acid encoding the polypeptide of SEQ ID NO: 3 *[Caldicellulosiruptor bescii* endoxylanase (Cb193)], b) a nucleic acid encoding the polypeptide of SEQ ID NO: 7 *[Caldicellulosiruptor bescii* endoxylanase (Cb195)], c) a nucleic acid encoding the polypeptide of SEQ ID NO: 13 *[Caldicellulosiruptor bescii* α-arabinofuranosidase (Cb1172)], d) a nucleic acid encoding the polypeptide of SEQ ID NO: 19 *[Caldicellulosiruptor bescii* α-glucuronidase (Cb909)], e) a nucleic acid encoding the polypeptide of SEQ ID NO: 27 *[Caldicellulosiruptor bescii* β-xylosidase (Cb2487)], f) a nucleic acid encoding the polypeptide of SEQ ID NO: 33 *[Caldicellulosiruptor bescii* acetyl xylan esterase (Cb162)], g) a nucleic acid encoding the polypeptide of SEQ ID NO: 37 *[Caldicellulosiruptor bescii* endoxylanase (Cb193) lacking signal peptide], wherein at least one of the two or more recombinant nucleic acids is selected from the group consisting of: a nucleic acid encoding the polypeptide of SEQ ID NO: 7 *[Caldicellulosiruptor bescii* endoxylanase (Cb195)], a nucleic acid encoding the polypeptide of SEQ ID NO: 13 *[Caldicellulosiruptor bescii* α-arabinofuranosidase (Cb1172)], a nucleic acid encoding the polypeptide of SEQ ID NO: 19 *[Caldicellulosiruptor bescii* α-glucuronidase (Cb909)], a nucleic acid encoding the polypeptide of SEQ ID NO: 27 *[Caldicellulosiruptor bescii* β-xylosidase (Cb2487)], and a nucleic acid encoding the polypeptide of SEQ ID NO: 33 *[Caldicellulosiruptor bescii* acetyl xylan esterase (Cb162)], and culture medium.

In another embodiment, the disclosure provides a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33.

In another embodiment, the disclosure provides a composition comprising six recombinant proteins, the recombinant proteins selected from the group consisting of the polypeptides of SEQ ID NOs: 3, 7, 13, 19, 27, 33 and 37, wherein five of the six recombinant proteins are selected from the group consisting of the polypeptide sequences of SEQ ID NOs: 7, 13, 19, 27, and 33.

In another embodiment, the disclosure provides a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition further comprises one or more recombinant cellulases.

In yet another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fermentation product.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fermentation product, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fermentation product, wherein the biomass comprises a plant material.

In another embodiment, the disclosure provides a method of converting biomass to fermentation product comprising contacting the biomass with a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fermentation product, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fuel.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fuel, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fuel, wherein the biomass comprises a plant material.

In another embodiment, the disclosure provides a method of converting biomass to fuel comprising contacting the biomass with the composition a composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution; and culturing the sugar solution with a fermentative microorganism under conditions sufficient to produce a fuel, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution, and wherein the biomass is subjected to pretreatment prior to being contacted with the composition comprising two or more recombinant proteins, wherein the pretreatment comprises one or more of the treatments selected from the group consisting of: ammonia fiber expansion (AFEX), steam explosion, treatment with alkaline aqueous solutions, treatment with acidic solutions, treatment with organic solvents, treatment with ionic liquids (IL), treatment with electrolyzed water, and treatment with phosphoric acid.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution, wherein the biomass comprises a plant material.

In another embodiment, the disclosure provides a method of degrading biomass comprising contacting the biomass with the composition comprising two or more recombinant proteins, the recombinant proteins selected from the group consisting of the polypeptide sequences of SEQ ID NOs: 3, 7, 13, 19, 27, 33 and 37, wherein at least one of the two or more recombinant proteins is selected from the group consisting of the polypeptide sequences of SEQ ID NOs: 7, 13, 19, 27, and 33, and wherein the composition may further comprise one or more recombinant cellulases, to yield a sugar solution, wherein the biomass comprises a plant material selected from the group consisting of *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, birch, willow, aspen, poplar wood, and energy cane.

In yet another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said one or more functional groups are selected from the group consisting of arabinose, glucuronyl, and acetyl.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said treating is conducted at a temperature between 40 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said treating is conducted at a temperature between 60 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said one or more functional groups are selected from the group consisting of arabinose, glucuronyl, and acetyl.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said treating is conducted at a temperature between 40 and 80° C.

In another embodiment, the disclosure provides a method for degrading hemicellulose, said method comprising the steps of: a) providing plant material comprising hemicellulose, wherein said hemicellulose comprises a xylose backbone comprising β-1,4-linkages and one or more functional groups; and b) treating said hemicellulose with a transgenic host cell that secretes two or more enzymes selected from the group consisting of the polypeptides of SEQ ID NOs: 3, 7, 13, 19, 27, 33, and 37, wherein at least one of the two or more enzymes is selected from the group consisting of the polypeptide of SEQ ID NOs: 7, 13, 19, 27, and 33, and wherein said treating cleaves said one or more functional groups from said xylose backbone to form cleaved hemicellulose, wherein said treating is conducted at a temperature between 60 and 80° C.

In one aspect, provided herein is a host cell containing one, two, three, four, five, six or more recombinant nucleic acids, wherein the recombinant nucleic acids encode one, two, three, four, five, or six polypeptides selected from: Cb1952, Cb1953, Cb1954, Cb1946, Cb629 and Cb486 polypeptides.

In another aspect, provided herein is a host cell containing one, two, three, four, five, six or more recombinant nucleic acids, wherein the recombinant nucleic acids encode one, two, three, four, five, or six polypeptides selected from: Cb1952, Cb1953, Cb1954, Cb1946, Cb629 and Cb486 polypeptides, and wherein the Cb1952 polypeptide has a sequence selected from SEQ ID NOs: 44, 114, 124, 126, 128, and 46, wherein the Cb1953 polypeptide has a sequence selected from SEQ ID NOs: 60, 61, and 111. wherein the Cb1954 polypeptide has a sequence selected from SEQ ID NOs: 74, 121, and 76; wherein the Cb1946 polypeptide has a sequence selected from SEQ ID NOs: 86, 87, and 113; wherein the Cb629 polypeptide has a sequence selected from SEQ ID NOs: 98, 119, and 100; and wherein the Cb486 polypeptide has a sequence of SEQ ID NO: 106.

Also provided herein is a host cell containing one, two, three, four, five, six or more recombinant nucleic acids, wherein the recombinant nucleic acids encode one, two, three, four, five, or six polypeptides selected from polypeptides having the sequence of: SEQ ID NO: 46, 111, 76, 113, 100, and 106.

Also provided herein is a host cell containing one, two, three, four, five, six or more recombinant nucleic acids, wherein the recombinant nucleic acids encode one, two, three, four, five, or six polypeptides selected from: Cb1952, Cb1953, Cb1954, Cb1946, Cb629 and Cb486 polypeptides, and wherein the recombinant nucleic acid encoding a Cb1952 polypeptide has a sequence selected from SEQ ID NOs: 45, 115, 125, 127, 129, and 47; wherein the recombinant nucleic acid encoding a Cb1953 polypeptide has a sequence selected from SEQ ID NOs: 62, 63, and 110; wherein the recombinant nucleic acid encoding a Cb1954 polypeptide has a sequence selected from SEQ ID NOs: 116, 75, and 77; wherein the recombinant nucleic acid encoding a Cb1946 polypeptide has a sequence selected from SEQ ID NOs: 88, 89, and 112; wherein the recombinant nucleic acid encoding a Cb629 polypeptide has a sequence selected from SEQ ID NOs: 99, 120, and 101; and, wherein the recombinant nucleic acid encoding a Cb486 polypeptide has the sequence of SEQ ID NO: 107.

Also provided herein is a host cell containing one, two, three, four, five, six, or more recombinant nucleic acids, wherein the recombinant nucleic acids encode one, two, three, four, five, or six polypeptides selected from: Cb1952, Cb1953, Cb1954, Cb1946, Cb629 and Cb486 polypeptides, and wherein the recombinant nucleic acids have a sequence selected from SEQ ID NOs: 47, 110, 77, 112, 101, and 107.

Also provided herein host cell containing six recombinant nucleic acids, wherein the nucleic acids have the sequences of SEQ ID NOs: 47, 110, 77, 112, 101, and 107.

Any of the host cells provided herein may also contain one or more recombinant nucleic acids encoding a hemicellulase, wherein the hemicellulase has a sequence selected from SEQ ID NOs: 3, 7, 13, 19, 27, 33, and 37. In some aspects, a nucleic acid encoding a hemicellulase has a sequence selected from SEQ ID NOs: 4, 8, 14, 20, 28, 34, and 38. In some aspects, host cells provided herein may contain recombinant nucleic acids having the sequences of SEQ ID NOs: 8, 14, 20, 28, 34, and 38, or recombinant nucleic acids having the sequences of SEQ ID NOs: 8, 14, 20, 28, and 38.

Further provided herein is a composition containing one, two, three, four, five, six, or more recombinant polypeptides, wherein the recombinant polypeptides are selected from Cb1952, Cb1953, Cb1954, Cb1946, Cb629 and Cb486 polypeptides.

In another aspect, provided herein is a composition containing one, two, three, four, five, six, or more recombinant polypeptides, wherein the recombinant polypeptides are selected from Cb1952, Cb1953, Cb1954, Cb1946, Cb629 and Cb486 polypeptides, and wherein the Cb1952 polypeptide has a sequence selected from SEQ ID NOs: 44, 114, 124, 126, 128, and 46, wherein the Cb1953 polypeptide has a sequence selected from SEQ ID NOs: 60, 61, and 111. wherein the Cb1954 polypeptide has a sequence selected from SEQ ID NOs: 74, 121, and 76; wherein the Cb1946 polypeptide has a sequence selected from SEQ ID NOs: 86, 87, and 113; wherein the Cb629 polypeptide has a sequence selected from SEQ ID NOs: 98, 119, and 100; and wherein the Cb486 polypeptide has a sequence of SEQ ID NO: 106.

Also provided herein is a composition containing one, two, three, four, five, six, or more recombinant polypeptides, wherein the recombinant polypeptides have a sequence selected from SEQ ID NOs: 46, 111, 76, 113, 100, and 106.

Also provided herein is a composition containing six recombinant polypeptides, wherein the recombinant polypeptides have the sequences of SEQ ID NOs: 46, 111, 76, 113, 100, and 106.

Also provided herein is a composition containing one or more recombinant polypeptides, wherein the one or more recombinant polypeptides are selected from the group consisting of the polypeptides of SEQ ID NOs: 46, 111, 76, 113, 124, 126, 128, and 100.

Any of the compositions provided herein may also contain one or more hemicellulase polypeptides, wherein the hemicellulase has a sequence selected from SEQ ID NOs: 3, 7, 13, 19, 27, 33, and 37. In some aspects, compositions provided herein contain polypeptides having the sequences of SEQ ID NOs: 7, 13, 19, 27, 33, and 37 or polypeptides having the sequences of SEQ ID NOs: 7, 13, 19, 27, and 37.

In another aspect, provided herein is a method for producing one or more cellulases, the method including: a) culturing any of the host cells disclosed herein which contain one or more recombinant nucleic acids encoding one or more Cb1952, Cb1953, Cb1954, Cb1946, Cb629 and Cb486 polypeptides, in culture media under conditions sufficient to support the expression of the recombinant nucleic acid(s), and collecting one or more cellulases from said media and/or said host cell.

In another aspect, provided herein is a method for degrading a cellulose-containing material, the method including: a) contacting the cellulose-containing material with any host cell or composition disclosed herein, and, b) incubating the host cell or composition and cellulose-containing material under conditions that support cellulose degradation.

Cellulose-containing material may be pretreated prior to being contacted with a composition or host cell disclosed herein. Pre-treatment steps may include one or more of the treatments of: ammonia fiber expansion (AFEX), steam explosion, treatment with alkaline aqueous solutions, treatment with acidic solutions, treatment with organic solvents, treatment with high pressure, treatment with high temperature, treatment with ionic liquids (IL), treatment with electrolyzed water, and treatment with phosphoric acid.

Also provided herein is a method of reducing the viscosity of a pretreated cellulose-containing material, the method including contacting pretreated cellulose-containing material with any host cell or composition provided herein.

Also provided herein is a method of converting a cellulose-containing material to fermentation product, the method including: a) contacting the cellulose-containing material with any host cell or composition provided herein, to yield a sugar solution, and culturing the sugar solution with a fermentative microorganism under conditions sufficient to produce a fermentation product.

Also provided herein is a method for degrading a cellulose-containing material, the method including: a) contacting the cellulose-containing material with one or more polypeptides selected from SEQ ID NOs: 46, 111, 76, 113, 124, 126, 128, and 100, and b) incubating the one or more polypeptides and cellulose-containing material under conditions that support cellulose degradation.

In some aspects, cellulose-containing material provided herein is a plant material. Plant material may include, without limitation, *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, rye hulls, wheat hulls, sugarcane bagasse, copra meal, copra pellets, palm kernel meal, corn fiber, Distillers Dried Grains with Solubles (DDGS), Blue Stem, corncobs, pine wood, birch wood, willow wood, aspen wood, poplar wood, energy cane, waste paper, sawdust, forestry wastes, waste paper, and crop residues.

In some aspects, at least a portion of any of the methods provided herein may be conducted at a temperature above 50° C. In some aspects, at least a portion of any of the methods provided herein may be conducted at a temperature between 40° and 80°, 50° and 80°, 60° and 80°, 70° and 80°, 45° and 55°, 50° and 60°, 55° and 65°, 60° and 70°, 65° and 75°, 75° and 85°, or 80° and 90° C.

In some aspects, in any host cells disclosed herein that contain two or more recombinant nucleic acids, two or more of the recombinant nucleic acids may be present in a contiguous polydeoxyribonucleotide chain.

In any of the compositions or methods above, a Cb1581 polypeptide may be provided in the composition or the method with the cellulases and/or hemicellulases. In some aspects, the Cb1581 polypeptide is a polypeptide containing the sequence of SEQ ID NO: 146. Also provided herein are any of the above host cells that further contain a nucleic acid encoding a Cb1581 polypeptide. In some aspects, a nucleic acid encoding a Cb1581 polypeptide is a nucleic acid containing the sequence of SEQ ID NO: 147.

BRIEF DESCRIPTION OF THE DRAWINGS

FIG. 2A shows the putative domain architecture of the Cb193 and Cb195 proteins. FIG. 2B shows an SDS-PAGE of purified Cb193 and Cb195; the molecular markers are in the lane marked M. The proteins were purified by metal affinity chromatography, followed by ion exchange chromatography and then gel filtration. The predicted molecular masses of Cb193 and Cb195 were 77.7 kDa and 42.0 kDa, respectively. FIG. 2C shows the enzymatic activity of Cb193 on natural substrates using TLC analysis. Various substrates were tested: soluble wheat arabinoxylan (SWAX), oat-spelt xylan (OSX), Birchwood xylan (BWX), carboxymethyl cellulose (CMC), lichenan, glucomannan, 1,4 β-mannan, and arabinan. In the case of SWAX, OSX, and BWX, in the presence of Cb193 (+), short xylose chains were released. In the minus (−) lanes, no enzyme was added and therefore no products of hydrolysis were released. X1 (xylose monomer), X2 (xylose dimer or a disaccharide), X3 (trisaccharide), X4 (tetrasaccharide), and pentasaccharide (X5) were loaded in the first lane (M) as markers. The results showed that this enzyme releases shorter chains or oligosaccharides from the complex substrates (SWAX, OSX, and BWX). FIG. 2D shows the enzymatic activity of Cb195 on natural substrates using TLC analysis. Various substrates were tested: SWAX, OSX, BWX, CMC, lichenan, glucomannan, 1,4 β-mannan, and arabinan. In the case of SWAX, OSX, and BWX, in the presence of Cb195 (+), short xylose chains were released. In the minus (−) lanes, no enzyme was added and therefore no products of hydrolysis were released. X1 (xylose monomer), X2 (xylose dimer or a disaccharide), X3 (trisaccharide), X4 (tetrasaccharide), and pentasaccharide (X5) were loaded in the first lane (M) as markers. The results showed that this enzyme releases shorter chains or oligosaccharides from the complex substrates (SWAX, OSX, and BWX). FIG. 2E shows the enzymatic activity of Cb193 and Cb195 on natural substrates from a reducing sugar assay. In this experiment, a different assay for reducing sugars was used to determine the release of products from the substrates. A standard was made based on known glucose concentrations and their absorbance (color development) in the presence of para-hydroxy-benzoic acid hydrazide (Cann et al. 1999. J. Bacterial. 181:1643-1651 and other reference above-Laver, M. 1972.). Incubation of enzymes with the substrates led to release of products that were quantified as a concentration of glucose equivalents.

FIG. 3A shows the thermostability of Cb193, and FIG. 3B shows the thermostability of Cb195. 5 nM of Cb193 and Cb195 were incubated at different temperatures ranging from 65~90° C. For Cb193, the enzymes were incubated at 70° C., 75° C., 80° C., 85° C., and 90° C.; for Cb195, the enzymes were incubated at 65° C., 70° C., 75° C., and 80° C. The incubated enzymes were taken out at certain time points (0 h, 0.5 h, 1 h, 2 h, 4 h, 7 h, 11 h, 16 h, and 24 h) as indicated, and immediately incubated with wheat arabinoxylan (final 1%, w/v) to measure the enzyme activity. The initial velocity of reaction was calculated. The residue activity (%) was calculated by dividing the activity of each samples by the initial activity at zero time. Bars are shown with standard errors for three independent experiments.

In FIGS. 4AA, 4AB, and 4AC, the experiment was conducted at 75° C. with 50 mM citrate buffer (pH 6.0).

In FIGS. 5AA, 5AB, and 5AC, the experiment was conducted at 75° C. with 50 mM citrate buffer (pH 6.0).

were incubated with Cb195 (final 5 nM for wheat arabinoxylan and final 50 nM for oat spelt xylan and birchwood xylan). The initial velocity of reaction was calculated. The initial velocities were then plotted against the concentrations of xylan substrates. The $K_m$ and $k_{cat}$ were calculated by non-linear fit using the Graphpad software. Bars are shown with standard errors for three independent experiments.

Figure 6A:
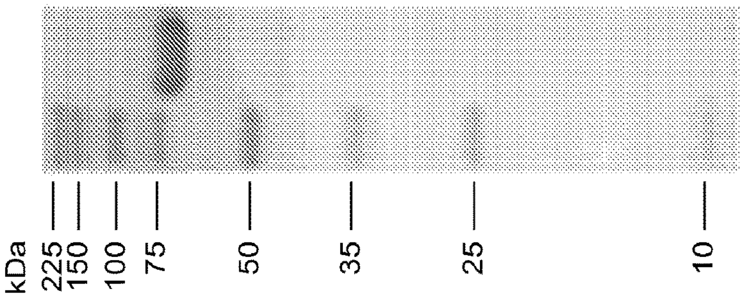
Figure 6B:
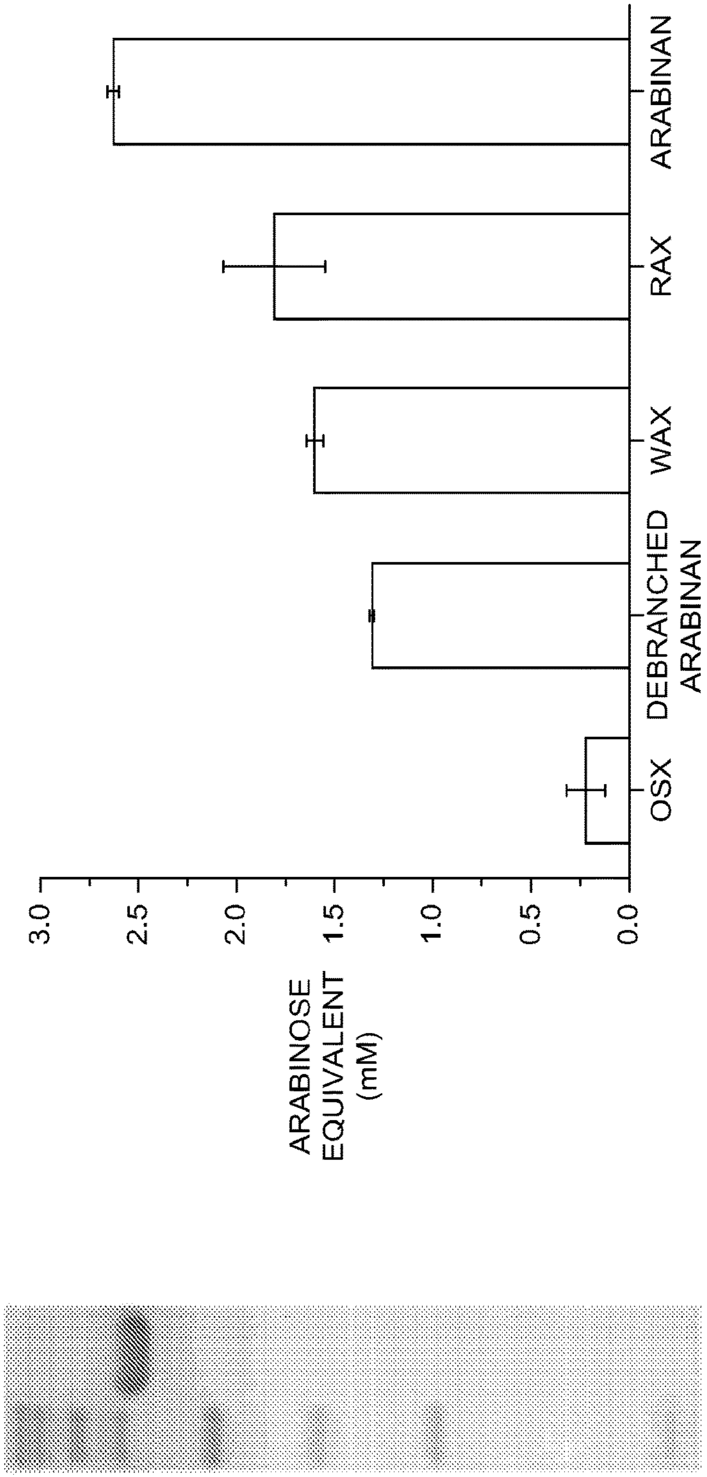
Figure 6C:
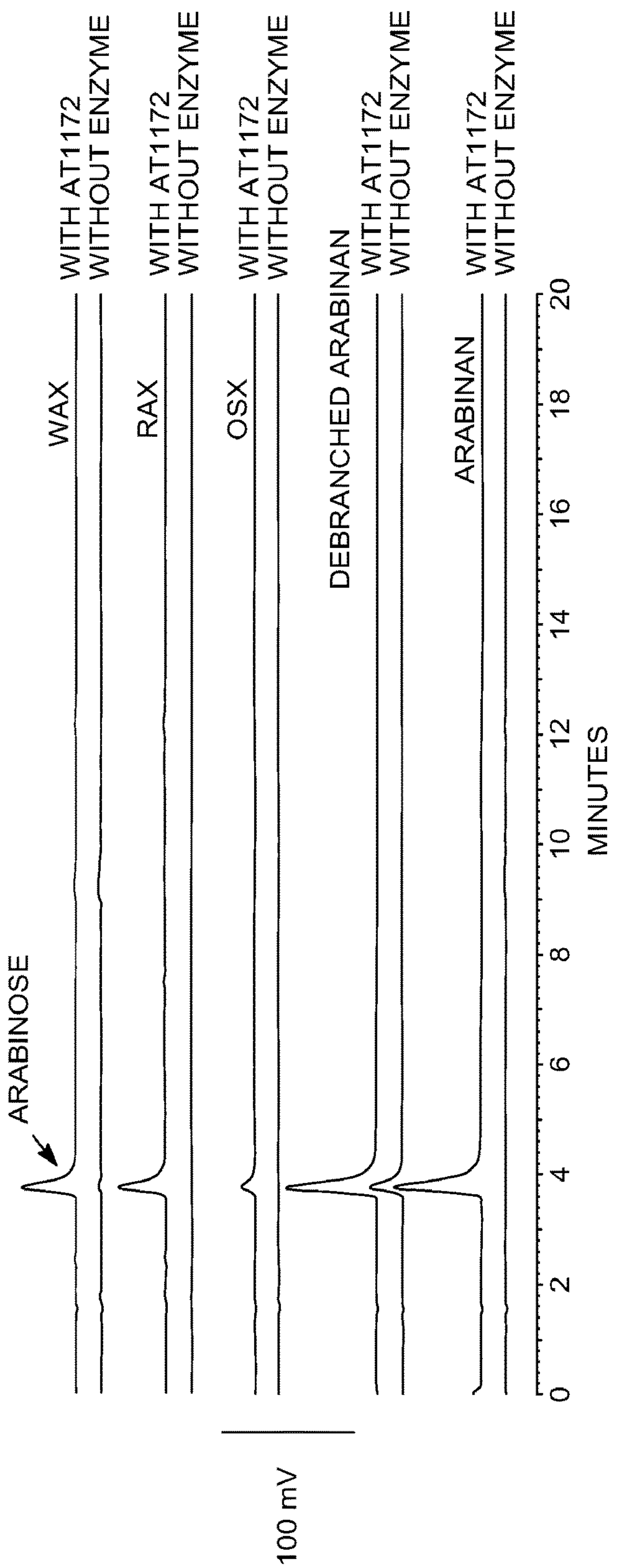
Figure 6D:
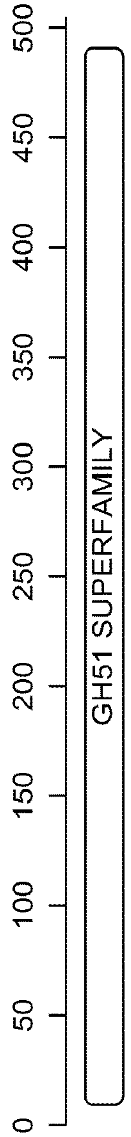
Figure 6E:
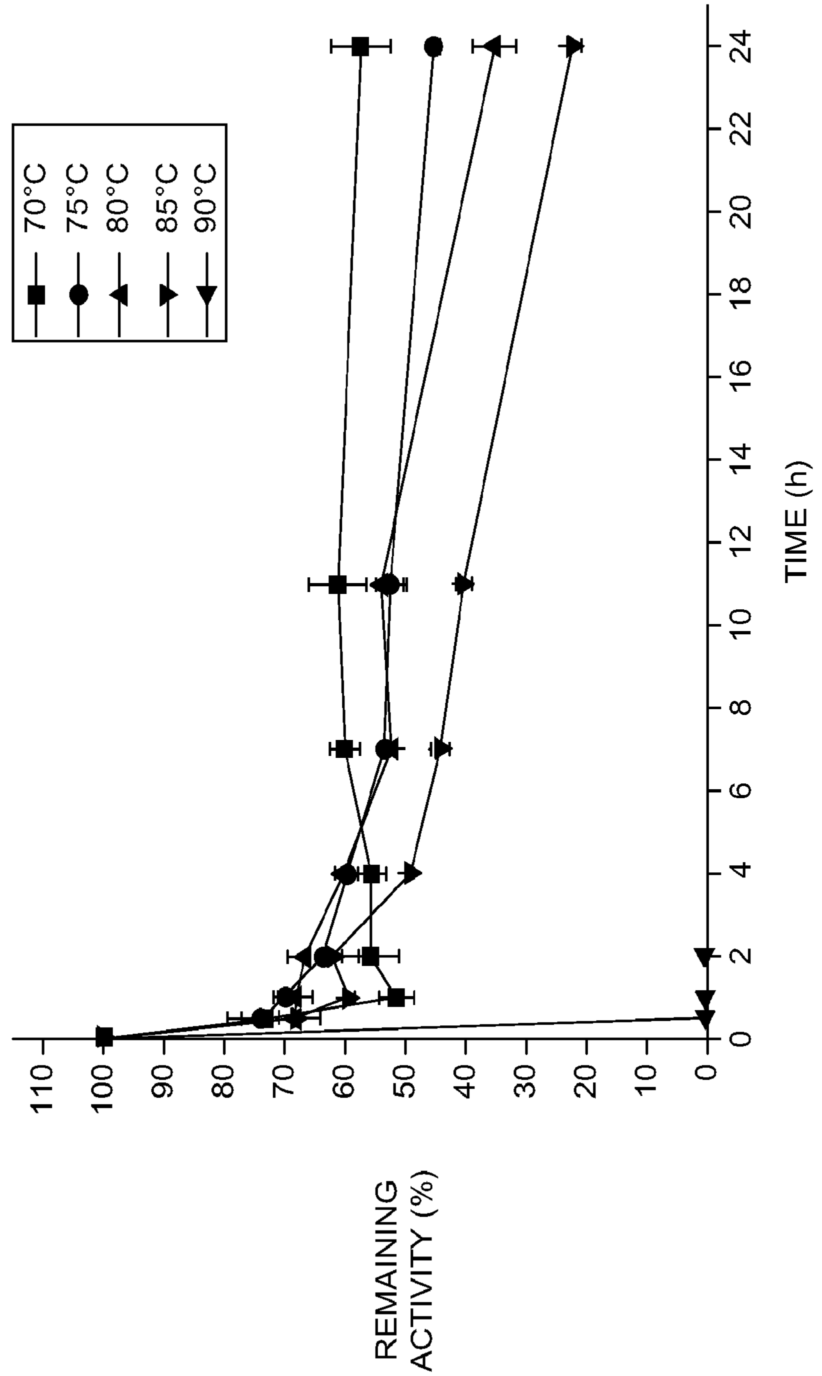

FIGS. 6A to 6E: FIG. 6A shows an SDS-PAGE of purified Cb1172. FIG. 6B shows the enzymatic activity of Cb1172 on natural substrates from a reducing sugar assay. Five different hemicellulosic substrates were tested: arabinan (sugar beet), SWAX, rye arabinoxylan (RAX), OSX and debranched arabinan. Incubation of enzymes with the substrates led to release of products that were quantified as a concentration of arabinose equivalents. Hydrolysis of arabinan was higher than hydrolysis of other natural substrates. FIG. 6C shows the enzymatic activity of Cb1172 on natural substrates using HPLC analysis. Five different hemicellulosic substrates were tested: arabinan (sugar beet), SWAX, RAX, OSX and debranched arabinan. In each case, in the presence of Cb1172, arabinose was released. In the absence of Cb1172, only minor amount of arabinose was observed for debranched arabinan; no products of hydrolysis were released for other natural polysaccharides. The results showed that this enzyme releases arabinose from complex substrates (arabinan, SWAX, RAX, OSX and debranched arabinan). FIG. 6D shows the domain architecture of the Cb1172 protein; it has a glycoside hydrolase (GH) family 51 catalytic domain. FIG. 6E shows the thermostability of Cb1172. Cb1172 has 57%, 45%, 35% and 22% activity after incubation at 70° C., 75° C., 80° C. and 85° C. for 24 h, respectively. Fifty nM Cb1172 was kept at different temperatures (70° C., 75° C., 80° C., 85° C. and 90° C.). The samples were taken out at the following time points (0 h, 0.5 h, 1 h, 2 h, 4 h, 7 h, 11 h and 24 h) and immediately applied to enzyme activity measurement.

Figure 7A:
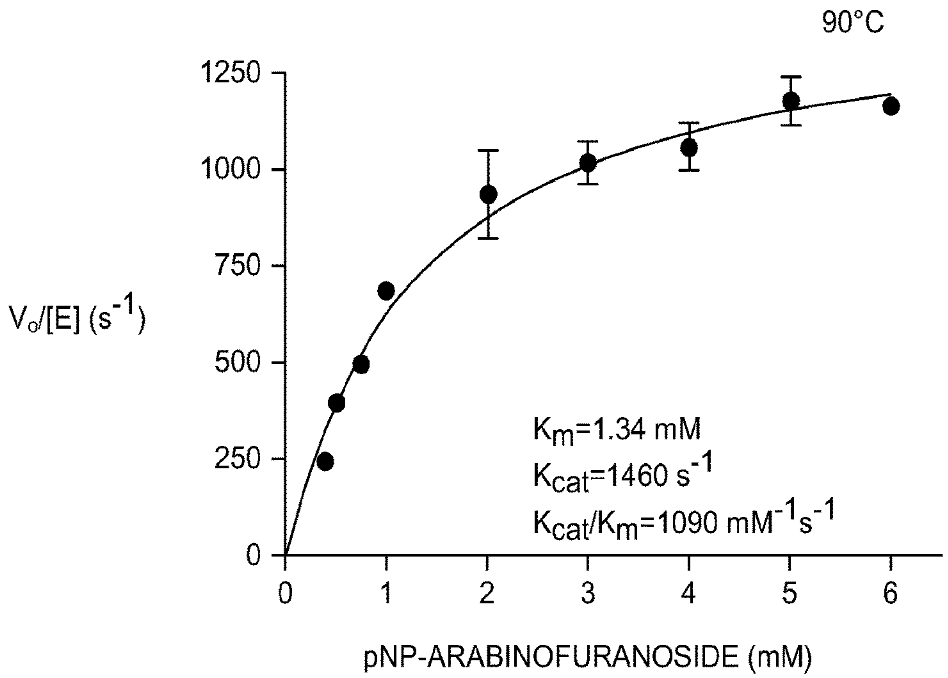
Figure 7B:
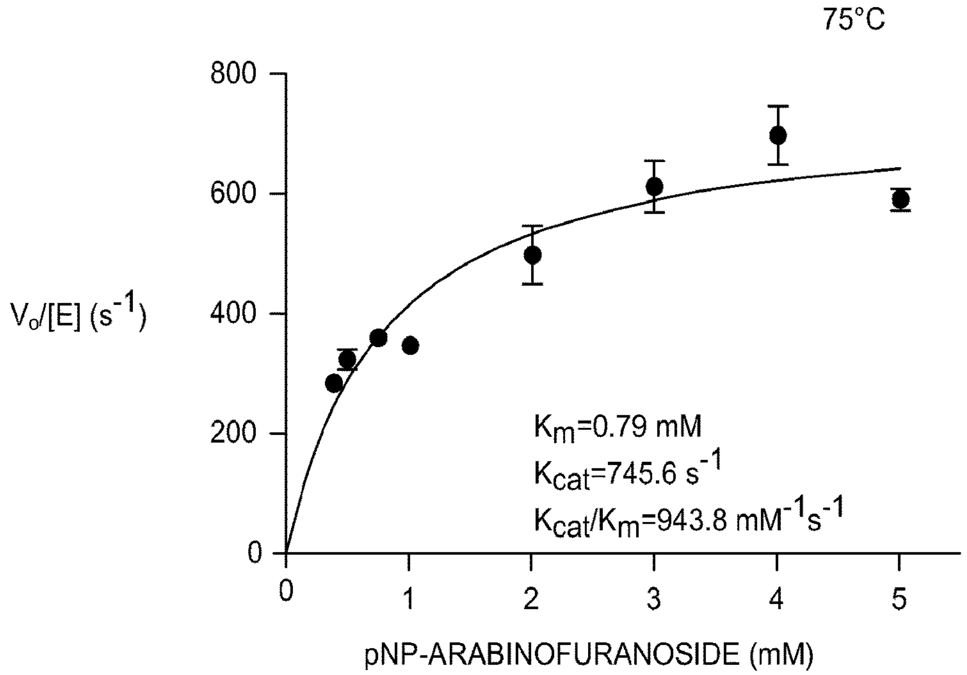

FIGS. 7A and 7B show the kinetic data of Cb1172 on hydrolysis of pNP-α-L-arabinofuranoside. The $K_m$, $k_{cat}$, and $k_{cat}/K_m$ are indicated as well. In FIG. 7A, the experiment was conducted at 90° C.; in FIG. 7B, the experiment was conducted at 75° C. One hundred μl pNP-α-L-arabinofuranoside substrate of different concentrations was kept at 85° C. for three minutes to equilibrate. Then twenty five μl of the protein sample (fifty nM) was added to the substrate and mixed by pipetting up and down for several times. The optical density at 400 nm was recorded by a Cary 300 UV-Visible spectrophotometer for 2.5 minutes. The initial velocity of reaction in the first minute was calculated. The initial velocities were then plotted against the concentrations of pNP-α-L-arabinofuranoside. The $K_m$ and $k_{cat}$ were calculated by non-linear fit using the Graphpad software.

Figure 8A:
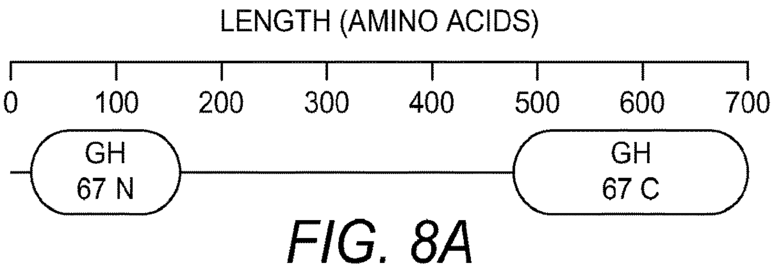
Figure 8B:
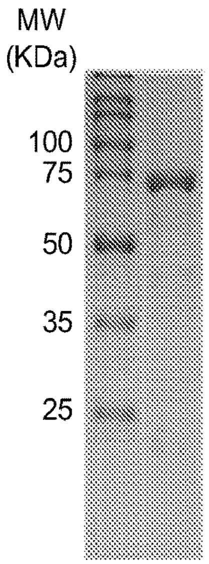
Figure 8C:
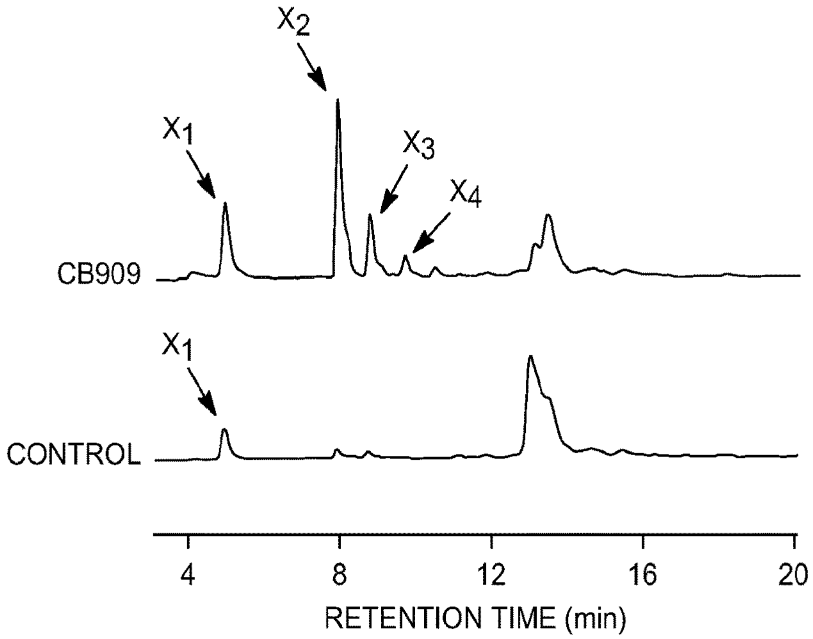
Figure 8D:
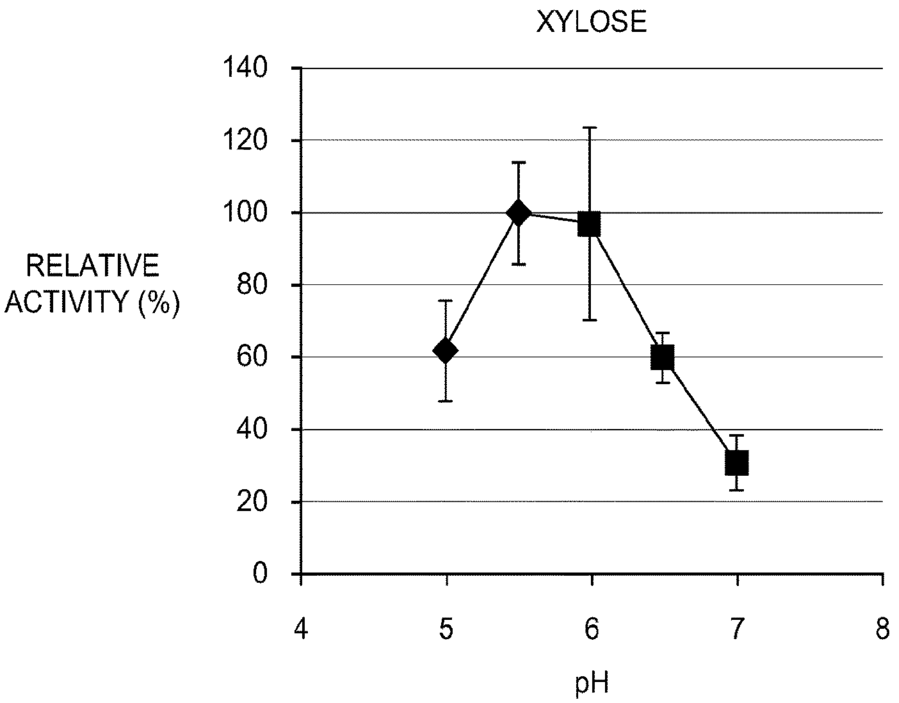
Figure 8D:
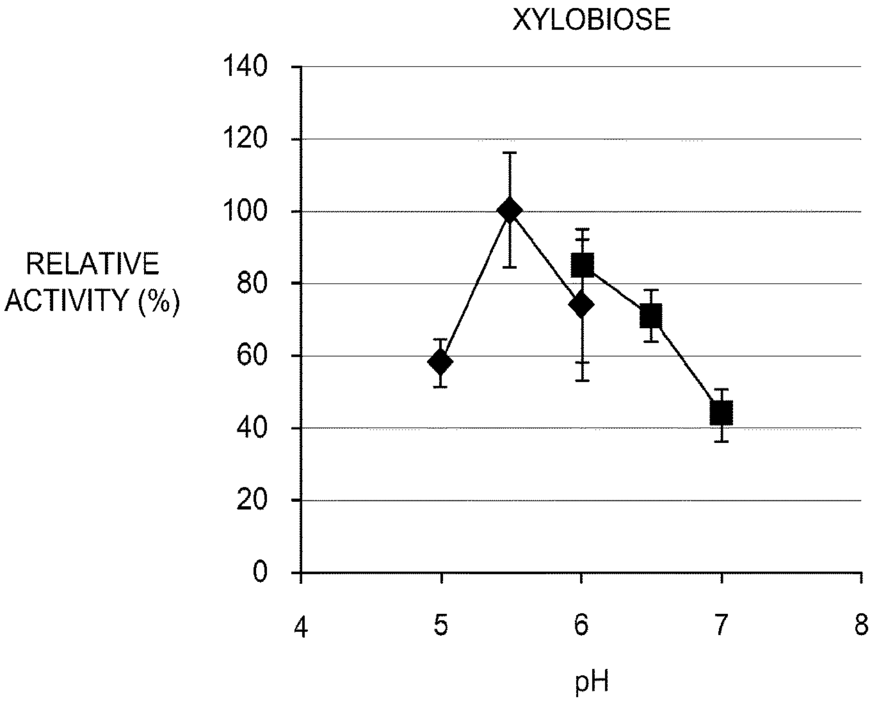
Figure 8D:
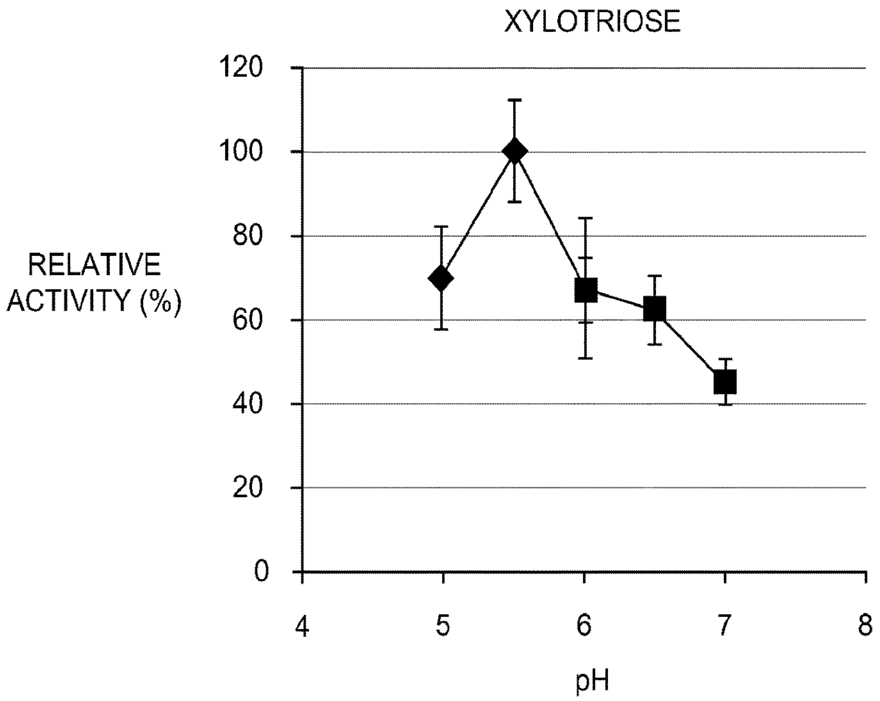
Figure 8E:
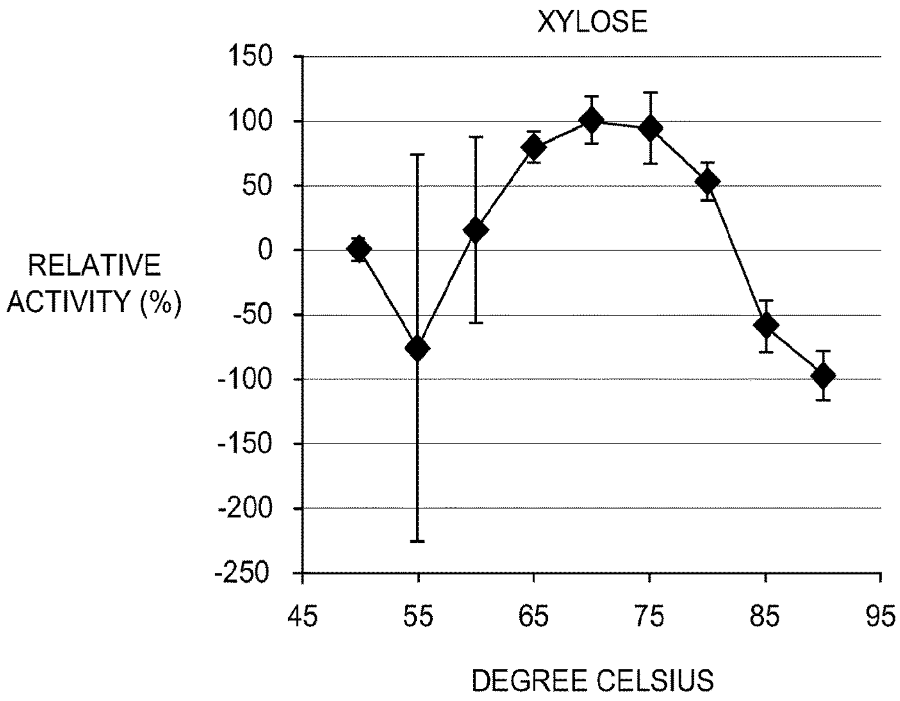
Figure 8E:
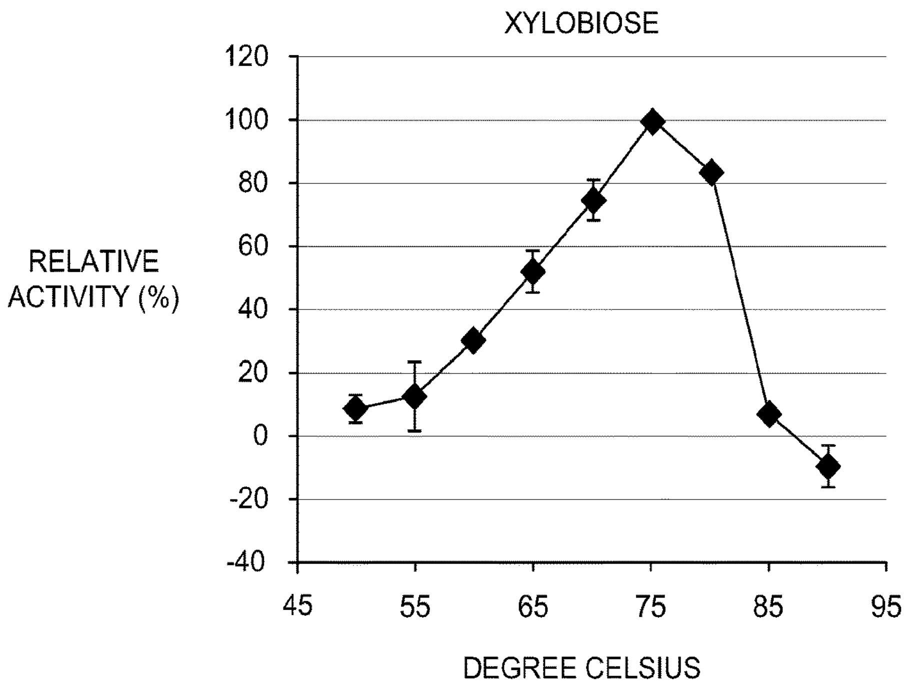
Figure 8E:
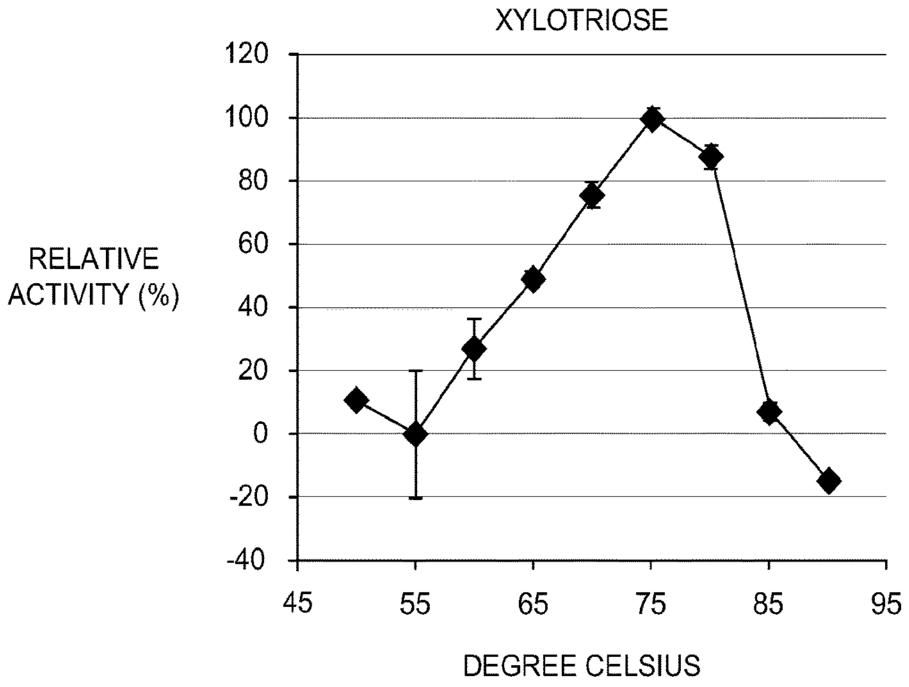

FIGS. 8A to 8EC: FIG. 8A shows putative domain architecture of Cb909. FIG. 8B shows SDS-PAGE of purified Cb909. FIG. 8C shows the activity of Cb909. The substrate is aldouronic acids, that is a mixture of xylo-oligosaccharides decorated with MeGlcA. After incubation with Cb909 at 75° C. for 60 minutes, MeGlcA group was cleaved by Cb909 from aldouronic acids to release undecorated xylose, xylobiose, xylotriose and xylotetraose as products. The condition of the reaction was as follows: 6 nM Cb909, 50 mM Phosphate buffer pH 6.0, 150 mM NaCl, 1 mg/ml aldouronic acids. FIGS. 8DA, 8DB, and 8DC show the results of a pH optimization assay. The maximum activity was detected at pH 5.5. This assay was carried out as follows: 1 mg/ml aldouronic acids solution was incubated with 6 nM Cb909 for 10 minutes at 75° C. at each pH. 50 mM citrate buffer containing 150 mM NaCl was used in the range from pH 5 to pH 6.50 mM phosphate buffer containing 150 mM NaCl was used in the range of pH 6 to pH 7. After the reaction, the temperature was quickly increased to 100° C. to terminate the reaction. The amounts of products were detected by HPLC. FIGS. 8EA, 8EB, and 8EC show the results of optimum temperature assay. The maximum activity of Cb909 was detected at 75° C. (xylobiose and xylotriose). Xylose was produced most efficiently at 70° C. but the amounts of produced xylose at 70° C. and 75° C. were almost the same. This assay was carried out as follows: 1 mg/ml aldouronic acids solution was incubated with 6 nM Cb909 for 10 minutes in 50 mM citrate buffer pH 5.5 that contained 150 mM NaCl. After the reaction the temperature was quickly increased to 100° C. to terminate the reaction. The amounts of products were detected by HPLC.

Figure 9A:
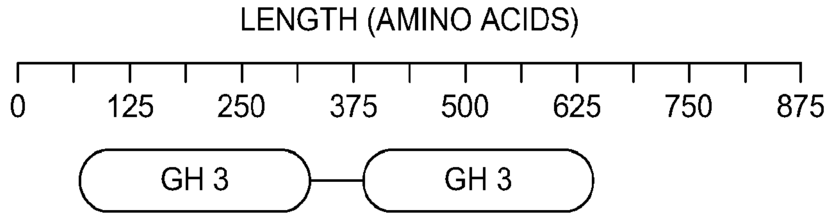
Figure 9B:
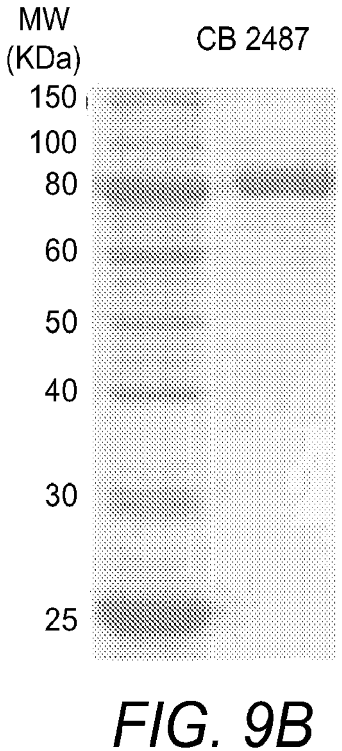
Figure 9C:
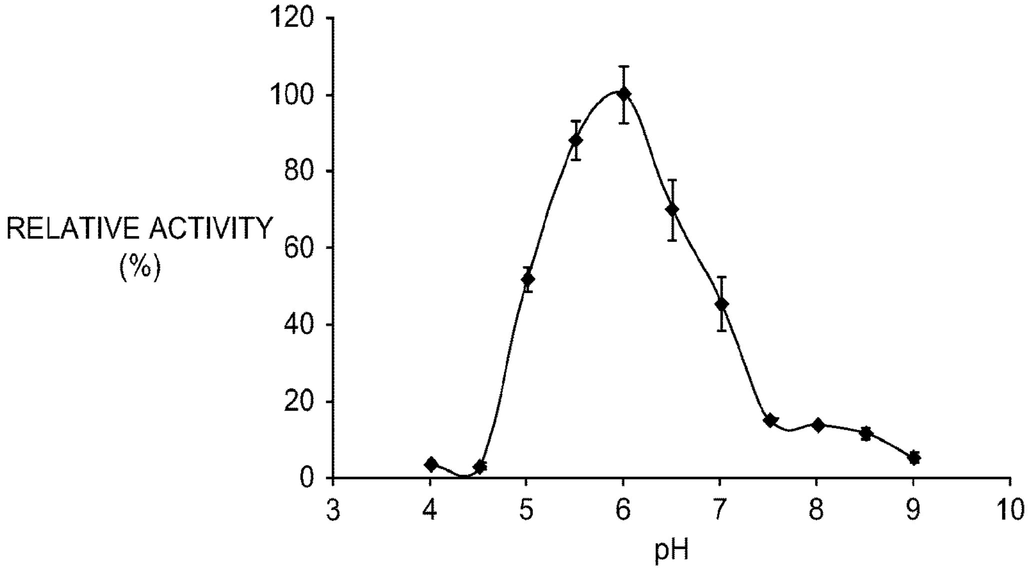
Figure 9D:
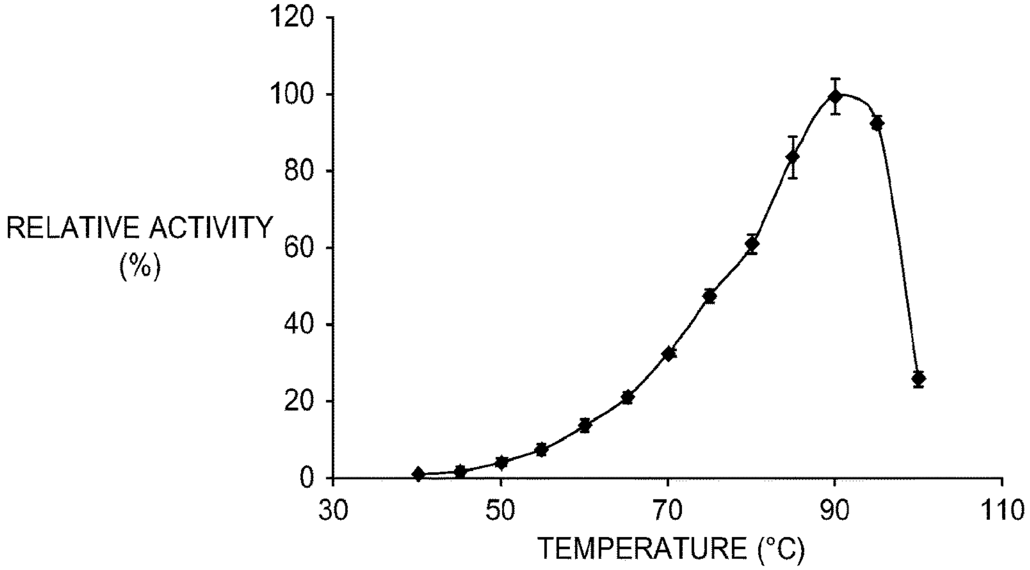
Figure 9E:
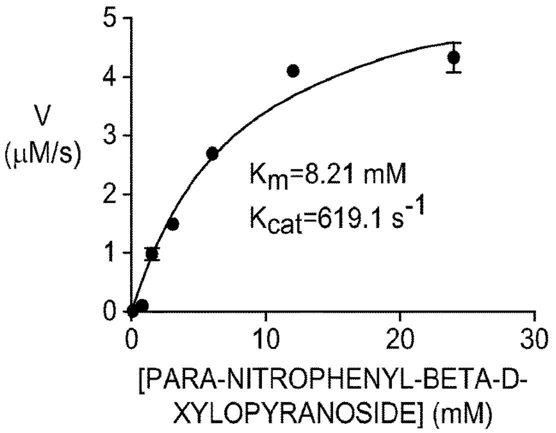
Figure 9E:
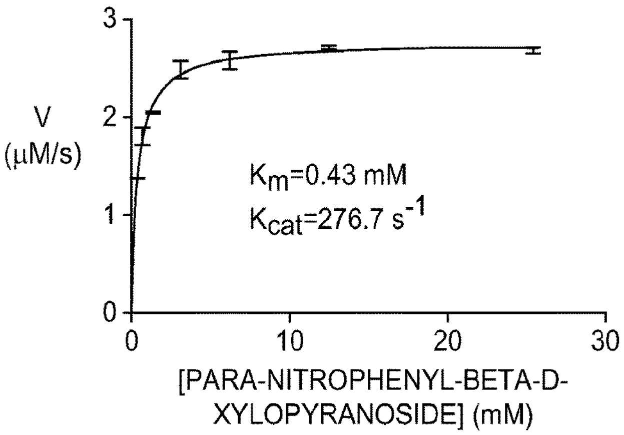
Figure 9F:
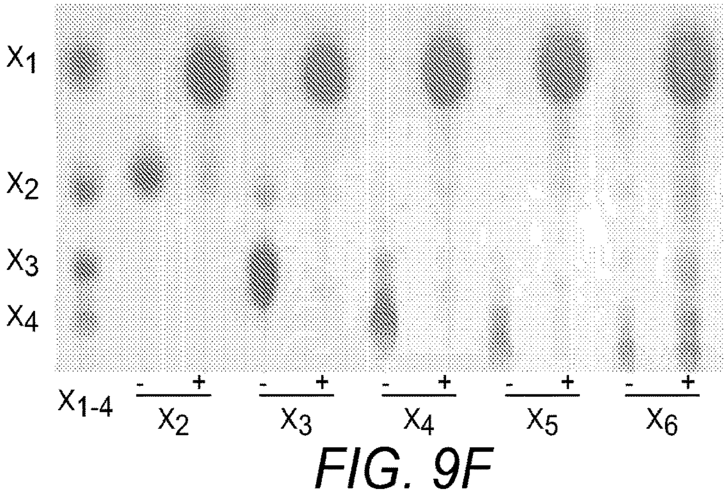
Figure 9G:
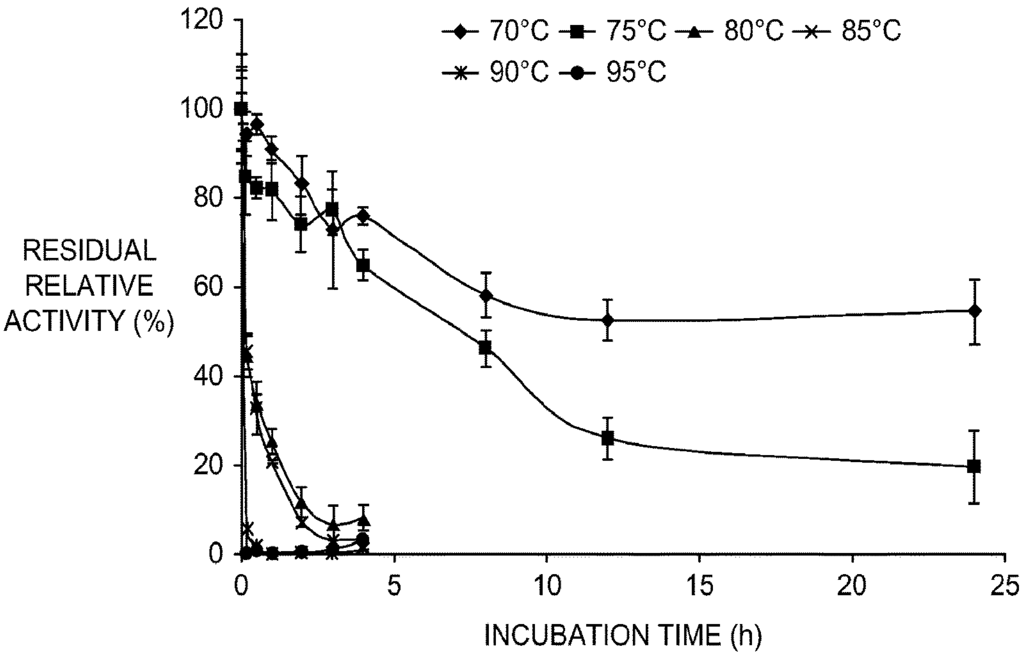
Figure 9H:
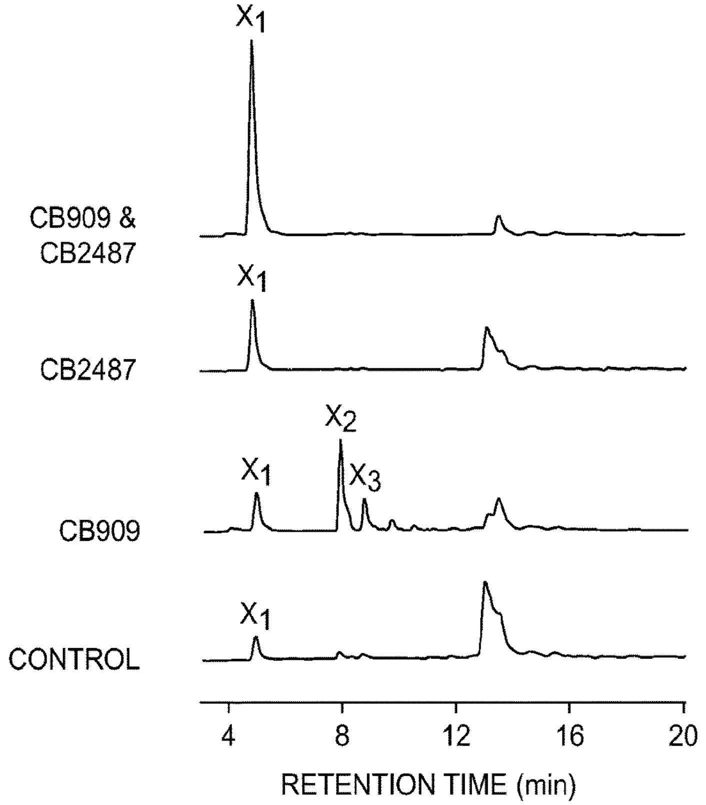

FIGS. 9A to 9H: FIG. 9A shows the putative domain architecture of Cb2487. The putative conserved domains of Cb2487 were analyzed through the NCBI Conserved Domains Database search tool. FIG. 9B shows SDS-PAGE of purified Cb2487. FIG. 9C shows a biochemical assay to determine the optimum pH of Cb2487. For pH optimum assay, para-nitrophenyl-beta-D-xylopyranoside (pNP-X, 0.8 mM) was incubated with Cb2487 (concentration 10 nM) at 75° C. in different buffers: pH 4.0-6.0 (citrate buffer, 50 mM, 150 mM NaCl), pH 6.0-8.0 (phosphate buffer, 50 mM, 150 mM NaCl), pH 8.5-9.0 (Tris-HCl, 50 mM, 150 mM NaCl). FIG. 9D shows a biochemical assay to determine the optimum temperature of Cb2487. For temperature optimum assay, pNP-X (0.8 mM) was incubated with Cb2487 (10 nM) in citrate buffer (50 mM, pH 6.0, 150 mM NaCl) at different temperatures (40, 45, 50, 55, 60, 65, 70, 75, 80, 85, 90, 95, 100° C.). FIGS. 9EA and 9EB show the kinetic parameters of Cb2487 with pNP-β-D-xylopyranoside as substrate. For the left side panel (FIG. 9EA), the kinetic parameters were determined at 90° C., pH 6.0. For the right side panel (FIG. 9EB), the kinetic parameters were determined at 75° C., pH 6.0. For these assays, different concentrations of pNP-X (0.08-24 mM) were incubated with Cb2487 (10 nM) in citrate buffer (50 mM, pH 6.0, 150 mM NaCl) at 75 and 90° C. FIG. 9F shows hydrolytic activity of Cb2487 on xylo-oligosaccharides. Cb2487 (0.5 μM) was incubated with different xylo-oligosaccharides ($X_{2-6}$) at 75° C. for 15 hr and then the products were separated by TLC. FIG. 9G shows thermostability assay for Cb2487. Cb2487 was incubated in citrate buffer (pH 6.0, 50 mM) at different temperatures (70, 75, 80, 85, 90, 95° C.) without substrate addition, the protein was taken at different times (0, 10 min, 30 min, 1 h, 3 h, 4, 8 h, 12 h, 24 h) and the residual activity was assayed with pNP-X as substrate. FIG. 9H shows synergism of β-xylosidase (Cb2487) and α-glucuronidase (Cb909). Aldouronic acids were incubated with Cb2487 (0.5 μM) and Cb909 (0.5 μM) in citrate buffer (pH 6.0) at 75° C. overnight, then assayed with HPLC. Adding Cb909 cleaved off the methylglucuronic acid decorations in aldouronic acids to release xylose and xylo-oligosaccharides. Adding Cb2487 cleaved available beta-1,4-xylosidic linkages to release more xylose. Mixing the two enzymes led to the conversion of the xylo-oligosaccharides released by Cb909 to xylose by Cb2487.

Figure 10A:
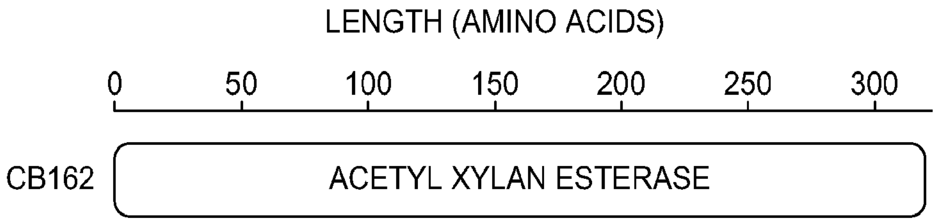
Figure 10B:
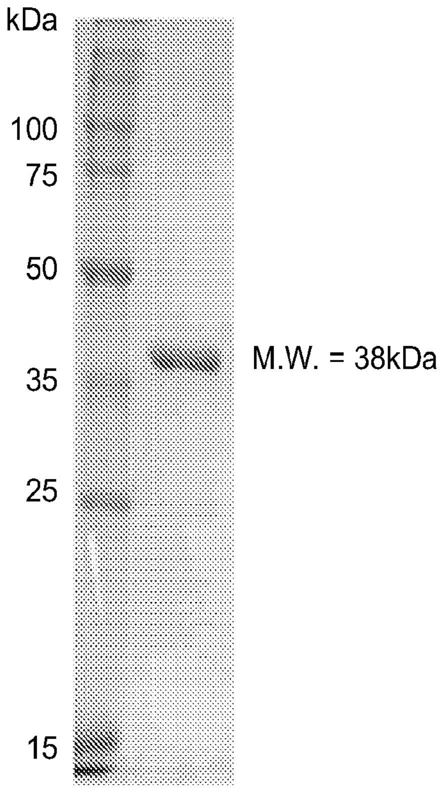
Figure 10C:
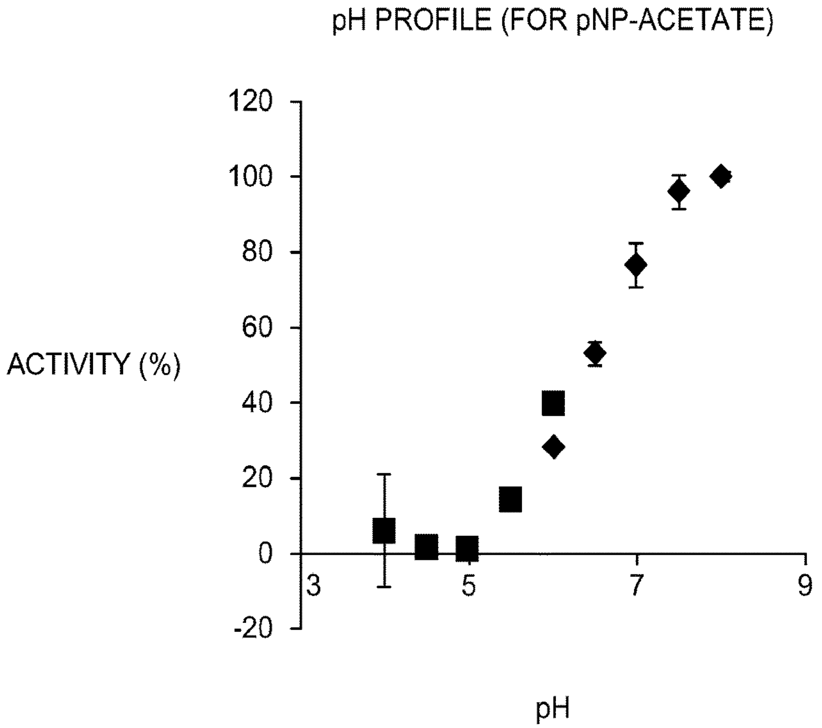
Figure 10D:
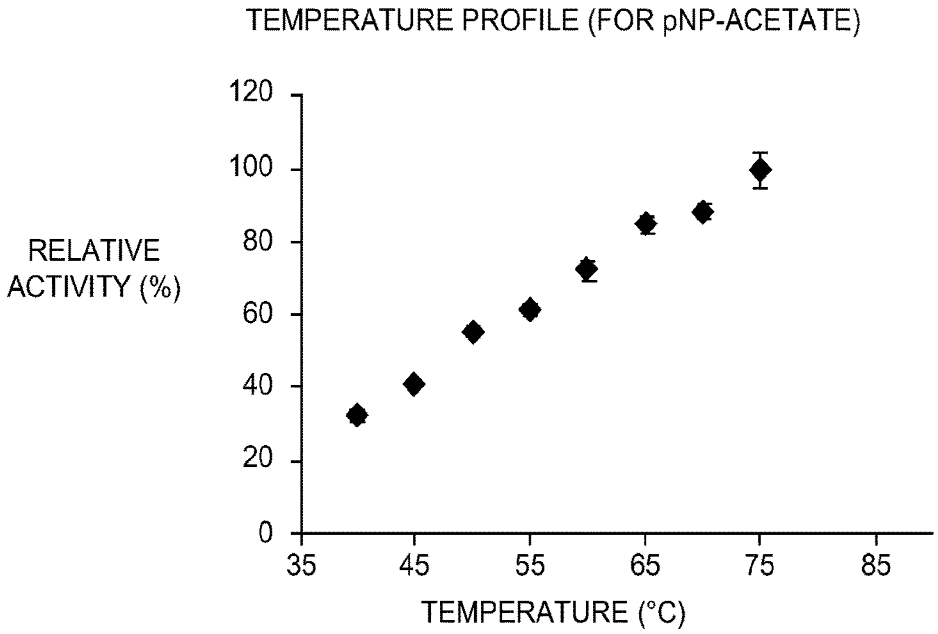
Figure 10E:
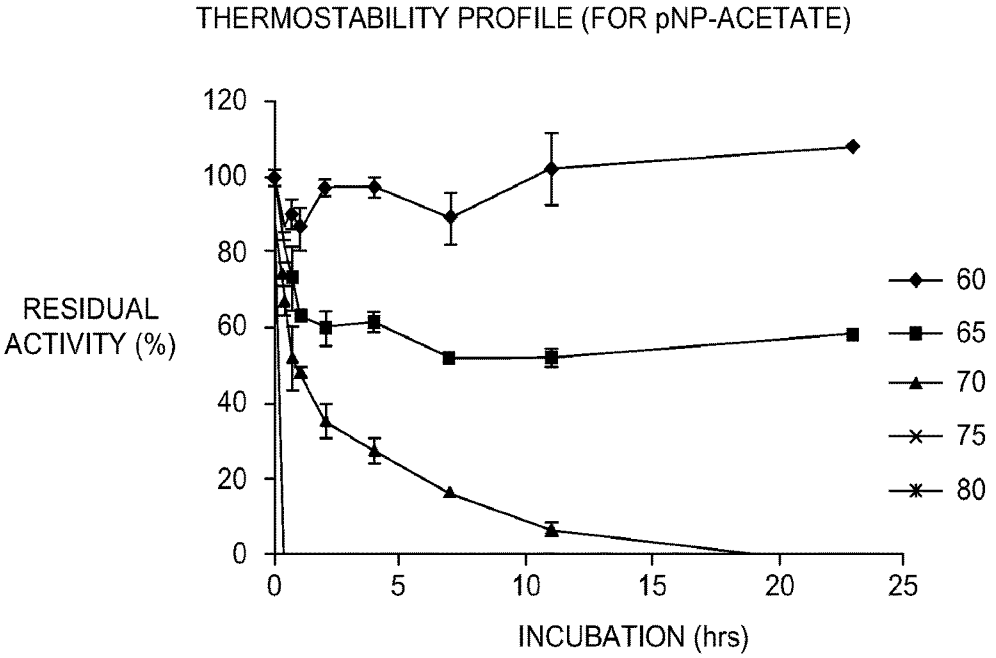
Figure 10F:
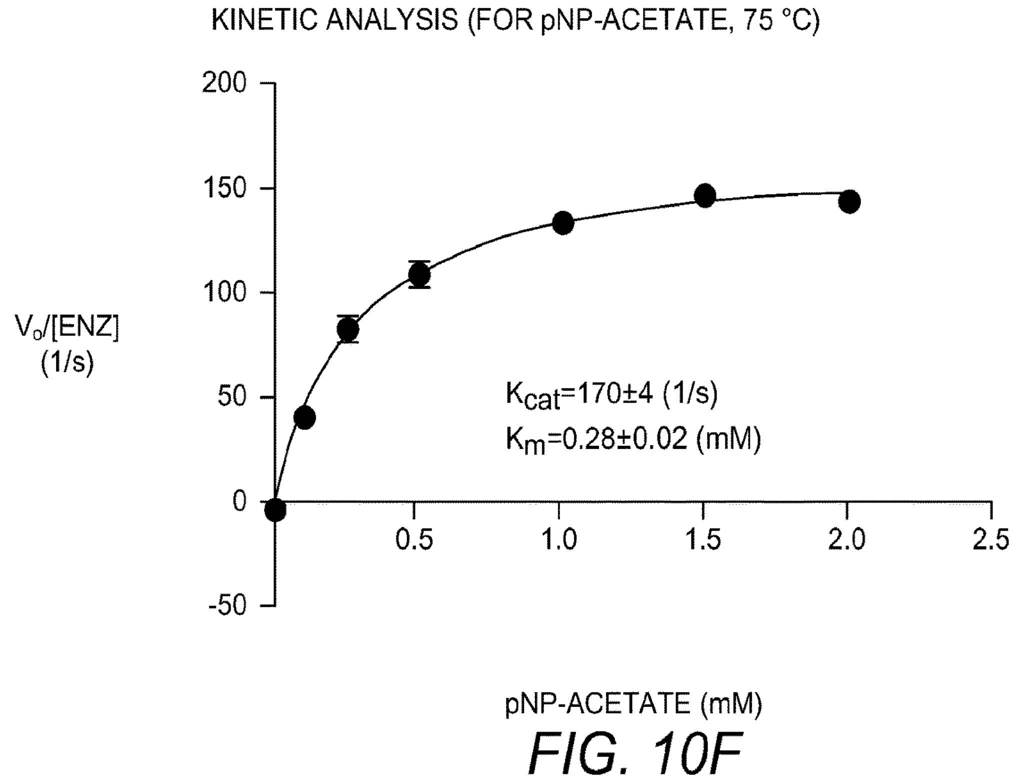

FIGS. 10A to 10F: FIG. 10A shows the domain structure of Cb162; the protein has a single domain of acetyl xylan esterase. FIG. 10B shows an SDS-PAGE of purified Cb162. FIG. 10C shows the pH profile of Cb162 on pNP-acetate using para-nitrophenol adducted acetate (pNP-acetate) as a substrate. The released pNP was monitored continuously at an absorbance of 400 nm using Synergy 2 Microplate reader (BioTek). The initial rate of hydrolysis was adopted as an enzyme activity. The pH effect on the Cb162 was examined at 50° C. in the presence of 50 mM citrate-NaOH (pH 4.0 to 6.0) or 50 mM $Na_2HPO_4$—HCl (pH 6.0 to 8.0), with 150 mM NaCl. 0.1 μM of purified Cb162 and 2 mM pNP-acetate were used for this assay. FIG. 10D shows the temperature profile of Cb162 on pNP-acetate. The temperature profile was performed in 50 mM $Na_2HPO_4$—HCl, pH 7.0 and 150 mM NaCl, at temperatures between 40° C. and 75° C. with 5° C. increments. 0.04 μM of purified Cb162 and 2 mM pNP-acetate were used for this assay. FIG. 10E shows the thermostability profile of Cb162 on pNP-acetate; 0.02 μM of purified Cb162 in 50 mM $Na_2HPO_4$—HCl, pH 7.0 and 150 mM NaCl was incubated for 0 to 24 hours at temperatures between 60° C. and 80° C. with 5° C. intervals, and the residual activities were measured. FIG. 10F shows a kinetic study of Cb162. 0.04 μM of purified Cb162 in 50 mM $Na_2HPO_4$—HCl, pH 6.0, and 150 mM NaCl was incubated with various concentrations of pNP-acetate, and the initial rate of hydrolysis was plotted on the graph. The kinetic parameters were determined by Michaelis-Menten equation utilizing Graph Pad Prism v5.01 (GraphPad Software).

Figure 11A:
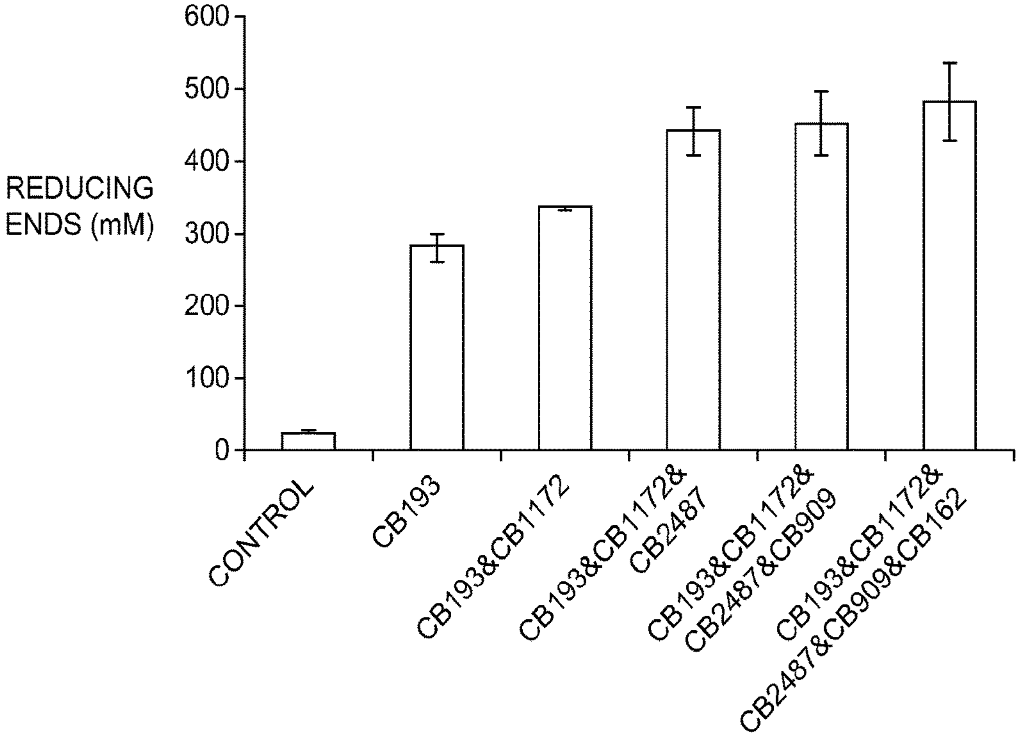
Figure 11B:
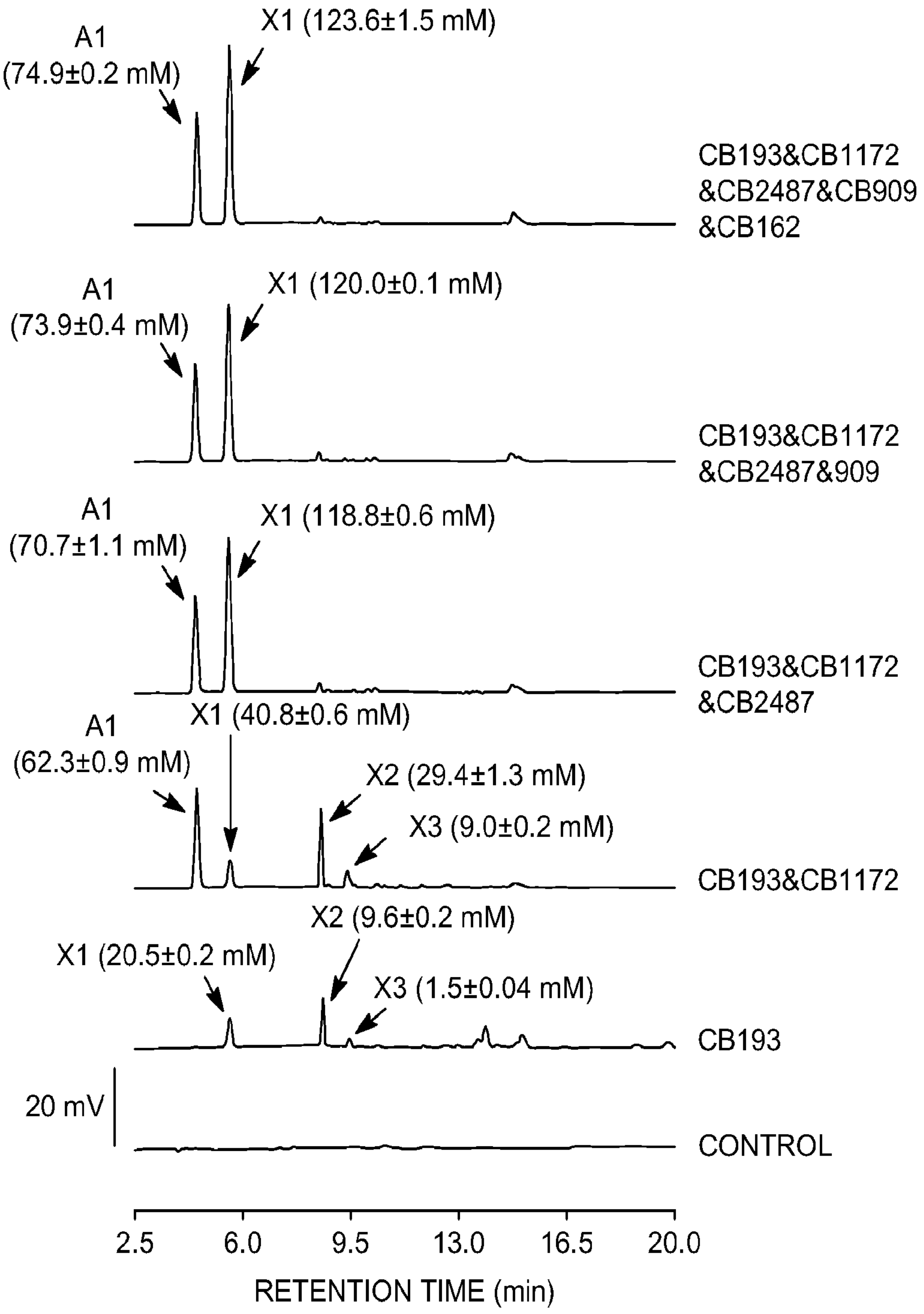

FIGS. 11A and 11B show synergy of *C. bescii* hemicellulolytic enzymes on soluble wheat arabinoxylan (SWAX) hydrolysis. SWAX (8.0%, w/v) was incubated with different hemicellulase mixes at 75° C. for 15 hr in citrate buffer (50 mM, pH 6.0, 150 mM NaCl), and subjected to reducing sugar [FIG. 11A] and HPLC [FIG. 11B] analysis. The hemicellulases applied include Cb193 (0.5 μM), Cb1172 (0.5 μM), Cb2487 (4 μM), Cb909 (0.5 μM), and Cb162 (0.5 μM).

Figure 12A:
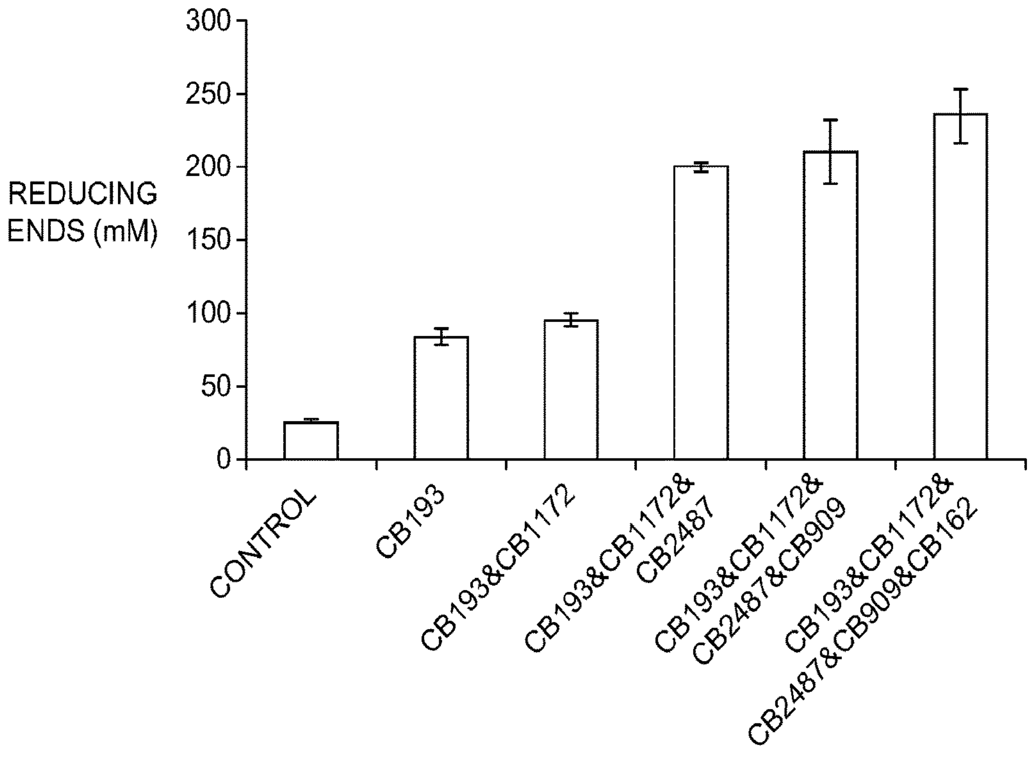
Figure 12B:
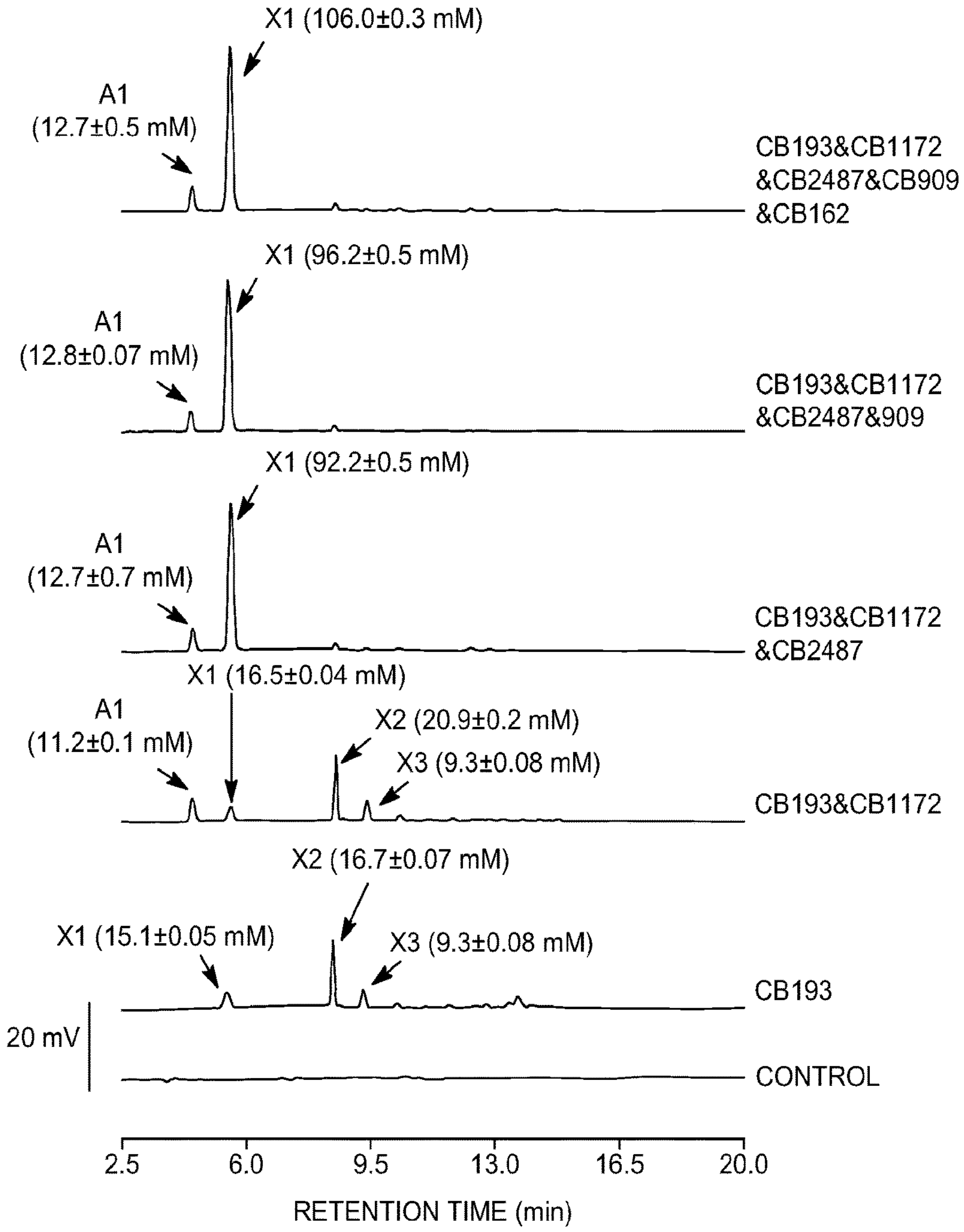

FIGS. 12A and 12B show synergy of *C. bescii* hemicellulolytic enzymes on oatspelt xylan (OSX) hydrolysis. OSX (8.0%, w/v) was incubated with different hemicellulase mixes at 75° C. for 15 hr in citrate buffer (50 mM, pH 6.0, 150 mM NaCl), and subjected to reducing sugar [FIG. 12A] and HPLC [FIG. 12B] analysis. The hemicellulases applied include Cb193 (0.5 μM), Cb1172 (0.5 μM), Cb2487 (4 μM), Cb909 (0.5 μM), and Cb162 (0.5 μM).

Figure 13A:
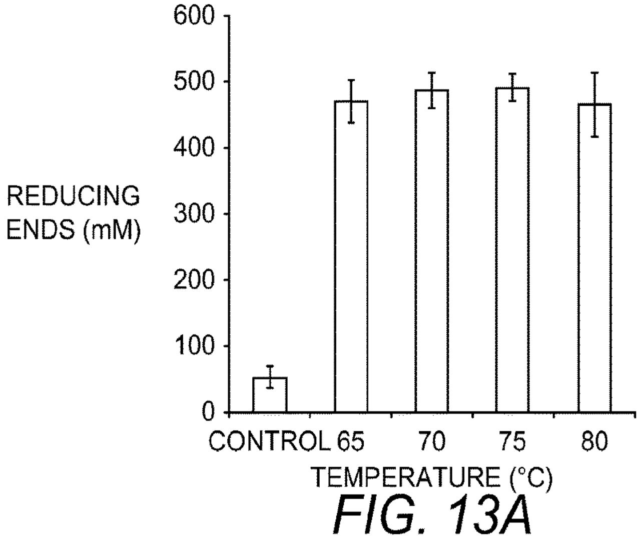
Figure 13B:
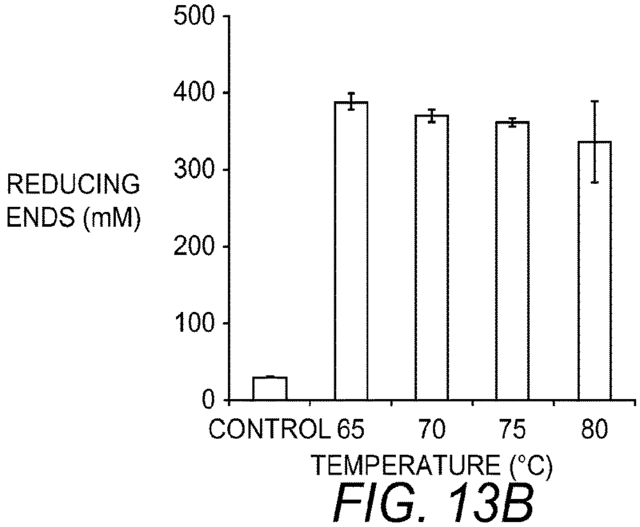
Figure 13C:
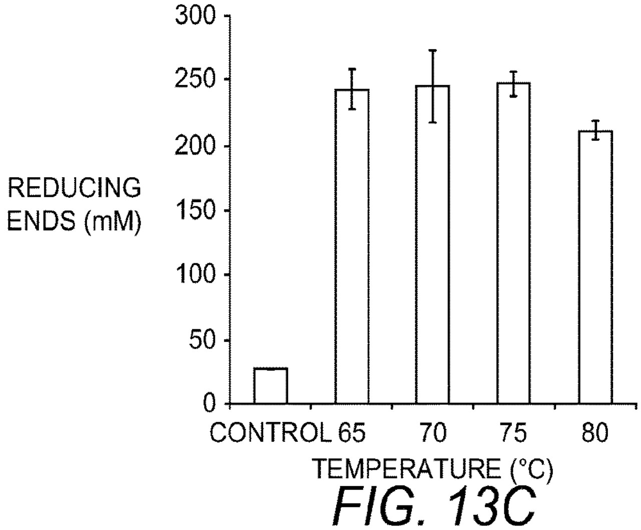

FIGS. 13A to 13C: FIG. 13A shows soluble wheat arabinoxylan hydrolysis with hemicellulase cocktail at different temperatures. SWAX (8.0%, w/v) was incubated with Cb193 (0.5 μM), Cb2487 (4 μM), Cb1172 (0.5 μM), Cb162 (0.5 μM), and Cb909 (0.5 μM) at 65° C., 70° C., 75° C., 80° C. for 15 hr in citrate buffer (50 mM, pH 6.0, 150 mM NaCl), and subjected to reducing sugar assay. FIG. 13B shows birch wood xylan hydrolysis with hemicellulase cocktail at different temperatures. BWX (8.0%, w/v) was incubated with Cb193 (0.5 μM), Cb1172 (0.5 μM), Cb2487 (4 μM), Cb909 (0.5 μM), and Cb162 (0.5 μM) at 65° C., 70° C., 75° C., 80° C. for 15 hr in citrate buffer (50 mM, pH 6.0, 150 mM NaCl), and subjected to reducing sugar assay. FIG. 13C shows oat spelt xylan hydrolysis with hemicellulase cocktail at different temperatures. OSX (8.0%, w/v) was incubated with Cb193 (0.5 μM), Cb1172 (0.5 μM), Cb2487 (4 μM), Cb909 (0.5 μM), and Cb162 (0.5 μM) at 65° C., 70° C., 75° C., 80° C. for 15 hr in citrate buffer (50 mM, pH 6.0, 150 mM NaCl), and subjected to reducing sugar assay.

Figure 14A:
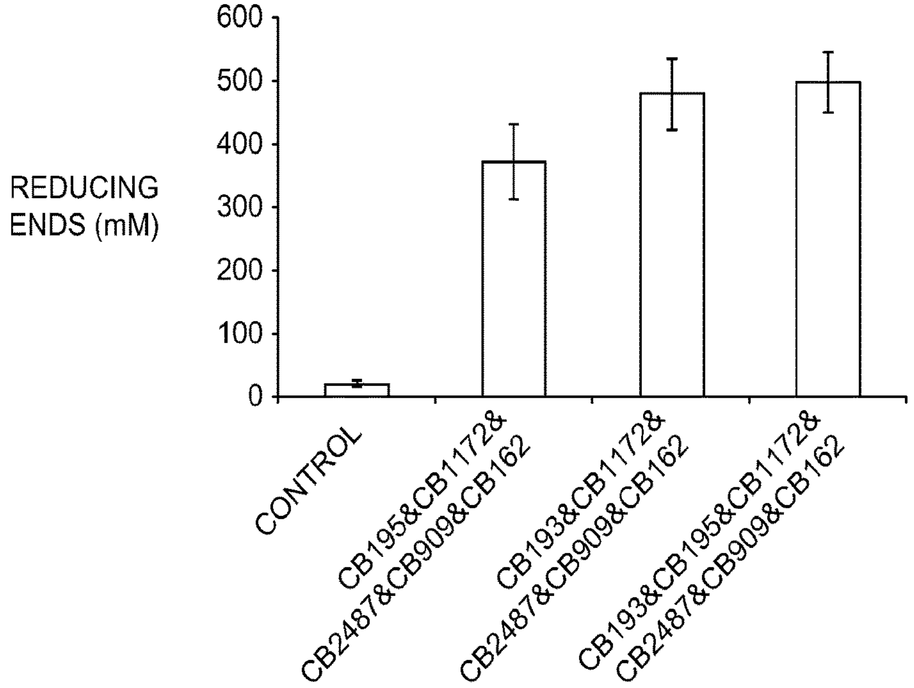
Figure 14B:
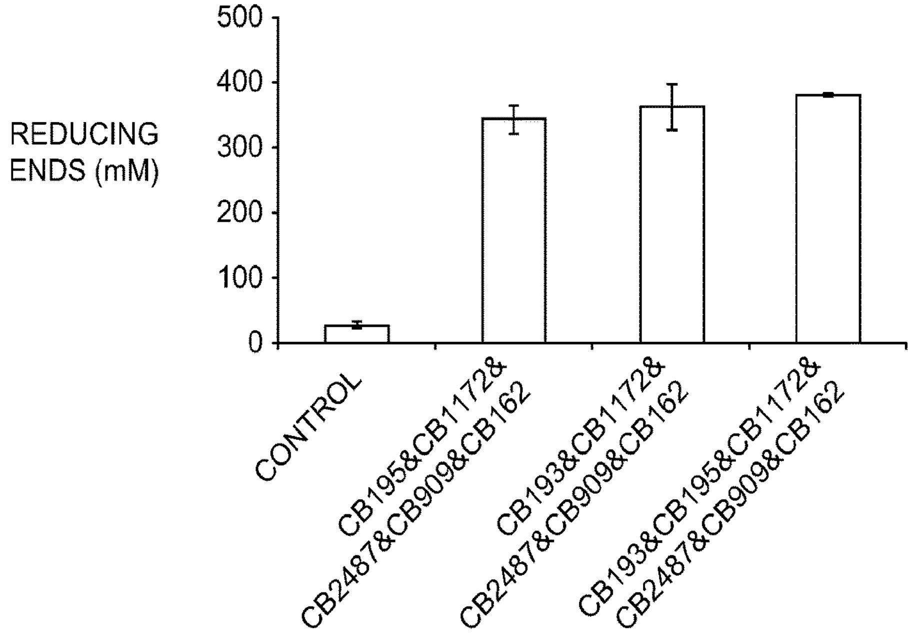
Figure 14C:
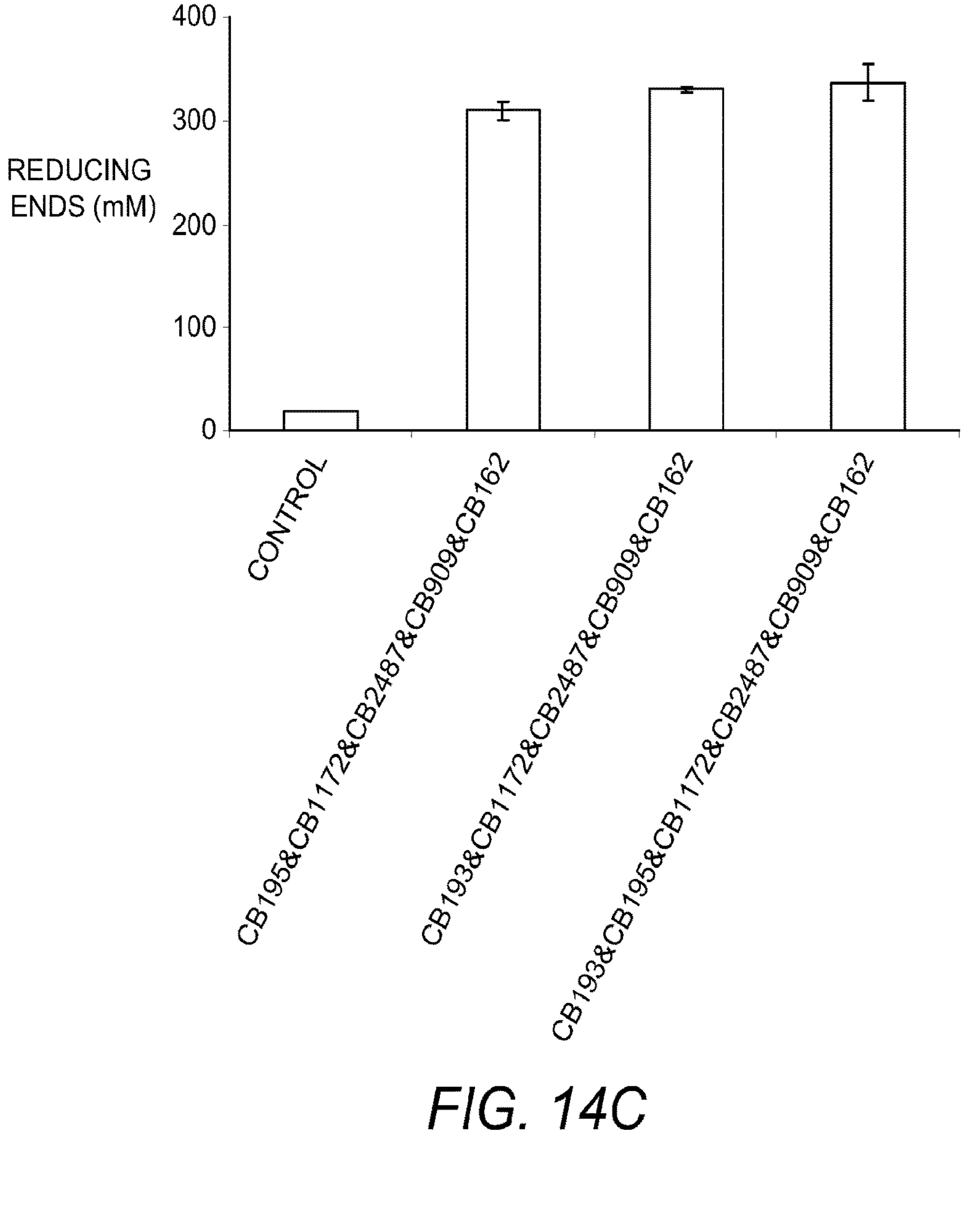

FIGS. 14A to 14C: FIG. 14A shows SWAX hydrolysis was improved by adding two xylanases (Cb195 and Cb193) in the hemicellulase mixture. SWAX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); or Mix III) Cb195 (0.25 μM), Cb193 (0.25 μM), Cb1172 (0.5 μM), Cb2487 (4 μM), Cb909 (0.5 μM), and Cb162 (0.5 μM). FIG. 14B shows BWX hydrolysis was improved by adding two xylanases (Cb195 and Cb193) in the hemicellulase mixture. BWX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); or Mix III) Cb195 (0.25 μM), Cb193 (0.25 μM), Cb1172 (0.5 μM), Cb2487 (4 μM), Cb909 (0.5 μM), and Cb162 (0.5 μM).

FIG. 14C shows OSX hydrolysis was improved by adding two xylanases (Cb195 and Cb193) in the hemicellulase mixture. OSX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); or Mix III) Cb195 (0.25 μM), Cb193 (0.25 μM), Cb1172 (0.5 μM), Cb2487 (4 μM), Cb909 (0.5 μM), and Cb162 (0.5 μM).

Figure 15A:
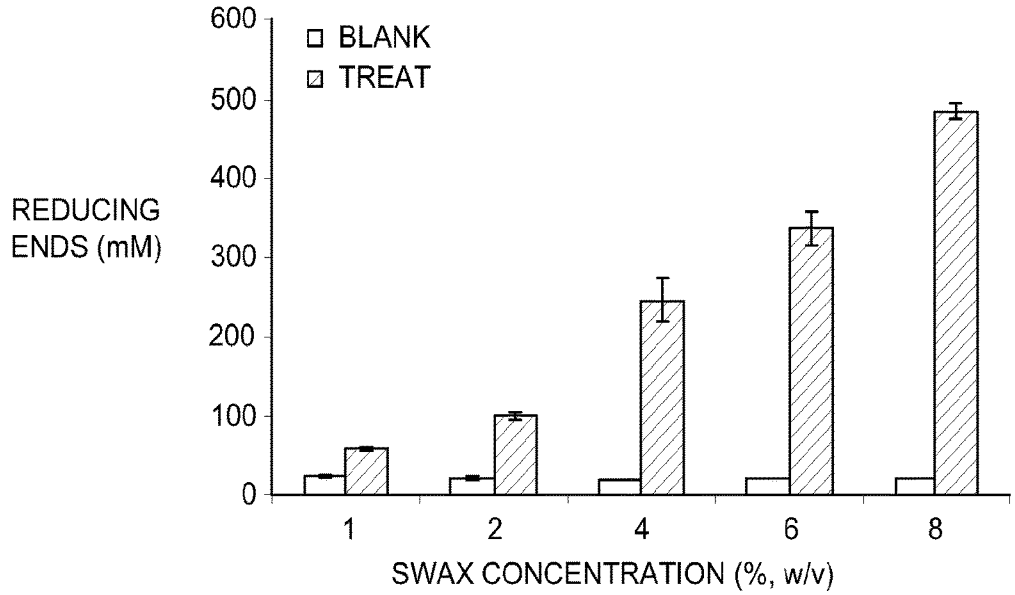
Figure 15B:
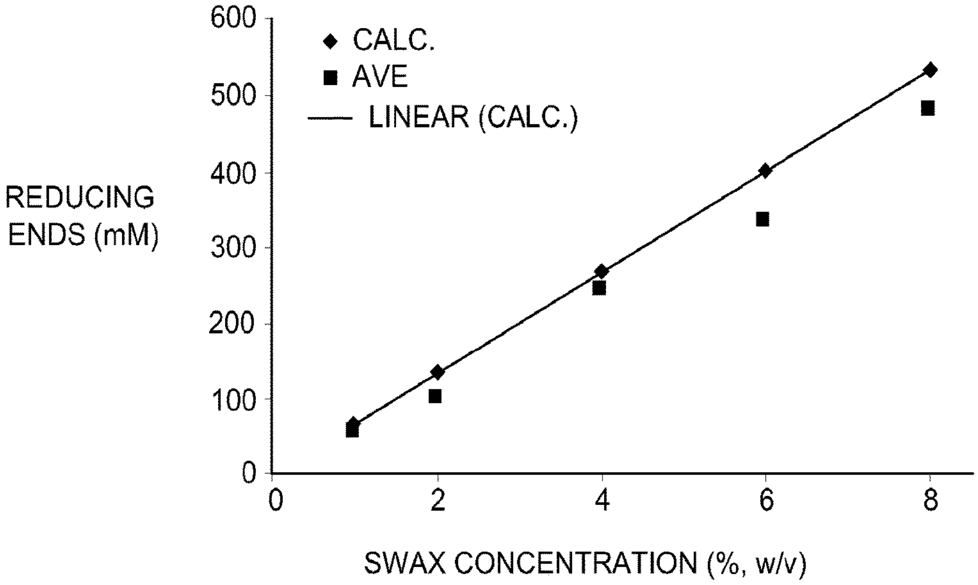

FIGS. 15A and 15B show soluble wheat arabinoxylan hydrolysis with hemicellulase cocktail of *Caldicellulosiruptor bescii*. Different concentrations of SWAX (1.0, 2.0, 4.0, 6.0, 8.0%, w/v) were incubated with Cb193 (0.5 μM), Cb195 (0.5 μM), Cb1172 (0.5 μM), Cb2487 (4 μM), Cb162 (0.5 μM), and Cb909 (0.5 μM) for 15 hr at 75° C. in citrate buffer (50 mM, pH 6.0, 150 mM NaCl), and subjected to reducing sugar assay. FIG. 15A shows reducing sugar in the control and hydrolysis mixtures, and FIG. 15B shows comparison of calculated and average of actual reducing sugar in hydrolysis mixtures with different substrate concentrations.

Figure 16A:
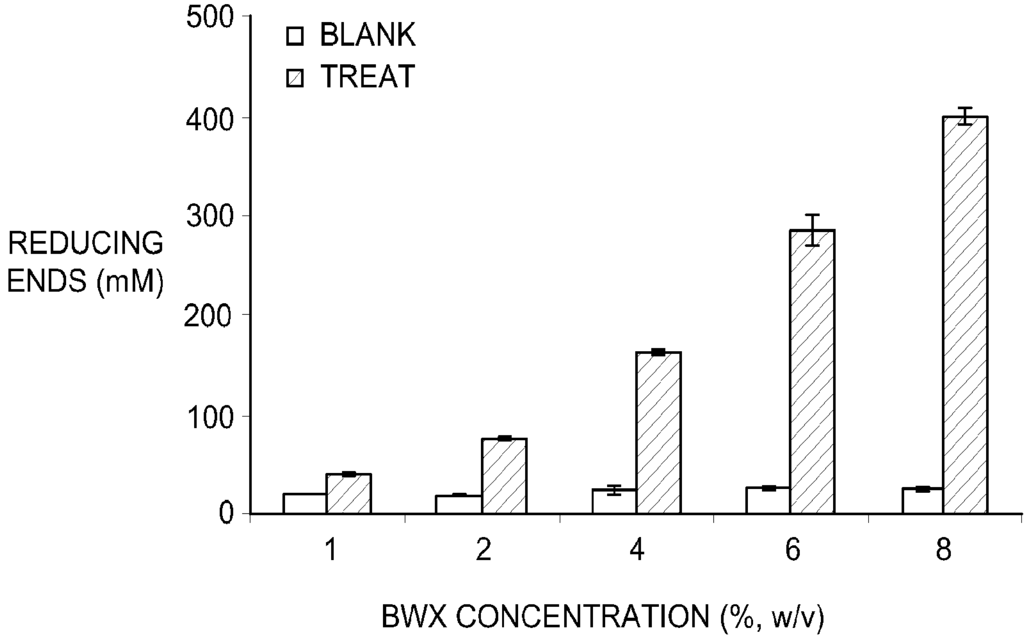
Figure 16B:
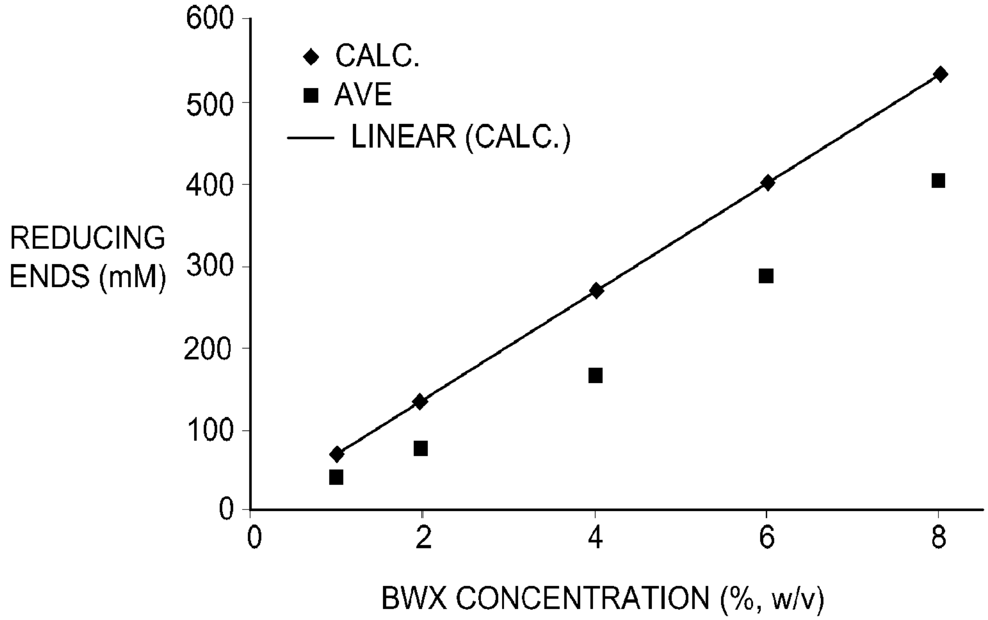

FIGS. 16A and 16B show birch wood xylan hydrolysis with hemicellulase cocktails of *Caldicellulosiruptor bescii*. Different concentrations of BWX (1.0, 2.0, 4.0, 6.0, 8.0%, w/v) were incubated with Cb193 (0.5 μM), Cb195 (0.5 μM), Cb1172 (0.5 μM), Cb2487 (4 μM), Cb162 (0.5 μM), and Cb909 (0.5 μM) at 75° C. for 15 hr in citrate buffer (50 mM, pH 6.0, 150 mM NaCl), and subjected to reducing sugar assay. FIG. 16A shows reducing sugar in the control and hydrolysis mixtures, and FIG. 16B shows comparison of calculated and average of actual reducing sugar in hydrolysis mixtures with different substrate concentrations.

Figure 17A:
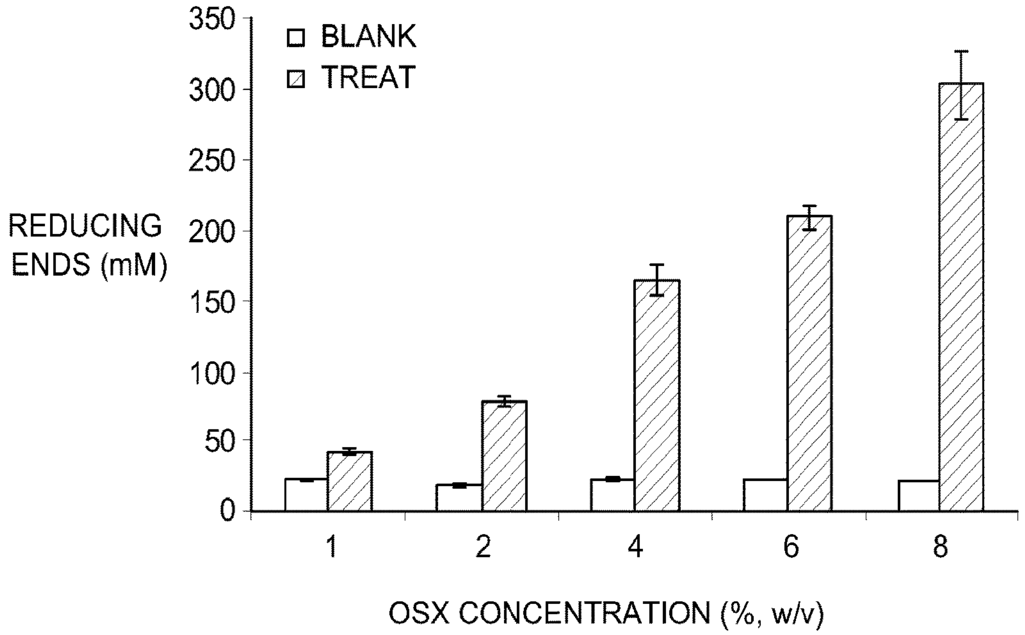
Figure 17B:
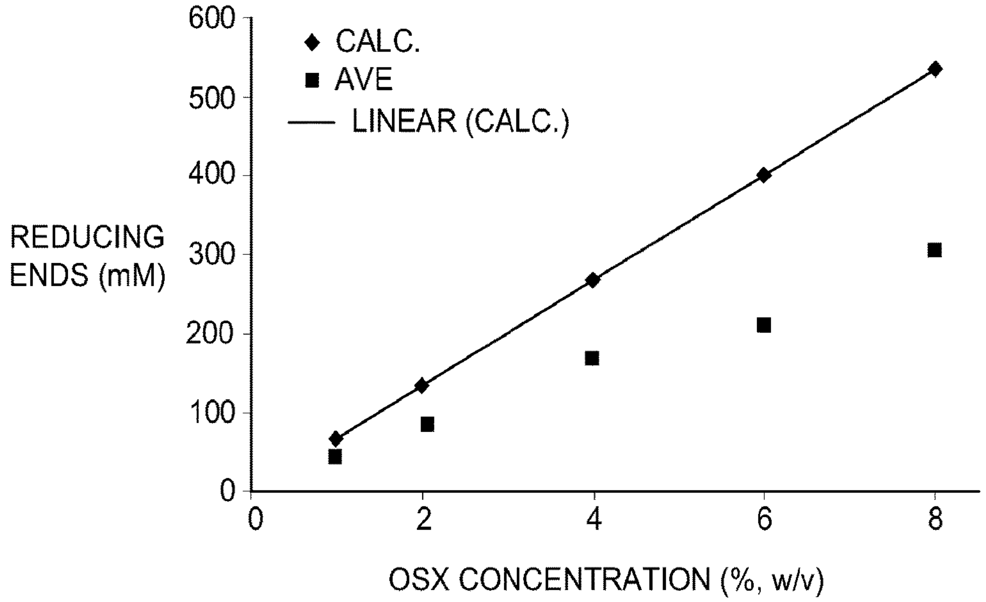

FIGS. 17A and 17B show oat spelt xylan hydrolysis with hemicellulase cocktail of *Caldicellulosiruptor bescii*. Different concentrations of OSX (1.0, 2.0, 4.0, 6.0, 8.0%, w/v) were incubated with Cb193 (0.5 μM), Cb195 (0.5 μM), Cb1172 (0.5 μM), Cb2487 (4 μM), Cb162 (0.5 μM), and Cb909 (0.5 μM) at 75° C. for 15 hr in citrate buffer (50 mM, pH 6.0, 150 mM NaCl), and subjected to reducing sugar assay. FIG. 17A shows reducing sugar in the control and hydrolysis mixtures, and FIG. 17B shows comparison of calculated and average of actual reducing sugar in hydrolysis mixtures with different substrate concentrations.

Figure 18:
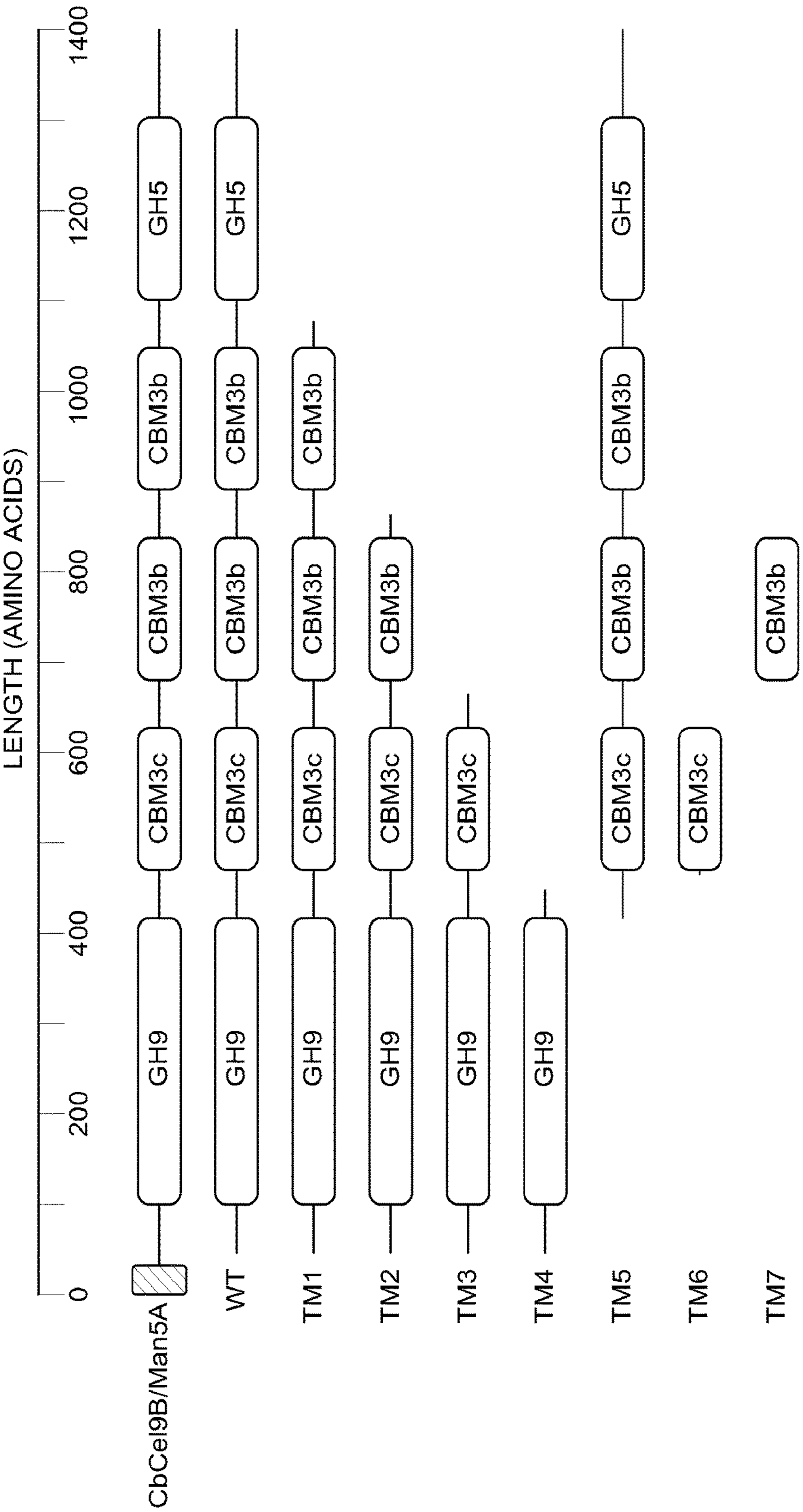

FIG. 18: Schematic structures of wild-type Cb1952 and its truncation mutants. The signal peptide is shown in filled rectangle. GH9: family 9 glycoside hydrolase domain; GH5: family 5 glycoside hydrolase domain; CBM3c: family 3 type C carbohydrate binding module; CBM3b: family 3 type B carbohydrate binding module.

Figure 19:
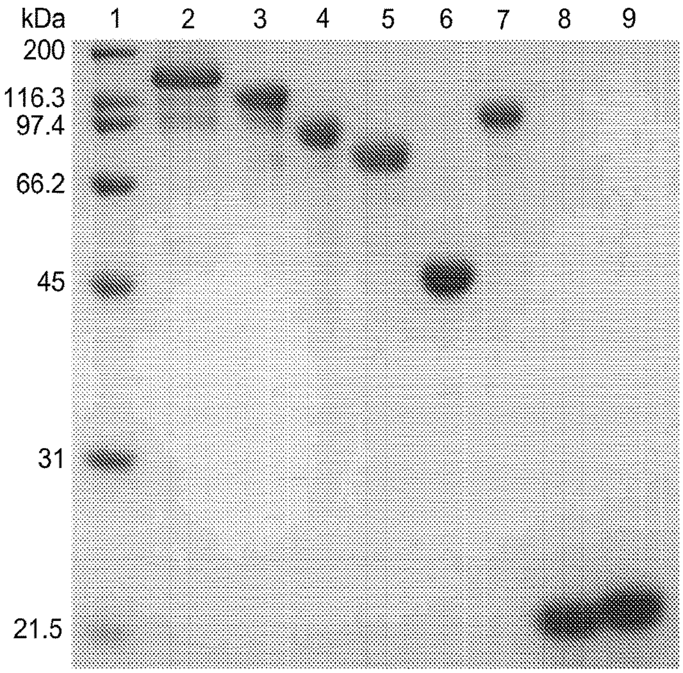

FIG. 19: SDS-PAGE of Cb1952 wild-type and its truncation mutants. Lane 1: protein molecular mass marker; lane 2: Cb1952 wild-type; lane 3: Cb1952TM1; lane 4: Cb1952TM2; lane 5: Cb1952TM3; lane 6: Cb1952TM4; lane 7: Cb1952TM5; lane 8: Cb1952TM6; lane 9: Cb1952TM7. Two μg of each enzyme was resolved on a 12% SDS polyacrylamide gel.

Figure 20:
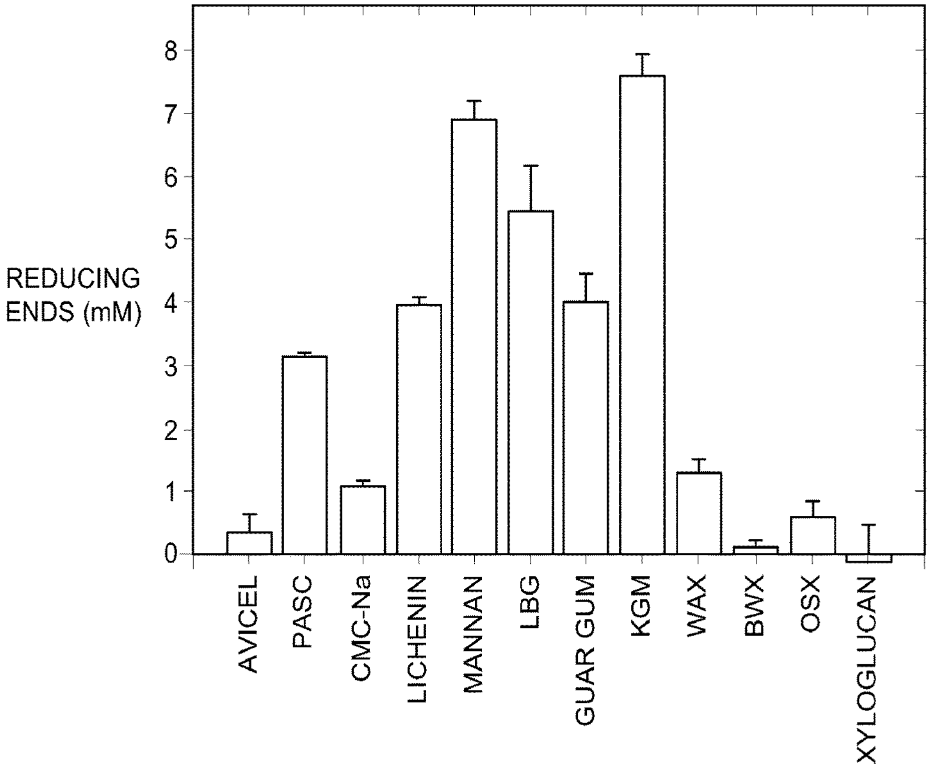

FIG. 20: Enzymatic activity of Cb1952WT on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan. Incubation of enzymes with Avicel, PASC, CMC-Na, lichenin, mannan, LBG, guar gum, KGM, WAX and OSX substrates led to release of products that were quantified as a concentration of glucose equivalents. The Cb1952WT mainly hydrolyzes glucose- and mannose-configured substrates, but not xylose-configured substrates.

Figure 21:
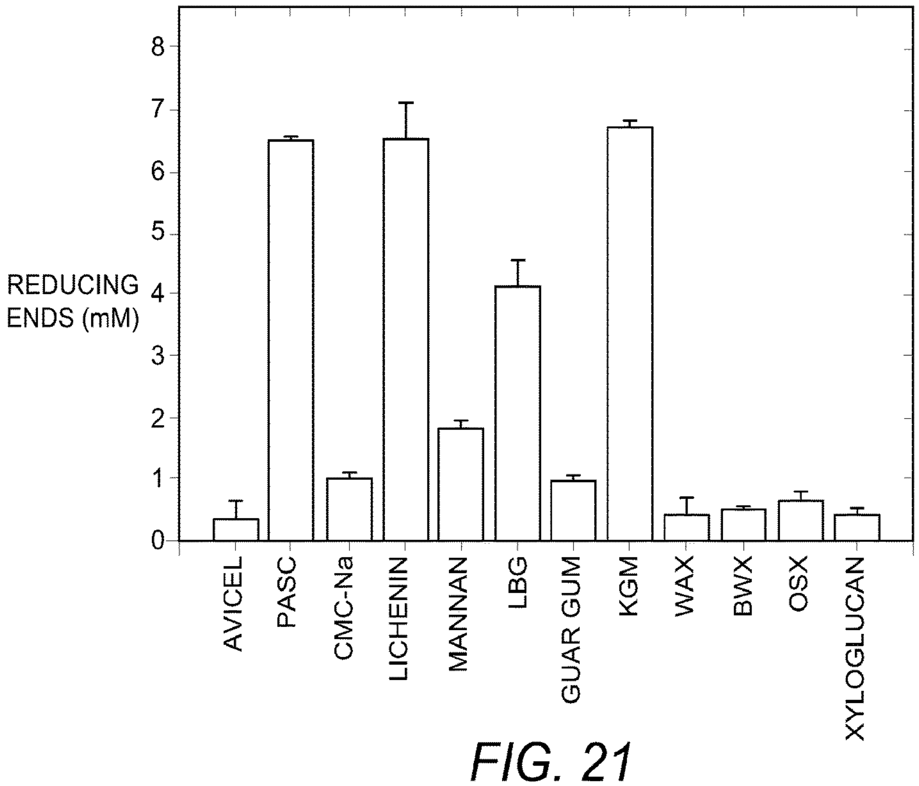

FIG. 21: Enzymatic activity of Cb1952TM1 on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan. Incubation of enzymes with Avicel, PASC, CMC-Na, lichenin, mannan, LBG, guar gum, KGM, WAX, BWX, OSX and xyloglucan substrates led to release of products that were quantified as a concentration of glucose equivalents. The results show that Cb1952TM1 mainly hydrolyzes glucose-configured substrates. It also has some activities on mannose-configured substrates. It has low activities on xylose-configured substrates.

Figure 22:
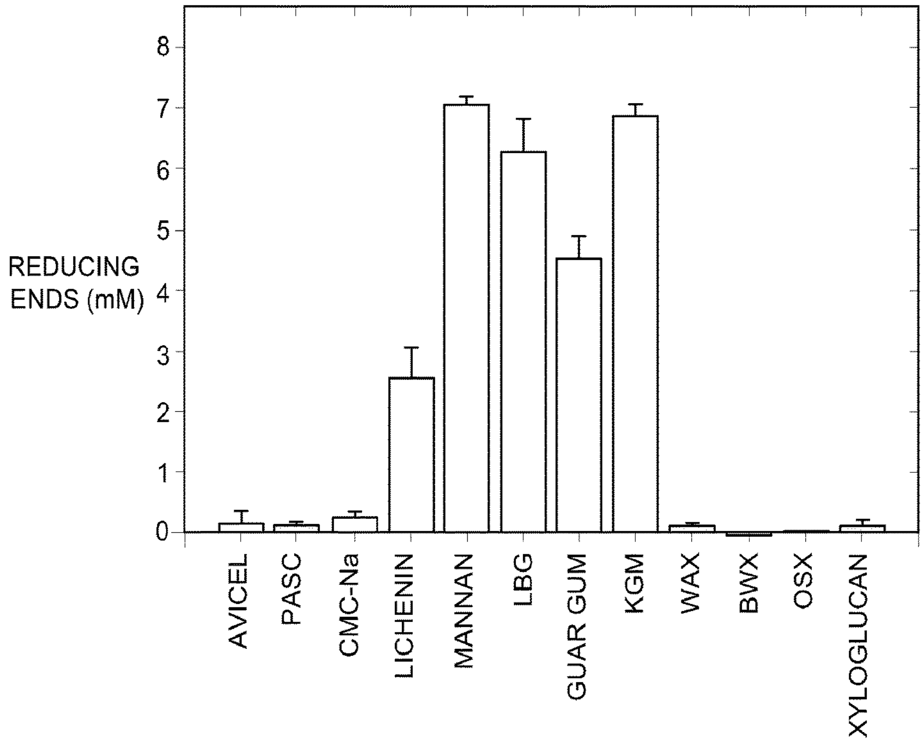

FIG. 22: Enzymatic activity of Cb1952TM5 on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan. Incubation of enzymes with CMC-Na, lichenin, mannan, LBG, guar gum and KGM substrates led to release of products that were quantified as a concentration of mannose equivalents. The Cb1952TM5 mainly hydrolyzes mannose-configured substrates, but does not have obvious activity on glucose- or xylose-configured substrates.

Figure 23:
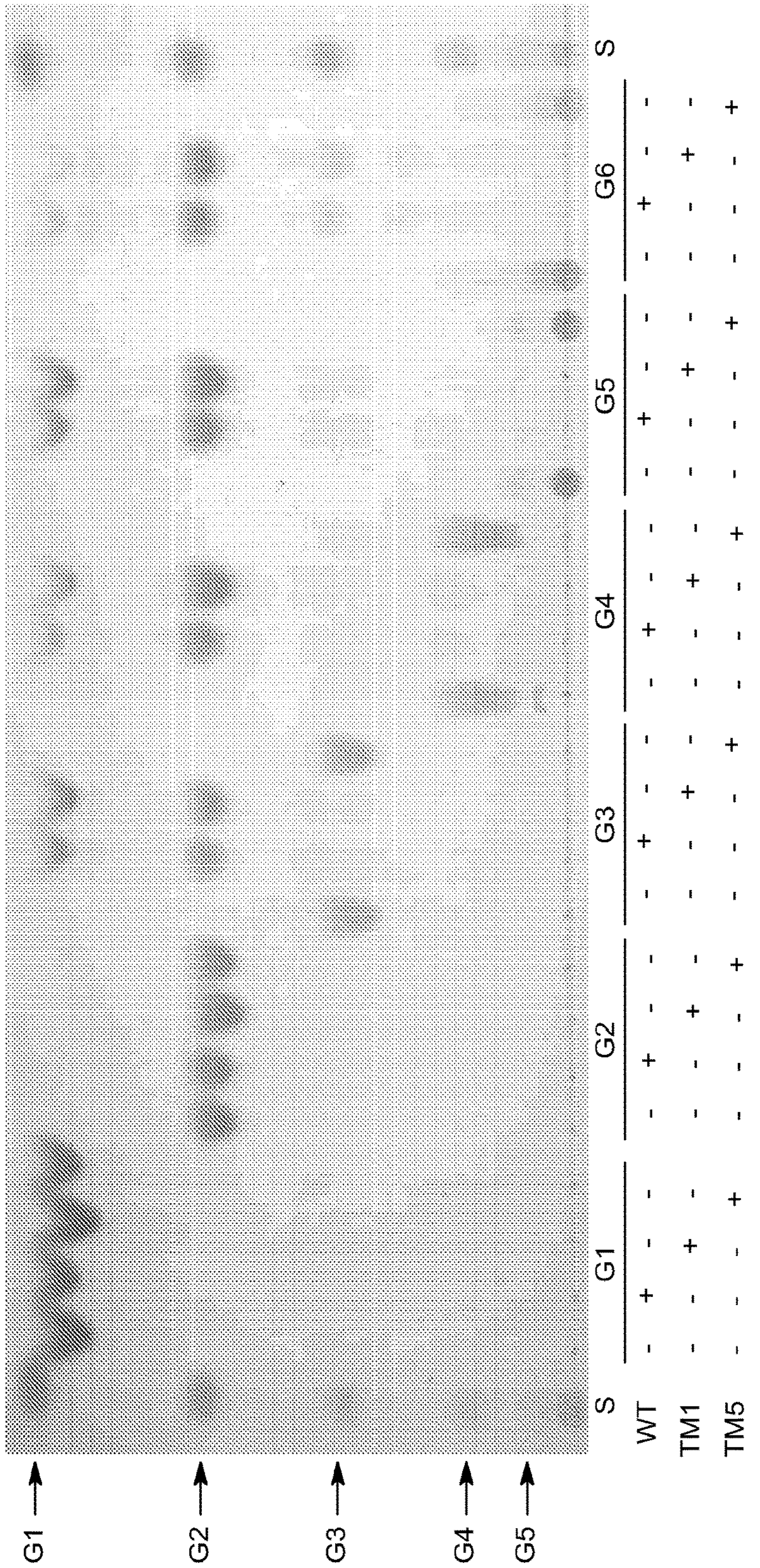

FIG. 23: Thin Layer Chromatography (TLC) analysis of enzymatic activity of Cb1952WT, Cb1952TM1 and Cb1952TM5 on glucose and cellooligosaccharides. G1, G2, G3, G4, G5, and G6 refer to glucose, cellobiose, cellotriose, cellotetraose, cellopentaose, and cellohexaose, respectively. Cb1952WT and Cb1952TM1 hydrolyze cellotriose, cellotetraose, cellopentaose and cellohexaose into glucose and cellobiose, but have no activity on cellobiose. Cb1952TM5 has no activity on glucose and any of the cellooligosaccharides tested. None of the enzyme has transglycosylation activity on glucose and cellooligosaccharides.

Figure 24:
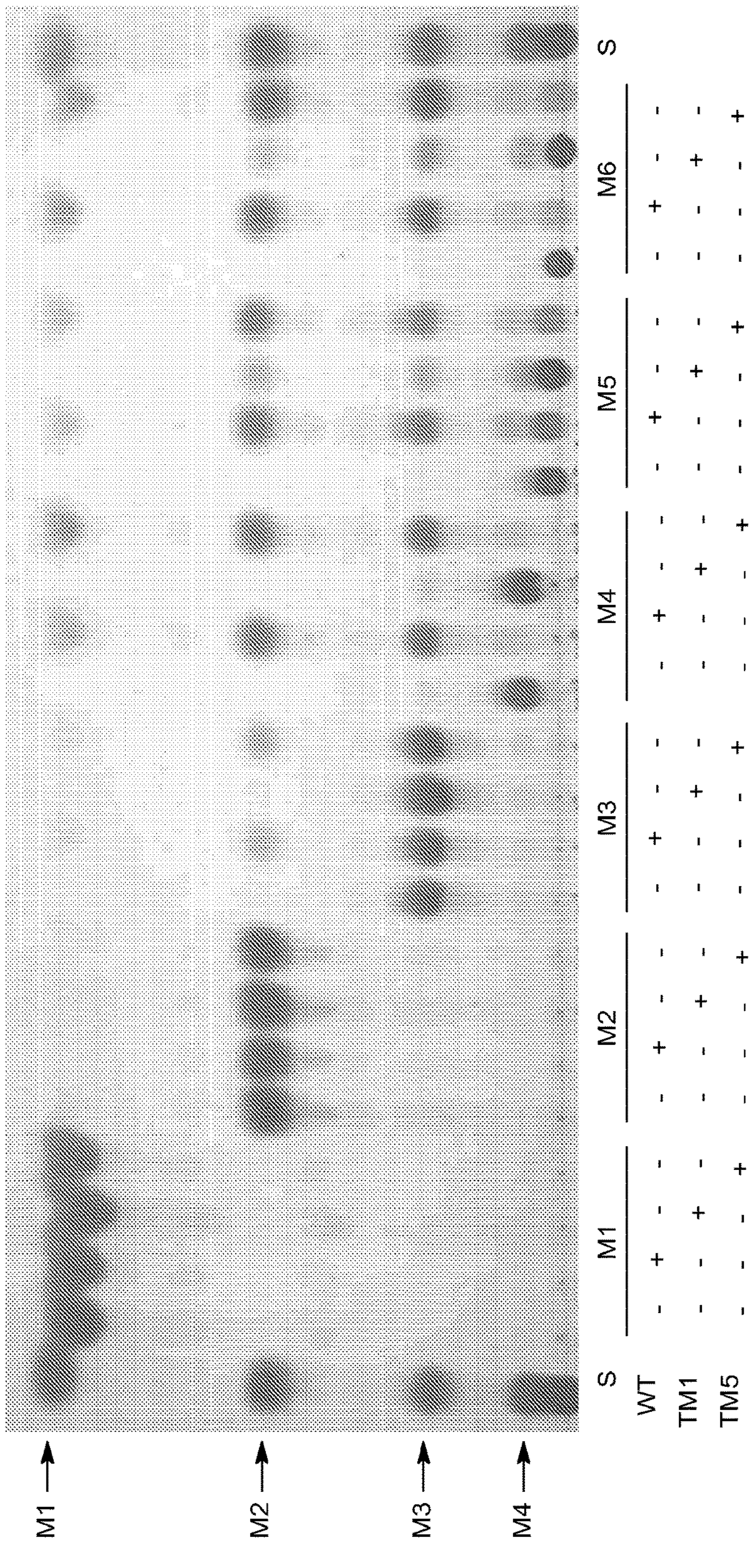

FIG. 24: Thin Layer Chromatography (TLC) analysis of enzymatic activity of Cb1952WT, Cb1952TM1 and Cb1952TM5 on mannose and mannooligosaccharides. M1, M2, M3, M4, M5, and M6 refer to mannose, mannobiose, mannotriose, mannotetraose, mannopentaose and mannohexaose, respectively. Cb1952WT and Cb1952TM5 hydrolyze mannotriose, mannootetraose, mannopentaose and mannohexaose into mannose and smaller mannooligosaccharides, but have no hydrolyzing activity on mannobiose. Cb1952TM1 hydrolyzes mannopentaose and mannohexaose into smaller oligosaccharides but has no hydrolyzing activity on mannobiose, mannotriose, mannotriose and mannotetraose. None of the enzyme has transglycosylation activity on mannose and mannooligosaccharides.

Figure 25:
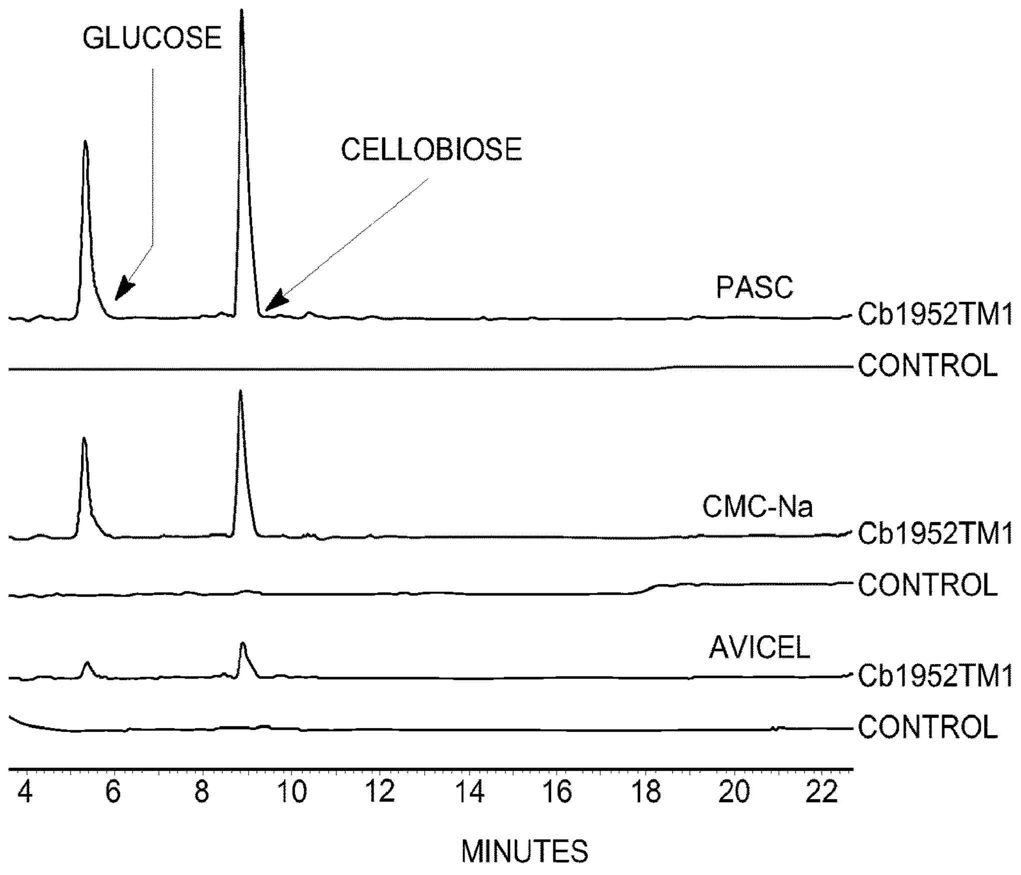

FIG. 25: HPLC analysis of enzymatic activity of Cb1952TM1 on cellulose substrates. Three different cellulosic substrates were tested: Avicel, CMC-Na and PASC. In each case, in the presence of Cb1952TM1, glucose and cellobiose were released. In the absence of Cb1952TM1, neither glucose nor cellobiose was observed for all the substrates. The results showed that this part of the enzyme or polypeptide (Cb1952) cleaves glucose and cellobiose as end products from cellulosic substrates (Avicel, CMC-Na and PASC).

Figure 26:
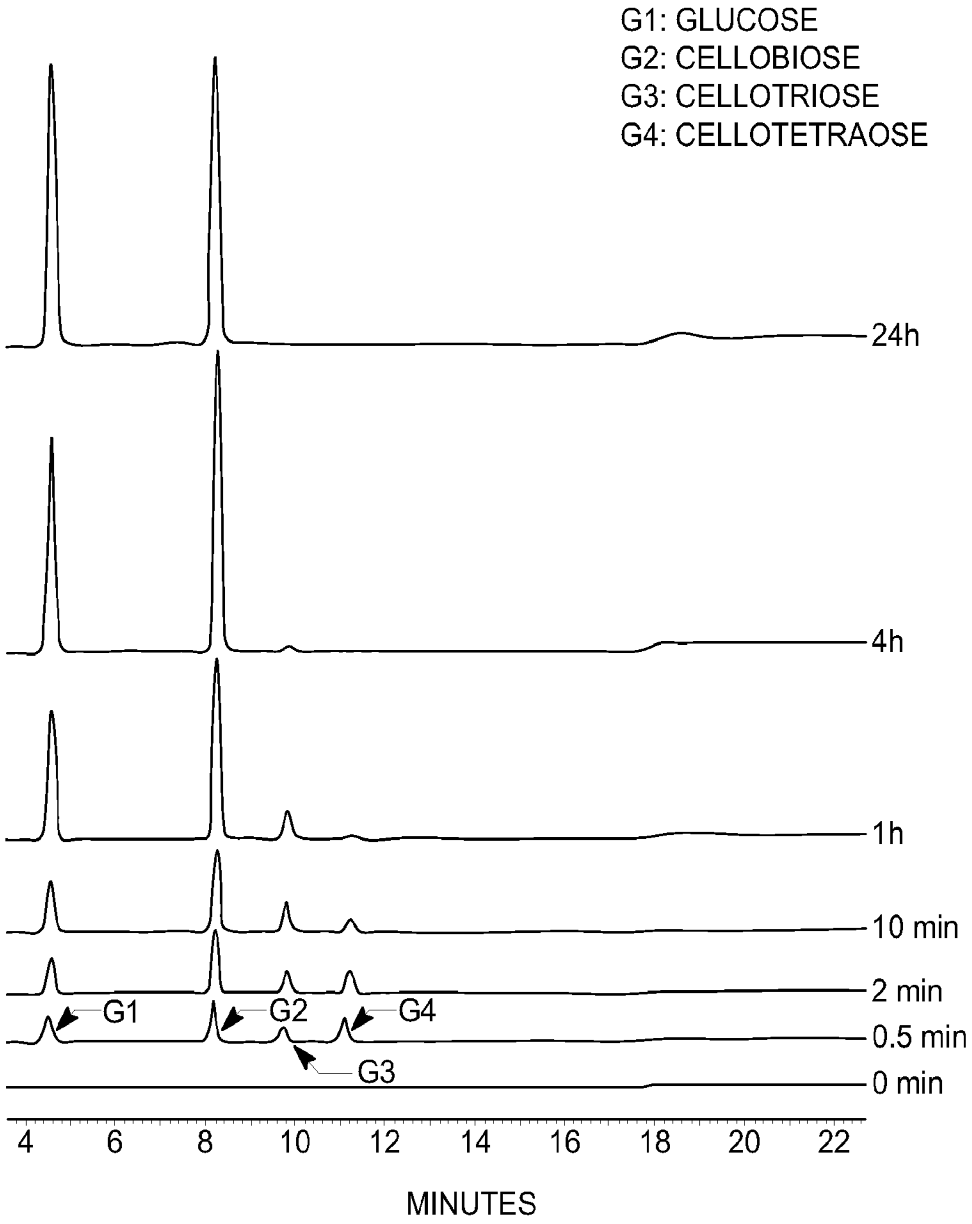

FIG. 26: HPLC analysis of time-course hydrolysis of PASC by Cb1952TM1. 100 nanomolar of Cb1952TM1 was incubated with 2.5 mg/ml PASC at 75° C. At different time intervals (0, 0.5 min, 2 min, 10 min, 1 h, 4 h and 24 h), samples were taken out and immediately boiled for 10 min to inactivate the enzyme. After centrifugation, the supernatants of the samples were appropriately diluted with water and applied to HPLC analysis. The results show that Cb1952TM1 initially releases glucose, cellobiose, cellotriose and cellotetraose. With increasing time, only glucose and cellobiose were left in the reaction mixture.

Figure 27:
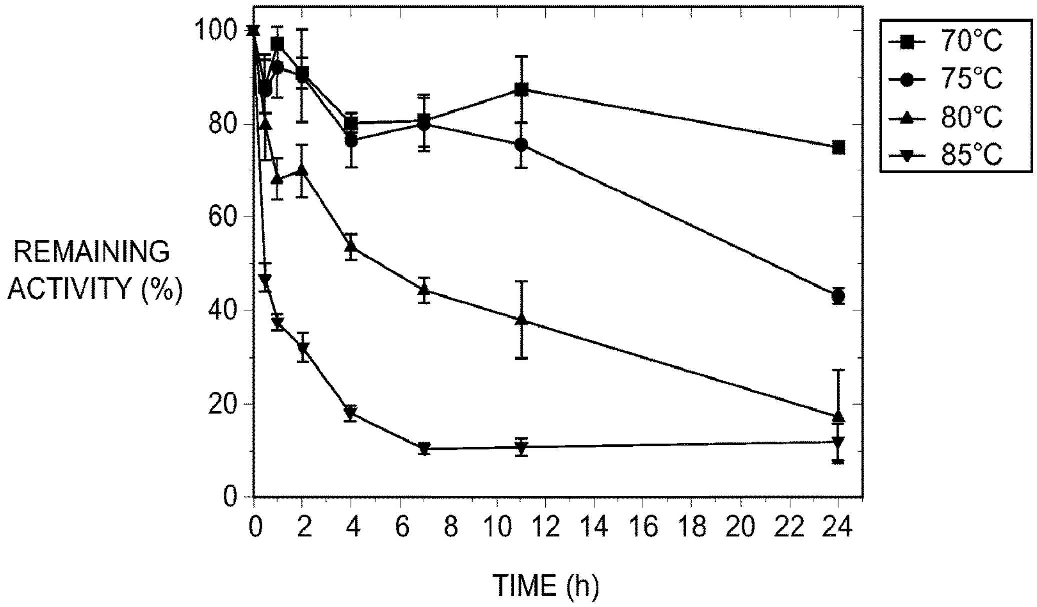

FIG. 27: Thermostability of Cb1952WT using PASC as substrate for activity measurement. Cb1952WT has 75%, 43%, 17% and 12% activity after incubation at 70° C., 75° C., 80° C. and 85° C. for 24 h, respectively. 500 nM Cb1952WT was kept at different temperatures (70° C., 75° C., 80° C. and 85° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 85° C. on a thermomixer. 2.5 mg/ml final concentration of PASC was used for measurement, and 8.31 μl of the protein sample was added to the substrate and mixed by pipetting up and down for several times. The total volume was 100 μl. The reducing ends corresponding to glucose equivalents were measured according to the methods of Lever, M. (A new reaction for colorimetric determination carbohydrates. Anal. Biochem. 1972: 47; 273-279). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Figure 28:
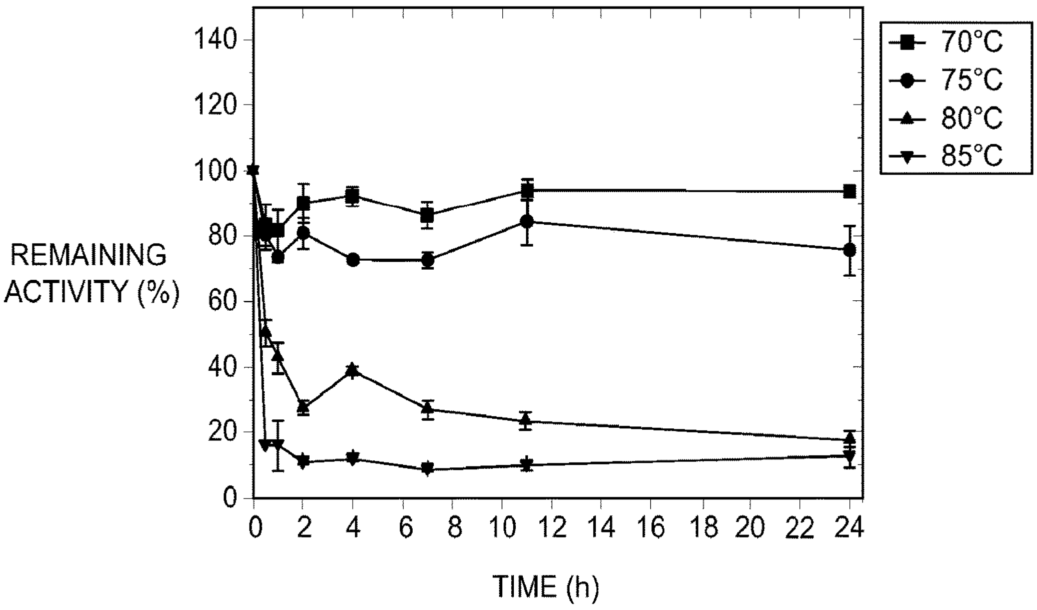

FIG. 28: Thermostability of Cb1952TM1 using PASC as substrate for activity measurement. Cb1952TM1 has 94%, 76%, 18% and 13% activity after incubation at 70° C., 75° C., 80° C. and 85° C. for 24 h, respectively. 500 nM Cb1952TM1 was kept at different temperatures (70° C., 75° C., 80° C. and 85° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 85° C. on a thermomixer. 2.5 mg/ml final concentration of PASC was used for measurement, and 8.31 μl of the protein sample was added to the substrate and mixed by pipetting up and down for several times. The total volume was 100 μl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Figure 29:
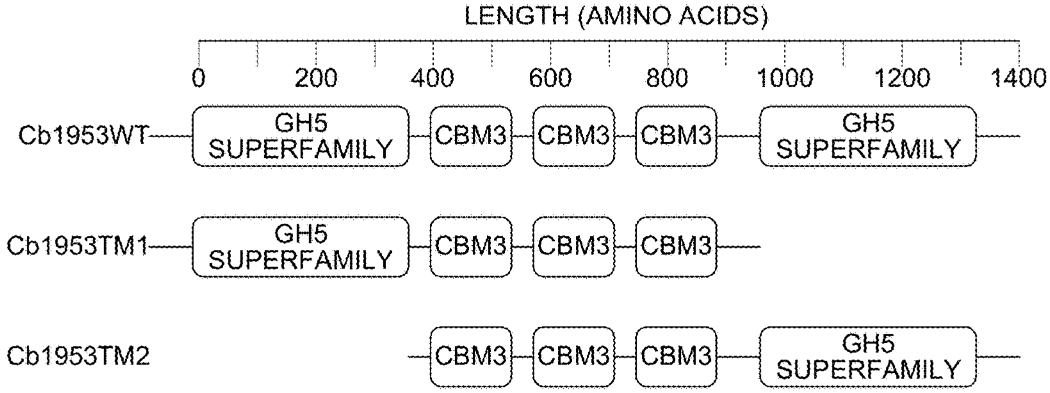

FIG. 29: Domain architecture of wild-type (WT) Cb1953, Cb1953TM1 and Cb1953TM2.

Figure 30:
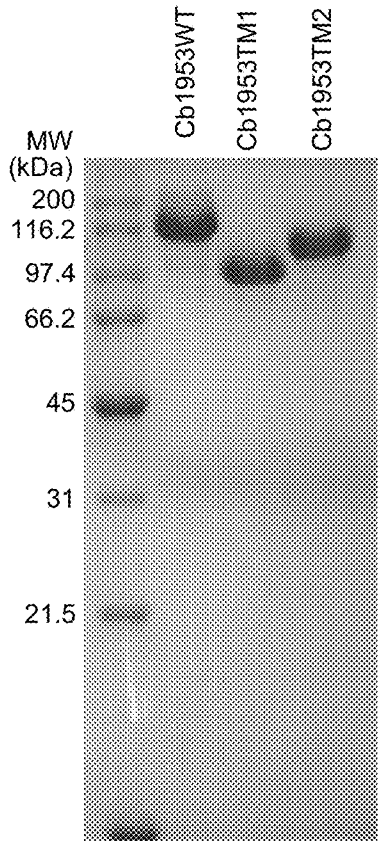

FIG. 30: SDS-polyacrylamide gel with purified wild-type Cb1953, Cb1953TM1 and Cb1953TM2 proteins.

Figure 31:
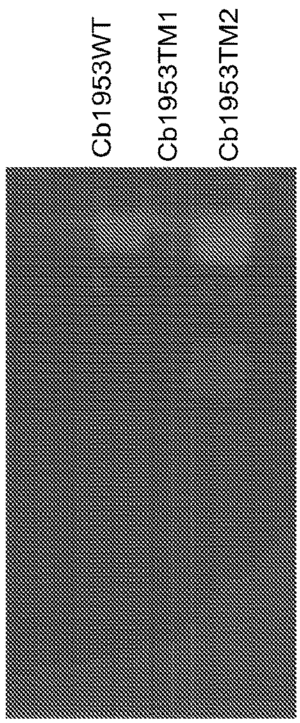

FIG. 31: A zymogram of Cb1953WT, Cb1953TM1, Cb1953TM2 on carboxylmethyl cellulose (CMC). The gel was prepared as in standard dodecyl sulfate polyacrylamide gel electrophoresis (SDS-PAGE) with CMC substrate (final 0.1%, w/v). After electrophoretic fractionation of the proteins, gels were washed twice in distilled water and incubated in 30 mL of refolding buffer (20 mM citrate buffer, pH 6.0, 2.5% Triton X-100, 2 mM dithiothreitol, 2.5 mM $CaCl_2$) for 1 hour at 25° C. and then held overnight in fresh buffer at 37° C. The gel was washed twice in 50 mM Citrate buffer (pH 6.0) and then the results were visualized by staining with 0.1% Congo red and destaining with 1M NaCl. As shown in FIG. 31, Cb1953WT and Cb1953TM2 showed significant white bands at the positions of their expected sizes indicating cellulase activity, but not Cb1953TM1 protein.

Figure 32:
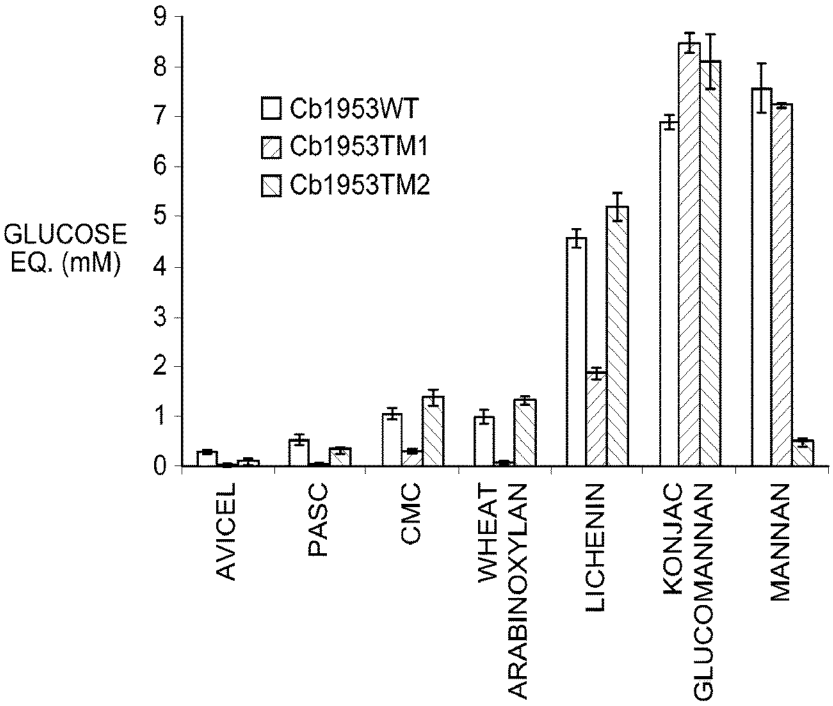
Figure 33:
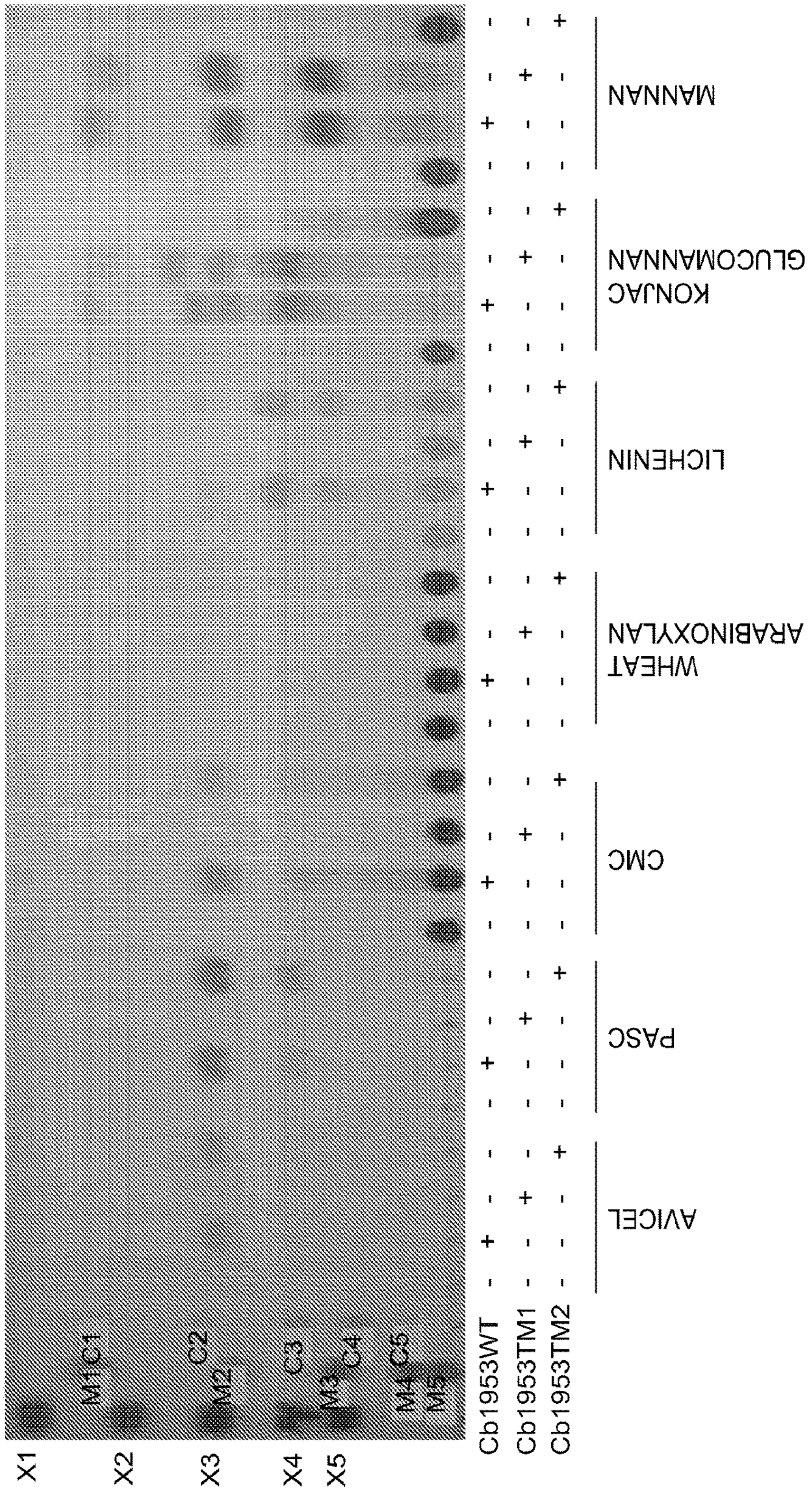

FIGS. 32 and 33: Enzymatic activity of Cb1953WT, Cb1953TM1, and Cb1953TM2 on natural substrates from a reducing sugar assay. Seven different substrates were tested: Avicel, Phosphoric acid swollen cellulose (PASC), carboxylmethyl cellulose (CMC), wheat arabinoxylan (WAX), lichenin, konjac glucomannan, and mannan. Incubation of enzymes with the substrates led to release of products that were quantified as a concentration of glucose equivalents. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay. The wavelength at 410 nm was measured for the standards and samples. The $A_{410nm}$ and glucose concentrations were plotted against each other, and linear regression was used to fit a line to the data. The reactions were resolved by thin layer chromatography (TLC), The mobile phase consisted of n-butanol:acetic acid: H2O, 10:5:1 (vol/vol/vol) and 10 cm×20 cm plates were used. The reducing sugar assay (FIG. 32) and TLC (FIG. 33) results show that Cb1953WT and Cb1953TM2 have cellulase activity whereas Cb1953TM1 has mannanase activity.

Figure 34:
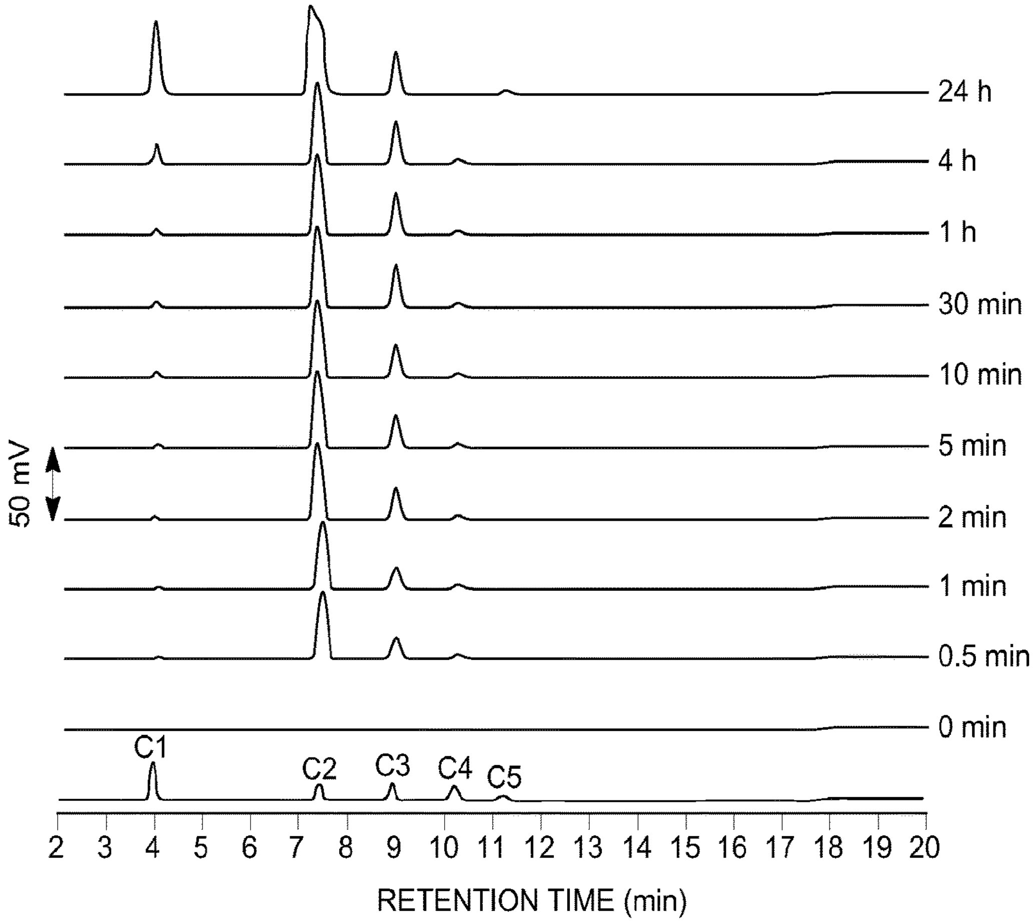

FIG. 34: HPLC analysis of time course of enzymatic activity of Cb1953TM2 on PASC. For analysis of the products of hydrolysis, the samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.). For the analysis, glucose and five different cellooligosaccharides (cellobiose, cellotriose, cellotetraose, cellopentaose, and cellohexaose) were used as standards. In the reaction, Cb1953TM2 started to release cellooligosaccharides (C2-C4) and then glucose was released later. The results showed that this enzyme releases mainly cellobiose from PASC.

Figure 35:
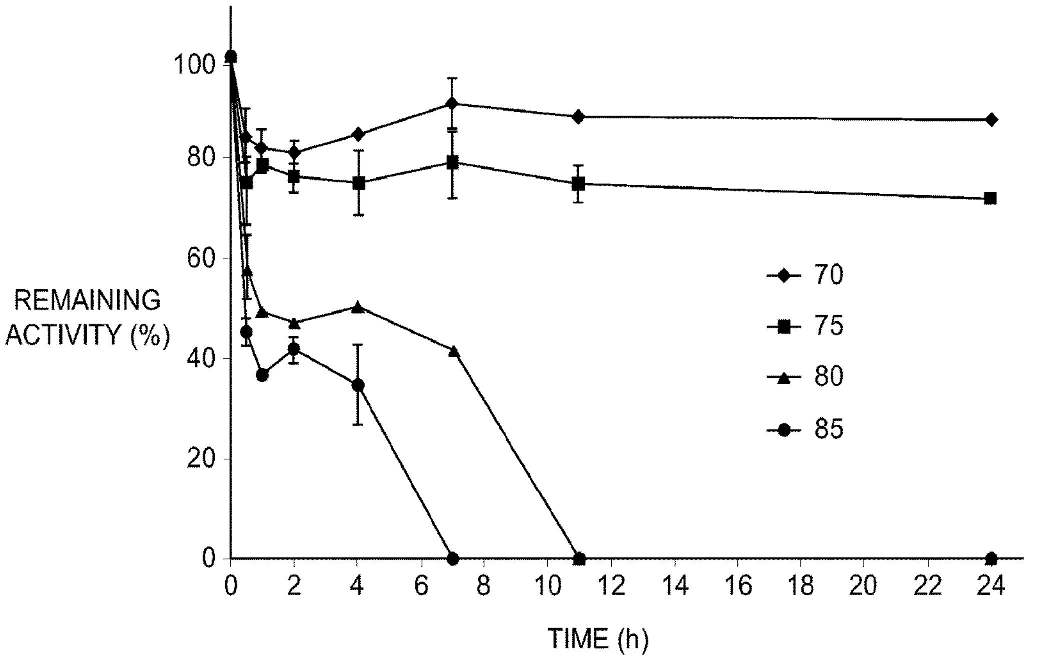
Figure 36:
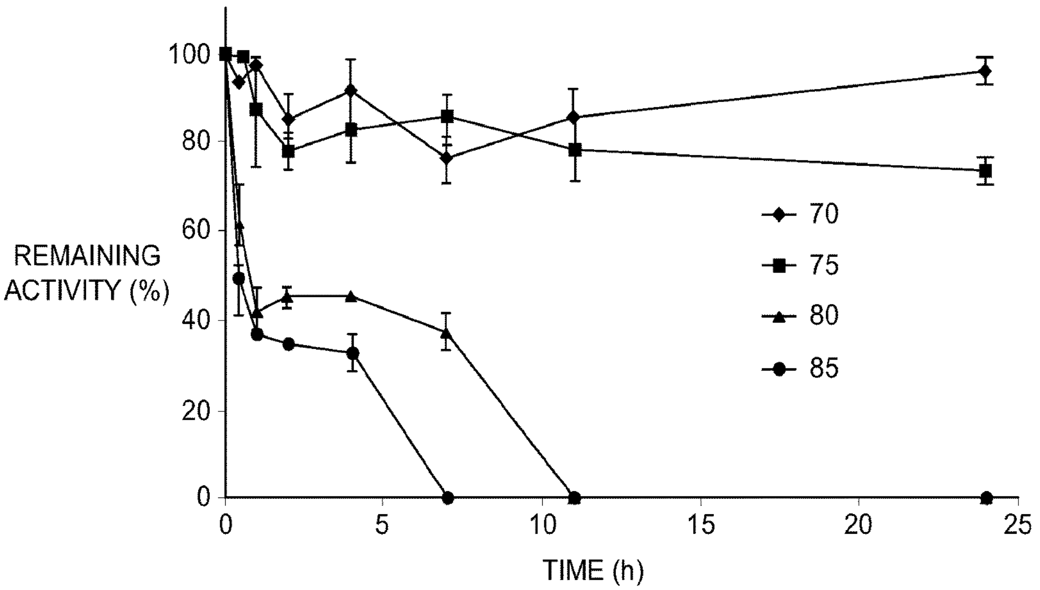

FIGS. 35 and 36: Thermostability of Cb1953WT (FIG. 35) and Cb1953TM2 (FIG. 36) on PASC. Fifty nM Cb1953WT and Cb1953TM2 were kept at different temperatures (70° C., 75° C., 80° C., 85° C. and 90° C.). The samples were taken out at different time points (0 h, 0.5 h, 1 h, 2 h, 4 h, 7 h, 11 h and 24 h) and immediately used in enzyme activity measurement. The enzyme activity was measured at 85° C. using Cary 300 UV-Vis spectrophotometer (Varian). The initial velocity of reaction in the first minute was calculated. The initial velocity of reaction for time 0 was set as 100; then the remaining activities (percentage) for time 0.5 h, 1 h, 2 h, 4 h, 7 h, 11 h and 24 h were calculated by dividing the initial velocities of reaction for time 0.5 h, 1 h, 2 h, 4 h, 7 h, 11 h and 24 h by the initial velocity of reaction at time 0, then multiplied by 100. From the results, Cb1953WT (FIG. 35) and Cb1953TM2 (FIG. 36) were quite stable at 70° C. and 75° C., maintaining activity of 75~90% of heat non-treated proteins.

Figure 37A:
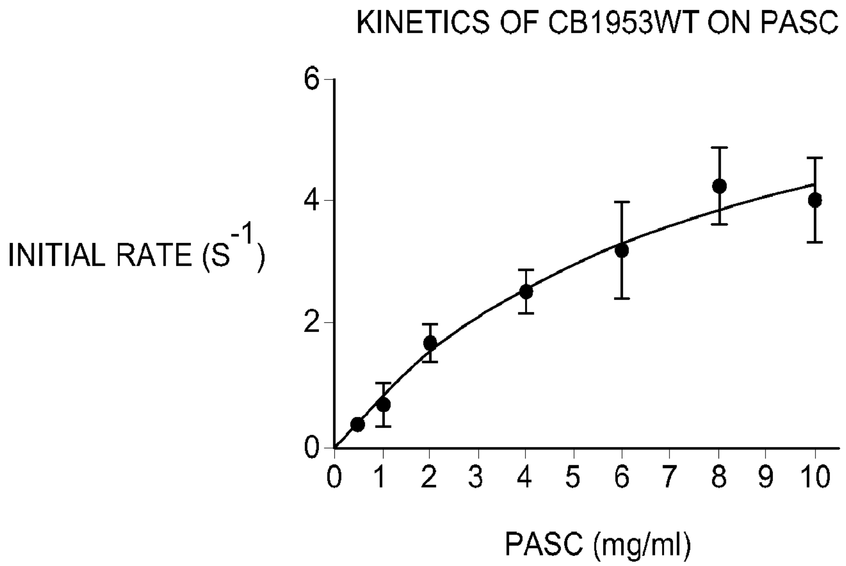
Figure 37B:
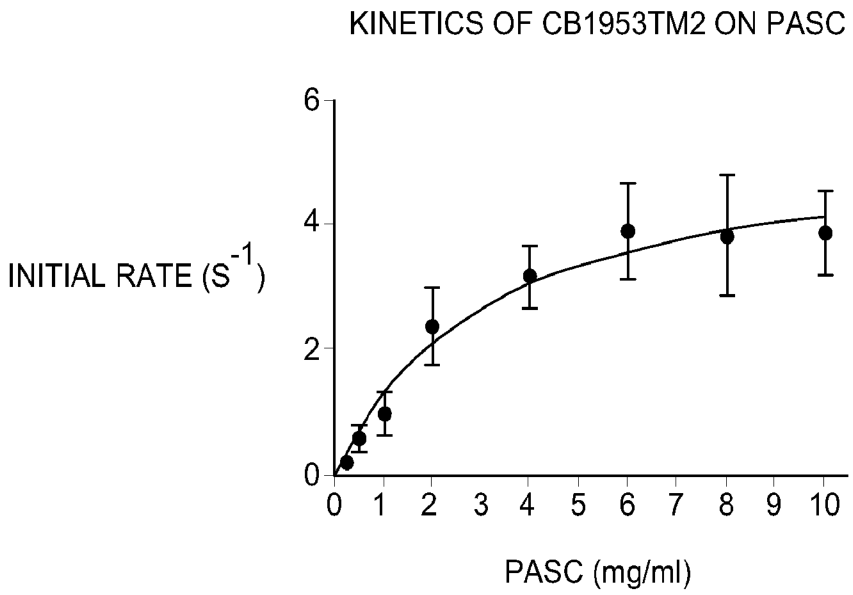

FIGS. 37A and 37B: Kinetic studies of Cb1953WT (FIG. 37A) and Cb1953TM2 (FIG. 37B) on PASC. 0.05 μM of purified Cb1953WT or Cb1953TM2 in 50 mM $Na_2HPO_4$—HCl, pH 6.0, and 150 mM NaCl was incubated with various concentrations of phosphoric acid swollen cellulose (PASC), and the initial rate of hydrolysis was plotted against substrate concentration. The kinetic parameters ($K_m$: 7.603 mg/mL, $k_{cat}$: 7.513 $s^{-1}$ and $k_{cat}/K_m$: 0.988 $s^{-1}$ mL/mg for Cb1953WT and $K_m$: 3.032 mg/mL, $k_{cat}$: 5.411 $s^{-1}$ and $k_{cat}/K_m$: 1.785 $s^{-1}$ mL/mg for Cb1953TM2) were determined by fitting the data to the Michaelis-Menten equation (Graph Pad Prism v5.01).

Figure 38:
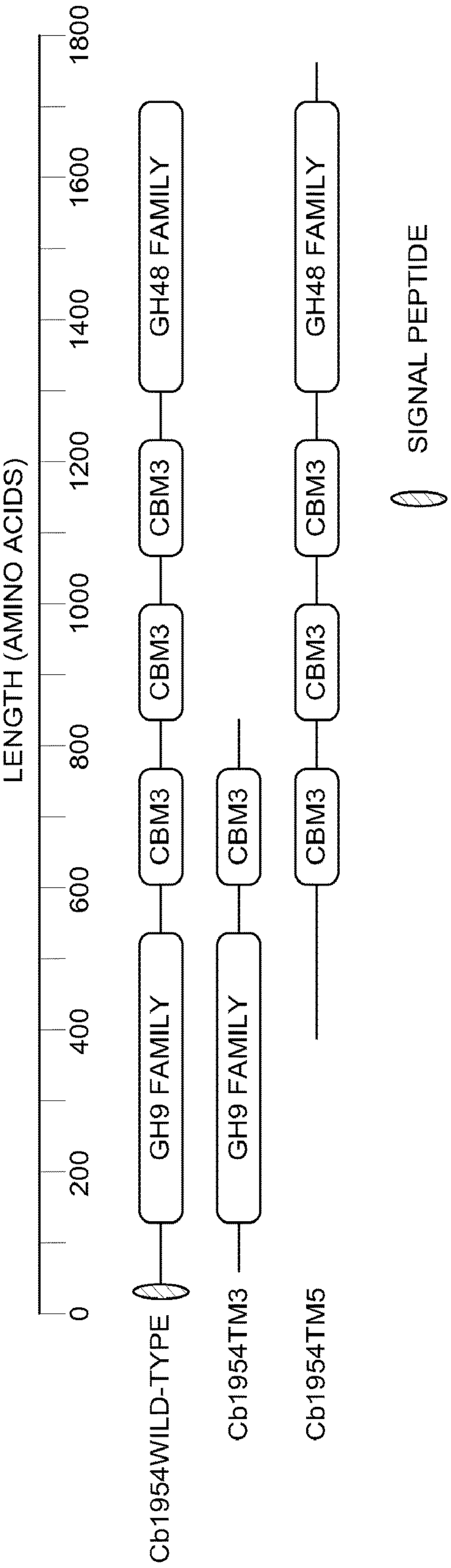

FIG. 38: Domain architecture of wild-type (WT) Cb1954, Cb1954TM3 and Cb1954TM5 polypeptides.

Figure 39A:
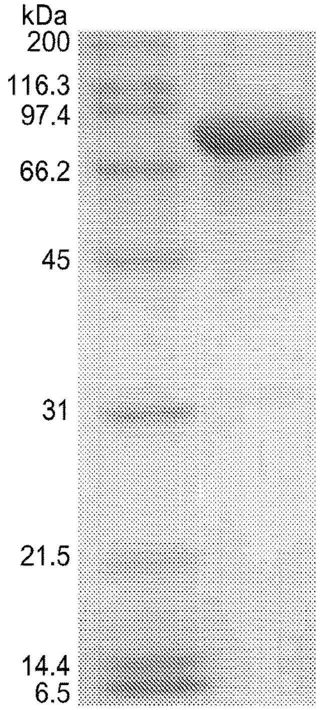
Figure 39B:
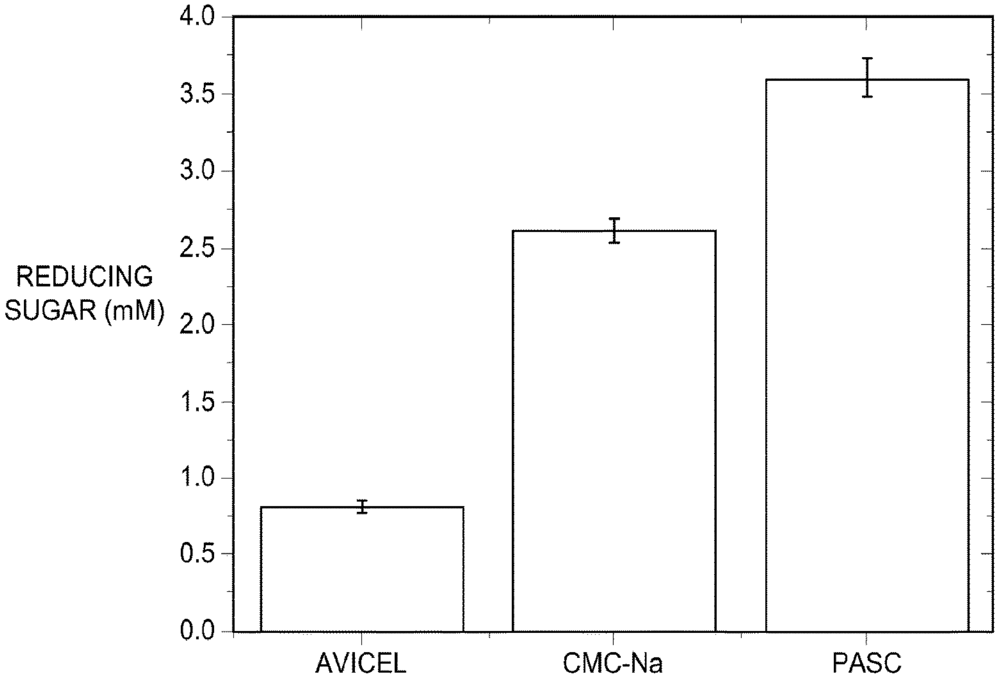

FIGS. 39A and 39B: FIG. 39A: SDS-polyacrylamide gel with purified Cb1954TM3 protein. FIG. 39B: Enzymatic activity of Cb1954TM3 on natural substrates from a reducing sugar assay. Three different cellulose substrates were tested: Avicel, sodium carboxymethyl cellulose (CMC-Na) and phosphoric acid swollen cellulose (PASC). Incubation of enzymes with the substrates led to release of products that were quantified as a concentration of glucose equivalents. Hydrolysis of PASC was higher than hydrolysis of other substrates.

Figure 40:
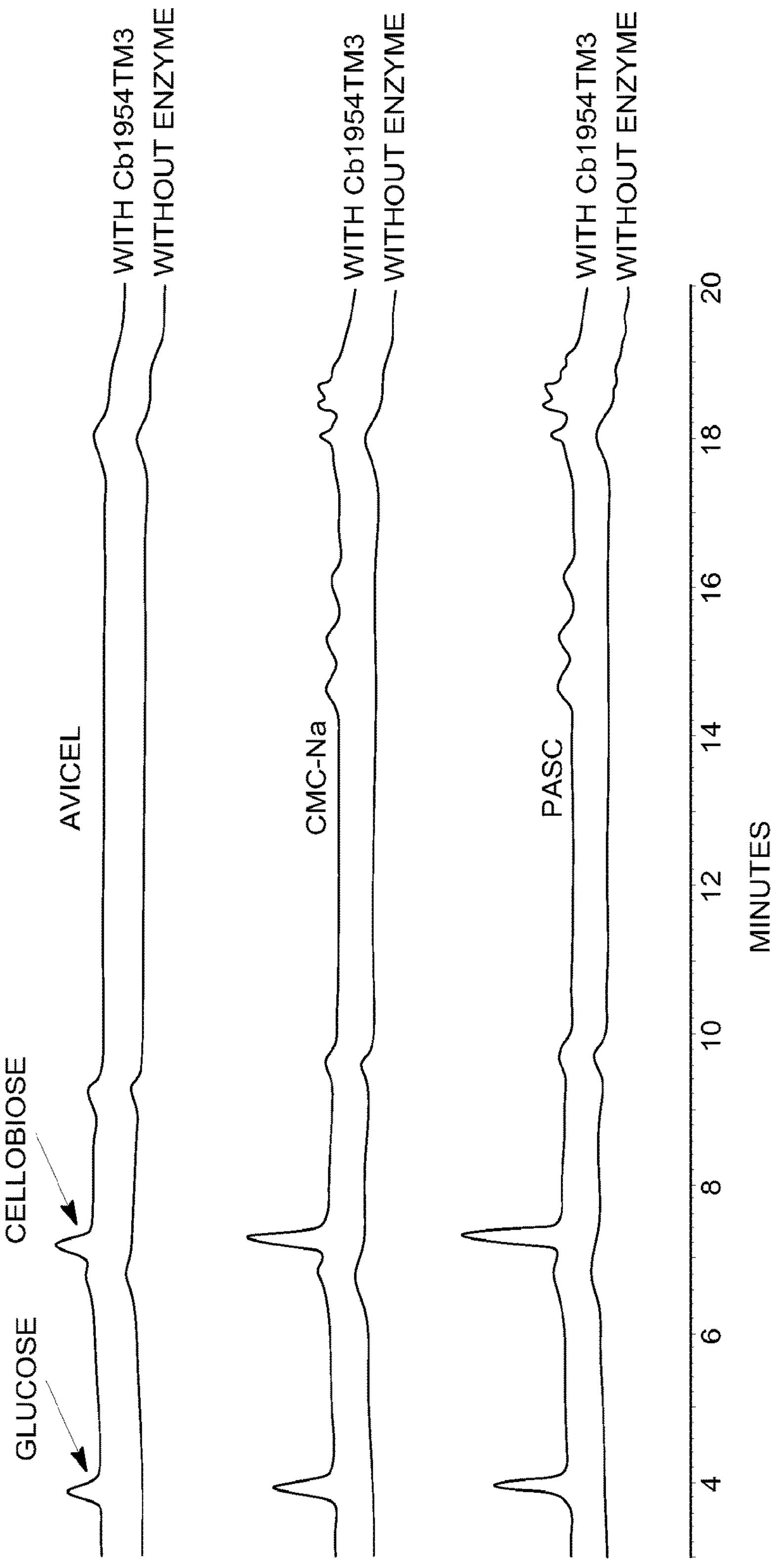

FIG. 40: HPLC analysis of enzymatic activity of Cb1954TM3 on cellulosic substrates. Three different cellulosic substrates were tested: Avicel, CMC-Na and PASC. In each case, in the presence of Cb1954TM3, glucose and cellobiose were released. In the absence of Cb1954TM3, neither glucose nor cellobiose was observed for all the substrates. The results showed that this enzyme releases glucose and cellobiose, and also longer chain oligosaccharides as end products from cellulosic substrates (CMC-Na and PASC).

Figure 41:
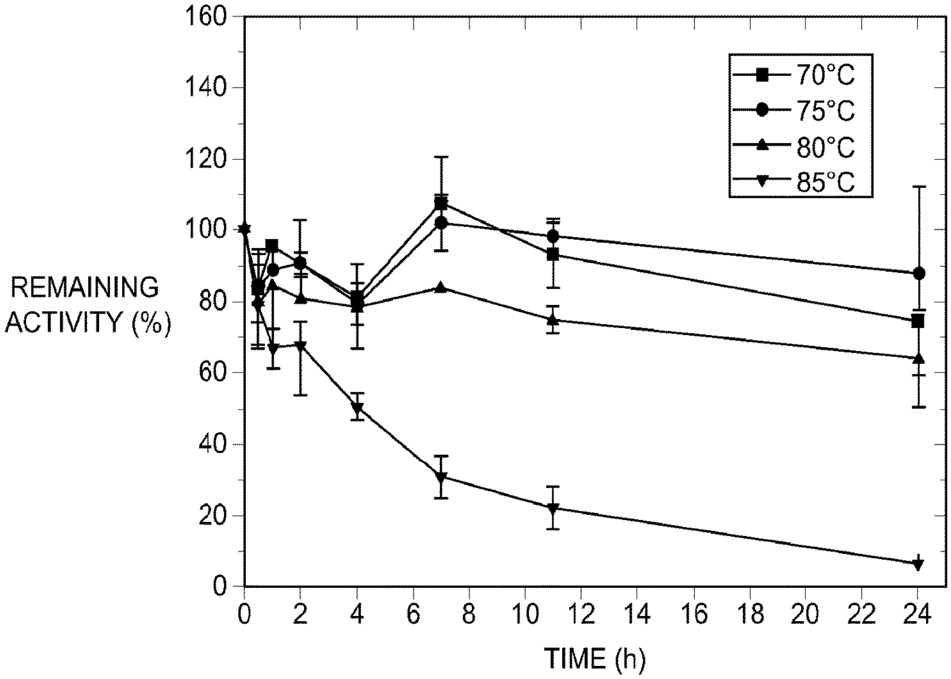

FIG. 41: Thermostability of Cb1954TM3. Cb1954TM3 has 75%, 87%, 64% and 7% activity after incubation at 70° C., 75° C., 80° C. and 85° C. for 24 h, respectively. 500 nM Cb1954TM3 was kept at different temperatures (70° C., 75° C., 80° C. and 85° C.). The enzyme activity was measured at pH 5.5 and at 95° C. on a thermomixer. 2.5 mg/ml final concentration of PASC was used for measurement, and 10 μl of the protein sample was added to the substrate and mixed by pipetting up and down for several times. The total volume was 100 μl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Figure 42:
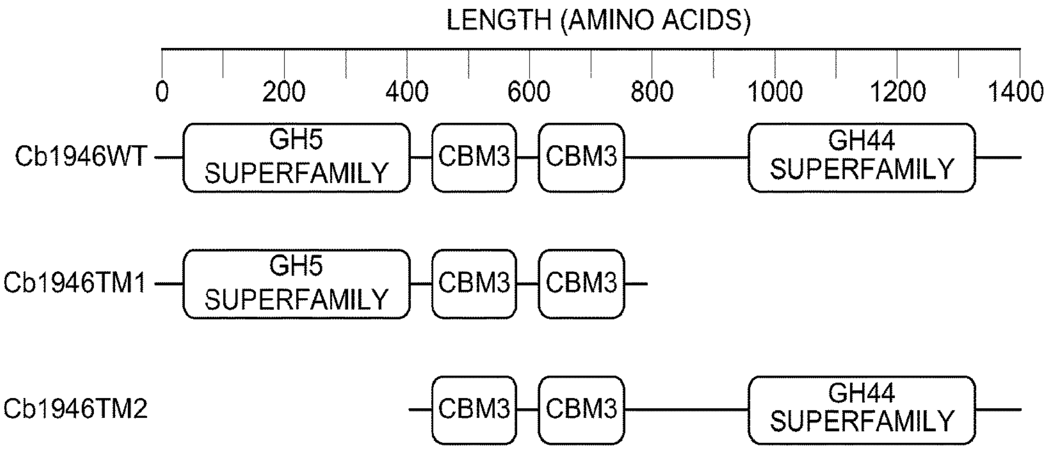

FIG. 42: Domain architecture of wild-type (WT) Cb1946, Cb1946TM1 and Cb1946TM2 polypeptides.

Figure 43:
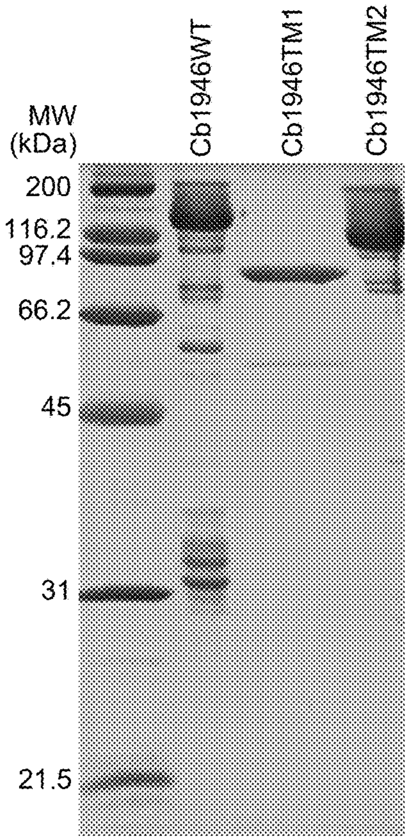

FIG. 43: SDS-polyacrylamide gel with purified wild-type Cb1946, Cb1946TM1 and Cb1946TM2 proteins.

Figure 44:
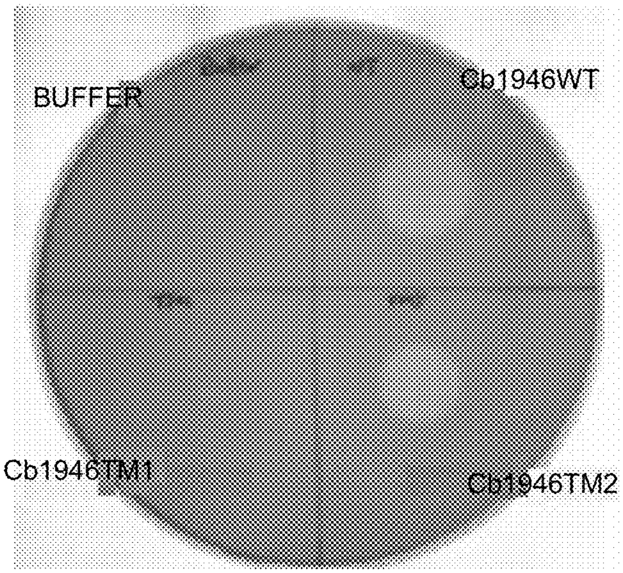

FIG. 44: Zymogram of Cb1946WT, Cb1946TM1, and Cb1946TM2 on carboxylmethyl cellulose (CMC) agar plate. The agar plate was prepared with CMC substrate (final 0.25%, w/v). After spotting 1 μg of each protein on agar-CMC plates, the plate was incubated at 37° C. overnight and then the gel was visualized by staining with 0.1% Congo red and destaining with 1M NaCl. As shown in FIG. 44, Cb1946WT and Cb1946TM2 showed significant halos on the agar plate indicating cellulase activity, but not Cb1953TM1 proteins.

Figure 45:
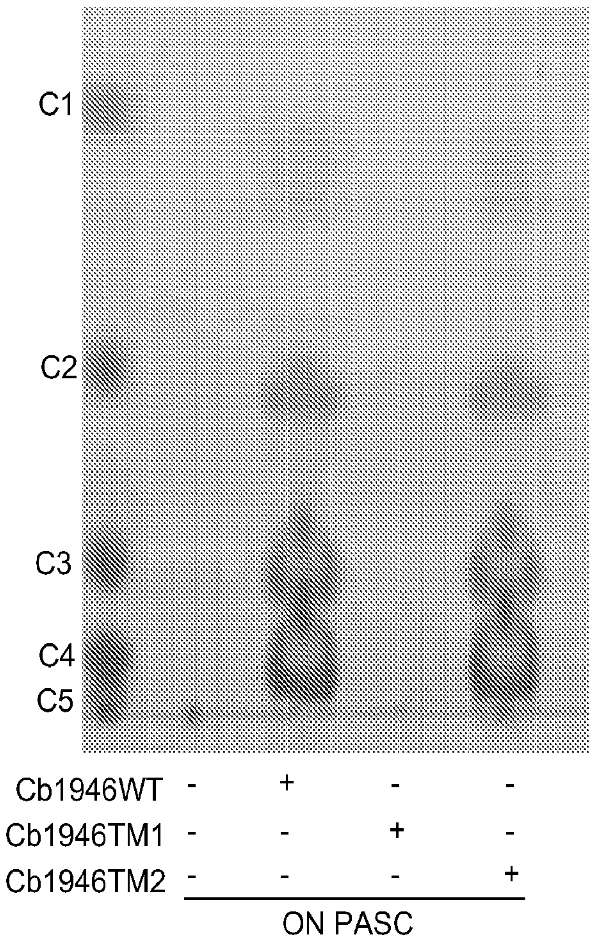
Figure 46:
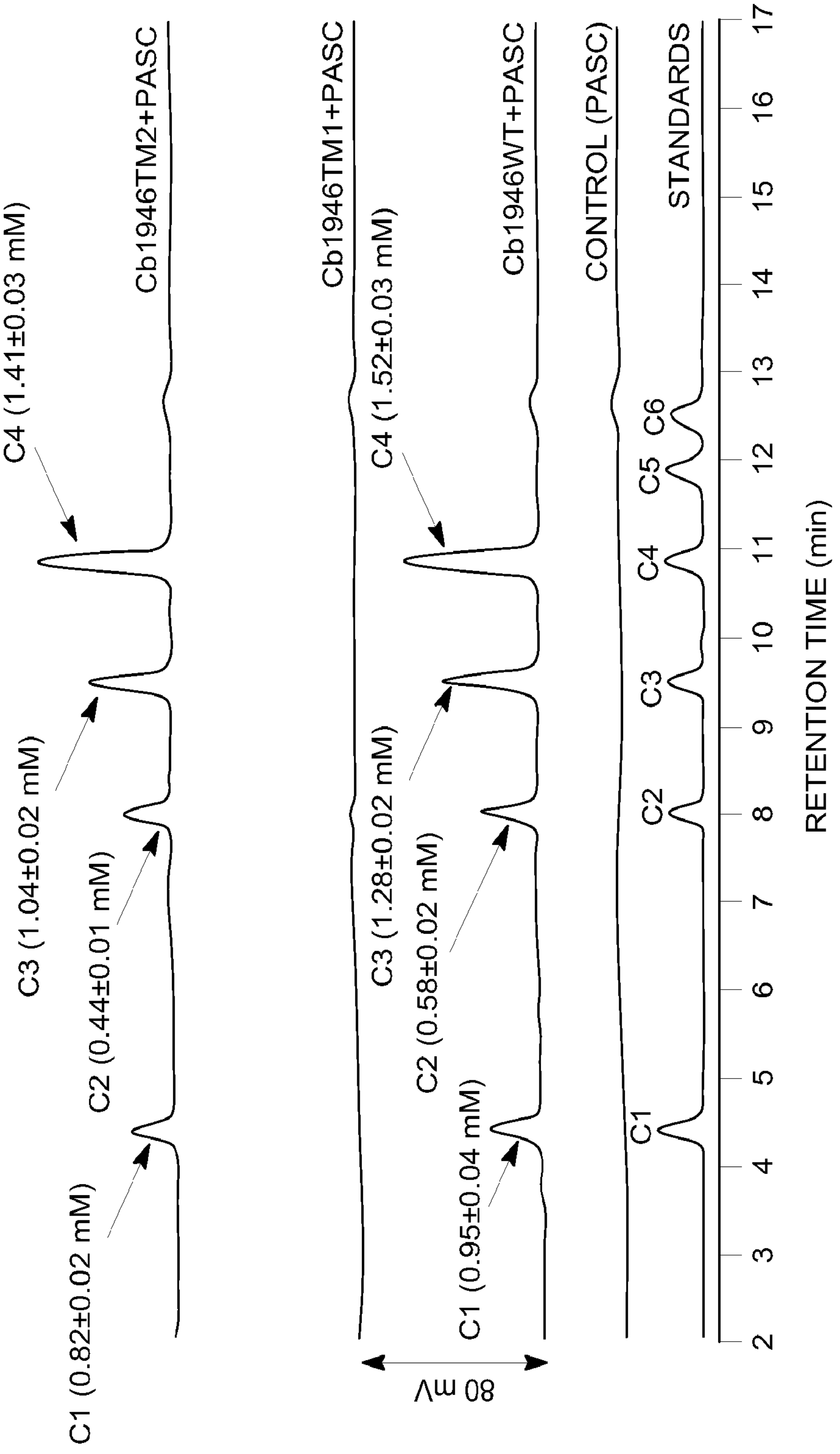

FIGS. 45 and 46: Thin Layer Chromatography (TLC) (FIG. 45) and High Performance Liquid Chromatography (HPLC) (FIG. 46) analysis of enzymatic activity of Cb1946WT, Cb1946TM1, Cb1946TM2 on phosphoric acid swollen cellulose (PASC). Each enzyme (final 0.5 μM) was reacted with phosphoric acid swollen cellulose (PASC) at 1% final concentration in 50 mM citrate-150 mM NaCl, pH 6.0 at 75° C. for 16 hours. The reactions were resolved by thin layer chromatography (TLC) (FIG. 45). The mobile phase consisted of n-butanol:acetic acid:H2O, 10:5:1 (vol/vol/vol) and 10 cm×20 cm plates were used. In FIG. 45, C1, C2, C3, C4, and C5 refer to glucose, cellobiose, cellotriose, cellotetraose and cellopentaose, respectively. For more quantitative analysis of the products of hydrolysis, the samples were analyzed by high performance anion-exchange chromatography (HPAEC) (FIG. 46). For HPAEC analyses, 100 μL of each diluted sample was injected into a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.). For the TLC and HPLC analysis, glucose and five different cellooligosaccharides were used: cellobiose, cellotriose, cellotetraose, cellopentaose, and cellohexaose as standards. Based on the results of TLC and HPLC, Cb1953WT and Cb1953TM2 showed significant release of products such as glucose, cellobiose, cellotriose, and cellotetraose from PASC substrate, indicating that Cb1946WT and Cb1953TM2 have cellulase activities, but not Cb1953TM1.

Figure 47:
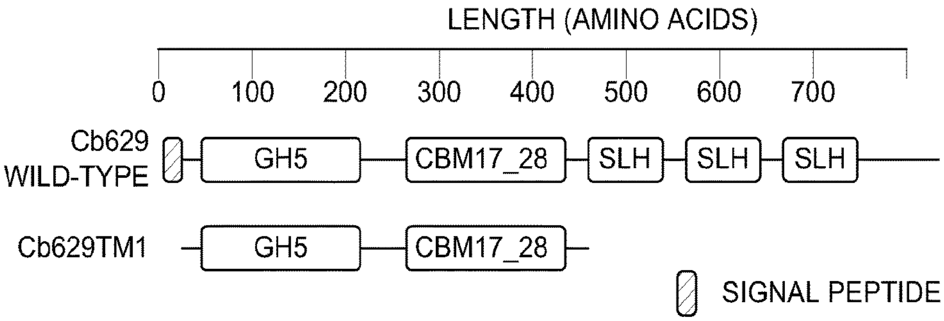

FIG. 47: Domain architecture of wild-type Cb629 and Cb629TM1 polypeptides.

Figure 48:
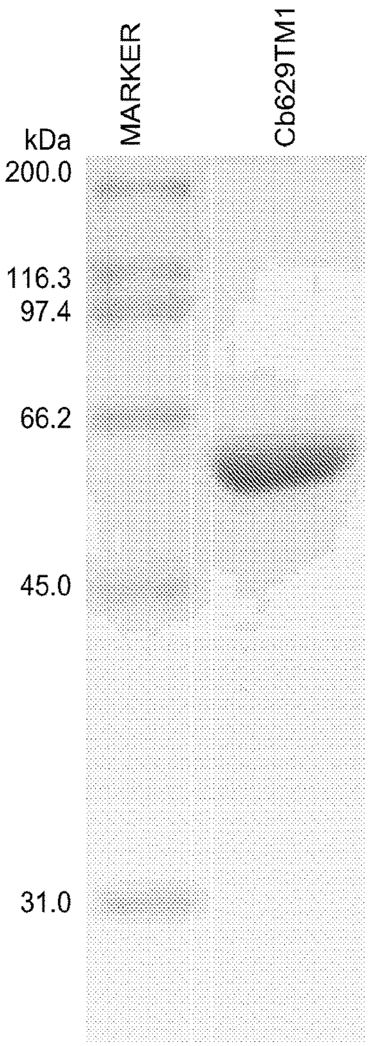

FIG. 48: SDS-polyacrylamide gel with purified Cb629TM1 protein.

Figure 49:
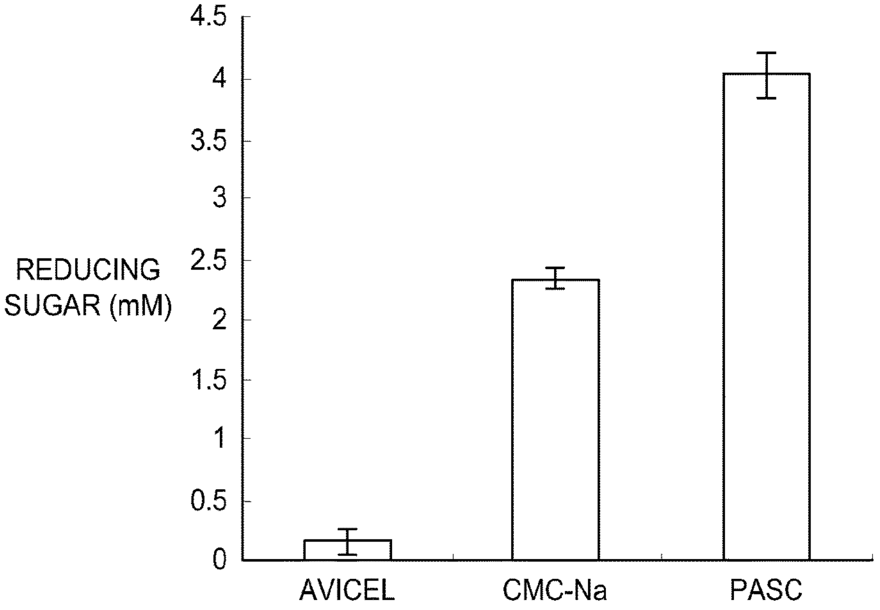

FIG. 49: Enzymatic activity of Cb629TM1 on substrates with products determined through a reducing sugar assay. Three different cellulose substrates were tested: Avicel, sodium carboxymethyl cellulose (CMC-Na) and phosphoric acid swollen cellulose (PASC). Incubation of enzymes with the substrates led to release of products that were quantified as a concentration of glucose equivalents. Hydrolysis of PASC was higher than hydrolysis of the other substrates.

Figure 50:
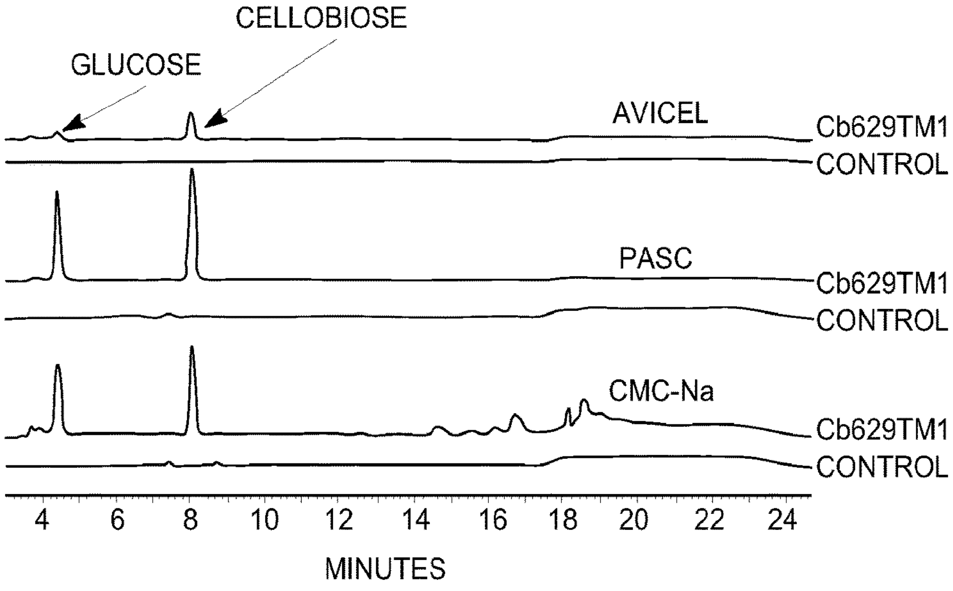

FIG. 50: HPLC analysis of enzymatic activity of Cb629TM1 on substrates. Three different cellulosic substrates were tested: Avicel, CMC-Na and PASC. In each case, in the presence of Cb629TM1, glucose and cellobiose were released. In the absence of Cb629TM1, neither glucose nor cellobiose was observed from all the substrates. The results showed that this enzyme releases glucose and cellobiose as end products from cellulosic substrates (Avicel, CMC-Na and PASC).

Figure 51:
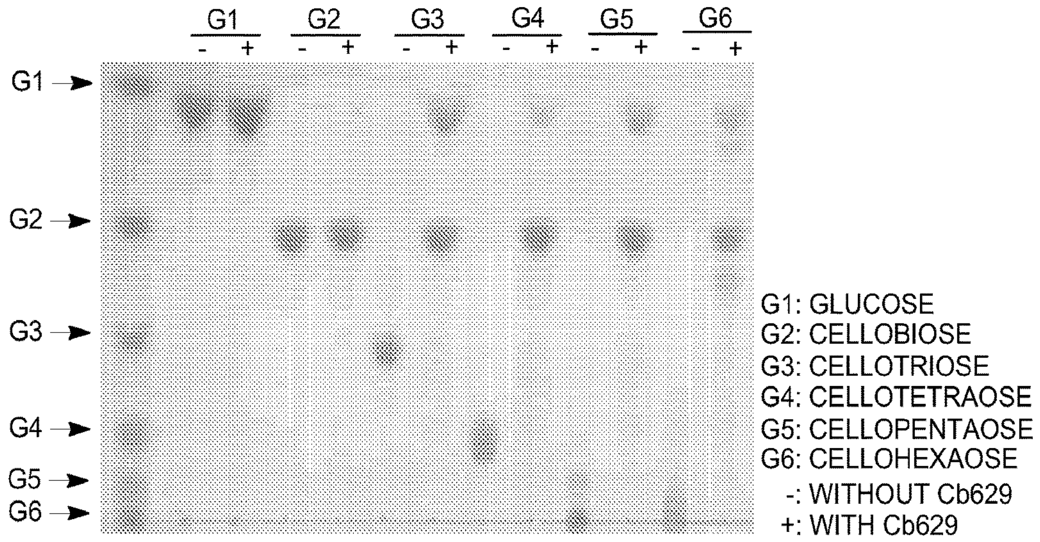

FIG. 51: TLC analysis of enzymatic activity of Cb629TM1 on cello-oligosaccharides. G1, G2, G3, G4, G5, and G6 refer to glucose, cellobiose, cellotriose, cellotetraose, cellopentaose, and cellohexaose respectively.

Figure 52:
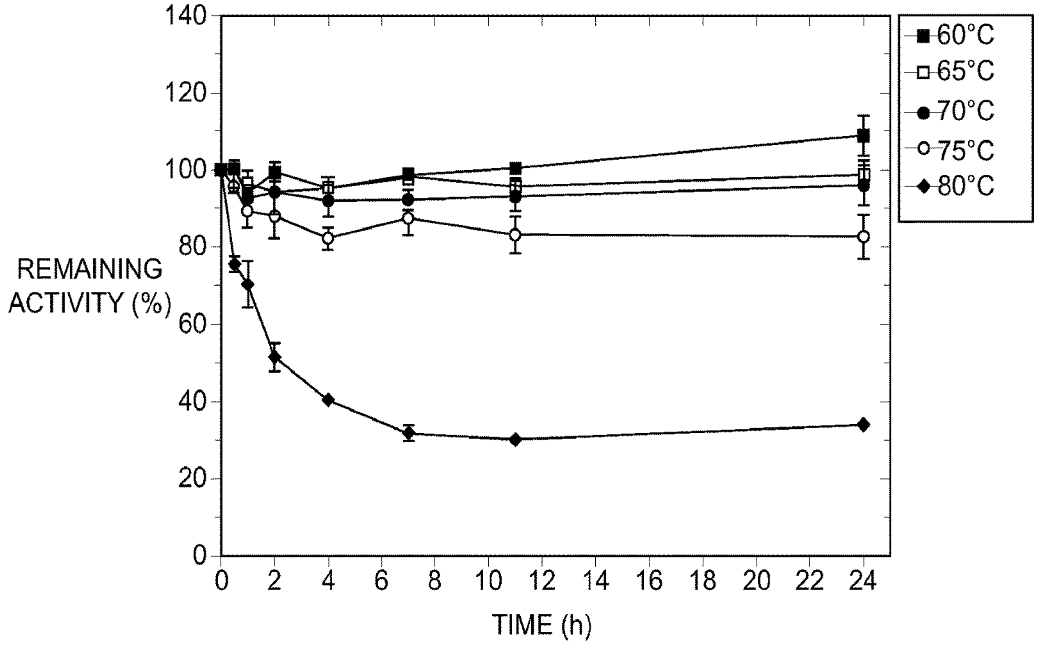

FIG. 52: Thermostability of Cb629TM1. Cb629TM1 has 109%, 99%, 96%, 83% and 34% activity after incubation at 60° C., 65° C., 70° C., 75° C. and 80° C. for 24 h, respectively. 500 nM Cb629TM1 was kept at different temperatures (60° C., 65° C., 70° C., 75° C. and 80° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 70° C. on a thermomixer. 2.5 mg/ml final concentration of PASC was used for measurement, and 8.31 μl of the protein sample was added to the substrate and mixed by pipetting up and down for several times. The total volume was 100 μl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Figure 53A:
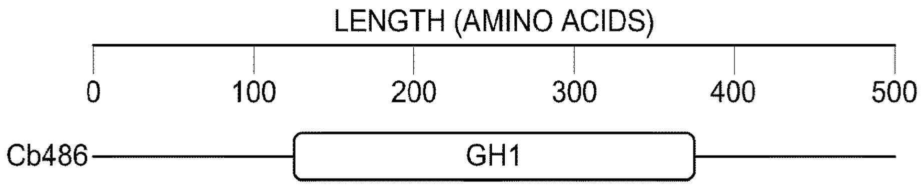
Figure 53B:
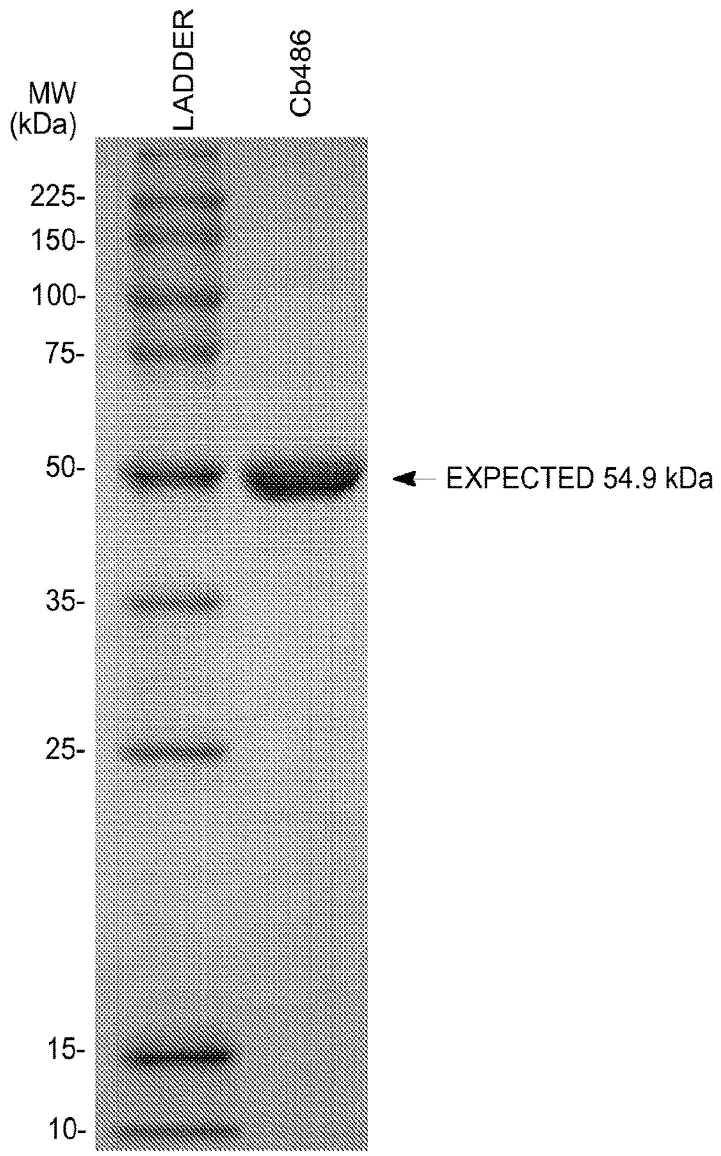

FIGS. 53A and 53B: FIG. 53A: Domain architecture of wild-type Cb486. FIG. 53B: SDS-polyacrylamide gel with purified wild-type Cb486 protein.

Figure 54:
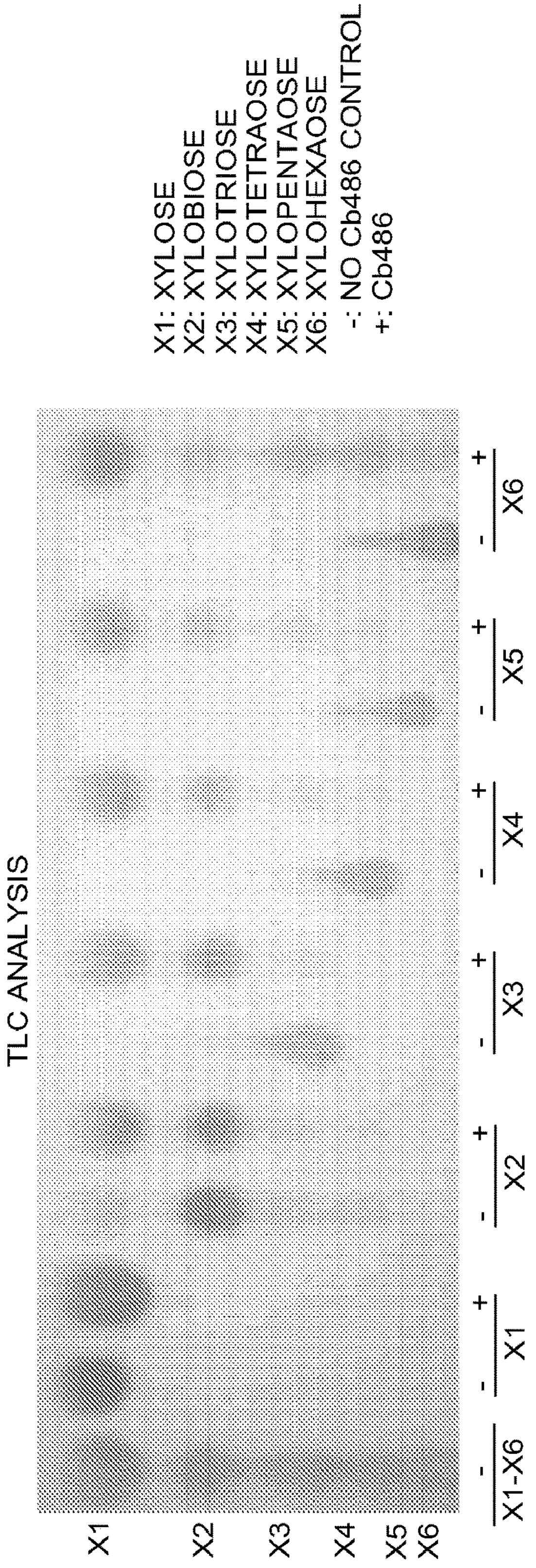

FIG. 54: TLC analysis of enzymatic activity of Cb486 on xylo-oligosaccharides ($X_2$-$X_6$). The following xylo-oligosaccharides ($X_2$-$X_6$) were tested: xylobiose, xylotriose, xylotetraose, xylopentaose and xylohexaose. This was done by an overnight hydrolysis of the xylo-oligosaccharides followed by resolving of the products with TLC. In each case, in the presence of Cb486, xylose and xylobiose were released. In the absence of Cb486, only minor amount of xylose was observed for xylobiose; no products of hydrolysis were released for other xylo-oligosaccharides. The results showed that this enzyme releases xylose and xylobiose from xylo-oligosaccharides (xylobiose, xylotriose, xylotetraose, xylopentaose and xylohexaose). X1, X2, X3, X4, X5, and X6 refer to xylose, xylobiose, xylotriose, xylotetraose, xylopentaose, and xylohexaose, respectively.

Figure 55:
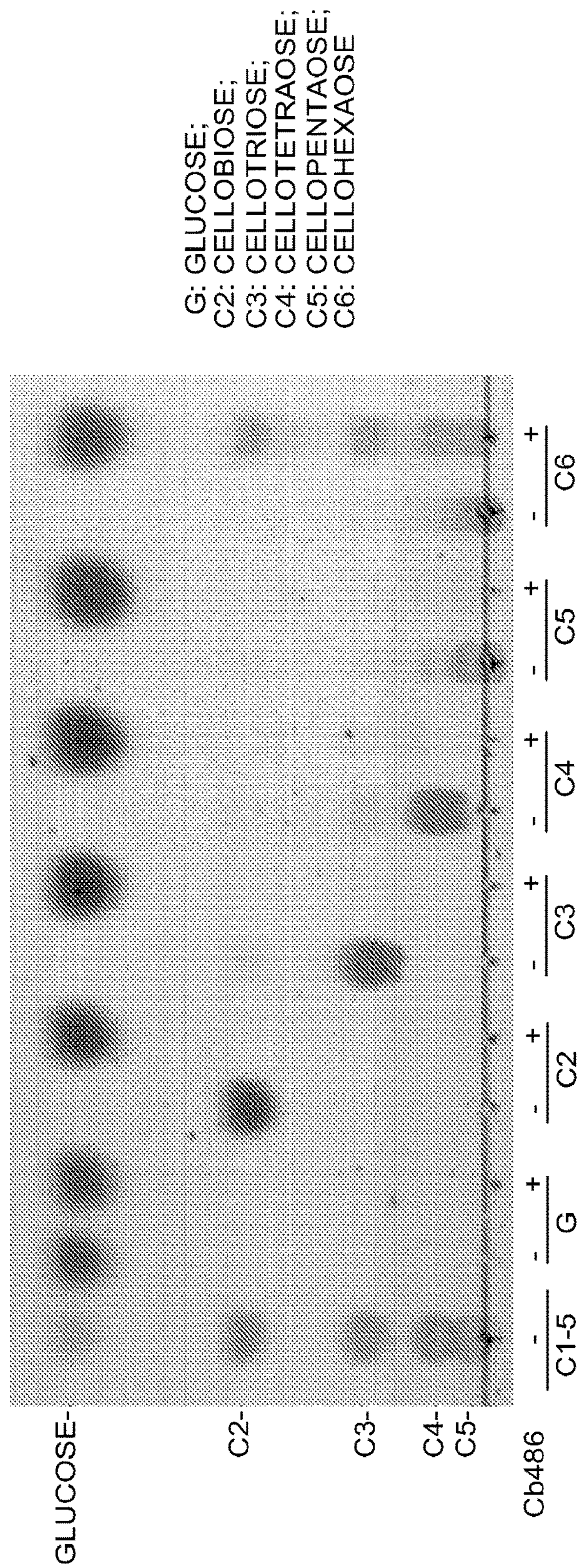

FIG. 55: TLC analysis of enzymatic activity of Cb486 on glucose and cellooligosaccharides. Glucose and five different cellooligosaccharides were used for the assay: cellobiose, cellotriose, cellotetraose, cellopentaose and cellohexaose. C2, C3, C4, and C5 refer to cellobiose, cellotriose, cellotetraose and cellopentaose, respectively.

Figure 56A:
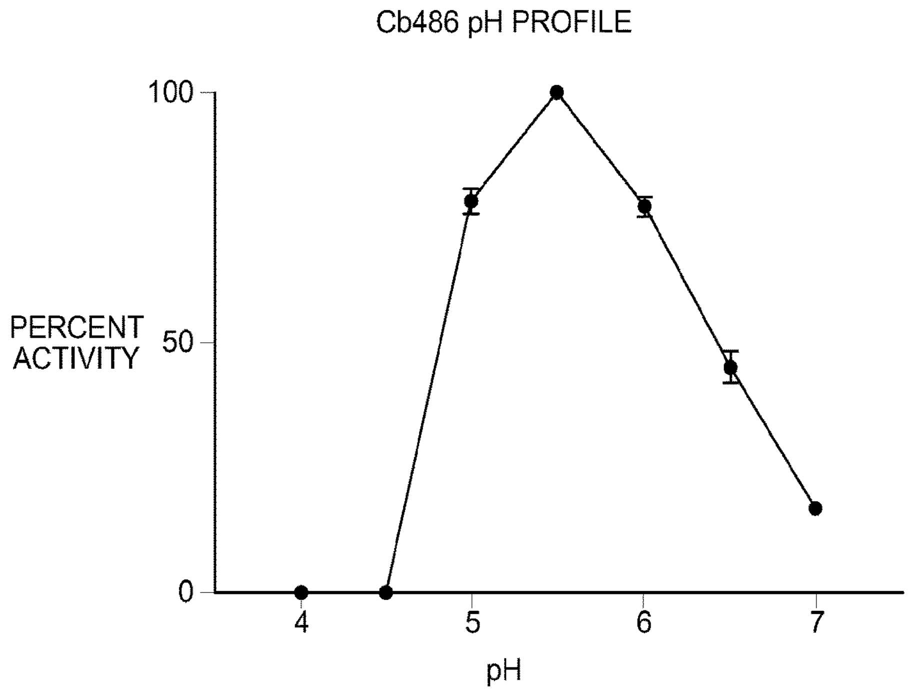
Figure 56B:
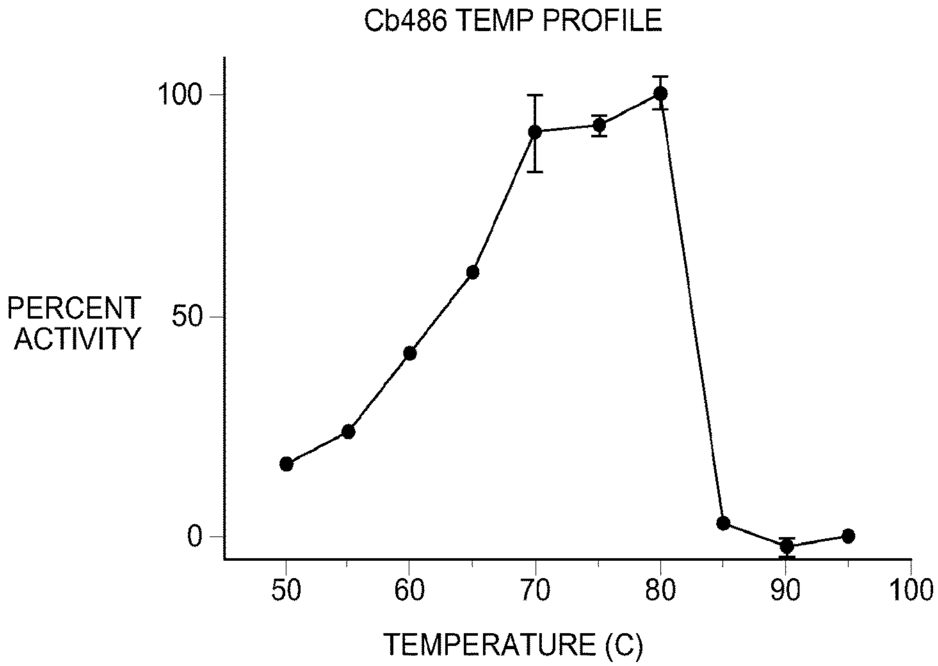

FIGS. 56A and 56B: FIGS. 56A and 56B show the pH and temperature profiles, respectively of the activity of Cb486. For these assays, the enzyme concentration of Cb486 was 10 nM. For pH profiling, the reactions were carried out in two buffers: 50 mM sodium citrate, 150 mM NaCl (pH 4.0-pH 6.0) and 50 mM $Na_2HPO_4$—$NaH_2PO_4$, 150 mM NaCl (pH 6.5-pH 8.0). The enzyme was incubated with 1 mM pNP-β-D-galactopyranoside in each buffer at a given pH at 75° C., and the activities in a 30 min assay were determined. For determination of optimal temperature, 10 nM of Cb486 was incubated with 1 mM pNP-β-D-galactopyranoside at pH 5.5 at different temperatures ranging from 40° C. to 95° C. with a 5° C. interval. The releasing of pNP was recorded by monitoring the increase of optical density at 410 nM with a Cary 300 UV-Visible spectrophotometer (Agilent, Santa Clara Calif.).

Figure 57A:
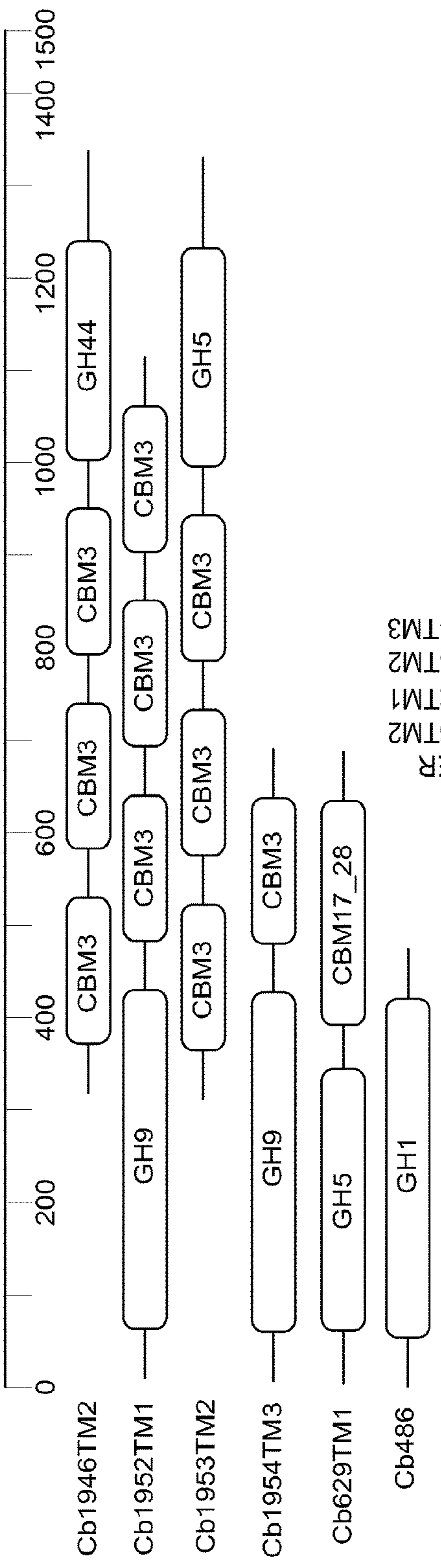
Figure 57B:
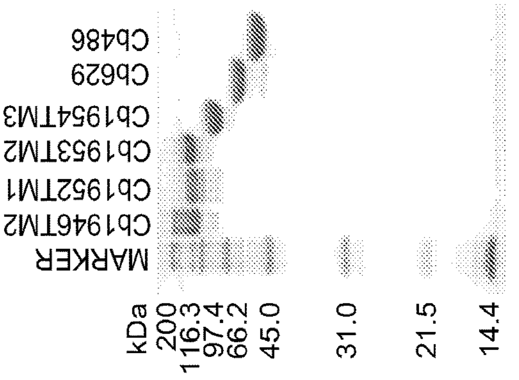

FIGS. 57A and 57B: Domain architecture (FIG. 57A) and SDS-polyacrylamide gels containing purified proteins (FIG.

57B) of a cellulase mixture composed of Cb629TM1, Cb486, Cb1946TM2, Cb1952TM1, Cb1953TM2, and Cb1954TM3 cellulases.

Figure 58:
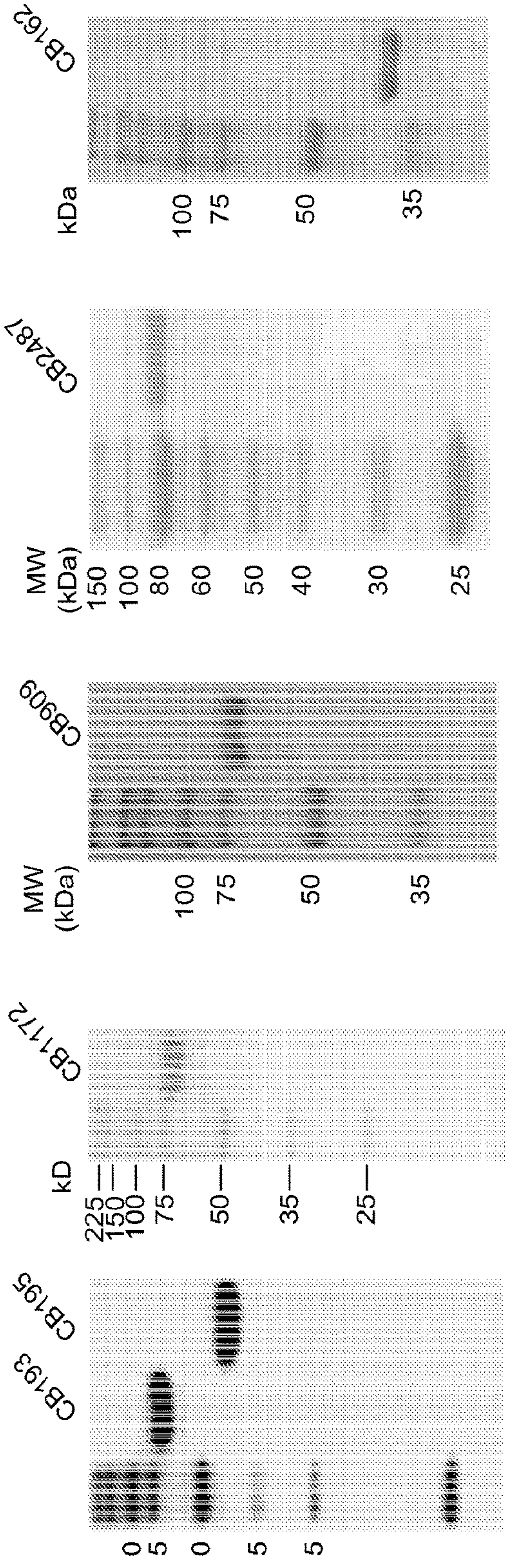

FIG. 58: SDS-polyacrylamide gels containing purified proteins of the hemicellulases Cb193, Cb195, Cb1172, Cb909, Cb2487, and Cb162.

Figure 59:
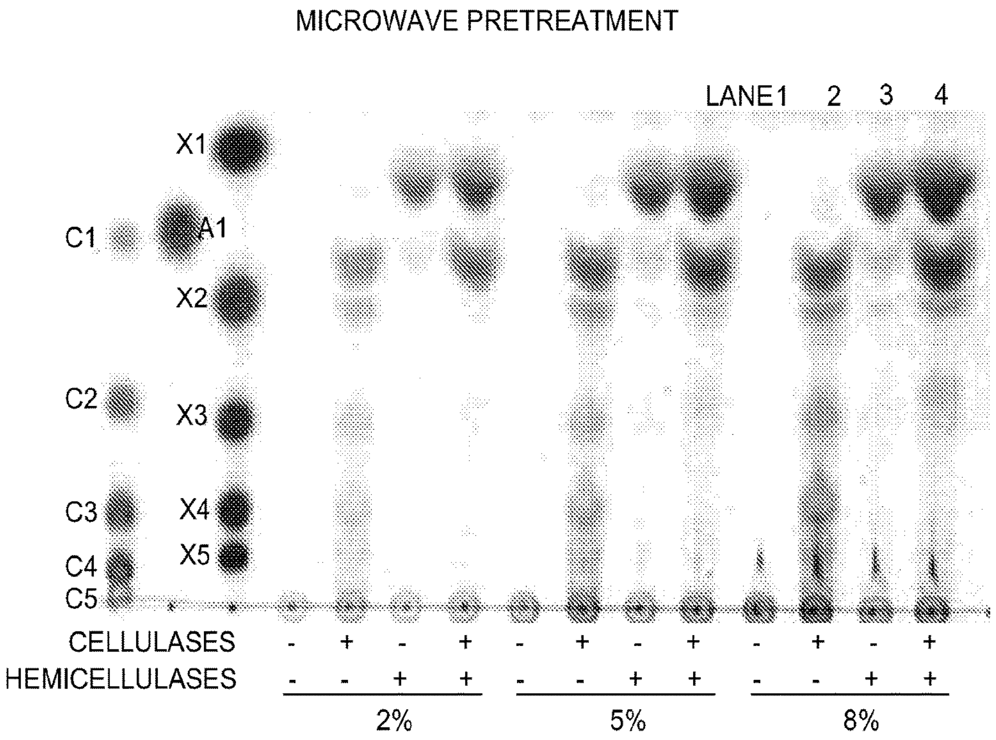
Figure 60:
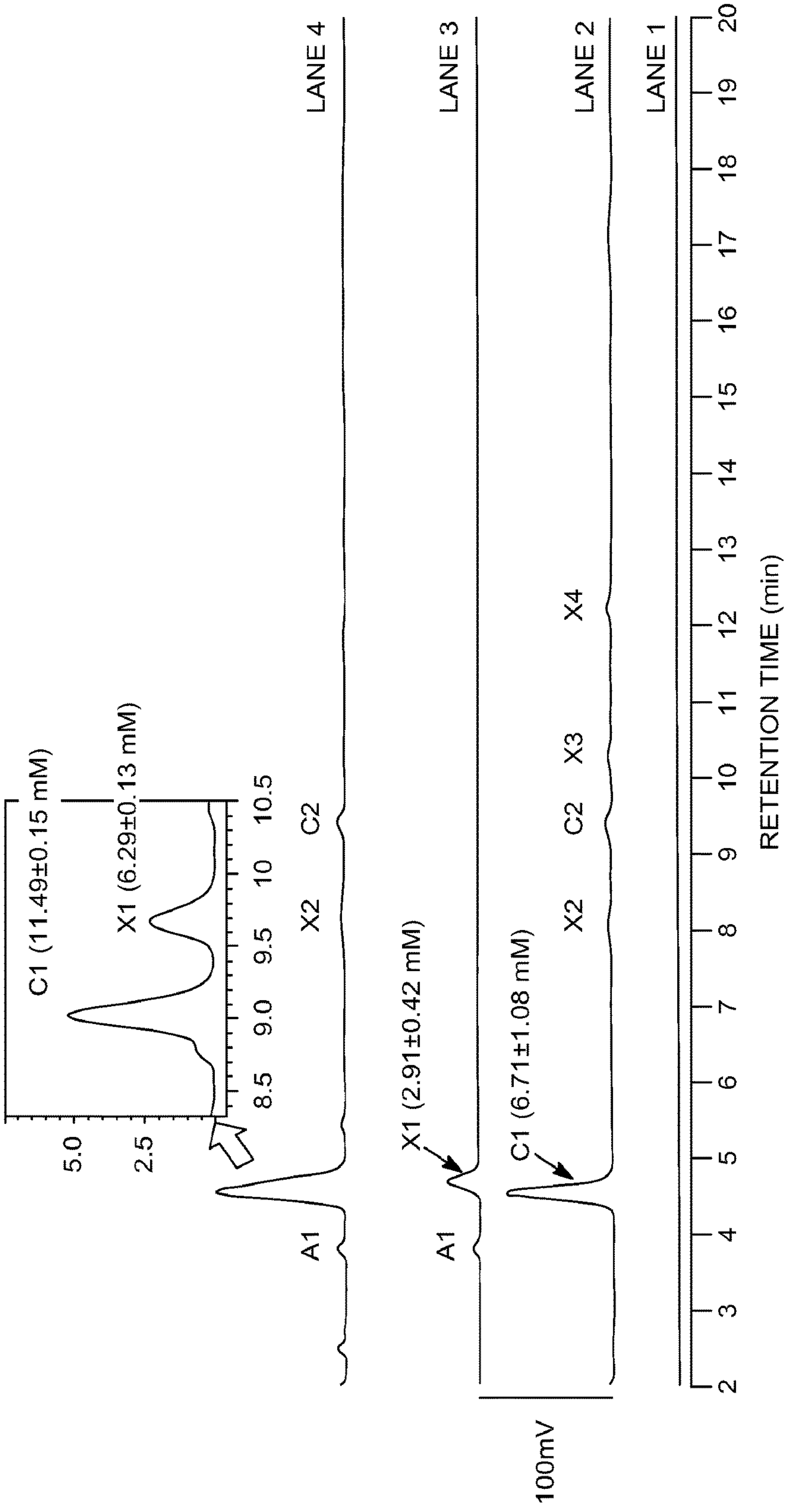

FIGS. 59 and 60: TLC (FIG. 59) and HPLC (FIG. 60) analysis of samples of microwave-pretreated *Miscanthus* that were treated with a cellulase mixture containing Cb629TM1, Cb486, Cb1946TM2, Cb1952TM1, Cb1953TM2, and Cb1954TM3 cellulases and/or a hemicellulase mixture containing Cb193, Cb195, Cb1172, Cb909, and Cb2487 hemicellulases. FIG. 59 shows analysis of assays with samples containing 2%, 5%, or 8% *Miscanthus*, and FIG. 60 shows analysis of an assay with a sample containing 8% *Miscanthus*. In FIG. 59, C1, C2, C3, C4, and C5 refer to glucose, cellobiose, cellotriose, cellotetraose and cellopentaose, respectively. X1, X2, X3, X4, and X5 refer to xylose, xylobiose, xylotriose, xylotetraose and xylopentaose, respectively. A1 refers to arabinose. For FIG. 60, the 8% substrate reaction samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.).

Figure 61:
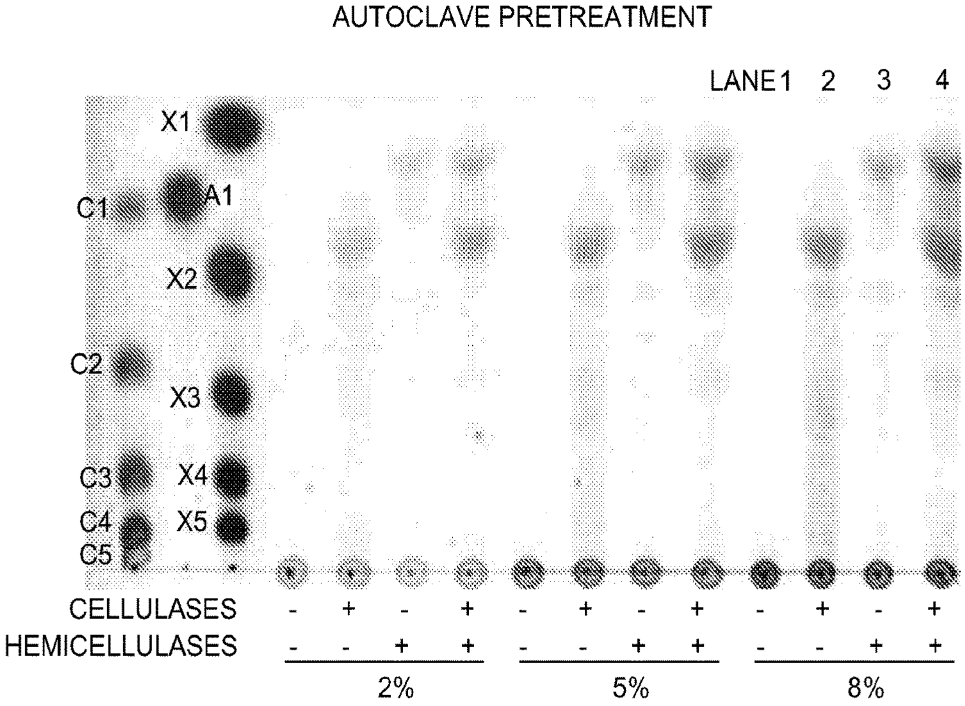
Figure 62:
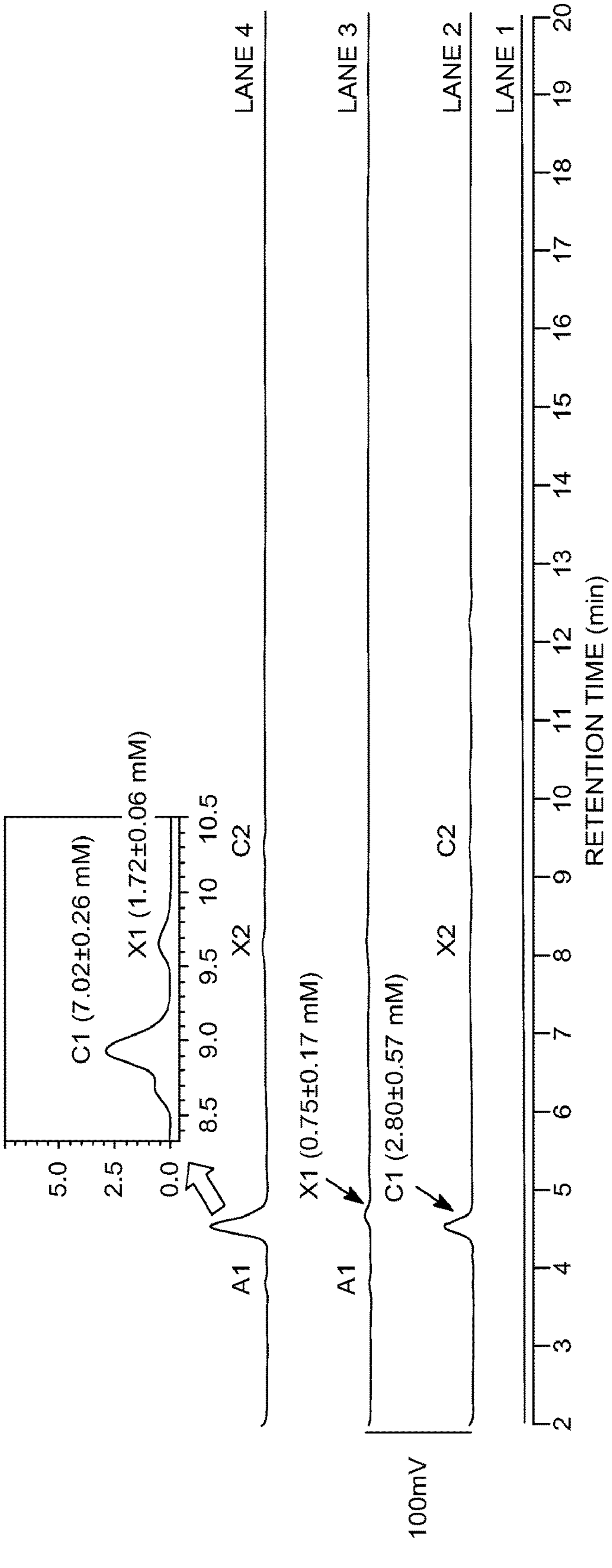

FIGS. 61 and 62: TLC (FIG. 61) and HPLC (FIG. 62) analysis of samples of autoclave-pretreated *Miscanthus* that were treated with a cellulase mixture containing Cb629TM1, Cb486, Cb1946TM2, Cb1952TM1, Cb1953TM2, and Cb1954TM3 cellulases and/or a hemicellulase mixture containing Cb193, Cb195, Cb1172, Cb909, and Cb2487 hemicellulases. FIG. 61 shows analysis of assays with samples containing 2%, 5%, or 8% *Miscanthus*, and FIG. 62 shows analysis of an assay with a sample containing 8% *Miscanthus*. In FIG. 61, C1, C2, C3, C4, and C5 refer to glucose, cellobiose, cellotriose, cellotetraose and cellopentaose, respectively. X1, X2, X3, X4, and X5 refer to xylose, xylobiose, xylotriose, xylotetraose and xylopentaose, respectively. For FIG. 62, the 8% substrate reaction samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.).

Figure 63:
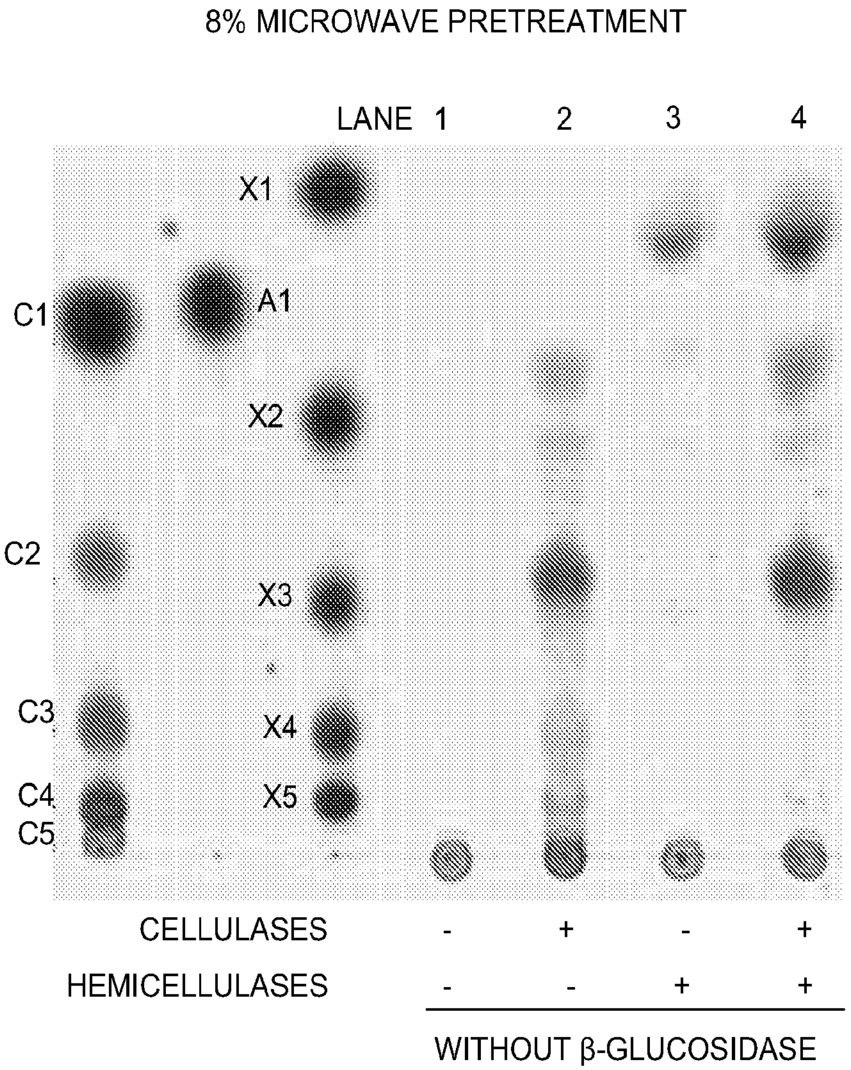
Figure 64:
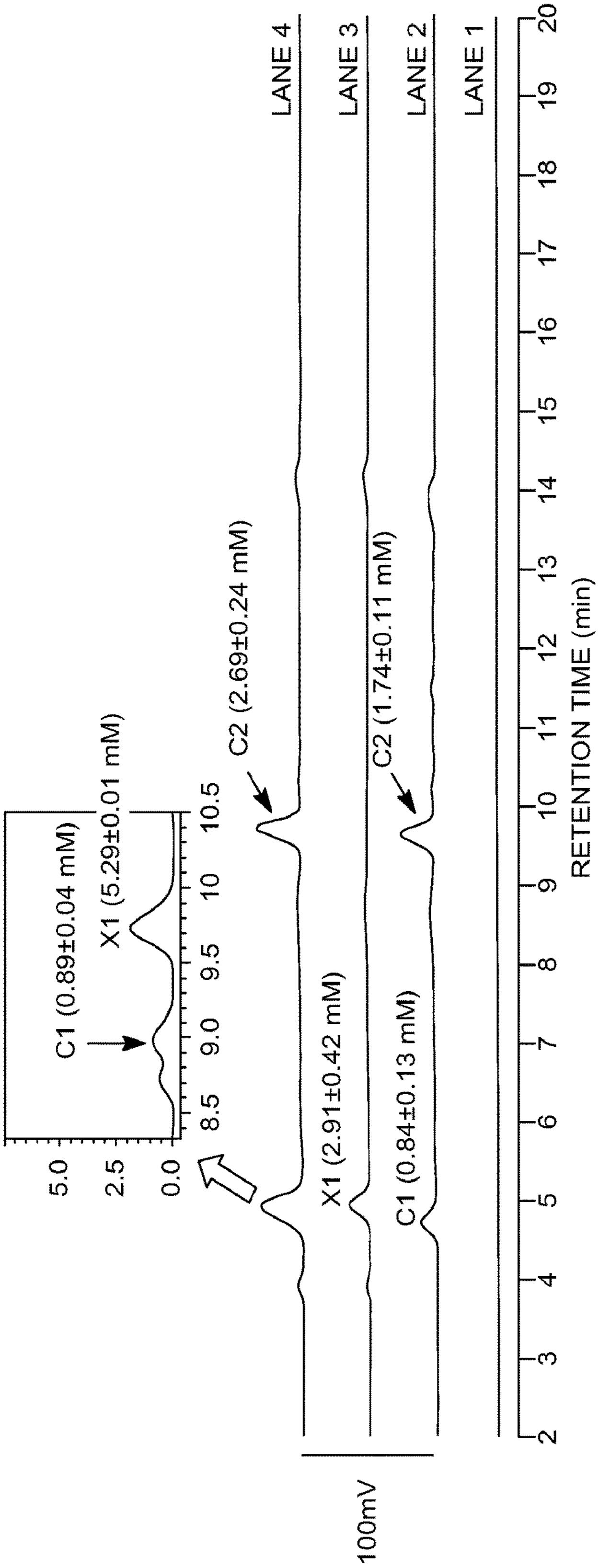

FIGS. 63 and 64: TLC (FIG. 63) and HPLC (FIG. 64) analysis of samples of microwave-pretreated 8% *Miscanthus* samples that were treated with a cellulase mixture containing Cb629TM1, Cb1946TM2, Cb1952TM1, Cb1953TM2, and Cb1954TM3 cellulases (the mixture lacks the β-glucosidase Cb486), and/or a hemicellulase mixture containing Cb193, Cb195, Cb1172, Cb909, and Cb2487 hemicellulases. In FIG. 63, C1, C2, C3, C4, and C5 refer to glucose, cellobiose, cellotriose, cellotetraose and cellopentaose, respectively. X1, X2, X3, X4, and X5 refer to xylose, xylobiose, xylotriose, xylotetraose and xylopentaose, respectively. For FIG. 64, the reaction samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.).

Figure 65:
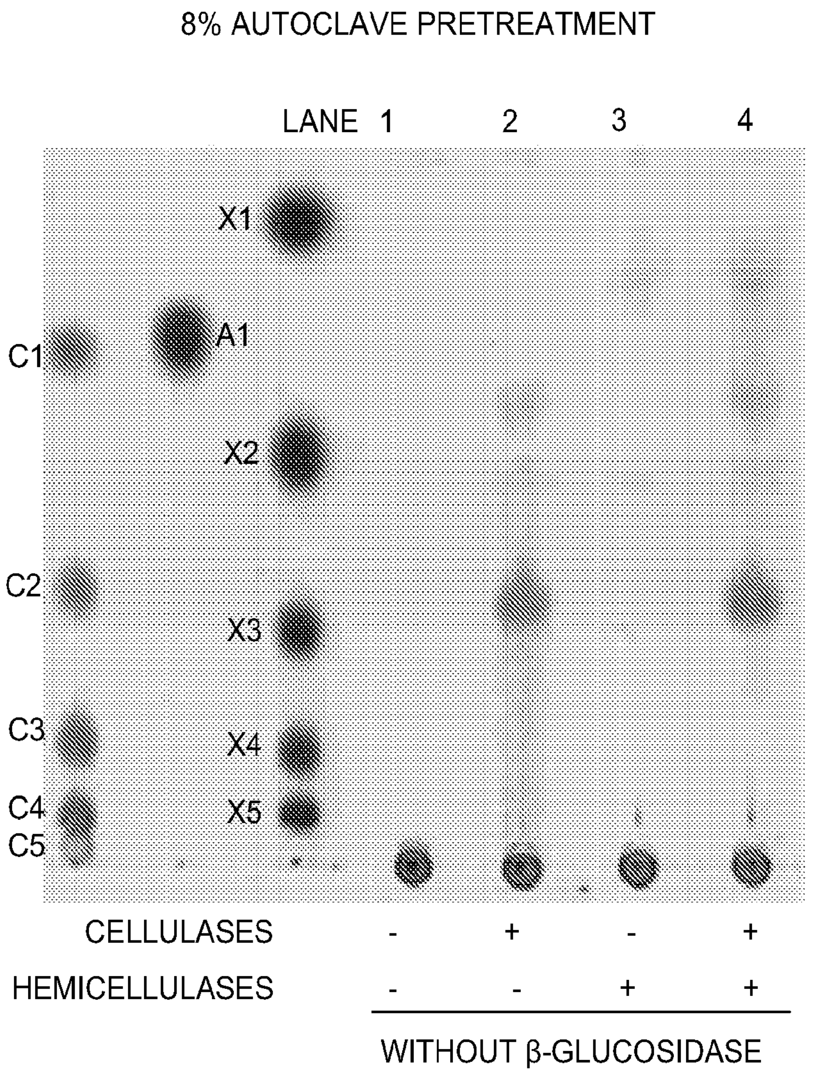
Figure 66:
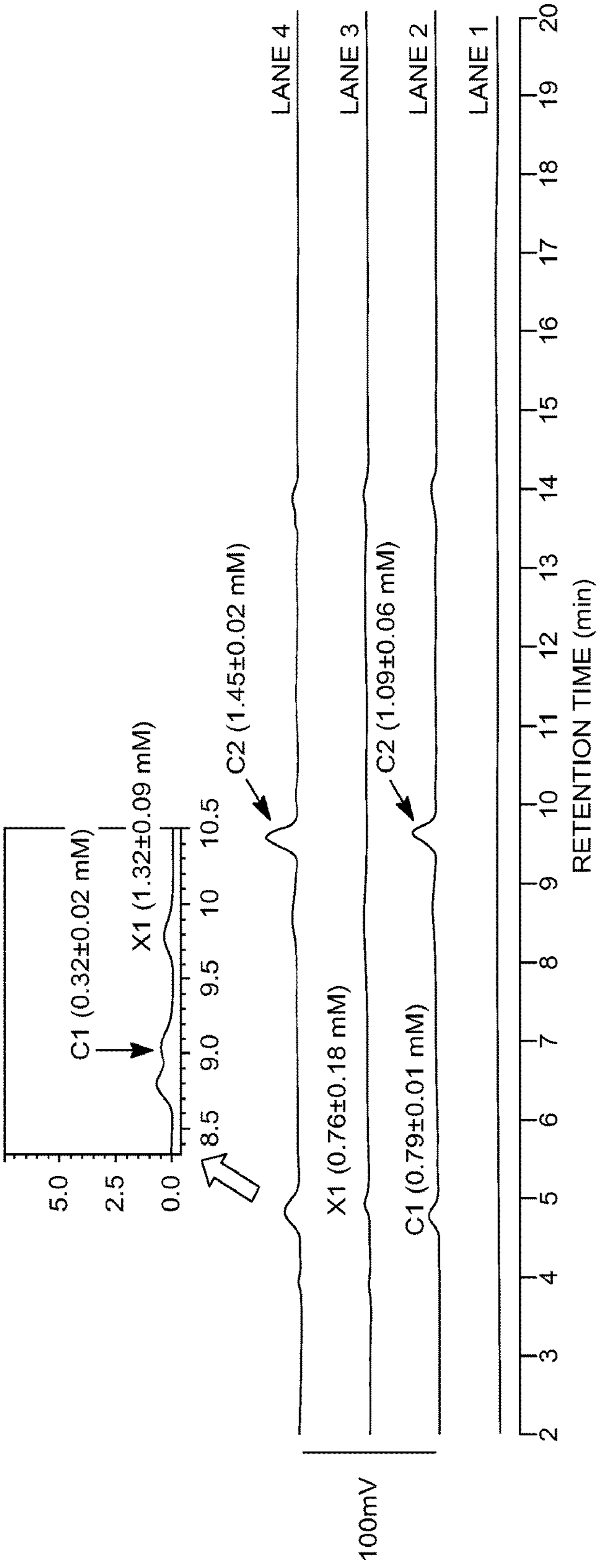

FIGS. 65 and 66: TLC (FIG. 65) and HPLC (FIG. 66) analysis of samples of autoclave-pretreated 8% *Miscanthus* samples that were treated with a cellulase mixture containing Cb629TM1, Cb1946TM2, Cb1952TM1, Cb1953TM2, and Cb1954TM3 cellulases (the mixture lacks the β-glucosidase Cb486), and/or a hemicellulase mixture containing Cb193, Cb195, Cb1172, Cb909, and Cb2487 hemicellulases. In FIG. 65, C1, C2, C3, C4, and C5 refer to glucose, cellobiose, cellotriose, cellotetraose and cellopentaose, respectively. X1, X2, X3, X4, and X5 refer to xylose, xylobiose, xylotriose, xylotetraose and xylopentaose, respectively. For FIG. 66, the reaction samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.).

Figure 67A:
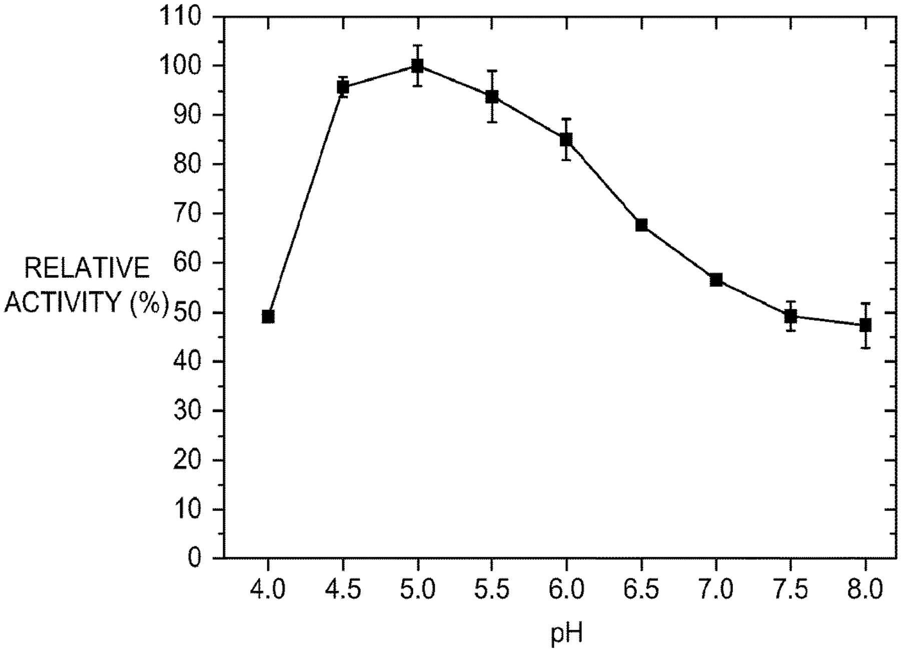
Figure 67B:
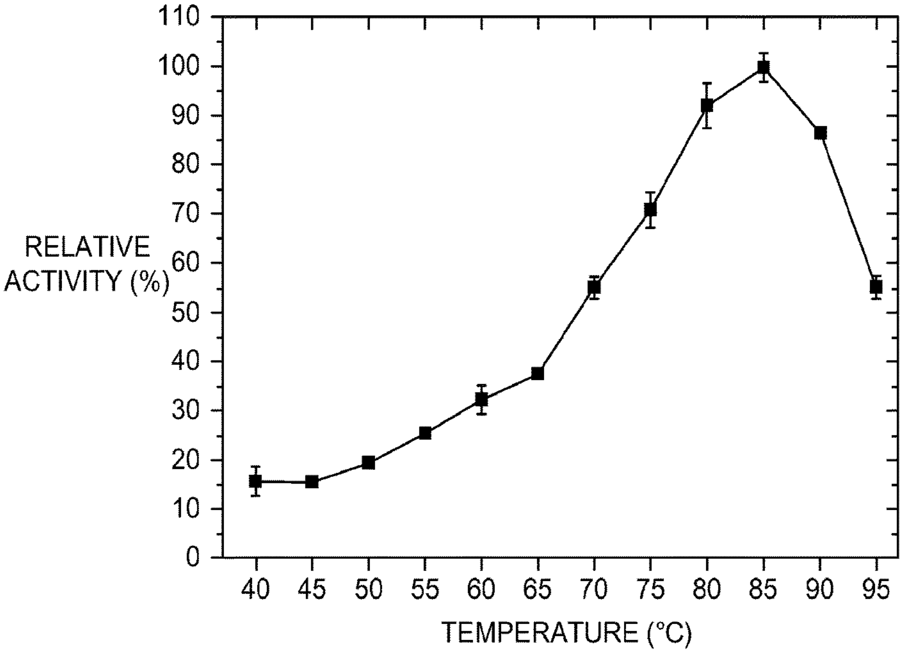

FIGS. 67A and 67B show the pH and temperature profiles, respectively of the activity of Cb1952TM1. For pH profiling, the reactions were carried out in two buffers: 50 mM sodium citrate, 150 mM NaCl (pH 4.0-pH 6.0) and 50 mM $Na_2HPO_4$—$NaH_2PO_4$, 150 mM NaCl (pH 6.5-pH 8.0). The enzyme concentration of Cb1952TM1 was 0.5 μM. The enzyme was incubated with 2.5 mg/ml PASC in each buffer at a given pH at 75° C., and the activities in a 10 min assay were determined. The reducing sugars released were measured using the pHBAH assay. For determination of optimal temperature, 0.5 μM of Cb1952TM1 enzyme was incubated with 2.5 mg/ml PASC at pH 5.5 at different temperatures ranging from 40° C. to 95° C. with a 5° C. interval.

Figure 68A:
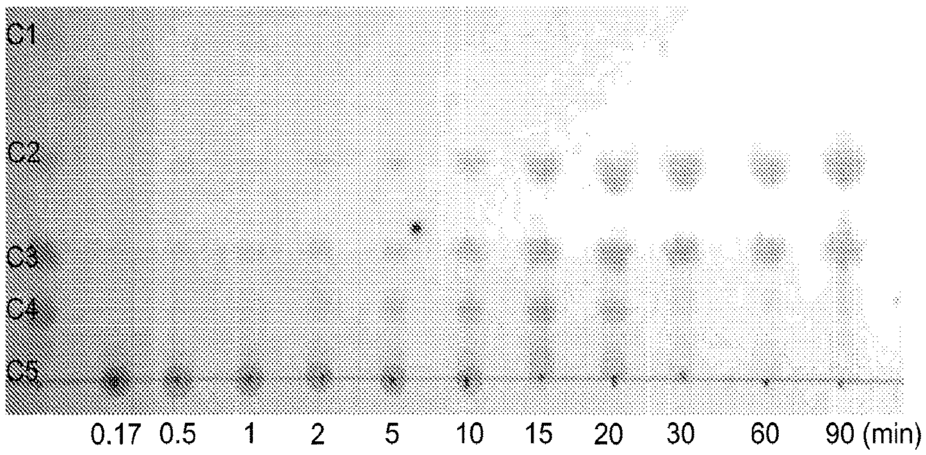
Figure 68B:
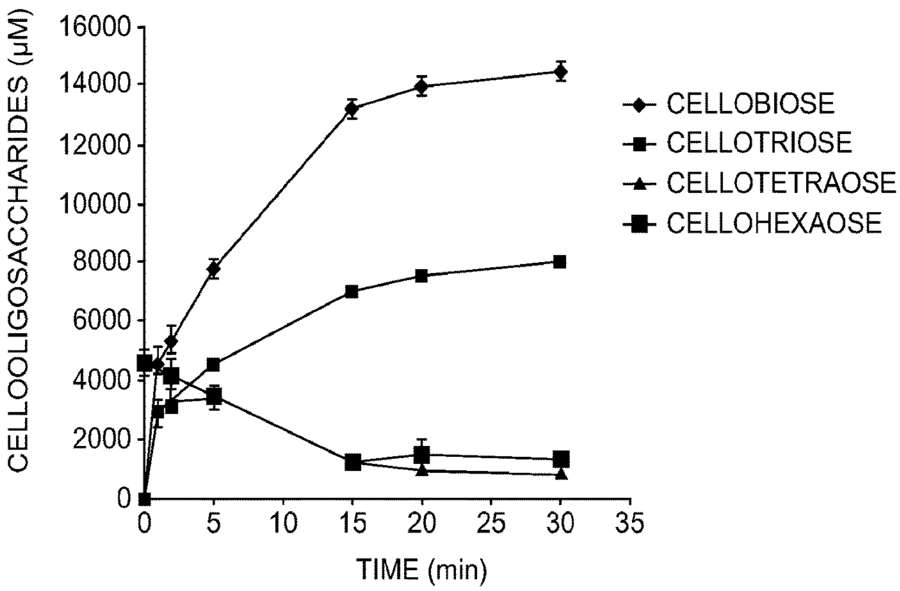

FIGS. 68A and 68B: Cleavage products resulting from the incubation of Cb1953TM2 with cellohexaose. FIG. 68A: TLC analysis of reaction products; FIG. 68B: HPLC analysis of reaction products. The data indicates that Cb1953TM2 hydrolyzes cellohexaose randomly.

Figure 69A:
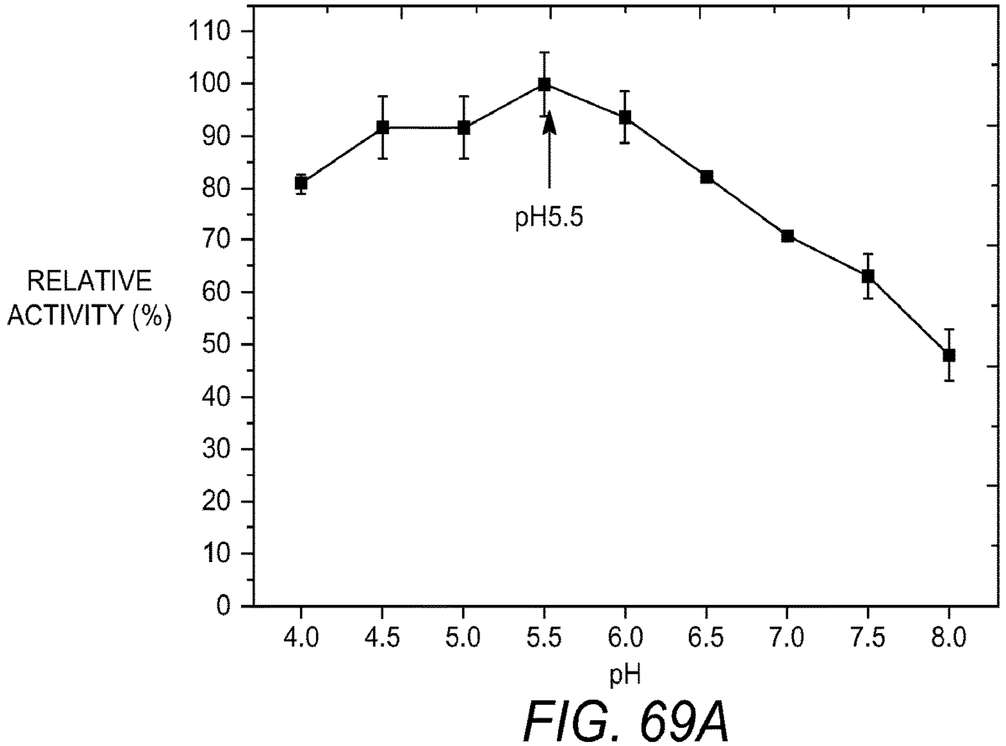
Figure 69B:
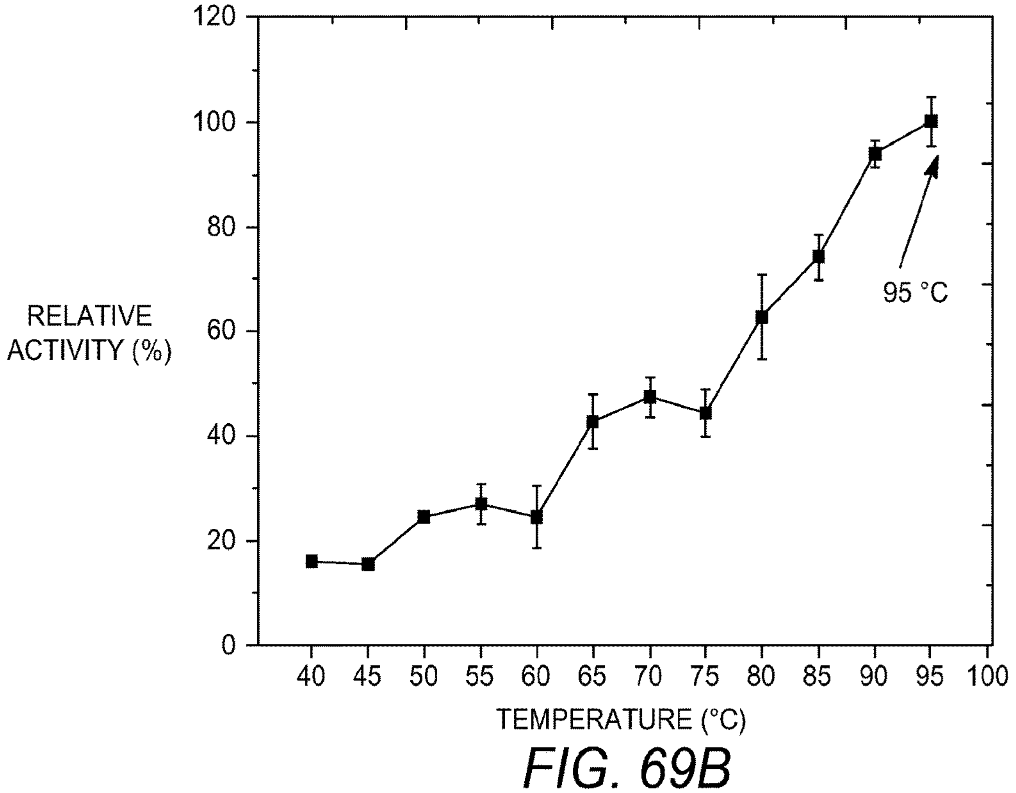

FIGS. 69A and 69B show the pH and temperature profiles, respectively of the activity of Cb1954TM3.

Figure 70A:
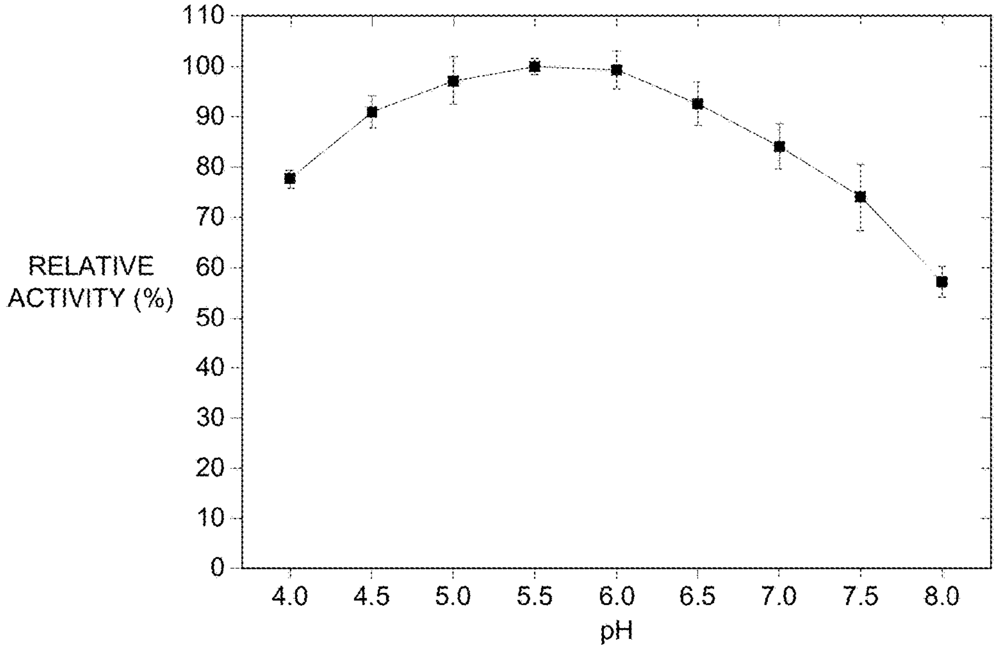
Figure 70B:
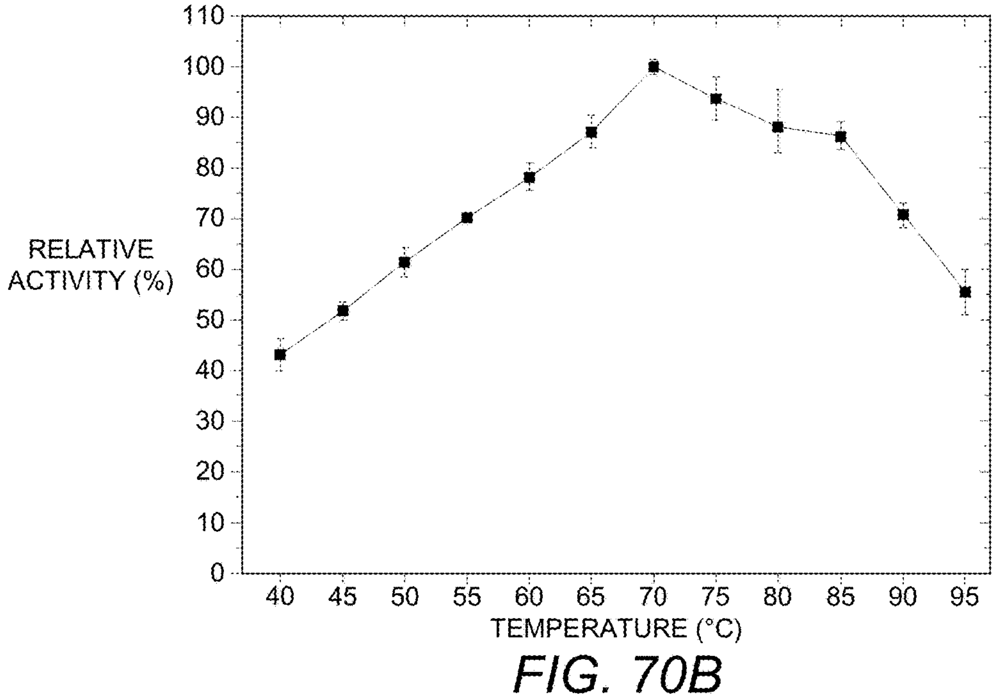

FIGS. 70A and 70B show the pH and temperature profiles, respectively of the activity of Cb629TM1.

Figure 71:
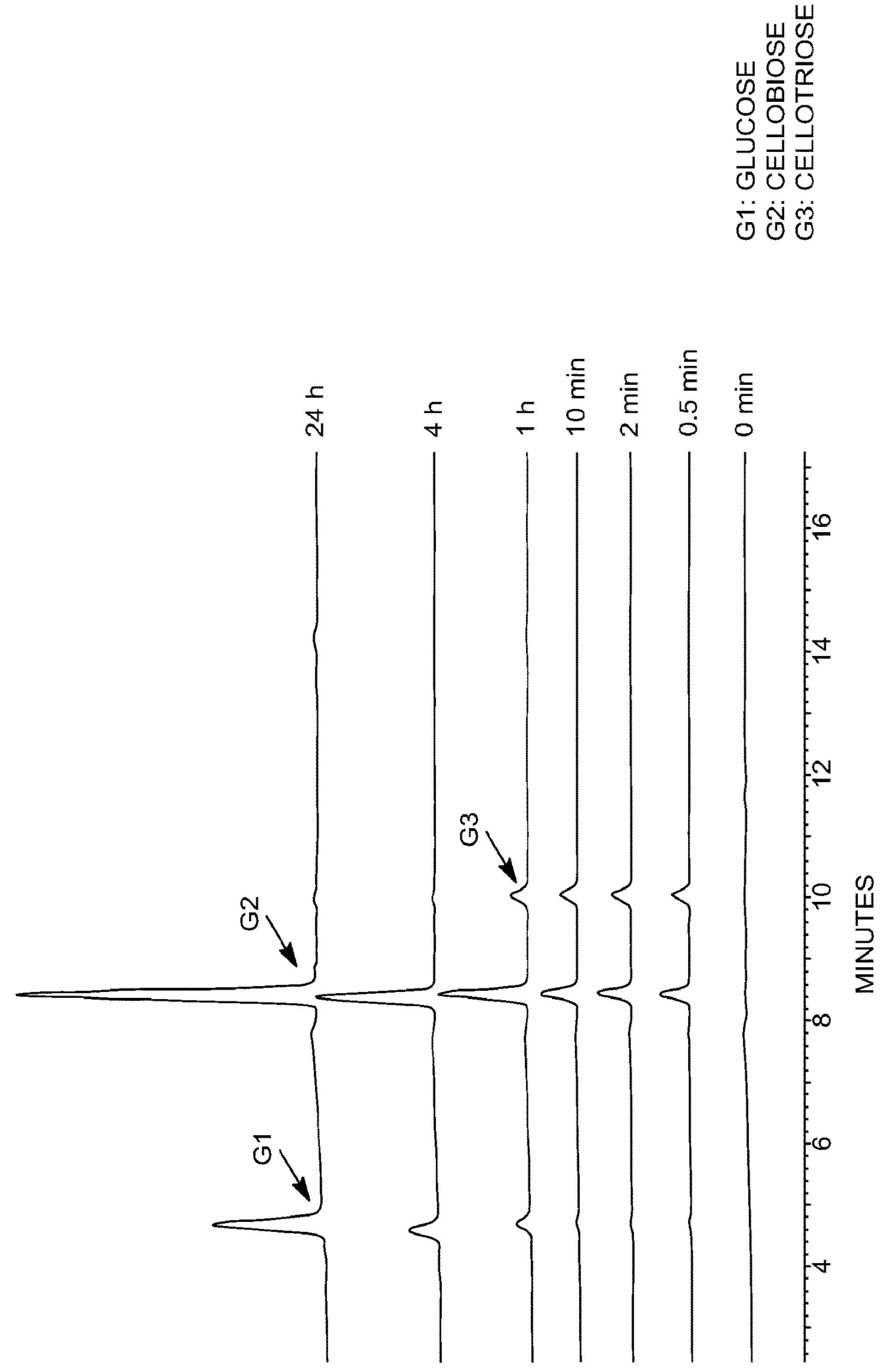

FIG. 71: HPLC analysis of time course of enzymatic activity of Cb629TM1 on PASC. For analysis of the products of hydrolysis, the samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.). For the analysis, glucose, cellobiose, and cellotriose were used as standards.

Figure 72:
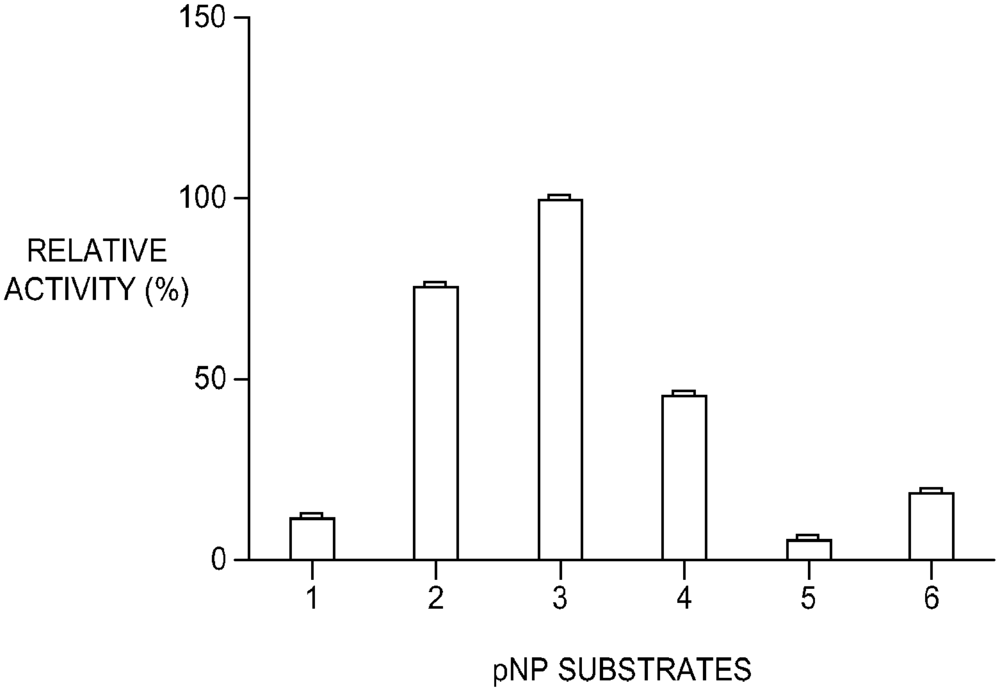

FIG. 72: Substrate specificity analysis of Cb486. 50 nM of Cb486 was incubated at 75° C. in its optimal buffer (50 mM sodium citrate, 150 mM NaCl, pH5.5) with 1 mM each of pNP-α-L-arabinopyranoside, pNP-β-D-fucopyranoside, pNP-β-D-galactopyranoside, pNP-β-D-glucopyranoside, pNP-βD-xylopyranoside, and pNP-β-D-cellobiose, respectively, for 30 min. The release of pNP was recorded by monitoring the increase in optical density at 410 nM with a Cary 300 UV-Visible spectrophotometer (Agilent, Santa Clara Calif.).

Figure 73A:
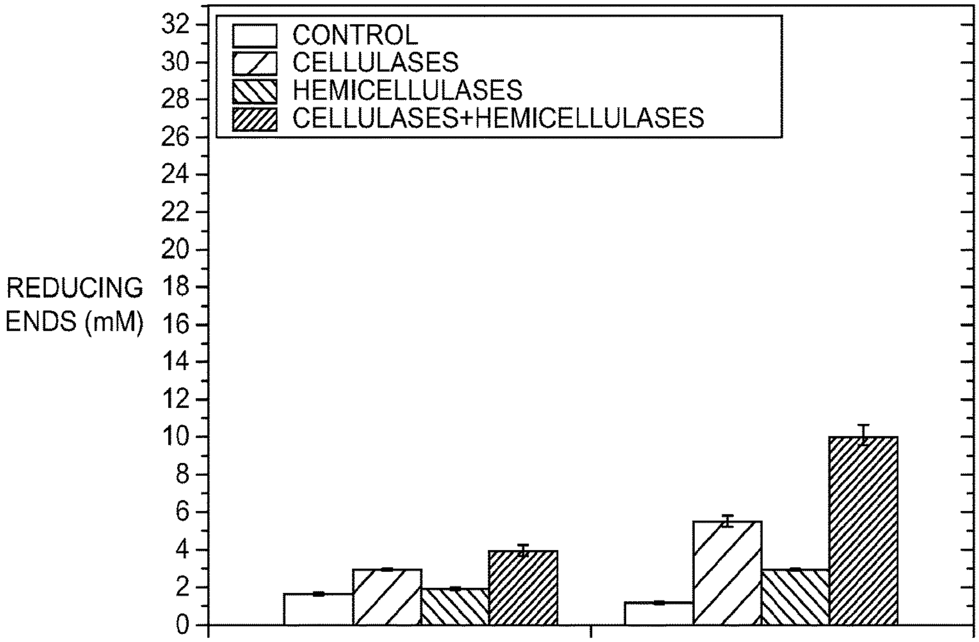
Figure 73B:
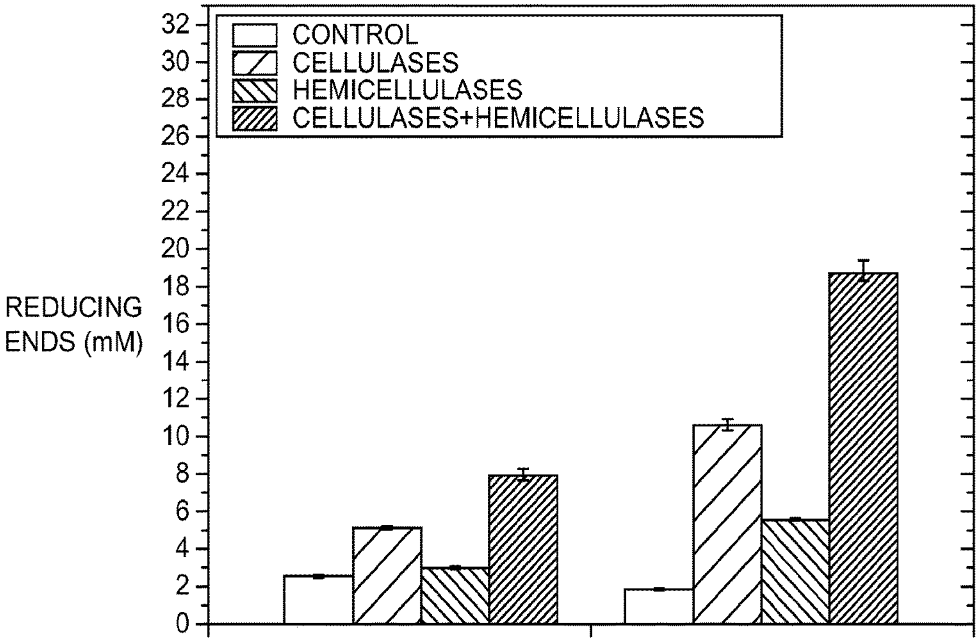
Figure 73C:
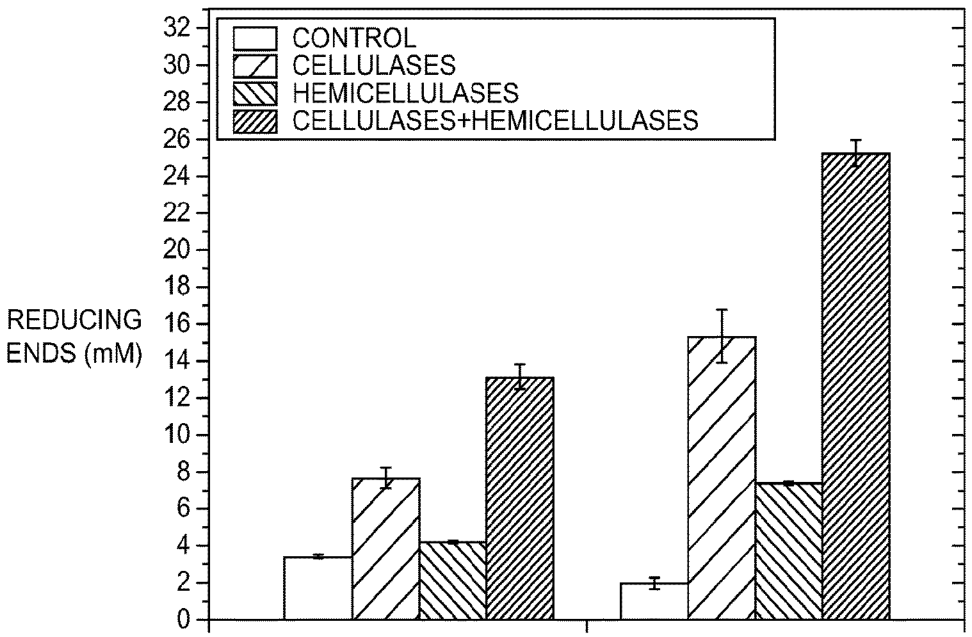
Figure 73D:
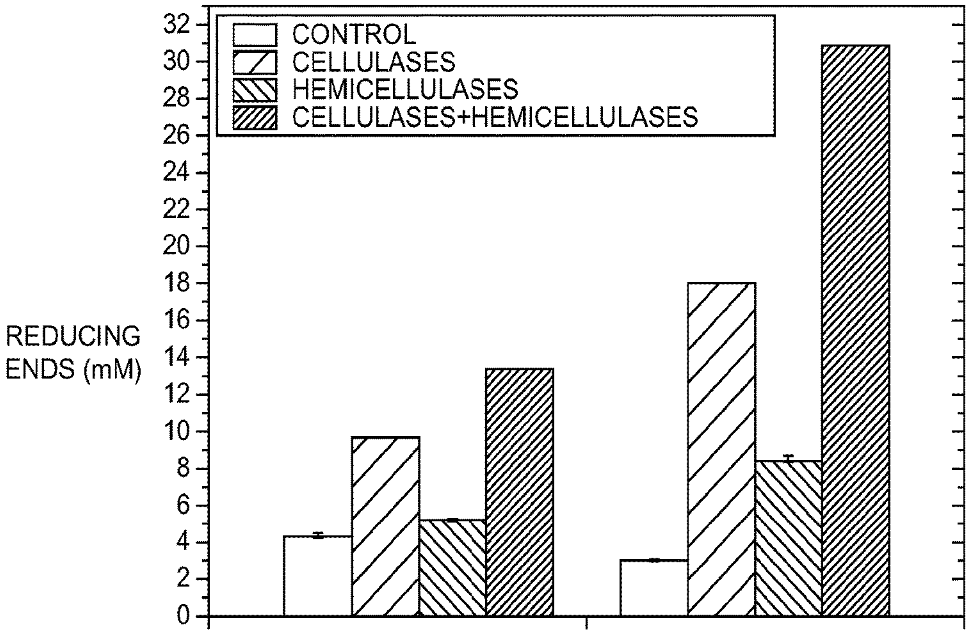

FIGS. 73A to 73D: Hydrolysis of treated *miscanthus* with cellulase and/or hemicellulase mixtures. FIG. 73A: 0.5 μM enzyme; 2% substrate; FIG. 73B: 0.5 μM enzyme; 5% substrate; FIG. 73C: 0.5 μM enzyme; 8% substrate; FIG. 73D: 1.0 μM enzyme; 10% substrate. Different concentrations (2%, 5%, and 8%) of *Miscanthus* pre-treated using two different methods (autoclaving or microwaving) were incubated with either the cellulase mix (containing 0.5 μM each of Cb1946TM2, Cb1952TM1, Cb1953TM2, Cb1954TM3, Cb629TM1, and Cb486) or the hemicellulase mix (containing 0.5 μM each of Cb193, Cb195, Cb1172, Cb2487, and Cb909), or both enzyme mixtures in a total volume of 500 μl at 75° C. with an end-over-end shaking manner for 15 hours. Further, increased concentration (10%) of pretreated *Miscanthus* of both pretreatment types was incubated with an increased enzyme concentration of 1.0 μM at 75° C. with an end-over-end shaking manner for 15 hours. The reducing ends were measured using the pHBAH method.

Figure 74:
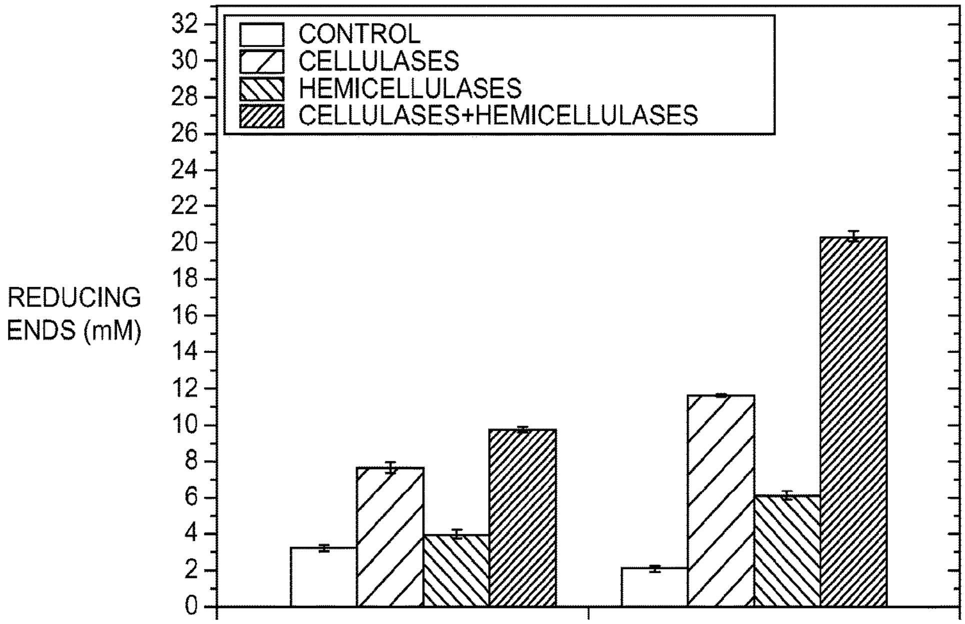

FIG. 74: Hydrolysis of treated *miscanthus* with enzyme mixtures lacking Cb486. For these assays, reaction mixtures with 0.5 μM enzyme and 8% substrate were used. Pretreated *Miscanthus* (8%) using two different methods (autoclaving or microwaving) was incubated with either the cellulase mix (containing 0.5 μM each of Cb1946TM2, Cb1952TM1, Cb1953TM2, Cb1954TM3, and Cb629TM1, but without Cb486) or the hemicellulase mix (containing 0.5 μM each of Cb193, Cb195, Cb1172, Cb2487, and Cb909), or both enzyme mixtures in a total volume of 500 μl at 75° C. with an end-over-end shaking manner for 15 hours. The reducing ends were measured using pHBAH method.

Figure 75A:
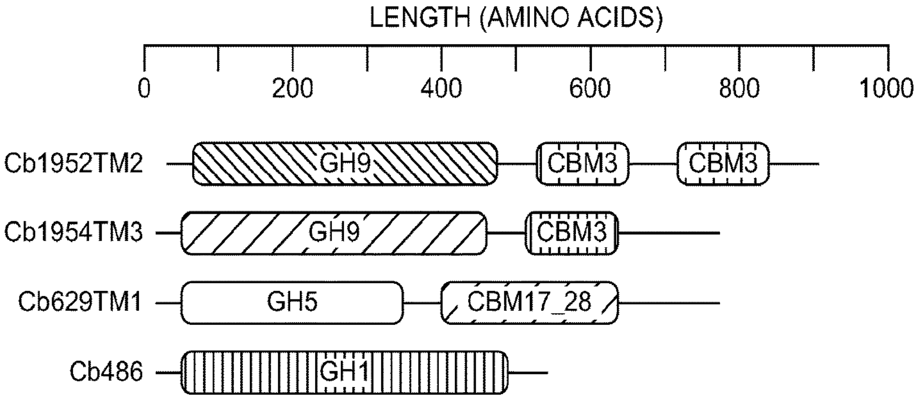
Figure 75B:
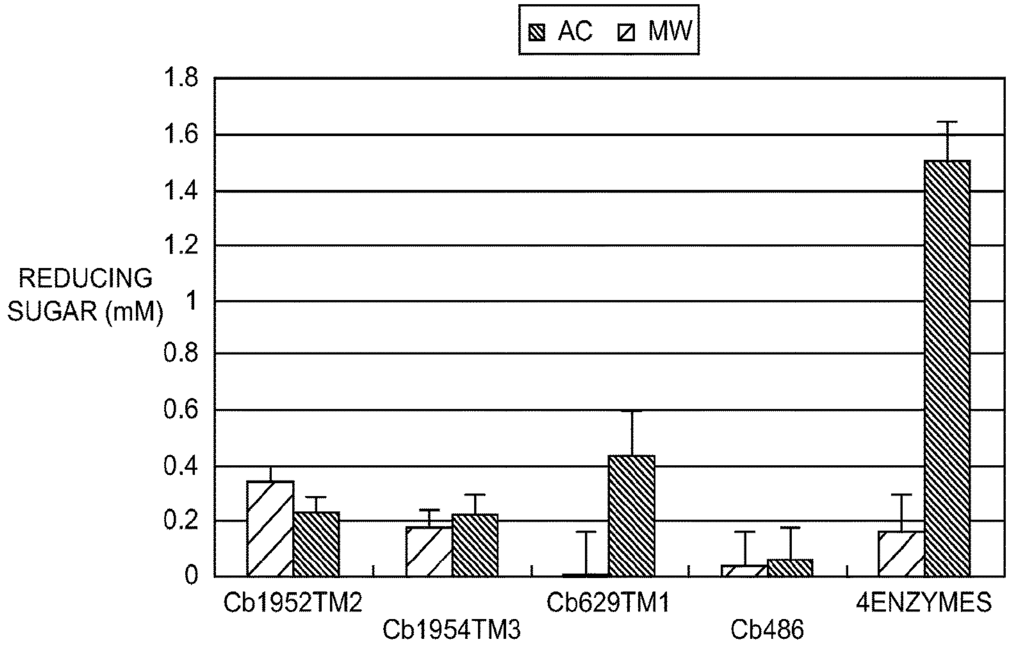

FIGS. 75A and 75B: FIG. 75A: Domain architecture of Cb1952TM2, Cb1954TM3, Cb629TM1, and Cb486 polypeptides. FIG. 75B: Analysis of samples of pretreated *Miscanthus* (AC=autoclaved; MW=microwaved) that were treated with Cb1952TM2, Cb1954TM3, Cb629TM1, Cb486, or a mixture containing Cb1952TM2, Cb1954TM3, Cb629TM1, and Cb486 cellulases. Pre-treated *Miscanthus*, using two different methods (autoclaving or microwaving), at a final concentration of 2% was incubated with an individual cellulase (Cb1952TM2, Cb1954TM3, Cb629TM1, or Cb486, 0.5 μM each) or a mixture containing all four cellulases in a total volume of 500 μl at 75° C. with an end-over-end shaking manner for 15 hours. The reducing ends were measured using pHBAH method.

Figure 76:
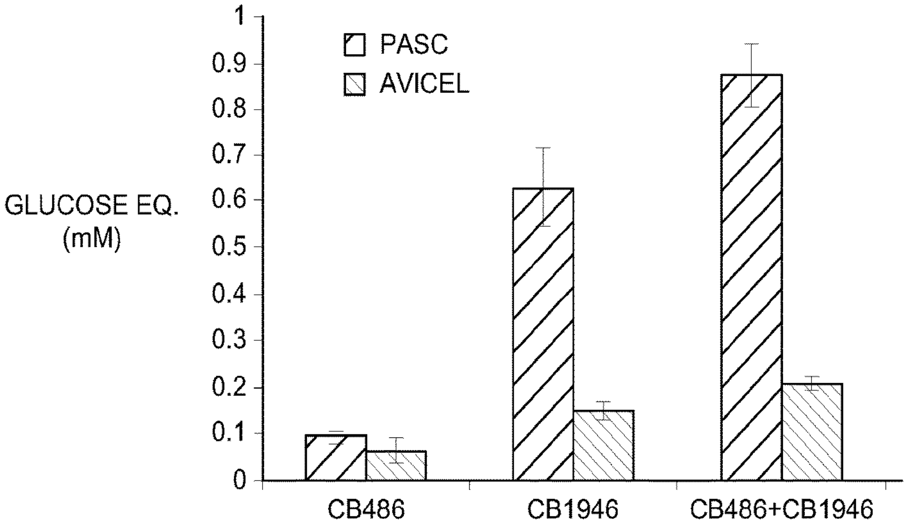

FIG. 76: Reducing sugar assay with Cb1946WT, Cb486, or a mixture containing Cb1946WT and Cb486 cellulases. The reactions were carried out using 0.5 μM of Cb1946WT, Cb486 or both enzymes in a phosphate buffer (50 mM sodium phosphate, 150 mM NaCl, pH 6.5) at a total volume of 500 μl in a 16-hours incubation with an end-over-end shaking manner at 75° C.

Figure 77A:
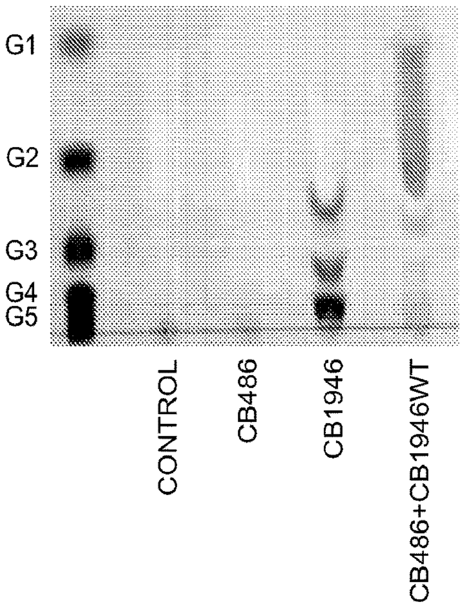
Figure 77B:
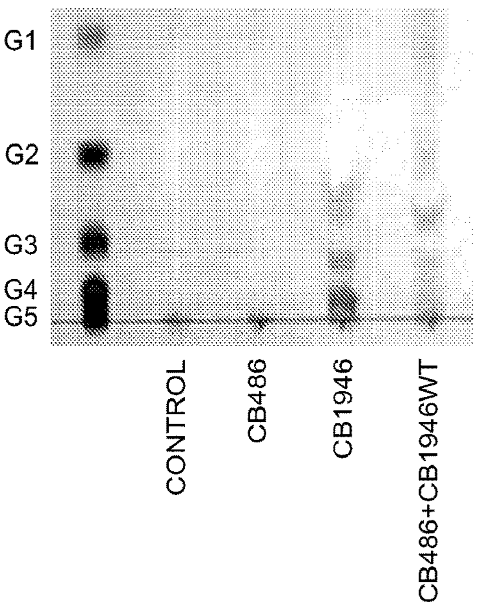

FIGS. 77A and 77B: Analysis of PASC (FIG. 77A) or Avicel (FIG. 77B) samples treated with Cb1946WT, Cb486, or a mixture containing Cb1946WT and Cb486 cellulases. The reactions were carried out using 0.5 μM of either Cb1946WT or Cb486 or both enzymes in a phosphate buffer (50 mM sodium phosphate, 150 mM NaCl, pH 6.5) in a total volume of 500 μl in a 16-hours incubation with an end-over-end shaking manner at 75° C. Seven μl of the hydrolysis products were applied to TLC analysis.

Figure 78A:
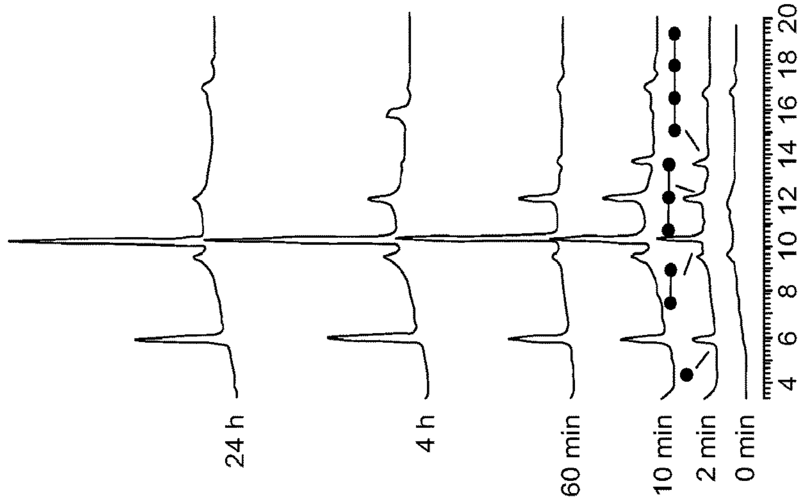
Figure 78B:
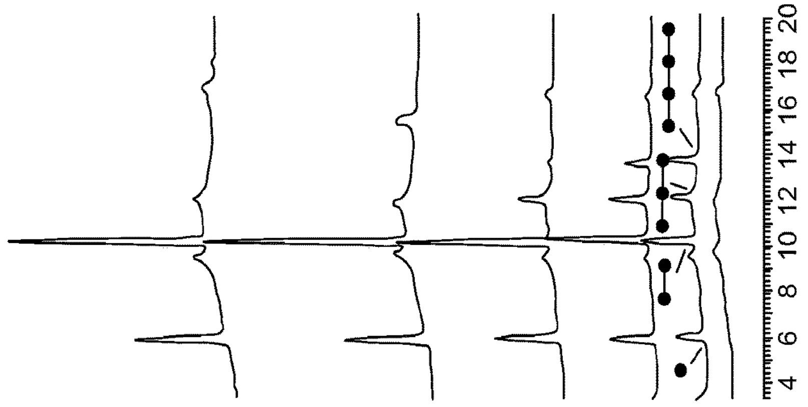
Figure 78C:
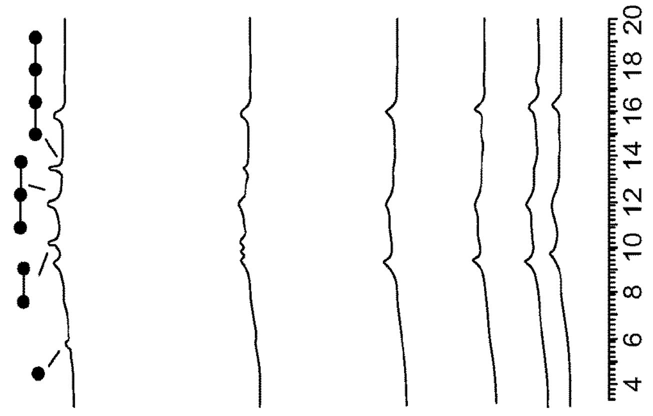

FIGS. 78A to 78C: Time course hydrolysis of PASC by Cb1952 WT (FIG. 78A), TM1 (FIG. 78B), and TM5 (FIG. 78C). Two point five mg/ml PASC was incubated with 0.5 μM Cb1952 WT, TM1, and TM5 at 75° C. At different time intervals (0 min, 2 min, 10 min, 60 min, 4 h, and 24 h), samples were taken out and applied to HPAEC-PAD analysis.

FIG. 79: Amino acid sequence alignment of the GH9 domain of Cb1952 (SEQ ID NO: 150) with those of CloceCel9G (*Clostridium cellulolyticum* Cel9G, GenBank accession number: AAA73868, (SEQ ID NO: 151)) (26) and ThefuCel9A (*Thermobifida fusca* Cel9A, GenBank accession number: AAB42155, (SEQ ID NO: 152)) (34). CloceCel9G (non-processive) and ThefuCel9A (processive) represent the two types of family 9 theme B1 endoglucanases whose enzyme-cello-oligosaccharide complex structures have been resolved. The asterisks indicate the identical or similar amino acid residues within the three sequences. The filled triangles indicate non-conserved residues. The numbers under a specific amino acid residue indicate the subsites of the cello-oligosaccharides interacting with this amino acid residue based on the CloceCel9G and ThefuCel9A enzyme-substrate complex structures.

Figure 80A:
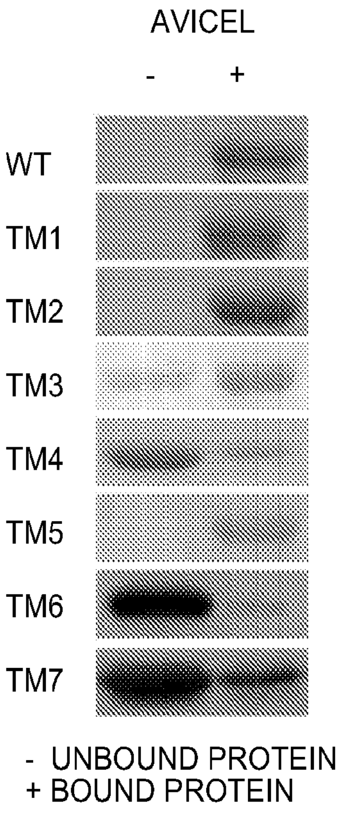
Figure 80B:
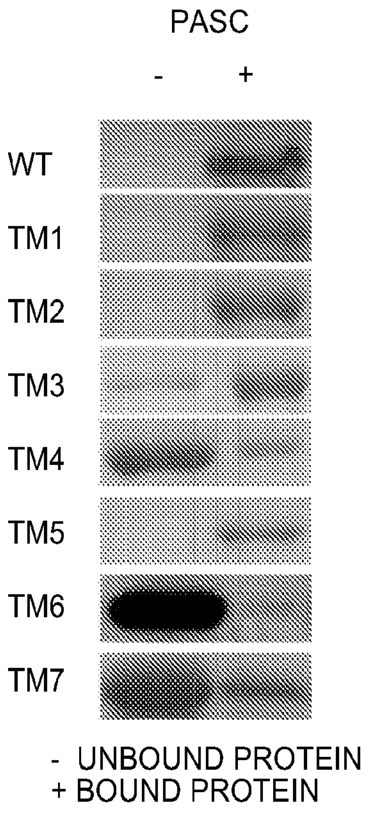

FIGS. 80A and 80B: Qualitative binding of Cb1952 wild-type and its truncation mutants with Avicel (FIG. 80A) and phosphoric acid swollen cellulose (PASC) (FIG. 80B). Thirty micrograms of each protein were incubated with 40 mg/ml Avicel cellulose or 2.5 mg/ml PASC in 50 mM Tris buffer, 150 mM NaCl (pH 7.5). The mixture was shaken end-over-end at 4° C. for 1 h. Then the bound and unbound proteins were separated by centrifugation of the mixture at 16,400 rpm for 3 min. The cellulose pellet was washed with 1 ml buffer (50 mM Tris buffer, 150 mM NaCl, pH 7.5) for 4 times. Then the pellet was added with 70 μl of 1×SDS-PAGE loading buffer and boiled for 5 min. The protein corresponding to one tenth volume of each fraction was applied to a 12% SDS-PAGE.

Figure 81A:
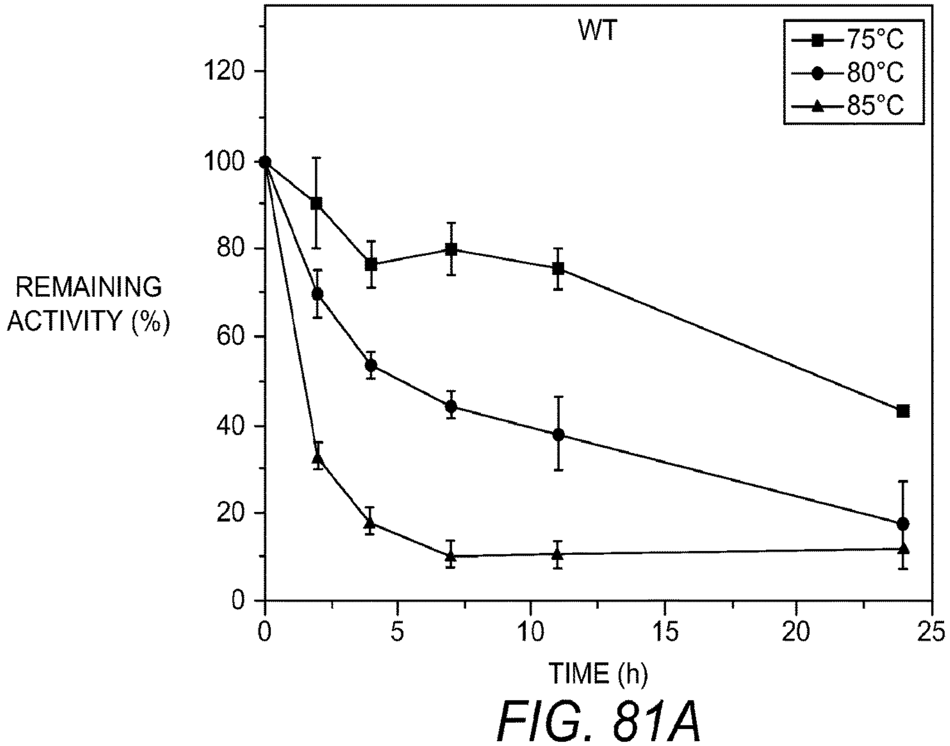
Figure 81B:
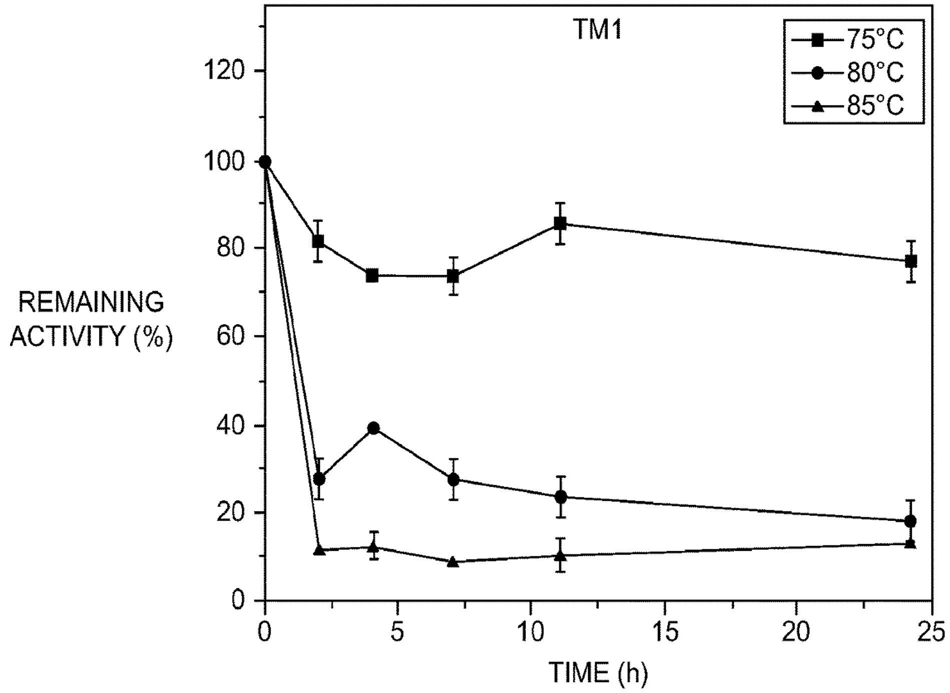
Figure 81C:
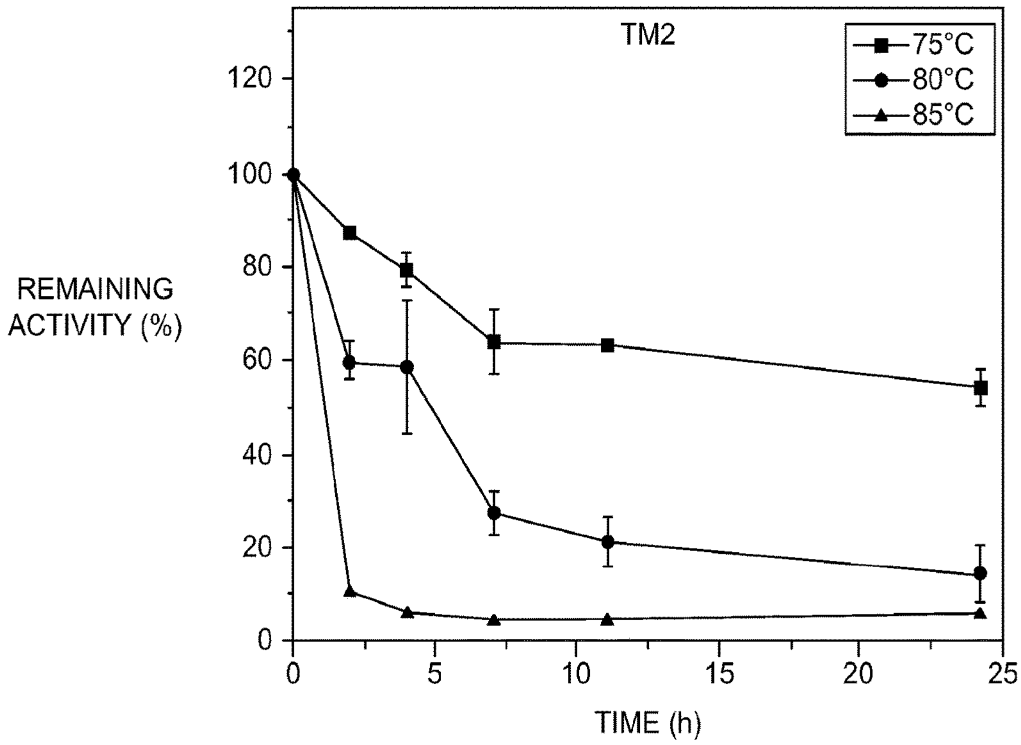

FIGS. 81A to 81C: Thermostability of Cb1952 and its truncation mutants harboring cellulase activities. FIG. 81A: Cb1952 TM2; FIG. 81B: Cb1952 TM3; FIG. 81C: Cb1952 TM4. The enzymes were incubated at 75° C., 80° C., and 85° C. (WT, TM1, TM2, and TM3) or at 45° C., 50° C., and 55° C. (TM4) on a Veriti 96-well thermal cycle. At different time points, samples were taken out and measured for their remaining activity using PASC as the substrate.

FIG. 82: Amino acid sequence alignment of the CBM3c of Cb1952 with those from other family 9 glycoside hydrolases. The amino acid residues proposed to be involved in cellulose ligand binding based on the works of Jindou et al. (2006) and Li et al. (2010) are indicated with a filled triangle. The sources of the enzymes used for comparison are as follows. Cb1952 (SEQ ID NO: 153): bifunctional cellulase/mannanase of *Caldicellulosiruptor bescii* (this study); ADQ45731(SEQ ID NO: 154): putative cellulase of *Caldicellulosiruptor kronotskyensis*; ABP66693 (SEQ ID NO: 155): putative cellulase of *Caldicellulosiruptor saccharolyticus*; ADL42950 (SEQ ID NO: 156): putative *Caldicellulosiruptor obsidiansis* cellulase/mannan endo-1,4-beta-mannosidase; AAK06394 (SEQ ID NO: 157): CelE of *Caldicellulosiruptor* sp. Tok7B.1 (11); AAA73868 (SEQ ID NO: 158): Cel9G of *Clostridium cellulolyticum* (26); AAC38572 (SEQ ID NO: 159): EngH of *Clostridium cellulovorans* (38); CAA39010 (SEQ ID NO: 160): Cel9Z of *Clostridium stercorarium* (18); ABX43720 (SEQ ID NO: 161): Cel9 of *Clostridium phytofermentans* (39, 48); ABN51860 (SEQ ID NO: 162): Cel9I of *Clostridium thermocellum* DSM 1313 (50); CAB38941 (SEQ ID NO: 163): Cel9B of *Paenibacillus barcinonensis* (32); BAB33148 (SEQ ID NO: 164): CelQ of *Clostridium thermocellum* F1 (2); AAA23086 (SEQ ID NO: 165): CenB of *Cellulomonas fimi* (27); AAW62376 (SEQ ID NO: 166): CBP105 of

*Cellulomonas flavigena* (28); AAB42155 (SEQ ID NO: 167): Cel9A of *Thermobifida fusca* (16, 34).

Figure 83:
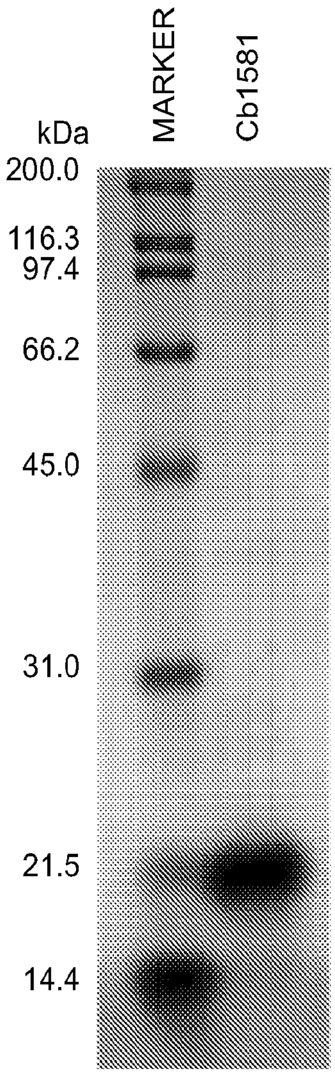

FIG. 83: SDS-PAGE of purified Cb1581.

Figure 84A:
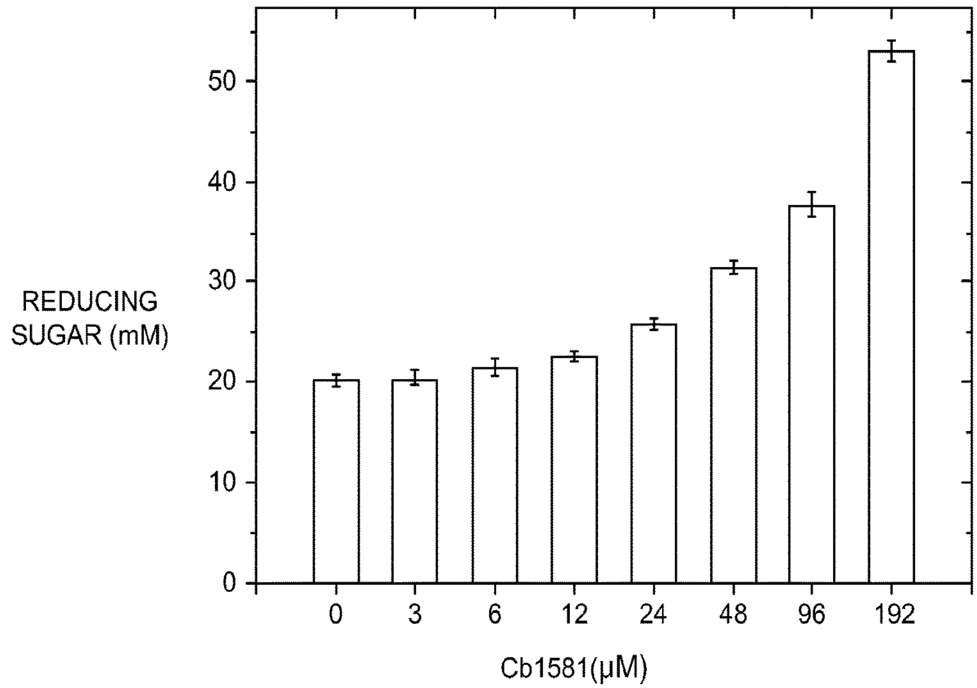
Figure 84B:
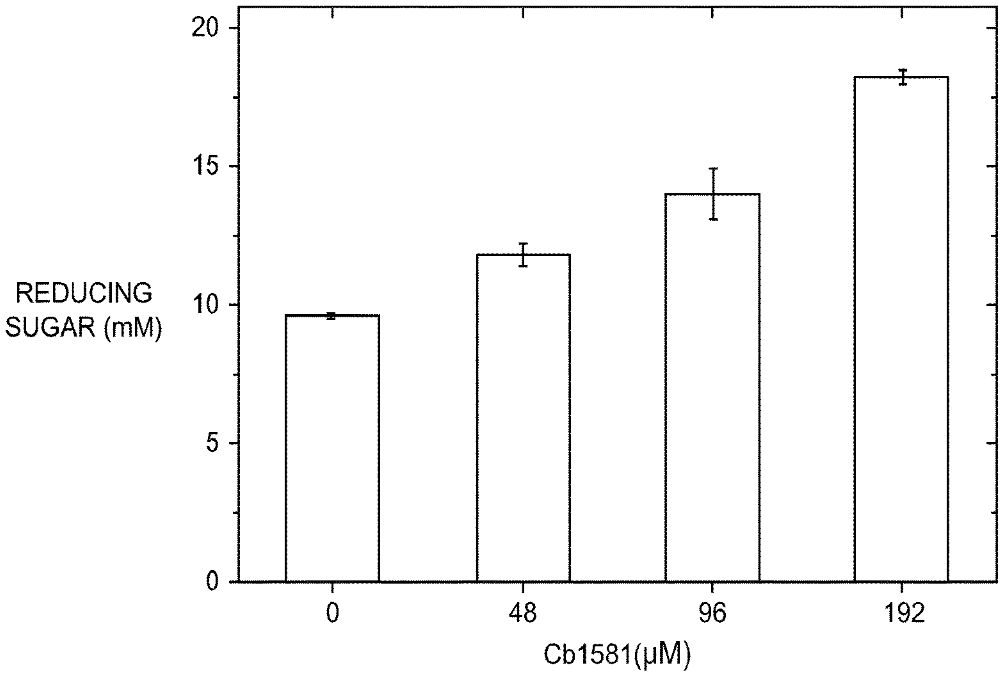

FIGS. 84A and 84B: Shows the enhancing effect of Cb1581 on enzymatic hydrolysis of microwave pretreated *miscanthus* at 70° C. (FIG. 84A) or 80° C. (FIG. 84B). Enzymatic hydrolysis of pretreated *miscanthus* was carried out at pH 6.0 using 0.5 μM each of the cellulase/hemicellulase enzyme mixture in a total volume of 500 μl with 10% *miscanthus* as the substrate. The enzymes in the mixture include Cb1946TM2, Cb1952TM1, Cb1953TM2, Cb1954TM3, Cb629TM1, Cb486, Cb193, Cb195, Cb2487, Cb1172, Cb909, and Cb162, and variable amounts of recombinant Cb1581, as indicated. The concentration of glucose equivalents was determined following enzymatic hydrolysis of microwave pretreated *miscanthus*, according to the methods of Lever, M. The releasing of sugars is enhanced with the increasing amount of Cb1581 in the reaction mixture at both 70° C. and 80° C.

DETAILED DESCRIPTION OF PREFERRED EMBODIMENTS

The present disclosure relates to thermostable cellulose and hemicellulose-degrading enzymes and to methods of using these enzymes for the degradation of cellulose, hemicellulose, and cellulose and hemicellulose-containing materials. The present disclosure also relates to nucleic acids encoding the enzymes disclosed herein, and enzyme cocktails containing various enzymes disclosed herein.

In one aspect, the disclosure provides enzymes having cellulase activity. Provided herein are truncated enzymes that have improved cellulase activity over wild-type cellulase proteins. Also provided herein are truncated enzymes that have similar cellulase activity to wild-type cellulase proteins. Truncated proteins may be advantageous over wild-type proteins, for example, due to lower cost or improved ease of production of truncated proteins.

In another aspect, the disclosure provides enzymes having hemicellulase activity. The hemicellulose-degrading enzymes of the present disclosure can be used alone, or in combination to degrade hemicellulose, i.e., convert hemicellulose into its structural components by cleavage of bonds, or linkages, between the component subunits present in hemicellulose. Bonds or linkages may include bonds between xylose subunits, or bonds between xylose and functional groups, or bonds between functional groups.

In another aspect, the disclosure provides enzymes that enhance the activity of enzymes having cellulase or hemicellulase activity, and/or mixtures thereof. Enzymes that enhance the activity of cellulases and/or hemicellulases may be provided alone, with cellulases, with hemicellulases, or with mixtures of cellulases and hemicellulases.

Cellulose or hemicellulose treated with the methods of the present disclosure may be at least 70%, 75%, 80%, 85%, 90%, 91%, 92%, 93%, 94%, 95%, 96%, 97%, 98%, 99%, or 100% degraded. Degradation products may include glucose, cellobiose, cellodextrins, xylose, arabinose, glucuronyl groups, and acetyl groups, in addition to other functional groups and hydrocarbons. The degradation products may find use as biofuels or other value-added compounds. For example, sugars released from the cellulose or hemicellulose may be fermented for the production of ethanol.

The cellulose and hemicellulose-degrading enzymes of the present disclosure are thermostable, and are optimally able to degrade cellulose and/or hemicellulose into sugars such as glucose, xylose, or arabinose at temperatures above 50° C. In addition, the enzymes retain substantial activity when maintained at various temperatures above 50° C.

Without wishing to be bound by theory, another important feature of the enzyme cocktails described herein are that they are derived from the same organism, ensuring that the enzymes will function together to degrade cellulose and/or hemicellulose. *Caldicellulosiruptor bescii* contains a complete set of enzymes for degrading cellulose, and hemicelluloses such as xylan. Xylan is the main hemicellulose in perennial grasses, such as switchgrass, and is most likely the main hemicellulose in the giant grass *Miscanthus.*

In one aspect, the present disclosure provides nucleotide and amino acid sequences for thermostable enzymes that degrade hemicellulose, including Cb193, Cb195, Cb1172, Cb909, Cb2487, and Cb162. Cb193 and Cb195 function as endoxylanases. Cb1172 functions as an α-arabinofuranosidase. Cb909 functions as a glucuronidase. Cb2487 functions as a β-xylosidase. Cb162 functions as an acetyl xylan esterase. Variants of the enzymes that retain partial or complete functional activity are also encompassed by the present disclosure. The enzymes disclosed herein can be used in various combinations.

In one aspect, the disclosure provides improved enzyme mixtures for the degradation of cellulose-containing materials. Improved enzyme mixtures for the degradation of cellulose-containing materials may contain, for example, improved mixtures of cellulases and/or truncated cellulase enzymes.

In another aspect, the disclosure provides improved enzyme mixtures for the degradation of materials containing both cellulose and hemicellulose. Enzyme mixtures disclosed herein containing both cellulases and hemicellulases provide the surprising result of synergistic activity on plant material containing both cellulose and hemicellulose. For example, as shown in Example 15 below, an enzyme cocktail provided herein containing a mixture of cellulases and a mixture of hemicellulases has greater cellulase activity on plant material than the same mixture of cellulases alone. Additionally, the enzyme cocktail containing a mixture of cellulases and a mixture of hemicellulases has greater hemicellulase activity on plant material than the same mixture of hemicellulases alone.

Combinations of enzymes, i.e., an enzyme cocktail, can be tailored to the cellulose and/or hemicellulose structure of a specific feedstock to increase the level of degradation. Initial analysis of the enzyme cocktails described herein suggests that the components have a long shelf life, an important characteristic in an industrial enzyme mix.

Abbreviations/Definitions

The following abbreviations are used in the present disclosure: TLC (thin layer chromatography); SWAX (soluble wheat arabinoxylan); OSX (oat-spelt xylan); BWX (birchwood xylan); CMC (carboxymethyl cellulose); RAX (rye arabinoxylan); MeGlcA (4-O-methyl-D-glucuronosyl); pNP-X (para-nitrophenyl-beta-D-xylopyranoside); GH (glycoside hydrolase); CBM (carbohydrate binding module); SDS-PAGE (sodium dodecyl sulfate polyacrylamide gel electrophoresis); PASC (phosphoric acid swollen cellulose); CMC-Na (sodium carboxymethyl cellulose); LBG (locust bean gum); KGM (konjac glucomannan); WAX (wheat arabinoxylan); HPAEC (high performance anion-exchange chromatography); HPLC (high performance liquid chromatography)

As used herein, a "polypeptide" is a chain of consecutive polymerized amino acid residues (e.g., at least about 5 consecutive polymerized amino acid residues). As used herein, the terms "polypeptide", "protein", and "amino acid sequence" are used interchangeably.

As used herein, "cellulase" activity refers to enzymatic activity which cleaves 1-4 β-D-glycosidic linkages between glucose molecules in cellulose and/or cellooligosaccharides. Cellulase activity includes endoglucanase, exoglucanase, and beta-glucosidase activity.

As used herein, "hemicellulase" activity refers to enzymatic activity which cleaves a bond in a molecule that is a component of hemicellulose, including endoxylanase, α-arabinofuranosidase, glucuronidase, β-xylosidase, and acetyl xylan esterase activity.

Polypeptides of the Disclosure

In some aspects, polypeptides of the disclosure relate to recombinant polypeptides of the thermophilic bacterium *Caldicellulosiruptor bescii* (formerly *Anaerocellum thermophilum* DSMZ 6725), truncations, and variations thereof.

In one aspect, the present disclosure provides recombinant polypeptides related to the degradation of cellulose. In some aspects, the disclosure provides recombinant Cb1952, Cb1953, Cb1954, Cb1946, Cb629, and Cb486 polypeptides which have cellulase activity.

In one aspect, the present disclosure provides recombinant polypeptides related to the degradation of hemicellulose. In some aspects, the disclosure provides recombinant Cb193, Cb195, Cb1172, Cb909, Cb2487, and Cb162 polypeptides which have hemicellulase activity.

In one aspect, the present disclosure provides recombinant polypeptides that enhance the hydrolysis of cellulose and/or hemicellulose during treatment of cellulose and/or hemicellulose with cellulase and/or hemicellulases. In one aspect, the disclosure provides recombinant Cb1581 polypeptide, which is a heat shock protein that enhances the hydrolysis of cellulose and/or hemicellulose during treatment of cellulose and/or hemicellulose with cellulase and/or hemicellulases.

Cellulases

Cb1952 Polypeptides

In some aspects, the present disclosure relates to recombinant Cb1952 polypeptides. As used herein, a "Cb1952 polypeptide" refers to the polypeptide of SEQ ID NO: 44, and truncational mutants thereof, homologs thereof, and truncational mutants of homologs thereof, which have cellulase activity. "Cb1952 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 44, 114, 124, 126, 128, and 46. As used herein, "Cb1952 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 44, 114, 124, 126, 128, and 46.

The polypeptide of SEQ ID NO: 44 is the product of the Cb1952 gene in *Caldicellulosiruptor bescii*, where Cb stands for *Caldicellulosiruptor bescii*. The Cb1952 polypeptide of SEQ ID NO: 44 is an endocellulase that has a glycoside hydrolase (GH) family 9 catalytic domain (cellulase domain), three family 3 carbohydrate binding modules (CBMs) and one GH5 catalytic domain (mannanase domain) (FIG. 18)

The present disclosure also includes the Cb1952 polypeptide of SEQ ID NO: 114, which is the Cb1952 polypeptide of SEQ ID NO: 44 without the signal peptide sequence. The signal peptide is produced as part of the initially translated Cb1952 protein to target the protein for secretion from the cell, and it may be cleaved from the protein during the secretion process. The disclosure also includes the Cb1952 polypeptide of SEQ ID NO: 114 with a methionine residue at the start of the polypeptide chain.

The disclosure further includes the Cb1952 polypeptide of SEQ ID NO: 46 ("Cb1952TM1"), which is a truncational mutant ("TM") of wild-type Cb1952. The Cb1952TM1 polypeptide includes the cellulase domain and CBMs of wt Cb1952, but does not include the mannase domain (FIG. 18).

The disclosure also includes the Cb1952 polypeptide of SEQ ID NO: 124 ("Cb1952TM2"), which is a truncational mutant of wild-type Cb1952 that does not include the mannase domain or the C-terminal CBM (FIG. 18).

The disclosure also includes the Cb1952 polypeptide of SEQ ID NO: 126 ("Cb1952TM3"), which is a truncational mutant of wild-type Cb1952 that does not include the mannase domain or the 2 most C-terminal CBMs (FIG. 18).

The disclosure also includes the Cb1952 polypeptide of SEQ ID NO: 128 ("Cb1952TM4"), which is a truncational mutant of wild-type Cb1952 that includes the GH9 cellulase domain, but that does not contain any of the CBMs or the mannose domain (FIG. 18).

Cb1952 polypeptides of the present disclosure are thermophilic and thermostable. In some aspects, a Cb1952 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1952 polypeptide of the present disclosure retains at least 60% of its initial rate of enzymatic activity for a period of at least 24 hours when incubated at a temperature of about 55, 60, 65, 70, 75, 80, 85, or 90° C.

Cb1953 Polypeptides

In some aspects, the present disclosure relates to recombinant Cb1953 polypeptides. As used herein, a "Cb1953 polypeptide" refers to the polypeptide of SEQ ID NO: 60, and truncational mutants thereof, homologs thereof, and truncational mutants of homologs thereof, which have cellulase activity. "Cb1953 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 60, 61, and 111. As used herein, "Cb1953 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 60, 61, and 111.

The Cb1953 polypeptide of SEQ ID NO: 60 is the product of the Cb1953 gene in *Caldicellulosiruptor bescii*, where Cb stands for *Caldicellulosiruptor bescii*. The Cb1953 polypeptide of SEQ ID NO: 60 is an endoglucanase that cleaves mostly cellobiose from cellulose, and it has two glycoside hydrolase (GH) family 5 catalytic domains and 3 carbohydrate binding modules (CBM) (FIG. 29).

The present disclosure also includes the Cb1953 polypeptide of SEQ ID NO: 61, which is the Cb1953 polypeptide of SEQ ID NO: 60 without the signal peptide sequence. The signal peptide is produced as part of the initially translated Cb1953 protein to target the protein for secretion from the cell, and it may be cleaved from the protein during the secretion process. The disclosure also includes the Cb1953 polypeptide of SEQ ID NO: 61 with a methionine residue at the start of the polypeptide chain.

The disclosure further includes the Cb1953 polypeptide of SEQ ID NO: 111 ("Cb1953TM2"), which is a truncational mutant ("TM") of wild-type Cb1953. The Cb1953TM2 polypeptide includes the C-terminal GH5 domain and the 3 CBMs of wt Cb1953, but does not include the N-terminal GH5 domain. (FIG. 29).

Cb1953 polypeptides of the present disclosure are thermophilic and thermostable. In some aspects, a Cb1953 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1953 polypeptide of the present disclosure retains at least 60% of its initial rate of enzymatic activity for a period of at least 24 hours when incubated at a temperature of about 55, 60, 65, 70, 75, 80, 85, or 90° C.

Cb1954 Polypeptides

In some aspects, the present disclosure relates to recombinant Cb1954 polypeptides. As used herein, a "Cb1954 polypeptide" refers to the polypeptide of SEQ ID NO: 74, and truncational mutants thereof, homologs thereof, and truncational mutants of homologs thereof, which have cellulase activity. "Cb1954 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 74, 121, and 76. As used herein, "Cb1954 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 74, 121, and 76.

The Cb1954 polypeptide of SEQ ID NO: 74 is the product of the Cb1954 gene in *Caldicellulosiruptor bescii*, where Cb stands for *Caldicellulosiruptor bescii*. The Cb1954 polypeptide of SEQ ID NO: 74 is an endoglucanase that has a glycoside hydrolase (GH) family 9 catalytic domain (a cellulase domain), 3 carbohydrate binding modules (CBM), and one GH48 catalytic domain (FIG. 38).

The present disclosure also includes the Cb1954 polypeptide of SEQ ID NO: 121, which is the Cb1954 polypeptide of SEQ ID NO: 74 without the signal peptide sequence. The signal peptide is produced as part of the initially translated Cb1954 protein to target the protein for secretion from the cell, and it may be cleaved from the protein during the secretion process. The disclosure also includes the Cb1954 polypeptide of SEQ ID NO: 121 with a methionine residue at the start of the polypeptide chain.

The disclosure further includes the Cb1954 polypeptide of SEQ ID NO: 76 ("Cb1954TM3"), which is a truncational mutant ("TM") of wild-type Cb1954. The Cb1954TM3 polypeptide includes the GH9 domain and the N-terminal-most CBM of wt Cb1954, but does not include the middle or C-terminal CBM, or the GH48 domain. (FIG. 38).

Cb1954 polypeptides of the present disclosure are thermophilic and thermostable. In some aspects, a Cb1954 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1954 polypeptide of the present disclosure retains at least 60% of its initial rate of enzymatic activity for a period of at least 24 hours when incubated at a temperature of about 55, 60, 65, 70, 75, 80, 85, or 90° C.

Cb1946 Polypeptides

In some aspects, the present disclosure relates to recombinant Cb1946 polypeptides. As used herein, a "Cb1946 polypeptide" refers to the polypeptide of SEQ ID NO: 86, and truncational mutants thereof, homologs thereof, and truncational mutants of homologs thereof, which have cellulase activity. "Cb1946 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 86, 87, and 113. As used herein, "Cb1946 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 86, 87, and 113.

The Cb1946 polypeptide of SEQ ID NO: 86 is the product of the Cb1946 gene in *Caldicellulosiruptor bescii*, where Cb stands for *Caldicellulosiruptor bescii*. The Cb1946 polypeptide of SEQ ID NO: 86 is an endoglucanase that has a glycoside hydrolase (GH) family 5 catalytic domain at the N-terminal region, a GH family 44 catalytic domain at the C-terminal region and 2 carbohydrate binding modules (CBMs) between the two GH catalytic domains (FIG. 42).

The present disclosure also includes the Cb1946 polypeptide of SEQ ID NO: 87, which is the Cb1946 polypeptide of SEQ ID NO: 86 without the signal peptide sequence. The signal peptide is produced as part of the initially translated Cb1946 protein to target the protein for secretion from the cell, and it may be cleaved from the protein during the secretion process. The disclosure also includes the Cb1946 polypeptide of SEQ ID NO: 87 with a methionine residue at the start of the polypeptide chain.

The disclosure further includes the Cb1946 polypeptide of SEQ ID NO: 113 ("Cb1946TM2"), which is a truncational mutant ("TM") of wild-type Cb1946. The Cb1946TM2 polypeptide includes the C-terminal GH44 domain and the 2 CBMs of wt Cb1946, but does not include the N-terminal GH5 domain. (FIG. 42).

Cb1946 polypeptides of the present disclosure are thermophilic and thermostable. In some aspects, a Cb1946 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1946 polypeptide of the present disclosure retains at least 60% of its initial rate of enzymatic activity for a period of at least 24 hours when incubated at a temperature of about 55, 60, 65, 70, 75, 80, 85, or 90° C.

Cb629 Polypeptides

In some aspects, the present disclosure relates to recombinant Cb629 polypeptides. As used herein, a "Cb629 polypeptide" refers to the polypeptide of SEQ ID NO: 98, and truncational mutants thereof, homologs thereof, and truncational mutants of homologs thereof, which have cellulase activity. "Cb629 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 98, 119, and 100. As used herein, "Cb629 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 98, 119, and 100.

The Cb629 polypeptide of SEQ ID NO: 98 is the product of the Cb629 gene in *Caldicellulosiruptor bescii*, where Cb stands for *Caldicellulosiruptor bescii*. The Cb629 polypeptide of SEQ ID NO: 98 is an endocellulase that initially cleaves glucose, cellobiose, and cellotriose from cellulose, and it has a glycoside hydrolase (GH) family 5 catalytic domain, a Carbohydrate Binding Module (CBM) family 17_28 domain, and three surface layer homology (SLH) modules likely used in anchoring the enzyme to the cell surface (FIG. 47).

The present disclosure also includes the Cb629 polypeptide of SEQ ID NO: 119, which is the Cb629 polypeptide of SEQ ID NO: 98 without the signal peptide sequence. The signal peptide is produced as part of the initially translated Cb629 protein to target the protein for secretion from the cell, and it may be cleaved from the protein during the secretion process. The disclosure also includes the Cb629 polypeptide of SEQ ID NO: 119 with a methionine residue at the start of the polypeptide chain.

The disclosure further includes the Cb629 polypeptide of SEQ ID NO: 100 ("Cb629TM1"), which is a truncational mutant ("TM") of wild-type Cb629. The Cb629TM1 polypeptide includes the N-terminal GH5 domain and the CBM17_28 domain of wt Cb629, but does not include the C-terminal SLH modules (FIG. 47).

Cb629 polypeptides of the present disclosure are thermophilic and thermostable. In some aspects, a Cb629 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb629 polypeptide of the present disclosure retains at least 60% of its initial rate of enzymatic activity for a period of at least 24 hours when incubated at a temperature of about 55, 60, 65, 70, 75, 80, 85, or 90° C.

Cb486 Polypeptides

In some aspects, the present disclosure relates to recombinant Cb486 polypeptides.

As used herein, a "Cb486 polypeptide" refers to the polypeptide of SEQ ID NO: 106, and truncational mutants thereof, homologs thereof, and truncational mutants of homologs thereof, which have cellulase activity. "Cb486 polypeptide" also refers to a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 106. As used herein, "Cb486 polypeptide" also refers to a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 106.

The Cb486 polypeptide of SEQ ID NO: 106 is the product of the Cb486 gene in *Caldicellulosiruptor bescii*, where Cb stands for *Caldicellulosiruptor bescii*. The Cb486 polypeptide of SEQ ID NO: 106 is a β-glucosidase that catalyzes the hydrolysis of cellobiose (a disaccharide of glucose) into two units of glucose, and it has a glycoside hydrolase (GH) family 1 catalytic domain (FIG. 53A).

Cb486 polypeptides of the present disclosure are thermophilic and thermostable. In some aspects, a Cb486 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb486 polypeptide of the present disclosure retains at least 60% of its initial rate of enzymatic activity for a period of at least 24 hours when incubated at a temperature of about 55, 60, 65, 70, 75, 80, 85, or 90° C.

Hemicellulases

The disclosure also provides for polypeptides of thermostable hemicellulose-degrading enzymes Cb193 (SEQ ID NO: 3), Cb195 (SEQ ID NO: 7), Cb1172 (SEQ ID NO: 13), Cb909 (SEQ ID NO: 19), Cb2487 (SEQ ID NO: 27), and Cb162 (SEQ ID NO: 33), or subsequences thereof. The disclosure further provides for an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to Cb193, Cb195, Cb1172, Cb2487, Cb909 or Cb162.

Hemicellulases of the present disclosure may contain one or more glycoside hydrolase (GH) domains. Hemicellulases may also contain one or more carbohydrate binding modules (CBM). The CBM modules may interrupt a GH domain or be located in between two GH domains. Hemicellulases may also contain an acetyl xylan esterase domain. In certain embodiments, the GH, CBM and/or acetyl xylan esterase domain sequence is conserved in polypeptide variants.

Cb193 Polypeptides

In some aspects, the present disclosure relates to recombinant Cb193 polypeptides. As used herein, a "Cb193 polypeptide" refers to the polypeptide of SEQ ID NO: 3, and truncational mutants thereof, homologs thereof, and truncational mutants of homologs thereof, which have hemicellulase activity. "Cb193 polypeptide" also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 3 and/or 37. As used herein, "Cb193 polypeptide" also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 3 and/or 37.

Figure 1:
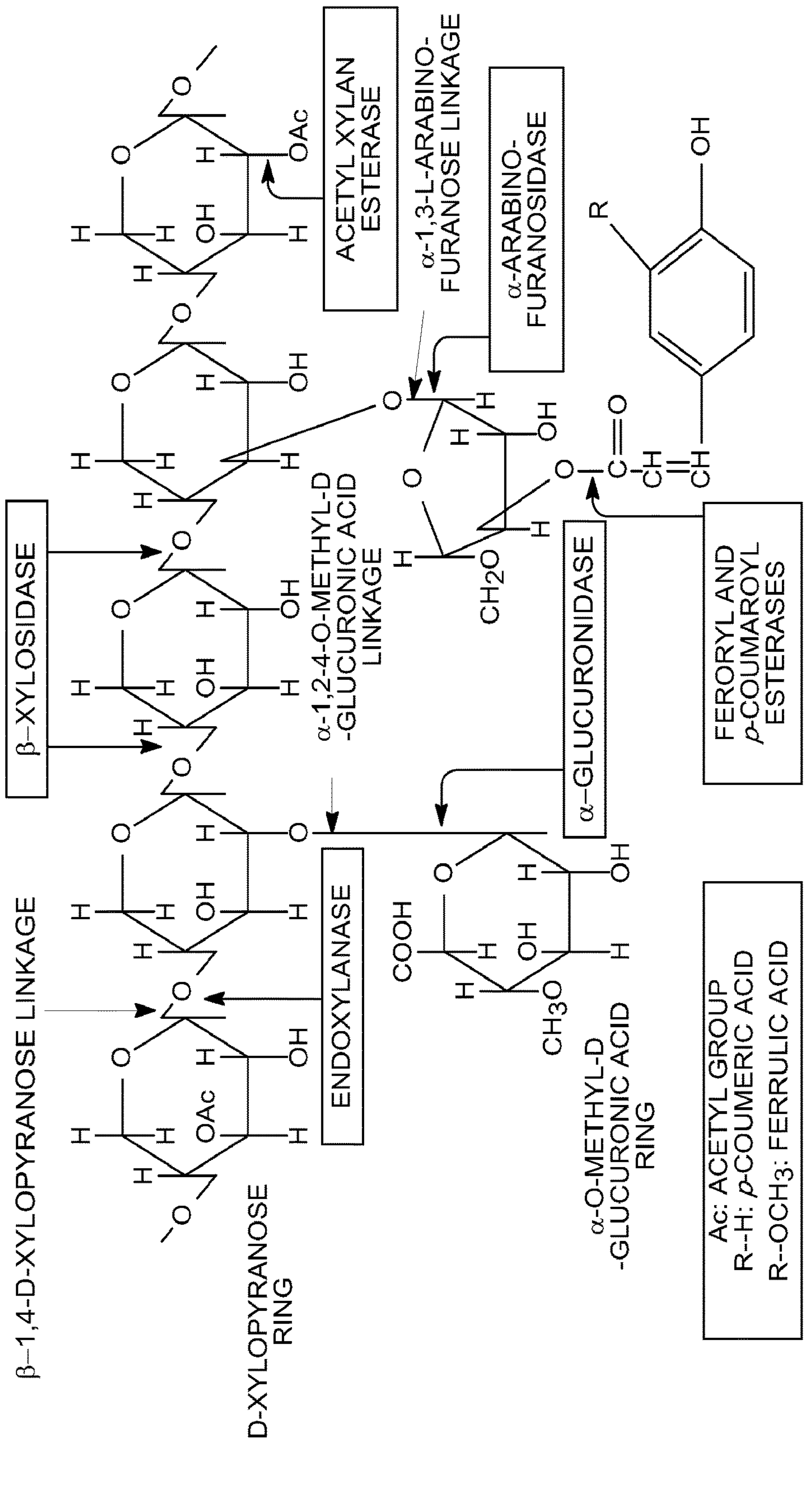
FIG. 1 shows a model of a typical hemicellulose such as xylan.
Figure 2A:
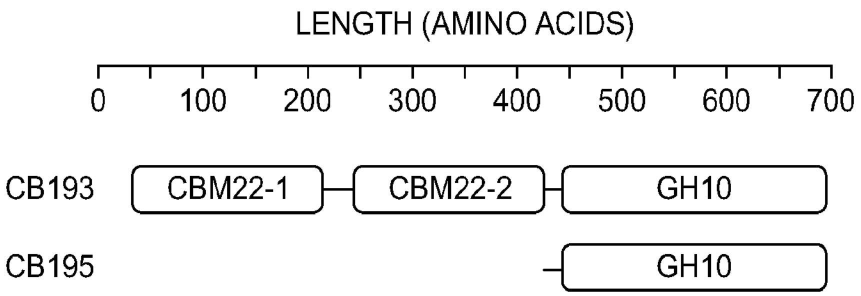
FIGS. 2A to 2E.

The Cb193 polypeptide of SEQ ID NO: 3 is the product of the Cb193 gene in *Caldicellulosiruptor bescii*, where Cb stands for *Caldicellulosiruptor bescii*. The Cb193 polypeptide of SEQ ID NO: 3 or 37 is an endoxylanase cleaves the xylose backbone of hemicellulose at random to generate shorter chains of xylose in β-1,4-linkages. These xylo-oligosaccharides can range from two or more sugar subunits. Cb193 has a signal peptide (corresponding to amino acids 1-41 of SEQ ID NO: 3), which may be removed. The amino acid sequence of the Cb193 protein without the signal peptide is disclosed in SEQ ID NO: 37. The protein has two putative carbohydrate binding modules (CBM) inserted within the glycoside hydrolase (GH) family 10 catalytic domain (FIG. 2A).

The present disclosure also includes the Cb193 polypeptide of SEQ ID NO: 37, which is the Cb193 polypeptide of SEQ ID NO: 3 without the signal peptide sequence. The signal peptide is produced as part of the initially translated Cb193 protein to target the protein for secretion from the cell, and it may be cleaved from the protein during the secretion process. The disclosure also includes the Cb193 polypeptide of SEQ ID NO: 37 with a methionine residue at the start of the polypeptide chain.

Cb193 polypeptides of the present disclosure are thermophilic and thermostable. In some aspects, a Cb193 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb193 polypeptide of the present disclosure retains at least 60% of its initial rate of enzymatic activity for a period of at least 24 hours when incubated at a temperature of about 55, 60, 65, 70, 75, 80, 85, or 90° C.

Cb195 Polypeptides

In some aspects, the present disclosure relates to recombinant Cb195 polypeptides. As used herein, a "Cb195 polypeptide" refers to the polypeptide of SEQ ID NO: 7, and truncational mutants thereof, homologs thereof, and truncational mutants of homologs thereof, which have hemicellulase activity. "Cb195 polypeptide" also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 7. As used herein, "Cb195 polypeptide" also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 7.

The Cb195 polypeptide of SEQ ID NO: 7 is the product of the Cb195 gene in *Caldicellulosiruptor bescii*, where Cb stands for *Caldicellulosiruptor bescii*. The Cb195 polypeptide of SEQ ID NO: 7 is an endoxylanase that cleaves the xylose backbone of hemicellulose at random to generate shorter chains of xylose in β-1,4-linkages. These xylo-oligosaccharides can range from containing two or more sugar subunits.

Cb195 polypeptides of the present disclosure are thermophilic and thermostable. In some aspects, a Cb195 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb195 polypeptide of the present disclosure retains at least 60% of its initial rate of enzymatic activity for a period of at least 24 hours when incubated at a temperature of about 55, 60, 65, 70, 75, 80, 85, or 90° C.

Cb1172 Polypeptides

In some aspects, the present disclosure relates to recombinant Cb1172 polypeptides. As used herein, a "Cb1172 polypeptide" refers to the polypeptide of SEQ ID NO: 13, and truncational mutants thereof, homologs thereof, and truncational mutants of homologs thereof, which have hemicellulase activity. "Cb1172 polypeptide" also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 13. As used herein, "Cb1172 polypeptide" also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 13.

The Cb1172 polypeptide of SEQ ID NO: 13 is the product of the Cb1172 gene in *Caldicellulosiruptor bescii*, where Cb stands for *Caldicellulosiruptor bescii*. The Cb1172 polypeptide of SEQ ID NO: 13 is an α-L-arabinofuranosidase that cleaves arabinose moiety from the xylose backbone or from branched or debranched arabinan of hemicellulose to generate exclusively arabinose. The protein has a glycoside hydrolase (GH) family 51 catalytic domain (FIG. 6D).

Cb1172 polypeptides of the present disclosure are thermophilic and thermostable. In some aspects, a Cb1172 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1172 polypeptide of the present disclosure retains at least 60% of its initial rate of enzymatic activity for a period of at least 24 hours when incubated at a temperature of about 55, 60, 65, 70, 75, 80, 85, or 90° C.

Cb909 Polypeptides

In some aspects, the present disclosure relates to recombinant Cb909 polypeptides. As used herein, a "Cb909 polypeptide" refers to the polypeptide of SEQ ID NO: 19, and truncational mutants thereof, homologs thereof, and truncational mutants of homologs thereof, which have hemicellulase activity. "Cb909 polypeptide" also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 19. As used herein, "Cb909 polypeptide" also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 19.

The Cb909 polypeptide of SEQ ID NO: 19 is the product of the Cb909 gene in *Caldicellulosiruptor bescii*, where Cb stands for *Caldicellulosiruptor bescii*. The Cb909 polypeptide of SEQ ID NO: 19 is an α-glucuronidase that cleaves the α-1,2-glycosidic bond between 4-O-methyl-D-glucuronic acid and the β-1,4-xylosidic linkage backbone of xylan.

Cb909 polypeptides of the present disclosure are thermophilic and thermostable. In some aspects, a Cb909 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb909 polypeptide of the present disclosure retains at least 60% of its initial rate of enzymatic activity for a period of at least 24 hours when incubated at a temperature of about 55, 60, 65, 70, 75, 80, 85, or 90° C.

Cb2487 Polypeptides

In some aspects, the present disclosure relates to recombinant Cb2487 polypeptides. As used herein, a “Cb2487 polypeptide” refers to the polypeptide of SEQ ID NO: 27, and truncational mutants thereof, homologs thereof, and truncational mutants of homologs thereof, which have hemicellulase activity. “Cb2487 polypeptide” also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 27. As used herein, “Cb2487 polypeptide” also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 27.

The Cb2487 polypeptide of SEQ ID NO: 27 is the product of the Cb2487 gene in *Caldicellulosiruptor bescii*, where Cb stands for *Caldicellulosiruptor bescii*. The Cb2487 polypeptide of SEQ ID NO: 27 is a β-xylosidase.

Cb2487 polypeptides of the present disclosure are thermophilic and thermostable. In some aspects, a Cb2487 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb2487 polypeptide of the present disclosure retains at least 60% of its initial rate of enzymatic activity for a period of at least 24 hours when incubated at a temperature of about 55, 60, 65, 70, 75, 80, 85, or 90° C.

Cb162 Polypeptides

In some aspects, the present disclosure relates to recombinant Cb162 polypeptides. As used herein, a “Cb162 polypeptide” refers to the polypeptide of SEQ ID NO: 33, and truncational mutants thereof, homologs thereof, and truncational mutants of homologs thereof, which have hemicellulase activity. “Cb162 polypeptide” also refers to a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 33. As used herein, “Cb162 polypeptide” also refers to a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 33.

The Cb162 polypeptide of SEQ ID NO: 33 is the product of the Cb162 gene in *Caldicellulosiruptor bescii*, where Cb stands for *Caldicellulosiruptor bescii*. The Cb162 polypeptide of SEQ ID NO: 33 is an acetyl xylan esterase that cleaves the linkages between xylose and the side chain of acetyl groups in hemicellulose to provide more accessibility to other hemicellulases such as xylanase and beta-xylosidase to the backbone of xylan. The protein has a single domain of acetyl xylan esterase (FIG. 10A).

Cb162 polypeptides of the present disclosure are thermophilic and thermostable. In some aspects, a Cb162 polypeptide of the present disclosure has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb162 polypeptide of the present disclosure retains at least 60% of its initial rate of enzymatic activity for a period of at least 24 hours when incubated at a temperature of about 55, 60, 65, 70, 75, 80, 85, or 90° C.

Polypeptides that Enhance Enzymatic Hydrolysis of Cellulose and/or Hemicellulose In some aspects, the disclosure provides for recombinant polypeptides that enhance the enzymatic hydrolysis of cellulose and/or hemicellulose.

In one aspect, a recombinant polypeptide that enhances the enzymatic hydrolysis of cellulose and/or hemicellulose is a recombinant Cb1581 polypeptide.

As used herein, a “Cb1581 polypeptide” refers to the polypeptide of SEQ ID NO: 146, and truncational mutants thereof, homologs thereof, and truncational mutants of homologs thereof, which have enzymatic hydrolysis of cellulose and/or hemicellulose-enhancing activity. “Cb1581 polypeptide” also refers to a polypeptide that has enzymatic hydrolysis of cellulose and/or hemicellulose-enhancing activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 146. As used herein, “Cb1581 polypeptide” also refers to a polypeptide that has enzymatic hydrolysis of cellulose and/or hemicellulose-enhancing activity, and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 146.

The Cb1581 polypeptide of SEQ ID NO: 146 is the product of the Cb1581 gene in *Caldicellulosiruptor bescii*, where Cb stands for *Caldicellulosiruptor bescii*. The Cb1581 polypeptide is a small heat shock protein.

Cb1581 polypeptides of the present disclosure are thermophilic and thermostable. In some aspects, a Cb1581 polypeptide of the present disclosure has peak enzymatic hydrolysis of cellulose and/or hemicellulose-enhancing activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, a Cb1581 polypeptide of the present disclosure retains at least 60% of its initial rate of enzymatic hydrolysis of cellulose and/or hemicellulose-enhancing activity for a period of at least 24 hours when incubated at a temperature of about 55, 60, 65, 70, 75, 80, 85, or 90° C.

Polypeptides with Protein “Tags”

Polypeptides of the disclosure further include any of the recombinant polypeptides disclosed herein with a polypeptide “tag.” Polypeptide tags are polypeptides that may be attached to a protein of interest through gene cloning, and may be used to facilitate the purification, increase the solubility, and/or increase the stability of the “tagged” protein. Protein tags are well known in the art and include, without limitation, poly-histidine (e.g. 6 consecutive His-residues), glutathione S-transferase (GST), T7, FLAG, hemagglutinin (HA), MYC and maltose-binding protein (MBP) tags.

Production of Polypeptides

The polypeptides can be expressed in and purified from their native host, *Caldicellulosiruptor bescii*. Polypeptides may also be expressed in and purified from transgenic expression systems. Transgenic expression systems can be prokaryotic or eukaryotic. Transgenic host cells may include yeast and *E. coli*. Transgenic host cells may secrete the polypeptide out of the host cell. In certain embodiments, the isolated or recombinant polypeptide lacks a signal sequence. Methods for the production of recombinant polypeptides are further discussed infra.

Nucleic Acids of the Disclosure

The present disclosure further provides recombinant nucleic acids that encode any of the polypeptides disclosed herein. Nucleic acids that encode a polypeptide are also referred to herein as "genes". Methods for determining the relationship between a polypeptide and a nucleic acid that encodes the polypeptide are well known to one of skill in the art. Similarly, methods of determining the polypeptide sequence encoded by a polynucleotide sequence are well known to one of skill in the art. Due to codon degeneracy, multiple different nucleic acid sequences may encode the same polypeptide sequence.

As used herein, the terms, "nucleic acid" "polynucleotide", and variations thereof are generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

As used herein, more than one "nucleic acid" or "polynucleotide" may be present in a single contiguous polydeoxyribonucleotide chain/strand of DNA. Thus, a single strand of DNA (such as in a plasmid) may contain more than one "nucleic acid" or "polynucleotide", and thus, may contain sequences encoding more than one different polypeptide.

The nucleic acids may be synthesized, isolated, or manipulated using standard molecular biology techniques such as those described in Sambrook, J. et al. 2000. Molecular Cloning: A Laboratory Manual (Third Edition). Techniques may include cloning, expression of cDNA libraries, and amplification of mRNA or genomic DNA.

The nucleic acids of the present disclosure, or subsequences thereof, may be incorporated into a cloning vehicle comprising an expression cassette or vector. The cloning vehicle can be a viral vector, a plasmid, a phage, a phagemid, a cosmid, a fosmid, a bacteriophage, or an artificial chromosome. The viral vector can comprise an adenovirus vector, a retroviral vector, or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The nucleic acids may be operably linked to a promoter. The promoter can be a viral, bacterial, mammalian or plant promoter. The promoter can be a constitutive promoter, an inducible promoter, a tissue-specific promoter, or an environmentally regulated or a developmentally regulated promoter.

Nucleic Acids that Encode Cellulases

Cb1952 Polynucleotides

The present disclosure includes recombinant polynucleotides that encode a Cb1952 polypeptide of the disclosure. In some aspects, the disclosure includes recombinant polynucleotides that encode a polypeptide of SEQ ID NOs: 44, 114, 124, 126, 128, or 46.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 44, 114, 124, 126, 128, and 46. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 44, 114, 124, 126, 128, and 46.

In some aspects, the disclosure includes the recombinant polynucleotides of SEQ ID NOs: 45, 115, 125, 127, 129, and 47. The polynucleotide of SEQ ID NO: 45 encodes the polypeptide of SEQ ID NO: 44. The polynucleotide of SEQ ID NO: 115 encodes the polypeptide of SEQ ID NO: 45. The polynucleotide of SEQ ID NO: 47 encodes the polypeptide of SEQ ID NO: 46. The polynucleotide of SEQ ID NO: 125 encodes the polypeptide of SEQ ID NO: 124. The polynucleotide of SEQ ID NO: 127 encodes the polypeptide of SEQ ID NO: 126. The polynucleotide of SEQ ID NO: 129 encodes the polypeptide of SEQ ID NO: 128.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 45, 115, 125, 127, 129, and 47, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 44, 114, 124, 126, 128, and 46. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 45, 115, 125, 127, 129, and 47, and that encode a polypeptide that has cellulase activity and that has at least 60%, at least 65%, at least 70%, at least 75%, at least 80%, at least 85%, least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 44, 114, 124, 126, 128, and 46.

Polynucleotides of the disclosure further include recombinant polynucleotides that are complementary to polynucleotides that encode Cb1952 polypeptides disclosed herein.

Cb1953 Polynucleotides

The present disclosure includes recombinant polynucleotides that encode a Cb1953 polypeptide of the disclosure. In some aspects, the disclosure includes recombinant polynucleotides that encode a polypeptide of SEQ ID NOs: 60, 61, or 111.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 60, 61, and 111. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 60, 61, and 111.

In some aspects, the disclosure includes the recombinant polynucleotides of SEQ ID NOs: 62, 63, or 110. The polynucleotide of SEQ ID NO: 62 encodes the polypeptide of SEQ ID NO: 60. The polynucleotide of SEQ ID NO: 63 encodes the polypeptide of SEQ ID NO: 61. The polynucleotide of SEQ ID NO: 110 encodes the polypeptide of SEQ ID NO: 111.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 62, 63, and 110, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 60, 61, and 111. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 62, 63, or 110, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 60, 61, and 111.

Polynucleotides of the disclosure further include recombinant polynucleotides that are complementary to polynucleotides that encode Cb1953 polypeptides disclosed herein.

Cb1954 Polynucleotides

The present disclosure includes recombinant polynucleotides that encode a Cb1954 polypeptide of the disclosure. In some aspects, the disclosure includes recombinant polynucleotides that encode a polypeptide of SEQ ID NOs: 74, 121, or 76.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 74, 121, and 76. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 74, 121, and 76.

In some aspects, the disclosure includes the recombinant polynucleotides of SEQ ID NOs: 116, 75, or 77. The polynucleotide of SEQ ID NO: 116 encodes the polypeptide of SEQ ID NO: 74. The polynucleotide of SEQ ID NO: 75 encodes the polypeptide of SEQ ID NO: 121. The polynucleotide of SEQ ID NO: 77 encodes the polypeptide of SEQ ID NO: 76.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 116, 75, and 77, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 74, 121, and 76. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 116, 75, and 77, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 74, 121, and 76.

Polynucleotides of the disclosure further include recombinant polynucleotides that are complementary to polynucleotides that encode Cb1954 polypeptides disclosed herein.

Cb1946 Polynucleotides

The present disclosure includes recombinant polynucleotides that encode a Cb1946 polypeptide of the disclosure. In some aspects, the disclosure includes recombinant polynucleotides that encode a polypeptide of SEQ ID NOs: 86, 87, or 113.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 86, 87, and 113. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 86, 87, and 113.

In some aspects, the disclosure includes the recombinant polynucleotides of SEQ ID NOs: 88, 89, or 112. The polynucleotide of SEQ ID NO: 88 encodes the polypeptide of SEQ ID NO: 86. The polynucleotide of SEQ ID NO: 89 encodes the polypeptide of SEQ ID NO: 87. The polynucleotide of SEQ ID NO: 112 encodes the polypeptide of SEQ ID NO: 113.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 88, 89, and 112, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 86, 87, and 113. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 88, 89, or 112, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 86, 87, and 113.

Polynucleotides of the disclosure further include recombinant polynucleotides that are complementary to polynucleotides that encode Cb1946 polypeptides disclosed herein.

Cb629 Polynucleotides

The present disclosure includes recombinant polynucleotides that encode a Cb629 polypeptide of the disclosure. In some aspects, the disclosure includes recombinant polynucleotides that encode a polypeptide of SEQ ID NOs: 98, 119, or 100.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 98, 119, and 100. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 98, 119, and 100.

In some aspects, the disclosure includes the recombinant polynucleotides of SEQ ID NOs: 99, 120, or 101. The polynucleotide of SEQ ID NO: 99 encodes the polypeptide of SEQ ID NO: 98. The polynucleotide of SEQ ID NO: 120 encodes the polypeptide of SEQ ID NO: 119. The polynucleotide of SEQ ID NO: 101 encodes the polypeptide of SEQ ID NO: 100.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 99, 120, or 101, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 98, 119, and 100. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 99, 120, or 101, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 98, 119, and 100.

Polynucleotides of the disclosure further include recombinant polynucleotides that are complementary to polynucleotides that encode Cb629 polypeptides disclosed herein.

Cb486 Polynucleotides

The present disclosure includes recombinant polynucleotides that encode a Cb486 polypeptide of the disclosure. In some aspects, the disclosure includes recombinant polynucleotides that encode the polypeptide of SEQ ID NO: 106.

Polynucleotides of the disclosure include recombinant polynucleotides that encode a polypeptide that has cellulase activity and that has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 106. Polynucleotides of the disclosure also include recombinant polynucleotides that encode a polypeptide that has cellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 106.

In some aspects, the disclosure includes the recombinant polynucleotide of SEQ ID NO: 107. The polynucleotide of SEQ ID NO: 107 encodes the polypeptide of SEQ ID NO: 106.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 107, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 106. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 107, and that encode a polypeptide that has cellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 106.

Polynucleotides of the disclosure further include recombinant polynucleotides that are complementary to polynucleotides that encode Cb486 polypeptides disclosed herein.

Nucleic Acids that Encode Hemicellulases

The present disclosure provides nucleotide sequences encoding the hemicellulose-degrading enzymes Cb193 (SEQ ID NO: 4), Cb195 (SEQ ID NO: 8), Cb1172 (SEQ ID NO: 14), Cb909 (SEQ ID NO: 20), Cb2487 (SEQ ID NO: 28), and Cb162 (SEQ ID NO: 34), or subsequences thereof.

The disclosure also provides for nucleotide sequences having at least about 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the nucleic acid sequences encoding Cb193, Cb195, Cb1172, Cb909, Cb2487, and Cb162.

Nucleotide sequences of the present disclosure may encode polypeptides with one or more glycoside hydrolase (GH) domains. Nucleotide sequences may also encode polypeptides with one or more carbohydrate binding modules (CBM). The CBM modules may interrupt a GH domain or be located in between two GH domains. Nucleotide sequences may also encode polypeptides with an acetyl xylan esterase domain. In certain embodiments, the GH, CBM and/or acetyl xylan esterase domain sequence is conserved in nucleotide variants.

Cb193 Polynucleotides

The present disclosure includes recombinant polynucleotides that encode a Cb193 polypeptide of the disclosure. In some aspects, the disclosure includes recombinant polynucleotides that encode a polypeptide of SEQ ID NOs: 3 or 37.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 3 and/or 37. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of any of the polypeptides of SEQ ID NOs: 3 and/or 37.

In some aspects, the disclosure includes the recombinant polynucleotides of SEQ ID NOs: 4 or 38. The polynucleotide of SEQ ID NO: 4 encodes the polypeptide of SEQ ID NO: 3. The polynucleotide of SEQ ID NO: 38 encodes the polypeptide of SEQ ID NO: 37.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to any of the sequences of SEQ ID NOs: 4 and/or 38, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 3 and/or 37. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of any of the sequences of SEQ ID NOs: 4 or 38, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of any of the polypeptides of SEQ ID NOs: 3 and/or 37.

Polynucleotides of the disclosure further include recombinant polynucleotides that are complementary to polynucleotides that encode Cb193 polypeptides disclosed herein.

Cb195 Polynucleotides

The present disclosure includes recombinant polynucleotides that encode a Cb195 polypeptide of the disclosure. In some aspects, the disclosure includes a recombinant polynucleotide that encodes a polypeptide of SEQ ID NO: 7.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 7. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 7.

In some aspects, the disclosure includes the recombinant polynucleotide of SEQ ID NO: 8. The polynucleotide of SEQ ID NO: 8 encodes the polypeptide of SEQ ID NO: 7.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 8, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 7. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 8, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence the polypeptide of SEQ ID NO: 7.

Polynucleotides of the disclosure further include recombinant polynucleotides that are complementary to polynucleotides that encode Cb195 polypeptides disclosed herein.

Cb1172 Polynucleotides

The present disclosure includes recombinant polynucleotides that encode a Cb1172 polypeptide of the disclosure. In some aspects, the disclosure includes a recombinant polynucleotide that encodes a polypeptide of SEQ ID NO: 13.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 13. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 13.

In some aspects, the disclosure includes the recombinant polynucleotide of SEQ ID NO: 14. The polynucleotide of SEQ ID NO: 14 encodes the polypeptide of SEQ ID NO: 13.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 14, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 13. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 14, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence the polypeptide of SEQ ID NO: 13.

Polynucleotides of the disclosure further include recombinant polynucleotides that are complementary to polynucleotides that encode Cb1172 polypeptides disclosed herein.

Cb909 Polynucleotides

The present disclosure includes recombinant polynucleotides that encode a Cb909 polypeptide of the disclosure. In some aspects, the disclosure includes a recombinant polynucleotide that encodes a polypeptide of SEQ ID NO: 19.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 19. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 19.

In some aspects, the disclosure includes the recombinant polynucleotide of SEQ ID NO: 20. The polynucleotide of SEQ ID NO: 20 encodes the polypeptide of SEQ ID NO: 19.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 20, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 19. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 20, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence the polypeptide of SEQ ID NO: 19.

Polynucleotides of the disclosure further include recombinant polynucleotides that are complementary to polynucleotides that encode Cb909 polypeptides disclosed herein.

Cb2487 Polynucleotides

The present disclosure includes recombinant polynucleotides that encode a Cb2487 polypeptide of the disclosure. In some aspects, the disclosure includes a recombinant polynucleotide that encodes a polypeptide of SEQ ID NO: 27.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 27. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 27.

In some aspects, the disclosure includes the recombinant polynucleotide of SEQ ID NO: 28. The polynucleotide of SEQ ID NO: 28 encodes the polypeptide of SEQ ID NO: 27.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 28, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 27. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 28, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence the polypeptide of SEQ ID NO: 27.

Polynucleotides of the disclosure further include recombinant polynucleotides that are complementary to polynucleotides that encode Cb2487 polypeptides disclosed herein.

Cb162 Polynucleotides

The present disclosure includes recombinant polynucleotides that encode a Cb162 polypeptide of the disclosure. In some aspects, the disclosure includes a recombinant polynucleotide that encodes a polypeptide of SEQ ID NO: 33.

Polynucleotides of the disclosure include recombinant polynucleotides that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 33. Polynucleotides of the disclosure also include recombinant polynucleotides that encode a polypeptide that has hemicellulase activity and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 33.

In some aspects, the disclosure includes the recombinant polynucleotide of SEQ ID NO: 34. The polynucleotide of SEQ ID NO: 34 encodes the polypeptide of SEQ ID NO: 33.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 34, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 33. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 34, and that encode a polypeptide that has hemicellulase activity and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence the polypeptide of SEQ ID NO: 33.

Polynucleotides of the disclosure further include recombinant polynucleotides that are complementary to polynucleotides that encode Cb162 polypeptides disclosed herein.

Nucleic Acids that Encode Polypeptides that Enhance Enzymatic Hydrolysis of Cellulose and/or Hemicellulose The present disclosure includes recombinant polynucleotides that encode a Cb1581 polypeptide of the disclosure. In some aspects, the disclosure includes recombinant polynucleotides that encode the polypeptide of SEQ ID NO: 146.

Polynucleotides of the disclosure include recombinant polynucleotides that encode a polypeptide that enhances enzymatic hydrolysis of cellulose and/or hemicellulose and that has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 146. Polynucleotides of the disclosure also include recombinant polynucleotides that encode a polypeptide that enhances enzymatic hydrolysis of cellulose and/or hemicellulose and that has at least 10, at least 20, at least 30, at least 40, at least 50, at least 60, at least 80, at least 100, at least 120, at least 140, at least 160, at least 180, or at least 200 consecutive amino acids of the polypeptide of SEQ ID NO: 146.

In some aspects, the disclosure includes the recombinant polynucleotide of SEQ ID NO: 147. The polynucleotide of SEQ ID NO: 147 encodes the polypeptide of SEQ ID NO: 146.

Polynucleotides of the disclosure also include recombinant polynucleotides having at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of SEQ ID NO: 147, and that encode a polypeptide that enhances enzymatic hydrolysis of cellulose and/or hemicellulose and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 146. Polynucleotides of the disclosure also include recombinant polynucleotides that have at least 10, at least 12, at least 14, at least 16, at least 18, at least 20, at least 22, at least 24, at least 26, at least 28, or at least 30 consecutive nucleotides of the sequence of SEQ ID NO: 147, and that encode a polypeptide that enhances enzymatic hydrolysis of cellulose and/or hemicellulose and that has at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99%, or 100% identity to the sequence of the polypeptide of SEQ ID NO: 146.

Polynucleotides of the disclosure further include recombinant polynucleotides that are complementary to polynucleotides that encode Cb1581 polypeptides disclosed herein.

Recombinant Polynucleotides Encoding Polypeptides with Protein “Tags”

Further disclosed herein are recombinant polynucleotides that encode polypeptides of the disclosure with a polypeptide “tag.” Polynucleotides that encode a polypeptide “tag” may be added to a polynucleotide encoding a polypeptide of the disclosure by standard molecular biology cloning techniques. (See, for example, Sambrook et al., Molecular Cloning: A Laboratory Manual, 3rd Ed., Vol. 1-3, Cold Spring Harbor Laboratory, Cold Spring Harbor, N.Y. (2001)).

Variants, Sequence Identity, and Sequence Similarity

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller (1988) CABIOS 4:11 17; the local homology algorithm of Smith et al. (1981) Adv. Appl. Math. 2:482; the homology alignment algorithm of Needleman and Wunsch (1970) J. Mol. Biol. 48:443 453; the search-for-similarity-method of Pearson and Lipman (1988) Proc. Natl. Acad. Sci. 85:2444 2448; the algorithm of Karlin and Altschul (1990) Proc. Natl. Acad. Sci. USA 872264, modified as in Karlin and Altschul (1993) Proc. Natl. Acad. Sci. USA 90:5873 5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237 244 (1988); Higgins et al. (1989) CABIOS 5:151 153; Corpet et al. (1988) Nucleic Acids Res. 16:10881 90; Huang et al. (1992) CABIOS 8:155 65; and Pearson et al. (1994) Meth. Mol. Biol. 24:307 331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used. BLAST is available, for example, from the National Center for Biotechnology Information (NCBI). Alignment may also be performed manually by inspection.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

The functional activity of enzyme variants can be evaluated using standard molecular biology techniques including thin layer chromatography or a reducing sugar assay. Enzymatic activity can be determined using cellulose, hemicellulose or an artificial substrate.

Compositions

The present disclosure further includes compositions containing one or more recombinant polypeptides disclosed herein. In some aspects, provided herein are compositions containing two or more recombinant polypeptides disclosed herein. Compositions containing two or more recombinant polypeptides may be referred to as a "cocktail" of polypeptides and/or enzymes.

In some aspects, disclosed herein are compositions that contain one or more recombinant polypeptides disclosed herein, wherein the one or more recombinant polypeptides are selected from Cb1952, Cb1953, Cb1954, Cb1946, Cb629 or Cb486 polypeptides.

In some aspects, disclosed herein are compositions that contain two or more recombinant polypeptides disclosed herein, wherein the two or more recombinant polypeptides are selected from Cb1952, Cb1953, Cb1954, Cb1946, Cb629 or Cb486 polypeptides.

In some aspects, disclosed herein are compositions that contain three or more recombinant polypeptides disclosed herein, wherein the three or more recombinant polypeptides are selected from Cb1952, Cb1953, Cb1954, Cb1946, Cb629 or Cb486 polypeptides.

In some aspects, disclosed herein are compositions that contain four or more recombinant polypeptides disclosed herein, wherein the four or more recombinant polypeptides are selected from Cb1952, Cb1953, Cb1954, Cb1946, Cb629 or Cb486 polypeptides.

In some aspects, disclosed herein are compositions that contain five or more recombinant polypeptides disclosed herein, wherein the five or more recombinant polypeptides are selected from Cb1952, Cb1953, Cb1954, Cb1946, Cb629 or Cb486 polypeptides.

In some aspects, disclosed herein are compositions that contain six or more recombinant polypeptides disclosed herein, wherein the six or more recombinant polypeptides are selected from Cb1952, Cb1953, Cb1954, Cb1946, Cb629 or Cb486 polypeptides.

In some aspects, disclosed herein are compositions that contain one or more recombinant polypeptides disclosed herein, wherein the one or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain two or more recombinant polypeptides disclosed herein, wherein the two or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain three or more recombinant polypeptides disclosed herein, wherein the three or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain four or more recombinant polypeptides disclosed herein, wherein the four or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain five or more recombinant polypeptides disclosed herein, wherein the five or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain six or more recombinant polypeptides disclosed herein, wherein the six or more recombinant polypeptides are selected from Cb1952, Cb1953, Cb1954, Cb1946, Cb629 and Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, disclosed herein are compositions that contain two or more recombinant polypeptides disclosed herein, wherein the two or more polypeptides are selected from the polypeptides of SEQ ID NOs: 46, 76, 100, 106, 111, and 113.

In some aspects, disclosed herein are compositions that contain three or more recombinant polypeptides disclosed herein, wherein the three or more polypeptides are selected from the polypeptides of SEQ ID NOs: 46, 76, 100, 106, 111, and 113.

In some aspects, disclosed herein are compositions that contain four or more recombinant polypeptides disclosed herein, wherein the four or more polypeptides are selected from the polypeptides of SEQ ID NOs: 46, 76, 100, 106, 111, and 113.

In some aspects, disclosed herein are compositions that contain five or more recombinant polypeptides disclosed herein, wherein the five or more polypeptides are selected from the polypeptides of SEQ ID NOs: 46, 76, 100, 106, 111, and 113.

In some aspects, disclosed herein are compositions that contain six recombinant polypeptides disclosed herein, wherein the six polypeptides are the polypeptides of SEQ ID NOs: 46, 76, 100, 106, 111, and 113.

Any of the compositions disclosed herein containing one or more recombinant cellulases disclosed herein may further contain one or more recombinant hemicellulases. Hemicellulases include, without limitation, endoxylanases, exoxylanases, α-arabinofuranosidases, glucuronidases, β-xylosidases, and acetyl xylan esterases. In some aspects, hemicellulases include the polypeptides that contain the amino acid sequence of any of SEQ ID NOs: 3, 7, 13, 19, 27, 33, or 37. Any of the compositions disclosed herein containing one or more recombinant cellulases disclosed herein may further contain an enzyme that enhances enzymatic hydrolysis of cellulose and/or hemicellulose. In one aspect, an enzyme that enhances enzymatic hydrolysis of cellulose and/or hemicellulose contains the amino acid sequence of SEQ ID NO: 146.

The present disclosure provides for compositions including the recombinant amino acid sequence of Cb193 alone or in combination with one or more of the recombinant amino acid sequences of Cb195, Cb1172, Cb909, Cb2487 and Cb162. The present disclosure also provides for compositions including the recombinant amino acid sequence of Cb195 alone or in combination with one or more of the recombinant amino acid sequences of Cb193, Cb1172, Cb909, Cb2487 and Cb162. The present disclosure also provides for compositions including the recombinant amino acid sequence of Cb1172 alone or in combination with one or more of the recombinant amino acid sequences of Cb193, Cb195, Cb909, Cb2487 and Cb162. The present disclosure also provides for compositions including the recombinant amino acid sequence of Cb909 alone or in combination with one or more of the recombinant amino acid sequences of Cb193, Cb195, Cb1172, Cb2487 and Cb162. The present disclosure also provides for compositions including the recombinant amino acid sequence of Cb2487 alone or in combination with one or more of the recombinant amino acid sequences of Cb193, Cb195, Cb1172, Cb909 and Cb162. The present disclosure also provides for compositions including the recombinant amino acid sequence of Cb162 alone or in combination with one or more of the recombinant amino acid sequences of Cb193, Cb195, Cb1172, Cb2487 and Cb909.

The present disclosure also provides for compositions including two or more of the recombinant amino acid sequences of Cb193, Cb195, Cb1172, Cb909, Cb2487, and Cb162. One composition includes the recombinant amino acid sequences of Cb193, Cb195, Cb1172, Cb909, Cb2487, and Cb162. Another composition includes the recombinant amino acid sequences of Cb195, Cb1172, Cb909, Cb2487, and Cb162. Another composition includes the recombinant amino acid sequences of Cb193, Cb1172, Cb909, Cb2487, and Cb162. Another composition includes the recombinant amino acid sequences of Cb193, Cb195, Cb909, Cb2487, and Cb162. Another composition includes the recombinant amino acid sequences of Cb193, Cb195, Cb1172, Cb2487, and Cb162. Another composition includes the recombinant amino acid sequences of Cb193, Cb195, Cb1172, Cb909, and Cb162. Another composition includes the recombinant amino acid sequences of Cb193, Cb195, Cb1172, Cb909, and Cb2487. Another composition includes the recombinant amino acid sequences of Cb1172, Cb909, Cb2487, and Cb162. Another composition includes the recombinant amino acid sequences of Cb195, Cb909, Cb2487, and Cb162. Another composition includes the recombinant amino acid sequences of Cb195, Cb1172, Cb2487, and Cb162. Another composition includes the recombinant amino acid sequences of Cb195, Cb1172, Cb909, and Cb162. Another composition includes the recombinant amino acid sequences of Cb195, Cb1172, Cb909, and Cb2487. Another composition includes the recombinant amino acid sequences of Cb193, Cb909, Cb2487, and Cb162. Another composition includes the recombinant amino acid sequences of Cb193, Cb1172, Cb2487, and Cb162. Another composition includes the recombinant amino acid sequences of Cb193, Cb1172, Cb909, and Cb162. Another composition includes the recombinant amino acid sequences of Cb193, Cb1172, Cb909, and Cb2487. Another composition includes the recombinant amino acid sequences of Cb193, Cb195, Cb2487, and Cb162. Another composition includes the recombinant amino acid sequences of Cb193, Cb195, Cb909, and Cb162. Another composition includes the recombinant amino acid sequences of Cb193, Cb195, Cb909, and Cb2487. Another composition includes the recombinant amino acid sequences of Cb193, Cb195, Cb1172, and Cb162. Another composition includes the recombinant amino acid sequences of Cb193, Cb195, Cb1172, and Cb2487. Another composition includes the recombinant amino acid sequences of Cb193, Cb195, Cb1172, and Cb909. Another composition includes the recombinant amino acid sequences of Cb909, Cb2487, and Cb162. Another composition includes the recombinant amino acid sequences of Cb1172, Cb2487, and Cb162. Another composition includes the recombinant amino acid sequences of Cb1172, Cb909, and Cb162. Another composition includes the recombinant amino acid sequences of Cb1172, Cb909, and Cb2487. Another composition includes the recombinant amino acid sequences of Cb195, Cb2487, and Cb162. Another composition includes the recombinant amino acid sequences of Cb195, Cb909, and Cb162. Another composition includes the recombinant amino acid sequences of Cb195, Cb909, and Cb2487. Another composition includes the recombinant amino acid sequences of Cb195, Cb1172, and Cb162. Another composition includes the recombinant amino acid sequences of Cb195, Cb1172, and Cb2487. Another composition includes the recombinant amino acid sequences of Cb195, Cb1172, and Cb909. Another composition includes the recombinant amino acid sequences of Cb193, Cb2487, and Cb162. Another composition includes the recombinant amino acid sequences of Cb193, Cb909, and Cb162. Another composition includes the recombinant amino acid sequences of Cb193, Cb909, and Cb2487. Another composition includes the recombinant amino acid sequences of Cb193, Cb1172, and Cb162. Another composition includes the recombinant amino acid sequences of Cb193, Cb1172, and Cb2487. Another composition includes the recombinant amino acid sequences of Cb193, Cb1172, and Cb909. Another composition includes the recombinant amino acid sequences of Cb193, Cb195, and Cb162. Another composition includes the recombinant amino acid sequences of Cb193, Cb195, and Cb2487. Another composition includes the recombinant amino acid sequences of Cb193, Cb195, and Cb909. Another composition includes the recombinant amino acid sequences of Cb193, Cb195, and Cb1172. Another composition includes the recombinant amino acid sequences of Cb195 and Cb909. Another composition includes the recombinant amino acid sequences of Cb193 and Cb195. Another composition includes the recombinant amino acid sequences of Cb193 and Cb1172. Another composition includes the recombinant amino acid sequences of Cb193 and Cb909. Another composition includes the recombinant amino acid sequences of Cb193 and Cb2487. Another composition includes the recombinant amino acid sequences of Cb193 and Cb162. Another composition includes the recombinant amino acid sequences of Cb195 and Cb1172. Another composition includes the recombinant amino acid sequences of Cb195 and Cb2487. Another composition includes the recombinant amino acid sequences of Cb195 and Cb162. Another composition includes the recombinant amino acid sequences of Cb1172 and Cb909. Another composition includes the recombinant amino acid sequences of Cb1172 and Cb2487. Another composition includes the recombinant amino acid sequences of Cb1172 and Cb162. Another composition includes the recombinant amino acid sequences of Cb909 and Cb2487. Another composition includes the recombinant amino acid sequences of Cb909 and Cb162. Another composition includes the recombinant amino acid sequences of Cb2487 and Cb162.

Compositions may include a transgenic host cell comprising one or more of the amino acid sequences encoding Cb193, Cb195, Cb1172, Cb2487, Cb909, and Cb162. The one or more polypeptides may be secreted from the transgenic host cell.

The present disclosure provides for compositions including the recombinant nucleotide sequence encoding Cb193 alone or in combination with one or more of the recombinant nucleotide sequences encoding Cb195, Cb1172, Cb909, Cb2487 and Cb162. The present disclosure also provides for compositions including the recombinant nucleotide sequence encoding Cb195 alone or in combination with one or more of the recombinant nucleotide sequences encoding Cb193, Cb1172, Cb909, Cb2487 and Cb162. The present disclosure also provides for compositions including the recombinant nucleotide sequence encoding Cb1172 alone or in combination with one or more of the recombinant nucleotide sequences encoding Cb193, Cb195, Cb909, Cb2487 and Cb162. The present disclosure also provides for compositions including the recombinant nucleotide sequence encoding Cb909 alone or in combination with one or more of the recombinant nucleotide sequences encoding Cb193, Cb195, Cb1172, Cb2487 and Cb162. The present disclosure also provides for compositions including the recombinant nucleotide sequence encoding Cb2487 alone or in combination with one or more of the recombinant nucleotide sequences encoding Cb193, Cb195, Cb1172, Cb909 and Cb162. The present disclosure also provides for compositions including the recombinant nucleotide sequence encoding Cb162 alone or in combination with one or more of the recombinant nucleotide sequences encoding Cb193, Cb195, Cb1172, Cb2487 and Cb909.

The present disclosure also provides for compositions including two or more of the recombinant nucleotide sequences encoding Cb162, Cb193, Cb195, Cb1172, Cb2487 and Cb909. Compositions may include vectors comprising the nucleotide sequence encoding one or more of Cb193, Cb195, Cb1172, Cb2487, Cb909, and Cb162.

Any of the compositions disclosed herein containing one or more recombinant hemicellulases disclosed herein may further contain one or more recombinant cellulases. In some aspects, cellulases include the polypeptides that contain the amino acid sequence of any of SEQ ID NOs: 44, 114, 124, 126, 128, 46, 60, 61, 111, 74, 121, 76, 86, 87, 113, 98, 119, 100, and 106. Any of the compositions disclosed herein containing one or more recombinant hemicellulases disclosed herein may further contain an enzyme that enhances enzymatic hydrolysis of cellulose and/or hemicellulose. In one aspect, an enzyme that enhances enzymatic hydrolysis of cellulose and/or hemicellulose contains the amino acid sequence of SEQ ID NO: 146.

Compositions disclosed herein containing one or more recombinant polypeptides disclosed herein may contain the proteins in any form. In some aspects, the polypeptides are in a liquid solution. In some aspects, the polypeptides are lyophilized. In some aspects, additional material is included in compositions containing one or more recombinant polypeptides disclosed herein to help preserve the stability of the polypeptides. In some aspects, additional material is included in compositions containing one or more recombinant polypeptides disclosed herein to help preserve the stability of the polypeptides, wherein the additional material is additional polypeptides. In some aspects, the compositions are stable for at least six months. In some aspects, the compositions are stable for at least one year.

Host Cells

The present disclosure further provides host cells that contain a recombinant nucleic acid encoding a recombinant polypeptide of the disclosure. In some aspects, the disclosure provides host cells containing two or more recombinant nucleic acids encoding two or more recombinant polypeptides of the disclosure.

"Host cell" and "host microorganism" are used interchangeably herein to refer to a living biological cell that can be transformed via insertion of recombinant DNA or RNA. Such recombinant DNA or RNA can be in an expression vector. A host organism or cell as described herein may be a prokaryotic organism or a eukaryotic cell.

Any prokaryotic or eukaryotic host cell may be used in the present disclosure so long as it remains viable after being transformed with a sequence of nucleic acids. Preferably, the host cell is not adversely affected by the transduction of the necessary nucleic acid sequences, the subsequent expression of the proteins (e.g., transporters), or the resulting intermediates.

In some aspects, the host cell is a prokaryotic cell. Any prokaryotic cell suitable for expression of a recombinant polypeptide may be used to produce recombinant polypeptides of the present disclosure. Prokaryotic host cells of the disclosure include, without limitation, *Escherichia coli, Bacillus subtilis, Corynebacterium* spp., *Pseudomonas* spp., *Proteus* spp., *Ralstonia* spp., *Streptomyces* spp., *Staphylococcus* spp., *Lactococcus* spp., *Zymomonas mobilis, Clostridium* spp., *Thermoanaerobacterium* spp., *Caldicellulosiruptor* spp. and *Klebsiella* spp.

In some aspects, the host cell is a eukaryotic cell. Any eukaryotic cell suitable for expression of a recombinant polypeptide may be used to produce recombinant polypeptides of the present disclosure. Suitable eukaryotic cells include, but are not limited to, fungal, plant, insect or mammalian cells.

In certain aspects, the host cell is a fungal strain. "Fungi" as used herein includes the phyla Ascomycota, Basidiomycota, Chytridiomycota, and Zygomycota as well as the Oomycota and all mitosporic fungi.

In certain embodiments, the fungal host is a yeast strain. "Yeast" as used herein refers to any single cell fungus that reproduces asexually by budding or division, and it includes fungi of both Ascomycota and Basidiomycota.

In certain embodiments, the fungal host is of the genus *Saccharomyces, Schizosaccharomyces, Leucosporidium, Dekkera/Brettanomyces, Zygosaccharomyces, Yarrowia, Hansenula, Kluyveromyces, Scheffersomyces* (*Pichia*), *Neurospora* or *Candida.*

In some aspects, the host cell is a thermophilic microorganism.

The host cells of the present disclosure may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

"Recombinant nucleic acid" or "heterologous nucleic acid" or "recombinant polynucleotide", "recombinant nucleotide" or "recombinant DNA" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; (c) the sequence of nucleic acids contains two or more subsequences that are not found in the same relationship to each other in nature; (d) the polynucleotide is isolated from an organism in which the polynucleotide naturally occurs; or (e) the polynucleotide is synthetically prepared. For example, regarding instance (c), a recombinant nucleic acid sequence will have two or more sequences from unrelated genes arranged to make a new functional nucleic acid. Specifically, the present disclosure describes the introduction of an expression vector into a host cell, wherein the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. As used herein, the term "recombinant polypeptide" refers to a polypeptide generated from a "recombinant nucleic acid" or "heterologous nucleic acid" or "recombinant polynucleotide", "recombinant nucleotide" or "recombinant DNA" as described above.

In some aspects, the host cell naturally produces a protein encoded by a polynucleotide of the disclosure. A gene encoding the desired protein may be heterologous to the host cell or the gene may be endogenous to the host cell but is operatively linked to a heterologous promoters and/or control region which results in the higher expression of the gene in the host cell.

Host Cell Components

In some aspects, host cells disclosed herein contain one or more recombinant nucleic acids, wherein the recombinant nucleic acids encode one or more polypeptides selected from Cb1952, Cb1953, Cb1954, Cb1946, Cb629, or Cb486 polypeptides.

In some aspects, host cells disclosed herein contain two or more recombinant nucleic acids, wherein the recombinant nucleic acids encode two or more polypeptides selected from Cb1952, Cb1953, Cb1954, Cb1946, Cb629, or Cb486 polypeptides.

In some aspects, host cells disclosed herein contain three or more recombinant nucleic acids, wherein the recombinant nucleic acids encode three or more polypeptides selected from Cb1952, Cb1953, Cb1954, Cb1946, Cb629, or Cb486 polypeptides.

In some aspects, host cells disclosed herein contain four or more recombinant nucleic acids, wherein the recombinant nucleic acids encode four or more polypeptides selected from Cb1952, Cb1953, Cb1954, Cb1946, Cb629, or Cb486 polypeptides.

In some aspects, host cells disclosed herein contain five or more recombinant nucleic acids, wherein the recombinant nucleic acids encode five or more polypeptides selected from Cb1952, Cb1953, Cb1954, Cb1946, Cb629, or Cb486 polypeptides.

In some aspects, host cells disclosed herein contain six or more recombinant nucleic acids, wherein the recombinant nucleic acids encode six or more polypeptides selected from Cb1952, Cb1953, Cb1954, Cb1946, Cb629, and Cb486 polypeptides.

In some aspects, host cells disclosed herein contain one or more recombinant nucleic acids, wherein the recombinant nucleic acids encode one or more recombinant polypeptides disclosed herein, wherein the one or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain two or more recombinant nucleic acids, wherein the recombinant nucleic acids encode two or more recombinant polypeptides disclosed herein, wherein the two or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain three or more recombinant nucleic acids, wherein the recombinant nucleic acids encode three or more recombinant polypeptides disclosed herein, wherein the three or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain four or more recombinant nucleic acids, wherein the recombinant nucleic acids encode four or more recombinant polypeptides disclosed herein, wherein the four or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain five or more recombinant nucleic acids, wherein the recombinant nucleic acids encode five or more recombinant polypeptides disclosed herein, wherein the five or more recombinant polypeptides are selected from Cb1952, Cb1953, Cb1954, Cb1946, Cb629 or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain six or more recombinant nucleic acids, wherein the recombinant nucleic acids encode six or more recombinant polypeptides disclosed herein, wherein the six or more recombinant polypeptides are selected from Cb1952, Cb1953, Cb1954, Cb1946, Cb629 and Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106.

In some aspects, host cells disclosed herein contain two or more recombinant nucleic acids encoding two or more recombinant polypeptides disclosed herein, wherein the two or more polypeptides are selected from the polypeptides of SEQ ID NOs: 46, 76, 100, 106, 111, and 113.

In some aspects, host cells disclosed herein contain three or more recombinant nucleic acids encoding three or more recombinant polypeptides disclosed herein, wherein the three or more polypeptides are selected from the polypeptides of SEQ ID NOs: 46, 76, 100, 106, 111, and 113.

In some aspects, host cells disclosed herein contain four or more recombinant nucleic acids encoding four or more recombinant polypeptides disclosed herein, wherein the four or more polypeptides are selected from the polypeptides of SEQ ID NOs: 46, 76, 100, 106, 111, and 113.

In some aspects, host cells disclosed herein contain five or more recombinant nucleic acids encoding five or more recombinant polypeptides disclosed herein, wherein the five or more polypeptides are selected from the polypeptides of SEQ ID NOs: 46, 76, 100, 106, 111, and 113.

In some aspects, host cells disclosed herein contain six recombinant nucleic acids encoding six recombinant polypeptides disclosed herein, wherein the six polypeptides are the polypeptides of SEQ ID NOs: 46, 76, 100, 106, 111, and 113.

In some aspects, host cells disclosed herein contain one or more recombinant nucleic acids, wherein the recombinant nucleic acids encode one or more recombinant polypeptides disclosed herein, wherein the one or more recombinant polypeptides are selected from Cb1952, Cb1953, Cb1954, Cb1946, Cb629 or Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain two or more recombinant nucleic acids, wherein the recombinant nucleic acids encode two or more recombinant polypeptides disclosed herein, wherein the two or more recombinant polypeptides are selected from Cb1952, Cb1953, Cb1954, Cb1946, Cb629 or Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain three or more recombinant nucleic acids, wherein the recombinant nucleic acids encode three or more recombinant polypeptides disclosed herein, wherein the three or more recombinant polypeptides are selected from Cb1952, Cb1953, Cb1954, Cb1946, Cb629 or Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain four or more recombinant nucleic acids, wherein the recombinant nucleic acids encode four or more recombinant polypeptides disclosed herein, wherein the four or more recombinant polypeptides are selected from Cb1952, Cb1953, Cb1954, Cb1946, Cb629 or Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain five or more recombinant nucleic acids, wherein the recombinant nucleic acids encode five or more recombinant polypeptides disclosed herein, wherein the five or more recombinant polypeptides are selected from Cb1952, Cb1953, Cb1954, Cb1946, Cb629 or Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain six or more recombinant nucleic acids, wherein the recombinant nucleic acids encode six or more recombinant polypeptides disclosed herein, wherein the six or more recombinant polypeptides are selected from Cb1952, Cb1953, Cb1954, Cb1946, Cb629 and Cb486 polypeptides, and wherein the recombinant nucleic acid encoding a Cb1952 polypeptide is selected from the polynucleotides of SEQ ID NOs: 45, 115, 125, 127, 129, and 47, wherein the recombinant nucleic acid encoding a Cb1953 polypeptide is selected from the polynucleotides of SEQ ID NOs: 62, 63, and 110, wherein the recombinant nucleic acid encoding a Cb1954 polypeptide is selected from the polynucleotides of SEQ ID NOs: 116, 75, and 77, wherein the recombinant nucleic acid encoding a Cb1946 polypeptide is selected from the polynucleotides of SEQ ID NOs: 88, 89, and 112, wherein the recombinant nucleic acid encoding a Cb629 polypeptide is selected from the polynucleotides of SEQ ID NOs: 99, 120, and 101, and wherein the recombinant nucleic acid encoding a Cb486 polypeptide is the polynucleotide of SEQ ID NO: 107.

In some aspects, host cells disclosed herein contain two or more recombinant nucleic acids encoding two or more recombinant polypeptides disclosed herein, wherein the two or more recombinant nucleic acids are selected from the polynucleotides of SEQ ID NOs: 47, 110, 77, 112, 101, and 107.

In some aspects, host cells disclosed herein contain three or more recombinant nucleic acids encoding three or more recombinant polypeptides disclosed herein, wherein the three or more recombinant nucleic acids are selected from the polynucleotides of SEQ ID NOs: 47, 110, 77, 112, 101, and 107.

In some aspects, host cells disclosed herein contain four or more recombinant nucleic acids encoding four or more recombinant polypeptides disclosed herein, wherein the four or more recombinant nucleic acids are selected from the polynucleotides of SEQ ID NOs: 47, 110, 77, 112, 101, and 107.

In some aspects, host cells disclosed herein contain five or more recombinant nucleic acids encoding five or more recombinant polypeptides disclosed herein, wherein the five or more recombinant nucleic acids are selected from the polynucleotides of SEQ ID NOs: 47, 110, 77, 112, 101, and 107.

In some aspects, host cells disclosed herein contain six recombinant nucleic acids encoding six recombinant polypeptides disclosed herein, wherein the six recombinant nucleic acids are the polynucleotides of SEQ ID NOs: 47, 110, 77, 112, 101, and 107.

Any of the host cells disclosed herein containing one or more recombinant nucleic acids encoding one or more recombinant cellulases disclosed herein may further contain one or more recombinant nucleic acids encoding one or more recombinant hemicellulases. In some aspects, polynucleotides that encode hemicellulases include nucleic acids that contain the polynucleotide sequence of any of SEQ ID NOs: 4, 8, 14, 20, 28, 34, or 38. Any of the host cells disclosed herein containing one or more recombinant cellulases disclosed herein may further contain an enzyme that enhances enzymatic hydrolysis of cellulose and/or hemicellulose. In one aspect, an enzyme that enhances enzymatic hydrolysis of cellulose and/or hemicellulose contains the amino acid sequence of SEQ ID NO: 146.

The disclosure further provides for a transformed transgenic host cell comprising one or more of the nucleic acids encoding Cb193, Cb195, Cb1172, Cb2487, Cb909, and Cb162. The transformed cell can be, without limitation, a bacterial cell, a mammalian cell, a fungal cell, a yeast cell, an insect cell, or a plant cell. In certain embodiments, the transformed cell is *E. coli*. In certain embodiments, the transformed cell is a thermophilic microorganism.

Any of the host cells disclosed herein containing one or more recombinant nucleic acids encoding one or more recombinant hemicellulases disclosed herein may further contain one or more recombinant nucleic acids encoding one or more recombinant cellulases. In some aspects, polynucleotides that encode cellulases include nucleic acids that contain the polynucleotide sequence of any of SEQ ID NOs: 44, 114, 124, 126, 128, 46, 60, 61, 111, 74, 121, 76, 86, 87, 113, 98, 119, 100, and 106. Any of the host cells disclosed herein containing one or more recombinant hemicellulases disclosed herein may further contain an enzyme that enhances enzymatic hydrolysis of cellulose and/or hemicellulose. In one aspect, an enzyme that enhances enzymatic hydrolysis of cellulose and/or hemicellulose contains the amino acid sequence of SEQ ID NO: 146.

Methods of Producing and Culturing Host Cells of the Disclosure

Methods of producing and culturing host cells of the disclosure may include the introduction or transfer of expression vectors containing the recombinant nucleic acids of the disclosure into the host cell. Such methods for transferring expression vectors into host cells are well known to those of ordinary skill in the art. For example, one method for transforming cells with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Cells also may be transformed through the use of spheroplasts (Schweizer, M, Proc. Natl. Acad. Sci., 78: 5086-5090 (1981)). Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

In some cases, cells are prepared as protoplasts or spheroplasts prior to transformation. Protoplasts or spheroplasts may be prepared, for example, by treating a cell having a cell wall with enzymes to degrade the cell wall. Fungal cells may be treated, for example, with zymolyase or chitinase.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids which together contain the total DNA to be introduced into the genome of the host, or a transposon may be used.

The vectors preferably contain one or more selectable markers which permit easy selection of transformed hosts. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, tet, camR and hyg genes.

Selectable markers for use in fungal host cells include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Suitable markers for *S. cerevisiae* hosts include, for example, ADE2, HIS3, LEU2, LYS2, MET3, TRP1, and URA3.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should contain a sufficient number of nucleic acids, such as 100 to 10,000 base pairs, 400 to 10,000 base pairs, or 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further contain an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo.

The vector may further contain a promoter for regulation of expression of a recombinant nucleic acid in the vector. Promoters for the regulation of expression of a gene are well-known in the art, and include constitutive promoters, and inducible promoters. Promoters are described, for example, in Sambrook, et al. *Molecular Cloning: A Laboratory Manual, $3^{rd}$ edition*, Cold Spring Harbor Laboratory Press, (2001). In some aspects, vectors for use in *Saccharomyces* spp. may include the TDH1 or PGK1 promoter, which are strong and constitutive promoters.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 2001, supra).

Once the host cell has been transformed with the expression vector, the host cell is allowed to grow. Growth of a host cell in a medium may involve the process of fermentation. Methods of the disclosure may include culturing the host cell such that recombinant nucleic acids in the cell are expressed. Media, temperature ranges and other conditions suitable for growth are known in the art.

Expression of Recombinant Polypeptides of the Disclosure

The disclosure further provides for the expression of polypeptides of the disclosure. Polypeptides of the disclosure may be prepared by standard molecular biology techniques such as those described herein and in Sambrook, et al. *Molecular Cloning: A Laboratory Manual, $3^{rd}$ edition*, Cold Spring Harbor Laboratory Press, (2001). Recombinant polypeptides may be expressed in and purified from transgenic expression systems. Transgenic expression systems can be prokaryotic or eukaryotic. In some aspects, transgenic host cells may secrete the polypeptide out of the host cell. In some aspects, transgenic host cells may retain the expressed polypeptide in the host cell.

In certain aspects, recombinant polypeptides of the disclosure are partially or substantially isolated from a host cell, or from the growth media of the host cell. In certain aspects, a recombinant polypeptide of the disclosure is prepared with a protein "tag" to facilitate protein purification, such as a GST-tag or poly-His tag. In some aspects, a recombinant polypeptide of the disclosure is prepared with a signal sequence to direct the export of the polypeptide out of the cell. In some aspects, recombinant polypeptides may be only partially purified (e.g. <80% pure, <70% pure, <60% pure, <50% pure, <40% pure, <30% pure, <20% pure, <10% pure, <5% pure). In some aspects, recombinant polypeptides of the present disclosure may be purified to a high degree of purity (e.g. >99% pure, >98% pure, >95% pure, >90% pure, etc.). Recombinant polypeptides may be purified through a variety of techniques known to those of skill in the art, including for example, ion-exchange chromatography, size exclusion chromatography, and affinity chromatography.

In one aspect, a method for producing any of the recombinant polypeptides disclosed herein (including cellulases, hemicellulases, and enzymes that enhances enzymatic hydrolysis of cellulose and/or hemicellulose) includes the steps of: A) culturing a host cell containing one or more recombinant nucleic acids encoding the one or more recombinant polypeptides disclosed herein in media under conditions necessary to support the expression of the recombinant nucleic acid(s), and collecting the one or more polypeptides from the media and/or host cell.

In one aspect, a method for producing cellulases includes the steps of: A) culturing a host cell containing one or more recombinant nucleic acids encoding one or more recombinant polypeptides disclosed herein, wherein the one or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acid(s), and collecting the one or more polypeptides from the media and/or host cell. In another aspect, a method for producing cellulases includes the steps of: A) culturing a host cell containing two or more recombinant nucleic acids encoding two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and collecting the one or more polypeptides from the media and/or host cell. In another aspect, a method for producing cellulases includes the steps of: A) culturing a host cell containing three or more recombinant nucleic acids encoding three or more recombinant polypeptides disclosed herein, wherein the three or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and collecting the one or more polypeptides from the media and/or host cell. In another aspect, a method for producing cellulases includes the steps of: A) culturing a host cell containing four or more recombinant nucleic acids encoding four or more recombinant polypeptides disclosed herein, wherein the four or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and collecting the one or more polypeptides from the media and/or host cell. In another aspect, a method for producing cellulases includes the steps of: A) culturing a host cell containing five or more recombinant nucleic acids encoding five or more recombinant polypeptides disclosed herein, wherein the five or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and collecting the one or more polypeptides from the media and/or host cell. In another aspect, a method for producing cellulases includes the steps of: A) culturing a host cell containing six or more recombinant nucleic acids encoding six or more recombinant polypeptides disclosed herein, wherein the six or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and collecting the one or more polypeptides from the media and/or host cell.

In another aspect, a method for producing cellulases includes the steps of: A) culturing a host cell containing one or more recombinant nucleic acids encoding one or more of the recombinant polypeptides of SEQ ID NOs: 46, 76, 100, 106, 111, and 113, in media under conditions necessary to support the expression of the recombinant nucleic acid(s), and collecting the one or more polypeptides from the media and/or host cell. In another aspect, a method for producing cellulases includes the steps of: A) culturing a host cell containing two or more recombinant nucleic acids encoding two or more of the recombinant polypeptides of SEQ ID NOs: 46, 76, 100, 106, 111, and 113, in media under conditions necessary to support the expression of the recombinant nucleic acids, and collecting the one or more polypeptides from the media and/or host cell. In another aspect, a method for producing cellulases includes the steps of: A) culturing a host cell containing three or more recombinant nucleic acids encoding three or more of the recombinant polypeptides of SEQ ID NOs: 46, 76, 100, 106, 111, and 113, in media under conditions necessary to support the expression of the recombinant nucleic acids, and collecting the one or more polypeptides from the media and/or host cell. In another aspect, a method for producing cellulases includes the steps of: A) culturing a host cell containing four or more recombinant nucleic acids encoding four or more of the recombinant polypeptides of SEQ ID NOs: 46, 76, 100, 106, 111, and 113, in media under conditions necessary to support the expression of the recombinant nucleic acids, and collecting the one or more polypeptides from the media and/or host cell. In another aspect, a method for producing cellulases includes the steps of: A) culturing a host cell containing five or more recombinant nucleic acids encoding five or more of the recombinant polypeptides of SEQ ID NOs: 46, 76, 100, 106, 111, and 113, in media under conditions necessary to support the expression of the recombinant nucleic acids, and collecting the one or more polypeptides from the media and/or host cell. In another aspect, a method for producing cellulases includes the steps of: A) culturing a host cell containing six or more recombinant nucleic acids encoding six of the recombinant polypeptides of SEQ ID NOs: 46, 76, 100, 106, 111, and 113, in media under conditions necessary to support the expression of the recombinant nucleic acids, and collecting the one or more polypeptides from the media and/or host cell.

Thermostability of Enzymes

The enzymes of the present disclosure are thermophilic and thermostable. As used herein, "thermophilic" refers to the characteristic of an enzyme to have peak activity at a high temperature (e.g. above 50° C.). As used herein, "thermostable" refers to the characteristic of an enzyme to retain activity at high temperatures (e.g. above 50° C.) for a significant period of time. For Cb1952, Cb1953, Cb1954, Cb1946, Cb629 and Cb486 polypeptides of the disclosure, "enzymatic" activity refers to cellulase activity (including β-glucosidase activity). For Cb193, Cb195, Cb1172, Cb2487, Cb909, and Cb162 polypeptides of the disclosure, "enzymatic" activity refers to hemicellulase activity. For Cb1581 polypeptides of the disclosure, "enzymatic" activity refers to activity that enhances enzymatic hydrolysis of cellulose and/or hemicellulose.

Cellulases

In certain aspects, one or more of the Cb1952, Cb1953, Cb1954, Cb1946, Cb629 and Cb486 polypeptides of the disclosure has a peak rate of enzymatic activity on cellulose or cellulose-containing material at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail has a peak rate of enzymatic activity on cellulose or a cellulose-containing material at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In another aspect, an enzyme cocktail is provided herein, wherein the cocktail contains the polypeptides of SEQ ID NOs: 46, 76, 100, 106, 111, and 113 has a peak rate of enzymatic activity on cellulose or a cellulose-containing material at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C.

In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 55° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 60° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 65° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 70° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 75° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 90% of its initial rate of enzymatic activity for a period of at least 24 hours when incubated at a temperature of about 80° C.

In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 55° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 60° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 65° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 70° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 75° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 75% of its initial rate of enzymatic activity for a period of at least 24 hours when incubated at a temperature of about 80° C.

In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 55° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 60° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 65° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 70° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 75° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 50% of its initial rate of enzymatic activity for a period of at least 24 hours when incubated at a temperature of about 80° C.

In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 55° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 60° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 65° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 70° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 75° C. In another aspect, an enzyme cocktail is provided herein, wherein the cocktail contains two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the cocktail retains at least 25% of its initial rate of enzymatic activity for a period of at least 24 hours when incubated at a temperature of about 80° C.

In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 55° C. In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 60° C. In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 65° C. In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 70° C. In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 75° C. In another aspect, an enzyme cocktail is provided herein, wherein the cocktail contains the polypeptides of SEQ ID NOs: 46, 76, 100, 106, 111, and 113 retains at least 90% of its initial rate of enzymatic activity for a period of at least 24 hours when incubated at a temperature of about 80° C.

In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 55° C. In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 60° C. In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 65° C. In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 70° C. In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 75° C. In another aspect, an enzyme cocktail is provided herein, wherein the cocktail contains the polypeptides of SEQ ID NOs: 46, 76, 100, 106, 111, and 113 retains at least 75% of its initial rate of enzymatic activity for a period of at least 24 hours when incubated at a temperature of about 80° C.

In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 55° C. In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 60° C. In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 65° C. In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 70° C. In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 75° C. In another aspect, an enzyme cocktail is provided herein, wherein the cocktail contains the polypeptides of SEQ ID NOs: 46, 76, 100, 106, 111, and 113 retains at least 50% of its initial rate of enzymatic activity for a period of at least 24 hours when incubated at a temperature of about 80° C.

In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 55° C. In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 60° C. In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 65° C. In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 70° C. In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 75° C. In another aspect, an enzyme cocktail is provided herein, wherein the cocktail contains the polypeptides of SEQ ID NOs: 46, 76, 100, 106, 111, and 113 retains at least 25% of its initial rate of enzymatic activity for a period of at least 24 hours when incubated at a temperature of about 80° C.

Hemicellulases

In certain embodiments, one or more of the enzymes Cb193, Cb195, Cb1172, Cb2487, Cb909, and Cb162 has peak rate of enzymatic activity at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In other embodiments, an enzyme 'cocktail' that contains two or more of the enzymes Cb193, Cb195, Cb1172, Cb2487, Cb909, and Cb162 has peak rate of enzymatic activity on hemicellulose or a hemicellulose-derived substrate at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In one embodiment, an enzyme 'cocktail' that contains all six of the enzymes Cb193, Cb195, Cb1172, Cb2487, Cb909, and Cb162 has peak rate of enzymatic activity on hemicellulose or a hemicellulose-derived substrate at a temperature of about 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C.

Enzymes of the present disclosure retain significant enzymatic activity for significant periods of time at high temperatures. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 55° C. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 60° C. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 65° C. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 70° C. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 75° C. In one embodiment, an enzyme cocktail containing two or more of the enzymes Cb193, Cb195, Cb1172, Cb2487, Cb909, and Cb162 retains at least 90% of its initial rate of enzymatic activity for a period of at least 24 hours when incubated at a temperature of about 80° C.

In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 55° C. In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 60° C. In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 65° C. In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 70° C. In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 75° C. In one embodiment, an enzyme cocktail containing two or more of the enzymes Cb193, Cb195, Cb1172, Cb2487, Cb909, and Cb162 retains at least 75% of its initial rate of enzymatic activity for a period of at least 24 hours when incubated at a temperature of about 80° C.

In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 55° C. In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 60° C. In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 65° C. In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 70° C. In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 75° C. In one embodiment, an enzyme cocktail containing two or more of the enzymes Cb193, Cb195, Cb1172, Cb2487, Cb909, and Cb162 retains at least 50% of its initial rate of enzymatic activity for a period of at least 24 hours when incubated at a temperature of about 80° C.

In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 55° C. In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 60° C. In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 65° C. In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 70° C. In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 75° C. In one embodiment, an enzyme cocktail containing two or more of the enzymes Cb193, Cb195, Cb1172, Cb2487, Cb909, and Cb162 retains at least 25% of its initial rate of enzymatic activity for a period of at least 24 hours when incubated at a temperature of about 80° C.

In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 55° C. In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 60° C. In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 65° C. In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 70° C. In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 75° C. In one embodiment, an enzyme cocktail containing all six of the enzymes Cb193, Cb195, Cb1172, Cb2487, Cb909, and Cb162 retains at least 90% of its initial rate of enzymatic activity for a period of at least 24 hours when incubated at a temperature of about 80° C.

In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 55° C. In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 60° C. In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 65° C. In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 70° C. In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 75° C. In one embodiment, an enzyme cocktail containing all six of the enzymes Cb193, Cb195, Cb1172, Cb2487, Cb909, and Cb162 retains at least 75% of its initial rate of enzymatic activity for a period of at least 24 hours when incubated at a temperature of about 80° C.

In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 55° C. In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 60° C. In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 65° C. In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 70° C. In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 75° C. In one embodiment, an enzyme cocktail containing all six of the enzymes Cb193, Cb195, Cb1172, Cb2487, Cb909, and Cb162 retains at least 50% of its initial rate of enzymatic activity for a period of at least 24 hours when incubated at a temperature of about 80° C.

In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 55° C. In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 60° C. In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 65° C. In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 70° C. In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 75° C. In one embodiment, an enzyme cocktail containing all six of the enzymes Cb193, Cb195, Cb1172, Cb2487, Cb909, and Cb162 retains at least 25% of its initial rate of enzymatic activity for a period of at least 24 hours when incubated at a temperature of about 80° C.

Any of the cellulase cocktails disclosed herein having the thermophilic and thermostable characteristics disclosed herein may further include any of the hemicellulases disclosed herein and/or an enzyme that enhances enzymatic hydrolysis of cellulose and/or hemicellulose disclosed herein. Additionally, any of the hemicellulase cocktails disclosed herein having the thermophilic and thermostable characteristics disclosed herein may further include any of the cellulases disclosed herein and/or an enzyme that enhances enzymatic hydrolysis of cellulose and/or hemicellulose disclosed herein.

Applications

Methods of Degrading Cellulose-Containing Material

In one aspect, provided herein are methods for degrading cellulose-containing material.

In one aspect, a method for degrading a cellulose-containing material includes contacting a cellulose-containing material with a composition containing one or more recombinant polypeptides disclosed herein, wherein the one or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptide(s) and cellulose-containing material under conditions that support cellulose degradation. In another aspect, a method for degrading a cellulose-containing material includes contacting a cellulose-containing material with a composition containing two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptides and cellulose-containing material under conditions that support cellulose degradation. In another aspect, a method for degrading a cellulose-containing material includes contacting a cellulose-containing material with a composition containing three or more recombinant polypeptides disclosed herein, wherein the three or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptides and cellulose-containing material under conditions that support cellulose degradation. In another aspect, a method for degrading a cellulose-containing material includes contacting a cellulose-containing material with a composition containing four or more recombinant polypeptides disclosed herein, wherein the four or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptides and cellulose-containing material under conditions that support cellulose degradation. In another aspect, a method for degrading a cellulose-containing material includes contacting a cellulose-containing material with a composition containing five or more recombinant polypeptides disclosed herein, wherein the five or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptides and cellulose-containing material under conditions that support cellulose degradation. In another aspect, a method for degrading a cellulose-containing material includes contacting a cellulose-containing material with a composition containing six or more recombinant polypeptides disclosed herein, wherein the six or more polypeptides are selected from: Cb1952 polypeptides, Cb1953 polypeptides, Cb1954 polypeptides, Cb1946 polypeptides, Cb629 polypeptides, or Cb486 polypeptides, and incubating the polypeptides and cellulose-containing material under conditions that support cellulose degradation.

In another aspect, a method for degrading a cellulose-containing material includes contacting a cellulose-containing material with a composition containing one or more recombinant polypeptides disclosed herein, wherein the one or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptide(s) and cellulose-containing material under conditions that support cellulose degradation. In another aspect, a method for degrading a cellulose-containing material includes contacting a cellulose-containing material with a composition containing two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptides and cellulose-containing material under conditions that support cellulose degradation. In another aspect, a method for degrading a cellulose-containing material includes contacting a cellulose-containing material with a composition containing three or more recombinant polypeptides disclosed herein, wherein the three or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptides and cellulose-containing material under conditions that support cellulose degradation. In another aspect, a method for degrading a cellulose-containing material includes contacting a cellulose-containing material with a composition containing four or more recombinant polypeptides disclosed herein, wherein the four or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptides and cellulose-containing material under conditions that support cellulose degradation. In another aspect, a method for degrading a cellulose-containing material includes contacting a cellulose-containing material with a composition containing five or more recombinant polypeptides disclosed herein, wherein the five or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptides and cellulose-containing material under conditions that support cellulose degradation. In another aspect, a method for degrading a cellulose-containing material includes contacting a cellulose-containing material with a composition containing six or more recombinant polypeptides disclosed herein, wherein the six or more polypeptides are selected from: Cb1952 polypeptides, Cb1953 polypeptides, Cb1954 polypeptides, Cb1946 polypeptides, Cb629 polypeptides, or Cb486 polypeptides, and wherein the Cb1952 polypeptide is selected from the polypeptides of SEQ ID NOs: 44, 114, 124, 126, 128, and 46, wherein the Cb1953 polypeptide is selected from the polypeptides of SEQ ID NOs: 60, 61, and 111, wherein the Cb1954 polypeptide is selected from the polypeptides of SEQ ID NOs: 74, 121, and 76, wherein the Cb1946 polypeptide is selected from the polypeptides of SEQ ID NOs: 86, 87, and 113, wherein the Cb629 polypeptide is selected from the polypeptides of SEQ ID NOs: 98, 119, and 100, and wherein the Cb486 polypeptide is the polypeptide of SEQ ID NO: 106, and incubating the polypeptides and cellulose-containing material under conditions that support cellulose degradation.

In another aspect, a method for degrading a cellulose-containing material includes contacting a cellulose-containing material with a composition containing one or more of the recombinant polypeptides of SEQ ID NOs: 46, 76, 100, 106, 111, and 113, and incubating the polypeptide(s) and cellulose-containing material under conditions that support cellulose degradation. In another aspect, a method for degrading a cellulose-containing material includes contacting a cellulose-containing material with a composition containing two or more of the recombinant polypeptides of SEQ ID NOs: 46, 76, 100, 106, 111, and 113, and incubating the polypeptides and cellulose-containing material under conditions that support cellulose degradation. In another aspect, a method for degrading a cellulose-containing material includes contacting a cellulose-containing material with a composition containing three or more of the recombinant polypeptides of SEQ ID NOs: 46, 76, 100, 106, 111, and 113, and incubating the polypeptides and cellulose-containing material under conditions that support cellulose degradation. In another aspect, a method for degrading a cellulose-containing material includes contacting a cellulose-containing material with a composition containing four or more of the recombinant polypeptides of SEQ ID NOs: 46, 76, 100, 106, 111, and 113, and incubating the polypeptides and cellulose-containing material under conditions that support cellulose degradation. In another aspect, a method for degrading a cellulose-containing material includes contacting a cellulose-containing material with a composition containing five or more of the recombinant polypeptides of SEQ ID NOs: 46, 76, 100, 106, 111, and 113, and incubating the polypeptides and cellulose-containing material under conditions that support cellulose degradation. In another aspect, a method for degrading a cellulose-containing material includes contacting a cellulose-containing material with a composition containing six of the recombinant polypeptides of SEQ ID NOs: 46, 76, 100, 106, 111, and 113, and incubating the polypeptides and cellulose-containing material under conditions that support cellulose degradation.

In another aspect, a method for degrading a cellulose-containing material includes contacting a cellulose-containing material with a host cell containing one or more recombinant nucleic acids encoding one or more recombinant polypeptides disclosed herein, wherein the one or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acid(s), and incubating the cell and cellulose-containing material under conditions that support cellulose degradation. In another aspect, a method for degrading a cellulose-containing material includes contacting a cellulose-containing material with a host cell containing two or more recombinant nucleic acids encoding two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing three or more recombinant nucleic acids encoding three or more recombinant polypeptides disclosed herein, wherein the three or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing four or more recombinant nucleic acids encoding four or more recombinant polypeptides disclosed herein, wherein the four or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing five or more recombinant nucleic acids encoding five or more recombinant polypeptides disclosed herein, wherein the five or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing six or more recombinant nucleic acids encoding six or more recombinant polypeptides disclosed herein, wherein the six or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, and incubating the cell and cellulose-containing material under conditions that support cellulose degradation.

In another aspect, a method for degrading a cellulose-containing material includes contacting a cellulose-containing material with a host cell containing one or more recombinant nucleic acids encoding one or more of the recombinant polypeptides of SEQ ID NOs: 46, 76, 100, 106, 111, and 113, in media under conditions necessary to support the expression of the recombinant nucleic acid(s), and incubating the cell and cellulose-containing material under conditions that support cellulose degradation. In another aspect, a method for degrading a cellulose-containing material includes contacting a cellulose-containing material with a host cell containing two or more recombinant nucleic acids encoding two or more of the recombinant polypeptides of SEQ ID NOs: 46, 76, 100, 106, 111, and 113, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing three or more recombinant nucleic acids encoding three or more of the recombinant polypeptides of SEQ ID NOs: 46, 76, 100, 106, 111, and 113, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing four or more recombinant nucleic acids encoding four or more of the recombinant polypeptides of SEQ ID NOs: 46, 76, 100, 106, 111, and 113, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing five or more recombinant nucleic acids encoding five or more of the recombinant polypeptides of SEQ ID NOs: 46, 76, 100, 106, 111, and 113, in media under conditions necessary to support the expression of the recombinant nucleic acids, and incubating the cell and cellulose-containing material under conditions that support cellulose degradation. In another aspect, a method for degrading a cellulose-containing material includes contacting a cellulose-containing material with a host cell containing six or more recombinant nucleic acids encoding six of the recombinant polypeptides of SEQ ID NOs: 46, 76, 100, 106, 111, and 113, in media under conditions necessary to support the expression of the recombinant nucleic acids, and incubating the cell and cellulose-containing material under conditions that support cellulose degradation.

In another aspect, a method for degrading a cellulose-containing material includes contacting a cellulose-containing material with a composition containing one or more recombinant polypeptides disclosed herein, wherein the one or more polypeptides are selected from: Cb1952 polypeptides, Cb1953 polypeptides, Cb1954 polypeptides, Cb1946 polypeptides, or Cb629 polypeptides, and wherein the composition does not contain a Cb486 polypeptide, and incubating the polypeptides and cellulose-containing material under conditions that support cellulose degradation. In another aspect, a method for degrading a cellulose-containing material includes contacting a cellulose-containing material with a host cell containing one or more recombinant nucleic acids encoding one or more recombinant polypeptides disclosed herein, wherein the one or more polypeptides are selected from: Cb1952 polypeptides, Cb1953 polypeptides, Cb1954 polypeptides, Cb1946 polypeptides, or Cb629 polypeptides, and wherein the host cell does not contain a recombinant nucleic acid encoding a Cb486 polypeptide, in media under conditions necessary to support the expression of the recombinant nucleic acid(s), and incubating the cell and cellulose-containing material under conditions that support cellulose degradation. Contacting a cellulose-containing material with one or more cellulases disclosed herein, but not Cb486, may lead to the accumulation of cellobiose and/or other oligosaccharides during the degradation of the cellulose-containing material. Products containing cellobiose and/or oligosaccharides may be useful as feedstocks for organisms or processes that effectively utilize cellobiose and/or oligosaccharides to generate desired end products, such as biofuels.

As used herein, a "cellulose-containing material" is any material that contains cellulose, including biomass. Biomass suitable for use with the currently disclosed methods include any cellulose-containing material, and includes, without limitation, *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, rye hulls, wheat hulls, sugarcane bagasse, copra meal, copra pellets, palm kernel meal, corn fiber, Distillers Dried Grains with Solubles (DDGS), Blue Stem, corncobs, pine wood, birch wood, willow wood, aspen wood, poplar wood, energy cane, waste paper, sawdust, forestry wastes, municipal solid waste, waste paper, crop residues, other grasses, and other woods. In some aspects, biomass is lignocellulosic material.

Commonly, cellulose-containing materials also contain hemicellulose. For example, unprocessed or partially processed plant materials generally contain hemicellulose. In some aspects, any of the methods for degrading a cellulose-containing material disclosed herein may further include contacting a cellulose-containing material with one or more hemicellulases.

Any of the methods disclosed herein for degrading a cellulose-containing material that includes contacting a cellulose-containing material with a composition containing one, two, three, four, five, six or more polypeptides selected from: Cb1952 polypeptides, Cb1953 polypeptides, Cb1954 polypeptides, Cb1946 polypeptides, Cb629 polypeptides, or Cb486 polypeptides, may further include contacting the cellulose-containing material with one or more, two or more, three or more, four or more, five or more, or the six recombinant polypeptides of SEQ ID NOs: 7, 13, 19, 27, 33, and 37. In one aspect, a method for degrading a cellulose-containing material includes contacting a cellulose-containing material with a composition containing the recombinant polypeptides of SEQ ID NOs: 46, 76, 100, 106, 111, and 113 and the recombinant polypeptides of SEQ ID NOs: 7, 13, 19, 27, 33, and 37. In one aspect, provided herein is a method for degrading a biomass-containing material, including contacting a cellulose-containing material with a composition containing the recombinant polypeptides of SEQ ID NOs: 46, 76, 100, 106, 111, and 113 and the recombinant polypeptides of SEQ ID NOs: 3, 7, 13, 19, 27, 33, and 37, and incubating the polypeptides and biomass-containing material under conditions that support cellulose degradation.

Any of the methods disclosed herein for degrading a cellulose-containing material that includes contacting a cellulose-containing material with a host cell containing one, two, three, four, five, or six recombinant nucleic acids encoding one, two, three, four, five, or six recombinant polypeptides disclosed herein, wherein the one, two, three, four, five, six or more polypeptides are selected from: Cb1952 polypeptides, Cb1953 polypeptides, Cb1954 polypeptides, Cb1946 polypeptides, Cb629 polypeptides, or Cb486 polypeptides, in media under conditions necessary to support the expression of the recombinant nucleic acids, may further include contacting the cellulose-containing material with one or more, two or more, three or more, four or more, five or more, or six or more recombinant polypeptides of SEQ ID NOs: 7, 13, 19, 27, 33, and 37. In one aspect, a method for degrading a cellulose-containing material includes contacting a cellulose-containing material with a host cell containing recombinant nucleic acids encoding the recombinant polypeptides of SEQ ID NOs: 46, 76, 100, 106, 111, and 113 and the recombinant polypeptides of SEQ ID NOs: 7, 13, 19, 27, 33, and 37. In one aspect, provided herein is a method for degrading a biomass-containing material, including contacting a cellulose-containing material with a host cell containing recombinant nucleic acids encoding the recombinant polypeptides of SEQ ID NOs: 46, 76, 100, 106, 111, and 113 and the recombinant polypeptides of SEQ ID NOs: 7, 13, 19, 27, 33, and 37, and incubating the host cell and biomass-containing material under conditions that support cellulose degradation.

In some aspects, any of the methods disclosed herein for degrading a cellulose-containing material may be carried out at a high temperature. In some aspects, any of the methods disclosed herein for degrading a cellulose-containing material may be carried out at about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, any of the methods disclosed herein for degrading a cellulose-containing material may be carried out for at least 1, 2, 3, 4, 5, 6, 7, 8, 9, 10, 11, 12, 14, 16, 18, 20, 22, or 24 hours at about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. If a method disclosed herein for degrading a cellulose containing material is carried out at a high temperature and it uses host cells expressing recombinant polypeptides disclosed herein, in some aspects, the host cell is a thermophilic organism.

Methods of Reducing Viscosity of Pretreated Biomass Mixtures

Further provided herein are methods for reducing the viscosity of pre-treated biomass.

Biomass that that is used for degradation into component sugars or oligosaccharides may contains high levels of lignin, which can block hydrolysis of the cellulosic component of the biomass. Typically, biomass is pretreated with, for example, high temperature and/or high pressure to increase the accessibility of the cellulosic component to hydrolysis. Other pretreatments include, without limitation, ammonia fiber expansion (AFEX), steam explosion, and treatment with alkaline aqueous solutions, acidic solutions, organic solvents, ionic liquids (IL), electrolyzed water, phosphoric acid, or combinations thereof. However, pretreatment generally results in a biomass mixture that is highly viscous. The high viscosity of the pretreated biomass mixture can increase the difficulty in handling the pretreated biomass, and it can also interfere with effective hydrolysis of the pretreated biomass. Advantageously, recombinant polypeptides disclosed herein can be used to reduce the viscosity of pretreated biomass mixtures prior to further degradation of the biomass.

Accordingly, certain aspects of the present disclosure relate to methods of reducing the viscosity of a pretreated biomass mixture, by contacting a pretreated biomass mixture having an initial viscosity with a composition containing one or more recombinant polypeptides disclosed herein, wherein the one or more polypeptides are selected from one or more of the cellulases, hemicellulases, and polypeptides that enhance enzymatic hydrolysis of cellulose and/or hemicellulose, and incubating the contacted biomass mixture under conditions sufficient to reduce the initial viscosity of the pretreated biomass mixture.

Certain aspects of the present disclosure relate to methods of reducing the viscosity of a pretreated biomass mixture, by contacting a pretreated biomass mixture having an initial viscosity with a composition containing one or more recombinant polypeptides disclosed herein, wherein the one or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing two or more recombinant polypeptides disclosed herein, wherein the two or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing three or more recombinant polypeptides disclosed herein, wherein the three or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing four or more recombinant polypeptides disclosed herein, wherein the four or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing five or more recombinant polypeptides disclosed herein, wherein the five or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing six or more recombinant polypeptides disclosed herein, wherein the six or more polypeptides are selected from: Cb1952 polypeptides, Cb1953 polypeptides, Cb1954 polypeptides, Cb1946 polypeptides, Cb629 polypeptides, or Cb486 polypeptides, and incubating the contacted biomass mixture under conditions sufficient to reduce the initial viscosity of the pretreated biomass mixture.

In another aspect, the disclosure includes a method of reducing the viscosity of a pretreated biomass mixture, by contacting a pretreated biomass mixture having an initial viscosity with a composition containing one or more of the recombinant polypeptides of SEQ ID NOs: 46, 76, 100, 106, 111, and 113, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing two or more of the recombinant polypeptides of SEQ ID NOs: 46, 76, 100, 106, 111, and 113, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing three or more of the recombinant polypeptides of SEQ ID NOs: 46, 76, 100, 106, 111, and 113, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing four or more of the recombinant polypeptides of SEQ ID NOs: 46, 76, 100, 106, 111, and 113, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing five or more of the recombinant polypeptides of SEQ ID NOs: 46, 76, 100, 106, 111, and 113, and incubating the contacted biomass mixture under conditions sufficient to reduce the initial viscosity of the pretreated biomass mixture. In another aspect, the disclosure includes a method of reducing the viscosity of a pretreated biomass mixture, by contacting a pretreated biomass mixture having an initial viscosity with a composition containing six of the recombinant polypeptides of SEQ ID NOs: 46, 76, 100, 106, 111, and 113, and incubating the contacted biomass mixture under conditions sufficient to reduce the initial viscosity of the pretreated biomass mixture.

In some aspects, the disclosed methods are carried out as part of a pretreatment process. The pretreatment process may include the additional step of adding a composition containing one, two, three, four, five, six or more recombinant polypeptides disclosed herein, wherein the one, two, three, four, five, six or more polypeptides are selected from: Cb1952 polypeptides, Cb1953 polypeptides, Cb1954 polypeptides, Cb1946 polypeptides, Cb629 polypeptides, or Cb486 polypeptides, to pretreated biomass mixtures after a step of pretreating the biomass, and incubating the pretreated biomass with the polypeptides under conditions sufficient to reduce the viscosity of the mixture. The polypeptides or compositions may be added to pretreated biomass mixture while the temperature of the mixture is high, or after the temperature of the mixture has decreased. In some aspects, the methods are carried out in the same vessel or container where the pretreatment was performed. In other aspects, the methods are carried out in a separate vessel or container where the pretreatment was performed.

In some aspects, the methods are carried out in the presence of high salt, such as solutions containing saturating concentrations of salts, solutions containing sodium chloride (NaCl) at a concentration of at least at or about 0.1 M, 0.2 M, 0.3 M, 0.4 M, 0.5 M, 1 M, 1.5 M, 2 M, 2.5 M, 3 M, 3.5 M, or 4 M sodium chloride, or potassium chloride (KCl), at a concentration at or about 0.1 M, 0.2 M, 0.3 M, 0.4 M, 0.5 M, 1 M, 1.5 M, 2 M, 2.5 M 3.0 M or 3.2 M KCl and/or ionic liquids, such as 1,3-dimethylimidazolium dimethyl phosphate ([DMIM]DMP) or [EMIM]OAc, or in the presence of one or more detergents, such as ionic detergents (e.g., SDS, CHAPS), sulfydryl reagents, such as in saturating ammonium sulfate or ammonium sulfate between at or about 0 and 1 M. In some aspects, the methods are carried out at a temperature of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90° C. In some aspects, the methods are carried out over a broad temperature range, such as between at or about 20° C. and 50° C., 25° C. and 55° C., 30° C. and 60° C., 40° C. and 80° C., 60° C. and 80° C., or 60° C. and 100° C. In some aspects, the methods may be performed over a broad pH range, for example, at a pH of between about 4.5 and 8.75, at a pH of greater than 7 or at a pH of 8.5, or at a pH of at least 5.0, 5.5, 6.0, 6.5, 7.0, 7.5, 8.0, or 8.5.

Any of the methods disclosed herein for reducing the viscosity of a pretreated biomass mixture that includes contacting a pretreated biomass mixture with a composition containing one, two, three, four, five, six or more polypeptides selected from: Cb1952 polypeptides, Cb1953 polypeptides, Cb1954 polypeptides, Cb1946 polypeptides, Cb629 polypeptides, or Cb486 polypeptides, may further include contacting the pretreated biomass mixture with one or more, two or more, three or more, four or more, five or more, or six recombinant polypeptides of SEQ ID NOs: 7, 13, 19, 27, 33, and 37. In one aspect, a method for reducing the viscosity of a pretreated biomass mixture includes contacting a pre-treated biomass mixture with a composition containing the recombinant polypeptides of SEQ ID NOs: 46, 76, 100, 106, 111, and 113 and the recombinant polypeptides of SEQ ID NOs: 7, 13, 19, 27, 33, and 37. In one aspect, provided herein is a method for reducing the viscosity of a pretreated biomass mixture, including contacting a pretreated biomass mixture with a composition containing the recombinant polypeptides of SEQ ID NOs: 46, 76, 100, 106, 111, and 113 and the recombinant polypeptides of SEQ ID NOs: 7, 13, 19, 27, 33, and 37, and incubating the polypeptides and reducing the viscosity of a pretreated biomass mixture to reduce the viscosity of the pretreated biomass mixture.

Methods of Converting Cellulose-Containing Materials to Fermentation Product

Further provided herein are methods for converting cellulose-containing materials to a fermentation production. In one aspect, a method for converting a cellulose-containing material into a fermentation product includes the steps of: A) contacting a cellulose-containing material with a composition containing one, two, three, four, five, six or more polypeptides selected from: Cb1952 polypeptides, Cb1953 polypeptides, Cb1954 polypeptides, Cb1946 polypeptides, Cb629 polypeptides, or Cb486 polypeptides; B) incubating the cellulose-containing material with the composition containing one, two, three, four, five, six or more polypeptides under conditions that support cellulose degradation, in order to obtain sugars; and C) culturing the sugars with a fermentative microorganism under conditions sufficient to produce a fermentation product.

In another aspect, a method for converting a cellulose-containing material into a fermentation product includes the steps of: A) contacting a cellulose-containing material with a composition containing the polypeptides of SEQ ID NOs: 46, 76, 100, 106, 111, and 113; B) incubating the cellulose-containing material with the composition containing the polypeptides of SEQ ID NOs: 46, 76, 100, 106, 111, and 113, under conditions that support cellulose degradation, in order to obtain sugars; and C) culturing the sugars with a fermentative microorganism under conditions sufficient to produce a fermentation product.

Any of the methods disclosed herein for converting a cellulose-containing material into a fermentation product may further include contacting the pretreated biomass mixture with one or more, two or more, three or more, four or more, five or more, or six recombinant polypeptides of SEQ ID NOs: 7, 13, 19, 27, 33, and 37. In one aspect, a method for converting a cellulose-containing material into a fermentation product includes contacting a cellulose-containing material with a composition containing the recombinant polypeptides of SEQ ID NOs: 46, 76, 100, 106, 111, and 113, and the recombinant polypeptides of SEQ ID NOs: 7, 13, 19, 27, 33, and 37. In one aspect, provided herein is a method for converting a cellulose-containing material into a fermentation product including the steps of: A) contacting a cellulose-containing material with a composition containing the recombinant polypeptides of SEQ ID NOs: 46, 76, 100, 106, 111, and 113 and the recombinant polypeptides of SEQ ID NOs: 7, 13, 19, 27, 33, and 37; B) incubating the cellulose-containing material with the composition containing the polypeptides of SEQ ID NOs: 46, 76, 100, 106, 111, 113, 7, 13, 19, 27, 33, and 37 under conditions that support cellulose degradation, in order to obtain sugars; and C) culturing the sugars with a fermentative microorganism under conditions sufficient to produce a fermentation product.

Sugars that may be obtained from the degradation of cellulose-containing materials include, without limitation, glucose, cellobiose, xylose, arabinose, galactose, glucuronic acid, and mannose.

Fermentation products that may be produced from sugars obtained from the degradation of cellulose-containing materials include, without limitation, ethanol, n-propanol, n-butanol, iso-butanol, 3-methyl-1-butanol, 2-methyl-1-butanol, 3-methyl-1-pentanol, and octanol.

Fermentative organisms include, without limitation, *Saccharomyces* spp.

Methods of Consolidated Bioprocessing

Further provided herein are methods for converting cellulose-containing materials to a fermentation production, by consolidated bioprocessing. Consolidated bioprocessing combines enzyme generation, biomass hydrolysis, and biofuel production into a single stage. In one aspect, a method for converting a cellulose-containing material into a fermentation product by consolidated bioprocessing includes the steps of: A) contacting a cellulose-containing material with a cell having recombinant nucleic acids encoding one, two, three, four, five, six or more polypeptides selected from: Cb1952 polypeptides, Cb1953 polypeptides, Cb1954 polypeptides, Cb1946 polypeptides, Cb629 polypeptides, or Cb486 polypeptides, and one or more recombinant nucleic acids encoding one or more polypeptides involved in a biochemical pathway for the production of a biofuel, under conditions sufficient to support expression of the nucleic acids; B) incubating the cellulose-containing material with the cell expressing recombinant nucleic acids under conditions that support cellulose degradation and fermentation, in order to produce a fermentation product.

In another aspect, a method for converting a cellulose-containing material into a fermentation product by consolidated bioprocessing includes the steps of: A) contacting a cellulose-containing material with a cell having recombinant nucleic acids encoding the polypeptides of SEQ ID NOs: 46, 76, 100, 106, 111, and 113, and one or more recombinant nucleic acids encoding one or more polypeptides involved in a biochemical pathway for the production of a biofuel, under conditions sufficient to support expression of the nucleic acids; B) incubating the cellulose-containing material with the cell expressing recombinant nucleic acids under conditions that support cellulose degradation and fermentation, in order to produce a fermentation product.

In another aspect, a method for converting a cellulose-containing material into a fermentation product by consolidated bioprocessing includes the steps of: A) contacting a cellulose-containing material with a cell having recombinant nucleic acids encoding the polypeptides of SEQ ID NOs: 46, 76, 100, 106, 111, 113, 7, 13, 19, 27, 33, and 37, and one or more recombinant nucleic acids encoding a polypeptide involved in a biochemical pathway for the production of a biofuel under conditions sufficient to support expression of the nucleic acids; B) incubating the cellulose-containing material with the cell expressing recombinant nucleic acids under conditions that support cellulose degradation and fermentation, in order to produce a fermentation product.

Fermentation products that may be produced from sugars obtained from the degradation of cellulose-containing materials include, without limitation, ethanol, n-propanol, n-butanol, iso-butanol, 3-methyl-1-butanol, 2-methyl-1-butanol, 3-methyl-1-pentanol, and octanol.

Concentration of Polypeptides

In certain aspects, polypeptides of the disclosure are provided with a substrate at a concentration of at least 0.01 nM of each polypeptide. In certain aspects, the polypeptides are provided with a substrate at a concentration of at least 0.1 nM of each polypeptide. In certain aspects, the polypeptides are provided with a substrate at a concentration of at least 1 nM of each polypeptide. In certain aspects, the polypeptides are provided with a substrate at a concentration of at least 10 nM of each polypeptide. In certain aspects, the polypeptides are provided with a substrate at a concentration of at least 0.1

μM of each polypeptide. In certain aspects, the polypeptides are provided with a substrate at a concentration of at least 10 μM of each polypeptide. In certain aspects, the polypeptides are provided with a substrate at a concentration of at least 100 μM of each polypeptide.

Combination of Thermostable Cellulases with Thermostable Hemicellulose-Degrading Enzymes In some aspects, thermostable cellulose-degrading enzymes of the present disclosure are provided with thermostable hemicellulases. Thermostable hemicellulases may be provided with the thermostable cellulose-degrading enzymes of the present disclosure in order to increase the degradation of materials containing both cellulose and hemicellulose, such as biomass from terrestrial plants.

In some aspects disclosed herein, mixtures of cellulases of the present disclosure exhibit surprising synergistic effects when combined with mixtures of hemicellulases. In such examples, mixtures containing multiple cellulases have greater cellulase activity when they are combined in a cocktail with a mixture containing multiple hemicellulases, as compared to when the mixture of cellulases is not combined with a mixture containing multiple hemicellulases. Also, in some examples, mixtures containing multiple hemicellulases have greater hemicellulase activity when they are combined in a cocktail with a mixture containing multiple cellulases, as compared to the activity of the mixture of hemicellulases when it is not combined with a mixture containing multiple cellulases. Thus, cellulase and hemicellulase mixtures provided herein may have surprising synergistic effects together, wherein each enzyme mixture has greater activity when combined with the other than when either enzyme mixture is provided with a substrate alone.

Thermostable hemicellulases may be obtained from organisms capable of degrading hemicellulose. In one aspect, thermostable hemicellulases may be isolated directly from organisms capable of degrading cellulose. In another aspect, thermostable hemicellulases are produced recombinantly, through the use of host cells and expression vectors containing genes encoding thermostable hemicellulases. Thermostable hemicellulases and/or genes encoding thermostable hemicellulases may be isolated from various organisms capable of degrading hemicellulose including, for example and without limitation, archaeal, bacterial, fungal, and protozoan organisms.

In some aspects, thermostable hemicellulases are recombinant polypeptides related to thermostable hemicellulases of *C. bescii*. In some aspects, thermostable hemicellulases contain the amino acid sequence of any of SEQ ID NOs: 3, 7, 13, 19, 27, 33, and 37. In some aspects, polynucleotides encoding thermostable hemicellulases contain the nucleic acid sequence of any of SEQ ID NOs: 4, 8, 14, 20, 28, 34, and 38.

Synergy of Hemicellulase Enzymatic Activity

In certain embodiments, the enzymes of the present disclosure are provided as an enzyme 'cocktail' wherein two or more of the enzymes Cb193, Cb195, Cb1172, Cb2487, Cb909, and Cb162 are provided together to degrade hemicellulose or a hemicellulose-derived substrate. In certain embodiments, the enzymes function synergistically and the combination of two or more of the enzymes Cb193, Cb195, Cb1172, Cb2487, Cb909, and Cb162 is more effective at degrading hemicellulose and releasing monosaccharides from hemicellulose than the activity of a single enzyme. Similarly, in certain embodiments, enzyme cocktails with three or more of the enzymes Cb193, Cb195, Cb1172, Cb2487, Cb909, and Cb162 are more effective at degrading hemicellulose and releasing monosaccharides from hemicellulose than enzyme cocktails with one or two of the enzymes. In certain embodiments, enzyme cocktails with four or more of the enzymes Cb193, Cb195, Cb1172, Cb2487, Cb909, and Cb162 are more effective at degrading hemicellulose and releasing monosaccharides from hemicellulose than enzyme cocktails with one, two, or three of the enzymes. In certain embodiments, enzyme cocktails with five or more of the enzymes Cb193, Cb195, Cb1172, Cb2487, Cb909, and Cb162 are more effective at degrading hemicellulose and releasing monosaccharides from hemicellulose than enzyme cocktails with one, two, three, or four of the enzymes. In certain embodiments, enzyme cocktails with all six of the enzymes Cb193, Cb195, Cb1172, Cb2487, Cb909, and Cb162 are more effective at degrading hemicellulose and releasing monosaccharides from hemicellulose than enzyme cocktails with one, two, three, four, or five of the enzymes.

In other embodiments, enzyme cocktails with two or more of the enzymes Cb193, Cb195, Cb1172, Cb2487, Cb909, and Cb162 are more effective at degrading hemicellulose and releasing monosaccharides from hemicellulose than enzyme cocktails with the same total amount of enzyme units but with only one of the species of enzymes. In other embodiments, enzyme cocktails with three or more of the enzymes Cb193, Cb195, Cb1172, Cb2487, Cb909, and Cb162 are more effective at degrading hemicellulose and releasing monosaccharides from hemicellulose than enzyme cocktails with the same total amount of enzyme units but with only one or two of the species of enzymes. In other embodiments, enzyme cocktails with four or more of the enzymes Cb193, Cb195, Cb1172, Cb2487, Cb909, and Cb162 are more effective at degrading hemicellulose and releasing monosaccharides from hemicellulose than enzyme cocktails with the same total amount of enzyme units but with only one, two, or three of the species of enzymes. In other embodiments, enzyme cocktails with five or more of the enzymes Cb193, Cb195, Cb1172, Cb2487, Cb909, and Cb162 are more effective at degrading hemicellulose and releasing monosaccharides from hemicellulose than enzyme cocktails with the same total amount of enzyme units but with only one, two, three, or four of the species of enzymes. In other embodiments, enzyme cocktails with all six of the enzymes Cb193, Cb195, Cb1172, Cb2487, Cb909, and Cb162 are more effective at degrading hemicellulose and releasing monosaccharides from hemicellulose than enzyme cocktails with the same total amount of enzyme units but with only one, two, three, four, or five of the species of enzymes.

Treatment Methods of Hemicellulose and Hemicellulose-Containing Materials

The above-described hemicellulase enzymes and variants can be used alone or in combination to degrade hemicellulose by cleaving one or more functional groups from the xylose backbone to form cleaved hemicellulose.

Hemicellulose treated with the methods of the present disclosure may be at least 91%, 92%, 93%, 94%, 95%, 96%, 97%, 98%, 99%, or 100% degraded. The hemicellulose substrate is degraded when the enzymes cleave the bonds or linkages present between the subunits present in the hemicellulose. Degradation products may comprise xylose, arabinose, glucuronyl groups, acetyl groups, in addition to other functional groups and hydrocarbons.

In one aspect, plant material containing hemicellulose, or isolated hemicellulose, is treated with one or more of the above-described enzymes, such as Cb193, Cb195, Cb1172, Cb2487, Cb909, and Cb162. In one embodiment, hemicellulose is treated with Cb193 in combination with one or more enzymes including Cb195, Cb1172, Cb2487, Cb909, and Cb162. In one embodiment, hemicellulose is treated with Cb195 in combination with one or more enzymes including Cb193, Cb1172, Cb909, Cb2487, and Cb162.

Without wishing to be bound by theory, Applicants believe that the methods of the present disclosure degrade hemicellulose via the following mechanisms. Treatment of hemicellulose with endoxylanases Cb193, Cb195, or a variant cleaves β-1,4-xylose linkages in the xylose backbone to generate shorter chains of xylose in β-1,4-linkages. Treatment of hemicellulose with the α-L-arabinofuranosidase Cb1172 or a variant cleaves arabinose moiety from the xylose backbone or from branched or debranched arabinan of hemicelluloses to generate exclusively arabinose. Treatment of hemicellulose with the α-glucuronidase Cb909 or a variant cleaves the alpha-1,2,-glycosidic bond between 4-O-methyl-D-glucuronic acid and the beta-1,4-xylosidic linkage backbone of xylan. Treatment of hemicellulose with the β-xylosidase Cb2487 or a variant cleaves beta-1,4-xylosidic linkages in the xylose backbone. Treatment of hemicellulose with Cb162 or a variant cleaves the linkages between xylose and the side chain of acetyl groups in hemicellulose to provide more accessibility to other hemicellulases such as xylanase and β-xylosidase to the backbone of xylan. Using a combination or two or more enzymes is believed to provide synergistic hemicellulose degradation activity.

In certain embodiments, plant material containing hemicellulose, or isolated hemicellulose, may be treated with one or more isolated or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity/sequence similarity to Cb193, Cb195, Cb1172, Cb2487, Cb909, and Cb162.

The polypeptides may be administered directly, either alone, or as a composition.

In other methods of the present disclosure, hemicellulose is degraded by contact with a transgenic host cell secreting one or more polypeptides including Cb193, Cb195, Cb1172, Cb2487, Cb909, and Cb162. In some embodiments, the transgenic host cell may be *Escherichia, Pseudomonas, Proteus, Ralstonia, Streptomyces, Staphylococcus, Lactococcus, Bacillus, Saccharomyces cerevisiae, Schizosaccharomyces pombe, Yarrowia lipolytica, Hansenula polymorpha, Kluyveromyces lactis, Pichia pastoris, Aspergillus, Chrysosporium lucknowense*, or *Trichoderma reesei*. In some embodiments, the transgenic host cell may be a thermophilic microorganism. In one embodiment, the thermophilic host cell is *Caldicellulosiruptor bescii.*

The transgenic host cell may contain a vector encoding Cb193, Cb195, Cb1172, Cb909, Cb2487, Cb162 or variants thereof. In some embodiments, the hemicellulose is degraded by treating with Cb193 or a variant alone, or in combination with one or more of Cb195, Cb1172, Cb909, Cb2487, Cb162, and variants thereof. In some embodiments, the hemicellulose is degraded by treating with Cb195 or a variant alone, or in combination with one or more of Cb193, Cb1172, Cb909, Cb2487, Cb162, and variants thereof.

The methods of the present disclosure can be practiced with any plant material that contains hemicellulose. Plant material suitable for use with the currently disclosed methods include *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, rye hulls, wheat hulls, sugarcane bagasse, corn fiber, Distillers Dried Grains with Solubles (DDGS), Blue Stem, corncobs, pine, birch, willow, aspen, poplar wood, and energy cane. The methods may also be practiced on isolated hemicellulose.

In certain embodiments, thermophilic enzymes of the present disclosure are provided with a substrate at a concentration of at least 0.01 nM enzyme of each enzyme. In certain embodiments, the enzymes are provided with a substrate at a concentration of at least 0.1 nM enzyme of each enzyme. In certain embodiments, the enzymes are provided with a substrate at a concentration of at least 1 nM enzyme of each enzyme. In certain embodiments, the enzymes are provided with a substrate at a concentration of at least 10 nM enzyme of each enzyme. In certain embodiments, the enzymes are provided with a substrate at a concentration of at least 0.1 μM enzyme of each enzyme. In certain embodiments, the enzymes are provided with a substrate at a concentration of at least 10 μM enzyme of each enzyme. In certain embodiments, the enzymes are provided with a substrate at a concentration of at least 100 μM enzyme of each enzyme.

The methods of the present disclosure can be practiced at any pH and temperature at which hemicellulose can be degraded; however, in certain embodiments, the methods of the present disclosure are practiced in a pH range of about 5 to about 7 and at or between a temperature between about 60 and about 80° C.

Combination of Thermostable Hemicellulose-Degrading Enzymes with Thermostable Cellulases In some embodiments, thermostable hemicellulose-degrading enzymes of the present disclosure are provided with thermostable cellulases. Cellulases are enzymes that can hydrolyze cellulose, and they include, but are not limited to, exoglucanases, endoglucanases, and β-glucosidases. In some aspects, thermostable cellulases have optimal enzymatic activity at temperatures above 55° C. Thermostable cellulases may be provided with the thermostable hemicellulose-degrading enzymes of the present disclosure in order to increase the degradation of materials containing both cellulose and hemicellulose, such as biomass from terrestrial plants. For example and without limitation, in one aspect, microorganisms can be provided that express hemicellulose-degrading enzymes of the present disclosure and thermostable cellulases. In one aspect, compositions containing hemicellulose-degrading enzymes of the present disclosure may also contain thermostable cellulases. In other aspects, methods of degrading biomass, of converting biomass into fermentation product, and of converting biomass to fuel are provided, in which biomass is contacted with hemicellulose-degrading enzymes of the present disclosure and with thermostable cellulases Thermostable cellulases may be obtained from organisms capable of degrading cellulose. In one aspect, thermostable cellulases are obtained directly from organisms capable of degrading cellulose. In another aspect, thermostable cellulases are produced recombinantly, through the use of host cells and expression vectors containing genes encoding thermostable cellulases. Thermostable cellulases and/or genes encoding thermostable cellulases may be isolated from various organisms capable of degrading cellulose including, for example and without limitation, archaeal, bacterial, fungal, and protozoan organisms.

Organisms capable of degrading cellulose include for example and without limitation, those belonging to the genera *Aquifex, Bacillus, Rhodothermus, Thermobifida,*

*Thermotoga, Anaerocellum, Sulfolobus, Pyrococcus* and *Caldicellulosiruptor*. A recombinant thermostable endoglucanase of *Aquifex aeolicus* produced in *E. coli* showed maximal activity at 80° C. and pH 7.0 with a half-life of 2 h at 100° C. (Kim J S, Lee Y Y, Torget, R W. (2001). Cellulose hydrolysis under extremely low sulfuric acid and high-temperature conditions. Appl. Biochem. Biotechnol. 91-93. 331-340)). The endoglucanases produced by *Anaerocellum thermophilum* and *Caldicellulosiruptor saccharolyticus* are multidomain enzymes composed of two catalytic domains, linked to carbohydrate binding domains by proline-threonine-rich regions (Zverlov V, Mahr S, Riedel K, Bronnenmeier K (1998a), "Properties and gene structure of a bifunctional cellulolytic enzyme (CelA) from the extreme thermophile '*Anaerocellum thermophilum*' with separate glycosyl hydrolase family 9 and 48 catalytic domains," *Microbiology* 144 (Pt 2): 457-465; Te'o V S, Saul D J, Bergquist P L (1995), "celA, another gene coding for a multidomain cellulase from the extreme thermophile *Caldocellum saccharolyticum," Appl Microbiol Biotechnol* 43: 291-296; Saul et al. 1990. The recombinant endoglucanase of *Rhodothermus marinus* has a pH optimum of 6.0-7.0 and a temperature optimum at 100° C. (Halldórsdóttir S, Thórólfsdóttir ET, Spilliaert R, Johansson M, Thorbjarnardóttir S H, Palsdottir A, Hreggvidsson G O, Kristjánsson J K, Holst O, Eggertsson G. (1998), "Cloning, sequencing and overexpression of a *Rhodothermus marinus* gene encoding a thermostable cellulase of glycosyl hydrolase family 12," *Appl Microbiol Biotechnol* 49: 277-284). The aerobic thermophilic bacterium *Thermus caldophilus* also produces an endoglucanase which exhibits high activity on CMC with cellobiose and cellotriose as products (Kim D, Park B H, Jung B-W, Kim M-K, Hong S I, Lee, D S (2006) Identification and molecular modeling of a family 5 endocellulase from *Thermus caldophilus* GK24, a cellulolytic strain of *Thermus thermophilus*. Int J Mol Sci 7: 571-589). Thermostable cellulases have also been described from *Bacillus subtilis* (Mawadza, C, Hatti-Kaul, R., Zvauya, R. and Mattiasson, B., 2000. Purification and characterization of cellulases produced by two *Bacillus* strains. J. Biotechnol. 83, pp. 177-187), from *Pyrococcus furiosus* (Kengen, S., Luesink, E., Stams, A. and Zehnder, A., 1993. Purification and characterization of an extremely thermostable β-glucosidase from the hyperthermophilic archaeon *Pyrococccus furiosus*. Eur. J. Biochem. 213, pp. 305-312.), from *Pyrococcus horikoshi* (Ando, S., Ishida, H., Kosugi, Y. and Ishikawa, K., 2002. Hyperthermostable endoglucanase from *Pyrococcus horikoshi*. Appl. Environ. Microbiol. 68, pp. 430-433.), from *Rhodothermus marinus* (Hreggvidsson, G O., Kaiste, E., Hoist, O., Eggertsson, G., Palsdottir, A. and Kristjansson, J. K., 1996. An extremely thermostable cellulase from the thermophilic eubacterium *Rhodothermus marinus*. Appl. Environ. Microbiol. 62, pp. 3047-3049.), from *Thermatoga maritema* (Bronnenmeier, K., Kern, A., Libel, W. and Staudenbauer, W., 1995. Purification of *Thermatoga maritema* enzymes for the degradation of cellulose materials. Appl. Environ. Microbiol. 61, pp. 1399-1407.), and from *Thermatoga neapolitana* (Bok, J., Goers, S. and Eveleigh, D., 1994. Cellulase and xylanase systems of *Thermatoga neapolitana*. ACS Symp. Ser. 566, pp. 54-65; Bok, J., Dienesh, A., Yernool, D. and Eveleigh, D., 1998. Purification, characterization and molecular analysis of thermostable cellulases CeIA and CeIB from *Thermatoga neapolitana*. Appl. Environ. Microbiol. 64, pp. 4774-4781.).

In some aspects, the thermostable cellulases are any of Cb1952, Cb1953, Cb1954, Cb1946, Cb629, or Cb486 polypeptides.

In some aspects, any mixture of hemicellulases or hemicellulase with cellulases provided herein may further be provided with Cb1581 polypeptides.

Additional Applications

The methods described herein can be practiced in combination with other methods useful for converting lignocellulosic materials into biofuels.

For example, plant material may be subjected to pretreatment including ammonia fiber expansion (AFEX), steam explosion, treatment with alkaline aqueous solutions, acidic solutions, organic solvents, ionic liquids (IL), electrolyzed water, phosphoric acid, and combinations thereof. Pretreatments that remove lignin from the plant material may increase the overall amount of sugar released from the hemicellulose.

In certain embodiments, where a cellulase mixture is being used to release glucose from plant cell walls, a hemicellulase enzyme cocktail of the present disclosure may be used to hydrolyze the hemicellulosic component of the plant material and increase accessibility of the cellulase cocktail to the cellulose fraction of the plant material.

Typically, the compositions and methods of the present disclosure are used to generate biofuels or specialty chemicals. In one aspect, the compositions and methods of the present disclosure are used to degrade hemicellulose into fermentable sugars. The fermentable sugars are then converted into biofuel components, such as ethanol, propanol, and butanol, or specialty chemicals, such as ketones and aldehydes. The fermentable sugars may be converted by a microorganism, such as yeast, or by isolated enzymes.

The hemicellulose-related methods described herein can be practiced in combination with cellulases. Additional methods are provided for the use of the polypeptides and compositions as feed additives for monogastric animal agriculture, including pigs and poultry production.

EXAMPLES

The following Examples are merely illustrative and are not meant to limit any aspects of the present disclosure in any way.

Example 1: Endoxylanase Cb193 (SEQ ID NOs: 3 and 4)

An endoxylanase, Cb193, was identified in *Caldicellulosiruptor bescii*. The enzyme is the gene product of Cb193, where Cb stands for *C. bescii*. The endoxylanase cleaves the xylose backbone of hemicellulose at random to generate shorter chains of xylose in β-1,4-linkages. These xylooligosaccharides can range from two or more sugar subunits. The Cb193 protein is 671 amino acids long and has a molecular mass of 77.7 kDa (His-tag+truncated Cb193 protein). The protein has two putative carbohydrate binding modules (CBM) inserted within the glycoside hydrolase (GH) family 10 catalytic domain (FIG. 2A).

Cloning of Cb193

The gene for Cb193 was amplified from *Caldicellulosiruptor bescii* genomic DNA by PCR using iProof HF DNA polymerase (BIO-RAD). The Cb193 gene was amplified using the following primer set:

```
Cb193For
                                    (SEQ ID NO: 134)
5'-GACGACGACAAGATGAACTTTGAAGGAAGAGAC-3'
```

-continued

```
Cb193Rev
                                         (SEQ ID NO: 135)
5'-GAGGAGAAGCCCGGTTATTTT TTAGCCTTTAC-3'
```

The polymerase chain reaction mixture contained the following:

| PCR reaction | |
|---|---|
| 2 U/μL iProof HF DNA polymerase | 0.5 |
| 13.7 ng/μL *C. bescii* gDNA | 1 |
| 50 μM Fw Primer | 0.5 |
| 50 μM Rv Primer | 0.5 |
| 10 mM dNTP Mixture | 1 |
| 5x iProof HF Buffer | 10 |
| $dH_2O$ | 36.5 |
| Total | 50 μL |

To amplify the gene from the genomic DNA, the following PCR cycling was used:

| PCR protocol | | | |
|---|---|---|---|
| Denaturing | 98° C. | 10 sec | |
| Annealing | 62° C. | 30 sec | 35 cycles |
| Elongation | 72° C. | 120 sec | |
| Last | 4° C. | ∞ | |

After the PCR amplification described above, the amplification of Cb193 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/mL T4 DNA Polymerase | 0.2 | 22° C. | 30 min |
| Purified PCR Product | 2.1 | 75° C. | 20 min |
| 25 mM dATP | 1 | 4° C. | ∞ |
| 100 mM DTT | 0.5 | | |
| 10x T4 DNA Polymerase Buffer | 1 | | |
| $dH_2O$ | 5.2 | | |
| Total | 10 μL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 μL | | |

After the incubation, EDTA was added to the reaction.

| Annealing | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 μL | | |

The annealing mixture for Cb193-pET46 Ek/LIC was introduced into *E. coli* JM109 by electroporation and the cells were plated on LB-ampicillin. After overnight incubation at 37° C., three colonies were selected and used to inoculate 10 mL cultures of LB-ampicillin. The cultures were grown at 37° C. with vigorous aeration for 16 hours and minipreps were made of the cell cultures. The plasmids were then electrophoresed on a 1% agarose gel to confirm the size of plasmid/insert DNA. Next, the integrity of the gene was confirming by nucleotide sequencing.

For gene expression, one of the plasmids was transformed into *E. coli* BL21 codon plus DE3 RIL by the heat shock method and plated on LB plates supplemented with chloramphenicol and ampicillin at 100 μg/ml and 50 μg/ml and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.5 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed several times to remove the unbound proteins. The bound protein (6-Histidine-tagged Cb193) was then eluted from the resin with an elution buffer composed of the lysis buffer supplemented with 150 mM imidazole.

The gene product of Cb193 was expressed in a truncated form. The first 41 amino acids, which represent a signal peptide, were removed. In the native organism, *C. bescii*, the signal peptide facilitates transport of the Cb193 out of the cell so that it can act on its target substrate (xylan or plant cell wall) in the medium. Usually after transportation outside the cell, the signal peptide is processed (cleaved) off the protein. Signal peptides can often become a problem during production of recombinant proteins. To circumvent this potential problem, i.e., to prevent secretion of the protein into the periplasm, the PCR primers were designed to remove the signal peptide. The signal peptide does not influence catalytic activity. The design of the PCR primers also ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

Cb193 (Amino Acid Sequence)

The Cb193 [ENDO-1,4-BETA-XYLANASE A PRECURSOR (EC 3.2.1.8)] amino acid sequence is disclosed in SEQ ID NO: 3. The signal peptide of Cb193, corresponding to amino acid numbers 1-41 of SEQ ID NO: 3 was removed to create the Cb193 protein expression vector. Thus, the expressed Cb193 protein did not contain amino acids 1-41 of SEQ ID NO: 3. The amino acid sequence of the Cb193 protein without the signal peptide is disclosed in SEQ ID NO: 37.

Cb193 (Nucleotide Sequence)

The Cb193 nucleotide sequence is disclosed in SEQ ID NO: 4. Nucleotide numbers 1-123 of SEQ ID NO: 4 correspond to the signal peptide of Cb193, and were not present in the gene cloned to make Cb193. The Cb193 gene without the first 123 nucleotides is disclosed in SEQ ID NO: 38, which encodes the amino acid sequence of SEQ ID NO: 37.

The procedure of cloning the gene for Cb193 into the plasmid pET46 Ek/LIC led to fusion of the gene to a short nucleotide sequence encoding a peptide that contains six histidines. The short peptide comprises the first 15 amino acids of SEQ ID NO: 6. The nucleotide sequence encoding SEQ ID NO: 6 is SEQ ID NO: 5.

Figure 2B:
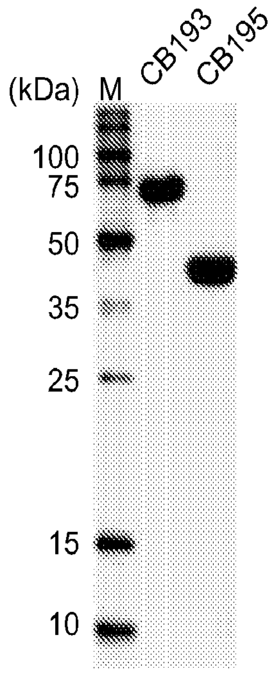

The Cb193 gene was expressed in *E. coli* cells, and the protein was purified in three steps (TALON affinity chromatography, ion exchange chromatography, and gel filtration). FIG. 2B shows an SDS-PAGE of purified Cb193. The molecular markers are in the lane marked M.

Enzyme Activity

The enzymatic activity of Cb193 was measured according to the methods of Morag, E., Bayer, E. A., and Lamed, R. (Relationship of cellulosomal and non-cellulosomal xylanases of *Clostridium thermocellum* to cellulose degrading enzymes. J. Bacteriol. 1990: 172; 6098-6105). 1 μL of sample supernatant (substrate reacted with enzyme) was spotted on TLC plate. A marker mixture was made by combining each 0.2 μL of 1% xylose/xylobiose/xylotriose/xylotetraose/xylopentaose. All sugars were purchased from Megazyme. The spots were dried and the TLC plate was developed in a developing tank for 1 hour. The plate was dried in a chamber for 30 min. The plate was sprayed with visualizing reagent and incubated for 5 to 10 min at 75° C. to visualize the results.

Figure 2C:
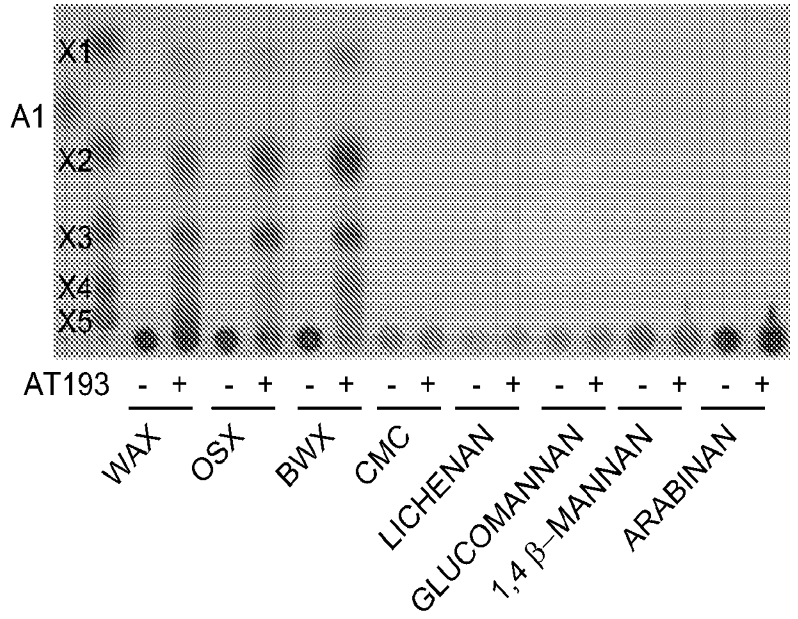

FIG. 2C shows the enzymatic activity of Cb193 on natural substrates using TLC analysis. Various substrates were tested: soluble wheat arabinoxylan (SWAX), oat-spelt xylan (OSX), birchwood xylan (BWX), carboxymethyl cellulose (CMC), lichenan, glucomannan, 1,4 β-mannan, arabinan. In the case of SWAX, OSX, and BWX, in the presence of Cb193 (+), short xylose chains were released. In the minus (−) lanes, no enzyme was added and therefore no products of hydrolysis were released. X1 (xylose monomer), X2 (xylose dimer or a disaccharide), X3 (trisaccharide), X4 (tetrasaccharide), and pentasaccharide (X5) were loaded in the first lane (M) as markers. The results showed that this enzyme releases shorter chains or oligosaccharides from the complex substrates (SWAX, OSX, and BWX).

The concentration of glucose equivalents was determined following enzymatic hydrolysis of SWAX and OSX according to the methods of Lever, M. (A new reaction for colorimetric determination carbohydrates. Anal. Biochem. 1972: 47; 273-279). 1.5 mL microcentrifuge tubes were "zeroed" in an analytical balance. Next, 5±0.1 mg SWAX or OSX were added to each tube, and the mass measured and recorded. The volumes needed to be added to each tube were calculated based on the mass. Sodium phosphate reaction buffer and enzymes were added to each tube beginning with the reaction buffer. The tubes were incubated with constant mixing in a Rotisserie-style tube mixer at 37° C. for 15 h. The tubes were centrifuged at 10,000 rpm for 5 min at 4° C. 100 μL of sample supernatant was transferred to a clean 1.5 mL centrifuge tube for the pHBAH assay, and 150 μL of sodium citrate reaction buffer was added for a final volume of 250 μL. 1 mL of a stock solution of glucose was made at a concentration of 20 mM in sodium citrate buffer, and then serial dilutions were made in sodium citrate buffer to the following concentrations (20 mM, 10 mM, 5 mM, 2.5 mM, 1.25 mM, 0.625 mM, 0.3125 mM). 50 mg of pHBAH was dissolved in 50 mL of ice-cold citrate/NaOH solution for a final concentration of 0.1% (w/v), and the solution kept on ice. 112.5 μL of pHBAH solution was added to 37.5 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbances.

Figure 2D:
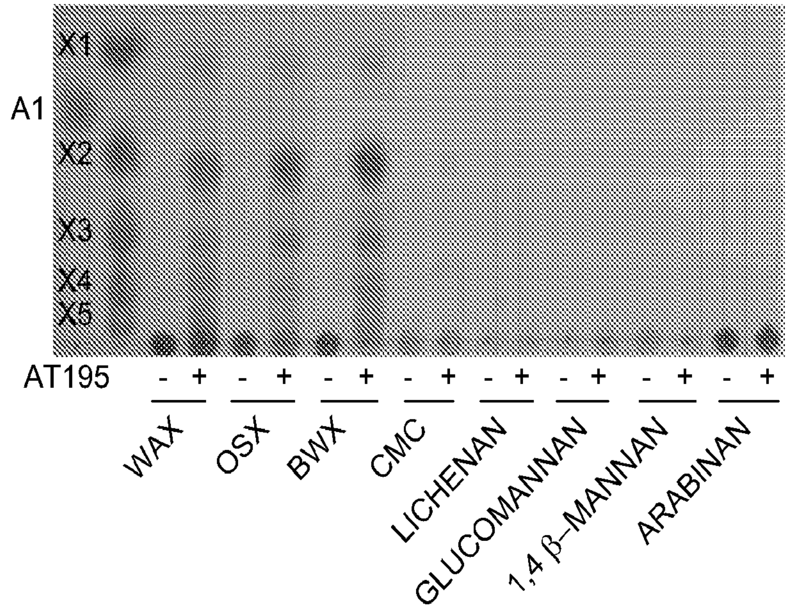
Figure 2E:
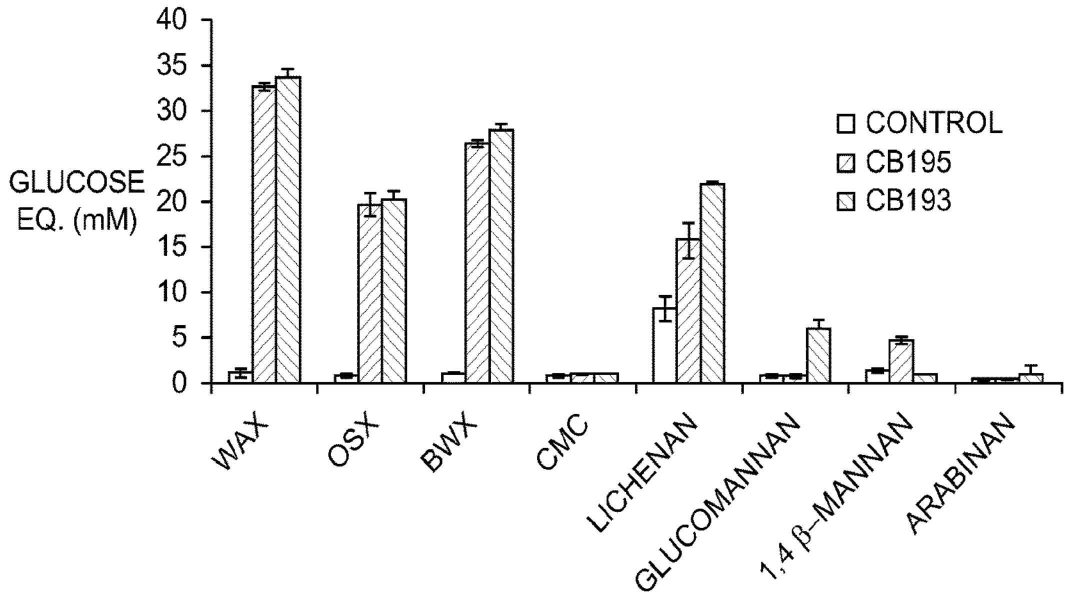

FIG. 2E shows the enzymatic activity of Cb193 on natural substrates from a reducing sugar assay. In this experiment, a different assay for reducing sugars was used to determine the release of products from the substrates. A standard was made based on known glucose concentrations and their absorbance (color development) in the presence of para-hydroxy-benzoic acid hydrazide (Cann et al. 1999. J. Bacterial. 181:1643-1651 and other reference above—Laver, M. 1972.). Incubation of enzymes with the substrates led to release of products that were quantified as a concentration of glucose equivalents.

Figure 3A:
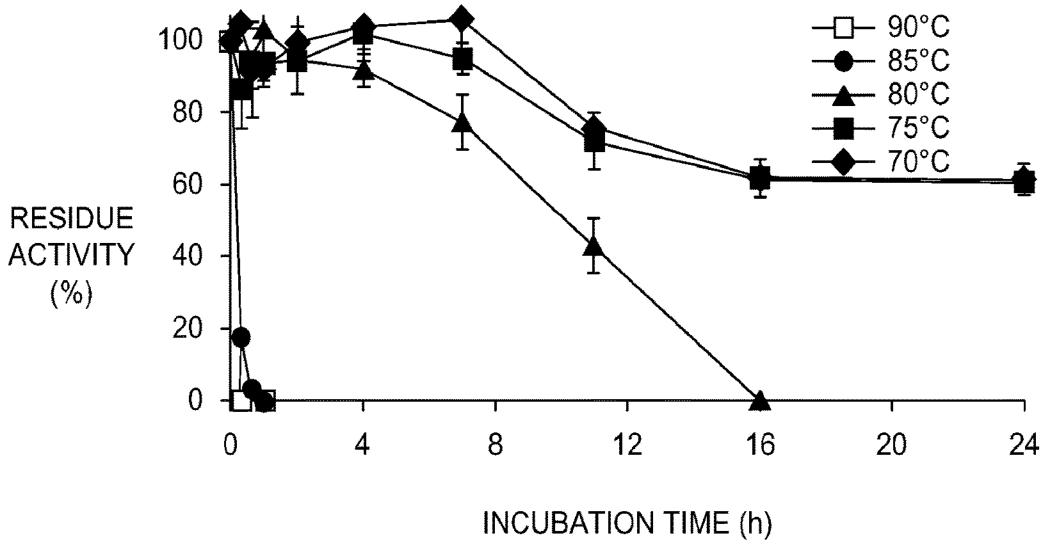
FIGS. 3A and 3B.

FIG. 3A shows the thermostability of Cb193. Final 5 nM of Cb193 was incubated at different temperatures from 70~90° C. The Cb193 enzymes were incubated at 70° C., 75° C., 80° C., 85° C., 90° C. The incubated enzymes were taken out at certain time points (0 h, 0.5 h, 1 h, 2 h, 4 h, 7 h, 11 h, 16 h, and 24 h) and immediately incubated with wheat arabinoxylan (final 1%, w/v) to measure the enzyme activity. The initial velocity of reaction was calculated. The residue activity (%) was calculated by dividing the activity of each sample by the initial activity at zero time. Bars are shown with standard errors for three independent experiments.

FIG. 4 shows the kinetic data of Cb193 on hydrolysis of wheat arabinoxylan, oat spelt xylan, and birchwood xylan. The $K_m$, $k_{cat}$, and $k_{cat}/K_m$ are indicated as well. In FIGS. 4AA, AB, and AC, the experiment was conducted at 75° C. with 50 mM citrate buffer (pH 6.0). In FIGS. BA, BB, and BC, the experiment was conducted at 85° C. with 50 mM citrate buffer (pH 6.0). Xylan substrates (final 2.5-50 mg/mL) were incubated with CB193 (final 5 nM for wheat arabinoxylan and final 50 nM for oat spelt xylan and birchwood xylan). The initial velocity of reaction was calculated. The initial velocities were then plotted against the concentrations of xylan substrates. The $K_m$ and $k_{cat}$ were calculated by non-linear fit using the Graphpad software. Bars are shown with standard errors for three independent experiments.

Example 2: Endoxylanase Cb195 (SEQ ID NOs: 7 and 8)

An endoxylanase, Cb195, was identified in *Caldicellulosiruptor bescii*. The enzyme is the gene product of Cb195, where Cb stands for *C. bescii*. The endoxylanase cleaves the xylose backbone of hemicellulose at random to generate shorter chains of xylose in β-1,4-linkages. These xylo-oligosaccharides can range from containing two or more sugar subunits. The Cb195 protein is 351 amino acids long and has a molecular weight of 41.9 kDa (His-tag+Cb195 protein) (FIG. 2A).

Cloning of Cb195

The gene for Cb195 was amplified from *Caldicellulosiruptor bescii* genomic DNA by PCR using iProof HF DNA polymerase (BIO-RAD).

The polymerase chain reaction mixture contained the following:

| PCR reaction | |
|---|---|
| 2 U/μL iProof HF DNA polymerase | 0.5 |
| 13.7 ng/μL *C. bescii* gDNA | 1 |
| 50 μM Fw Primer | 0.5 |
| 50 μM Rv Primer | 0.5 |
| 10 mM dNTP Mixture | 1 |
| 5x iProof HF Buffer | 10 |
| $dH_2O$ | 36.5 |
| Total | 50 μL |

To amplify the gene from the genomic DNA, the following PCR cycling was used:

| PCR protocol | | | |
|---|---|---|---|
| Denaturing | 98° C. | 10 sec | |
| Annealing | 62° C. | 30 sec | 35 cycles |
| Elongation | 72° C. | 120 sec | |
| Last | 4° C. | ∞ | |

After the PCR amplification described above, the amplification of Cb195 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/mL T4 DNA Polymerase | 0.2 | 22° C. | 30 min |
| Purified PCR Product | 2.1 | 75° C. | 20 min |
| 25 mM dATP | 1 | 4° C. | ∞ |
| 100 mM DTT | 0.5 | | |
| 10x T4 DNA Polymerase Buffer | 1 | | |
| $dH_2O$ | 5.2 | | |
| Total | 10 μL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 μL | | |

After the incubation, EDTA was added to the reaction.

| Annealing | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 μL | | |

The annealing mixtures for Cb195-pET46 Ek/LIC was introduced into *E. coli* JM109 by electroporation and the cells were plated on LB-ampicillin. After overnight incubation at 37° C., three colonies were selected and used to inoculate 10 mL cultures of LB-ampicillin. The cultures were grown at 37° C. with vigorous aeration for 16 hours and minipreps were made of the cell cultures. The plasmids were then electrophoresed on a 1% agarose gel to confirm the size of plasmid/insert DNA. Next, the integrity of the gene was confirming by nucleotide sequencing.

For gene expression, one of the plasmids was transformed into *E. coli* BL21 codon plus DE3 RIL by the heat shock method and plated on LB plates supplemented with chloramphenicol and ampicillin at 100 μg/ml and 50 μg/ml and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.5 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed several times to remove the unbound proteins. The bound protein (6-Histidine-tagged Cb195) was then eluted from the resin with an elution buffer composed of the lysis buffer supplemented with 150 mM imidazole. The protein was purified in three steps (TALON affinity chromatography, ion exchange chromatography, and gel filtration). FIG. 2B shows an SDS-PAGE of purified Cb195. The molecular mass markers are in the lane marked M.

The Cb195 [ENDO-1,4-BETA-XYLANASE A PRECURSOR (EC 3.2.1.8)] amino acid sequence is disclosed in SEQ ID NO: 7. The nucleotide sequence encoding Cb195 is disclosed in SEQ ID NO: 8.

For protein expression, Cb195 was cloned into the plasmid pET46 Ek/LIC. The amino acid sequence of Cb195-pET46 Ek/LIC is SEQ ID NO: 10. Amino acid numbers 1-15 of SEQ ID NO: 10 are from the pET46 Ek/LIC plasmid, and include a sequence of six histidines to facilitate protein purification. The nucleotide sequence encoding SEQ ID NO: 10 is disclosed in SEQ ID NO: 9. Nucleotide numbers 1-45 of SEQ ID NO: 9 are from the pET46 Ek/LIC plasmid.

Enzyme Activity

The enzymatic activity of Cb195 was measured according to the methods of Morag, E., Bayer, E. A., and Lamed, R. (Relationship of cellulosomal and non-cellulosomal xylanases of *Clostridium thermocellum* to cellulose degrading enzymes. J. Bacteriol. 1990: 172; 6098-6105). 1 μL of sample supernatant (substrate reacted with enzyme) was spotted on TLC plate. A marker mixture was made by combining each 0.2 μL of 1% xylose/xylobiose/xylotriose/xylotetraose/xylopentaose. All sugars were purchased from Megazyme. The spots were dried and the TLC plate was developed in a developing tank for 1 hour. The plate was dried in a chamber for 30 min. The plate was sprayed with visualizing reagent and incubated for 5 to 10 min at 75° C. to visualize the results.

FIG. 2D shows the enzymatic activity of Cb195 on natural substrates using TLC analysis. Various substrates were tested: soluble wheat arabinoxylan (SWAX), oat-spelt xylan (OSX), birchwood xylan (BWX), carboxymethyl cellulose (CMC), lichenan, glucomannan, 1,4 β-mannan, arabinan. In the case of SWAX, OSX, and BWX, in the presence of Cb195 (+), short xylose chains were released. In the minus (−) lanes, no enzyme was added and therefore no products of hydrolysis were released. X1 (xylose monomer), X2 (xylose dimer or a disaccharide), X3 (trisaccharide), X4

(tetrasaccharide), and pentasaccharide (X5) were loaded in the first lane (M) as markers. The results showed that this enzyme releases shorter chains or oligosaccharides from the complex substrates (SWAX, OSX, and BWX).

The concentration of glucose equivalents was determined following enzymatic hydrolysis of soluble wheat arabinoxylan (SWAX) and oat-spelt xylan (OSX) according to the methods of Lever, M. (A new reaction for colorimetric determination carbohydrates. Anal. Biochem. 1972: 47; 273-279). 1.5 mL microcentrifuge tubes were "zeroed" in an analytical balance. Next, 5±0.1 mg SWAX or OSX were added to each tube, and the mass measured and recorded. The volumes needed to be added to each tube were calculated based on the mass. Sodium phosphate reaction buffer and enzymes were added to each tube beginning with the reaction buffer. The tubes were incubated with constant mixing in a Rotisserie-style tube mixer at 37° C. for 15 h. The tubes were centrifuged at 10,000 rpm for 5 min at 4° C. 100 μL of sample supernatant was transferred to a clean 1.5 mL centrifuge tube for the pHBAH assay, and 150 μL of sodium citrate reaction buffer was added for a final volume of 250 μL. 1 mL of a stock solution of glucose was made at a concentration of 20 mM in sodium citrate buffer, and then serial dilutions were made in sodium citrate buffer to the following concentrations (20 mM, 10 mM, 5 mM, 2.5 mM, 1.25 mM, 0.625 mM, 0.3125 mM). 50 mg of pHBAH was dissolved in 50 mL of ice-cold citrate/NaOH solution for a final concentration of 0.1% (w/v), and the solution kept on ice. 112.5 μL of pHBAH solution was added to 37.5 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbances.

FIG. 2E shows the enzymatic activity of Cb195 on natural substrates from a reducing sugar assay. In this experiment, a different assay for reducing sugars was used to determine the release of products from the substrates. A standard was made based on known glucose concentrations and their absorbance (color development) in the presence of para-hydroxy-benzoic acid hydrazide (Cann et al. 1999. J. Bacterial. 181:1643-1651 and other reference above-Laver, M. 1972.). Incubation of enzymes with the substrates led to release of products that were quantified as a concentration of glucose equivalents.

Figure 3B:
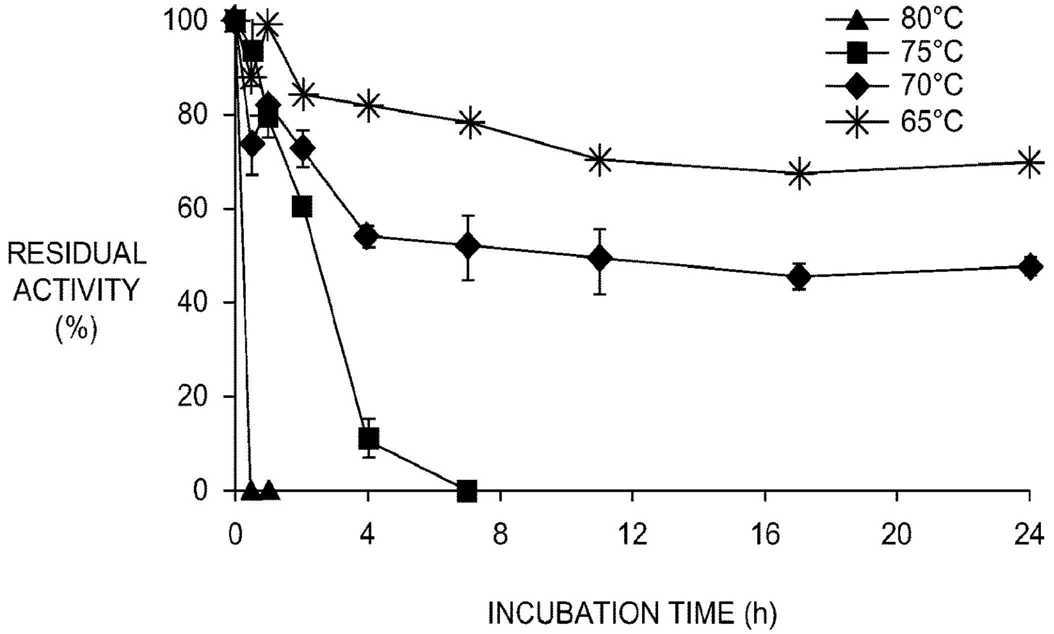
Figure 4A:
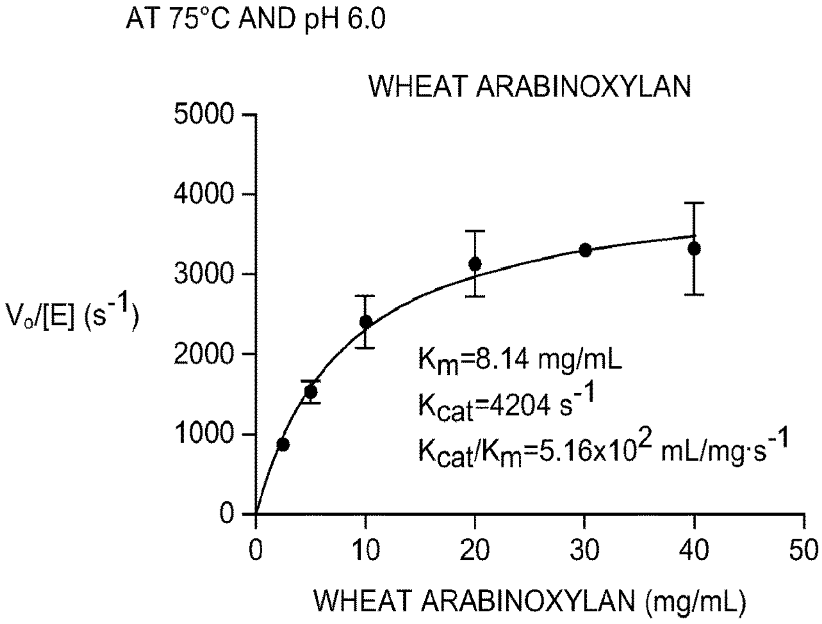
FIGS. 4AA to 4BC show the kinetic data of Cb193 on hydrolysis of wheat arabinoxylan (FIGS. 4AA and 4BA), oat spelt xylan (FIGS. 4AB and 4BB), and birchwood xylan (FIGS. 4AC and 4BC). The $K_m$, $k_{cat}$, and $k_{cat}/K_m$ are indicated as well.
Figure 4A:
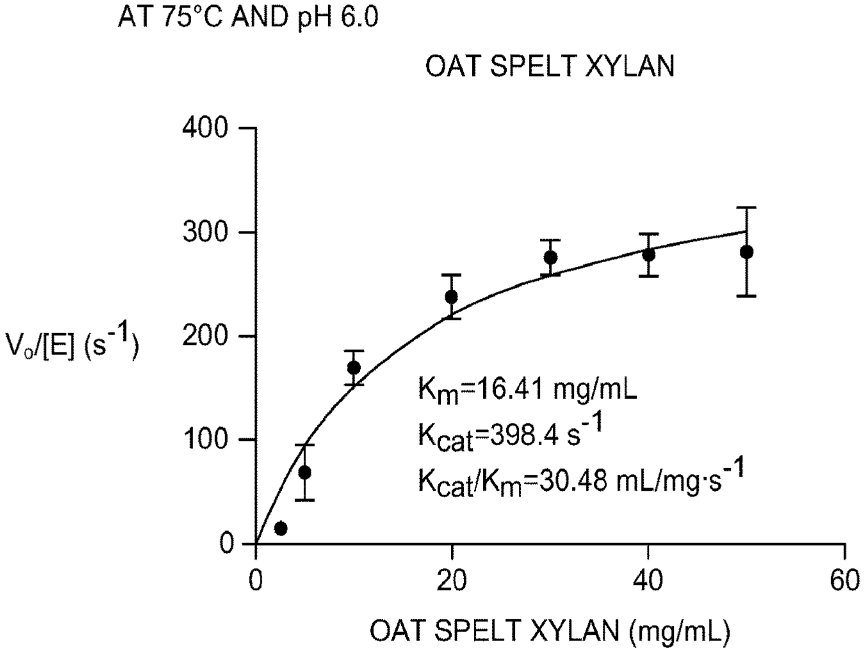
Figure 4A:
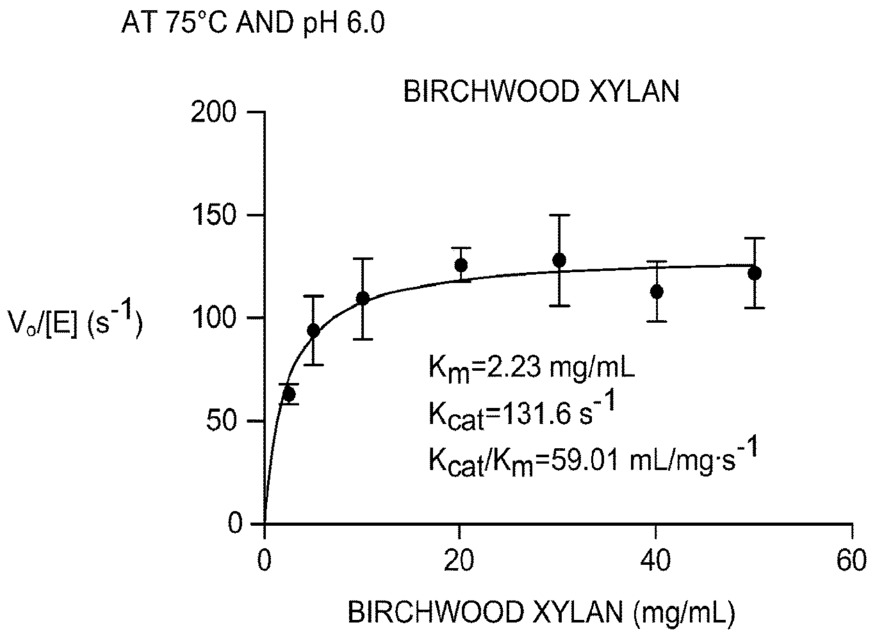
Figure 4B:
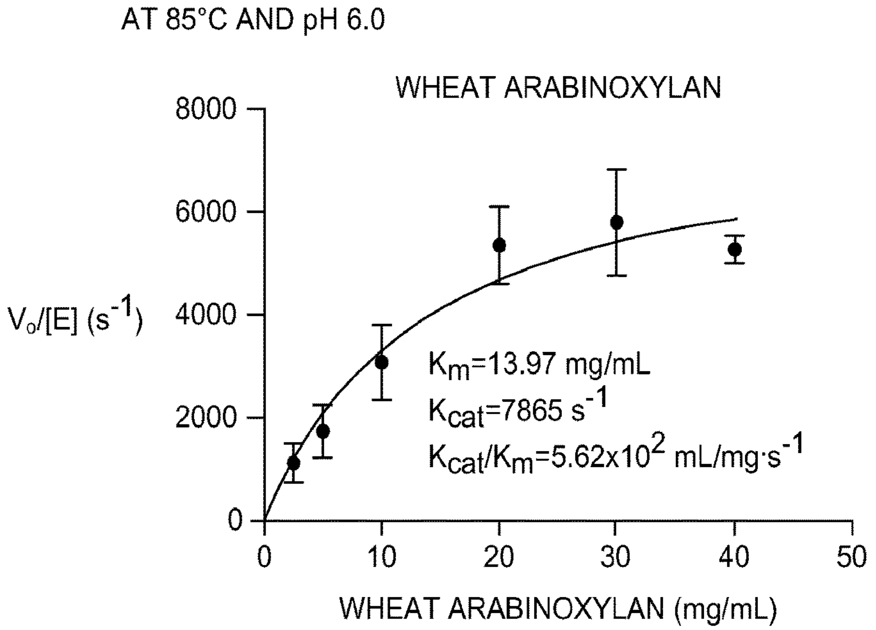
In FIGS. 4BA, 4BB, and 4BC the experiment was conducted at 85° C. with 50 mM citrate buffer (pH 6.0). Xylan substrates (final 2.5-50 mg/mL) were incubated with Cb193 (final 5 nM for wheat arabinoxylan and final 50 nM for oat spelt xylan and birchwood xylan). The initial velocity of reaction was calculated. The initial velocities were then plotted against the concentrations of xylan substrates. The $K_m$ and $k_{cat}$ were calculated by non-linear fit using the Graphpad software. Bars are shown with standard errors for three independent experiments.
Figure 4B:
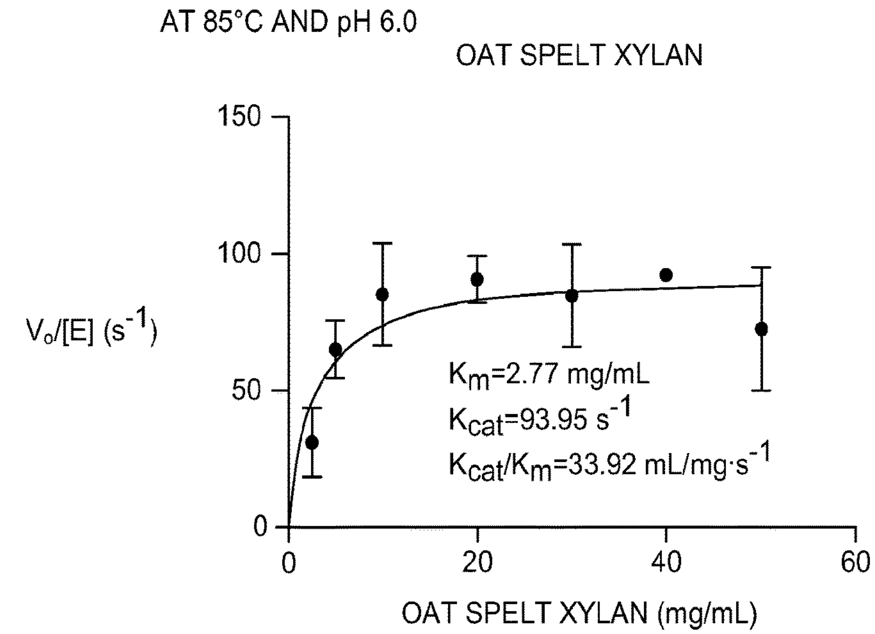
Figure 4B:
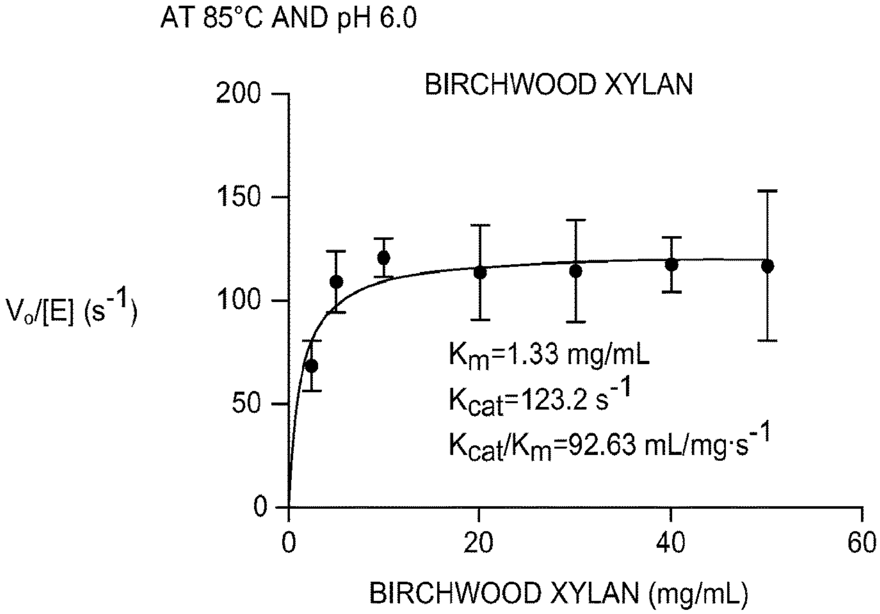
Figure 5A:
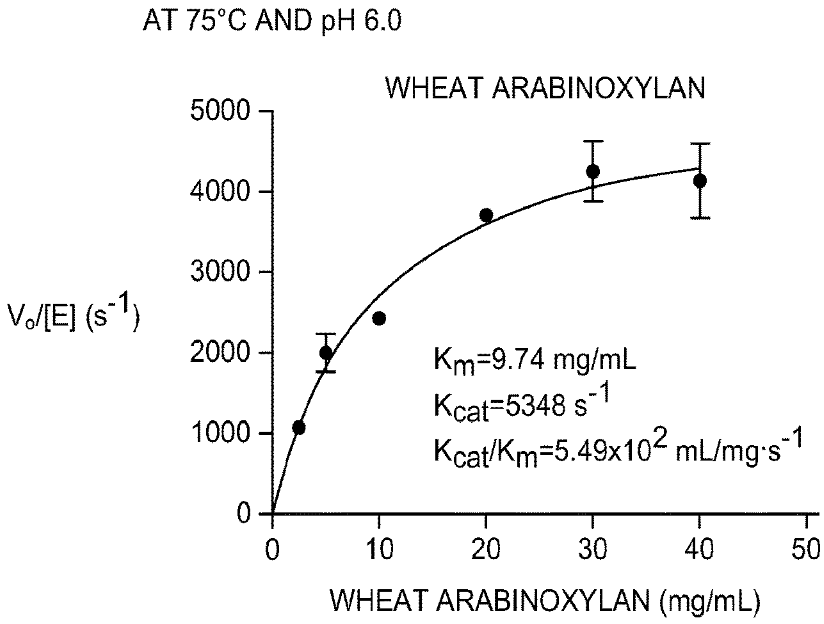
FIGS. 5AA to 5BC show the kinetic data of Cb195 on hydrolysis of wheat arabinoxylan (FIGS. 5AA and 5BA), oat spelt xylan (FIGS. 5AB and 5BB), and birchwood xylan (FIGS. 5AC and 5BC). The $K_m$, $k_{cat}$, and $k_{cat}/K_m$ are indicated as well.
Figure 5A:
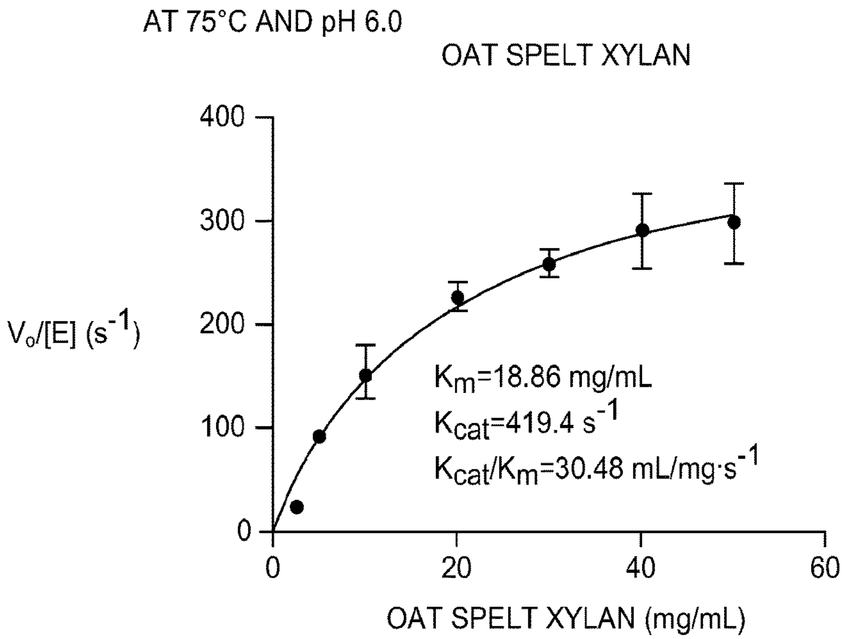
Figure 5A:
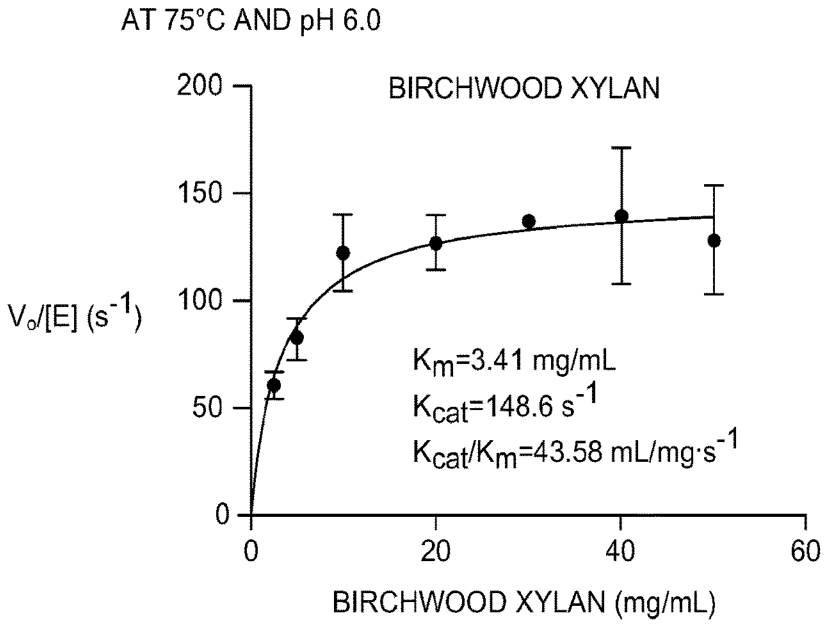
Figure 5B:
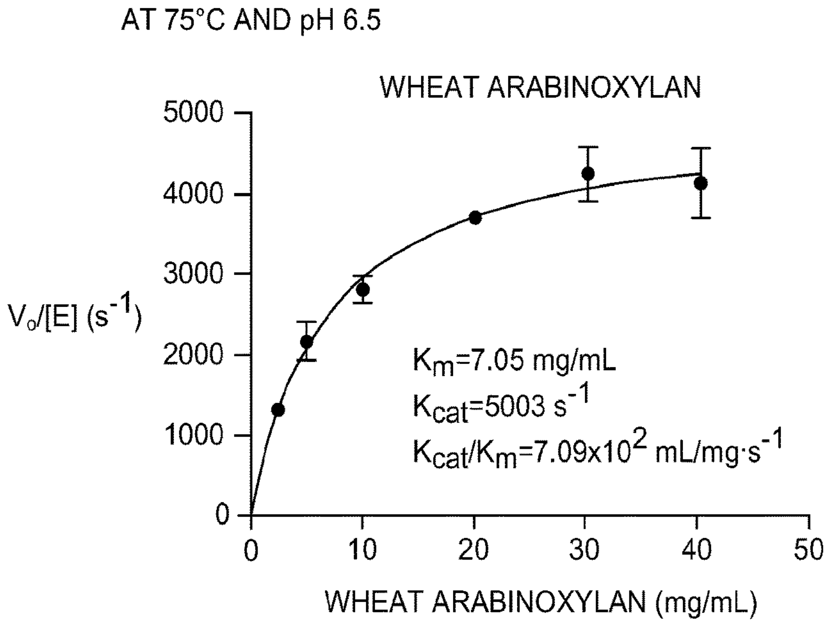
In FIGS. 5BA, 5BB, and 5BC, the experiment was conducted at 75° C. with 50 mM sodium phosphate buffer (pH 6.5). Xylan substrates (final 2.5-50 mg/mL)
Figure 5B:
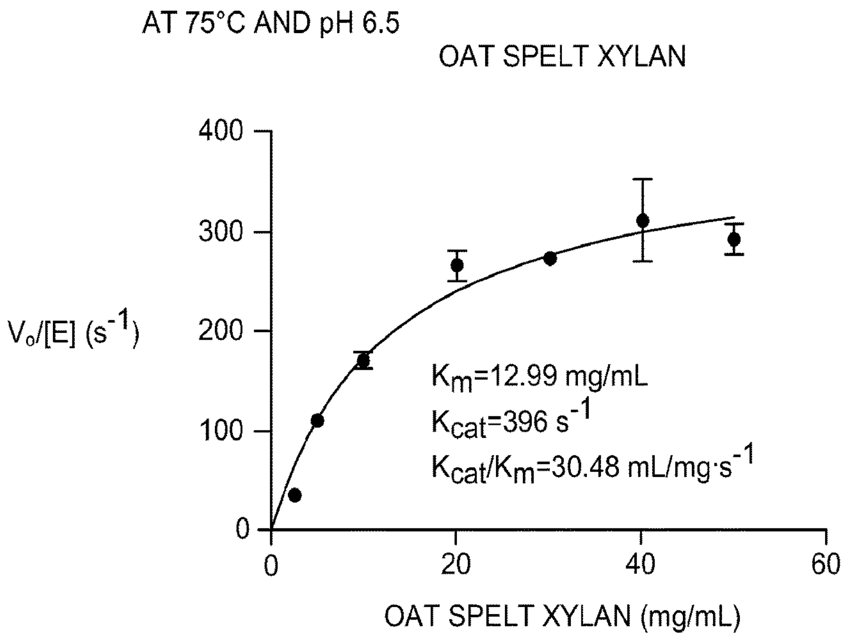
Figure 5B:
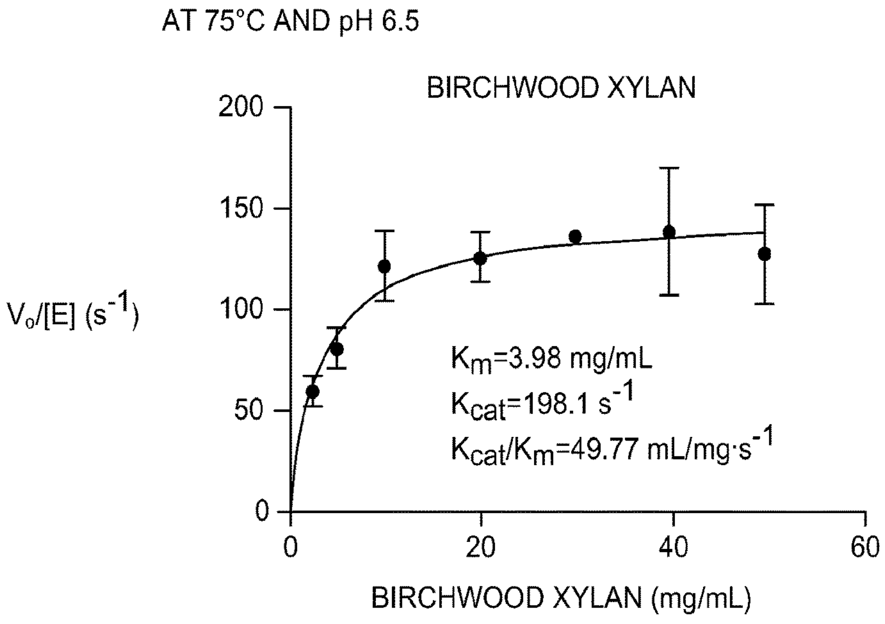

FIG. 3B shows the thermostability of Cb195. Final 5 nM of Cb195 were incubated at different temperatures ranging from 65~80° C. The Cb195 enzymes were incubated at 65° C., 70° C., 75° C., and 80° C. The incubated enzymes were taken out at certain time points (0 h, 0.5 h, 1 h, 2 h, 4 h, 7 h, 11 h, 16 h, and 24 h) and immediately incubated with wheat arabinoxylan (final 1%, w/v) to measure the enzyme activity. The initial velocity of reaction was calculated. The residue activity (%) was calculated by dividing the activity of each sample by the initial activity at zero time. Bars are shown with standard errors for three independent experiments.

FIG. 5 shows the kinetic data of Cb195 on hydrolysis of wheat arabinoxylan, oat spelt xylan, and birchwood xylan. The $K_m$, $k_{cat}$, and $k_{cat}/K_m$ are indicated as well. In FIGS. 5AA, 5AB, and 5AC, the experiment was conducted at 75° C. with 50 mM citrate buffer (pH 6.0). In FIGS. 5BA, 5BB, and 5BC, the experiment was conducted at 75° C. with 50 mM sodium phosphate buffer (pH 6.5). Xylan substrates (final 2.5-50 mg/mL) were incubated with Cb195 (final 5 nM for wheat arabinoxylan and final 50 nM for oat spelt xylan and birchwood xylan). The initial velocity of reaction was calculated. The initial velocities were then plotted against the concentrations of xylan substrates. The $K_m$ and $k_{cat}$ were calculated by non-linear fit using the Graphpad software. Bars are shown with standard errors for three independent experiments.

Example 3: α-L-Arabinofuranosidase Cb1172 (SEQ ID NOs: 13 and 14)

An α-L-arabinofuranosidase, Cb1172, was identified in *Caldicellulosiruptor bescii*. The enzyme is the gene product of Cb1172. The α-L-arabinofuranosidase cleaves arabinose moiety from the xylose backbone or from branched or debranched arabinan of hemicellulose to generate exclusively arabinose. The Cb1172 protein is 505 amino acids long and has a molecular mass of 59.6 kDa (His-tag+Cb1172 protein). The protein has a glycoside hydrolase (GH) family 51 catalytic domain (FIG. 6D).

Cloning of Cb1172

The gene for Cb1172 was amplified from *Caldicellulosiruptor bescii* DSM 6725T genomic DNA by PCR using iProof™ High-Fidelity DNA Polymerase (BIO-RAD). The Cb1172 gene was amplified using the following primer set:

```
Cb1172Forward
                                        (SEQ ID NO: 136)
5'-GAC GAC GAC AAG ATG AAA AAA GCA AAA GTC
ATC TAC-3'

Cb1172Reverse
                                        (SEQ ID NO: 137)
5'-GAG GAG AAG CCC GGT TAA TTT TCT TTC TTC
TTT AAC CTG-3'
```

The polymerase chain reaction mixture contained the following:

| PCR reaction | |
|---|---|
| 2 U/μL iProoF ™ High-Fidelity DNA Polymerase | 0.5 |
| 17 ng/μL *Caldicellulosiruptor bescii* genomic DNA | 1 |
| 50 μM Fw Primer | 0.5 |
| 50 μM Rv Primer | 0.5 |
| 10 mM dNTP Mixture | 1 |
| 5 × iProof HF Buffer | 10 |
| $dH_2O$ | 36.5 |
| Total | 50 μL |

To amplify the gene from the genomic DNA, the following PCR cycling was used:

| PCR protocol | | | |
|---|---|---|---|
| Denaturing | 98° C. | 30 sec | 1 cycle |
| Denaturing | 98° C. | 10 sec | 35 cycles |
| Annealing | 62° C. | 30 sec | |
| Elongation | 72° C. | 2 min | |
| Elongation | 72° C. | 10 min | 1 cycle |
| Last | 4° C. | ∞ | |

After the PCR reaction described above, the amplification of Cb1172 gene was confirmed by 1% agarose gel electrophoresis. The DNA corresponding to the expected band on the gel was cut out and applied to a Qiagen Gel Extraction kit to extract the DNA out of the gel.

The Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was deactivated by incubating at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for Cb1172-pET-46 Ek/LIC was introduced into *E. coli* JM109 by electroporation method, and the cells were plated on LB-ampicillin. After overnight incubation at 37° C., four colonies were selected and used individually to inoculate 6 mL cultures of LB-ampicillin. The cultures were grown at 37° C. with vigorous aeration for 16 hours, and plasmid minipreps (QIAGEN) were made from the cell cultures. The plasmids were then electrophoresed on a 1% agarose gel to confirm the size of the plasmid DNA. The plasmid inserts (genes) were sequenced to confirm their identity.

For gene expression, one of the correct plasmids was transformed into *E. coli* BL21 codon plus DE3 RIL by the heat shock method and plated on LB plates supplemented with chloramphenicol (100 μg/ml) and ampicillin (50 μg/ml) and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.01 mM final concentration, and the culturing continued at 16° C. overnight.

Protein Purification

Cultures were centrifuged to collect the cell pellet. The pellet was then suspended in a lysis buffer (25 mM Tris-HCL pH 7.8, 750 mM of NaCl, 5% glycerol, 20 mM imidazole, 1.25% Tween-20). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged Cb1172) was then eluted from the resin with an elution buffer (50 mM Tris-HCL, pH7.5, 250 mM imidazole).

The gene product of Cb1172 was expressed in its full length form. The design of the PCR primers ensured that the protein was fused to 6-histidines encoded in the plasmid. The six histidines will bind to either a nickel-charged resin or a cobalt-charged resin. The bound protein can then be displaced from the resin with a buffer containing imidazole. This method facilitated quick purification of the protein.

The Cb1172 [α-L-arabinofuranosidase (EC 3.2.1.55)] amino acid sequence is disclosed in SEQ ID NO: 13. The nucleotide sequence encoding Cb1172 is disclosed in SEQ ID NO: 14.

For protein expression, Cb1172 was cloned into the plasmid pET46 Ek/LIC. The amino acid sequence of Cb195-pET46 Ek/LIC is SEQ ID NO: 16. Amino acid numbers 1-15 of SEQ ID NO: 16 are from the pET46 Ek/LIC plasmid, and include a sequence of six histidines to facilitate protein purification. The nucleotide sequence encoding SEQ ID NO: 16 is disclosed in SEQ ID NO: 15. Nucleotide numbers 1-45 of SEQ ID NO: 15 are from the pET46 Ek/LIC plasmid.

The Cb1172 gene was expressed in *E. coli* cells, and the protein was purified in two steps, including a talon resin purification (immobilized metal affinity chromatography) step making use of the 6-histidines encoded by the plasmid and an anion exchange step using Hitrap Q column. FIG. 6A shows an SDS-PAGE of purified Cb1172.

Enzyme Activity

FIG. 6B shows the enzymatic activity of Cb1172 on natural substrates from a reducing sugar assay. Five different hemicellulosic substrates were tested: arabinan (sugar beet), soluble wheat arabinoxylan (SWAX), rye arabinoxylan (RAX), oat spelt xylan (OSX) and debranched arabinan. Incubation of enzymes with the substrates led to release of products that were quantified as a concentration of arabinose equivalents. Hydrolysis of arabinan (from sugar beet) was higher than hydrolysis of other natural substrates.

The concentration of arabinose equivalents was determined following enzymatic hydrolysis of arabinan (sugar beet), soluble wheat arabinoxylan (SWAX), rye arabinoxylan (RAX), oat spelt xylan (OSX) and debranched arabinan, according to the methods of Lever, M. (A new reaction for colorimetric determination carbohydrates. Anal. Biochem. 1972: 47; 273-279). 1.5 mL microcentrifuge tubes were "zeroed" in an analytical balance. Next, 2±0.1 mg arabinan (sugar beet), SWAX, RAX, OSX and debranched arabinan were added to each tube, and the mass measured and recorded. The volumes needed to be added to each tube were calculated based on the mass. Sodium citrate reaction buffer and enzymes were added to each tube beginning with the reaction buffer. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay. 1 mL of a stock solution of arabinose was made at a concentration of 100 mM in sodium citrate buffer, and then serial dilutions were made in sodium citrate buffer to the following concentrations (50 mM, 25 mM, 12.5 mM and 6.25 mM). 50 mg of pHBAH was dissolved in 50 mL of ice-cold citrate/NaOH solution for a final concentration of 0.1% (w/v), and the solution was kept on ice. 150 μL of pHBAH solution was added to 50 μL of the sample and arabinose standard solutions, and the tubes were incubated at 100° C. for 10 min. The tubes were incubated at room temperature for 5 min. The wavelength at 410 nm was measured for the standards and samples. The $A_{410nm}$ and arabinose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbances.

FIG. 6C shows the enzymatic activity of Cb1172 on natural substrates using HPLC analysis. Five different hemicellulosic substrates were tested: arabinan (sugar beet), soluble wheat arabinoxylan (SWAX), rye arabinoxylan (RAX), oat spelt xylan (OSX) and debranched arabinan. In each case, in the presence of Cb1172, arabinose was released. In the absence of Cb1172, only minor amount of arabinose was observed for debranched arabinan; no products of hydrolysis were released for other natural polysaccharides. The results showed that this enzyme releases arabinose from complex substrates (arabinan, SWAX, RAX, OSX and debranched arabinan).

FIG. 6E shows the thermostability of Cb1172. Cb1172 has 57%, 45%, 35% and 22% activity after incubation at 70° C., 75° C., 80° C. and 85° C. for 24 h, respectively. Fifty nM Cb1172 was kept at different temperatures (70° C., 75° C., 80° C., 85° C. and 90° C.). The samples were taken out at the following time points (0 h, 0.5 h, 1 h, 2 h, 4 h, 7 h, 11 h and 24 h) and immediately applied to enzyme activity measurement. The enzyme activity was measured at 85° C. using Cary 300 UV-Vis spectrophotometer (Varian). One hundred μl 1.25 mM pNP-α-L-arabinofuranoside substrate was kept at 85° C. for three minutes to equilibrate. Then twenty five μl of the protein sample was added to the substrate and mixed by pipetting up and down for several times. The optical density at 400 nm was recorded by the spectrophotometer for 2.5 minutes. And the initial velocity of reaction in the first minute was calculated. The initial velocity of reaction for time 0 was set as 100; then the remaining activities (percentage) for time 0.5 h, 1 h, 2 h, 4 h, 7 h, 11 h and 24 h were calculated by dividing the initial velocities of reaction for time 0.5 h, 1 h, 2 h, 4 h, 7 h, 11 h and 24 h by the initial velocity of reaction at time 0, then multiplied by 100, respectively.

FIG. 7 shows the kinetic data of Cb1172 on hydrolysis of pNP-α-L-arabinofuranoside. The $K_m$, $k_{cat}$, and $k_{cat}/K_m$ are indicated as well. In FIG. 7A, the experiment was conducted at 90° C.; in FIG. 7B, the experiment was conducted at 75° C. One hundred μl pNP-α-L-arabinofuranoside substrate of different concentrations was kept at 85° C. for three minutes to equilibrate. Then twenty five μl of the protein sample (fifty nM) was added to the substrate and mixed by pipetting up and down for several times. The optical density at 400 nm was recorded by a Cary 300 UV-Visible spectrophotometer for 2.5 minutes. The initial velocity of reaction in the first minute was calculated. The initial velocities were then plotted against the concentrations of pNP-α-L-arabinofuranoside. The $K_m$ and $k_{cat}$ were calculated by non-linear fit using the Graphpad software.

Example 4: α-Glucuronidase Cb909 (SEQ ID NOs: 19 and 20)

An α-glucuronidase, Cb909, was identified in *Caldicellulosiruptor bescii*. The α-glucuronidase cleaves the α-1,2-glycosidic bond between 4-O-methyl-D-glucuronic acid and the β-1,4-xylosidic linkage backbone of xylan.

The Cb909 gene was amplified by PCR using iProof™ High-Fidelity DNA Polymerase (Bio-Rad) and subcloned into pET46 Ek/LIC vector using Ek/LIC Cloning Kits (Novagen). The forward (For) and reverse (Rev) primer sequences are below:

```
CB909For
                                    (SEQ ID NO: 138)
5'-GAC GAC GAC AAG ATG ATT TTA TCA AGG AGC AGT
AAC-3'

CB909Rev
                                    (SEQ ID NO: 139)
5'-GAG GAG AAG CCC GGT TAC GGA TAT ATT AGT CTT
C-3'
```

The PCR mixture and the amplification procedure appear below:

| PCR mixture | μL |
|---|---|
| 2 U/μL iProoF ™ High-Fidelity DNA Polymerase | 0.5 |
| Genomic DNA | 1 |
| 50 μM Fw Primer | 0.5 |
| 50 μM Rv Primer | 0.5 |
| 10 mM dNTP Mixture | 1 |
| 5 x iProof HF Buffer | 10 |
| $dH_2O$ | 36.5 |
| Total | 50 |

| PCR Protocol | | | |
|---|---|---|---|
| Denature | 98° C. | 30 sec | |
| Denature | 98° C. | 10 sec | 35 Cycles |
| Anneal | 62° C. | 30 sec | |
| Elongate | 72° C. | 2 min | |
| Elongate | 72° C. | 10 min | |
| Final | 4° C. | ∞ | |

After the PCR amplification described above, the amplification of Cb909 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/μL T4 DNA Polymerase | 0.2 | 22° C. | 30 min |
| Purified PCR Product | 0.5 | 75° C. | 20 min |
| 25 mM dATP | 1 | 4° C. | ∞ |
| 100 mM DTT | 0.5 | | |
| 10x T4 DNA Polymerase Buffer | 1 | | |
| $dH_2O$ | 6.8 | | |
| Total | 10 μL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 μL | | |

After the incubation, EDTA was added to terminate the annealing reaction.

| Termination reaction | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 μL | | |

The annealing mixture for Cb909-pET46 Ek/LIC was used to transform *E. coli* JM109 by electroporation and the cells were plated on LB-ampicillin plates. After overnight incubation at 37° C., three colonies were selected and each was used to inoculate 10 mL cultures of LB-ampicillin. The cultures were grown at 37° C. with vigorous aeration for 16 hours and plasmid minipreps were made of each cell culture. The individual plasmid preparations were then electrophoresed on a 1% agarose gel to confirm the size of plasmid/insert DNA. Next, the integrity of the gene was confirmed by nucleotide sequencing.

The Cb909 (α-glucuronidase) amino acid sequence is disclosed in SEQ ID NO: 19.

The nucleotide sequence encoding Cb909 is disclosed in SEQ ID NO: 20.

For protein expression, Cb909 was cloned into the plasmid pET46Ek/LIC. The amino acid sequence of Cb909-pET46 Ek/LIC is SEQ ID NO: 24. Amino acid numbers 1-15 of SEQ ID NO: 24 are from the pET46 Ek/LIC plasmid, and include a sequence of six histidines to facilitate protein purification. The nucleotide sequence encoding SEQ ID NO: 24 is disclosed in SEQ ID NO: 23. Nucleotide numbers 1-45 of SEQ ID NO: 23 are from the pET46 Ek/LIC plasmid.

FIG. 8A shows putative domain architecture of Cb909. FIG. 8B show SDS-PAGE of purified Cb909.

FIG. 8C shows the activity of Cb909. The substrate is aldouronic acids, that is a mixture of xylo-oligosaccharides decorated with 4-O-methyl-D-glucuronosyl (MeGlcA). After incubation with Cb909 at 75° C. for 60 minutes, MeGlcA group was cleaved by Cb909 from aldouronic acids to release undecorated xylose, xylobiose, xylotriose and xylotetraose as products. The condition of the reaction was as follows: 6 nM Cb909, 50 mM Phosphate buffer pH 6.0, 150 mM NaCl, 1 mg/ml aldouronic acids.

FIG. 8D shows the results of pH optimization assay for Cb909. The maximum activity was detected at pH 5.5. This assay was carried out as follows: 1 mg/ml aldouronic acids solution was incubated with 6 nM Cb909 for 10 minutes at 75° C. at each pH. 50 mM citrate buffer containing 150 mM NaCl was used in the range from pH 5 to pH 6.50 mM phosphate buffer containing 150 mM NaCl was used in the range of pH 6 to pH 7. After the reaction, the temperature was quickly increased to 100° C. to terminate the reaction. The amounts of products were detected by HPLC.

FIG. 8E shows the results of optimum temperature assay. The maximum activity of Cb909 was detected at 75° C. (xylobiose and xylotriose). Xylose was produced most efficiently at 70° C. but the amounts of produced xylose at 70° C. and 75° C. were almost the same. This assay was carried out as follows: 1 mg/ml aldouronic acids solution was incubated with 6 nM Cb909 for 10 minutes in 50 mM citrate buffer pH 5.5 that contained 150 mM NaCl. After the reaction the temperature was quickly increased to 100° C. to terminate the reaction. The amounts of products were detected by HPLC.

Example 5: β-Xylosidase Cb2487 (SEQ ID NOs: 27 and 28)

Another enzyme in the enzyme cocktail is a β-xylosidase that was amplified from a *Caldicellulosiruptor bescii*, Cb2487.

The Cb2487 gene was amplified by PCR using iProof™ High-Fidelity DNA Polymerase (Bio-Rad) and subcloned into pET46 Ek/LIC vector using Ek/LIC Cloning Kits (Novagen). The forward (For) and reverse (Rev) primer sequences are below:

```
CB2487For
                                        (SEQ ID NO: 140)
5'-GACGACGACAAGATGTCAATTGAAAAAAGGGTAAAC-3'

CB2487Rev
                                        (SEQ ID NO: 141)
5'-GAGGAGAAGCCCGGTTATTCACACCATGCA-3'
```

The PCR mixture and the amplification procedure appear below:

| PCR mixture | |
|---|---|
| | μL |
| 2 U/μL iProoF ™ High-Fidelity DNA Polymerase | 0.5 |
| Genomic DNA | 1 |
| 50 μM Fw Primer | 0.5 |
| 50 μM Rv Primer | 0.5 |
| 10 mM dNTP Mixture | 1 |
| 5 x iProof HF Buffer | 10 |
| $dH_2O$ | 36.5 |
| Total | 50 |

| PCR Protocol | | | |
|---|---|---|---|
| Denature | 98° C. | 30 sec | |
| Denature | 98° C. | 10 sec | 35 Cycles |
| Anneal | 62° C. | 30 sec | |
| Elongate | 72° C. | 2 min | |
| Elongate | 72° C. | 10 min | |
| Final | 4° C. | ∞ | |

After the PCR amplification described above, the amplification of Cb2487 gene was confirmed by 1% agarose gel electrophoresis. T4 DNA polymerase (Novagen) was then added to the purified PCR product to generate compatible overhangs.

| T4 DNA polymerase treatment | | Incubation | |
|---|---|---|---|
| 2.5 U/μL T4 DNA Polymerase | 0.2 | 22° C. | 30 min |
| Purified PCR Product | 0.5 | 75° C. | 20 min |
| 25 mM dATP | 1 | 4° C. | ∞ |
| 100 mM DTT | 0.5 | | |
| 10x T4 DNA Polymerase Buffer | 1 | | |
| $dH_2O$ | 6.8 | | |
| Total | 10 μL | | |

After the reaction, the following annealing reaction was prepared with pET46 Ek/LIC vector.

| Annealing | | Incubation | |
|---|---|---|---|
| pET46 Ek/LIC vector | 0.5 | 22° C. | 5 min |
| Reaction Mixture | 1 | | |
| Total | 1.5 μL | | |

After the incubation, EDTA was added to terminate the reaction.

| Termination reaction | | Incubation | |
|---|---|---|---|
| 25 mM EDTA | 0.5 | 22° C. | 5 min |
| pET46 Ek/LIC vector | 0.5 | | |
| Reaction Mixture | 1 | | |
| Total | 2 μL | | |

The annealing mixtures for Cb2487-pET46 Ek/LIC was transformed into *E. coli* JM109 by electroporation and the cells were plated on LB-ampicillin plates. After overnight incubation at 37° C., three colonies were selected and each was used to inoculate 10 mL cultures of LB-ampicillin. The cultures were grown at 37° C. with vigorous aeration for 16 hours and plasmid minipreps were made from each cell culture. The individual plasmid preparations were then electrophoresed on a 1% agarose gel to confirm the size of plasmid/insert DNA. Next, the integrity of the gene was confirmed by nucleotide sequencing.

The Cb2487 (β-xylosidase) amino acid sequence is disclosed in SEQ ID NO: 27. The nucleotide sequence encoding Cb2487 is disclosed in SEQ ID NO: 28.

For protein expression, Cb2487 was cloned into the plasmid pET46 Ek/LIC. The amino acid sequence of Cb2487-pET46 Ek/LIC is SEQ ID NO: 30. Amino acid numbers 1-15 of SEQ ID NO: 30 are from the pET46 Ek/LIC plasmid, and include a sequence of six histidines to facilitate protein purification. The nucleotide sequence encoding SEQ ID NO: 30 is disclosed in SEQ ID NO: 29. Nucleotide numbers 1-45 of SEQ ID NO: 29 are from the pET46 Ek/LIC plasmid.

FIG. 9A shows putative domain architecture of Cb2487. FIG. 9B shows SDS-PAGE of purified Cb2487. FIG. 9C shows biochemical assay to determine the optimum pH of Cb2487. FIG. 9D shows biochemical assay to determine the optimum temperature of Cb2487. FIG. 9E shows the kinetic parameter of Cb2487 with pNP-β-D-xylopyranoside as substrate. FIG. 9F shows xylo-oligosaccharides hydrolysis products analysis through thin layer chromatography (TLC). FIG. 9G shows thermostability assay for Cb2487. FIG. 9H shows synergism of β-xylosidase (Cb2487) and α-glucuronidase (Cb909).

FIG. 9A shows putative domain architecture of Cb2487. The putative conserved domains of Cb2487 were analyzed through the NCBI Conserved Domains Database search tool.

FIG. 9B shows SDS-PAGE of purified Cb2487. The lane next to MW shows the protein molecular mass marker. The lane Cb2487 shows the purified protein.

Purification of Cb2487

For Cb2487 purification, the cell pellet was re-suspended in binding buffer (50 mM Tris-HCl, 300 mM NaCl, pH 7.5), then lysed by passing through an EmulsiFlex C-3 cell homogenizer. The lysate was centrifuged at 20,000×g for 20 min at 4° C. to remove cell debris. The supernatant was incubated at 75° C. for 30 min and centrifuged at 20,000×g for 15 min at 4° C. to remove heat labile proteins. The supernatant after heating was purified by Talon Metal Affinity Resin pre-equilibrated with binding buffer and incubated for 1 h at 4° C. The resin was washed with 50 column volumes of binding buffer, then eluted with 10 column volumes of elution buffer (50 mM Tris-HCl, 300 mM NaCl, 250 mM Imidazole, pH 7.5). The elution fractions were pooled and concentrated with Amicon Ultra-15 centrifugal filter units (50,000 MMCO), and exchanged into Tris-HCl buffer (20 mM, pH 7.5) by three successive concentration and dilution cycles, then purified with Hitrap Q HP column. The elution fractions were pooled and concentrated with Amicon Ultra-15 centrifugal filter units (50,000 MMCO), and exchanged into Tris-HCl buffer (50 mM, pH 7.5, 300 mM NaCl). The proteins were then purified with a Superdex™ 200 Hiload™ 16/60 size exclusion column using an AKTAxpress system equipped with a UV detector.

FIG. 9C shows a biochemical assay to determine the optimum pH of Cb2487. For the pH optimum assay, para-nitrophenyl-beta-D-xylopyranoside (pNP-X, 0.8 mM) was incubated with Cb2487 concentration (10 nM) at 75° C. in different buffer: pH 4.0-6.0 (citrate buffer, 50 mM, 150 mM NaCl), pH6.0-8.0 (phosphate buffer, 50 mM, 150 mM NaCl), pH 8.5-9.0 (Tris-HCl, 50 mM, 150 mM NaCl).

FIG. 9D shows a biochemical assay to determine the optimum temperature of Cb2487. For temperature optimum assay, pNP-X (0.8 mM) was incubated with Cb2487 (10 nM) in citrate buffer (50 mM, pH 6.0, 150 mM NaCl) at different temperatures (40, 45, 50, 55, 60, 65, 70, 75, 80, 85, 90, 95, 100° C.).

FIGS. 9EA and 9EB show a determination of kinetic parameters for Cb2487 with pNP-β-D-xylopyranose as substrate. For the left side panel (FIG. 9EA), the kinetic parameters were determined at 90° C., pH 6.0. For the right side panel (FIG. 9EB), the kinetic parameters were determined at 75° C., pH 6.0. For these assays, different concentrations of pNP-X (0.08-24 mM) were incubated with Cb2487 (10 nM) in citrate buffer (50 mM, pH 6.0, 150 mM NaCl) at 75 and 90° C., respectively.

FIG. 9F shows hydrolytic activity of Cb2487 on xylo-oligosaccharides. Cb2487 (0.5 μM) was incubated with different xylo-oligosaccharides ($X_{2-6}$) at 75° C. for 15 hr and then the products were separated by TLC.

FIG. 9G shows a thermostability assay for Cb2487. Cb2487 was incubated in citrate buffer (pH 6.0, 50 mM) at different temperatures (70, 75, 80, 85, 90, and 95° C.) without substrate addition, the protein was taken at different times (0, 10 min, 30 min, 1 h, 3 h, 4, 8 h, 12 h, 24 h) and the residual activity was assayed with pNP-X as substrate.

FIG. 9H shows synergism of β-xylosidase (Cb2487) & α-glucuronidase (Cb909). Aldouronic acids were incubated with Cb2487 (0.5 μM), Cb909 (0.5 μM) in citrate buffer (pH 6.0), 75° C. overnight, then assayed with HPLC. Adding Cb909 cleaved off the methylglucuronic acid decorations in aldouronic acids to release xylose and xylo-oligosaccharides. Adding Cb2487 cleaved available beta-1,4-xylosidic linkages to release more xylose. Mixing the two enzymes led to the conversion of the xylo-oligosaccharides released by Cb909 to xylose by Cb2487.

Example 6: Acetyl Xylan Esterase Cb162 (SEQ ID NOs: 33 and 34)

An acetyl xylan esterase, Cb162, was identified in *Caldicellulosiruptor bescii*. The enzyme is the gene product of Cb162, where Cb stands for *C. bescii*. The acetyl xylan esterase cleaves the linkages between xylose and the side chain of acetyl groups in hemicellulose to provide more accessibility to other hemicellulases such as xylanase and beta-xylosidase to the backbone of xylan. The Cb162 protein is 321 amino acids long and has a predicted molecular mass of 38.7 kDa (His-tag+Cb162 protein). The protein has a single domain of acetyl xylan esterase (FIG. 10A).

Cloning of Cb162

The gene for Cb162 was amplified from *Caldicellulosiruptor bescii* genomic DNA by PCR using PrimeSTAR HS DNA polymerase (TaKaRa). The Cb162 gene was amplified using the following primer set:

```
Cb162-Fw
                                        (SEQ ID NO: 142)
5'-GACGACGACAAGATGGTTTTTGAAATGCCACTTGAAAAG-3'

Cb162-Rv
                                        (SEQ ID NO: 143)
5'-GAGGAGAAGCCCGGTTATTTTATCATCTCCATAAGATACATAAA
TATCTTGTC-3'
```

The polymerase chain reaction mixture contained the following:

| PCR reaction | |
|---|---|
| 2.5 U/mL PrimeSTAR DNA polymerase | 0.5 |
| 19 ng/mL *C. bescii* gDNA | 1 |
| 10 mM Fw Primer | 1 |
| 10 mM Rv Primer | 1 |
| 2.5 mM dNTP Mixture | 4 |
| 5x PrimeSTAR Buffer | 10 |
| $dH_2O$ | 32.5 |
| Total | 50 μL |

To amplify the gene from the genomic DNA, the following PCR cycling was used:

| PCR protocol | | | |
|---|---|---|---|
| Denaturing | 98° C. | 10 sec | 30 cycles |
| Annealing | 55° C. | 5 sec | |
| Elongation | 72° C. | 60 sec | |
| Last | 4° C. | ∞ | |

The Ek/LIC cloning kit was utilized (Novagen). Both ends of the amplified gene fragment were digested, in the presence of dATP, with the 3' to 5' exonuclease activity of T4 DNA polymerase. The resultant fragment was annealed to the pET-46 Ek/LIC vector.

The ligation mixtures for Cb162-pET46 were introduced into *E. coli* JM109 by heat shock method and the cells were plated on LB-ampicillin. After overnight incubation at 37° C., four colonies were selected and used to inoculate, individually, 10 mL of LB-ampicillin. The cultures were grown at 37° C. with vigorous aeration for 16 hours, and minipreps were made of the cell cultures. The plasmids were then electrophoresed on a 1% agarose gel to check the size of the plasmid DNA. For gene expression, one of the plasmids was transformed into *E. coli* BL21 codon plus DE3 RIL by the heat shock method and plated on LB plates supplemented with chloramphenicol and ampicillin at 100 μg/ml and 50 μg/ml and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.1 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 20 mM imidazole and 300 mM of NaCl). The proteins in the cells were released through a French pressure cell. After centrifugation to pellet the cell debris, the supernatant was applied to a nickel-charged resin (GE Healthcare) and washed several times to remove the unbound proteins. The bound protein (6-Histidine-tagged Cb162) was then eluted from the resin with an elution buffer composed of the lysis buffer supplemented with 250 mM imidazole. The eluted protein was further purified by passing through Hiload 16/20 prepgrade gel-filtration column (GE Healthcare) under the 50 mM $Na_2HPO_4$—HCl pH 6.5 and 100 mM NaCl buffer.

The Cb162 (acetyl xylan esterase) amino acid sequence is disclosed in SEQ ID NO: 33. The nucleotide sequence encoding Cb162 is disclosed in SEQ ID NO: 34.

For protein expression, Cb162 was cloned into the plasmid pET46 Ek/LIC. The amino acid sequence of Cb162-pET46 Ek/LIC is SEQ ID NO: 36. Amino acid numbers 1-15 of SEQ ID NO: 36 are from the pET46 Ek/LIC plasmid, and include a sequence of six histidines to facilitate protein purification. The nucleotide sequence encoding SEQ ID NO: 36 is disclosed in SEQ ID NO: 35. Nucleotide numbers 1-45 of SEQ ID NO: 35 are from the pET46 Ek/LIC plasmid.

FIG. 10A shows the domain structure of Cb162; the protein has an acetyl xylan esterase domain.

The Cb162 gene was expressed in *E. coli* cells, and the protein was purified in two steps, making use of the 6-histidines encoded by the plasmid. FIG. 10B shows an SDS-PAGE of purified Cb162. The molecular markers are in the lane next to the purified Cb162.

FIG. 10C shows the enzymatic activity of Cb162 at different pHs using para-nitrophenol adducted acetate (pNP-acetate) as a substrate. The released pNP was monitored continuously at an absorbance of 400 nm using Synergy 2 Microplate reader (BioTek). The initial rate of hydrolysis was adopted as an enzyme activity. The figure shows the pH profile of Cb162 on pNP-acetate. The pH effect on the Cb162 was examined at 50° C. in the presence of 50 mM citrate-NaOH (pH 4.0 to 6.0), 50 mM $Na_2HPO_4$—HCl (pH 6.0 to 8.0), with 150 mM NaCl, respectively. 0.1 μM of purified Cb162 and 2 mM pNP-acetate were used for this assay.

FIG. 10D shows the temperature profile of Cb162 on pNP-acetate. The temperature profile was performed in 50 mM $Na_2HPO_4$—HCl, pH 7.0, and 150 mM NaCl, at temperatures between 40° C. and 75° C. with 5° C. increments. 0.04 μM of purified Cb162 and 2 mM pNP-acetate were used for this assay.

FIG. 10E shows the thermostability profile of Cb162 on pNP-acetate. 0.02 μM of purified Cb162 in 50 mM $Na_2HPO_4$—HCl, pH 7.0, and 150 mM NaCl was incubated for 0 to 24 hours at temperatures between 60° C. and 80° C. with 5° C. intervals, and the residual activities were measured.

FIG. 10F shows the kinetic study of Cb162. 0.04 μM of purified Cb162 in 50 mM $Na_2HPO_4$—HCl, pH 6.0, and 150 mM NaCl was incubated with a various concentration of pNP-acetate, and the initial rate of hydrolysis was plotted on the graph. The kinetic parameters were determined by Michaelis-Menten equation utilizing Graph Pad Prism v5.01 (GraphPad Software).

Example 7: Hydrolysis of Polysaccharides with Enzyme Cocktails of *Caldicellulosiruptor bescii* Hemicellulases Containing a Single Type of Endoxylanase Mixtures of one or more of the enzymes endoxylanase (Cb193), α-arabinofuranosidase (Cb1172), β-xylosidase (Cb2487), α-glucuronidase (Cb909), and acetyl xylan esterase (Cb162) were incubated with the polysaccharides soluble wheat arabinoxylan, birch wood xylan, and oat spelt xylan. For each substrate, incubation of the substrate with a cocktail containing all of the enzymes endoxylanase (Cb193), α-arabinofuranosidase (Cb1172), 3-xylosidase (Cb2487), α-glucuronidase (Cb909), and acetyl xylan esterase (Cb162) yielded a greater release of monosaccharides from xylan than incubating the substrate with an enzyme cocktail containing less than all of the enzymes.

FIG. 11 shows synergy of *C. bescii* hemicellulolytic enzymes on soluble wheat arabinoxylan (SWAX) hydrolysis. SWAX (8.0%, w/v) was incubated with different hemicellulase mixes at 75° C. for 15 hr in citrate buffer (50 mM, pH 6.0, 150 mM NaCl), and subjected to reducing sugar [FIG. 11A] and HPLC [FIG. 11B] analysis. The hemicellulases applied include Cb193 (0.5 μM), Cb1172 (0.5 μM), Cb2487 (4 μM), Cb909 (0.5 μM), and Cb162 (0.5 μM).

FIG. 12 shows synergy of *C. bescii* hemicellulolytic enzymes on oatspelt xylan (OSX) hydrolysis. OSX (8.0%, w/v) was incubated with different hemicellulase at 75° C. for 15 hr in citrate buffer (50 mM, pH 6.0, 150 mM NaCl), and subjected to reducing sugar [FIG. 12A] and HPLC [FIG. 12B] analysis. The hemicellulases applied include Cb193 (0.5 μM), Cb1172 (0.5 μM), Cb2487 (4 μM), Cb909 (0.5 μM), and Cb162 (0.5 μM).

FIG. 13A shows SWAX hydrolysis with a hemicellulase cocktail at different temperatures. SWAX (8.0%, w/v) was incubated with Cb193 (0.5 μM), Cb2487 (4 μM), Cb1172 (0.5 μM), Cb162 (0.5 μM), and Cb909 (0.5 μM) at 65° C., 70° C., 75° C., 80° C. for 15 hr in citrate buffer (50 mM, pH 6.0, 150 mM NaCl), and subjected to reducing sugar assay.

FIG. 13B shows BWX hydrolysis with a hemicellulase cocktail at different temperatures. BWX (8.0%, w/v) was incubated with Cb193 (0.5 μM), Cb1172 (0.5 μM), Cb2487 (4 μM), Cb909 (0.5 μM), and Cb162 (0.5 μM) at 65° C., 70° C., 75° C., 80° C. for 15 hr in citrate buffer (50 mM, pH 6.0, 150 mM NaCl), and subjected to reducing sugar assay.

FIG. 13C shows OSX hydrolysis with a hemicellulase cocktail at different temperatures. OSX (8.0%, w/v) was incubated with Cb193 (0.5 μM), Cb1172 (0.5 μM), Cb2487 (4 μM), Cb909 (0.5 μM), and Cb162 (0.5 μM) at 65° C., 70° C., 75° C., 80° C. for 15 hr in citrate buffer (50 mM, pH 6.0, 150 mM NaCl), and subjected to reducing sugar assay.

Example 8: Hydrolysis of Polysaccharides with Enzyme Cocktails of *Caldicellulosiruptor bescii* Hemicellulases Containing Two Types of Endoxylanase Mixtures containing the enzymes α-arabinofuranosidase (Cb1172), β-xylosidase (Cb2487), α-glucuronidase (Cb909), acetyl xylan esterase (Cb162), and one or both of the endoxylanases (Cb193 and Cb195) were incubated with the polysaccharides soluble wheat arabinoxylan, birch wood xylan, and oat spelt xylan. For each substrate, incubation of the substrate with a cocktail containing both of the endoxylanases (Cb193 and Cb195) yielded a greater release of monosaccharides from xylan than incubating the substrate with an enzyme cocktail containing only one of the endoxylanases.

FIG. 14A shows SWAX hydrolysis was improved by adding two xylanases (Cb195 and Cb193) in the hemicellulase mixture. SWAX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); Mix III) Cb195 (0.25 μM), Cb193 (0.25 μM), Cb1172 (0.5 μM), Cb2487 (4 μM), Cb909 (0.5 μM), and Cb162 (0.5 μM).

FIG. 14B shows BWX hydrolysis was improved by adding two xylanases (Cb195 and Cb193) in the hemicellulase mixture. BWX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); Mix III) Cb195 (0.25 μM), Cb193 (0.25 μM), Cb1172 (0.5 μM), Cb2487 (4 μM), Cb909 (0.5 μM), and Cb162 (0.5 μM).

FIG. 14C shows OSX hydrolysis was improved by adding two xylanases (Cb195 and Cb193) in the hemicellulase mixture. OSX (8.0%, w/v) was incubated with different hemicellulase mixes at 75° C. for 15 hr in citrate buffer (50 mM, pH 6.0, 150 mM NaCl), and subjected to reducing sugar analysis. Different hemicellulase mixtures were applied in the hydrolysis: Mix I) Cb195 (0.5 μM), Cb1172 (0.5 μM), Cb2487 (4 μM), Cb909 (0.5 μM), and Cb162 (0.5 μM); Mix II) Cb193 (0.5 μM), Cb1172 (0.5 μM), Cb2487 (4 μM), Cb909 (0.5 μM), and Cb162 (0.5 μM); Mix III) Cb195 (0.25 μM), Cb193 (0.25 μM), Cb1172 (0.5 μM), Cb2487 (4 μM), Cb909 (0.5 μM), and Cb162 (0.5 μM).

FIG. 15 shows soluble wheat arabinoxylan hydrolysis with hemicellulase cocktail of *Caldicellulosiruptor bescii*. Different concentrations of SWAX (1.0, 2.0, 4.0, 6.0, 8.0%, w/v) were incubated with Cb193 (0.5 μM), Cb195 (0.5 μM), Cb1172 (0.5 μM), Cb2487 (4 μM), Cb162 (0.5 μM), and Cb909 (0.5 μM) for 15 hr at 75° C. in citrate buffer (50 mM, pH 6.0, 150 mM NaCl), and subjected to reducing sugar assay. FIG. 15A shows reducing sugar in the control and hydrolysis mixtures, and FIG. 15B shows comparison of calculated and average of actual reducing sugar in hydrolysis mixtures with different substrate concentrations.

FIG. 16 shows birch wood xylan hydrolysis with hemicellulase cocktails of *Caldicellulosiruptor bescii*. Different concentrations of BWX (1.0, 2.0, 4.0, 6.0, 8.0%, w/v) were incubated with Cb193 (0.5 μM), Cb195 (0.5 μM), Cb1172 (0.5 μM), Cb2487 (4 μM), Cb162 (0.5 μM), and Cb909 (0.5 μM) at 75° C. for 15 hr in citrate buffer (50 mM, pH 6.0, 150 mM NaCl), and subjected to reducing sugar assay. FIG. 16A shows reducing sugar in the control and hydrolysis mixtures, and FIG. 16B shows comparison of calculated and average of actual reducing sugar in hydrolysis mixtures with different substrate concentrations.

FIG. 17 shows oat spelt xylan hydrolysis with hemicellulase cocktail of *Caldicellulosiruptor bescii*. Different concentrations of OSX (1.0, 2.0, 4.0, 6.0, 8.0%, w/v) were incubated with Cb193 (0.5 μM), Cb195 (0.5 μM), Cb1172

(0.5 μM), Cb2487 (4 μM), Cb162 (0.5 μM), and Cb909 (0.5 μM) at 75° C. for 15 hr in citrate buffer (50 mM, pH 6.0, 150 mM NaCl), and subjected to reducing sugar assay. FIG. 17A shows reducing sugar in the control and hydrolysis mixtures, and FIG. 17B shows comparison of calculated and average of actual reducing sugar in hydrolysis mixtures with different substrate concentrations.

Example 9: Endocellulase/Mannanase Cb1952

An endocellulase/mannanase, Cb1952, was identified in *Caldicellulosiruptor bescii*. The enzyme is the gene product of Cb1952, wherein Cb stands for *Caldicellulosiruptor bescii*. The protein has a Glycoside Hydrolase (GH) family 9 catalytic domain (cellulase domain), three family 3 carbohydrate binding modules (CBMs) (one CBM3c and two CBM3b modules) and one GH5 catalytic domain (mannanase domain) (FIG. 18).

A wild-type Cb1952 protein, lacking the signal peptide, and several truncational mutations (TM1, TM2, TM3, TM4, TM5, TM6, and TM7) were systematically constructed for functional analysis (FIG. 18).

As shown in FIG. 18, TM1 contained the GH9 module and the three CBMs, TM2 contained the GH9 module and two CBMs, TM3 contained the GH9 module and one CBM (CBM3c), and TM4 was made up of only the GH9 module. The truncated mutant TM5 was composed of the three CBMs linked to the GH5 module, whereas TM6 and TM7 were composed of the CBM3c and CBM3b, respectively. The SDS-PAGE results in FIG. 19 show that all protein constructs were successfully expressed as soluble proteins and highly purified.

Cloning of Cb1952 Wild-Type

The gene for Cb1952 wild-type was amplified from *Caldicellulosiruptor bescii* DSM 6725T genomic DNA by PCR using PrimeSTAR DNA Polymerase (TAKARA). The Cb1952 wild-type gene was amplified using the following primer set:

```
Cb1952 wild-type Forward:
                                  (SEQ ID NO: 39)
5'- GAC GAC GAC AAG ATG GCA ACA ACC TTT
AACTAT GGT GAA GCT C -3'

Cb1952 wild-type Reverse:
                                  (SEQ ID NO: 40)
5'- GA GGA GAA GCC CGG TTA TTC AGC ACC
AAT CGC ATT AGT TTT ATA CC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 5 min | |
| Elongation | 72° C. | 7 min | 1 cycle |
| Last | 4° C. | ∞ | |

Cloning of Cb1952TM1

The gene for Cb1952TM1 was amplified from *Caldicellulosiruptor bescii* DSM 6725T genomic DNA by PCR using PrimeSTAR DNA Polymerase (TAKARA). The Cb1952TM1 gene was amplified using the following primer set:

```
Cb1952TM1Forward:
                                  (SEQ ID NO: 41)
5'- GAC GAC GAC AAG ATG GCA ACA ACC TTT AAC
TAT GGT GAA GCT C -3'

Cb1952TM1Reverse:
                                  (SEQ ID NO: 42)
5'- GAG GAG AAG CCC GGT TAG CTA GTA TCT ATC
TTC ACT ATT CCA CTG -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

Cloning of Cb1952TM5

The gene for Cb1952TM5 was amplified from *Caldicellulosiruptor bescii* DSM 6725T genomic DNA by PCR using PrimeSTAR DNA Polymerase (TAKARA). The Cb1952TM5 gene was amplified using the following primer set:

```
Cb1952TM5Forward:
                                  (SEQ ID NO: 43)
5'- GAC GAC GAC AAG ATG A AT TTC AAA GCT
ATC GAA AAG CCA AC -3'

Cb1952TM5Reverse:
                                  (SEQ ID NO: 40)
5'- GA GGA GAA GCC CGG TTA TTC AGC ACC AAT
CGC ATT AGT TTT ATA CC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

After the PCR reactions described above, the amplification of Cb1952 wild-type, Cb1952TM1 and Cb1952TM5 gene was confirmed by 1% agarose gel electrophoresis. The DNA corresponding to the expected band on the gel was cut out and applied to a Qiagen Gel Extraction kit to extract the DNA out of the gel.

A Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was inactivated by incubating at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixtures for Cb1952 wild-type, Cb1952TM1- or Cb1952TM5-pET-46 Ek/LIC were introduced into *E. coli* NovaBlue competent cells by chemical transformation method, and the cells were plated on LB-ampicillin. After overnight incubation at 37° C., four colonies were selected and each was used to inoculate 6 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene has been inserted into plasmids, the genes were sequenced to confirm their identity. The plasmids with the right insertion sequences were selected for recombinant protein production.

Cb1952TM2, Cb1952TM3, Cb1952TM4, Cb1952TM6, and Cb19527 were prepared through similar steps as above, with different steps as appropriate (e.g. primer sequences).

For expression of each enzyme, plasmid containing the wild type, TM1, TM2, TM3, TM4, TM5, TM6, or TM7 was transformed into *E. coli* BL21 codon plus DE3 RIL by the heat shock method and plated on LB plates supplemented with chloramphenicol (50 μg/ml) and ampicillin (100 μg/ml) and incubated at 37° C. overnight. Five to six colonies were inoculated into 10 ml of LB broth supplemented with the two antibiotics at the same concentration and cultured for 6 hours. Ten mL of the culture was added to 1000 mL of LB broth supplemented with the two antibiotics at the same concentration and cultured at 37° C. until the absorbance at 600 nm reached ~0.3. The inducer, IPTG, was then added at 0.1 mM final concentration, and the culturing continued at 16° C. overnight.

Protein Purification

Cultures were centrifuged to collect the cell pellet. For Cb1952 wild-type, the pellet was then suspended in a lysis buffer (25 mM Tris-HCL pH 7.8, 750 mM of NaCl, 5% glycerol, 20 mM imidazole, 1.25% Tween-20). For Cb1952TM1, the pellet was then suspended in a lysis buffer (25 mM Tris-HCL pH 7.8, 100 mM of NaCl, 10% glycerol, 10 mM imidazole, 1.25% Tween-20). For the other Cb1952 TM mutants, the pellet was then suspended in a lysis buffer without imidazole (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed three times to remove the unbound proteins. The bound protein was then eluted from the resin with an elution buffer (50 mM Tris-HCL, pH7.5, 250 mM imidazole).

The design of the PCR primers ensured that each of the proteins was fused to 6-histidines (N-terminal tag) encoded in the plasmid. The six histidines will bind to either a nickel-charged resin or a cobalt-charged resin. The bound protein can be displaced from the resin with a buffer containing imidazole. This method facilitates quick purification of the protein of interest. All recombinant proteins were purified by immobilized metal ion affinity chromatography (IMAC) using talon resin (Clontech, Mountain View, Calif.) according to the manufacturer's instructions. For Cb1952 wild-type, the eluted protein was dialyzed against a protein storage buffer (50 mM Tris-HCl, 150 mM NaCl, pH7.5). The protein was heated at 75° C. for 10 min and centrifuged at 16,400 rpm for 20 min to precipitate any co-eluting thermo-labile host proteins. The recombinant protein was further purified by gel filtration using an ÄKTAxpress TWIN fast protein liquid chromatograph (FPLC) system equipped with a Hiload 16/60 Superdex 200 column (GE Healthcare, Piscataway, N.J.). For Cb1952TM1, the eluted protein was dialyzed against the protein storage buffer. The protein was then heated at 75° C. for 20 min and centrifuged at 16,400 rpm for 20 min. The supernatant was further purified by gel filtration as described above. For the other mutants, the recombinant proteins eluted from Talon resin were directly applied to gel filtration for purification close to homogeneity. FIG. 19 shows an SDS-PAGE of purified Cb1952 proteins.

Gene and Protein Sequences of Cb1952WT, Cb1952TM1, and Cb1952TM5

Cb1952 Full-Length Amino Acid Sequence

The full-length Cb1952 endocellulase/mannanase (EC 3.2.1.4/EC 3.2.1.78) amino acid sequence is disclosed in SEQ ID NO: 44. The signal peptide of Cb1952, corresponding to amino acid numbers 1-28 of SEQ ID NO: 44 was removed during all PCR amplifications. Thus, the expressed wild-type Cb1952 protein did not contain amino acid numbers 1-28 of SEQ ID NO: 44. The amino acid sequence of the wild-type Cb1952 protein without the signal peptide is disclosed in SEQ ID NO: 114.

The procedure of cloning the gene for wild-type Cb1952 (without the signal peptide) into the plasmid pET-46 Ek/LIC led to fusion of the gene to a short nucleotide sequence encoding a peptide that contains six histidines. The wild-type Cb1952 amino acid sequence (without the signal peptide) with the short peptide is disclosed in SEQ ID NO: 51. The amino acids of the short peptide are amino acids 1-14 of SEQ ID NO: 51.

Cb1952 Full-Length Nucleotide Sequence

The full-length Cb1952 nucleotide sequence is disclosed in SEQ ID NO: 45. The signal peptide of Cb1952, corresponding to nucleotide numbers 1-84 of SEQ ID NO: 45 was removed during all PCR amplifications. Thus, the nucleotide sequence used to express wild-type Cb1952 protein did not contain nucleotide numbers 1-84 of SEQ ID NO: 45. The nucleotide sequence encoding the wild-type Cb1952 protein without the signal peptide is disclosed in SEQ ID NO: 115.

The wild-type Cb1952 nucleotide sequence (without the signal peptide) with the coding sequence for the short peptide from the plasmid pET-46 Ek/LIC is disclosed in SEQ ID NO: 50. The nucleotides coding for the short peptide nucleotides are nucleotides 1-42 of SEQ ID NO: 50.

Cb1952TM1 Amino Acid Sequence

The Cb1952TM1 endocellulase (EC 3.2.1.4) amino acid sequence is disclosed in SEQ ID NO: 46. The procedure of cloning the gene for Cb1952TM1 into the plasmid pET-46 Ek/LIC led to fusion of the gene to a short nucleotide sequence encoding a peptide that contains six histidines. The Cb1952TM1 amino acid sequence with the short peptide is disclosed in SEQ ID NO: 53. The amino acids of the short peptide are amino acids 1-14 of SEQ ID NO: 53.

Cb1952TM1 Nucleotide Sequence

The Cb1952TM1 nucleotide sequence is disclosed in SEQ ID NO: 47. The Cb1952TM1 nucleotide sequence with the coding sequence for the short peptide from the plasmid pET-46 Ek/LIC is disclosed in SEQ ID NO: 52. The nucleotides coding for the short peptide nucleotides are nucleotides 1-42 of SEQ ID NO: 52.

Cb1952TM5 Amino Acid Sequence

The Cb1952TM5 amino acid sequence is disclosed in SEQ ID NO: 48. The procedure of cloning the gene for Cb1952TM5 into the plasmid pET-46 Ek/LIC led to fusion of the gene to a short nucleotide sequence encoding a peptide that contains six histidines. The Cb1952TM5 amino acid sequence with the short peptide is disclosed in SEQ ID NO: 55. The amino acids of the short peptide are amino acids 1-14 of SEQ ID NO: 55.

Cb1952TM5 Nucleotide Sequence

The Cb1952TM5 nucleotide sequence is disclosed in SEQ ID NO: 49. The Cb1952TM5 nucleotide sequence with the coding sequence for the short peptide from the plasmid pET-46 Ek/LIC is disclosed in SEQ ID NO: 54. The nucleotides coding for the short peptide nucleotides are nucleotides 1-42 of SEQ ID NO: 54.

Enzyme Activity

Determination of Optimal pH, Optimal Temperature, and Thermostability

The optimal pH for Cb1952 WT, TM1, TM2, and TM3 with PASC, as substrate, were in the range of pH5.0-5.5 and the optimal temperature for each of these proteins was 85° C. In the case of TM4, the optimal pH and temperature with PASC were 6.5 and 55° C., respectively. The thermostability assays were carried out on the wild type and truncation mutants harboring cellulase activities. At 80° C. and 85° C., the residual activities of WT, TM1, and TM2 after 24 h incubation were less than 20% except TM3, which retained 61.8% activity. At 75° C., the residual activities of WT, TM1, TM2, and TM3 after 24 h incubation were 43.1%, 75.7%, 53.6%, and 101.7%, respectively. Deletion of CBM3c dramatically reduced the thermostability of the enzyme. The truncated mutant TM4 remained stable at 45° C. and 50° C., but the enzyme rapidly lost its activity at temperatures above 55° C. (FIG. 81C). The pH and temperature optima were also determined for hydrolysis of mannan substrates. For the wild-type enzyme the optimal pH and temperature for mannan hydrolysis were 5.5-6.5 and 90° C., respectively, and for TM5 the values were 6.5 and 90° C., respectively (data not shown).

Hydrolysis of Phosphoric Acid Swollen Cellulose, Cello- and Manno-Oligosaccharides by Cb1952 and its Mutants The capacity of the wild-type Cb1952 and its TM1 and TM5 mutants, representing the mutants that harbored the GH9 module with the 3 CBMs and the GH5 module together with 3 CBMs (FIG. 18) were investigated in a time course approach for hydrolysis of PASC. As shown in the chromatograph in FIG. 78, release of products, mostly cellobiose and glucose, was observed for the wild-type (A) (FIG. 78A) and the TM1 (B) (FIG. 78B) mutant which contains the GH9 module. Very little to no hydrolysis of PASC was detected from TM5 (C) (FIG. 78C) (the construct with the GH5 module). By further testing hydrolysis of cello-oligosaccharides, it was confirmed that the β-1,4-glucose cleaving activity was present in the GH9 domain (FIG. 23). On manno-oligosaccharides hydrolysis, the wild-type and TM5 showed cleavage activity of oligosaccharides with degree of polymerization (DP) of 3 and above (FIG. 24). Interestingly, TM1 also showed activity on substrates of DP of 5 or higher, albeit the activity was lower than the wild-type enzyme and the TM5 mutant (FIG. 24). No transglycosylation activities were found for the wild-type, TM1, and TM5 on glucose, cello-oligosaccharides, mannose, and manno-oligosaccharides.

Activities and Kinetic Parameters of Cb1952 and its Mutants on Cellulosic Substrates Specific activities were determined for the wild-type protein and each of the mutants with Avicel, a model crystalline cellulose, and filter paper, as substrates. On Avicel, deletion of the individual CBMs led to a decrease in specific activity of the truncated mutant (TM1, TM2, and TM3) (Table 1). The truncated mutant with either two or one of the CBM3b (TM1 and TM2, respectively) only showed a slight decrease in specific activity compared with the WT enzyme. In contrast, deleting the two CBM3b's led to a protein with less than half the specific activity of the WT protein on Avicel. A similar trend was observed for specific activity on filter paper as substrate, although the decreases in activity were less pronounced (Table 1). On both substrates, a construct made up of the GH9 catalytic module alone had only 3.8% and 16.2% of the activities observed for the WT protein on Avicel and filter paper, respectively.

TABLE 1

Specific activities and kinetic parameters of Cb1952 wild-type, its truncation mutants, and the mutants of TM3 on cellulose substrates[a]

| Protein | Avicel (μmol sugar/ min/μmol protein) | Filter paper (μmol sugar/ min/μmol protein) | PASC[b] $k_{cat}$ ($s^{-1}$) | PASC[b] $K_m$ (mg/ml) | PASC[b] $k_{cat}/K_m$ ($s^{-1}$ ml/mg) |
|---|---|---|---|---|---|
| WT | 10.15 ± 0.51 | 16.12 ± 2.86 | 2.58 ± 0.15 | 0.36 ± 0.10 | 7.16 |
| TM1 | 8.53 ± 1.47 | 17.27 ± 2.06 | 2.12 ± 0.13 | 0.14 ± 0.07 | 15.14 |
| TM2 | 8.94 ± 0.89 | 14.31 ± 3.13 | 2.16 ± 0.18 | 0.19 ± 0.10 | 11.37 |
| TM3 | 4.47 ± 0.81 | 12.87 ± 1.44 | 3.09 ± 0.30 | 0.65 ± 0.24 | 4.75 |
| TM3G208WG | 3.68 ± 0.69 | 13.74 ± 1.80 | 7.92 ± 0.78 | 1.71 ± 0.45 | 4.63 |
| TM3G208W | 4.86 ± 0.49 | 14.61 ± 3.41 | 6.36 ± 0.74 | 1.35 ± 0.46 | 4.71 |
| TM3T298F | 5.53 ± 0.53 | 15.14 ± 1.71 | 8.53 ± 0.67 | 2.17 ± 0.42 | 3.93 |
| TM4 | 0.39 ± 0.02 | 2.62 ± 0.56 | 0.08 ± 0.01 | 3.73 ± 0.81 | 0.02 |

[a]The reactions were carried out at 75° C. except that for TM4, which was done at 45° C.
[b]PASC: phosphoric acid swollen cellulose.

The phosphoric acid swollen cellulose, derived from Avicel, was used to examine the kinetic parameters of the WT protein and its mutants (Table 1). The estimated $k_{cat}$ for the WT (2.58 $s^{-1}$) and its truncated mutants (2.12-3.09 $s^{-1}$) was very modest. Interestingly TM1 exhibited a catalytic efficiency twice higher than that of the wild type, suggesting that the catalytic activities of the GH9 and GH5 modules are functionally coupled. Similar functional coupling of different catalytic modules within a single polypeptide was proposed for another plant cell wall degrading enzyme *Prevotella ruminicola* Xyn10D-Fae1A (9), a two-domain arginine kinase from the deep-sea clam *Calyptogena kaikoi* (40), and a flagellar creatine kinase from *Chaetopterus variopedatus* (13). The kinetic parameters of TM4, the protein with only the GH9 catalytic module were very poor compared to the proteins linked to the CBMs, alluding to the importance of these auxiliary modules to the function of Cb1952.

were 1420 $s^{-1}$, 1068 $s^{-1}$, and 696 $s^{-1}$, respectively (Table 2). Based on the data in Table 2, the catalytic activity for degradation of mannan and mannose-configured substrates is located in the GH5 module. It was observed that cleaving the GH9 module from the polypeptide to create the TM5 mutant increased the $k_{cat}$ of this mutant, compared to the wild-type, by 2.4-, 2.8-, and 1.6-fold for locust bean gum, guar gum, and konjac glucomannan, respectively. Note that the standard error was quite high for the $k_{cat}$ for guar gum. A corresponding increase in the $K_m$ of TM5 on each mannose-configured substrate led to catalytic efficiencies that were lower than those determined for the wild-type protein (Table 2). The truncated mutants containing the GH9 catalytic module in addition to either all three CBMs (TM1) or only the CBM3c (TM3) were almost devoid of activity on both locust bean gum and guar gum. These mutants, however, exhibited very high activity on konjac glucomannan.

TABLE 2

Kinetic parameters of Cb1952 wild-type, its truncation mutants, and the mutants of TM3 on mannan substrates and konjac glucomannan[a]

| Protein | Locust bean gum $k_{cat}$ ($s^{-1}$) | Locust bean gum $K_m$ (mg/ml) | Locust bean gum $k_{cat}/K_m$ ($s^{-1}$ ml/mg) | Guar gum $k_{cat}$ ($s^{-1}$) | Guar gum $K_m$ (mg/ml) | Guar gum $k_{cat}/K_m$ ($s^{-1}$ ml/mg) | Konjac glucomannan $k_{cat}$ ($s^{-1}$) | Konjac glucomannan $K_m$ (mg/ml) | Konjac glucomannan $k_{cat}/K_m$ ($s^{-1}$ ml/mg) |
|---|---|---|---|---|---|---|---|---|---|
| WT | 1420 ± 158 | 0.62 ± 0.27 | 2290 | 696 ± 56.7 | 2.26 ± 0.42 | 308 | 1068 ± 271 | 1.84 ± 1.03 | 581 |
| TM1 | 0.23 ± 0.01 | 3.89 ± 0.41 | $5.9 \times 10^{-2}$ | n.d | n.d | n.d | 907 ± 50.7 | 1.85 ± 0.30 | 490 |
| TM3 | 0.15 ± 0.06 | 4.36 ± 2.82 | $3.5 \times 10^{-2}$ | $(1.03 \pm 0.17) \times 10^{-2}$ | 0.94 ± 0.50 | $1.10 \times 10^{-2}$ | 611 ± 68.9 | 1.30 ± 0.43 | 470 |
| TM3G208WG | 2.31 ± 0.15 | 1.93 ± 0.31 | 1.2 | 1.03 ± 0.35 | 9.28 ± 4.36 | $1.11 \times 10^{-1}$ | 1614 ± 143 | 2.37 ± 0.49 | 681 |
| TM3G208W | 0.12 ± 0.03 | 3.33 ± 1.49 | $3.7 \times 10^{-2}$ | $(1.01 \pm 0.01) \times 10^{-2}$ | 0.50 ± 0.20 | $2.01 \times 10^{-2}$ | 1119 ± 160 | 1.80 ± 0.68 | 621 |
| TM3T298F | 1.12 ± 0.55 | 12.58 ± 7.94 | $8.9 \times 10^{-2}$ | $(8.92 \pm 1.98) \times 10^{-2}$ | 3.62 ± 1.53 | $2.47 \times 10^{-2}$ | 1102 ± 77.4 | 2.61 ± 0.43 | 422 |
| TM5 | 3446 ± 367 | 1.82 ± 0.48 | 1893 | 1940 ± 570 | 11.98 ± 4.69 | 162 | 1710 ± 119 | 3.72 ± 0.48 | 460 |

[a]Konjac glucomannan is a polysaccharide with mixed linkage of glucose and mannose.

Activities and Kinetic Parameters of Cb1952 and its Mutants on Mannan-Like Substrates The enzymatic activities of Cb1952 and its mutants on mannan-like substrates were also investigated. The substrates tested were locust bean gum, guar gum, and konjac glucomannan. The wild type enzyme exhibited very high $k_{cat}$ on all tested mannose based substrates. On locust bean gum, konjac glucomannan, and guar gum, the $k_{cat}$ values Site-Directed Mutagenesis The architectural diversity of GH9 modules have been assigned to four different groups known as theme A, B, C, and D (19). In Cb1952, the GH9 catalytic module is linked to an accessory CBM3c at its C-terminus, and this is the architecture of the members of theme B1. In theme B1, there are both processive endoglucanases (7, 12, 34) and non-processive endoglucanases (2, 10). The distribution of reducing ends in the soluble and insoluble fractions of cellulase-hydrolyzed filter paper is commonly used to estimate the processivity of a cellulase (17). Our results, based on such an experiment, determined that Cb1952 and its truncation mutants (TM1, TM2, TM3, and TM4) do not harbor a processive GH9 catalytic module since their end products contained 40%-50% insoluble reducing ends (Table 3).

TABLE 3

Distribution of reducing sugars in soluble and insoluble fractions of filter paper hydrolyzed by Cb1952 wild-type, its truncation mutants, and the mutants of TM3[a]

| | | | Reducing sugar (%) | | Ratio (Sol./Insol.[b] |
|---|---|---|---|---|---|
| Protein | Soluble (mM) | Insoluble (mM) | Soluble | Insoluble | Reducing sugar) |
| WT[c] | 1.32 ± 0.07 | 1.32 ± 0.03 | 50.0 | 50.0 | 1.00 |
| TM1[c] | 2.02 ± 0.04 | 1.38 ± 0.08 | 59.4 | 40.6 | 1.46 |
| TM2[c] | 2.13 ± 0.11 | 1.42 ± 0.06 | 60.0 | 40.0 | 1.50 |
| TM3[c] | 1.98 ± 0.08 | 1.56 ± 0.12 | 55.9 | 44.1 | 1.27 |
| TM4[d] | 3.18 ± 0.15 | 2.72 ± 0.40 | 53.9 | 46.1 | 1.17 |
| TM3G208WG[c] | 1.80 ± 0.12 | 1.44 ± 0.13 | 55.6 | 44.4 | 1.25 |
| TM3G208W[c] | 1.74 ± 0.08 | 1.57 ± 0.11 | 52.6 | 47.4 | 1.11 |
| TM3T298F[c] | 1.87 ± 0.10 | 1.52 ± 0.12 | 55.2 | 44.8 | 1.23 |

[a]The reactions were carried out at 75° C. for 16 h for all enzymes except TM4, which was carried out at 45° C.
[b]Sol./Insol.: soluble versus insoluble.
[c]Enzyme concentration was 0.5 μM.
[d]Enzyme concentration was 10 μM.

An amino acid sequence alignment of the GH9 domain of Cb1952 with those of *Clostridium cellulolyticum* Cel9G (a non-processive endoglucanase) and *Thermobifida fusca* Cel9A (a processive endoglucanase) was examined. The *C. cellulolyticum* and *T. fusca* proteins represent two types of family 9 theme B1 endoglucanases with enzyme-cello-oligosaccharides co-crystal structures solved (26, 34). The amino acid sequence alignment showed that most of the residues involved in cellulose substrate binding are well conserved in the GH9 module of Cb1952 (FIG. 79). However, neither of two aromatic residues (Trp-209 in *T. fusca* and Phe-308 in *C. cellulolyticum*) responsible for hydrophobic stacking at subsite −3, is present in Cb1952 (FIG. 79). As aromatic residues involved in hydrophobic stacking interactions with the substrates contribute to the processivity of the enzyme during hydrolysis of crystalline substrate (15, 47), we mutated the corresponding amino acid residue in Cb1952TM3 to an aromatic residue by changing Gly-208 to Trp-208 or by inserting a tryptophan before Gly-208 to obtain a TM3G208W and a TM3G208WG mutant, respectively. These mutants mimicked the *T. fusca* enzyme. In addition, T-298 was also changed to Phe-298 to obtain TM3T298F mutant, which mimicked the *C. cellulolyticum* enzyme.

The secondary structures of the three mutants did not show any gross differences compared to Cb1952TM3 as revealed by circular dichroism (CD) scans (Table 4), suggesting that the mutations did not result in gross changes in the secondary structural elements of the proteins compared to Cb1952TM3. Compared to parental protein (TM3), the specific activities of the three mutants on Avicel and filter paper were not different (Table 1). The mutations also did not aid us in modifying TM3 into a processive endoglucanase, as the ratio of soluble versus insoluble reducing ends remained unchanged (Table 3). The $k_{cat}$ values of the mutants with PASC as substrate increased by about 2-fold. However, the $K_m$ values also increased leading to catalytic efficiencies ($k_{cat}/K_m$) that were similar to that of Cb1952TM3 (Table 1).

TABLE 4

CD spectroscopy analysis of CbCelB/Man5ATM3 and its mutants

| Protein | α-helix (%) | β-sheet (%) | Turn (%) | Unordered (%) |
|---|---|---|---|---|
| TM3 | 35.0 ± 1.7 | 24.0 ± 1.0 | 16.0 ± 1.0 | 25.0 ± 1.0 |
| TM3G208WG | 36.0 ± 1.0 | 22.7 ± 2.0 | 16.3 ± 1.1 | 25.3 ± 0.6 |
| TM3G208W | 35.7 ± 1.5 | 23.3 ± 1.1 | 16.3 ± 1.1 | 25.3 ± 0.6 |
| TM3T298F | 32.7 ± 0.6 | 23.7 ± 0.6 | 17.3 ± 0.6 | 26.7 ± 0.6 |

Unexpectedly, the $k_{cat}$ values of TM3G208WG with locust bean gum and guar gum, as substrates, were increased 15- and 100-fold compared with the values determined for TM3 (Table 2). Moreover, the catalytic efficiencies of this mutant for locust bean gum and guar gum also increased by 34-fold and 10-fold, respectively, (Table 2). The site-directed mutagenesis of the TM3 truncated mutant also increased its $k_{cat}$ on konjac glucomannan by two-fold or higher (Table 2).

Binding of Cb1952 to Insoluble Cellulose Substrates

The Cb1952 wild-type, TM1, and TM5, which harbored all three CBMs (one CBM3c and two CBM3b) bound tightly to Avicel (FIG. 80A) and PASC (FIG. 80B). The truncated mutant TM2, which harbored the CBM3c and one CBM3b, also bound tightly to the two cellulosic substrates. The binding of TM3, which was composed of the GH9 module and the CBM3c, to the insoluble cellulose was weaker than those for wild-type, TM1, TM2, and TM5 (FIGS. 80A and 80B). Depletion binding isotherms were used to estimate the dissociation constant and maximal binding capacity of TM3 to Avicel as 0.52±0.20 $M^{-1}$ and 423.9±50.7 nmol protein/g Avicel, respectively. The two components of TM3, i.e., the GH9 module and CBM3c, were observed to weakly bind to insoluble cellulose (FIGS. 80A and 80B). The binding of the CBM3c of CbCel9AMan5B (TM6) to insoluble cellulose was unexpected since this binding was not observed for other CBM3c characterized by this method (7, 10, 12, 16). Note, however, that the bindings were weak and thus preventing us from obtaining the binding constants of the GH9 and CBM3c modules for Avicel. The CBM3b (TM7) also bound to Avicel and PASC (FIGS. 80A and 80B), although in this case also the binding constants could not be determined.

Methods Used with Cb1952 Polypeptides

Methods used with the experiments above for Cb1952 polypeptides include the following:

Determination of Optimal pH and Temperature:

Two buffers were used for pH profiling of Cb1952: 50 mM sodium citrate, 150 mM NaCl (pH 4.0-pH 6.0) and 50 mM $Na_2HPO_4$—$NaH_2PO_4$, 150 mM NaCl (pH 6.5-pH 8.0). To measure the optimal pH of the enzymes on cellulose substrate, 0.5 μM Cb1952 wild-type or one of its truncation mutants was incubated with 2.5 mg/ml PASC in each buffer at a given pH at 75° C., and the activities in a 10 min assay were determined. The reducing sugars released were measured using the pHBAH assay. For determination of optimal temperature, 0.5 μM of each enzyme was incubated with 2.5 mg/ml PASC at pH 5.5 at different temperatures ranging from 40° C. to 95° C. with a 5° C. interval. The optimal pH and temperature for mannanase activity were determined as described above, except for the replacement of PASC with mannan as the substrate and change of the enzyme concentration to 12.5 nM.

Enzymatic Assays:

The specific activities of Cb1952 wild-type and its mutants on Avicel and filter paper were determined at 75° C. in the optimal buffer for the enzymes. The enzyme concentrations were 0.3 μM for each protein except for TM4 (5 μM). At different time intervals in a 90 min assay, samples were taken out and the products released determined as the amount of reducing ends present in the reaction mixture. The specific activities were determined in the region where the relation of reducing sugar versus time was linear.

The kinetics of Cb1952 wild-type and its mutants on PASC, locust bean gum, guar gum, and konjac glucomannan were determined in a 30 min assay. Different concentrations of the enzymes were incubated with a range of concentrations of substrates at 75° C. The velocities of release of reducing ends were determined and plotted against the concentrations of the substrates to estimate the kinetic parameters using the software GraphPad Prism 5.01 (GraphPad, San Diego, Calif.).

Time Course Hydrolysis of Phosphoric Acid Swollen Cellulose (PASC):

Two point five mg/ml PASC was incubated with 0.5 μM Cb1952 WT, TM1, and TM5 at 75° C. At different time intervals (0 min, 2 min, 10 min, 60 min, 4 h, and 24 h), samples were taken out and applied to HPAEC-PAD analysis as described earlier (29).

Analyses of Oligosaccharides Hydrolysis and Transglycosylation Activity:

Glucose, cello-oligosaccharides (cellobiose, cellotriose, cellotetraose, cellopentaose, and cellohexaose), mannose, and manno-oligosaccharides (mannobiose, mannotriose, mannotetraose, mannopentaose, and mannohexaose), each at a final concentration of 1 mg/ml were incubated with 0.1 μM Cb1952 wild-type, Cb1952TM1, and Cb1952TM5 in a citrate buffer (10 mM sodium citrate, 150 mM NaCl, pH5.5) at 75° C. for 14 h. The total reaction volume was 40 μl. The reaction products were dried using a SpeedVac concentrator (Thermo Fisher Scientific, Pittsburgh, Pa.) and dissolved in 3.5 μl of $H_2O$, and 1 μl of the products were analyzed by thin-layer chromatography (TLC) using a 250 μm thick Whatman silica gel 60A (Maidstone, England). The TLC method was the same as described in our earlier report (29).

Thermostability Assay:

The thermostability of Cb1952 and its truncation mutants harboring cellulase activity were determined by incubating the enzymes at 75° C., 80° C., and 85° C. (WT, TM1, TM2, and TM3) or at 45° C., 50° C., and 55° C. (TM4) on a Veriti 96-well thermal cycler (Applied Biosystems, Carlsbad, Calif.). At different time points, aliquots were taken from the reaction mixture and residual enzymatic activity was determined with PASC as the substrate.

Site-Directed Mutagenesis and Circular Dichroism:

For site-directed mutagenesis, the QuikChange Multi Site-Directed Mutagenesis Kit (Stratagene, La Jolla, Calif.) was used according to the manufacturer's instructions. One hundred nanograms of the plasmid encoding Cb1952TM3 were used as the template in the PCR amplification. The reaction mixture contained 100 ng of the mutagenic primer, 1 μl dNTP mix, 0.75 μl QuikSolution and 1 μl QuikChange Multi enzyme blend. The nucleotide sequences of the mutagenic primers used for mutagenesis are shown in Supplemental Table 1. The PCR amplification steps were carried out as follows: an initial denaturation at 95° C. for 1 min, followed by 30 cycles of 95° C. for 1 min, 55° C. for 1 min, and 65° C. for 15 min. The PCR product was digested with DpnI (New England Biolabs) at 37° C. for 4 hours to degrade the parental plasmid DNA. The product from the DpnI digestion was used in electrotransforming JM109 competent cells using a Gene Pulser Xcell electroporation system (BioRAD, Hercules, Calif.). The *E. coli* cells were spread on LB plates containing 100 μg/ml ampicillin and incubated at 37° C. overnight. Single colonies were inoculated in 7 ml LB medium supplemented with 100 μg/ml ampicillin and cultured for 10 h. The plasmids were extracted from the recombinant *E. coli* cells and the inserts were sequenced (W. M. Keck Center for Comparative and Functional Genomics, UIUC) to confirm the presence of the desired mutation. Circular dichroism scans of mutated proteins were carried out as described in our previous report (37).

Measurement of Reducing Sugar in the Soluble and Insoluble Fraction of Hydrolyzed Filter Paper:

The reducing sugars in the soluble and insoluble fractions of filter paper hydrolysis products were determined as described by Irwin et al. (17). The Cb1952 wild-type and its mutants (0.5 μM each except TM4, which was 10 μM) were incubated with five plates of Whatman No. 1 filter paper (0.6 cm in diameter) in a citrate buffer (pH5.5) at 75° C. (for TM4, the temperature was 45° C., since this construct has lower thermostability) in 200 μl. The mixtures were shaken end-over-end for 16 h. The reaction products were centrifuged, and the supernatants (soluble fractions) were analyzed for the amounts of reducing ends. For reducing sugar determination in the insoluble fraction, the filter papers were initially washed four times each with 1 ml of the citrate buffer. Two hundred microliters of the citrate buffer was then added to the insoluble fraction (precipitated filter paper) followed by assaying for reducing ends through the pHBAH method.

Binding of Cb1952 Wild-Type and its Truncated Mutants to Cellulose:

For qualitative measurements of the capacity of the individual polypeptides to bind to cellulose, thirty micrograms of Cb1952 wild-type and its mutants were incubated with 40 mg/ml Avicel cellulose or 2.5 mg/ml PASC in 50 mM Tris-HCl, 150 mM NaCl (pH 7.5). The mixture was shaken end-over-end at 4° C. for 1 h. Then the bound and unbound proteins were separated by centrifugation of the mixture at 16,400 rpm for 3 min. The cellulose pellet was washed four times with 1 ml buffer (50 mM Tris buffer, 150 mM NaCl, pH 7.5). Seventy microliters of 1×SDS-PAGE loading buffer was added to the pellet and boiled for 5 min to release bound proteins. The protein present in one tenth of the volume of the supernatant (unbound protein) and the cellulose pellet (bound protein) was examined by a 12% SDS-PAGE.

For quantitative binding assay, different concentrations of proteins were mixed with 2 mg/ml Avicel in 50 mM Tris-HCl, 150 mM NaCl, pH7.5 buffer in a 2-ml tube. As a control, proteins with the same concentrations were incubated without Avicel in the tube. After 1.5 h end-over-end incubation at 4° C., the mixtures were centrifuged at 16,400 rpm for 3 min. The protein concentrations in the supernatant were determined using a bicinchoninic acid (BCA) Protein Assay Reagent Kit (Thermo Scientific, Rockford, Ill.). Taking the protein concentration from the tube without cellulose as the total protein, the concentrations of bound protein were obtained by subtracting the protein concentration of the sample with cellulose from the total protein concentration. For determination of the binding parameters, the Michaelis/Langmuir equation ($q_{ad}/q=K_p \times q_{max}/(1+K_p \times q)$) as described in our previous report (46) was used. The $q_{ad}$ in the equation represents the amount of bound protein (nmol of protein per gram of Avicel), q is the free protein (μM), and $q_{max}$ is the maximal amount of bound protein to Avicel. The calculation of the binding parameters was carried out with GraphPad Prism 5.01.

Amino Acid Sequence Alignment:

The amino acid sequences of the family 9 glycoside hydrolase catalytic module of the *Clostridium cellulolyticum* Cel9G (GenBank accession number AAA73868)(26) and that of the *Thermobifida fusca* Cel9A (GenBank accession number: AAB42155)(34) were retrieved from Carbohydrate Active enZYme database and the Genbank database and aligned with the GH9 sequence of Cb1952 by using ClustalX. Similarly, the amino acid sequences of the CBM3c modules from the characterized cellulases of different bacterial sources in the published literatures were aligned. These include: ADQ45731: putative cellulase of *Caldicellulosiruptor kronotskyensis*; ABP66693: putative cellulase of *Caldicellulosiruptor saccharolyticus*; ADL42950: putative *Caldicellulosiruptor obsidiansis* cellulase/mannan endo-1,4-beta-mannosidase; AAK06394: CelE of *Caldicellulosiruptor* sp. Tok7B.1 (11); AAA73868: Cel9G of *Clostridium cellulolyticum* (26); AAC38572: EngH of *Clostridium cellulovorans* (38); CAA39010: Cel9Z of *Clostridium stercorarium* (18); ABX43720: Cel9 of *Clostridium phytofermentans* (39, 48); ABN51860: Cel9I of *Clostridium thermocellum* DSM 1313 (50); CAB38941: Cel9B of *Paenibacillus barcinonensis* (32); BAB33148: CelQ of *Clostridium thermocellum* F1 (2); AAA23086: CenB of *Cellulomonas fimi* (27); AAW62376: CBP105 of *Cellulomonas flavigena* (28); AAB42155: Cel9A of *Thermobifida fusca* (16, 34). The aligned sequences were analyzed using the BOXSHADE 3.21 with a default setting of the fraction of sequences parameter as 0.5.

Additional Assays

FIG. 20 shows the enzymatic activity of Cb1952 wild-type on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan were used. Incubation of enzymes with Avicel, PASC, CMC-Na, lichenin, mannan, LBG, guar gum, KGM, WAX and OSX substrates led to release of products that were quantified as a concentration of glucose equivalents. The Cb1952 wild-type mainly hydrolyzes glucose- and mannose-configured substrates, but not xylose-configured substrates.

FIG. 21 shows the enzymatic activity of Cb1952TM1 on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan were used. Incubation of enzymes with Avicel, PASC, CMC-Na, lichenin, mannan, LBG, guar gum, KGM, WAX, BWX, OSX and xyloglucan substrates led to release of products that were quantified as a concentration of glucose equivalents. The results show that Cb1952TM1 mainly hydrolyzes glucose-configured substrates. It also has some activities on mannose-configured substrates. Its activities on xylose-configured substrates are low.

FIG. 22 shows the enzymatic activity of Cb1952TM5 on natural substrates from a reducing sugar assay. Twelve different substrates were tested: Avicel, phosphoric acid swollen cellulose (PASC), sodium carboxymethyl cellulose (CMC-Na), lichenin, mannan, locust bean gum (LBG), guar gum, konjac glucomannan (KGM), wheat arabinoxylan (WAX), birchwood xylan (BWX), oat-spelt xylan (OSX) and xyloglucan were used. Incubation of enzymes with CMC-Na, lichenin, mannan, LBG, guar gum and KGM substrates led to release of products that were quantified as a concentration of mannose equivalents. The Cb1952TM5 mainly hydrolyzes mannose-configured substrates, but does not have obvious activity on glucose- or xylose-configured substrates.

FIG. 23 shows the enzymatic activity of Cb1952 wild-type, Cb1952TM1 and Cb1952TM5 on glucose and cellooligosaccharides from a thin-layer chromatography (TLC) assay. Glucose and five different cellooligosaccharides were used: cellobiose, cellotriose, cellotetraose, cellopentaose and cellohexaose. Cb1952 wild-type and Cb1952TM1 hydrolyze cellotriose, cellotetraose, cellopentaose and cellohexaose into glucose and cellobiose, but have no activity on cellobiose. Cb1952TM5 has no activity on glucose and any of the cellooligosaccharides tested. None of the enzyme has transglycosylation activity on glucose and cellooligosaccharides.

FIG. 24 shows the enzymatic activity of Cb1952 wild-type, Cb1952TM1 and Cb1952TM5 on mannose and mannooligosaccharides from a thin-layer chromatography (TLC) assay. Mannose and five different mannooligosaccharides were used: mannobiose, mannotriose, mannotetraose, mannopentaose and mannohexaose. Cb1952 wild-type and Cb1952TM5 hydrolyze mannotriose, mannootetraose, mannopentaose and mannohexaose into mannose and smaller mannooligosaccharides, but have no hydrolyzing activity on mannobiose. Cb1952TM1 hydrolyzes mannopentaose and mannohexaose into smaller oligosaccharides but has no hydrolyzing activity on mannobiose, mannotriose, mannotriose and mannotetraose. None of the enzyme has transglycosylation activity on mannose and mannooligosaccharides.

The concentration of glucose or mannose equivalents was determined following enzymatic hydrolysis of the natural polysaccharides, according to the methods of Lever, M. (A new reaction for colorimetric determination carbohydrates. Anal. Biochem. 1972: 47; 273-279). 1.5 mL microcentrifuge tubes were "zeroed" in an analytical balance. Next, 2±0.1 mg Avicel or mannan were added to each tube, and the mass measured and recorded. The volumes needed to be added to each tube were calculated based on the mass. For CMC-Na and PASC, a stock substrate solution of CMC-Na (2%) and PASC (6.11 mg/ml) were used. For lichenin, KGM, WAX, BWX, OSX and xyloglucan, 2% stock solution was used. For LBG and guar gum, 0.5% stock solution was used. Sodium citrate reaction buffer and enzymes were added to each tube beginning with the reaction buffer. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay. 1 mL of a stock solution of glucose was made at a concentration of 100 mM in sodium citrate buffer, and then serial dilutions were made in sodium citrate buffer to the following concentrations (20 mM, 10 mM and 5 mM). 50 mg of pHBAH was dissolved in 50 mL of ice-cold citrate/NaOH solution for a final concentration of 0.1% (w/v), and the solution was kept on ice. 150 μL of pHBAH solution was added to 50 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbances.

FIG. 25 shows the enzymatic activity of Cb1952TM1 on cellulose substrates using HPLC analysis. Three different cellulosic substrates were tested: Avicel, CMC-Na and PASC. In each case, in the presence of Cb1952TM1, glucose and cellobiose were released. In the absence of Cb1952TM1, neither glucose nor cellobiose was observed for all the substrates. The results showed that this part of the enzyme or polypeptide (Cb1952) cleaves glucose and cellobiose as end products from cellulosic substrates (Avicel, CMC-Na and PASC).

FIG. 26 shows a time-course hydrolysis of PASC by Cb1952TM1. 100 nanomolar of Cb1952TM1 was incubated with 2.5 mg/ml PASC at 75° C. At different time interval (0, 0.5 min, 2 min, 10 min, 1 h, 4 h and 24 h), samples were taken out and immediately boiled for 10 min to inactivate the enzyme. After centrifugation, the supernatants of the samples were appropriately diluted with water and applied to HPLC analysis. The results show that Cb1952TM1 initially releases glucose, cellobiose, cellotriose and cellotetraose. With increasing time, only glucose and cellobiose were left in the reaction mixture.

FIG. 27 shows the thermostability of Cb1952 wild-type using PASC as substrate for activity measurement. Cb1952 wild-type has 75%, 43%, 17% and 12% activity after incubation at 70° C., 75° C., 80° C. and 85° C. for 24 h, respectively. 500 nM Cb1952 wild-type was kept at different temperatures (70° C., 75° C., 80° C. and 85° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 85° C. on a thermomixer. 2.5 mg/ml final concentration of PASC was used for measurement, and 8.31 µl of the protein sample was added to the substrate and mixed by pipetting up and down for several times. The total volume was 100 µl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

FIG. 28 shows the thermostability of Cb1952TM1 using PASC as substrate for activity measurement. Cb1952TM1 has 94%, 76%, 18% and 13% activity after incubation at 70° C., 75° C., 80° C. and 85° C. for 24 h, respectively. 500 nM Cb1952TM1 was kept at different temperatures (70° C., 75° C., 80° C. and 85° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 85° C. on a thermomixer. 2.5 mg/ml final concentration of PASC was used for measurement, and 8.31 µl of the protein sample was added to the substrate and mixed by pipetting up and down for several times. The total volume was 100 µl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Discussion of Results with Cb1952 Polypeptides

Cb1952 is the first GH9 cellulase characterized with two tandem CBM3b modules linked to the GH9-CBM3c domains. The CBM3b module (TM7) binds to insoluble cellulose (FIGS. 80A and 80B). Deletion of one CBM3b (TM2) from TM1 did not significantly affect the binding to these substrates (FIGS. 80A and 80B). Correspondingly, the specific activities and kinetic parameters of TM1 and TM2 are similar for cellulose substrates (Table 1). Further deletion of another CBM3b (TM3) reduced both the binding to the insoluble substrates and the specific activities for Avicel and filter paper (Table 1). Therefore, the CBM3b modules facilitate the deconstruction of crystalline cellulose by Cb1952.

Cb1952 and its truncation mutants, especially TM3, retained considerable activities after incubation at 75° C. for 24 h. For other hyperthermophilic endoglucanases, Cel5A of *Thermoanaerobacter tengcongensis* has above 80% residual activity after incubation at 60° C. for 24 h (24), the Avicelase I of *Clostridium stercorarium* has above 60% residual activity after incubation at 80° C. for 12 h (6), and the CelB of *Caldicellulosiruptor saccharolyticus* has a half-life of 29 h at 70° C. (35). The thermostability property of the multifunctional enzyme can facilitate recycling during its use in releasing fermentable sugars from cellulosic substrates. Introduction of an enzyme recycling step in cellulosic ethanol production can significantly reduce the cost of production of the value added product.

The *C. bescii* Cb1954 (CelA) (ORF1954, GenBank accession number ACM60955) is the first cellulase characterized from this bacterium (49). It is the most highly secreted cellulase when *C. bescii* is grown on Avicel medium (25). Similar but not identical to Cb1952, Cb1954 is composed of an N-terminally located GH9 module, a C-terminally located GH48 module, and three CBM3 modules between the two catalytic domains. The specific activity of Cb1952 on Avicel (10.15 µmol sugar/min/µmol enzyme) was much lower than that of the full-length Cb1954/CelA (55.0 µmol sugar/min/µmol enzyme), but only slightly lower than that of its truncation mutant CelA' containing the GH9 catalytic module and CBMs (18.0 µmol sugar/min/µmol enzyme) (49). In a comparison with other hyperthermostable endoglucanases, this specific activity of Cb1952 was lower than those of Cel5A of *Thermoanaerobacter tengcongensis* (60.0 µmol sugar/min/µmol enzyme) (24) and Avicelase I of *Clostridium stercorarium* (30.2 µmol sugar/min/µmol enzyme) (6), comparable to that of EGPh of *Pyrococcus horikoshii* (12.7 µmol sugar/min/µmol enzyme) (1), but much higher than that of the *C. saccharolyticus* CelB (0.4 µmol sugar/min/µmol enzyme) (41). The specific activity of Cb1952 on filter paper was comparable to those of CelB of *Thermotoga neapolitana* (20.8 µmol sugar/min/µmol enzyme) (5), Cel5A of *Thermoanaerobacter tengcongensis* (18.5 µmol sugar/min/µmol enzyme) (24), and EglA of *Pyrococcus furious* (18.7 µmol sugar/min/µmol enzyme) (3), but much higher than those of CelA of *Thermotoga neapolitana* (3.2 µmol sugar/min/µmol enzyme) (5) and CelB of *C. saccharolyticus* (1.8 µmol sugar/min/µmol enzyme) (41). Note that the assay conditions (reaction temperature, buffer, reaction period, method for measuring reducing sugar, and lab equipment) for these specific activities may vary among the enzymes described above. Nevertheless, Cb1952 is an effective enzyme for releasing fermentable sugars from cellulosic substrates at high temperatures.

Interestingly, seven out of the nine genes in the gene cluster in which the Cb1952 encoding gene is located also contain CBM3b modules identical to or highly similar to (identity >98%) the CBM3b of Cb1952. Six of the polypeptides in the gene cluster have either two or three tandem CBM3b repeats. It is reasonable to postulate that these CBM3b modules aid in plant cell wall hydrolysis.

The mannanase activity of Cb1952 was mainly located in the GH5 module; however, limited mannanase activity was also observed with the construct containing the GH9 domain as the catalytic module. In most cases, family 9 glycoside hydrolases are described as endoglucanase (10, 16), cellobiohydrolase (36), 1,4-β-D-glucan glucohydrolase (33), β-glucosidase (30), and exo-β-glucosaminidase (14). The *Bacillus licheniformis* Cel9 is the only member of this family reported to have mannanase activity (42); however, its kinetic data and hydrolysis pattern on mannose-configured substrates are unknown. The TM1 mutant of Cb1952 showed different hydrolysis patterns compared with the TM5 mutant, in that the GH9 needed a minimal chain length of five and released mannobiose as the shortest end-product, while the GH5 needed a minimal chain length of three and released mannose as the shortest end-product. The ability of the GH9 module of Cb1952 to hydrolyze mannose-configured substrates suggests that the catalytic module can both accommodate the equatorial C-2 hydroxyl of glucose and also tolerate the axial C-2 hydroxyl of mannose.

The absence of a tryptophan for −3 subsite hydrophobic interaction was proposed to destabilize the non-productive binding which might impair the processivity of a GH9 cellulase (31). The mutations of G208 and T298 into aromatic residues (TM3G208WG, TM3G208W, and TM3T298F), however, did not change the processivity of TM3 as reflected by the unaltered ratios of soluble versus insoluble reducing ends. The specific activities of the mutants on crystalline cellulose (Avicel and filter paper) were also comparable to that of the parental TM3. However, for non-crystalline PASC, all turnover numbers of the mutants were increased by roughly 2 folds while the catalytic efficiencies remained unchanged. The different structures of crystalline and non-crystalline cellulose might affect the performance of these enzymes. One of the mutants, TM3G208WG, increased its substrate specificity for locust bean gum by 35 folds (TM3: $[k_{cat}/K_m]_{LBG}/[k_{cat}/K_m]_{PASC}$=7 $0.4\times10^{-3}$, TM3G208WG: $[k_{cat}/K_m]_{LBG}/[k_{cat}/K_m]_{PASC}$=0.26), suggesting that residues for subsite −3 interaction might be involved in substrate selection.

CBM3c has been proposed to bind loosely to the cellulose ligand and feed a cellulose chain into the GH9 catalytic module (34). However, no biochemical data was provided for this binding. In the co-crystal structure of family 9 cellulase in complex with cello-oligosaccharides, the binding of the cello-oligosaccharide to CBM3c has not been observed so far (26, 34). Our results suggest that a CBM3c can indeed bind to insoluble cellulose although the binding appeared weak. A sequence alignment of Cb1952 with its homologs revealed that considerable differences exist in the amino acid residues proposed to interact with the ligand (19, 22, 23) between Cb1952 CBM3c with its homologues. The conserved Q553, R557, E559, and R563 residues in ThefuCel9A proposed to interact with the ligand are correspondingly replaced by E545, K549, Q561, and K565, respectively, in the CBM3c of Cb1952 (FIG. 82). This observation may be akin to the fine-tuning demonstrated in a *Caldanaerobius polysaccharolyticus* family 16 CBM by mutating one polar residue (Q121 to E121) involved in hydrogen bonding with the ligand (37). The E545, K549, Q561, and K565 residues can also be found in four CBM3 modules from the related organisms *C. kronotskyensis, C. saccharolyticus, C. obsidiansis*, and *Caldicellulosiruptor* sp. Tok7B.1 (FIG. 82). A three-dimensional structure of a CBM3c in complex with a ligand is still lacking, which hinders accurate designation of residues important for ligand binding. Due to the diversity of CBM3c modules (19), one may postulate that other variants of CBM3c might exist which could hold a cello-oligosaccharide tightly enough to capture this complex in a crystal.

Example 10: Endo-Glucanase/Mannanase Cb1953

A putative endoglucanase, Cb1953WT, was identified in *Caldicellulosiruptor bescii*. The enzyme is the gene product of cb1953, where Cb stands for *Caldicellulosiruptor bescii*. The endoglucanase cleaves mostly cellobiose from cellulose. The Cb1953WT protein is 1391 amino acids long and has a molecular weight of 153.6 kDa (His-tag+Cb1953 protein). The Cb1953WT has two Glycoside Hydrolase (GH) family 5 catalytic domain and 3 carbohydrate binding proteins (FIG. 29). Two truncated mutants were made, as shown in FIG. 29, to determine the activity in each GH5 module. For the truncated mutants, Cb1953TM1 (961 amino acids, 103.9 kDa) has N-terminal GH 5 catalytic domains with 3 carbohydrate binding modules, whereas Cb1953TM2 (1108 amino acids, 121.7 kDa) has C-terminal GH5 catalytic domains with 3 carbohydrate binding modules as like shown in FIG. 29.

PCR Amplification of Cb1953WT

The genes were amplified from *Caldicellulosiruptor bescii* DSM 6725T genomic DNA by PCR using PrimeSTAR DNA Polymerase (TAKARA). The Cb1953WT, Cb1953TM1, and Cb1953TM2 coding sequences were amplified using the following respective primer set:

```
Cb1953WTForward:
                                   (SEQ ID NO: 56)
5'-GAC GAC GAC AAG ATG GCT ACA TCT AAT
GATGGA GTA GTG AAG -3'

Cb1953WTReverse:
                                   (SEQ ID NO: 57)
5'-GAG GAG AAG CCC GGT TAA TTT TGC GGC TGG
AAC TGG CGC TGG TTC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 5 min | |
| Elongation | 72° C. | 7 min | 1 cycle |
| Last | 4° C. | ∞ | |

Cloning of Cb1953TM1

```
Cb1953TM1Forward:
                                        (SEQ ID NO: 56)
5'-GAC GAC GAC AAG ATG GCT ACA TCT AAT
GATGGA GTA GTG AAG -3'

Cb1953TM1Reverse:
                                        (SEQ ID NO: 58)
5'-GAG GAG AAG CCC GGT TAT GGC ATT GGT ATT
ACT GTC TGC ACC GG -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

Cloning of Cb1953TM2

```
Cb1953TM2Forward:
                                        (SEQ ID NO: 59)
5'-GAC GAC GAC AAG ATG
GGTGCCTCTTCAGTACCTACTTCAACACC -3'

Cb1953TM2Reverse:
                                        (SEQ ID NO: 57)
5'- GAG GAG AAG CCC GGT TAA TTT TGC GGC TGG
AAC TGG CGC TGG TTC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

-continued

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

After the PCR amplification described above, the products of Cb1953WT, Cb1953TM1, and Cb1953TM2 were confirmed by 1% agarose gel electrophoresis. The DNA corresponding to the expected band on the gel was cut out and applied to a Qiagen Gel Extraction kit to extract the DNA out of the gel.

The Novagen pET-46 Ek/LIC kit was used to treat each purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was inactivated by incubation at 75° C. for 20 min.

The following protocol was used to anneal the insert into the pET-46 Ek/LIC vector:

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for Cb1953-pET-46 Ek/LIC was introduced into *E. coli* JM109 by electroporation, and the cells were plated on LB-ampicillin. After overnight incubation at 37° C., four colonies were selected and each was used to inoculate 6 mL cultures of LB-ampicillin. The cultures were grown at 37° C. with vigorous aeration for 16 hours, and minipreps (QIAGEN) were made from the cell cultures. The plasmids were then electrophoresed on a 1% agarose gel to check the size of the plasmid DNA. After confirmation of insertion of the gene into the plasmid, the inserts were sequenced to confirm the integrity of their sequences.

For gene expression, one of the plasmids was transformed into *E. coli* BL21 codon plus DE3 RIL by the heat shock method and plated on LB plates supplemented with chloramphenicol (100 μg/ml) and ampicillin (50 μg/ml) and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.1 mM final concentration, and the culturing continued at 16° C. overnight.

Gene and Protein Sequences of Cb1953WT, Cb1953TM1, and Cb1953TM2

Wild Type Cb1953 Amino Acid Sequence

The wild-type Cb1953 amino acid sequence is disclosed in SEQ ID NO: 60. The signal peptide of Cb1953, corresponding to amino acid numbers 1-38 of SEQ ID NO: 60 was removed during all PCR amplifications. Thus, the expressed wild-type Cb1953 protein did not contain amino acid numbers 1-38 of SEQ ID NO: 60. The amino acid sequence of the wild-type Cb1953 protein without the signal peptide is disclosed in SEQ ID NO: 61.

The procedure of cloning the gene for wild-type Cb1953 (without the signal peptide) into the plasmid pET-46 Ek/LIC led to fusion of the gene to a short nucleotide sequence encoding a peptide that contains six histidines. The wild-type Cb1953 amino acid sequence (without the signal peptide) with the short peptide is disclosed in SEQ ID NO: 65. The amino acids of the short peptide are amino acids 1-14 of SEQ ID NO: 65.

Wild Type Cb1953 Nucleotide Sequence

The wild-type Cb1953 nucleotide sequence is disclosed in SEQ ID NO: 62. The signal peptide of Cb1953, corresponding to nucleotide numbers 1-114 of SEQ ID NO: 62 was removed during all PCR amplifications. Thus, the nucleotide sequence used to express wild-type Cb1953 protein did not contain nucleotide numbers 1-114 of SEQ ID NO: 62. The nucleotide sequence encoding the wild-type Cb1953 protein without the signal peptide is disclosed in SEQ ID NO: 63.

The wild-type Cb1953 nucleotide sequence (without the signal peptide) with the coding sequence for the short peptide from the plasmid pET-46 Ek/LIC is disclosed in SEQ ID NO: 64. The nucleotides coding for the short peptide nucleotides are nucleotides 1-42 of SEQ ID NO: 64.

Cb1953TM1 Amino Acid Sequence

The Cb1953TM1 amino acid sequence is disclosed in SEQ ID NO: 122. The procedure of cloning the gene for Cb1953TM1 into the plasmid pET-46 Ek/LIC led to fusion of the gene to a short nucleotide sequence encoding a peptide that contains six histidines. The Cb1953TM1 amino acid sequence with the short peptide from pET-46 Ek/LIC is disclosed in SEQ ID NO: 67. The amino acids of the short peptide are amino acids 1-14 of SEQ ID NO: 67.

Cb1953TM1 Nucleotide Sequence

The Cb1953TM1 nucleotide sequence is disclosed in SEQ ID NO: 123. The Cb1953TM1 nucleotide sequence with the coding sequence for the short peptide from the plasmid pET-46 Ek/LIC is disclosed in SEQ ID NO: 66. The nucleotides coding for the short peptide nucleotides are nucleotides 1-42 of SEQ ID NO: 66.

Cb1953TM2 Amino Acid Sequence

The Cb1953TM2 amino acid sequence is disclosed in SEQ ID NO: 111. The procedure of cloning the gene for Cb1953TM2 into the plasmid pET-46 Ek/LIC led to fusion of the gene to a short nucleotide sequence encoding a peptide that contains six histidines. The Cb1953TM2 amino acid sequence with the short peptide is disclosed in SEQ ID NO: 69. The amino acids of the short peptide are amino acids 1-14 of SEQ ID NO: 69.

Cb1953TM2 Nucleotide Sequence

The Cb1953TM2 nucleotide sequence is disclosed in SEQ ID NO: 110. The Cb1953TM2 nucleotide sequence with the coding sequence for the short peptide from the plasmid pET-46 Ek/LIC is disclosed in SEQ ID NO: 68. The nucleotides coding for the short peptide nucleotides are nucleotides 1-42 of SEQ ID NO: 68.

Purification of Cb1953WT, Cb1953TM1, and Cb1953TM2 Proteins

The Cb1953WT, Cb1953TM1, Cb1953TM2 were expressed in *E. coli* BL-21 CodonPlus (DE3) RIL competent cells by heat shock. The recombinant cells were then grown overnight in LB agar plates supplemented with ampicillin (100 μg/mL) and chloramphenicol (50 μg/ml) at 37° C. After 8 h, the starter cultures were diluted into fresh LB supplemented with ampicillin (100 μg/mL) and chloramphenicol (50 μg/ml) at 37° C. with aeration until the absorbance at 600 nm reached 0.5. Gene expression was then induced by addition of IPTG at a final concentration of 0.1 mM and the temperature for culturing was lowered to 16° C. After 16 hours, the cells were centrifuged to collect the cell pellet. The pellet was then suspended in a lysis buffer (25 mM Tris-HCL pH 7.8, 750 mM of NaCl, 5% glycerol, 20 mM imidazole, 1.25% Tween-20). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged target proteins) was then eluted from the resin with an elution buffer (50 mM Tris-HCL, pH7.5, 250 mM imidazole). The eluted fractions were then heat-treated at 65° C. for 30 minutes and then centrifuged to remove the precipitated proteins. The proteins were then purified by gel filtration chromatography (HiLoad 16/20 Superdex 200, GE Healthcare) with a Tris-HCl elution buffer (50 mM Tris-HCl, 150 mM NaCl, pH 7.5). Aliquots of eluted fractions were analyzed by sodium dodecyl sulfate-polyacrylamide gel electrophoresis (SDS-PAGE) and proteins bands were visualized by staining with Coomassie brilliant blue G-250 (FIG. 30).

Enzyme Activity

FIG. 31 shows the zymogram of Cb1953WT, Cb1953TM1, Cb1953TM2 on carboxylmethyl cellulose (CMC). The gel was prepared as in standard dodecyl sulfate polyacrylamide gel electrophoresis (SDS-PAGE) with CMC substrate (final 0.1%, w/v). After electrophoretic fractionation of the proteins, gels were washed twice in distilled water and incubated in 30 mL of refolding buffer (20 mM citrate buffer, pH 6.0, 2.5% Triton X-100, 2 mM dithiothreitol, 2.5 mM $CaCl_2$) for 1 hour at 25° C. and then held overnight in fresh buffer at 37° C. The gel was washed twice in 50 mM Citrate buffer (pH 6.0) and then the results were visualized by staining with 0.1% Congo red and destaining with 1M NaCl. As shown in FIG. 31, Cb1953WT and Cb1953TM2 showed significant white bands at the positions of their expected sizes indicating cellulase activity, but not Cb1953TM1 protein.

FIGS. 32 and 33 show the enzymatic activity of Cb1953WT, Cb1953TM1, and Cb1953TM2 on natural substrates from a reducing sugar assay. Seven different substrates were tested: Avicel, Phosphoric acid swollen cellulose (PASC), carboxylmethyl cellulose (CMC), wheat arabinoxylan (WAX), lichenin, konjac glucomannan, and mannan. Incubation of enzymes with the substrates led to release of products that were quantified as a concentration of glucose equivalents. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay. The wavelength at 410 nm was measured for the standards and samples. The $A_{410nm}$ and glucose concentrations were plotted against each other, and linear regression was used to fit a line to the data. The reactions were resolved by thin layer chromatography (TLC), The mobile phase consisted of n-butanol:acetic acid: H2O, 10:5:1 (vol/vol/vol) and 10 cm×20 cm plates were used. The reducing sugar assay (FIG. 32) and TLC (FIG. 33) results show that Cb1953WT and Cb1953TM2 have cellulase activity whereas Cb1953TM1 has mannanase activity. Through the zymogram, reducing assay, and TLC analysis on various substrates, we concluded that the C-terminal GH5 in Cb1953WT functions as a cellulase whereas the N-terminal GH5 functions as mannase.

FIG. 34 shows the time course of enzymatic activity of Cb1953TM2 on PASC using HPLC analysis. For analysis of the products of hydrolysis, the samples were analyzed by high performance anion-exchange chromatography (HPAEC). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.). For the TLC and HPLC analysis, glucose and five different cellooligosaccharides (cellobiose, cellotriose, cellotetraose, cellopentaose, and cellohexaose) were used as standards. In the reaction, Cb1953 started to release cellooligosaccharides (C2-C4) and then glucose was released later. The results showed that this enzyme releases mainly cellobiose from PASC.

FIGS. 35 and 36 show the thermostability of Cb1953WT and Cb1953TM2 on PASC. 50 nM Cb1953WT and Cb1953TM2 were kept at different temperatures (70° C., 75° C., 80° C., 85° C. and 90° C.). The samples were taken out at different time points (0 h, 0.5 h, 1 h, 2 h, 4 h, 7 h, 11 h and 24 h) and immediately used in enzyme activity measurement. The enzyme activity was measured at 85° C. using Cary 300 UV-Vis spectrophotometer (Varian). The initial velocity of reaction in the first minute was calculated. The initial velocity of reaction for time 0 was set as 100; then the remaining activities (percentage) for time 0.5 h, 1 h, 2 h, 4 h, 7 h, 11 h and 24 h were calculated by dividing the initial velocities of reaction for time 0.5 h, 1 h, 2 h, 4 h, 7 h, 11 h and 24 h by the initial velocity of reaction at time 0, then multiplied by 100. From the results, Cb1953WT (FIG. 35) and Cb1953TM2 (FIG. 36) were quite stable at 70° C. and 75° C., maintaining activity of 75~90% of heat non-treated proteins.

FIG. 37 shows the kinetic studies of Cb1953WT and Cb1953TM2 on PASC. 0.05 μM of purified Cb1953WT or Cb1953TM2 in 50 mM $Na_2HPO_4$—HCl, pH 6.0, and 150 mM NaCl was incubated with various concentrations of phosphoric acid swollen cellulose (PASC), and the initial rate of hydrolysis was plotted against substrate concentration. The kinetic parameters ($K_m$: 7.603 mg/mL, $k_{cat}$: 7.513 $s^{-1}$ and $k_{cat}/K_m$: 0.988 $s^{-1}$ mL/mg for Cb1953WT and $K_m$: 3.032 mg/mL, $k_{cat}$: 5.411 $s^{-1}$ and $k_{cat}/K_m$: 1.785 $s^{-1}$ mL/mg for Cb1953TM2) were determined by fitting the data to the Michaelis-Menten equation (Graph Pad Prism v5.01).

Example 11: Endocellulase Cb1954

A putative endoglucanase, Cb1954, was identified in *Caldicellulosiruptor bescii*, where Cb stands for *Caldicellulosiruptor bescii*. The protein has a Glycoside Hydrolase (GH) family 9 catalytic domain (putative cellulase domain), three family 3 carbohydrate binding modules (CBMs) and one GH48 catalytic domain (FIG. 38). The Cb1954 wild-type is 1746 amino acids long and has a predicted molecular mass of 193.6 kDa (His-tag+Cb1954 wild-type protein). The enzyme Cb1954TM3 and Cb1954TM5 are the truncational mutants of the gene product of Cb1954, where Cb stands for *Caldicellulosiruptor bescii*. The endocellulase cleaves glucose and cellobiose from cellulose as end products. The Cb1954TM3 protein is 709 amino acids long and has a molecular weight of 78.57 kDa (His-tag+Cb1954TM3 protein). The protein has a Glycoside Hydrolase (GH) family 9 catalytic domain and one family 3 carbohydrate binding module (CBM3). The Cb1954TM5 protein is 1294 amino acids long and has a molecular weight of 142.82 kDa (His-tag+Cb1954TM5 protein). The protein has a Glycoside Hydrolase (GH) family 48 catalytic domain and three family 3 Carbohydrate binding modules (CBM3).

Cloning of Cb1954 Wild-Type

The gene for Cb1954 wild-type was amplified from *Caldicellulosiruptor bescii* DSM 6725T genomic DNA by PCR using PrimeSTAR DNA Polymerase (TAKARA). The Cb1954 wild-type gene was amplified using the following primer set:

The Cb1954 wild-type gene was amplified using the following primer set:

```
Cb1954 wild-type Forward:
                                    (SEQ ID NO: 70)
5'- GAC GAC GAC AAG ATG CAA GAG GTT AGG
GCT GGT TCG TTT AAC -3'

Cb1954 wild-type Reverse:
                                    (SEQ ID NO: 71)
5'- GA GGA GAA GCC CGG TTA TTG ATT GCC
AAA CAG TAT TTC ATA TG -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |

-continued

| PCR protocol | | | |
|---|---|---|---|
| Elongation | 72° C. | 6 min | |
| Elongation | 72° C. | 7 min | 1 cycle |
| Last | 4° C. | ∞ | |

Cloning of Cb1954TM3

The gene for Cb1954 was amplified from *Caldicellulosiruptor bescii* DSM 6725T genomic DNA by PCR using Pfu Turbo® DNA Polymerase. The Cb1954TM3 gene was amplified using the following primer set:

```
Cb1954TM3Forward:
                                        (SEQ ID NO: 70)
5'- GAC GAC GAC AAG ATG CAA GAG GTT AGG
GCTGGT TCG TTT AAC -3'

Cb1954TM3Reverse:
                                        (SEQ ID NO: 72)
5'- GA GGA GAA GCC CGG TTA TAC CTT TAT CTG
TCC ACC TGC TAC-3'
```

The polymerase chain reaction mixture contained the following:

| PCR reaction | |
|---|---|
| 2.5 U/μL Pfu Turbo ® DNA Polymerase | 0.5 |
| 17 ng/μL *Caldicellulosiruptor bescii* genomic DNA | 1 |
| 20 μM Fw Primer | 1 |
| 20 μM Rv Primer | 1 |
| 10 mM dNTP Mixture | 1 |
| 10 × Cloned Pfu Turbo DNA Polymerase Buffer | 5 |
| $dH_2O$ | 40.5 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 2.5 min | |
| Elongation | 72° C. | 10 min | 1 cycle |
| Last | 4° C. | ∞ | |

Cloning of Cb1954TM5

The gene for Cb1954 was amplified from *Caldicellulosiruptor bescii* DSM 6725T genomic DNA by PCR using Pfu Turbo® DNA Polymerase. The Cb1954TM3 gene was amplified using the following primer set:

```
Cb1954TM5Forward: 5'-
                                        (SEQ ID NO: 73)
GAC GAC GAC AAG ATG TTC AAA GCT ATT GAA
ACT CCA ACA AAC -3'

Cb1954TM5Reverse:
                                        (SEQ ID NO: 71)
5'- GA GGA GAA GCC CGG TTA TTG ATT GCC AAA
CAG TAT TTC ATA TG -3'
```

The polymerase chain reaction mixture contained the following:

| PCR reaction | |
|---|---|
| 2.5 U/μL Pfu Turbo ® DNA Polymerase | 0.5 |
| 17 ng/μL *Caldicellulosiruptor bescii* genomic DNA | 1 |
| 20 μM Fw Primer | 1 |
| 20 μM Rv Primer | 1 |
| 10 mM dNTP Mixture | 1 |
| 10 × Cloned Pfu Turbo DNA Polymerase Buffer | 5 |
| $dH_2O$ | 40.5 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 10 min | 1 cycle |
| Last | 4° C. | ∞ | |

After the PCR described above, the amplification of Cb1954 wild-type, Cb1954TM3 and Cb1954TM5 gene was confirmed by 1% agarose gel electrophoresis. The DNA corresponding to the expected band on the gel was cut out and the amplified fragment was extracted using the Qiagen Gel Extraction kit.

A Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was inactivated by incubation at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

Each of the ligation mixture for Cb1954 wild-type-, Cb1954TM3- or Cb1954TM5-pET-46 Ek/LIC was introduced into *E. coli* NovaBlue competent cells by chemical transformation method, and the cells were plated on LB-ampicillin. After overnight incubation at 37° C., four colonies were selected and used to inoculate 6 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene had been inserted into the plasmid, the genes were sequenced to confirm their identities.

For all the constructs of Cb1954, only Cb1954TM3 could be cloned. Thus for the expression of this protein, one of the recombinant plasmids was transformed into *E. coli* BL21 codon plus DE3 RIL by the heat shock method and plated on LB plates supplemented with chloramphenicol (50 μg/ml) and ampicillin (100 μg/ml) and incubated at 37° C. overnight. Five colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.1 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged Cb1954TM3) was then eluted from the resin with an elution buffer (50 mM Tris-HCL, pH7.5, 250 mM imidazole).

The design of the PCR primers ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

The Cb1954TM3 gene was expressed in *E. coli* cells, and the protein was purified in three steps, including a talon resin purification step making use of the 6-histidines encoded by the plasmid, an anion exchange step using Hitrap Q column and a gel filtration step using Hiload 16/60 Superdex 200 column. FIG. 39A shows an SDS-PAGE of purified Cb1954TM3.

Gene and Protein Sequences of Cb1954WT, Cb1954TM3, and Cb1954TM5

Wild Type Cb1954 Amino Acid Sequence

The wild-type Cb1954 endocellulase (EC 3.2.1.4) amino acid sequence is disclosed in SEQ ID NO: 74. The signal peptide of Cb1954, corresponds to amino acid numbers 1-27 of SEQ ID NO: 74. The amino acid sequence of the wild-type Cb1954 protein without the signal peptide is disclosed in SEQ ID NO: 121.

Wild Type Cb1954 Nucleotide Sequence

The wild-type Cb1954 nucleotide sequence is disclosed in SEQ ID NO: 116. The signal peptide of Cb1954 corresponds to nucleotide numbers 1-81 of SEQ ID NO: 116. The nucleotide sequence encoding the wild-type Cb1954 protein without the signal peptide is disclosed in SEQ ID NO: 75.

Cb1954TM3 Amino Acid Sequence

The Cb1954TM3 amino acid sequence is disclosed in SEQ ID NO: 76. The procedure of cloning the gene for Cb1954TM3 into the plasmid pET-46 Ek/LIC led to fusion of the gene to a short nucleotide sequence encoding a peptide that contains six histidines. The Cb1954TM3 amino acid sequence with the short peptide from pET-46 Ek/LIC is disclosed in SEQ ID NO: 81. The amino acids of the short peptide are amino acids 1-14 of SEQ ID NO: 81.

Cb1954TM3 Nucleotide Sequence

The Cb1954TM3 nucleotide sequence is disclosed in SEQ ID NO: 77. The Cb1954TM3 nucleotide sequence with the coding sequence for the short peptide from the plasmid pET-46 Ek/LIC is disclosed in SEQ ID NO: 80. The nucleotides coding for the short peptide nucleotides are nucleotides 1-42 of SEQ ID NO: 80.

Cb1954TM5 Amino Acid Sequence

The Cb1954TM5 amino acid sequence is disclosed in SEQ ID NO: 78.

Cb1954TM5 Nucleotide Sequence

The Cb1954TM5 nucleotide sequence is disclosed in SEQ ID NO: 79.

Enzyme Activity

FIG. 39B shows the enzymatic activity of Cb1954TM3 on natural substrates from a reducing sugar assay. Three different cellulose substrates were tested: Avicel, sodium carboxymethyl cellulose (CMC-Na) and phosphoric acid swollen cellulose (PASC). Incubation of enzymes with the substrates led to release of products that were quantified as a concentration of glucose equivalents. Hydrolysis of PASC was higher than hydrolysis of other substrates.

The concentration of glucose equivalents was determined following enzymatic hydrolysis of Avicel, CMC-Na and PASC, according to the methods of Lever, M. (supra). 1.5 mL microcentrifuge tubes were "zeroed" in an analytical balance. Next, 2±0.1 mg Avicel were added to each tube, and the mass measured and recorded. For CMC-Na and PASC, a stock substrate solution of CMC-Na (2%) and PASC (6.11 mg/ml) were used. Sodium citrate reaction buffer and enzymes were added to each tube beginning with the reaction buffer. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay to determine the reducing ends released by the enzyme. 1 mL of a stock solution of glucose was made at a concentration of 100 mM in sodium citrate buffer, and then serial dilutions were made in sodium citrate buffer to the following concentrations (20 mM, 10 mM and 5 mM). 50 mg of pHBAH was dissolved in 50 mL of ice-cold citrate/NaOH solution for a final concentration of 0.1% (w/v), and the solution was kept on ice. 150 μL of pHBAH solution was added to 50 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a prediction equation to the data. The coefficient of determination ($R^2$) value was between 0.98 and 1.0. The equation from the standard curve was used to calculate the concentrations of reducing ends in the samples based upon their absorbances.

FIG. 40 shows the enzymatic activity of Cb1954TM3 on cellulosic substrates using HPLC analysis. Three different cellulosic substrates were tested: Avicel, CMC-Na and PASC. In each case, in the presence of Cb1954TM3, glucose and cellobiose were released. In the absence of Cb1954TM3, neither glucose nor cellobiose was observed for all the substrates. The results showed that this enzyme releases glucose and cellobiose, and also longer chain oligosaccharides as end products from cellulosic substrates (CMC-Na and PASC).

FIG. 41 shows the thermostability of Cb1954TM3. Cb1954TM3 has 75%, 87%, 64% and 7% activity after incubation at 70° C., 75° C., 80° C. and 85° C. for 24 h, respectively. 500 nM Cb1954TM3 was kept at different temperatures (70° C., 75° C., 80° C. and 85° C.). The enzyme activity was measured at pH 5.5 and at 95° C. on a thermomixer. 2.5 mg/ml final concentration of PASC was used for measurement, and 10 μl of the protein sample was added to the substrate and mixed by pipetting up and down for several times. The total volume was 100 μl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Example 12: Endo-Glucanase Cb1946

A putative endoglucanase, Cb1946WT, was identified in *Caldicellulosiruptor bescii*. The enzyme is the gene product of Cb1946WT, where Cb stands for *Caldicellulosiruptor bescii*. The Cb1946WT protein is 1271 amino acids long and has a molecular mass of 139.8 kDa (His-tag+Cb1946 protein). The Cb1946WT has a Glycoside Hydrolase (GH) family 5 catalytic domain at the N-terminal region and Glycoside Hydrolase (GH) family 44 catalytic domain at the C-terminal region and 2 carbohydrate binding modules are positioned between the two catalytic domains (FIG. 42). For the truncated mutants, Cb1946TM1 (653 amino acids, 71.3 kDa) has N-terminal GH5 catalytic domain with 2 carbohydrate binding modules, whereas Cb1946TM2 (1015 amino acids, 111.0 kDa) has C-terminal GH44 catalytic domains with 2 carbohydrate binding modules as shown in FIG. 42.

Cloning of Cb1946WT

The wild type gene and its two truncated mutants (FIG. 42) were amplified from *Caldicellulosiruptor bescii* DSM 6725T genomic DNA by PCR using PrimeSTAR DNA Polymerase (TAKARA). The nucleotide sequences encoding Cb1946WT, Cb1946TM1, and Cb1946TM2 were amplified using the following primer set and procedures:

```
Cb1946WT Forward:
                                       (SEQ ID NO: 82)
5'-GAC GAC GAC AAG ATG GCT ACA TCT AAT GAT
GGA GTA GTG AAG -3'

Cb1946WT Reverse:
                                       (SEQ ID NO: 83)
5'-GAG GAG AAG CCC GGT TAA TTT AGT TTG TAC
TGA GGT TGA ATA TAA AAC GAT ATG G -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |

-continued

| PCR reaction | |
|---|---|
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 5 min | |
| Elongation | 72° C. | 7 min | 1 cycle |
| Last | 4° C. | ∞ | |

Cloning of Cb1946TM1

```
Cb1946TM1 Forward:
                                       (SEQ ID NO: 82)
5'-GAC GAC GAC AAG ATG GCT ACA TCT AAT GAT
GGA GTA GTG AAG -3'

Cb1946TM1 Reverse:
                                       (SEQ ID NO: 84)
5'-GAG GAG AAG CCC GGT TAG TTA AAC CTT ATC
TGT ATC TCC CCT GTG TC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

Cloning of Cb1946TM2

```
Cb1946TM2 Forward:
                                       (SEQ ID NO: 85)
5'-GAC GAC GAC AAG ATG GTA GGG TAC TTG GAC
ATG GTA AAC AAT TGG GA -3'

Cb1946TM2 Reverse:
                                       (SEQ ID NO: 83)
5'-GAG GAG AAG CCC GGT TAA TTT AGT TTG TAC
TGA GGT TGA ATA TAA AAC GAT ATG G -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |
| 5 × PrimeSTAR Buffer | 10 |
| $dH_2O$ | 35.6 |
| Total | 50 μL |

To amplify the coding sequence from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 4 min | |
| Elongation | 72° C. | 7 min | 1 cycle |
| Last | 4° C. | ∞ | |

After the PCR described above, the amplification of Cb1946 gene was confirmed by 1% agarose gel electrophoresis. The DNA corresponding to the expected band on the gel was cut out and applied to a Qiagen Gel Extraction kit to extract the DNA out of the gel.

A Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was inactivated by incubation at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for Cb1946-pET-46 Ek/LIC was introduced into *E. coli* JM109 by electroporation, and the cells were plated on LB-ampicillin. After overnight incubation at 37° C., four colonies were selected and used to inoculate 6 mL cultures of LB-ampicillin. The cultures were grown at 37° C. with vigorous aeration for 16 hours, and minipreps (QIAGEN) were made from the cell cultures. The plasmids were then electrophoresed on a 1% agarose gel to confirm the size of the plasmid DNA. After confirmation of the insert in the plasmid, the gene or coding sequences were sequenced to confirm their identity and integrity.

For gene expression, one of the plasmids was transformed into *E. coli* BL21 codon plus DE3 RIL by the heat shock method and plated on LB plates supplemented with chloramphenicol (50 μg/ml) and ampicillin (100 μg/ml) and incubated at 37° C. overnight. Five colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.1 mM final concentration, and the culturing continued at 16° C. overnight.

Gene and Protein Sequences of Cb1946WT, Cb1946TM1, and Cb1946TM2

Cb1946 Wild-Type Amino Acid Sequence

The wild-type Cb1946 amino acid sequence is disclosed in SEQ ID NO: 86. The signal peptide of Cb1946, corresponding to amino acid numbers 1-38 of SEQ ID NO: 86 was removed during all PCR amplifications. Thus, the expressed wild-type Cb1946 protein did not contain amino acid numbers 1-38 of SEQ ID NO: 86. The amino acid sequence of the wild-type Cb1946 protein without the signal peptide is disclosed in SEQ ID NO: 87.

The procedure of cloning the gene for wild-type Cb1946 (without the signal peptide) into the plasmid pET-46 Ek/LIC led to fusion of the gene to a short nucleotide sequence encoding a peptide that contains six histidines. The wild-type Cb1946 amino acid sequence (without the signal peptide) with the short peptide is disclosed in SEQ ID NO: 91. The amino acids of the short peptide are amino acids 1-14 of SEQ ID NO: 91.

Cb1946 Wild-Type Nucleotide Sequence

The wild-type Cb1946 nucleotide sequence is disclosed in SEQ ID NO: 88. The signal peptide of Cb1946, corresponding to nucleotide numbers 1-114 of SEQ ID NO: 88 was removed during all PCR amplifications. Thus, the nucleotide sequence used to express wild-type Cb1946 protein did not contain nucleotide numbers 1-114 of SEQ ID NO: 88. The nucleotide sequence encoding the wild-type Cb1946 protein without the signal peptide is disclosed in SEQ ID NO: 89.

The wild-type Cb1946 nucleotide sequence (without the signal peptide) with the coding sequence for the short peptide from the plasmid pET-46 Ek/LIC is disclosed in SEQ ID NO: 90. The nucleotides coding for the short peptide nucleotides are nucleotides 1-42 of SEQ ID NO: 90.

Cb1946TM1 Amino Acid Sequence

The Cb1946TM1 amino acid sequence is disclosed in SEQ ID NO: 117. The procedure of cloning the gene for Cb into the plasmid pET-46 Ek/LIC led to fusion of the gene to a short nucleotide sequence encoding a peptide that contains six histidines. The Cb1946TM1 amino acid sequence with the short peptide is disclosed in SEQ ID NO: 93. The amino acids of the short peptide are amino acids 1-14 of SEQ ID NO: 93.

Cb1946TM1 Nucleotide Sequence

The Cb1946TM1 nucleotide sequence is disclosed in SEQ ID NO: 118. The Cb1946TM1 nucleotide sequence with the coding sequence for the short peptide from the plasmid pET-46 Ek/LIC is disclosed in SEQ ID NO: 92. The nucleotides coding for the short peptide nucleotides are nucleotides 1-42 of SEQ ID NO: 92.

Cb1946TM2 Amino Acid Sequence

The Cb1946TM2 amino acid sequence is disclosed in SEQ ID NO: 113. The procedure of cloning the gene for Cb1946TM2 into the plasmid pET-46 Ek/LIC led to fusion of the gene to a short nucleotide sequence encoding a peptide that contains six histidines. The Cb1946TM2 amino acid sequence with the short peptide is disclosed in SEQ ID NO: 95. The amino acids of the short peptide are amino acids 1-14 of SEQ ID NO: 95.

Cb1946TM2 Nucleotide Sequence

The Cb1946TM2 nucleotide sequence is disclosed in SEQ ID NO: 112. The Cb1946TM2 nucleotide sequence with the coding sequence for the short peptide from the plasmid pET-46 Ek/LIC is disclosed in SEQ ID NO: 94. The nucleotides coding for the short peptide nucleotides are nucleotides 1-42 of SEQ ID NO: 94.

Purification of Cb1946WT, Cb1946TM1, and Cb1946TM2 Proteins

The Cb1946WT and its truncated mutants Cb1946TM1 and Cb1946TM2 were expressed in *E. coli* BL-21 Codon-Plus (DE3) RIL competent cells by heat shock. The recombinant cells were then grown overnight in LB agars supplemented with ampicillin (100 μg/mL) and chloramphenicol (50 μg/ml) at 37° C. After 8 h, the starter cultures were diluted into fresh LB supplemented with ampicillin (100 μg/mL) and chloramphenicol (50 μg/ml) at 37° C. with aeration until the absorbance at 600 nm reached 0.5. Gene expression was then induced by addition of IPTG at a final concentration of 0.1 mM and the temperature for culturing was lowered to 16° C. After 16 hours, the cells were centrifuged to collect the cell pellet. The pellet was then suspended in a lysis buffer (25 mM Tris-HCL pH 7.8, 750 mM of NaCl, 5% glycerol, 20 mM imidazole, 1.25% Tween-20). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged target proteins) was then eluted from the resin with an elution buffer (50 mM Tris-HCL, pH7.5, 250 mM imidazole). The eluted fractions was then heat-treated at 65° C. for 30 minutes and then centrifuged to remove the precipitated proteins. The proteins were then purified by gel filtration chromatography (HiLoad 16/20 Superdex 200, GE Healthcare) with a Tris-HCl elution buffer (50 mM Tris-HCl, 150 mM NaCl, pH 7.5). Aliquots of eluted fractions were analyzed by sodium dodecyl sulfate-polyacrylamide gel electrophoresis (SDS-PAGE) and proteins bands were visualized by staining with Coomassie brilliant blue G-250 (FIG. 43).

Enzyme Activity

FIG. 44 shows the zymogram of Cb1946WT, Cb1946TM1, and Cb1946TM2 on carboxylmethyl cellulose (CMC) agar plate. The agar plate was prepared with CMC substrate (final 0.25%, w/v). After spotting 1 μg of each protein on agar-CMC plates, the plate was incubated at 37° C. overnight and then the gel was visualized by staining with 0.1% Congo red and destaining with 1M NaCl. As shown in FIG. 44, Cb1946WT and Cb1946TM2 showed significant halos on the agar plate indicating cellulase activity, but not Cb1953TM1 proteins.

FIG. 45 shows the enzymatic activity of Cb1946WT, Cb1946TM1, Cb1946TM2 on phosphoric acid swollen cellulose (PASC). Each enzyme (final 0.5 μM) was reacted with phosphoric acid swollen cellulose (PASC) at 1% final concentration in 50 mM citrate-150 mM NaCl, pH 6.0 at 75° C. for 16 hours. The reactions were resolved by thin layer chromatography (TLC). The mobile phase consisted of n-butanol:acetic acid:H2O, 10:5:1 (vol/vol/vol) and 10 cm×20 cm plates were used. For more quantitative analysis of the products of hydrolysis, the samples were analyzed by high performance anion-exchange chromatography (HPAEC) (FIG. 46). For HPAEC analyses, 100 μL of each diluted sample was injected into a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.). For the TLC and HPLC analysis, glucose and five different cellooligosaccharides were used: cellobiose, cellotriose, cellotetraose, cellopentaose, and cellohexaose as standards. Based on the results of TLC and HPLC, Cb1953WT and Cb1953TM2 showed significant release of products such as glucose, cellobiose, cellotriose, and cellotetraose from PASC substrate, indicating that Cb1946WT and Cb1953TM2 have cellulase activities, but not Cb1953TM1.

Example 13: Endocellulase Cb629

An endocellulase, Cb629, was identified in *Caldicellulosiruptor bescii*. The enzyme Cb629TM1 is the truncational mutant of the gene product of cb629, where Cb stands for *Caldicellulosiruptor bescii*. The endocellulase initially cleaves glucose, cellobiose and cellotriose from cellulose. The Cb629TM1 protein is 562 amino acids long and has a molecular weight of 63.7 kDa (His-tag+Cb629TM1 protein). The protein has a Glycoside Hydrolase (GH) family 5 catalytic domain and a Carbohydrate Binding Module (CBM) family 17_28 domain (FIG. 47). In addition there is a N-terminal signal peptide (SP) for secretion and three surface layer homology (SLH) modules likely used in anchoring the enzyme to the cell surface. Since the SP and SLH are non-catalytic, they were cleaved from the polypeptide through the PCR amplification described below and the gene product was named Cb629TM1.

Cloning of Cb629TM1

The gene for Cb629TM1 was amplified from *Caldicellulosiruptor bescii* DSM 6725T genomic DNA by PCR using PrimeSTAR DNA Polymerase (TAKARA). The Cb629TM1 gene was amplified using the following primer set:

```
Cb629TM1Forward:
                                    (SEQ ID NO: 96)
5'- GAC GAC GAC AAG ATG CAG AGC ATA CTG TAT
GAA AAG G -3'

Cb629TM1Reverse:
                                    (SEQ ID NO: 97)
5'- GAG GAG AAG CCC GGT TAC TCA AAA AGG ATA
TTG GTA AAT C -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 50 μM Fw Primer | 1 |
| 50 μM Rv Primer | 1 |
| 10 mM dNTP Mixture | 1 |

-continued

| PCR reaction | |
|---|---|
| 5 × PrimeSTAR Buffer | 10 |
| $dH_2O$ | 35.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 2 min | |
| Elongation | 72° C. | 7 min | 1 cycle |
| Last | 4° C. | ∞ | |

After the PCR amplification described above, the amplification of Cb629TM1 was confirmed by 1% agarose gel electrophoresis. The DNA corresponding to the expected band on the gel was cut out and applied to a Qiagen Gel Extraction kit to extract the DNA out of the gel.

A Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, inactivate the enzyme by incubating at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for Cb629TM1-pET-46 Ek/LIC were introduced into *E. coli* NovaBlue competent cells by chemical transformation method, and the cells were plated on LB-ampicillin. After overnight incubation at 37° C., four colonies were selected and each was used to inoculate 6 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene had been inserted into the plasmid, the genes were sequenced to confirm the integrity of the coding sequence.

For gene expression, one of the plasmids was transformed into *E. coli* BL21 codon plus DE3 RIL by the heat shock method and plated on LB plates supplemented with chloramphenicol (50 μg/ml) and ampicillin (100 μg/ml) and incubated at 37° C. overnight. Five to six colonies were inoculated into 10 ml of LB broth supplemented with the two antibiotics at the same concentration and cultured for 6 hours. Ten mL of the culture was added to 1000 mL of LB broth supplemented with the two antibiotics at the same concentration and cultured at 37° C. until the absorbance at 600 nm reached ~0.3. The inducer, IPTG, was then added at 0.1 mM final concentration, and the culturing continued at 16° C. overnight.

Protein Purification

Cultures were centrifuged to collect the cell pellet. The pellet was then suspended in a lysis buffer (50 mM Tris-HCL pH 7.5, 300 mM of NaCl). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged Cb629TM1) was then eluted from the resin with an elution buffer (50 mM Tris-HCL, pH7.5, 250 mM imidazole).

The design of the PCR primers ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

Gene and Protein Sequences of Cb629WT and Cb629TM1

Cb629 Wild-Type Amino Acid Sequence

The wild-type Cb629 endocellulase (EC 3.2.1.4) amino acid sequence is disclosed in SEQ ID NO: 98. The signal peptide of Cb629 corresponds to amino acid numbers 1-29 of SEQ ID NO: 98. The amino acid sequence of the wild-type Cb629 protein without the signal peptide is disclosed in SEQ ID NO: 119.

Cb629 Wild-Type Nucleotide Sequence

The wild-type Cb629 nucleotide sequence is disclosed in SEQ ID NO: 99. The signal peptide of Cb629 corresponds to nucleotide numbers 1-87 of SEQ ID NO: 99. The nucleotide sequence encoding the wild-type Cb629 protein without the signal peptide is disclosed in SEQ ID NO: 120.

Cb629TM1 Amino Acid Sequence

The Cb629TM1 endocellulase (EC 3.2.1.4) amino acid sequence is disclosed in SEQ ID NO: 100. The procedure of cloning the gene for Cb629TM1 into the plasmid pET-46 Ek/LIC led to fusion of the gene to a short nucleotide sequence encoding a peptide that contains six histidines. The Cb629TM1 amino acid sequence with the short peptide is disclosed in SEQ ID NO: 103. The amino acids of the short peptide are amino acids 1-14 of SEQ ID NO: 103.

Cb629TM1 Nucleotide Sequence

The Cb629TM1 nucleotide sequence is disclosed in SEQ ID NO: 101. The Cb629TM1 nucleotide sequence with the coding sequence for the short peptide from the plasmid pET-46 Ek/LIC is disclosed in SEQ ID NO: 102. The nucleotides coding for the short peptide nucleotides are nucleotides 1-42 of SEQ ID NO: 102.

The Cb629TM1 coding sequence was expressed in *E. coli* cells, and the protein was purified in one step, i.e. the talon resin purification step making use of the 6-histidines encoded by the plasmid. FIG. 48 shows an SDS-PAGE of purified Cb629TM1.

Enzyme Activity

FIG. 49 shows the enzymatic activity of Cb629TM1 on substrates with products determined through a reducing sugar assay. Three different cellulose substrates were tested: Avicel, sodium carboxymethyl cellulose (CMC-Na) and phosphoric acid swollen cellulose (PASC). Incubation of enzymes with the substrates led to release of products that were quantified as a concentration of glucose equivalents. Hydrolysis of PASC was higher than hydrolysis of the other substrates.

The concentration of glucose equivalents was determined following enzymatic hydrolysis of Avicel, CMC-Na and PASC, according to the methods of Lever, M. (supra). 1.5 mL microcentrifuge tubes were "zeroed" in an analytical balance. Next, 2±0.1 mg Avicel were added to each tube, and the mass measured and recorded. The volumes that should be added to each tube were calculated based on the mass. For CMC-Na and PASC, a stock substrate solution of CMC-Na (2%) and PASC (6.11 mg/ml) were used. Sodium citrate reaction buffer and enzymes were added to each tube beginning with the reaction buffer. The tubes were incubated with constant mixing in a Thermomixer R (Eppendorf) at 75° C. for 16 h. The tubes were centrifuged at 10,000 rpm for 5 min at 4° C. 50 μL of sample supernatant was transferred to a clean 1.5 mL centrifuge tube for the pHBAH assay. 1 mL of a stock solution of glucose was made at a concentration of 100 mM in sodium citrate buffer, and then serial dilutions were made in sodium citrate buffer to the following concentrations (20 mM, 10 mM and 5 mM). 50 mg of pHBAH was dissolved in 50 mL of ice-cold citrate/NaOH solution for a final concentration of 0.1% (w/v), and the solution was kept on ice. 150 μL of pHBAH solution was added to 50 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The coefficient of determination ($R^2$) value was between 0.98 and 1.0. The equation from the standard curve was used to calculate the concentrations of reducing ends in the samples based on absorbance data.

FIG. 50 shows the enzymatic activity of Cb629TM1 on substrates using HPLC analysis. Three different cellulosic substrates were tested: Avicel, CMC-Na and PASC. In each case, in the presence of Cb629TM1, glucose and cellobiose were released. In the absence of Cb629TM1, neither glucose nor cellobiose was observed from all the substrates. The results showed that this enzyme releases glucose and cellobiose as end products from cellulosic substrates (Avicel, CMC-Na and PASC).

FIG. 51 shows that this enzyme is also able to release mostly disaccharides (cellobiose) and glucose from cello-oligosaccharide. The enzyme does not cleave hydrolyze cellobiose (G2 in the figure).

FIG. 52 shows the thermostability of Cb629TM1. Cb629TM1 has 109%, 99%, 96%, 83% and 34% activity after incubation at 60° C., 65° C., 70° C., 75° C. and 80° C. for 24 h, respectively. 500 nM Cb629TM1 was kept at different temperatures (60° C., 65° C., 70° C., 75° C. and 80° C.). The samples were taken out at different time points (0 h, 0.5 h, 1 h, 2 h, 4 h, 7 h, 11 h and 24 h) and immediately used for enzyme activity measurement. The enzyme activity was measured at pH 5.5 and at 70° C. on a thermomixer. 2.5 mg/ml final concentration of PASC was used for measurement, and 8.31 μl of the protein sample was added to the substrate and mixed by pipetting up and down for several times. The total volume was 100 μl. The reducing ends corresponding to glucose equivalents were measured according to the methods of Lever, M. (supra). The velocity of reaction in 10 minutes was calculated. The velocity of reaction for time 0 was set as 100; then the remaining activities (percentage) for time 0.5 h, 1 h, 2 h, 4 h, 7 h, 11 h and 24 h were calculated by dividing the velocities of reaction for time 0.5 h, 1 h, 2 h, 4 h, 7 h, 11 h and 24 h by the velocity of reaction at time 0, then multiplied by 100, respectively.

Example 14: β-Glucosidase Cb486

A putative β-glucosidase Cb486, was identified in *Caldicellulosiruptor bescii*. The enzyme is the gene product of Cb486, where Cb stands for *Caldicellulosiruptor bescii*. β-glucosidases catalyze the hydrolysis of cellobiose (a disaccharide of glucose) into two units of glucose. The Cb486 protein is 466 amino acids long and has a predicted molecular weight of 54.9 kDa (His-tag+Cb486 protein). The protein has a Glycoside Hydrolase (GH) family 1 catalytic domain (FIG. 53A).

Cloning of Cb486

The gene for Cb486 was amplified from *Caldicellulosiruptor bescii* DSM 6725T genomic DNA by PCR using iProof™ High-Fidelity DNA Polymerase (BIO-RAD). The Cb486 gene was amplified using the following primer set:

```
Cb486Forward:
                                        (SEQ ID NO: 104)
5'-GAC GAC GAC AAG ATG AGT TTA CCA AAA GGA TTT
CTG TGG GGT GC -3'

Cb1172Reverse:
                                        (SEQ ID NO: 105)
5'-GAG GAG AAG CCC GGT TAT GAG TTT TCC TTT ATA
TAC TGC TG -3'
```

The polymerase chain reaction mixture contained the following:

| PCR reaction | |
|---|---|
| 2 U/μL iProoF ™ High-Fidelity DNA Polymerase | 0.5 |
| 17 ng/μL *Caldicellulosiruptor bescii* genomic DNA | 1 |
| 50 μM Fw Primer | 0.5 |
| 50 μM Rv Primer | 0.5 |
| 10 mM dNTP Mixture | 1 |
| 5 × iProof HF Buffer | 10 |
| $dH_2O$ | 36.5 |
| Total | 50 μL |

To amplify the gene from the genomic DNA, the following PCR cycling was used:

| PCR protocol | | | |
|---|---|---|---|
| Denaturing | 98° C. | 30 sec | 1 cycle |
| Denaturing | 98° C. | 10 sec | 35 cycles |
| Annealing | 62° C. | 30 sec | |
| Elongation | 72° C. | 2 min | |
| Elongation | 72° C. | 10 min | 1 cycle |
| Last | 4° C. | ∞ | |

After the PCR described above, the amplification of the gene for Cb486 was confirmed by 1% agarose gel electrophoresis. The DNA corresponding to the expected band on the gel was cut out and applied to a Qiagen Gel Extraction kit to extract the DNA out of the gel.

A Novagen pET-46 Ek/LIC kit was used to treat the purified DNA and ligate it into the pET-46 Ek/LIC vector. The treatment of the purified DNA was as follows:

| Reaction | Unit (μl) | Incubation | |
|---|---|---|---|
| 0.1 pmol purified PCR product | X | | |
| 10X T4 DNA Polymerase buffer | 1 | | |
| 25 mM dATP | 1 | | |
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, the enzyme was inactivated by incubation at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for Cb486-pET-46 Ek/LIC was introduced into *E. coli* JM109 by electroporation, and the cells were plated on LB-ampicillin. After overnight incubation at 37° C., four colonies were selected and each was used to inoculate 6 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene had been inserted into the plasmid, the inserts were sequenced to confirm their identity and integrity of the sequence.

For gene expression, one of the plasmids was transformed into *E. coli* BL21 codon plus DE3 RIL by the heat shock method and plated on LB plates supplemented with chloramphenicol (100 μg/ml) and ampicillin (50 μg/ml) and incubated at 37° C. overnight. Five to six colonies were inoculated into 3 ml of LB broth supplemented with the two antibiotics at the same concentration and cultured for 4 hours. One mL of the culture was added to 500 mL of LB broth supplemented with the two antibiotics at the same concentration and cultured at 37° C. until the absorbance at 600 nm reached ~0.25. The inducer, IPTG, was then added at 0.1 mM final concentration, and the culturing continued at 16° C. overnight.

Protein Purification

Cultures were centrifuged to collect the cell pellet. The pellet was then suspended in a lysis buffer (25 mM Tris-HCL pH 7.8, 750 mM of NaCl, 5% glycerol, 20 mM imidazole, 1.25% Tween-20). The proteins in the cells were released through a French pressure cell. After centrifugation to pellet the cell debris, the supernatant was applied to a cobalt-charged resin (TALON, Clontech) and washed three times to remove the unbound proteins. The bound protein (6-Histidine-tagged Cb486) was then eluted from the resin with an elution buffer (50 mM Tris-HCL, pH7.5, 250 mM imidazole).

The gene product of Cb486 was expressed in its full-length form. The design of the PCR primers ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

Gene and Protein Sequences of Cb486WT

Cb486 Wild-Type Amino Acid Sequence

The wild-type Cb486 β-glucosidase (EC 3.2.1.21) amino acid sequence is disclosed in SEQ ID NO: 106. The procedure of cloning the gene for wild-type Cb486 into the plasmid pET-46 Ek/LIC led to fusion of the gene to a short nucleotide sequence encoding a peptide that contains six histidines. The wild-type Cb486 amino acid sequence with the short peptide is disclosed in SEQ ID NO: 109. The amino acids of the short peptide are amino acids 1-14 of SEQ ID NO: 109.

Cb486 Wild-Type Nucleotide Sequence

The wild-type Cb486 nucleotide sequence is disclosed in SEQ ID NO: 107. The wild-type Cb486 nucleotide sequence with the coding sequence for the short peptide from the plasmid pET-46 Ek/LIC is disclosed in SEQ ID NO: 108. The nucleotides coding for the short peptide nucleotides are nucleotides 1-42 of SEQ ID NO: 108.

The Cb486 gene was expressed in *E. coli* cells, and the protein was purified in one step, using the talon resin purification step making use of the 6-histidines encoded by the plasmid. FIG. 53B shows an SDS-PAGE of purified Cb486.

Enzyme Activity

FIG. 54 shows the enzymatic activity of Cb486 on xylo-oligosaccharides ($X_2$-$X_6$) through Thin Layer Chromatography (TLC) analysis. The following xylo-oligosaccharides ($X_2$-$X_6$) were tested: xylobiose, xylotriose, xylotetraose, xylopentaose and xylohexaose. This was done by an overnight hydrolysis of the xylo-oligosaccharides followed by resolving of the products with TLC. In each case, in the presence of Cb486, xylose and xylobiose were released. In the absence of Cb486, only minor amount of xylose was observed for xylobiose; no products of hydrolysis were released for other xylo-oligosaccharides. The results showed that this enzyme releases xylose and xylobiose from xylo-oligosaccharides (xylobiose, xylotriose, xylotetraose, xylopentaose and xylohexaose).

FIG. 55 shows that this enzyme is also capable of cleaving cello-oligosaccharides from cellobiose (2 glucose units joined by beta 1,4-linkage) to cellohexaose (six glucose units linked together by beta 1,4-linkages) to glucose. Thus this enzyme when coupled with an endoglucanase that release short chains of glucose should be able to convert the short chains to the monosaccharides glucose. The multi-functional activity (cleavage of different linkages) should make this enzyme an important enzyme in enzyme mixes used in hydrolyzing complex polysaccharides.

FIGS. 56A and 56B show the pH and temperature profiles, respectively of the activity of Cb486.

Example 15: Cellulase Mixture from *Caldicellulosiruptor bescii* for the Hydrolysis of *Miscanthus*

Based on the analyses above, a cellulase mixture containing Cb629TM1, Cb486, Cb1946TM2, Cb1952TM1, Cb1953TM2, and Cb1954TM3 was reconstituted to represent *Caldicellulosiruptor bescii* cellulases (FIG. 57). A previously reconstituted hemicellulase of *Caldicellulosiruptor bescii* (FIG. 58) was also prepared to test synergistic effects with the cellulase mixture. All enzyme mixtures (each 0.5 μM) were reacted with 2%, 5%, and 8% pretreated (autoclaved *Miscanthus* & 1% NaOH treated+microwaved *Miscanthus*) samples in 50 mM citrate-150 mM NaCl buffer (pH 6.5) at 75° C. overnight with shaking.

The reactions were resolved by thin layer chromatography (TLC). The mobile phase consisted of n-butanol:acetic acid: $H_2O$, 10:5:1 (vol/vol/vol), and 10 cm×20 cm plates were used. (FIGS. 59, 61, 63, and 65).

For further analysis of the products of hydrolysis, the 8% substrate reaction samples were analyzed by high performance anion-exchange chromatography (HPAEC) (FIGS. 60, 62, 64, and 66; i.e. FIG. 60 is HPAEC data of samples from FIG. 59, FIG. 62 is HPAEC data of samples from FIG. 61, etc.). For HPAEC analyses, 100 μL of each diluted sample was injected onto a System Gold HPLC instrument from Beckman Coulter (Fullerton, Calif.) equipped with CarboPac™ PA1 guard (4×50 mm) and analytical (4×250 mm) columns from Dionex Corporation (Sunnyvale, Calif.) and a Coulochem III electrochemical detector from ESA Biosciences (Chelmsford, Mass.).

For the TLC (FIGS. 59, 61, 63, and 65) and HPLC (FIGS. 60, 62, 64, and 66) analysis, glucose (C1) and five different cellooligosaccharides were used: cellobiose (C2), cellotriose (C3), cellotetraose (C4), cellopentaose (C5), and cellohexaose (C6) as standards. For the separation of xylose and glucose, Aminex HPX-87H column (300×7.8 mm, BioRad) was used with LC-20AT HPLC (SHIMADZU) with 5 mM sulfuric acid as mobile phase and 0.6 mL/mL flow rate at 65° C.

Based on TLC and HPLC data in FIGS. 59-62, in the presence of both cellulases and hemicellulases, the cellulase and hemicellulase mixtures released more glucose and xylose synergistically on pretreated *Miscanthus* samples than the amount of glucose released by the same cellulase mixture alone or the amount of xylose released by the same hemicellulase mixture alone. For example, as shown in FIG. 60, more glucose was released from the microwave pretreated *Miscanthus* by the cellulase mixture while in the presence of the hemicellulase mixture (lane 4, C1 peak; ~11 mM) than when the cellulase mixture acted on *Miscanthus* alone (lane 2, C1 peak; ~7 mM). Also, as shown in FIG. 60, more xylose was released from the pretreated *Miscanthus* by the hemicellulase mixture while in the presence of the cellulase mixture (lane 4, X1 peak; ~6 mM) than when the hemicellulase mixture acted on *Miscanthus* alone (lane 2, X1 peak; ~3 mM). As shown in FIGS. 61 and 62, synergistic effects between the cellulase and hemicellulase mixtures were also obtained with the autoclave pretreated *Miscanthus*. Thus, the results provided herein show the surprising result that an enzyme cocktail containing a cellulase mixture disclosed herein and a hemicellulase mixture disclosed herein shows synergistic activity between the cellulase and hemicellulase mixtures.

The results in FIGS. 59-62 also show that more products were released from the microwave pretreated *Miscanthus* (FIGS. 59 and 60) than the autoclave pretreated *Miscanthus* samples (FIGS. 61 and 62).

In FIGS. 63-66, the enzyme mixture without Cb486 (β-glucosidase) was tested on both pretreated samples. The results show that the enzyme mixtures released mainly cellobiose in the mix without β-glucosidase (Cb486). The results in lane 4 of FIG. 63 and FIG. 64 shows that the mixture of hemicellulase and cellulose without the beta-glucosidase will lead to xylose and mostly cellobiose from the microwaved sample. Similar data is obtained for the same experiment but with autoclaved *Miscanthus* as the substrate (FIGS. 65 and 66).

Example 16: Heat Shock Protein Cb1581

A small heat shock protein, Cb1581, was identified in *Caldicellulosiruptor bescii*. The protein is the gene product of Cb1581, where Cb stands for *Caldicellulosiruptor bescii*. The protein is 162 amino acids long and has a molecular weight of 19.68 kDa (His-tag+Cb1581 protein).

Cloning of Cb1581

The gene for Cb1581 was amplified from *Caldicellulosiruptor bescii* DSM 6725T genomic DNA by PCR using PrimeSTAR DNA Polymerase (TAKARA). The cb1581 gene was amplified using the following primer set:

```
Cb1581Forward: 5'-
                                          (SEQ ID NO: 144)
GACGACGACAAGATGCTCAGAGACATAGTTCCATTTGGC -3'

Cb1581Reverse: 5'-
                                          (SEQ ID NO: 145)
GAGGAGAAGCCCGGTTATTCTATATCAATTGTTCTTACATC -3'
```

The polymerase chain reaction mixture contained the following:

| PCR reaction | |
|---|---|
| 2.5 U/μL PrimeSTAR DNA Polymerase | 0.4 |
| 17 ng/μL *Caldicellulosiruptor bescii* genomic DNA | 1 |
| 20 μM Fw Primer | 1 |
| 20 μM Rv Primer | 1 |
| 2.5 mM dNTP Mixture | 4 |
| 5 × PrimeSTAR Buffer | 10 |
| $dH_2O$ | 32.6 |
| Total | 50 μL |

To amplify the gene from the genomic DNA, the following PCR cycling was used:

| PCR protocol | | | |
|---|---|---|---|
| Denaturing | 95° C. | 5 min | 1 cycle |
| Denaturing | 94° C. | 30 sec | 35 cycles |
| Annealing | 50° C. | 30 sec | |
| Elongation | 72° C. | 1 min | |
| Elongation | 72° C. | 7 min | 1 cycle |
| Last | 4° C. | ∞ | |

After the PCR reaction described above, the amplification of cb1581 gene was confirmed by 1% agarose gel electrophoresis. The DNA corresponding to the expected band on the gel was cut out and applied to a Qiagen Gel Extraction kit to extract the DNA out of the gel.

A Novagen pET-46 Ek/LIC kit was used to treat the purified DNA and ligate it into the pET-46 Ek/LIC vector. The treatment of the purified DNA was as follows:

| Reaction | Unit (μl) | Incubation |
|---|---|---|
| 0.1 pmol purified PCR product | X | |
| 10X T4 DNA Polymerase buffer | 1 | |
| 25 mM dATP | 1 | |

-continued

| Reaction | Unit (μl) | Incubation | |
|---|---|---|---|
| 100 mM DTT | 0.5 | | |
| Nuclease-free water | 7.3-X | | |
| 2.5 U/μl T4 DNA Polymerase | 0.2 | | |
| Total | 10 | 22° C. | 30 min |

After the reaction, inactivate the enzyme by incubating at 75° C. for 20 min.

The following protocol was used to anneal the insert into the pET-46 Ek/LIC vector.

| Reaction | Unit (μl) | Incubation | |
|---|---|---|---|
| pET-46 Ek/LIC vector | 0.5 | | |
| T4 DNA Polymerase treated EK/LIC insert | 1 | | |
| Total | 1.5 | 22° C. | 5 min |

Then add 0.5 μl 25 mM EDTA. Mix by stirring with pipet tip. Incubate at 22° C. for 5 min.

The ligation mixture for cb1581-pET-46 Ek/LIC were introduced into *E. coli* XL10-Gold by electroporation method, and the cells were plated on LB-ampicillin. After overnight incubation at 37° C., four colonies were selected and used to inoculate 6 mL cultures of LB-ampicillin. The cultures were grown at 37° C. with vigorous aeration for 16 hours, and minipreps (QIAGEN) were made of the cell cultures. The plasmids were then electrophoresed on a 1% agarose gel to check the size of the plasmid DNA. After confirmation that the gene had been inserted into the plasmid, the genes were sequenced to confirm their identity.

For gene expression, one of the plasmids was transformed into *E. coli* BL21-CodonPlus (DE3)-RIPL by the heat shock method and plated on LB plates supplemented with chloramphenicol (50 μg/ml) and ampicillin (100 μg/ml) and incubated at 37° C. overnight. Five to six colonies were inoculated into 10 ml of LB broth supplemented with the two antibiotics at the same concentration and cultured for 6 hours. Ten mL of the culture was added to 1000 mL of LB broth supplemented with the two antibiotics at the same concentration and cultured at 37° C. until the absorbance at 600 nm reached ~0.3. The inducer, IPTG, was then added at 0.1 mM final concentration, and the culturing continued at 16° C. overnight.

Protein Purification

Cultures were centrifuged to collect the cell pellet. The pellet was then suspended in a lysis buffer (50 mM Tris-HCl, 300 mM NaCl, pH 7.5). The proteins in the cells were released through a French pressure cell. After centrifugation at 10000 rpm for 30 minutes to pellet the cell debris, the supernatant was applied to a cobalt-charged resin (TALON, Clontech) and washed three times to remove the unbound proteins. The bound protein (6-Histidine-tagged Cb1581) was then eluted from the resin with an elution buffer (50 mM Tris-HCl, 300 mM NaCl, 250 mM imidazole, pH7.5).

The design of the PCR primers ensured that the protein was fused to 6-histidines encoded in the plasmid. The six histidines will bind to either a nickel-charged resin or a cobalt-charged resin. The bound protein can be displaced from the resin with a buffer containing imidazole. This method facilitates quick purification of the protein of interest.

Gene and Protein Sequences of Cb1581

Cb1581 Wild-Type Amino Acid Sequence

The wild-type Cb1581 amino acid sequence is disclosed in SEQ ID NO: 146. The procedure of cloning the gene for wild-type Cb1581 into the plasmid pET-46 Ek/LIC led to fusion of the gene to a short nucleotide sequence encoding a peptide that contains six histidines. The wild-type Cb486 amino acid sequence with the short peptide is disclosed in SEQ ID NO: 149. The amino acids of the short peptide are amino acids 1-14 of SEQ ID NO: 149.

Cb1581 Wild-Type Nucleotide Sequence

The wild-type Cb1581 nucleotide sequence is disclosed in SEQ ID NO: 147. The wild-type Cb1581 nucleotide sequence with the coding sequence for the short peptide from the plasmid pET-46 Ek/LIC is disclosed in SEQ ID NO: 148. The nucleotides coding for the short peptide nucleotides are nucleotides 1-42 of SEQ ID NO: 148.

The cb1581 gene was expressed in *E. coli* cells, and the protein was purified in one step, that is, a talon resin purification step making use of the 6-histidines encoded by the plasmid. FIG. 83 shows an SDS-PAGE of purified Cb1581.

Enhancing Enzymatic Hydrolysis of Microwave Pretreated *Miscanthus*

FIG. 84 shows the enhancing effect of Cb1581 on enzymatic hydrolysis of microwave pretreated *miscanthus* at 70° C. (FIG. 84A) or 80° C. (FIG. 84B). The hydrolysis was carried out at pH 6.0 using 0.5 μM each of the cellulase/hemicellulase enzyme mixture in a total volume of 500 μl with 10% *miscanthus* as the substrate. The enzymes in the mixture include Cb1946TM2, Cb1952TM1, Cb1953TM2, Cb1954TM3, Cb629TM1, Cb486, Cb193, Cb195, Cb2487, Cb1172, Cb909, and Cb162. Two mL microcentrifuge tubes were "zeroed" in an analytical balance. Next, 50±0.2 mg microwave pretreated *miscanthus* were added to each tube. The tubes were incubated with constant rotation in a Echo-Therm™RT11 Variable Speed Rotating Mixers (Torrey Pines Scientific) at 70° C. or 80° C. for 24 h.

The concentration of glucose equivalents was determined following enzymatic hydrolysis of microwave pretreated *miscanthus*, according to the methods of Lever, M. (A new reaction for colorimetric determination carbohydrates. Anal. Biochem. 1972: 47; 273-279). After the reaction, the tubes were centrifuged at 10,000 rpm for 5 min at 4° C. 45 μL of water and 5 μL of sample supernatant were transferred to a clean 1.5 mL centrifuge tube for the pHBAH assay. 1 mL of a stock solution of glucose was made at a concentration of 100 mM in sodium citrate buffer, and then serial dilutions were made in sodium citrate buffer to the following concentrations (20 mM, 10 mM and 5 mM). 50 mg of pHBAH was dissolved in 50 mL of ice-cold citrate/NaOH solution for a final concentration of 0.1% (w/v), and the solution was kept on ice. 150 μL of pHBAH solution was added to 50 μL of the sample and glucose standard solutions, and the tubes were incubated at 100° C. for 10 min. The tubes were incubated at room temperature for 5 min. The wavelength at 410 nm was measured for the standards and samples. The $A_{410nm}$ and glucose concentrations were plotted against each other, and linear regression was used to fit a line to the data. The correlation coefficient ($R^2$) value was between 0.98 and 1.0. The equation from the standard curve was used to calculate the concentrations of reducing ends in the samples based upon their absorbance. The releasing of sugars is enhanced with the increasing amount of Cb1581 in the reaction mixture at both 70° C. and 80° C.

REFERENCES

1. Ando, S., H. Ishida, Y. Kosugi, and K. Ishikawa. 2002. Hyperthermostable endoglucanase from *Pyrococcus horikoshii*. Appl Environ Microbiol 68:430-433.
2. Arai, T., et al. 2001. Sequence of celQ and properties of celQ, a component of the *Clostridium thermocellum* cellulosome. Appl Microbiol Biotechnol 57:660-666.
3. Bauer, M. W., et al. 1999. An endoglucanase, EglA, from the hyperthermophilic archaeon *Pyrococcus furiosus* hydrolyzes b-1,4 bonds in mixed-linkage (1→3),(1→4)-b-D-glucans and cellulose. J Bacteriol 181:284-290.
4. Blumer-Schuette, S. E., D. L. Lewis, and R. M. Kelly. 2010. Phylogenetic, microbiological, and glycoside hydrolase diversities within the extremely thermophilic, plant biomass-degrading genus *Caldicellulosiruptor*. Appl Environ Microbiol 76:8084-8092.
5. Bok, J. D., D. A. Yernool, and D. E. Eveleigh. 1998. Purification, characterization, and molecular analysis of thermostable cellulases CelA and CelB from *Thermotoga neapolitana*. Appl Environ Microbiol 64:4774-4781.
6. Bronnenmeier, K., and W. L. Staudenbauer. 1990. Cellulose hydrolysis by a highly thermostable endo-1,4-b-glucanase (Avicelase I) from *Clostridium stercorarlum*. Enzyme Microb Technol 12:431-436.
7. Chiriac, A. I., et al. 2010. Engineering a family 9 processive endoglucanase from *Paenibacillus barcinonensis* displaying a novel architecture. Appl Microbiol Biotechnol 86:1125-1134.
8. Dam, P., et al. 2011. Insights into plant biomass conversion from the genome of the anaerobic thermophilic bacterium *Caldicellulosiruptor bescii* DSM 6725. Nucleic Acids Res 39:3240-3254.
9. Dodd, D., et al. 2009. Biochemical analysis of a b-D-xylosidase and a bifunctional xylanase-ferulic acid esterase from a xylanolytic gene cluster in *Prevotella ruminicola* 23. J Bacteriol 191:3328-3338.
10. Gal, L., et al. 1997. CelG from *Clostridium cellulolyticum*: a multidomain endoglucanase acting efficiently on crystalline cellulose. J Bacteriol 179:6595-6601.
11. Gibbs, M. D., et al. 2000. Multidomain and multifunctional glycosyl hydrolases from the extreme thermophile *Caldicellulosiruptor* isolate Tok7B.1. Curr Microbiol 40:333-340.
12. Gilad, R., et al. 2003. CelI, a noncellulosomal family 9 enzyme from *Clostridium thermocellum*, is a processive endoglucanase that degrades crystalline cellulose. J Bacteriol 185:391-398.
13. Hoffman, G. G., O. Davulcu, S. Sona, and W. R. Ellington. 2008. Contributions to catalysis and potential interactions of the three catalytic domains in a contiguous trimeric creatine kinase. FEBS J 275:646-654.
14. Honda, Y., N. Shimaya, K. Ishisaki, M. Ebihara, and H. Taniguchi. 2011. Elucidation of exo-b-D-glucosaminidase activity of a family 9 glycoside hydrolase (PBPRA0520) from *Photobacterium profundum* SS9. Glycobiology 21:503-511.
15. Horn, S. J., et al. 2006. Costs and benefits of processivity in enzymatic degradation of recalcitrant polysaccharides. Proc Natl Acad Sci USA 103:18089-18094.
16. Irwin, D., et al. 1998. Roles of the catalytic domain and two cellulose binding domains of *Thermomonospora fusca* E4 in cellulose hydrolysis. J Bacteriol 180:1709-1714.
17. Irwin, D. C., M. Spezio, L. P. Walker, and D. B. Wilson. 1993. Activity studies of eight purified cellulases: Specificity, synergism, and binding domain effects. Biotechnol Bioeng 42:1002-1013.
18. Jauris, S., et al. 1990. Sequence analysis of the *Clostridium stercorarium* celZ gene encoding a thermoactive cellulase (Avicelase I): identification of catalytic and cellulose-binding domains. Mol Gen Genet 223:258-267.
19. Jindou, S., et al. 2006. Novel architecture of family-9 glycoside hydrolases identified in cellulosomal enzymes of *Acetivibrio cellulolyticus* and *Clostridium thermocellum*. FEMS Microbiol Lett 254:308-316.
20. Kataeva, I. A., et al. 2009. Genome sequence of the anaerobic, thermophilic, and cellulolytic bacterium "*Anaerocellum thermophilum*" DSM 6725. J Bacteriol 191:3760-3761.
21. Lever, M. 1972. A new reaction for colorimetric determination of carbohydrates. Anal Biochem 47:273-279.
22. Li, Y., D. C. Irwin, and D. B. Wilson. 2010. Increased crystalline cellulose activity via combinations of amino acid changes in the family 9 catalytic domain and family 3c cellulose binding module of *Thermobifida fusca* Cel9A. Appl Environ Microbiol 76:2582-2588.
23. Li, Y., D. C. Irwin, and D. B. Wilson. 2007. Processivity, substrate binding, and mechanism of cellulose hydrolysis by *Thermobifida fusca* Cel9A. Appl Environ Microbiol 73:3165-3172.
24. Liang, C., et al. 2011. Cloning and characterization of a thermostable and halo-tolerant endoglucanase from *Thermoanaerobacter tengcongensis* MB4. Appl Microbiol Biotechnol 89:315-326.
25. Lochner, A., et al. 2011. Use of label-free quantitative proteomics to distinguish the secreted cellulolytic systems of *Caldicellulosiruptor bescii* and *Caldicellulosiruptor obsidiansis*. Appl Environ Microbiol 77:4042-4054.
26. Mandelman, D., et al. 2003. X-Ray crystal structure of the multidomain endoglucanase Cel9G from *Clostridium cellulolyticum* complexed with natural and synthetic cello-oligosaccharides. J Bacteriol 185:4127-4135.
27. Meinke, A., et al. 1991. Unusual sequence organization in CenB, an inverting endoglucanase from *Cellulomonas fimi*. J Bacteriol 173:308-314.
28. Mejia-Castillo, T., M. E. Hidalgo-Lara, L. G. Brieba, and J. Ortega-Lopez. 2008. Purification, characterization and modular organization of a cellulose-binding protein, CBP105, a processive b-1,4-endoglucanase from *Cellulomonas flavigena*. Biotechnol Lett 30:681-687.
29. Moon, Y. H., M. Iakiviak, S. Bauer, R. I. Mackie, and I. K. Cann. 2011. Biochemical analyses of multiple endoxylanases from the rumen bacterium *Ruminococcus albus* 8 and their synergistic activities with accessory hemicellulose degrading enzymes. Appl Environ Microbiol doi: 10.1128/AEM.00353-11.
30. Park, J. K., L. X. Wang, H. V. Patel, and S. Roseman. 2002. Molecular cloning and characterization of a unique b-glucosidase from *Vibrio cholerae*. J Biol Chem 277: 29555-29560.
31. Parsiegla, G., A. Belaich, J. P. Belaich, and R. Haser. 2002. Crystal structure of the cellulase Cel9M enlightens structure/function relationships of the variable catalytic modules in glycoside hydrolases. Biochemistry 41:11134-11142.
32. Pastor, F. I., et al. 2001. Molecular cloning and characterization of a multidomain endoglucanase from *Paenibacillus* sp BP-23: evaluation of its performance in pulp refining. Appl Microbiol Biotechnol 55:61-68.

33. Qi, M., H. S. Jun, and C. W. Forsberg. 2008. Cel9D, an atypical 1,4-b-D-glucan glucohydrolase from *Fibrobacter succino* genes: characteristics, catalytic residues, and synergistic interactions with other cellulases. J Bacteriol 190:1976-1984.
34. Sakon, J., D. Irwin, D. B. Wilson, and P. A. Karplus. 1997. Structure and mechanism of endo/exocellulase E4 from *Thermomonospora fusca*. Nat Struct Biol 4:810-818.
35. Saul, D. J., et al. 1990. celB, a gene coding for a bifunctional cellulase from the extreme thermophile "*Caldocellum saccharolyticum*". Appl Environ Microbiol 56:3117-3124.
36. Schubot, F. D., et al. 2004. Structural basis for the exocellulase activity of the cellobiohydrolase CbhA from *Clostridium thermocellum*. Biochemistry 43:1163-1170.
37. Su, X., et al. 2010. Mutational insights into the roles of amino acid residues in ligand binding for two closely related family 16 carbohydrate binding modules. J Biol Chem 285:34665-34676.
38. Tamaru, Y., S. Karita, A. Ibrahim, H. Chan, and R. H. Doi. 2000. A large gene cluster for the *Clostridium cellulovorans* cellulosome. J Bacteriol 182:5906-5910.
39. Tolonen, A. C., A. C. Chilaka, and G. M. Church. 2009. Targeted gene inactivation in *Clostridium phytofermentans* shows that cellulose degradation requires the family 9 hydrolase Cphy3367. Mol Microbiol 74:1300-1313.
40. Uda, K., et al. 2008. Two-domain arginine kinase from the deep-sea clam *Calyptogena kaikoi*—evidence of two active domains. Comp Biochem Physiol B Biochem Mol Biol 151:176-182.
41. VanFossen, A. L., I. Ozdemir, S. L. Zelin, and R. M. Kelly. 2011. Glycoside hydrolase inventory drives plant polysaccharide deconstruction by the extremely thermophilic bacterium *Caldicellulosiruptor saccharolyticus*. Biotechnol Bioeng 108:1559-1569.
42. Vlasenko, E., M. Schulein, J. Cherry, and F. Xu. Substrate specificity of family 5, 6, 7, 9, 12, and 45 endoglucanases. Bioresour Technol 101:2405-2411.
43. Yang, S. J., et al. 2010. Classification of '*Anaerocellum thermophilum*' strain DSM 6725 as *Caldicellulosiruptor bescii* sp. nov. Int J Syst Evol Microbiol 60:2011-2015.
44. Yang, S. J., et al. 2009. Efficient degradation of lignocellulosic plant biomass, without pretreatment, by the thermophilic anaerobe "*Anaerocellum thermophilum*" DSM 6725. Appl Environ Microbiol 75:4762-4769.
45. Yeoman, C. J., et al. 2010. Thermostable enzymes as biocatalysts in the biofuel industry. Adv Appl Microbiol 70:1-55.
46. Yoshida, S., R. I. Mackie, and I. K. Cann. 2010. Biochemical and domain analyses of FSUAxe6B, a modular acetyl xylan esterase, identify a unique carbohydrate binding module in *Fibrobacter succinogenes* S85. J Bacteriol 192:483-493.
47. Zakariassen, H., et al. 2009. Aromatic residues in the catalytic center of chitinase A from *Serratia marcescens* affect processivity, enzyme activity, and biomass converting efficiency. J Biol Chem 284:10610-10617.
48. Zhang, X. Z., N. Sathitsuksanoh, and Y. H. Zhang. 2010. Glycoside hydrolase family 9 processive endoglucanase from *Clostridium phytofermentans*: heterologous expression, characterization, and synergy with family 48 cellobiohydrolase. Bioresour Technol 101:5534-5538.
49. Zverlov, V., S. Mahr, K. Riedel, and K. Bronnenmeier. 1998. Properties and gene structure of a bifunctional cellulolytic enzyme (CelA) from the extreme thermophile '*Anaerocellum thermophilum*' with separate glycosyl hydrolase family 9 and 48 catalytic domains. Microbiology 144 (Pt 2):457-465.
50. Zverlov, V. V., G. A. Velikodvorskaya, and W. H. Schwarz. 2003. Two new cellulosome components encoded downstream of cell in the genome of *Clostridium thermocellum*: the non-processive endoglucanase CelN and the possibly structural protein CseP. Microbiology 149:515-524.

What is claimed:

1. A method for producing a *Caldicellulosiruptor bescii* endoxylanase and a *Caldicellulosiruptor bescii* β-xylosidase comprising:

culturing a host cell comprising a nucleic acid encoding the *Caldicellulosiruptor bescii* endoxylanase of SEQ ID NO: 3, and a nucleic acid encoding the *Caldicellulosiruptor bescii* β-xylosidase of SEQ ID NO: 27 in a culture medium, under suitable conditions to produce the endoxylanase and the β-xylosidase, wherein the endoxylanase has a $K_m$ for xylan that ranges from about 1.3 mg/mL to about 13.9 mg/mL at a temperature of 85° C. and a pH of 6.0; a $K_{cat}$ for xylan that ranges from about 93 $s^{-1}$ to about 7865 $s^{-1}$ at a temperature of 85° C. and a pH of 6.0; and a $K_{cat}/K_m$ for xylan that ranges from about 33 ml/mg $s^{-1}$ to about 562 ml/mg $s^{-1}$ at a temperature of 85° C. and a pH of 6.0, wherein the β-xylosidase has an optimum temperature of about 90° C., a $K_m$ for xylo-oligosaccharides that is about 8.21 mM at a temperature of 90° C. and a pH of 6.0; a $K_{cat}$ for xylo-oligosaccharides that is about 619 $s^{-1}$ at a temperature of 90° C. and a pH of 6.0; and a $K_{cat}/K_m$ for xylo-oligosaccharides that is about 75 $mM^{-1}$ $s^{-1}$ at a temperature of 90° C. and a pH of 6.0, and wherein the host cell is an *E. coli* cell.

2. The method of claim 1, wherein the host cell further comprises one or more recombinant nucleic acids encoding one or more polypeptides selected from the group consisting of: *Caldicellulosiruptor bescii* endocellulase Cb629 and *Caldicellulosiruptor bescii* β-glucosidase Cb486 polypeptides.

3. The method of claim 2, wherein the *Caldicellulosiruptor bescii* endocellulase Cb629 polypeptide has the sequence of SEQ ID NO: 98 and wherein the *Caldicellulosiruptor bescii* β-glucosidase Cb486 polypeptide has the sequence of SEQ ID NO: 106.

4. The method of claim 2, the method further comprising:

a) culturing the host cell in culture media under conditions sufficient to support the expression of said recombinant nucleic acid(s); and b) collecting one or more cellulases from said media or said host cell.

5. The method of claim 1, wherein the host cell further comprises a recombinant nucleic acid encoding a *Caldicellulosiruptor bescii* heat shock protein Cb1581 polypeptide.

6. The method of claim 1, wherein the host cell further comprises one or more recombinant nucleic acids selected from the group consisting of:

a) a nucleic acid encoding the *Caldicellulosiruptor bescii* endoxylanase of SEQ ID NO: 7, b) a nucleic acid encoding the *Caldicellulosiruptor bescii* α-arabinofuranosidase of SEQ ID NO: 13, c) a nucleic acid encoding the *Caldicellulosiruptor bescii* α-glucuronidase of SEQ ID NO: 19, d) a nucleic acid encoding the *Caldicellulosiruptor bescii* acetyl xylan esterase of SEQ ID NO: 33, and e) a nucleic acid encoding the *Caldicellulosiruptor bescii* endoxylanase of SEQ ID NO: 37.

* * * * *

SEQUENCE LISTING

```
<160> NUMBER OF SEQ ID NOS: 167

<210> SEQ ID NO 1
<211> LENGTH: 33
<212> TYPE: DNA
<213> ORGANISM: Artificial Sequence
<220> FEATURE:
<223> OTHER INFORMATION: Synthesized Construct

<400> SEQUENCE: 1

gacgacgaca agatgaactt tgaaggaaga gac                                33


<210> SEQ ID NO 2
<211> LENGTH: 32
<212> TYPE: DNA
<213> ORGANISM: Artificial Sequence
<220> FEATURE:
<223> OTHER INFORMATION: Synthesized Construct

<400> SEQUENCE: 2

gaggagaagc ccggttattt tttagccttt ac                                 32


<210> SEQ ID NO 3
<211> LENGTH: 697
<212> TYPE: PRT
<213> ORGANISM: Caldicellulosiruptor bescii
```

<400> SEQUENCE: 3

Met Lys Lys Arg Lys Phe Lys Ile Leu Tyr Leu Phe Leu Ile Ile Val
1 5 10 15

Leu Ser Val Ser Phe Ile Ile Ser Ile Val Phe Pro Ser Phe Phe Lys
20 25 30

Ala Ala Gln Thr Thr Ser Thr Asn Ile Asn Phe Glu Gly Arg Asp Lys
35 40 45

Leu Thr Phe Phe Ala Tyr Gly Lys Ala Lys Ile Thr Ile Asp Gln Asn
50 55 60

Ile Ala Gln Glu Gly Lys Lys Ser Ile Lys Val Thr Asp Arg Lys Ser
65 70 75 80

Val Trp Asp Ser Phe Gly Ile Asp Val Lys Asp Val Leu Gln Arg Gly
85 90 95

Lys Thr Trp Val Val Ser Ala Tyr Val Lys His Lys Gly Lys Lys Pro
100 105 110

Ile Glu Phe Ser Ile Thr Ala Ile Tyr Asn Asp Gly Arg Gly Leu Lys
115 120 125

Tyr Leu Gln Leu Gly Glu Lys Ile Val Ile Pro Asn Lys Trp Asp Lys
130 135 140

Ile Val Ala Lys Trp Lys Pro Thr Leu Lys Asn Pro Met Asp Leu Ile
145 150 155 160

Ile Ala Ile His Pro Thr Val Asp Lys Thr Thr Ala Tyr Asn Val Asp
165 170 175

Asn Ile Gln Ile Met Thr Glu Glu Val Tyr Gln Ser Gln Ala Val Val
180 185 190

Phe Lys Asp Thr Phe Glu Ser Asn Leu Thr Asn Trp Gln Pro Arg Gly
195 200 205

Asp Thr Val Lys Leu Lys Ile Asp Asn Thr Lys Ser His Asn Gly Asn
210 215 220

Lys Ser Leu Tyr Val Ser Gly Arg Ser Ala Phe Trp His Gly Val Gln
225 230 235 240

Ile Pro Val Thr Lys Tyr Leu Val Ala Gly Lys Val Tyr Lys Phe Ser
245 250 255

Val Trp Leu Tyr His Gln Ser Ile Asp Lys Gln Gly Phe Gly Leu Thr
260 265 270

Ile Gln Arg Lys Met Ala Asn Asp Glu Gln Tyr Lys Tyr Asp Trp Ile
275 280 285

Thr Gly Ser Gln Ile Glu Gly Asp Gly Trp Val Glu Ile Ser Gly Asn
290 295 300

Tyr Tyr Val Pro Lys Asp Gly Lys Ile Glu Glu Leu Val Phe Cys Val
305 310 315 320

Ser Ser Trp Asn Pro Thr Leu Ala Phe Trp Val Asp Asp Val Thr Ile
325 330 335

Ser Asp Pro Phe Lys Leu Gln Gly Pro Asn Tyr Asn Leu Pro Ser Leu
340 345 350

Lys Glu Lys Tyr Lys Glu Asp Phe Lys Val Gly Val Ala Ile Gly Tyr
355 360 365

Gly Glu Leu Ile Ser Asp Ile Asp Thr Gln Phe Ile Lys Lys His Phe
370 375 380

Asn Ser Ile Thr Pro Gly Asn Glu Met Lys Pro Glu Ser Val Leu Lys
385 390 395 400

Gly Pro Asn Asn Tyr Asp Phe Thr Ile Ala Asp Ala Phe Val Asp Phe

-continued

```
                405                 410                 415

Ala Thr Lys Asn Lys Met Gly Ile Arg Gly His Thr Leu Val Trp His
            420                 425                 430

Asn Gln Thr Pro Asp Trp Phe Phe Lys Asp Glu Asn Gly Asn Phe Leu
        435                 440                 445

Lys Lys Asp Glu Leu Leu Lys Arg Leu Lys Asn His Ile Tyr Thr Val
    450                 455                 460

Val Ser Arg Tyr Lys Gly Lys Ile Tyr Ala Trp Asp Val Val Asn Glu
465                 470                 475                 480

Ala Ile Asp Glu Thr Gln Pro Asp Gly Tyr Arg Arg Ser Asn Trp Tyr
                485                 490                 495

Asn Ile Cys Gly Pro Glu Tyr Ile Glu Lys Ala Phe Ile Trp Ala His
            500                 505                 510

Glu Ala Asp Pro Gln Ala Lys Leu Phe Tyr Asn Asp Tyr Asn Thr Glu
        515                 520                 525

Ile Pro Gln Lys Arg Met Phe Ile Tyr Asn Met Ile Lys Asn Leu Lys
    530                 535                 540

Ala Lys Gly Val Pro Ile His Gly Ile Gly Leu Gln Cys His Ile Asn
545                 550                 555                 560

Ile Asp Asn Pro Ser Val Glu Asp Ile Glu Glu Thr Ile Lys Leu Phe
                565                 570                 575

Ser Thr Ile Pro Gly Leu Glu Ile Gln Ile Thr Glu Leu Asp Met Ser
            580                 585                 590

Phe Tyr Gln Trp Gly Ser Ser Val Tyr Tyr Ala Glu Pro Ser Arg Glu
        595                 600                 605

Met Leu Leu Lys Gln Ala Lys Lys Tyr Tyr Glu Leu Phe Asn Leu Phe
    610                 615                 620

Lys Lys Tyr Lys Asn Val Ile Lys Ser Val Thr Phe Trp Gly Leu Lys
625                 630                 635                 640

Asp Asp Asn Ser Trp Leu Arg Gly Val Phe Asn Lys Pro Asp Phe Pro
                645                 650                 655

Leu Leu Phe Asp Glu His Tyr Asp Gly Lys Pro Ala Phe Trp Ala Leu
            660                 665                 670

Ile Asp Tyr Ser Ile Leu Pro Gln Asn Ala Asn Leu Pro Thr Pro Pro
        675                 680                 685

Ala Ile Pro Lys Val Lys Ala Lys Lys
    690                 695


<210> SEQ ID NO 4
<211> LENGTH: 2094
<212> TYPE: DNA
<213> ORGANISM: Caldicellulosiruptor bescii

<400> SEQUENCE: 4

atgaaaaaaa ggaaattcaa aatattatat ttatttttaa ttatagtact ttctgtatca      60

tttattatat caatagtttt tccatcattt tttaaggcgg cacagacaac ctcaacaaac     120

ataaactttg aaggaagaga caagttaaca ttttttgcat atggcaaagc aaaaataaca     180

atagaccaaa acatagcaca agaaggaaaa aagagtataa aagttacaga caggaaaagt     240

gtatgggata gctttgggat agatgtaaaa gatgttttac aaagaggaaa aacatgggtg     300

gtatcagcct atgtaaaaca taaggggaag aagccgatag aattttcaat aacagctatt     360

tataatgacg gcagggggtt aaagtacctt cagcttggtg agaaaattgt cataccaaac     420

aaatgggaca aaattgttgc taagtggaaa ccaacgttaa aaaacccgat ggacttgatt     480
```

-continued attgcaattc atccaacagt tgataaaaca actgcatata atgtggacaa tattcaaata 540
atgacagaag aagtttatca atcacaagct gttgttttta aagatacatt tgaatcaaat 600
ttgacaaact ggcagccaag aggtgatact gtaaaactaa aaatagataa tacaaaatcg 660
cataatggaa ataagagtct ttatgtatca ggtcgttcgg cattctggca tggagttcaa 720
attcctgtga caaaatatct tgttgctggg aaggtataca aatttagcgt atggctgtat 780
catcaatcaa ttgacaagca aggttttggt cttaccattc aaagaaagat ggcaaacgat 840
gaacaatata aatatgattg gataactgga agccagattg aaggtgatgg ctgggttgag 900
ataagtggta attattatgt accaaaggat ggcaaaatag aagaacttgt attttgtgtt 960
tcttcgtgga acccaacatt agcattttgg gtagatgatg ttacaatatc tgatccgttt 1020
aagttacagg gacctaatta taatttgccg tctttaaaag agaaatataa agaagatttt 1080
aaagttggtg tagctattgg atatggtgaa cttattagtg atatagacac acaatttatc 1140
aaaaaacatt ttaacagtat aacaccaggc aacgagatga aacccgaaag tgtgctaaaa 1200
ggaccaaaca actatgactt tacaatagcg gatgcatttg tggattttgc aacaaaaaat 1260
aaaatgggta tacgcggaca tactcttgtc tggcacaacc agacacctga ttggttcttc 1320
aaagatgaga atggcaattt tttaaagaag gatgaacttt tgaaaaggtt aaaaaatcat 1380
atatacacag ttgttagccg gtataaaggc aaaatatatg cttgggatgt tgtcaatgaa 1440
gctattgatg aaacacaacc tgatggttac agaaggtcaa actggtacaa tatttgtgga 1500
cccgaatata tagaaaaagc gtttatttgg gcacatgagg cagatccaca agcaaagtta 1560
ttttacaatg attacaatac cgaaattcca caaaagagaa tgtttatata taacatgatt 1620
aaaaatttga aagcaaaagg tgttccaata catggtatag gtcttcaatg tcacataaat 1680
attgacaatc cttctgttga agatatagag gagacgataa aactatttag cacaattcca 1740
gggcttgaga ttcaaattac tgagcttgac atgagctttt atcaatgggg ttcttctgtt 1800
tattacgcag agccatcaag agaaatgtta ttaaaacagg caaagaaata ctatgagtta 1860
tttaacctat ttaagaagta caaaaatgtc ataaaaagcg ttacattctg ggggcttaag 1920
gatgacaact cttggctgag aggagttttt aacaaaccag attttccgct tttatttgat 1980
gagcattatg atggcaaacc tgctttctgg gcgttgatag actattcaat attaccacaa 2040
aatgccaatt tgcctacacc acctgctatt ccaaaagtaa aggctaaaaa ataa 2094

<210> SEQ ID NO 5
<211> LENGTH: 2016
<212> TYPE: DNA
<213> ORGANISM: Caldicellulosiruptor bescii

<400> SEQUENCE: 5
atggcacatc accaccacca tcacgtggat gacgacgaca agatgaactt tgaaggaaga 60
gacaagttaa catttttttgc atatggcaaa gcaaaaataa caatagacca aaacatagca 120
caagaaggaa aaaagagtat aaaagttaca gacaggaaaa gtgtatggga tagctttggg 180
atagatgtaa aagatgtttt acaaagagga aaaacatggg tggtatcagc ctatgtaaaa 240
cataagggga agaagccgat agaattttca ataacagcta tttataatga cggcaggggg 300
ttaaagtacc ttcagcttgg tgagaaaatt gtcataccaa acaaatggga caaaattgtt 360
gctaagtgga aaccaacgtt aaaaaacccg atggacttga ttattgcaat tcatccaaca 420
gttgataaaa caactgcata taatgtggac aatattcaaa taatgacaga agaagtttat 480

```
caatcacaag ctgttgtttt taaagataca tttgaatcaa atttgacaaa ctggcagcca    540

agaggtgata ctgtaaaact aaaaatagat aatacaaaat cgcataatgg aaataagagt    600

ctttatgtat caggtcgttc ggcattctgg catggagttc aaattcctgt gacaaaatat    660

cttgttgctg ggaaggtata caaatttagc gtatggctgt atcatcaatc aattgacaag    720

caaggttttg gtcttaccat tcaaagaaag atggcaaacg atgaacaata taaatatgat    780

tggataactg gaagccagat tgaaggtgat ggctgggttg agataagtgg taattattat    840

gtaccaaagg atggcaaaat agaagaactt gtattttgtg tttcttcgtg gaacccaaca    900

ttagcatttt gggtagatga tgttacaata tctgatccgt ttaagttaca gggacctaat    960

tataatttgc cgtctttaaa agagaaatat aaagaagatt ttaaagttgg tgtagctatt   1020

ggatatggtg aacttattag tgatatagac acacaattta tcaaaaaaca ttttaacagt   1080

ataacaccag gcaacgagat gaaacccgaa agtgtgctaa aaggaccaaa caactatgac   1140

tttacaatag cggatgcatt tgtggatttt gcaacaaaaa ataaaatggg tatacgcgga   1200

catactcttg tctggcacaa ccagacacct gattggttct tcaaagatga gaatggcaat   1260

tttttaaaga aggatgaact tttgaaaagg ttaaaaaatc atatatacac agttgttagc   1320

cggtataaag gcaaaatata tgcttgggat gttgtcaatg aagctattga tgaaacacaa   1380

cctgatggtt acagaaggtc aaactggtac aatatttgtg gacccgaata tatagaaaaa   1440

gcgtttattt gggcacatga ggcagatcca caagcaaagt tattttacaa tgattacaat   1500

accgaaattc cacaaaagag aatgtttata tataacatga ttaaaaattt gaaagcaaaa   1560

ggtgttccaa tacatggtat aggtcttcaa tgtcacataa atattgacaa tccttctgtt   1620

gaagatatag aggagacgat aaaactattt agcacaattc cagggcttga gattcaaatt   1680

actgagcttg acatgagctt ttatcaatgg ggttcttctg tttattacgc agagccatca   1740

agagaaatgt tattaaaaca ggcaaagaaa tactatgagt tatttaacct atttaagaag   1800

tacaaaaatg tcataaaaag cgttacattc tgggggctta aggatgacaa ctcttggctg   1860

agaggagttt ttaacaaacc agattttccg cttttatttg atgagcatta tgatggcaaa   1920

cctgctttct gggcgttgat agactattca atattaccac aaaatgccaa tttgcctaca   1980

ccacctgcta ttccaaaagt aaaggctaaa aaataa                             2016
```

<210> SEQ ID NO 6
<211> LENGTH: 671
<212> TYPE: PRT
<213> ORGANISM: Caldicellulosiruptor bescii

<400> SEQUENCE: 6

```
Met Ala His His His His His His Val Asp Asp Asp Asp Lys Met Asn
 1               5                  10                  15

Phe Glu Gly Arg Asp Lys Leu Thr Phe Phe Ala Tyr Gly Lys Ala Lys
            20                  25                  30

Ile Thr Ile Asp Gln Asn Ile Ala Gln Glu Gly Lys Lys Ser Ile Lys
        35                  40                  45

Val Thr Asp Arg Lys Ser Val Trp Asp Ser Phe Gly Ile Asp Val Lys
    50                  55                  60

Asp Val Leu Gln Arg Gly Lys Thr Trp Val Val Ser Ala Tyr Val Lys
65                  70                  75                  80

His Lys Gly Lys Lys Pro Ile Glu Phe Ser Ile Thr Ala Ile Tyr Asn
                85                  90                  95

Asp Gly Arg Gly Leu Lys Tyr Leu Gln Leu Gly Glu Lys Ile Val Ile
```

-continued

```
            100                 105                 110

Pro Asn Lys Trp Asp Lys Ile Val Ala Lys Trp Lys Pro Thr Leu Lys
        115                 120                 125

Asn Pro Met Asp Leu Ile Ile Ala Ile His Pro Thr Val Asp Lys Thr
    130                 135                 140

Thr Ala Tyr Asn Val Asp Asn Ile Gln Ile Met Thr Glu Glu Val Tyr
145                 150                 155                 160

Gln Ser Gln Ala Val Val Phe Lys Asp Thr Phe Glu Ser Asn Leu Thr
                165                 170                 175

Asn Trp Gln Pro Arg Gly Asp Thr Val Lys Leu Lys Ile Asp Asn Thr
            180                 185                 190

Lys Ser His Asn Gly Asn Lys Ser Leu Tyr Val Ser Gly Arg Ser Ala
        195                 200                 205

Phe Trp His Gly Val Gln Ile Pro Val Thr Lys Tyr Leu Val Ala Gly
    210                 215                 220

Lys Val Tyr Lys Phe Ser Val Trp Leu Tyr His Gln Ser Ile Asp Lys
225                 230                 235                 240

Gln Gly Phe Gly Leu Thr Ile Gln Arg Lys Met Ala Asn Asp Glu Gln
                245                 250                 255

Tyr Lys Tyr Asp Trp Ile Thr Gly Ser Gln Ile Glu Gly Asp Gly Trp
            260                 265                 270

Val Glu Ile Ser Gly Asn Tyr Tyr Val Pro Lys Asp Gly Lys Ile Glu
        275                 280                 285

Glu Leu Val Phe Cys Val Ser Ser Trp Asn Pro Thr Leu Ala Phe Trp
    290                 295                 300

Val Asp Asp Val Thr Ile Ser Asp Pro Phe Lys Leu Gln Gly Pro Asn
305                 310                 315                 320

Tyr Asn Leu Pro Ser Leu Lys Glu Lys Tyr Lys Glu Asp Phe Lys Val
                325                 330                 335

Gly Val Ala Ile Gly Tyr Gly Glu Leu Ile Ser Asp Ile Asp Thr Gln
            340                 345                 350

Phe Ile Lys Lys His Phe Asn Ser Ile Thr Pro Gly Asn Glu Met Lys
        355                 360                 365

Pro Glu Ser Val Leu Lys Gly Pro Asn Asn Tyr Asp Phe Thr Ile Ala
    370                 375                 380

Asp Ala Phe Val Asp Phe Ala Thr Lys Asn Lys Met Gly Ile Arg Gly
385                 390                 395                 400

His Thr Leu Val Trp His Asn Gln Thr Pro Asp Trp Phe Phe Lys Asp
                405                 410                 415

Glu Asn Gly Asn Phe Leu Lys Lys Asp Glu Leu Leu Lys Arg Leu Lys
            420                 425                 430

Asn His Ile Tyr Thr Val Val Ser Arg Tyr Lys Gly Lys Ile Tyr Ala
        435                 440                 445

Trp Asp Val Val Asn Glu Ala Ile Asp Glu Thr Gln Pro Asp Gly Tyr
    450                 455                 460

Arg Arg Ser Asn Trp Tyr Asn Ile Cys Gly Pro Glu Tyr Ile Glu Lys
465                 470                 475                 480

Ala Phe Ile Trp Ala His Glu Ala Asp Pro Gln Ala Lys Leu Phe Tyr
                485                 490                 495

Asn Asp Tyr Asn Thr Glu Ile Pro Gln Lys Arg Met Phe Ile Tyr Asn
            500                 505                 510

Met Ile Lys Asn Leu Lys Ala Lys Gly Val Pro Ile His Gly Ile Gly
        515                 520                 525
```

-continued

```
Leu Gln Cys His Ile Asn Ile Asp Asn Pro Ser Val Glu Asp Ile Glu
    530                 535                 540

Glu Thr Ile Lys Leu Phe Ser Thr Ile Pro Gly Leu Glu Ile Gln Ile
545                 550                 555                 560

Thr Glu Leu Asp Met Ser Phe Tyr Gln Trp Gly Ser Ser Val Tyr Tyr
                565                 570                 575

Ala Glu Pro Ser Arg Glu Met Leu Leu Lys Gln Ala Lys Lys Tyr Tyr
            580                 585                 590

Glu Leu Phe Asn Leu Phe Lys Lys Tyr Lys Asn Val Ile Lys Ser Val
        595                 600                 605

Thr Phe Trp Gly Leu Lys Asp Asp Asn Ser Trp Leu Arg Gly Val Phe
    610                 615                 620

Asn Lys Pro Asp Phe Pro Leu Leu Phe Asp Glu His Tyr Asp Gly Lys
625                 630                 635                 640

Pro Ala Phe Trp Ala Leu Ile Asp Tyr Ser Ile Leu Pro Gln Asn Ala
                645                 650                 655

Asn Leu Pro Thr Pro Pro Ala Ile Pro Lys Val Lys Ala Lys Lys
            660                 665                 670


<210> SEQ ID NO 7
<211> LENGTH: 337
<212> TYPE: PRT
<213> ORGANISM: Caldicellulosiruptor bescii

<400> SEQUENCE: 7

Met Ser Glu Asp Tyr Tyr Glu Lys Ser Thr Val Ser Leu Thr Glu Lys
 1               5                  10                  15

Tyr Lys Glu Phe Phe Lys Ile Gly Ala Ala Val Thr Val Lys Asp Phe
            20                  25                  30

Glu Gly Ile His Gly Arg Ile Leu Thr Lys His Phe Asn Ser Leu Thr
        35                  40                  45

Pro Glu Asn Asp Met Lys Phe Glu Arg Ile His Pro Lys Glu Asp Phe
    50                  55                  60

Tyr Asn Phe Glu Ala Thr Asp Lys Ile Lys Asp Phe Ala Leu Lys His
65                  70                  75                  80

Asn Met Gln Leu Arg Gly His Thr Leu Val Trp His Asn Gln Thr Pro
                85                  90                  95

Glu Trp Val Phe Arg Asp Asn Asp Lys Glu Ala Pro Lys Glu Leu Val
            100                 105                 110

Ile Glu Arg Leu Arg Glu His Ile Lys Thr Ile Cys Thr Arg Tyr Arg
        115                 120                 125

Asp Val Val Tyr Ser Trp Asp Val Val Asn Glu Ala Val Glu Asp Lys
    130                 135                 140

Thr Asp Val Leu Leu Arg Asp Ser Lys Trp Arg Arg Ile Ile Gly Asp
145                 150                 155                 160

Asp Tyr Ile Lys Ile Ala Phe Glu Ile Ala Lys Lys Tyr Thr Gly Asn
                165                 170                 175

Gly Lys Leu Phe Tyr Asn Asp Tyr Asn Asn Glu Met Pro Tyr Lys Leu
            180                 185                 190

Glu Lys Thr Tyr Lys Val Leu Lys Ser Leu Leu Glu Glu Gly Thr Pro
        195                 200                 205

Ile Asp Gly Val Gly Ile Gln Ala His Trp Asn Ile Trp Asp Lys Asn
    210                 215                 220

Leu Ile Asp Asn Leu Lys Arg Ala Ile Glu Thr Tyr Ala Ser Leu Gly
```

```
225                 230                 235                 240

Leu Glu Ile Gln Ile Thr Glu Leu Asp Ile Ser Val Phe Glu Phe Glu
                245                 250                 255

Asp Arg Arg Thr Asp Leu Leu Glu Pro Thr Glu Glu Met Val Glu Leu
            260                 265                 270

Gln Ala Lys Val Tyr Glu Asp Val Phe Arg Val Phe Arg Glu Tyr Arg
        275                 280                 285

Asp Val Ile Thr Ser Val Thr Leu Trp Gly Ile Ser Asp Arg His Thr
    290                 295                 300

Trp Lys Asp Asn Phe Pro Val Ile Gly Arg Lys Asp Trp Pro Leu Leu
305                 310                 315                 320

Phe Asp Ile Asp Gly Lys Pro Lys Lys Ala Phe Phe Arg Ile Ile Asp
                325                 330                 335

Phe
```

<210> SEQ ID NO 8
<211> LENGTH: 1014
<212> TYPE: DNA
<213> ORGANISM: Caldicellulosiruptor bescii

<400> SEQUENCE: 8

```
atgagcgaag attattatga aaagtctact gtatcactta cggaaaaata taaagagttc      60

tttaaaattg gtgcagctgt tacagtgaaa gattttgaag gaatacacgg aagaattctt     120

acaaagcatt ttaacagttt aacacctgag aatgatatga aatttgaaag aattcatccg     180

aaagaagatt tttacaactt tgaagctact gataagatta aagattttgc acttaaacat     240

aatatgcaac tgagaggaca tacacttgta tggcacaacc aaacacctga atgggttttt     300

cgtgacaatg acaaagaagc accaaaagag cttgtaatag aaagactgag ggaacacata     360

aagacaattt gcacaagata ccgcgatgtg gtttattcgt gggatgttgt gaatgaagct     420

gttgaggata aaacagatgt tctgctcaga gattcaaagt ggagaagaat cataggtgat     480

gattatatta agattgcctt tgaaatagct aaaaagtata caggaaatgg gaaactattt     540

tataacgact ataacaatga aatgccatac aagttagaaa agacatacaa ggtcttaaaa     600

agtcttttag aagaaggaac tccgattgat ggtgttggca tacaagcaca ctggaatatt     660

tgggataaga atttaataga caaccttaag agagctattg aaacatatgc atccttgggg     720

cttgaaatac aaataacaga gcttgatata tcagtatttg aatttgaaga cagaagaact     780

gacctattag agcccactga agagatggtg gagttgcaag ctaaggttta tgaggatgtg     840

tttagagtat ttagggagta tagagatgtt ataacgtcag ttacattatg gggattagc      900

gatagacata catggaaaga caattttccg gtaataggca gaaaagactg gccattgctg     960

tttgacattg atggaaagcc aaaaaaggca tttttcagaa taattgactt ttga          1014
```

<210> SEQ ID NO 9
<211> LENGTH: 1056
<212> TYPE: DNA
<213> ORGANISM: Caldicellulosiruptor bescii

<400> SEQUENCE: 9

```
atggcacatc accaccacca tcacgtggat gacgacgaca agatgagcga agattattat      60

gaaaagtcta ctgtatcact tacggaaaaa tataaagagt tctttaaaat tggtgcagct     120

gttacagtga aagattttga aggaatacac ggaagaattc ttacaaagca ttttaacagt     180

ttaacacctg agaatgatat gaaatttgaa agaattcatc cgaaagaaga tttttacaac     240
```

-continued

```
tttgaagcta ctgataagat taaagatttt gcacttaaac ataatatgca actgagagga    300

catacacttg tatggcacaa ccaaacacct gaatgggttt ttcgtgacaa tgacaaagaa    360

gcaccaaaag agcttgtaat agaaagactg agggaacaca taaagacaat ttgcacaaga    420

taccgcgatg tggtttattc gtgggatgtt gtgaatgaag ctgttgagga taaaacagat    480

gttctgctca gagattcaaa gtggagaaga atcataggtg atgattatat taagattgcc    540

tttgaaatag ctaaaaagta tacaggaaat gggaaactat tttataacga ctataacaat    600

gaaatgccat acaagttaga aaagacatac aaggtcttaa aaagtctttt agaagaagga    660

actccgattg atggtgttgg catacaagca cactggaata tttgggataa gaatttaata    720

gacaacctta agagagctat tgaaacatat gcatccttgg ggcttgaaat acaaataaca    780

gagcttgata tatcagtatt tgaatttgaa gacagaagaa ctgacctatt agagcccact    840

gaagagatgg tggagttgca agctaaggtt tatgaggatg tgtttagagt atttagggag    900

tatagagatg ttataacgtc agttacatta tgggggatta gcgatagaca tacatggaaa    960

gacaattttc cggtaatagg cagaaaagac tggccattgc tgtttgacat tgatggaaag   1020

ccaaaaaagg catttttcag aataattgac ttttga                             1056
```

<210> SEQ ID NO 10
<211> LENGTH: 351
<212> TYPE: PRT
<213> ORGANISM: Caldicellulosiruptor bescii

<400> SEQUENCE: 10

```
Met Ala His His His His His His Val Asp Asp Asp Asp Lys Met Ser
 1               5                  10                  15

Glu Asp Tyr Tyr Glu Lys Ser Thr Val Ser Leu Thr Glu Lys Tyr Lys
            20                  25                  30

Glu Phe Phe Lys Ile Gly Ala Ala Val Thr Val Lys Asp Phe Glu Gly
        35                  40                  45

Ile His Gly Arg Ile Leu Thr Lys His Phe Asn Ser Leu Thr Pro Glu
    50                  55                  60

Asn Asp Met Lys Phe Glu Arg Ile His Pro Lys Glu Asp Phe Tyr Asn
65                  70                  75                  80

Phe Glu Ala Thr Asp Lys Ile Lys Asp Phe Ala Leu Lys His Asn Met
                85                  90                  95

Gln Leu Arg Gly His Thr Leu Val Trp His Asn Gln Thr Pro Glu Trp
            100                 105                 110

Val Phe Arg Asp Asn Asp Lys Glu Ala Pro Lys Glu Leu Val Ile Glu
        115                 120                 125

Arg Leu Arg Glu His Ile Lys Thr Ile Cys Thr Arg Tyr Arg Asp Val
    130                 135                 140

Val Tyr Ser Trp Asp Val Val Asn Glu Ala Val Glu Asp Lys Thr Asp
145                 150                 155                 160

Val Leu Leu Arg Asp Ser Lys Trp Arg Arg Ile Ile Gly Asp Asp Tyr
                165                 170                 175

Ile Lys Ile Ala Phe Glu Ile Ala Lys Lys Tyr Thr Gly Asn Gly Lys
            180                 185                 190

Leu Phe Tyr Asn Asp Tyr Asn Asn Glu Met Pro Tyr Lys Leu Glu Lys
        195                 200                 205

Thr Tyr Lys Val Leu Lys Ser Leu Leu Glu Glu Gly Thr Pro Ile Asp
    210                 215                 220
```

-continued

```
Gly Val Gly Ile Gln Ala His Trp Asn Ile Trp Asp Lys Asn Leu Ile
225                 230                 235                 240

Asp Asn Leu Lys Arg Ala Ile Glu Thr Tyr Ala Ser Leu Gly Leu Glu
                245                 250                 255

Ile Gln Ile Thr Glu Leu Asp Ile Ser Val Phe Glu Phe Glu Asp Arg
            260                 265                 270

Arg Thr Asp Leu Leu Glu Pro Thr Glu Glu Met Val Glu Leu Gln Ala
        275                 280                 285

Lys Val Tyr Glu Asp Val Phe Arg Val Phe Arg Glu Tyr Arg Asp Val
    290                 295                 300

Ile Thr Ser Val Thr Leu Trp Gly Ile Ser Asp Arg His Thr Trp Lys
305                 310                 315                 320

Asp Asn Phe Pro Val Ile Gly Arg Lys Asp Trp Pro Leu Leu Phe Asp
                325                 330                 335

Ile Asp Gly Lys Pro Lys Lys Ala Phe Phe Arg Ile Ile Asp Phe
            340                 345                 350


<210> SEQ ID NO 11
<211> LENGTH: 36
<212> TYPE: DNA
<213> ORGANISM: Artificial Sequence
<220> FEATURE:
<223> OTHER INFORMATION: Synthesized Construct

<400> SEQUENCE: 11

gacgacgaca agatgaaaaa agcaaaagtc atctac                               36


<210> SEQ ID NO 12
<211> LENGTH: 39
<212> TYPE: DNA
<213> ORGANISM: Artificial Sequence
<220> FEATURE:
<223> OTHER INFORMATION: Synthesized Construct

<400> SEQUENCE: 12

gaggagaagc ccggttaatt ttctttcttc tttaacctg                            39


<210> SEQ ID NO 13
<211> LENGTH: 505
<212> TYPE: PRT
<213> ORGANISM: Caldicellulosiruptor bescii

<400> SEQUENCE: 13

Met Lys Lys Ala Lys Val Ile Tyr Asp Lys Glu Phe Val Ile Gly Gln
 1               5                  10                  15

Val Asp Lys Arg Ile Tyr Gly Ser Phe Leu Glu His Met Gly Arg Ala
            20                  25                  30

Ile Tyr Thr Gly Ile Tyr Glu Pro Asp His Pro Gln Ala Asp Glu Met
        35                  40                  45

Gly Phe Arg Lys Asp Val Leu Glu Leu Val Arg Lys Leu Asn Val Pro
    50                  55                  60

Ile Val Arg Tyr Pro Gly Gly Asn Phe Val Ser Gly Tyr Asn Trp Glu
65                  70                  75                  80

Asp Gly Ile Gly Pro Lys Glu Lys Arg Pro Arg Arg Leu Glu Leu Ala
                85                  90                  95

Trp Arg Ala Ile Glu Thr Asn Glu Val Gly Val Asn Glu Phe Val Glu
            100                 105                 110

Trp Ala Lys Arg Ala Asn Thr Ser Val Met Met Thr Val Asn Leu Gly
        115                 120                 125
```

```
Thr Arg Gly Ile Asp Ala Ala Arg Asn Leu Val Glu Tyr Cys Asn Phe
    130                 135                 140

Pro Gly Gly Thr Tyr Tyr Ser Asp Leu Arg Arg Gln His Gly Tyr Gln
145                 150                 155                 160

Gln Pro His Asn Ile Lys Val Trp Cys Leu Gly Asn Glu Met Asp Gly
                165                 170                 175

Asp Trp Gln Ile Gly His Lys Thr Ala Tyr Glu Tyr Gly Arg Leu Ala
            180                 185                 190

Arg Glu Thr Ala Lys Val Met Lys Trp Ile Asp Pro Ser Ile Glu Leu
        195                 200                 205

Val Ala Ala Gly Ser Ser Gly Pro Lys Met Pro Thr Phe Pro Glu Trp
    210                 215                 220

Glu Ala Ile Val Leu Asp His Thr Tyr Asp Leu Val Asp Tyr Val Ser
225                 230                 235                 240

Leu His Val Tyr Tyr Gly Asn Pro Glu Lys Asp Thr Lys Asn Phe Val
                245                 250                 255

Ala Lys Ser Leu Glu Met Glu Glu Phe Ile Lys Thr Val Ile Ser Thr
            260                 265                 270

Ile Asp Tyr Val Lys Ala Lys Lys Arg Ser Lys Lys Val Val Asn Ile
        275                 280                 285

Ser Phe Asp Glu Trp Asn Val Trp Tyr His Ala His Leu Glu Gly Lys
    290                 295                 300

Asp Gln Lys Ala Glu Pro Trp Ala Gln Val Arg Ala Ile Ala Glu Glu
305                 310                 315                 320

Asp Tyr Val Phe Glu Asp Ala Ile Leu Val Gly Cys Met Leu Ile Ala
                325                 330                 335

Leu Leu Lys His Cys Asp Arg Val Lys Met Ala Cys Met Ala Gln Leu
            340                 345                 350

Val Asn Val Ile Ala Pro Ile Thr Thr Val Lys Gly Gly Ile Ala Tyr
        355                 360                 365

Arg Gln Val Ile Tyr Tyr Pro Phe Met His Ala Ala Asn Phe Gly His
    370                 375                 380

Gly Val Ala Leu Leu Pro Lys Val Asn Ser Pro Lys Tyr Asp Ser Lys
385                 390                 395                 400

Asp Phe Thr Asp Val Pro Tyr Ile Glu Thr Val Ala Thr Tyr Asn Glu
                405                 410                 415

Glu Lys Asp Glu Ile Thr Ile Phe Ala Val Asn Arg Asp Leu Glu Glu
            420                 425                 430

Glu Met Gln Val Glu Phe Lys Leu Asp Gly Phe Glu Gly Phe Glu Val
        435                 440                 445

Val Glu His Ile Val Tyr Glu Ser Asp Asp Ile Tyr Lys Gly Asn Thr
    450                 455                 460

Gln Asp Lys Pro Asp Asn Val Val Pro His Lys Gly Gly Asn Ser Lys
465                 470                 475                 480

Ile Glu Gly Asn Val Leu Thr Ser Ile Leu Pro Lys Phe Ser Trp Asn
                485                 490                 495

Val Ile Arg Leu Lys Lys Lys Glu Asn
            500                 505
```

<210> SEQ ID NO 14
<211> LENGTH: 1518
<212> TYPE: DNA
<213> ORGANISM: Caldicellulosiruptor bescii

<400> SEQUENCE: 14

```
atgaaaaaag caaaagtcat ctacgataag gagttcgtaa tcgggcaagt agacaagaga     60
atctacggtt catttttaga acacatggga agagcaatat acacaggaat ctatgaacca    120
gaccatccgc aggctgatga aatggggttt agaaaggatg ttttagaact tgttcgcaag    180
ctgaatgttc ctattgtaag atatcctggc ggcaattttg tgtcggggta taactgggaa    240
gacggtattg gtccaaaaga aaaaagaccg agaagacttg agcttgcgtg gagagccatc    300
gagacaaatg aggttggtgt aaacgaattt gttgaatggg caaaaagagc aaacacctct    360
gttatgatga cagtaaacct tggcacacga ggaattgacg ctgcaagaaa cttagttgag    420
tattgcaact tcccaggcgg tacatactac agtgatttga gacgtcagca tggttatcag    480
cagccacaca acataaaagt atggtgtctt ggtaacgaga tggacgggga ctggcagata    540
ggtcataaaa ctgcatatga gtatggaagg cttgcaagag agacagcaaa ggttatgaag    600
tggatagatc cgagtattga gcttgttgca gcgggaagct caggtcccaa aatgccaaca    660
tttcctgagt gggaagcaat tgttttggac cacacatatg accttgtaga ttatgtgtcg    720
ctacatgtat actatggaaa tcctgaaaaa gacacaaaga attttgttgc aaaatcgctt    780
gaaatggaag agtttatcaa aacagttata tcaacaattg actatgtaaa ggctaaaaag    840
agaagcaaaa aggttgtcaa tatctcattt gacgaatgga atgtatggta ccatgctcat    900
cttgagggga aagaccagaa agcagaaccc tgggcacaag ttcgtgctat tgctgaagaa    960
gattatgtgt tcgaagatgc aattttggta ggatgcatgc tgattgcgct tttgaaacac   1020
tgtgatagag tcaagatggc gtgcatggca cagcttgtaa atgtaattgc tccaattacc   1080
actgtaaaag gtggaattgc ttacagacag gtaatctatt atcctttcat gcatgctgca   1140
aactttggac atggagttgc actgcttccc aaggtaaatt ctcctaaata tgattcaaaa   1200
gactttactg atgttccata tattgaaaca gttgcaacat acaatgagga aaaggatgaa   1260
ataacaatct ttgcagtcaa cagagattta gaagaggaga tgcaagttga gtttaagctt   1320
gatggttttg aaggctttga ggttgtggag cacattgtat atgaaagtga tgatatttac   1380
aaaggaaaca ctcaagataa gcctgacaat gttgtgcccc acaaaggtgg aaattcaaag   1440
atagaaggca atgttttaac atccatattg cccaaattct cctggaatgt tatcaggtta   1500
aagaagaaag aaaattaa                                                 1518
```

<210> SEQ ID NO 15
<211> LENGTH: 1560
<212> TYPE: DNA
<213> ORGANISM: Caldicellulosiruptor bescii

<400> SEQUENCE: 15

```
atggcacatc accaccacca tcacgtggat gacgacgaca agatgaaaaa agcaaaagtc     60
atctacgata aggagttcgt aatcgggcaa gtagacaaga gaatctacgg ttcattttta    120
gaacacatgg gaagagcaat atacacagga atctatgaac cagaccatcc gcaggctgat    180
gaaatggggt ttagaaagga tgttttagaa cttgttcgca agctgaatgt tcctattgta    240
agatatcctg gcggcaattt tgtgtcgggg tataactggg aagacggtat tggtccaaaa    300
gaaaaaagac cgagaagact tgagcttgcg tggagagcca tcgagacaaa tgaggttggt    360
gtaaacgaat ttgttgaatg ggcaaaaaga gcaaacacct ctgttatgat gacagtaaac    420
cttggcacac gaggaattga cgctgcaaga aacttagttg agtattgcaa cttcccaggc    480
ggtacatact acagtgattt gagacgtcag catggttatc agcagccaca caacataaaa    540
```

```
gtatggtgtc ttggtaacga gatggacggg gactggcaga taggtcataa aactgcatat    600

gagtatggaa ggcttgcaag agagacagca aaggttatga agtggataga tccgagtatt    660

gagcttgttg cagcgggaag ctcaggtccc aaaatgccaa catttcctga gtgggaagca    720

attgttttgg accacacata tgaccttgta gattatgtgt cgctacatgt atactatgga    780

aatcctgaaa aagacacaaa gaattttgtt gcaaaatcgc ttgaaatgga agagtttatc    840

aaaacagtta tatcaacaat tgactatgta aaggctaaaa agagaagcaa aaaggttgtc    900

aatatctcat ttgacgaatg gaatgtatgg taccatgctc atcttgaggg gaaagaccag    960

aaagcagaac cctgggcaca agttcgtgct attgctgaag aagattatgt gttcgaagat   1020

gcaattttgg taggatgcat gctgattgcg cttttgaaac actgtgatag agtcaagatg   1080

gcgtgcatgg cacagcttgt aaatgtaatt gctccaatta ccactgtaaa aggtggaatt   1140

gcttacagac aggtaatcta ttatcctttc atgcatgctg caaactttgg acatggagtt   1200

gcactgcttc ccaaggtaaa ttctcctaaa tatgattcaa aagactttac tgatgttcca   1260

tatattgaaa cagttgcaac atacaatgag gaaaaggatg aaataacaat ctttgcagtc   1320

aacagagatt tagaagagga gatgcaagtt gagtttaagc ttgatggttt tgaaggcttt   1380

gaggttgtgg agcacattgt atatgaaagt gatgatattt acaaaggaaa cactcaagat   1440

aagcctgaca atgttgtgcc ccacaaaggt ggaaattcaa agatagaagg caatgtttta   1500

acatccatat tgcccaaatt ctcctggaat gttatcaggt taaagaagaa agaaaattaa   1560
```

```
<210> SEQ ID NO 16
<211> LENGTH: 519
<212> TYPE: PRT
<213> ORGANISM: Caldicellulosiruptor bescii

<400> SEQUENCE: 16

Met Ala His His His His His His Val Asp Asp Asp Asp Lys Met Lys
1               5                   10                  15

Lys Ala Lys Val Ile Tyr Asp Lys Glu Phe Val Ile Gly Gln Val Asp
            20                  25                  30

Lys Arg Ile Tyr Gly Ser Phe Leu Glu His Met Gly Arg Ala Ile Tyr
        35                  40                  45

Thr Gly Ile Tyr Glu Pro Asp His Pro Gln Ala Asp Glu Met Gly Phe
    50                  55                  60

Arg Lys Asp Val Leu Glu Leu Val Arg Lys Leu Asn Val Pro Ile Val
65                  70                  75                  80

Arg Tyr Pro Gly Gly Asn Phe Val Ser Gly Tyr Asn Trp Glu Asp Gly
                85                  90                  95

Ile Gly Pro Lys Glu Lys Arg Pro Arg Arg Leu Glu Leu Ala Trp Arg
            100                 105                 110

Ala Ile Glu Thr Asn Glu Val Gly Val Asn Glu Phe Val Glu Trp Ala
        115                 120                 125

Lys Arg Ala Asn Thr Ser Val Met Met Thr Val Asn Leu Gly Thr Arg
    130                 135                 140

Gly Ile Asp Ala Ala Arg Asn Leu Val Glu Tyr Cys Asn Phe Pro Gly
145                 150                 155                 160

Gly Thr Tyr Tyr Ser Asp Leu Arg Arg Gln His Gly Tyr Gln Gln Pro
                165                 170                 175

His Asn Ile Lys Val Trp Cys Leu Gly Asn Glu Met Asp Gly Asp Trp
            180                 185                 190
```

Gln Ile Gly His Lys Thr Ala Tyr Glu Tyr Gly Arg Leu Ala Arg Glu
195 200 205

Thr Ala Lys Val Met Lys Trp Ile Asp Pro Ser Ile Glu Leu Val Ala
210 215 220

Ala Gly Ser Ser Gly Pro Lys Met Pro Thr Phe Pro Glu Trp Glu Ala
225 230 235 240

Ile Val Leu Asp His Thr Tyr Asp Leu Val Asp Tyr Val Ser Leu His
245 250 255

Val Tyr Tyr Gly Asn Pro Glu Lys Asp Thr Lys Asn Phe Val Ala Lys
260 265 270

Ser Leu Glu Met Glu Glu Phe Ile Lys Thr Val Ile Ser Thr Ile Asp
275 280 285

Tyr Val Lys Ala Lys Lys Arg Ser Lys Lys Val Val Asn Ile Ser Phe
290 295 300

Asp Glu Trp Asn Val Trp Tyr His Ala His Leu Glu Gly Lys Asp Gln
305 310 315 320

Lys Ala Glu Pro Trp Ala Gln Val Arg Ala Ile Ala Glu Glu Asp Tyr
325 330 335

Val Phe Glu Asp Ala Ile Leu Val Gly Cys Met Leu Ile Ala Leu Leu
340 345 350

Lys His Cys Asp Arg Val Lys Met Ala Cys Met Ala Gln Leu Val Asn
355 360 365

Val Ile Ala Pro Ile Thr Thr Val Lys Gly Gly Ile Ala Tyr Arg Gln
370 375 380

Val Ile Tyr Tyr Pro Phe Met His Ala Ala Asn Phe Gly His Gly Val
385 390 395 400

Ala Leu Leu Pro Lys Val Asn Ser Pro Lys Tyr Asp Ser Lys Asp Phe
405 410 415

Thr Asp Val Pro Tyr Ile Glu Thr Val Ala Thr Tyr Asn Glu Glu Lys
420 425 430

Asp Glu Ile Thr Ile Phe Ala Val Asn Arg Asp Leu Glu Glu Glu Met
435 440 445

Gln Val Glu Phe Lys Leu Asp Gly Phe Glu Gly Phe Glu Val Val Glu
450 455 460

His Ile Val Tyr Glu Ser Asp Asp Ile Tyr Lys Gly Asn Thr Gln Asp
465 470 475 480

Lys Pro Asp Asn Val Val Pro His Lys Gly Gly Asn Ser Lys Ile Glu
485 490 495

Gly Asn Val Leu Thr Ser Ile Leu Pro Lys Phe Ser Trp Asn Val Ile
500 505 510

Arg Leu Lys Lys Lys Glu Asn
515

<210> SEQ ID NO 17
<211> LENGTH: 36
<212> TYPE: DNA
<213> ORGANISM: Artificial Sequence
<220> FEATURE:
<223> OTHER INFORMATION: Synthesized Construct

<400> SEQUENCE: 17
gacgacgaca agatgatttt atcaaggagc agtaac 36

<210> SEQ ID NO 18
<211> LENGTH: 34
<212> TYPE: DNA

```
<213> ORGANISM: Caldicellulosiruptor bescii

<400> SEQUENCE: 18

gaggagaagc ccggttacgg atatattagt cttc                              34


<210> SEQ ID NO 19
<211> LENGTH: 693
<212> TYPE: PRT
<213> ORGANISM: Caldicellulosiruptor bescii

<400> SEQUENCE: 19

Met Ile Leu Ser Arg Ser Ser Asn Pro Asn Tyr Ser Met Cys Trp Leu
1               5                   10                  15

Ser Tyr Lys Pro Ile Gly Lys Lys Glu Tyr Val His Glu Val Glu Lys
            20                  25                  30

Phe Leu Gly Gln Ile Val Leu Leu Glu Lys Asn Ile Tyr Phe Glu Asn
        35                  40                  45

Ala Ala Asn Glu Leu Lys Lys Ala Leu Cys Val Leu Phe Glu Thr Glu
    50                  55                  60

Leu Arg Leu Asn Asn Ala Leu Ser Leu Tyr Val Asp Ser Gly Ile Ile
65                  70                  75                  80

Leu Gly Lys Val Thr Asn Glu Asn Leu Arg Gly Phe Ile Thr Asp Val
                85                  90                  95

Glu Lys Glu Ala Val Gly Glu Glu Gly Phe Ile Ile Lys Leu Val Asp
            100                 105                 110

Lys Ser Lys Lys Lys Tyr Ile Ile Val Ala Ser Lys Gly Glu Lys Gly
        115                 120                 125

Ile Ile Tyr Gly Ile Phe His Leu Ile Asn Lys Phe Arg Leu Lys Thr
    130                 135                 140

Gly Leu Lys Glu Leu Asn Cys Ile Glu Asn Pro Lys Ala Ser Leu Arg
145                 150                 155                 160

Ile Ile Asn His Trp Asp Asn Met Asp Gly Ser Ile Glu Arg Gly Tyr
                165                 170                 175

Ala Gly Lys Ser Ile Phe Phe Thr Asn Gly Arg Ile Lys Arg Asn Tyr
            180                 185                 190

Lys Arg Ile Trp Asp Tyr Ala Arg Leu Leu Ala Ser Ile Gly Ile Asn
        195                 200                 205

Gly Val Val Ile Asn Asn Val Asn Val Arg Asp Lys Ala Ile Trp Leu
    210                 215                 220

Ile Thr Pro Lys Tyr Leu Asn Asp Leu Ser Lys Ile Ala Glu Ile Phe
225                 230                 235                 240

Arg Leu Tyr Gly Ile Lys Leu Tyr Leu Ser Ile Asn Phe Ala Ser Pro
                245                 250                 255

Ile Tyr Ile Gly Gly Leu Asp Thr Ala Asp Pro Leu Asp Lys Asn Val
            260                 265                 270

Gln Lys Trp Trp Lys Asp Thr Val Lys Thr Ile Tyr Ser Tyr Ile Pro
        275                 280                 285

Asp Phe Gly Gly Phe Leu Val Lys Ala Asp Ser Glu Phe Asn Pro Gly
    290                 295                 300

Pro Tyr Val Tyr Gly Arg Thr His Ala Asp Gly Ala Asn Met Leu Ala
305                 310                 315                 320

Glu Ala Leu Leu Pro Tyr Gly Gly Val Val Ile Trp Arg Ala Phe Val
                325                 330                 335

Tyr Asn Cys Leu Gln Asp Trp Arg Asp Thr Lys Thr Asp Arg Ala Lys
            340                 345                 350
```

```
Ala Ala Tyr Asp Asn Phe Lys Pro Leu Asp Gly Met Phe Ser Lys Asn
        355                 360                 365

Val Ile Leu Gln Ile Lys Tyr Gly Pro Met Asp Phe Gln Val Arg Glu
    370                 375                 380

Pro Val Ser Pro Leu Phe Gly Ala Met Glu Lys Thr Asn Gln Met Ile
385                 390                 395                 400

Glu Phe Gln Ile Thr Gln Glu Tyr Thr Gly Gln Gln Ile His Leu Cys
                405                 410                 415

Tyr Leu Gly Thr Leu Trp Lys Glu Ile Leu Glu Phe Asp Thr Tyr Cys
            420                 425                 430

Lys Gly Lys Gly Ser Tyr Val Lys Arg Ile Val Asp Gly Ser Leu Phe
        435                 440                 445

Gly Met Lys Tyr Ala Gly Phe Ala Gly Val Ser Asn Ile Gly Asp Ser
    450                 455                 460

Ile Asn Trp Thr Gly His Asp Leu Ala Gln Ala Asn Leu Trp Thr Phe
465                 470                 475                 480

Gly Lys Leu Ala Trp Asp Pro Asp Lys Lys Ile Glu Asp Ile Ala Arg
                485                 490                 495

Glu Trp Ala Ile Leu Thr Phe Gly Asp Asp Lys Lys Val Val Asp Asn
            500                 505                 510

Ile Leu Trp Met Leu Leu Asn Ser His Gly Ile Tyr Glu Lys Tyr Thr
        515                 520                 525

Thr Pro Leu Gly Leu Gly Trp Met Val Asn Pro Gly His His Tyr Gly
    530                 535                 540

Pro Asn Pro Glu Gly Tyr Glu Tyr Ser Lys Trp Gly Thr Tyr His Arg
545                 550                 555                 560

Ser Asp Thr Lys Ala Ile Gly Val Asp Arg Thr Ser Arg Gly Thr Gly
                565                 570                 575

Tyr Thr Leu Gln Tyr His Lys Pro Trp Gln Glu Ile Phe Asp Asp Ile
            580                 585                 590

Asn Lys Cys Pro Glu Glu Leu Leu Leu Phe Phe His Arg Val Pro Tyr
        595                 600                 605

Asp Phe Arg Leu Lys Asn Gly Lys Thr Leu Leu Gln Phe Met Tyr Asp
    610                 615                 620

Ser His Phe Glu Gly Ala Asp Met Val Asp Lys Leu Ile Glu Lys Trp
625                 630                 635                 640

Glu Glu Leu Arg Gly Lys Ile Asp Glu Glu Ile Phe Asn Arg Val Tyr
                645                 650                 655

Glu Arg Leu Lys Met Gln Lys Glu His Ala Met Glu Trp Arg Asp Val
            660                 665                 670

Ile Asn Thr Tyr Phe Tyr Arg Lys Thr Gly Ile Pro Asp Glu Lys Gly
        675                 680                 685

Arg Leu Ile Tyr Pro
    690


<210> SEQ ID NO 20
<211> LENGTH: 2082
<212> TYPE: DNA
<213> ORGANISM: Caldicellulosiruptor bescii

<400> SEQUENCE: 20

atgattttat caaggagcag taacccaaac tattctatgt gttggctttc ttataaacct      60

ataggtaaga aagaatatgt acatgaagtt gaaaaatttt tagggcaaat agttttattg     120
```

-continued

```
gagaaaaata tttatttcga aaatgcggcg aatgaactta aaaaggcttt atgtgtattg    180
tttgaaactg aactaagatt gaacaatgct ttaagtcttt atgttgacag tggaattatt    240
ttaggtaaag tgacaaatga aaatcttaga ggttttataa ccgatgttga aaaagaagca    300
gtaggtgagg aagggtttat aataaaactt gtagataaaa gtaagaaaaa atacattatt    360
gttgcttcaa agggtgaaaa aggaataata tatgggatat ttcatttgat aaacaaattt    420
agacttaaaa caggattaaa agaactcaat tgtatagaaa atccaaaggc ctcgttacga    480
attattaacc attgggataa tatggatgga agtattgaaa gaggatatgc gggtaaatca    540
atatttttta caaatggtag aataaaacgc aattataaac gtatatggga ttatgcaagg    600
cttcttgcct caattggaat aaacggtgtt gtaataaata atgtgaatgt aagagataag    660
gctatatggt taattacgcc aaaatatcta aatgacctct cgaaaatagc agaaattttt    720
agactctatg ggataaaact ttaccttagc ataaactttg caagcccaat ttatatagga    780
ggtcttgaca ctgcagaccc acttgacaaa aacgttcaaa agtggtggaa ggacactgta    840
aaaactattt acagctacat accagacttt ggtggatttt tggtaaaagc cgattctgag    900
ttcaatccag ggccgtatgt atacggtaga acacatgcag atggagcaaa catgcttgca    960
gaggcacttt tgccttatgg aggagttgtt atatggcgtg cgtttgttta caactgcttg   1020
caggattgga gagatacaaa gacagacagg gcaaaggctg catatgacaa ttttaaacca   1080
cttgatggga tgttctctaa aaatgtcatt ttacagataa agtatggtcc gatggatttt   1140
caggtaagag aacctgtttc acctcttttt ggcgctatgg aaaagacaaa ccagatgata   1200
gagtttcaaa taacccaaga atatacgggg caacaaattc atctgtgcta tttggggacg   1260
ctatggaaag agattttaga gtttgacaca tattgtaaag gaaaaggttc gtacgtaaag   1320
agaatagtgg atggaagtct tttggaatg aaatatgcag gatttgcagg tgtttcgaat   1380
attggggata gcatcaactg gacaggtcat gaccttgcac aggcgaatct gtggacgttt   1440
ggaaaacttg catgggaccc agataaaaag attgaagata tagcaagaga gtgggccatt   1500
ttaacatttg gagatgacaa aaaagtggtt gacaacattt tatggatgct tcttaattct   1560
cacgggatct acgaaaaata tacaactccg cttgggcttg gctggatggt aaatccaggt   1620
catcactatg gtccaaaccc ggaagggtat gagtattcaa agtggggaac gtatcatcgg   1680
tcagatacaa aagcaattgg agttgacaga acttcaagag ggacaggtta tactttgcaa   1740
tatcacaagc cctggcagga aatattcgat gatataaata aatgtcctga agaacttctt   1800
ctatttttcc acagagtgcc gtatgatttt agactgaaaa atggaaaaac gctcctgcag   1860
tttatgtatg actctcactt tgaaggggct gatatggtag ataaacttat agaaaagtgg   1920
gaggaactga gaggaaagat tgatgaggag atcttcaaca gagtatatga aagattgaag   1980
atgcaaaaag aacatgcaat ggaatggaga gatgttatca acacatattt ttatagaaag   2040
acaggaatac ctgatgaaaa gggaagacta atatatccgt aa                      2082
```

<210> SEQ ID NO 21
<211> LENGTH: 42
<212> TYPE: DNA
<213> ORGANISM: Artificial Sequence
<220> FEATURE:
<223> OTHER INFORMATION: Synthesized Construct

<400> SEQUENCE: 21

```
atggcacatc accaccacca tcacgtggat gacgacgaca ag                        42
```

-continued

<210> SEQ ID NO 22
<211> LENGTH: 14
<212> TYPE: PRT
<213> ORGANISM: Artificial Sequence
<220> FEATURE:
<223> OTHER INFORMATION: Synthesized Construct

<400> SEQUENCE: 22

Met Ala His His His His His His Val Asp Asp Asp Asp Lys
1 5 10

<210> SEQ ID NO 23
<211> LENGTH: 2124
<212> TYPE: DNA
<213> ORGANISM: Caldicellulosiruptor bescii

<400> SEQUENCE: 23
atggcacatc accaccacca tcacgtggat gacgacgaca agatgatttt atcaaggagc 60
agtaacccaa actattctat gtgttggctt tcttataaac ctataggtaa gaaagaatat 120
gtacatgaag ttgaaaaatt tttagggcaa atagttttat tggagaaaaa tatttatttc 180
gaaaatgcgg cgaatgaact taaaaaggct ttatgtgtat tgtttgaaac tgaactaaga 240
ttgaacaatg ctttaagtct ttatgttgac agtggaatta ttttaggtaa agtgacaaat 300
gaaaatctta gaggttttat aaccgatgtt gaaaaagaag cagtaggtga ggaagggttt 360
ataataaaac ttgtagataa aagtaagaaa aaatacatta ttgttgcttc aaagggtgaa 420
aaaggaataa tatatgggat atttcatttg ataaacaaat ttagacttaa aacaggatta 480
aaagaactca attgtataga aaatccaaag gcctcgttac gaattattaa ccattgggat 540
aatatggatg gaagtattga aagaggatat gcgggtaaat caatattttt tacaaatggt 600
agaataaaac gcaattataa acgtatatgg gattatgcaa ggcttcttgc ctcaattgga 660
ataaacggtg ttgtaataaa taatgtgaat gtaagagata aggctatatg gttaattacg 720
ccaaaatatc taaatgacct ctcgaaaata gcagaaattt ttagactcta tgggataaaa 780
ctttacctta gcataaactt tgcaagccca atttatatag gaggtcttga cactgcagac 840
ccacttgaca aaaacgttca aaagtggtgg aaggacactg taaaaactat ttacagctac 900
ataccagact tggtggattt tttggtaaaa gccgattctg agttcaatcc agggccgtat 960
gtatacggta gaacacatgc agatggagca aacatgcttg cagaggcact tttgccttat 1020
ggaggagttg ttatatggcg tgcgtttgtt tacaactgct tgcaggattg gagagataca 1080
aagacagaca gggcaaaggc tgcatatgac aattttaaac cacttgatgg gatgttctct 1140
aaaaatgtca ttttacagat aaagtatggt ccgatggatt ttcaggtaag agaacctgtt 1200
tcacctcttt ttggcgctat ggaaaagaca aaccagatga tagagtttca aataacccaa 1260
gaatatacgg ggcaacaaat tcatctgtgc tatttgggga cgctatggaa agagatttta 1320
gagtttgaca catattgtaa aggaaaaggt tcgtacgtaa agagaatagt ggatggaagt 1380
ctttttggaa tgaaatatgc aggatttgca ggtgtttcga atattgggga tagcatcaac 1440
tggacaggtc atgaccttgc acaggcgaat ctgtggacgt ttggaaaact tgcatgggac 1500
ccagataaaa agattgaaga tatagcaaga gagtgggcca ttttaacatt tggagatgac 1560
aaaaaagtgg ttgacaacat tttatggatg cttcttaatt ctcacgggat ctacgaaaaa 1620
tatacaactc cgcttgggct tggctggatg gtaaatccag gtcatcacta tggtccaaac 1680
ccggaagggt atgagtattc aaagtgggga acgtatcatc ggtcagatac aaaagcaatt 1740
ggagttgaca gaacttcaag agggacaggt tatactttgc aatatcacaa gccctggcag 1800

```
gaaatattcg atgatataaa taaatgtcct gaagaacttc ttctattttt ccacagagtg   1860

ccgtatgatt ttagactgaa aaatggaaaa acgctcctgc agtttatgta tgactctcac   1920

tttgaagggg ctgatatggt agataaactt atagaaaagt gggaggaact gagaggaaag   1980

attgatgagg agatcttcaa cagagtatat gaaagattga agatgcaaaa agaacatgca   2040

atggaatgga gagatgttat caacacatat ttttatagaa agacaggaat acctgatgaa   2100

aagggaagac taatatatcc gtaa                                          2124
```

<210> SEQ ID NO 24
<211> LENGTH: 707
<212> TYPE: PRT
<213> ORGANISM: Caldicellulosiruptor bescii

<400> SEQUENCE: 24

```
Met Ala His His His His His His Val Asp Asp Asp Asp Lys Met Ile
 1               5                  10                  15

Leu Ser Arg Ser Ser Asn Pro Asn Tyr Ser Met Cys Trp Leu Ser Tyr
            20                  25                  30

Lys Pro Ile Gly Lys Lys Glu Tyr Val His Glu Val Glu Lys Phe Leu
        35                  40                  45

Gly Gln Ile Val Leu Leu Glu Lys Asn Ile Tyr Phe Glu Asn Ala Ala
    50                  55                  60

Asn Glu Leu Lys Lys Ala Leu Cys Val Leu Phe Glu Thr Glu Leu Arg
65                  70                  75                  80

Leu Asn Asn Ala Leu Ser Leu Tyr Val Asp Ser Gly Ile Ile Leu Gly
                85                  90                  95

Lys Val Thr Asn Glu Asn Leu Arg Gly Phe Ile Thr Asp Val Glu Lys
            100                 105                 110

Glu Ala Val Gly Glu Glu Gly Phe Ile Ile Lys Leu Val Asp Lys Ser
        115                 120                 125

Lys Lys Lys Tyr Ile Ile Val Ala Ser Lys Gly Glu Lys Gly Ile Ile
    130                 135                 140

Tyr Gly Ile Phe His Leu Ile Asn Lys Phe Arg Leu Lys Thr Gly Leu
145                 150                 155                 160

Lys Glu Leu Asn Cys Ile Glu Asn Pro Lys Ala Ser Leu Arg Ile Ile
                165                 170                 175

Asn His Trp Asp Asn Met Asp Gly Ser Ile Glu Arg Gly Tyr Ala Gly
            180                 185                 190

Lys Ser Ile Phe Phe Thr Asn Gly Arg Ile Lys Arg Asn Tyr Lys Arg
        195                 200                 205

Ile Trp Asp Tyr Ala Arg Leu Leu Ala Ser Ile Gly Ile Asn Gly Val
    210                 215                 220

Val Ile Asn Asn Val Asn Val Arg Asp Lys Ala Ile Trp Leu Ile Thr
225                 230                 235                 240

Pro Lys Tyr Leu Asn Asp Leu Ser Lys Ile Ala Glu Ile Phe Arg Leu
                245                 250                 255

Tyr Gly Ile Lys Leu Tyr Leu Ser Ile Asn Phe Ala Ser Pro Ile Tyr
            260                 265                 270

Ile Gly Gly Leu Asp Thr Ala Asp Pro Leu Asp Lys Asn Val Gln Lys
        275                 280                 285

Trp Trp Lys Asp Thr Val Lys Thr Ile Tyr Ser Tyr Ile Pro Asp Phe
    290                 295                 300

Gly Gly Phe Leu Val Lys Ala Asp Ser Glu Phe Asn Pro Gly Pro Tyr
```

305 310 315 320

Val Tyr Gly Arg Thr His Ala Asp Gly Ala Asn Met Leu Ala Glu Ala
325 330 335

Leu Leu Pro Tyr Gly Gly Val Val Ile Trp Arg Ala Phe Val Tyr Asn
340 345 350

Cys Leu Gln Asp Trp Arg Asp Thr Lys Thr Asp Arg Ala Lys Ala Ala
355 360 365

Tyr Asp Asn Phe Lys Pro Leu Asp Gly Met Phe Ser Lys Asn Val Ile
370 375 380

Leu Gln Ile Lys Tyr Gly Pro Met Asp Phe Gln Val Arg Glu Pro Val
385 390 395 400

Ser Pro Leu Phe Gly Ala Met Glu Lys Thr Asn Gln Met Ile Glu Phe
405 410 415

Gln Ile Thr Gln Glu Tyr Thr Gly Gln Gln Ile His Leu Cys Tyr Leu
420 425 430

Gly Thr Leu Trp Lys Glu Ile Leu Glu Phe Asp Thr Tyr Cys Lys Gly
435 440 445

Lys Gly Ser Tyr Val Lys Arg Ile Val Asp Gly Ser Leu Phe Gly Met
450 455 460

Lys Tyr Ala Gly Phe Ala Gly Val Ser Asn Ile Gly Asp Ser Ile Asn
465 470 475 480

Trp Thr Gly His Asp Leu Ala Gln Ala Asn Leu Trp Thr Phe Gly Lys
485 490 495

Leu Ala Trp Asp Pro Asp Lys Lys Ile Glu Asp Ile Ala Arg Glu Trp
500 505 510

Ala Ile Leu Thr Phe Gly Asp Asp Lys Lys Val Val Asp Asn Ile Leu
515 520 525

Trp Met Leu Leu Asn Ser His Gly Ile Tyr Glu Lys Tyr Thr Thr Pro
530 535 540

Leu Gly Leu Gly Trp Met Val Asn Pro Gly His His Tyr Gly Pro Asn
545 550 555 560

Pro Glu Gly Tyr Glu Tyr Ser Lys Trp Gly Thr Tyr His Arg Ser Asp
565 570 575

Thr Lys Ala Ile Gly Val Asp Arg Thr Ser Arg Gly Thr Gly Tyr Thr
580 585 590

Leu Gln Tyr His Lys Pro Trp Gln Glu Ile Phe Asp Asp Ile Asn Lys
595 600 605

Cys Pro Glu Glu Leu Leu Leu Phe Phe His Arg Val Pro Tyr Asp Phe
610 615 620

Arg Leu Lys Asn Gly Lys Thr Leu Leu Gln Phe Met Tyr Asp Ser His
625 630 635 640

Phe Glu Gly Ala Asp Met Val Asp Lys Leu Ile Glu Lys Trp Glu Glu
645 650 655

Leu Arg Gly Lys Ile Asp Glu Glu Ile Phe Asn Arg Val Tyr Glu Arg
660 665 670

Leu Lys Met Gln Lys Glu His Ala Met Glu Trp Arg Asp Val Ile Asn
675 680 685

Thr Tyr Phe Tyr Arg Lys Thr Gly Ile Pro Asp Glu Lys Gly Arg Leu
690 695 700

Ile Tyr Pro
705

<210> SEQ ID NO 25

<211> LENGTH: 36
<212> TYPE: DNA
<213> ORGANISM: Artificial Sequence
<220> FEATURE:
<223> OTHER INFORMATION: Synthesized Construct

<400> SEQUENCE: 25
gacgacgaca agatgtcaat tgaaaaaagg gtaaac 36

<210> SEQ ID NO 26
<211> LENGTH: 30
<212> TYPE: DNA
<213> ORGANISM: Artificial Sequence
<220> FEATURE:
<223> OTHER INFORMATION: Synthesized Construct

<400> SEQUENCE: 26
gaggagaagc ccggttattc acaccatgca 30

<210> SEQ ID NO 27
<211> LENGTH: 771
<212> TYPE: PRT
<213> ORGANISM: Caldicellulosiruptor bescii

<400> SEQUENCE: 27

Met Ser Ile Glu Lys Arg Val Asn Gln Leu Leu Gln Gln Met Thr Val
1 5 10 15

Glu Glu Lys Val Tyr Gln Leu Thr Ser Val Leu Val Lys Asp Ile Leu
20 25 30

Glu Asn Asn Gln Phe Ser Glu Glu Lys Ala Lys Lys Val Ile Pro His
35 40 45

Gly Ile Gly Gln Ile Thr Arg Val Ala Gly Ala Ser Asn Phe Thr Pro
50 55 60

Gln Gln Ala Leu Glu Ala Ala Asn Gln Ile Gln Lys Phe Leu Ile Glu
65 70 75 80

Asn Thr Arg Leu Lys Ile Pro Ala Ile Ile His Glu Glu Ser Cys Ser
85 90 95

Gly Phe Met Ala Ser Lys Ala Thr Val Phe Pro Gln Ser Ile Gly Val
100 105 110

Ala Cys Thr Phe Asp Asn Glu Leu Val Lys Glu Met Ala Lys Val Ile
115 120 125

Arg Leu Gln Met Lys Ala Val Gly Ala His Gln Ala Leu Ala Pro Leu
130 135 140

Ile Asp Val Ala Arg Asp Ala Arg Trp Gly Arg Val Glu Glu Thr Phe
145 150 155 160

Gly Glu Asp Pro Tyr Leu Val Ala Asn Met Ala Val Ser Tyr Val Glu
165 170 175

Gly Ile Gln Gly Lys Asn Phe Glu Glu Lys Ile Ile Ala Thr Gly Lys
180 185 190

His Phe Val Gly Tyr Ala Met Ser Glu Gly Gly Met Asn Trp Ala Pro
195 200 205

Val His Ile Pro Glu Arg Glu Leu Arg Glu Val Tyr Leu Tyr Pro Phe
210 215 220

Glu Val Ala Val Lys Val Ala Gly Leu Lys Ser Ile Met Pro Ala Tyr
225 230 235 240

His Glu Ile Asp Gly Ile Pro Cys His Ala Asn Arg Lys Leu Leu Thr
245 250 255

Glu Ile Ala Arg Asn Glu Trp Arg Phe Asp Gly Ile Phe Val Ser Asp

-continued

```
            260                 265                 270

Tyr Ser Gly Val Lys Asn Ile Leu Asp Tyr His Lys Ser Val Lys Thr
        275                 280                 285

Tyr Glu Glu Ala Ala Tyr Ile Ser Leu Trp Ala Gly Leu Asp Ile Glu
    290                 295                 300

Leu Pro Arg Ile Glu Cys Phe Thr Glu Lys Phe Ile Glu Ala Leu Lys
305                 310                 315                 320

Glu Gly Lys Phe Asp Met Ala Val Val Asp Ala Ala Val Lys Arg Val
                325                 330                 335

Leu Glu Met Lys Phe Arg Leu Gly Leu Phe Asp Asn Pro Phe Val Lys
            340                 345                 350

Thr Glu Asn Ile Leu Glu Leu Phe Asp Asn Glu Glu Gln Arg Ser Leu
        355                 360                 365

Ala Arg Lys Val Ala Gln Glu Ser Met Val Leu Leu Lys Asn Asp Gly
    370                 375                 380

Ile Leu Pro Leu Lys Glu Lys Glu Leu Lys Lys Val Ala Val Ile Gly
385                 390                 395                 400

Pro Asn Ala Asn Ser Val Arg Asn Leu Leu Gly Asp Tyr Ser Tyr Pro
                405                 410                 415

Ala His Ile Ser Thr Thr Glu Met Phe Phe Met Lys Glu Glu Val Asp
            420                 425                 430

Leu Gly Asp Glu Asp Ala Phe Val Lys Lys Val Val Asn Ile Lys Ser
        435                 440                 445

Val Tyr Glu Val Ile Lys Glu Arg Ile Gly Lys His Thr Glu Val Val
    450                 455                 460

Tyr Ala Lys Gly Cys Asp Val Asn Ser Gln Asp Lys Ser Ser Phe Glu
465                 470                 475                 480

Glu Ala Lys Lys Ala Ala Gln Gly Ala Asp Val Val Ile Val Val Val
                485                 490                 495

Gly Asp Lys Ala Gly Leu Lys Leu Asp Cys Thr Ser Gly Glu Ser Arg
            500                 505                 510

Asp Arg Ala Ser Leu Lys Leu Pro Gly Val Gln Glu Glu Leu Ile Glu
        515                 520                 525

Glu Ile Ser Lys Val Asn Gln Asn Ile Val Val Ile Leu Val Asn Gly
    530                 535                 540

Arg Pro Val Ala Leu Glu Asn Phe Trp Gln Lys Ser Lys Ala Ile Leu
545                 550                 555                 560

Glu Ala Trp Phe Pro Gly Glu Glu Gly Ala Glu Ala Ile Ala Asp Val
                565                 570                 575

Ile Phe Gly Lys Tyr Asn Pro Gly Gly Lys Leu Ala Ile Ser Phe Pro
            580                 585                 590

Arg Asp Val Gly Gln Val Pro Val Tyr Tyr Ser His Lys Pro Ser Gly
        595                 600                 605

Gly Lys Ser Cys Trp His Gly Asp Tyr Val Glu Met Ser Ser Lys Pro
    610                 615                 620

Phe Leu Pro Phe Gly Tyr Gly Leu Ser Tyr Thr Thr Phe Glu Tyr Lys
625                 630                 635                 640

Asn Leu Thr Ile Glu Lys Glu Lys Ile Thr Met Asp Glu Ser Ile Lys
                645                 650                 655

Ile Ser Val Glu Ile Glu Asn Thr Gly Asn Tyr Glu Gly Asp Glu Val
            660                 665                 670

Val Gln Leu Tyr Thr Arg Lys Glu Glu Phe Leu Val Thr Arg Pro Val
        675                 680                 685
```

```
Lys Glu Leu Lys Ala Tyr Lys Arg Val His Leu Lys Pro Gly Glu Lys
    690                 695                 700

Lys Lys Val Val Phe Glu Ile Phe Pro Asp Gln Phe Ala Tyr Tyr Asp
705                 710                 715                 720

Tyr Asp Met Asn Arg Val Ile Ser Pro Gly Thr Val Glu Val Met Val
                725                 730                 735

Gly Ala Ser Ser Glu Asp Ile Lys Phe Thr Gly Thr Phe Glu Ile Val
            740                 745                 750

Gly Glu Lys Lys Asp Ala Lys Glu Ile Lys Asn Tyr Leu Ser His Ala
        755                 760                 765

Trp Cys Glu
    770


<210> SEQ ID NO 28
<211> LENGTH: 2319
<212> TYPE: DNA
<213> ORGANISM: Caldicellulosiruptor bescii

<400> SEQUENCE: 28

gtggtgtcaa ttgaaaaaag ggtaaaccag cttttgcagc agatgacagt tgaagaaaag      60

gtgtatcagc tcacaagtgt gcttgtaaaa gatattttgg aaaacaacca attttctgag     120

gaaaaagcaa agaaagtcat tcctcatggt attggccaga ttacaagggt tgcaggtgcg     180

agcaatttca cacctcaaca ggctttagag gcagcaaacc aaatccaaaa gtttttgatt     240

gaaaacacaa ggctcaaaat tcctgcgata atccatgaag aatcttgttc tggttttatg     300

gcaagcaaag caacagtatt tccacagagc attggtgttg cctgcacttt tgacaatgaa     360

cttgtaaaag agatggcaaa ggttataagg ctgcagatga aagctgtagg tgcgcatcag     420

gctttggcac cacttattga tgttgcaagg gatgcacgat ggggaagggt tgaagagaca     480

tttggtgaag acccatatct tgttgcaaat atggcagtaa gttatgttga aggaattcag     540

ggcaagaact ttgaagaaaa gattattgca acaggcaaac attttgttgg ttatgcaatg     600

tcagaaggtg ggatgaactg ggcacctgtt catattcctg aaagagagct aagagaagtg     660

tatctttatc catttgaggt cgctgttaaa gtggcaggat taaaatcaat tatgccagct     720

taccatgaaa ttgacggaat tccttgtcat gcaaacagaa agcttttgac cgaaattgca     780

aggaatgaat ggagattcga tggaatattt gtgtctgact acagtggtgt taaaaatatc     840

ttagactatc ataagtcggt taaaacttat gaagaggcag cgtatatttc tctttgggca     900

ggacttgata ttgaacttcc aagaatagag tgttttactg agaagtttat tgaggcatta     960

aaagaaggca agtttgatat ggcagttgtt gatgctgctg tgaagagagt tttagagatg    1020

aagttcaggc tcggactttt tgacaatcca tttgtaaaaa cagaaaatat tttagaactt    1080

tttgacaatg aggagcaaag aagccttgca agaaaagttg cccaagagtc tatggttctt    1140

ttgaaaaacg acggtatatt gccacttaaa gaaaaagaac tcaagaaagt tgctgtgata    1200

ggacctaatg ccaactcagt tagaaatctt cttggtgatt attcttaccc agcacacata    1260

tcaacaacag aaatgttctt tatgaaagaa gaggttgacc tcggcgatga agatgcattt    1320

gtcaaaaagg ttgtaaatat taaatctgta tatgaagtta taaaagaaag aataggtaag    1380

catacagagg tagtctatgc aaaaggttgt gatgtaaact ctcaagataa gtccagcttt    1440

gaagaagcta aaaaagctgc ccagggcgca gatgttgtta tagttgtagt tggtgacaag    1500

gcagggttaa aacttgactg cacatctggt gagtcaagag atagagcaag cttaaaactt    1560
```

-continued ccaggtgttc aggaagagct gatagaagaa atttcaaaag taaatcaaaa cattgttgtt 1620
attcttgtaa acggtcgacc tgttgcgctc gaaaatttct ggcaaaagtc caaagctatt 1680
cttgaagctt ggttcccggg cgaagaaggt gcagaggcga ttgcagatgt tatctttgga 1740
aagtacaatc cgggtggaaa acttgcaatt tcattcccaa gagatgttgg gcaagtaccg 1800
gtatactata gtcacaaacc atccggtgga aaatcatgct ggcatgggga ctatgttgaa 1860
atgtcttcaa agccattttt accatttggt tacggtcttt cgtatacaac ttttgaatac 1920
aaaaatctta ccattgaaaa agaaaaaatt acaatggatg agagcataaa aatctcggtt 1980
gagatagaaa atacaggaaa ctatgaagga gatgaggtag ttcagctgta tacaagaaaa 2040
gaagagtttt tagtaacaag acctgtaaaa gagctaaagg catacaagag agttcactta 2100
aaacctggtg aaaagaagaa agttgtattt gaaatcttcc cagaccagtt tgcatactat 2160
gattatgata tgaacagggt aatctcaccc ggcactgttg aggtcatggt aggggcatct 2220
tcagaagaca taaagtttac agggacattt gagattgttg ggaaaaagaa agatgcaaaa 2280
gaaatcaaaa attatcttag ccatgcatgg tgtgaataa 2319

<210> SEQ ID NO 29
<211> LENGTH: 2361
<212> TYPE: DNA
<213> ORGANISM: Caldicellulosiruptor bescii

<400> SEQUENCE: 29
atggcacatc accaccacca tcacgtggat gacgacgaca agatggtgtc aattgaaaaa 60
agggtaaacc agcttttgca gcagatgaca gttgaagaaa aggtgtatca gctcacaagt 120
gtgcttgtaa aagatatttt ggaaaacaac caattttctg aggaaaaagc aaagaaagtc 180
attcctcatg gtattggcca gattacaagg gttgcaggtg cgagcaattt cacacctcaa 240
caggctttag aggcagcaaa ccaaatccaa aagtttttga ttgaaaacac aaggctcaaa 300
attcctgcga taatccatga agaatcttgt tctggtttta tggcaagcaa agcaacagta 360
tttccacaga gcattggtgt tgcctgcact tttgacaatg aacttgtaaa agagatggca 420
aaggttataa ggctgcagat gaaagctgta ggtgcgcatc aggctttggc accacttatt 480
gatgttgcaa gggatgcacg atggggaagg gttgaagaga catttggtga agacccatat 540
cttgttgcaa atatggcagt aagttatgtt gaaggaattc agggcaagaa ctttgaagaa 600
aagattattg caacaggcaa acattttgtt ggttatgcaa tgtcagaagg tgggatgaac 660
tgggcacctg ttcatattcc tgaaagagag ctaagagaag tgtatcttta tccatttgag 720
gtcgctgtta aagtggcagg attaaaatca attatgccag cttaccatga aattgacgga 780
attccttgtc atgcaaacag aaagcttttg accgaaattg caaggaatga atggagattc 840
gatggaatat ttgtgtctga ctacagtggt gttaaaaata tcttagacta tcataagtcg 900
gttaaaactt atgaagaggc agcgtatatt tctctttggg caggacttga tattgaactt 960
ccaagaatag agtgttttac tgagaagttt attgaggcat taaaagaagg caagtttgat 1020
atggcagttg ttgatgctgc tgtgaagaga gttttagaga tgaagttcag gctcggactt 1080
tttgacaatc catttgtaaa aacagaaaat attttagaac tttttgacaa tgaggagcaa 1140
agaagccttg caagaaaagt tgcccaagag tctatggttc ttttgaaaaa cgacggtata 1200
ttgccactta aagaaaaaga actcaagaaa gttgctgtga taggacctaa tgccaactca 1260
gttagaaatc ttcttggtga ttattcttac ccagcacaca tatcaacaac agaaatgttc 1320
tttatgaaag aagaggttga cctcggcgat gaagatgcat ttgtcaaaaa ggttgtaaat 1380
attaaatctg tatatgaagt tataaaagaa agaataggta agcatacaga ggtagtctat 1440
gcaaaaggtt gtgatgtaaa ctctcaagat aagtccagct ttgaagaagc taaaaaagct 1500
gcccagggcg cagatgttgt tatagttgta gttggtgaca aggcagggtt aaaacttgac 1560
tgcacatctg gtgagtcaag agatagagca agcttaaaac ttccaggtgt tcaggaagag 1620
ctgatagaag aaatttcaaa agtaaatcaa aacattgttg ttattcttgt aaacggtcga 1680
cctgttgcgc tcgaaaattt ctggcaaaag tccaaagcta ttcttgaagc ttggttcccg 1740
ggcgaagaag gtgcagaggc gattgcagat gttatctttg gaaagtacaa tccgggtgga 1800
aaacttgcaa tttcattccc aagagatgtt gggcaagtac cggtatacta tagtcacaaa 1860
ccatccggtg gaaaatcatg ctggcatggg gactatgttg aaatgtcttc aaagccattt 1920
ttaccatttg gttacggtct ttcgtataca acttttgaat acaaaaatct taccattgaa 1980
aaagaaaaaa ttacaatgga tgagagcata aaaatctcgg ttgagataga aaatacagga 2040
aactatgaag gagatgaggt agttcagctg tatacaagaa aagaagagtt tttagtaaca 2100
agacctgtaa aagagctaaa ggcatacaag agagttcact taaaacctgg tgaaaagaag 2160
aaagttgtat ttgaaatctt cccagaccag tttgcatact atgattatga tatgaacagg 2220
gtaatctcac ccggcactgt tgaggtcatg gtaggggcat cttcagaaga cataaagttt 2280
acagggacat ttgagattgt tggggaaaag aaagatgcaa aagaaatcaa aaattatctt 2340
agccatgcat ggtgtgaata a 2361

<210> SEQ ID NO 30
<211> LENGTH: 785
<212> TYPE: PRT
<213> ORGANISM: Caldicellulosiruptor bescii

<400> SEQUENCE: 30

Met Ala His His His His His His Val Asp Asp Asp Asp Lys Met Ser
1 5 10 15

Ile Glu Lys Arg Val Asn Gln Leu Leu Gln Gln Met Thr Val Glu Glu
20 25 30

Lys Val Tyr Gln Leu Thr Ser Val Leu Val Lys Asp Ile Leu Glu Asn
35 40 45

Asn Gln Phe Ser Glu Glu Lys Ala Lys Lys Val Ile Pro His Gly Ile
50 55 60

Gly Gln Ile Thr Arg Val Ala Gly Ala Ser Asn Phe Thr Pro Gln Gln
65 70 75 80

Ala Leu Glu Ala Ala Asn Gln Ile Gln Lys Phe Leu Ile Glu Asn Thr
85 90 95

Arg Leu Lys Ile Pro Ala Ile Ile His Glu Glu Ser Cys Ser Gly Phe
100 105 110

Met Ala Ser Lys Ala Thr Val Phe Pro Gln Ser Ile Gly Val Ala Cys
115 120 125

Thr Phe Asp Asn Glu Leu Val Lys Glu Met Ala Lys Val Ile Arg Leu
130 135 140

Gln Met Lys Ala Val Gly Ala His Gln Ala Leu Ala Pro Leu Ile Asp
145 150 155 160

Val Ala Arg Asp Ala Arg Trp Gly Arg Val Glu Glu Thr Phe Gly Glu
165 170 175

Asp Pro Tyr Leu Val Ala Asn Met Ala Val Ser Tyr Val Glu Gly Ile
180 185 190

-continued

```
Gln Gly Lys Asn Phe Glu Glu Lys Ile Ile Ala Thr Gly Lys His Phe
        195                 200                 205

Val Gly Tyr Ala Met Ser Glu Gly Gly Met Asn Trp Ala Pro Val His
    210                 215                 220

Ile Pro Glu Arg Glu Leu Arg Glu Val Tyr Leu Tyr Pro Phe Glu Val
225                 230                 235                 240

Ala Val Lys Val Ala Gly Leu Lys Ser Ile Met Pro Ala Tyr His Glu
                245                 250                 255

Ile Asp Gly Ile Pro Cys His Ala Asn Arg Lys Leu Leu Thr Glu Ile
            260                 265                 270

Ala Arg Asn Glu Trp Arg Phe Asp Gly Ile Phe Val Ser Asp Tyr Ser
        275                 280                 285

Gly Val Lys Asn Ile Leu Asp Tyr His Lys Ser Val Lys Thr Tyr Glu
    290                 295                 300

Glu Ala Ala Tyr Ile Ser Leu Trp Ala Gly Leu Asp Ile Glu Leu Pro
305                 310                 315                 320

Arg Ile Glu Cys Phe Thr Glu Lys Phe Ile Glu Ala Leu Lys Glu Gly
                325                 330                 335

Lys Phe Asp Met Ala Val Val Asp Ala Ala Val Lys Arg Val Leu Glu
            340                 345                 350

Met Lys Phe Arg Leu Gly Leu Phe Asp Asn Pro Phe Val Lys Thr Glu
        355                 360                 365

Asn Ile Leu Glu Leu Phe Asp Asn Glu Glu Gln Arg Ser Leu Ala Arg
    370                 375                 380

Lys Val Ala Gln Glu Ser Met Val Leu Leu Lys Asn Asp Gly Ile Leu
385                 390                 395                 400

Pro Leu Lys Glu Lys Glu Leu Lys Lys Val Ala Val Ile Gly Pro Asn
                405                 410                 415

Ala Asn Ser Val Arg Asn Leu Leu Gly Asp Tyr Ser Tyr Pro Ala His
            420                 425                 430

Ile Ser Thr Thr Glu Met Phe Phe Met Lys Glu Glu Val Asp Leu Gly
        435                 440                 445

Asp Glu Asp Ala Phe Val Lys Lys Val Val Asn Ile Lys Ser Val Tyr
    450                 455                 460

Glu Val Ile Lys Glu Arg Ile Gly Lys His Thr Glu Val Val Tyr Ala
465                 470                 475                 480

Lys Gly Cys Asp Val Asn Ser Gln Asp Lys Ser Ser Phe Glu Glu Ala
                485                 490                 495

Lys Lys Ala Ala Gln Gly Ala Asp Val Val Ile Val Val Val Gly Asp
            500                 505                 510

Lys Ala Gly Leu Lys Leu Asp Cys Thr Ser Gly Glu Ser Arg Asp Arg
        515                 520                 525

Ala Ser Leu Lys Leu Pro Gly Val Gln Glu Glu Leu Ile Glu Glu Ile
    530                 535                 540

Ser Lys Val Asn Gln Asn Ile Val Val Ile Leu Val Asn Gly Arg Pro
545                 550                 555                 560

Val Ala Leu Glu Asn Phe Trp Gln Lys Ser Lys Ala Ile Leu Glu Ala
                565                 570                 575

Trp Phe Pro Gly Glu Glu Gly Ala Glu Ala Ile Ala Asp Val Ile Phe
            580                 585                 590

Gly Lys Tyr Asn Pro Gly Gly Lys Leu Ala Ile Ser Phe Pro Arg Asp
        595                 600                 605

Val Gly Gln Val Pro Val Tyr Tyr Ser His Lys Pro Ser Gly Gly Lys
```

610 615 620

Ser Cys Trp His Gly Asp Tyr Val Glu Met Ser Ser Lys Pro Phe Leu
625 630 635 640

Pro Phe Gly Tyr Gly Leu Ser Tyr Thr Thr Phe Glu Tyr Lys Asn Leu
645 650 655

Thr Ile Glu Lys Glu Lys Ile Thr Met Asp Glu Ser Ile Lys Ile Ser
660 665 670

Val Glu Ile Glu Asn Thr Gly Asn Tyr Glu Gly Asp Glu Val Val Gln
675 680 685

Leu Tyr Thr Arg Lys Glu Glu Phe Leu Val Thr Arg Pro Val Lys Glu
690 695 700

Leu Lys Ala Tyr Lys Arg Val His Leu Lys Pro Gly Glu Lys Lys Lys
705 710 715 720

Val Val Phe Glu Ile Phe Pro Asp Gln Phe Ala Tyr Tyr Asp Tyr Asp
725 730 735

Met Asn Arg Val Ile Ser Pro Gly Thr Val Glu Val Met Val Gly Ala
740 745 750

Ser Ser Glu Asp Ile Lys Phe Thr Gly Thr Phe Glu Ile Val Gly Glu
755 760 765

Lys Lys Asp Ala Lys Glu Ile Lys Asn Tyr Leu Ser His Ala Trp Cys
770 775 780

Glu
785

<210> SEQ ID NO 31
<211> LENGTH: 39
<212> TYPE: DNA
<213> ORGANISM: Artificial Sequence
<220> FEATURE:
<223> OTHER INFORMATION: Synthesized Construct

<400> SEQUENCE: 31
gacgacgaca agatggtttt tgaaatgcca cttgaaaag 39

<210> SEQ ID NO 32
<211> LENGTH: 53
<212> TYPE: DNA
<213> ORGANISM: Artificial Sequence
<220> FEATURE:
<223> OTHER INFORMATION: Synthesized Construct

<400> SEQUENCE: 32
gaggagaagc ccggttattt tatcatctcc ataagataca taaatatctt gtc 53

<210> SEQ ID NO 33
<211> LENGTH: 321
<212> TYPE: PRT
<213> ORGANISM: Caldicellulosiruptor bescii

<400> SEQUENCE: 33

Met Val Phe Glu Met Pro Leu Glu Lys Leu Lys Thr Tyr Met Gly Thr
1 5 10 15

Asn Pro Cys Pro Pro Asp Phe Asp Glu Tyr Trp Gln Arg Ala Leu Lys
20 25 30

Glu Met Asp Glu Val Glu Pro Asn Val Glu Ile Val Lys Glu Glu Ser
35 40 45

Val Glu Ala Pro Tyr Ala Glu Cys Phe Asn Met Tyr Phe Thr Gly Val
50 55 60

-continued

```
Lys Gly Ala Arg Ile Arg Val Gln Leu Ile Lys Pro Lys Lys Ile Glu
65                  70                  75                  80

Lys Gln Cys Pro Ala Ile Leu Met Phe His Gly Tyr Lys Trp Tyr Ser
                85                  90                  95

Gly Asp Trp Ser Asp Lys Phe Gly Leu Val Ala Ala Gly Phe Ile Val
            100                 105                 110

Ala Ala Met Asp Val Arg Gly Gln Asn Gly Tyr Ser Glu Asp Val Gly
        115                 120                 125

Gly Val Lys Gly Asn Thr Val Gln Gly His Ile Ile Arg Gly Phe Asp
    130                 135                 140

Asp Asp Lys Asp Gln Leu Leu Tyr Arg Gln Ile Phe Leu Asp Thr Ala
145                 150                 155                 160

Glu Leu Ala Lys Ile Ile Ala Asn Met Pro Glu Val Asp Glu Lys Arg
                165                 170                 175

Ile Ala Ala Leu Gly Tyr Ser Gln Gly Gly Gly Leu Ala Leu Ala Cys
            180                 185                 190

Ala Ala Leu Ser Pro Tyr Ile Ser Arg Val Val Ser Val Tyr Pro Phe
        195                 200                 205

Leu Cys Asp Tyr Lys Arg Val Trp Glu Met Asp Leu Ala Lys Glu Ala
    210                 215                 220

Tyr Glu Glu Ile Arg Thr Tyr Phe Arg Phe Arg Asp Pro Leu His Glu
225                 230                 235                 240

Arg Glu Asp Glu Ile Phe Thr Lys Leu Gly Tyr Ile Asp Val Gln His
                245                 250                 255

Leu Ala Lys Trp Ile Arg Ala Glu Val Leu Met Val Thr Gly Leu Met
            260                 265                 270

Asp Thr Ile Cys Pro Pro Ser Thr Gln Phe Ala Ala Tyr Asn Lys Ile
        275                 280                 285

Gln Ser Lys Lys Gln Met Leu Ile Tyr Pro Asp Phe Gly His Glu Gln
    290                 295                 300

Ile Phe Tyr Leu Asn Asp Lys Ile Phe Met Tyr Leu Met Glu Met Ile
305                 310                 315                 320

Lys
```

<210> SEQ ID NO 34
<211> LENGTH: 966
<212> TYPE: DNA
<213> ORGANISM: Caldicellulosiruptor bescii

<400> SEQUENCE: 34

```
atggtttttg aaatgccact tgaaaagtta aaaacgtata tggggacaaa tccgtgtccg     60

ccagattttg atgagtactg gcaaagggcg ttaaaagaga tggatgaggt tgaacccaat    120

gtagagattg tcaaagaaga gtcagtagaa gctccatatg ctgagtgttt taatatgtat    180

tttaccggag taaaaggagc aagaataaga gttcagctta taaaacctaa gaaaattgaa    240

aagcaatgcc ctgcaatttt gatgtttcat ggatacaaat ggtactctgg cgactggagt    300

gacaaatttg gacttgttgc tgcaggtttc atagttgctg caatggatgt aagaggacaa    360

aatggttatt cagaagatgt tggtggcgtg aagggcaaca cggttcaagg acatataata    420

aggggttttg acgatgataa agaccagctt ttatacaggc agattttctt agatacagct    480

gagcttgcaa agataatagc taacatgcca gaagtagatg aaaaaagaat tgcagcatta    540

ggatattctc aaggtggcgg gcttgctctt gcctgtgcag ctttatctcc ttatatttca    600

agggttgtct ctgtttatcc ttttctttgt gactacaaga gagtttggga gatggattta    660
```

```
gcaaaagagg cttatgaaga aataagaaca tatttcagat ttagagaccc tcttcatgaa    720

agagaagatg agatatttac aaagcttggc tacatagatg ttcagcacct tgcaaagtgg    780

ataagagcag aggttttaat ggttacaggt cttatggaca caatctgccc accatctact    840

cagtttgctg cctacaataa aatacagtcc aaaaaacaaa tgctcatcta ccctgacttt    900

ggacatgaac agattttcta cttaaatgac aagatattta tgtatcttat ggagatgata    960

aaataa                                                               966
```

<210> SEQ ID NO 35
<211> LENGTH: 1008
<212> TYPE: DNA
<213> ORGANISM: Caldicellulosiruptor bescii

<400> SEQUENCE: 35

```
atggcacatc accaccacca tcacgtggat gacgacgaca agatggtttt tgaaatgcca     60

cttgaaaagt taaaaacgta tatggggaca aatccgtgtc cgccagattt tgatgagtac    120

tggcaaaggg cgttaaaaga gatggatgag gttgaaccca atgtagagat tgtcaaagaa    180

gagtcagtag aagctccata tgctgagtgt tttaatatgt attttaccgg agtaaaagga    240

gcaagaataa gagttcagct tataaaacct aagaaaattg aaaagcaatg ccctgcaatt    300

ttgatgtttc atggatacaa atggtactct ggcgactgga gtgacaaatt tggacttgtt    360

gctgcaggtt tcatagttgc tgcaatggat gtaagaggac aaaatggtta ttcagaagat    420

gttggtggcg tgaagggcaa cacggttcaa ggacatataa taaggggttt tgacgatgat    480

aaagaccagc ttttatacag gcagattttc ttagatacag ctgagcttgc aaagataata    540

gctaacatgc cagaagtaga tgaaaaaaga attgcagcat taggatattc tcaaggtggc    600

gggcttgctc ttgcctgtgc agctttatct ccttatattt caagggttgt ctctgtttat    660

ccttttcttt gtgactacaa gagagtttgg gagatggatt tagcaaaaga ggcttatgaa    720

gaaataagaa catatttcag atttagagac cctcttcatg aaagagaaga tgagatattt    780

acaaagcttg gctacataga tgttcagcac cttgcaaagt ggataagagc agaggtttta    840

atggttacag gtcttatgga cacaatctgc ccaccatcta ctcagtttgc tgcctacaat    900

aaaatacagt ccaaaaaaca aatgctcatc taccctgact ttggacatga acagattttc    960

tacttaaatg acaagatatt tatgtatctt atggagatga taaaataa                1008
```

<210> SEQ ID NO 36
<211> LENGTH: 335
<212> TYPE: PRT
<213> ORGANISM: Caldicellulosiruptor bescii

<400> SEQUENCE: 36

```
Met Ala His His His His His His Val Asp Asp Asp Asp Lys Met Val
1               5                   10                  15

Phe Glu Met Pro Leu Glu Lys Leu Lys Thr Tyr Met Gly Thr Asn Pro
            20                  25                  30

Cys Pro Pro Asp Phe Asp Glu Tyr Trp Gln Arg Ala Leu Lys Glu Met
        35                  40                  45

Asp Glu Val Glu Pro Asn Val Glu Ile Val Lys Glu Glu Ser Val Glu
    50                  55                  60

Ala Pro Tyr Ala Glu Cys Phe Asn Met Tyr Phe Thr Gly Val Lys Gly
65                  70                  75                  80

Ala Arg Ile Arg Val Gln Leu Ile Lys Pro Lys Lys Ile Glu Lys Gln
```

```
                85                  90                  95

Cys Pro Ala Ile Leu Met Phe His Gly Tyr Lys Trp Tyr Ser Gly Asp
            100                 105                 110

Trp Ser Asp Lys Phe Gly Leu Val Ala Ala Gly Phe Ile Val Ala Ala
        115                 120                 125

Met Asp Val Arg Gly Gln Asn Gly Tyr Ser Glu Asp Val Gly Gly Val
    130                 135                 140

Lys Gly Asn Thr Val Gln Gly His Ile Ile Arg Gly Phe Asp Asp Asp
145                 150                 155                 160

Lys Asp Gln Leu Leu Tyr Arg Gln Ile Phe Leu Asp Thr Ala Glu Leu
                165                 170                 175

Ala Lys Ile Ile Ala Asn Met Pro Glu Val Asp Glu Lys Arg Ile Ala
            180                 185                 190

Ala Leu Gly Tyr Ser Gln Gly Gly Gly Leu Ala Leu Ala Cys Ala Ala
        195                 200                 205

Leu Ser Pro Tyr Ile Ser Arg Val Val Ser Val Tyr Pro Phe Leu Cys
    210                 215                 220

Asp Tyr Lys Arg Val Trp Glu Met Asp Leu Ala Lys Glu Ala Tyr Glu
225                 230                 235                 240

Glu Ile Arg Thr Tyr Phe Arg Phe Arg Asp Pro Leu His Glu Arg Glu
                245                 250                 255

Asp Glu Ile Phe Thr Lys Leu Gly Tyr Ile Asp Val Gln His Leu Ala
            260                 265                 270

Lys Trp Ile Arg Ala Glu Val Leu Met Val Thr Gly Leu Met Asp Thr
        275                 280                 285

Ile Cys Pro Pro Ser Thr Gln Phe Ala Ala Tyr Asn Lys Ile Gln Ser
    290                 295                 300

Lys Lys Gln Met Leu Ile Tyr Pro Asp Phe Gly His Glu Gln Ile Phe
305                 310                 315                 320

Tyr Leu Asn Asp Lys Ile Phe Met Tyr Leu Met Glu Met Ile Lys
                325                 330                 335


<210> SEQ ID NO 37
<211> LENGTH: 656
<212> TYPE: PRT
<213> ORGANISM: Caldicellulosiruptor bescii

<400> SEQUENCE: 37

Asn Phe Glu Gly Arg Asp Lys Leu Thr Phe Phe Ala Tyr Gly Lys Ala
 1               5                  10                  15

Lys Ile Thr Ile Asp Gln Asn Ile Ala Gln Glu Gly Lys Lys Ser Ile
            20                  25                  30

Lys Val Thr Asp Arg Lys Ser Val Trp Asp Ser Phe Gly Ile Asp Val
        35                  40                  45

Lys Asp Val Leu Gln Arg Gly Lys Thr Trp Val Val Ser Ala Tyr Val
    50                  55                  60

Lys His Lys Gly Lys Lys Pro Ile Glu Phe Ser Ile Thr Ala Ile Tyr
65                  70                  75                  80

Asn Asp Gly Arg Gly Leu Lys Tyr Leu Gln Leu Gly Glu Lys Ile Val
                85                  90                  95

Ile Pro Asn Lys Trp Asp Lys Ile Val Ala Lys Trp Lys Pro Thr Leu
            100                 105                 110

Lys Asn Pro Met Asp Leu Ile Ile Ala Ile His Pro Thr Val Asp Lys
        115                 120                 125
```

```
Thr Thr Ala Tyr Asn Val Asp Asn Ile Gln Ile Met Thr Glu Glu Val
    130                 135                 140

Tyr Gln Ser Gln Ala Val Val Phe Lys Asp Thr Phe Glu Ser Asn Leu
145                 150                 155                 160

Thr Asn Trp Gln Pro Arg Gly Asp Thr Val Lys Leu Lys Ile Asp Asn
                165                 170                 175

Thr Lys Ser His Asn Gly Asn Lys Ser Leu Tyr Val Ser Gly Arg Ser
            180                 185                 190

Ala Phe Trp His Gly Val Gln Ile Pro Val Thr Lys Tyr Leu Val Ala
        195                 200                 205

Gly Lys Val Tyr Lys Phe Ser Val Trp Leu Tyr His Gln Ser Ile Asp
    210                 215                 220

Lys Gln Gly Phe Gly Leu Thr Ile Gln Arg Lys Met Ala Asn Asp Glu
225                 230                 235                 240

Gln Tyr Lys Tyr Asp Trp Ile Thr Gly Ser Gln Ile Glu Gly Asp Gly
                245                 250                 255

Trp Val Glu Ile Ser Gly Asn Tyr Tyr Val Pro Lys Asp Gly Lys Ile
            260                 265                 270

Glu Glu Leu Val Phe Cys Val Ser Ser Trp Asn Pro Thr Leu Ala Phe
        275                 280                 285

Trp Val Asp Asp Val Thr Ile Ser Asp Pro Phe Lys Leu Gln Gly Pro
    290                 295                 300

Asn Tyr Asn Leu Pro Ser Leu Lys Glu Lys Tyr Lys Glu Asp Phe Lys
305                 310                 315                 320

Val Gly Val Ala Ile Gly Tyr Gly Glu Leu Ile Ser Asp Ile Asp Thr
                325                 330                 335

Gln Phe Ile Lys Lys His Phe Asn Ser Ile Thr Pro Gly Asn Glu Met
            340                 345                 350

Lys Pro Glu Ser Val Leu Lys Gly Pro Asn Asn Tyr Asp Phe Thr Ile
        355                 360                 365

Ala Asp Ala Phe Val Asp Phe Ala Thr Lys Asn Lys Met Gly Ile Arg
    370                 375                 380

Gly His Thr Leu Val Trp His Asn Gln Thr Pro Asp Trp Phe Phe Lys
385                 390                 395                 400

Asp Glu Asn Gly Asn Phe Leu Lys Lys Asp Glu Leu Leu Lys Arg Leu
                405                 410                 415

Lys Asn His Ile Tyr Thr Val Val Ser Arg Tyr Lys Gly Lys Ile Tyr
            420                 425                 430

Ala Trp Asp Val Val Asn Glu Ala Ile Asp Glu Thr Gln Pro Asp Gly
        435                 440                 445

Tyr Arg Arg Ser Asn Trp Tyr Asn Ile Cys Gly Pro Glu Tyr Ile Glu
    450                 455                 460

Lys Ala Phe Ile Trp Ala His Glu Ala Asp Pro Gln Ala Lys Leu Phe
465                 470                 475                 480

Tyr Asn Asp Tyr Asn Thr Glu Ile Pro Gln Lys Arg Met Phe Ile Tyr
                485                 490                 495

Asn Met Ile Lys Asn Leu Lys Ala Lys Gly Val Pro Ile His Gly Ile
            500                 505                 510

Gly Leu Gln Cys His Ile Asn Ile Asp Asn Pro Ser Val Glu Asp Ile
        515                 520                 525

Glu Glu Thr Ile Lys Leu Phe Ser Thr Ile Pro Gly Leu Glu Ile Gln
    530                 535                 540

Ile Thr Glu Leu Asp Met Ser Phe Tyr Gln Trp Gly Ser Ser Val Tyr
```

-continued

```
545                 550                 555                 560

Tyr Ala Glu Pro Ser Arg Glu Met Leu Leu Lys Gln Ala Lys Lys Tyr
                565                 570                 575

Tyr Glu Leu Phe Asn Leu Phe Lys Lys Tyr Lys Asn Val Ile Lys Ser
            580                 585                 590

Val Thr Phe Trp Gly Leu Lys Asp Asp Asn Ser Trp Leu Arg Gly Val
        595                 600                 605

Phe Asn Lys Pro Asp Phe Pro Leu Leu Phe Asp Glu His Tyr Asp Gly
    610                 615                 620

Lys Pro Ala Phe Trp Ala Leu Ile Asp Tyr Ser Ile Leu Pro Gln Asn
625                 630                 635                 640

Ala Asn Leu Pro Thr Pro Pro Ala Ile Pro Lys Val Lys Ala Lys Lys
                645                 650                 655
```

<210> SEQ ID NO 38
<211> LENGTH: 1971
<212> TYPE: DNA
<213> ORGANISM: Caldicellulosiruptor bescii

<400> SEQUENCE: 38

```
aactttgaag gaagagacaa gttaacattt tttgcatatg gcaaagcaaa aataacaata     60

gaccaaaaca tagcacaaga aggaaaaaag agtataaaag ttacagacag gaaaagtgta    120

tgggatagct ttgggataga tgtaaaagat gttttacaaa gaggaaaaac atgggtggta    180

tcagcctatg taaaacataa ggggaagaag ccgatagaat tttcaataac agctatttat    240

aatgacggca gggggttaaa gtaccttcag cttggtgaga aaattgtcat accaaacaaa    300

tgggacaaaa ttgttgctaa gtggaaacca acgttaaaaa acccgatgga cttgattatt    360

gcaattcatc caacagttga taaaacaact gcatataatg tggacaatat tcaaataatg    420

acagaagaag tttatcaatc acaagctgtt gtttttaaag atacatttga atcaaatttg    480

acaaactggc agccaagagg tgatactgta aaactaaaaa tagataatac aaaatcgcat    540

aatggaaata agagtcttta tgtatcaggt cgttcggcat tctggcatgg agttcaaatt    600

cctgtgacaa aatatcttgt tgctgggaag gtatacaaat ttagcgtatg gctgtatcat    660

caatcaattg acaagcaagg ttttggtctt accattcaaa gaaagatggc aaacgatgaa    720

caatataaat atgattggat aactggaagc cagattgaag gtgatggctg ggttgagata    780

agtggtaatt attatgtacc aaaggatggc aaaatagaag aacttgtatt ttgtgtttct    840

tcgtggaacc caacattagc attttgggta gatgatgtta caatatctga tccgtttaag    900

ttacagggac ctaattataa tttgccgtct ttaaaagaga aatataaaga agattttaaa    960

gttggtgtag ctattggata tggtgaactt attagtgata tagacacaca atttatcaaa   1020

aaacatttta acagtataac accaggcaac gagatgaaac ccgaaagtgt gctaaaagga   1080

ccaaacaact atgactttac aatagcggat gcatttgtgg attttgcaac aaaaaataaa   1140

atgggtatac gcggacatac tcttgtctgg cacaaccaga cacctgattg gttcttcaaa   1200

gatgagaatg gcaatttttt aaagaaggat gaacttttga aaaggttaaa aaatcatata   1260

tacacagttg ttagccggta taaaggcaaa atatatgctt gggatgttgt caatgaagct   1320

attgatgaaa cacaacctga tggttacaga aggtcaaact ggtacaatat ttgtggaccc   1380

gaatatatag aaaaagcgtt tatttgggca catgaggcag atccacaagc aaagttattt   1440

tacaatgatt acaataccga aattccacaa aagagaatgt ttatatataa catgattaaa   1500

aatttgaaag caaaaggtgt tccaatacat ggtataggtc ttcaatgtca cataaatatt   1560
```

```
gacaatcctt ctgttgaaga tatagaggag acgataaaac tatttagcac aattccaggg   1620

cttgagattc aaattactga gcttgacatg agcttttatc aatggggttc ttctgtttat   1680

tacgcagagc catcaagaga aatgttatta aaacaggcaa agaaatacta tgagttattt   1740

aacctattta agaagtacaa aaatgtcata aaaagcgtta cattctgggg gcttaaggat   1800

gacaactctt ggctgagagg agtttttaac aaaccagatt ttccgctttt atttgatgag   1860

cattatgatg gcaaacctgc tttctgggcg ttgatagact attcaatatt accacaaaat   1920

gccaatttgc ctacaccacc tgctattcca aaagtaaagg ctaaaaaata a            1971
```

<210> SEQ ID NO 39
<211> LENGTH: 43
<212> TYPE: DNA
<213> ORGANISM: Artificial Sequence
<220> FEATURE:
<223> OTHER INFORMATION: Synthesized Construct

<400> SEQUENCE: 39

```
gacgacgaca agatggcaac aacctttaac tatggtgaag ctc                        43
```

<210> SEQ ID NO 40
<211> LENGTH: 46
<212> TYPE: DNA
<213> ORGANISM: Artificial Sequence
<220> FEATURE:
<223> OTHER INFORMATION: Synthesized Construct

<400> SEQUENCE: 40

```
gaggagaagc ccggttattc agcaccaatc gcattagttt tatacc                     46
```

<210> SEQ ID NO 41
<211> LENGTH: 43
<212> TYPE: DNA
<213> ORGANISM: Artificial Sequence
<220> FEATURE:
<223> OTHER INFORMATION: Synthesized Construct

<400> SEQUENCE: 41

```
gacgacgaca agatggcaac aacctttaac tatggtgaag ctc                        43
```

<210> SEQ ID NO 42
<211> LENGTH: 45
<212> TYPE: DNA
<213> ORGANISM: Artificial Sequence
<220> FEATURE:
<223> OTHER INFORMATION: Synthesized Construct

<400> SEQUENCE: 42

```
gaggagaagc ccggttagct agtatctatc ttcactattc cactg                      45
```

<210> SEQ ID NO 43
<211> LENGTH: 41
<212> TYPE: DNA
<213> ORGANISM: Artificial Sequence
<220> FEATURE:
<223> OTHER INFORMATION: Synthesized Construct

<400> SEQUENCE: 43

```
gacgacgaca agatgaattt caaagctatc gaaaagccaa c                          41
```

<210> SEQ ID NO 44
<211> LENGTH: 1360
<212> TYPE: PRT

<213> ORGANISM: Caldicellulosiruptor bescii

<400> SEQUENCE: 44

```
Met Ile Thr Phe Cys Val Ala Met Val Phe Leu Leu Gln Val Phe Phe
 1               5                  10                  15

Leu Phe Ser Gly Tyr Asn Asn Ser Glu Val Lys Ala Ala Thr Thr Phe
            20                  25                  30

Asn Tyr Gly Glu Ala Leu Gln Lys Ala Ile Met Phe Tyr Glu Phe Gln
        35                  40                  45

Met Ser Gly Lys Leu Pro Ser Trp Ile Arg Asn Asn Trp Arg Gly Asp
    50                  55                  60

Ser Gly Leu Asn Asp Gly Lys Asp Val Gly Leu Asp Leu Thr Gly Gly
65                  70                  75                  80

Trp His Asp Ala Gly Asp His Val Lys Phe Asn Leu Pro Met Ser Tyr
                85                  90                  95

Ser Ala Ser Met Leu Ser Trp Ala Val Tyr Glu Tyr Lys Ala Ala Phe
            100                 105                 110

Glu Lys Ser Gly Gln Leu Glu His Ile Leu Asn Gln Ile Glu Trp Val
        115                 120                 125

Asn Asp Tyr Phe Val Lys Cys His Pro Ser Lys Tyr Val Tyr Tyr Tyr
    130                 135                 140

Gln Val Gly Asp Pro Ile Glu Asp His Asn Phe Trp Gly Pro Ala Glu
145                 150                 155                 160

Val Met Gln Met Lys Arg Pro Ala Tyr Lys Cys Asp Leu Asn Asn Pro
                165                 170                 175

Ala Ser Ser Val Val Ala Glu Thr Ala Ala Ser Leu Ala Ala Ala Ser
            180                 185                 190

Ile Val Ile Arg Glu Arg Asn Ser Gln Lys Ala Asp Thr Tyr Leu Gln
        195                 200                 205

His Ala Met Val Leu Phe Asp Phe Ala Asp Arg Thr Arg Ser Asp Ala
    210                 215                 220

Gly Tyr Thr Ala Ala Thr Gly Phe Tyr Thr Ser Gly Gly Phe Ile Asp
225                 230                 235                 240

Asp Leu Gly Trp Ala Ala Val Trp Leu Tyr Leu Ala Thr Asn Asp Lys
                245                 250                 255

Ser Tyr Leu Asp Lys Ala Glu Ala Leu Met Ala Glu Tyr Ala Gly Gly
            260                 265                 270

Thr Asn Thr Trp Thr Gln Cys Trp Asp Asp Val Arg Tyr Gly Ala Ile
        275                 280                 285

Leu Leu Leu Ala Lys Ile Thr Asn Lys Asp Ile Tyr Lys Gly Ala Val
    290                 295                 300

Glu Arg Asn Leu Asp His Trp Thr Tyr Asn Ile Thr Tyr Thr Pro Lys
305                 310                 315                 320

Gly Leu Ala Trp Ile Thr Gly Trp Gly Ser Leu Arg Tyr Ala Thr Thr
                325                 330                 335

Ala Ala Phe Leu Ala Phe Val Tyr Ala Asp Trp Ser Gly Cys Pro Glu
            340                 345                 350

Asn Lys Arg Thr Ala Tyr Leu Lys Phe Gly Glu Ser Gln Ile Asn Tyr
        355                 360                 365

Ala Leu Gly Ser Thr Gly Arg Ser Phe Leu Val Gly Phe Gly Gln Asn
    370                 375                 380

Tyr Pro Gln His Pro His His Arg Asn Ala His Ser Ser Trp Ala Asn
385                 390                 395                 400
```

-continued

```
Ser Met Arg Ile Pro Glu Tyr His Arg His Ile Leu Tyr Gly Ala Leu
                405                 410                 415

Val Gly Gly Pro Gly Ser Asp Asp Ser Tyr Asn Asp Asp Ile Thr Asp
            420                 425                 430

Tyr Val Gln Asn Glu Val Ala Cys Asp Tyr Asn Ala Gly Ile Val Gly
        435                 440                 445

Ala Leu Ala Lys Met Tyr Leu Met Tyr Gly Gly Asp Pro Ile Pro Asn
    450                 455                 460

Phe Lys Ala Ile Glu Lys Pro Thr Asn Asp Glu Ile Phe Val Glu Ser
465                 470                 475                 480

Lys Phe Gly Asn Ser Gln Gly Thr Asn Tyr Thr Glu Ile Ile Ser Tyr
                485                 490                 495

Ile Tyr Asn Arg Thr Gly Trp Pro Pro Arg Val Thr Asp Asn Leu Asn
            500                 505                 510

Phe Lys Tyr Phe Ile Asp Leu Ser Glu Leu Ile Lys Ala Gly Tyr Gly
        515                 520                 525

Pro Asp Val Val Lys Val Glu Thr Tyr Tyr Ser Glu Gly Gly Lys Ile
    530                 535                 540

Ser Gly Pro Tyr Val Trp Asn Ala Ser Lys Asn Leu Tyr Tyr Ile Leu
545                 550                 555                 560

Val Asp Phe Thr Gly Thr Lys Ile Tyr Pro Gly Gly Glu Val Glu His
                565                 570                 575

Lys Lys Gln Ala Gln Phe Lys Ile Ser Val Pro Gln Gly Val Pro Trp
            580                 585                 590

Asp Pro Thr Asn Asp Pro Ser Tyr Ala Gly Leu Thr Lys Glu Leu Ser
        595                 600                 605

Lys Asn Lys Phe Ile Ala Ala Tyr Glu Gly Asn Val Leu Val Trp Gly
    610                 615                 620

Gln Glu Pro Glu Gly Ser Ser Ser Ser Thr Pro Thr Pro Thr Pro Thr
625                 630                 635                 640

Pro Thr Pro Thr Leu Thr Pro Thr Pro Thr Ser Thr Ala Thr Pro Thr
                645                 650                 655

Pro Thr Pro Thr Pro Thr Pro Thr Ser Thr Pro Thr Ala Thr Pro Thr
            660                 665                 670

Ala Thr Pro Thr Pro Thr Pro Thr Pro Ser Ser Thr Pro Val Ala Gly
        675                 680                 685

Gly Gln Ile Lys Val Leu Tyr Ala Asn Lys Glu Thr Asn Ser Thr Thr
    690                 695                 700

Asn Thr Ile Arg Pro Trp Leu Lys Val Val Asn Thr Gly Ser Ser Ser
705                 710                 715                 720

Ile Asp Leu Ser Arg Val Thr Ile Arg Tyr Trp Tyr Thr Val Asp Gly
                725                 730                 735

Asp Lys Ala Gln Ser Ala Ile Ser Asp Trp Ala Gln Ile Gly Ala Ser
            740                 745                 750

Asn Val Thr Phe Lys Phe Val Lys Leu Ser Ser Ser Val Ser Gly Ala
        755                 760                 765

Asp Tyr Tyr Leu Glu Ile Gly Phe Lys Ser Gly Ala Gly Gln Leu Gln
    770                 775                 780

Ala Gly Lys Asp Thr Gly Glu Ile Gln Ile Arg Phe Asn Lys Ser Asp
785                 790                 795                 800

Trp Ser Asn Tyr Asn Gln Gly Asn Asp Trp Ser Trp Met Gln Ser Met
                805                 810                 815

Thr Ser Tyr Gly Glu Asn Val Lys Val Thr Ala Tyr Ile Asp Gly Val
```

```
            820                 825                 830

Leu Val Trp Gly Gln Glu Pro Ser Gly Ala Thr Pro Thr Pro Thr Ala
        835                 840                 845

Thr Pro Ala Pro Thr Val Thr Pro Thr Pro Thr Pro Ala Pro Thr Pro
    850                 855                 860

Thr Pro Thr Pro Thr Pro Thr Ala Thr Pro Thr Pro Thr Pro Thr Pro
865                 870                 875                 880

Thr Pro Thr Pro Thr Ala Thr Pro Thr Pro Thr Pro Ser Ser Thr Pro
                885                 890                 895

Val Ala Gly Gly Gln Ile Lys Val Leu Tyr Ala Asn Lys Glu Thr Asn
            900                 905                 910

Ser Thr Thr Asn Thr Ile Arg Pro Trp Leu Lys Val Val Asn Thr Gly
        915                 920                 925

Ser Ser Ser Ile Asp Leu Ser Arg Val Thr Ile Arg Tyr Trp Tyr Thr
    930                 935                 940

Val Asp Gly Asp Lys Ala Gln Ser Ala Ile Ser Asp Trp Ala Gln Ile
945                 950                 955                 960

Gly Ala Ser Asn Val Thr Phe Lys Phe Val Lys Leu Ser Ser Ser Val
                965                 970                 975

Ser Gly Ala Asp Tyr Tyr Leu Glu Ile Gly Phe Lys Ser Gly Ala Gly
            980                 985                 990

Gln Leu Gln Ala Gly Lys Asp Thr Gly Glu Ile Gln Ile Arg Phe Asn
        995                 1000                1005

Lys Ser Asp Trp Ser Asn Tyr Asn Gln Gly Asn Asp Trp Ser Trp Met
    1010                1015                1020

Gln Ser Met Thr Ser Tyr Gly Glu Asn Val Lys Val Thr Ala Tyr Ile
1025                1030                1035                1040

Asp Gly Val Leu Val Trp Gly Gln Glu Pro Ser Gly Ala Thr Pro Thr
                1045                1050                1055

Pro Thr Ala Thr Pro Ala Pro Thr Val Thr Pro Thr Pro Thr Pro Thr
            1060                1065                1070

Pro Thr Pro Thr Pro Ser Ser Gly Ile Val Lys Ile Asp Thr Ser Thr
        1075                1080                1085

Leu Ile Gly Thr Asn His Ala His Cys Trp Tyr Arg Asp Lys Leu Glu
    1090                1095                1100

Thr Ala Leu Arg Gly Ile Arg Ser Trp Gly Met Asn Ser Val Arg Val
1105                1110                1115                1120

Val Leu Ser Asn Gly Tyr Arg Trp Thr Lys Ile Pro Ala Ser Glu Val
                1125                1130                1135

Ala Asn Ile Ile Ser Leu Ser Arg Ser Leu Gly Phe Arg Ala Ile Val
            1140                1145                1150

Leu Glu Val His Asp Thr Thr Gly Tyr Gly Glu Asp Gly Ala Ala Cys
        1155                1160                1165

Ser Leu Ala Gln Ala Val Glu Tyr Trp Lys Glu Ile Lys Ser Val Leu
    1170                1175                1180

Glu Gly Asn Glu Asp Phe Val Ile Ile Asn Ile Gly Asn Glu Pro Tyr
1185                1190                1195                1200

Gly Asn Asn Asn Tyr Gln Asn Trp Ile Asn Asp Thr Lys Asn Ala Ile
                1205                1210                1215

Lys Ala Leu Arg Asp Ala Gly Phe Lys His Thr Ile Met Val Asp Ala
            1220                1225                1230

Pro Asn Trp Gly Gln Asp Trp Ser Asn Thr Met Arg Asp Asn Ala Gln
        1235                1240                1245
```

Ser Ile Met Glu Ala Asp Pro Leu Arg Asn Leu Val Phe Ser Ile His
    1250                1255                1260

Met Tyr Gly Val Tyr Asn Thr Ala Ser Lys Val Glu Glu Tyr Ile Lys
1265                1270                1275                1280

Ser Phe Val Glu Lys Gly Leu Pro Leu Val Ile Gly Glu Phe Gly His
                1285                1290                1295

Gln His Thr Asp Gly Asp Pro Asp Glu Glu Ala Ile Val Arg Tyr Ala
            1300                1305                1310

Lys Gln Tyr Lys Ile Gly Leu Phe Ser Trp Ser Trp Cys Gly Asn Ser
        1315                1320                1325

Ser Tyr Val Gly Tyr Leu Asp Met Val Asn Asn Trp Asp Pro Asn Asn
    1330                1335                1340

Pro Thr Pro Trp Gly Gln Trp Tyr Lys Thr Asn Ala Ile Gly Ala Glu
1345                1350                1355                1360

<210> SEQ ID NO 45
<211> LENGTH: 4083
<212> TYPE: DNA
<213> ORGANISM: Caldicellulosiruptor bescii

<400> SEQUENCE: 45
atgattacat tttgtgttgc tatggtattt ctattgcagg ttttctttct attttcagga 60
tataataaca gtgaagtaaa agcagcaaca acctttaact atggtgaagc tcttcaaaaa 120
gcgatcatgt tttatgaatt tcagatgtca ggtaaactac catcatggat ccgtaacaac 180
tggcgcgggg attctggtct aaatgatggc aaagatgtag gtttagatct tactggtggc 240
tggcatgatg cgggcgacca tgtaaagttt aatctaccaa tgtcatacag tgcatcaatg 300
ctttcgtggg cagtttatga gtacaaagca gcatttgaga aaagtggtca gcttgaacat 360
atacttaacc agattgaatg ggtaaacgac tactttgtaa aatgccatcc atcaaagtat 420
gtatactact atcaagttgg tgacccaatt gaagatcata acttctgggg tccagcagaa 480
gttatgcaaa tgaaacgacc agcatacaag tgtgacttaa ataatccagc aagttcggtt 540
gttgcagaaa cagcagcatc cttagctgca gcttcaatcg tcatacgtga aagaaatagt 600
caaaaggcag acacatattt gcagcatgcg atggtactct ttgattttgc cgatagaact 660
cgtagtgatg cagggtatac cgcagcaaca ggcttttaca catcaggtgg ttttattgat 720
gatcttggtt gggcagcagt gtggttatat cttgcgacaa atgacaaatc atatttagat 780
aaagctgagg cacttatggc agaatatgcc ggtggcacaa atacatggac acagtgctgg 840
gacgatgtaa gatacggagc aatattgctt ttagcaaaaa ttactaataa agacatatat 900
aaaggtgctg ttgaaagaaa tcttgatcat tggacatata acataaccta tacacctaaa 960
ggtcttgcat ggataacagg gtggggctca cttaggtatg ccacaactgc agctttctta 1020
gcgtttgttt atgcagattg gtcaggatgt ccagaaaata agcgaacagc ttatctaaaa 1080
tttggtgaga gtcagattaa ctatgcatta ggttcaacag gaagaagctt tttggtagga 1140
tttgggcaaa attatccaca acatccacat cacagaaatg cacacagttc atgggcgaac 1200
agtatgcgaa tacctgaata tcatcgacac atactttatg gtgcattagt aggcggacca 1260
ggctctgatg atagttacaa tgatgatatt actgactatg ttcaaaacga ggtggcttgt 1320
gactacaatg ctggtattgt aggtgctctg gcaaaaatgt accttatgta tggaggagac 1380
ccaataccta atttcaaagc tatcgaaaag ccaactaatg atgaaatttt tgttgaatcc 1440
aagtttggta attcacaggg tacaaactat accgaaataa tttcatacat ttataacaga 1500

-continued

```
acgggatggc cgcctcgagt cacagataat ctaaacttta agtattttat tgacctaagt   1560
gagttaatca aggctgggta tggtcctgat gttgttaaag tagagacata ttattcagaa   1620
ggtggaaaaa tatctggacc atacgtatgg aatgcatcaa agaaccttta ctatatatta   1680
gttgatttta caggaacaaa aatatatcca ggtggggaag tagaacacaa aaaacaagct   1740
caatttaaga tatctgtgcc acaaggtgtt ccatgggatc caactaatga cccatcttat   1800
gcaggattaa caaaagaact tagtaaaaat aagttcatag cagcttatga aggtaacgtg   1860
ctggtatggg gacaagaacc agagggttcg tcaagttcaa ccccaacccc aacaccaaca   1920
ccaacaccaa cactgactcc aacaccgaca tcaactgcta caccaacacc gacacctaca   1980
ccaacaccaa cgtcaacacc aactgctaca ccaacagcaa cgccaacacc aacaccgacg   2040
ccgagcagca cacctgtagc aggcgggcag ataaaggtat tgtatgctaa caaggagaca   2100
aatagcacaa caaacacgat aaggccatgg ttgaaggtag tgaacactgg aagcagcagc   2160
atagatttaa gcagggtaac gataaggtac tggtacacgg tagatgggga caaggcacag   2220
agtgcgatat cagactgggc acagatagga gcaagcaatg tgacattcaa gtttgtgaag   2280
ctgagcagta gcgtaagtgg agcggactat tatttagaga taggatttaa gagtggagct   2340
gggcagttgc aggctggtaa agacacaggg gagatacaga taaggtttaa caagagtgac   2400
tggagcaatt acaatcaggg gaatgactgg tcatggatgc agagcatgac gagttatgga   2460
gagaatgtga aggtaacagc gtatatagat ggtgtattgg tatggggaca ggagccgagt   2520
ggagcgacac caacaccgac agcaacacca gcaccgacag tgacaccgac accaacacca   2580
gcaccaacac caaccccgac tccaacacca actgctacac caacgccaac accgactcca   2640
acaccaacac caactgctac cccaacaccg acgccgagca gcacacctgt agcaggtgga   2700
cagataaagg tattgtatgc taacaaggag acaaatagca caacaaacac gataaggcca   2760
tggttgaagg tagtgaacac tggaagcagc agcatagatt taagcagggt aacgataagg   2820
tactggtaca cggtagatgg ggacaaggca cagagtgcga tatcagactg ggcacagata   2880
ggagcaagca atgtgacatt caagtttgtg aagctgagca gtagcgtaag tggagcggac   2940
tattatttag agataggatt taagagtgga gctgggcagt tgcaggctgg taaagacaca   3000
ggggagatac agataaggtt taacaagagt gactggagca attacaatca ggggaatgac   3060
tggtcatgga tgcagagcat gacgagttat ggagagaatg tgaaggtaac agcgtatata   3120
gatggtgtat tggtatgggg acaggagccg agtggagcga caccaacacc gacagcaaca   3180
ccagcaccga cagtgacacc tacacctaca ccaactccaa ctccaacgcc gagcagtgga   3240
atagtgaaga tagatactag cacattaata ggaacaaatc acgcacattg ctggtacaga   3300
gataaacttg agacggcatt gcgaggaata aggtcatggg gtatgaactc tgtgagggta   3360
gtgttgagta atggctatcg atggacgaag ataccagcaa gtgaagtagc aaatattata   3420
tcattgtcaa gaagtcttgg attcagagcc attgtattag aagttcacga cacgacagga   3480
tatggtgagg acggtgcagc atgttcattg gcgcaagcag tagaatattg gaaagagata   3540
aagagtgtgt tagaaggcaa tgaggatttt gttataataa acattggtaa tgagccgtat   3600
gggaacaata actatcaaaa ctggattaat gacacgaaga atgctataaa agcgctaagg   3660
gatgcagggt tcaagcacac gataatggtt gatgcaccga actgggggca ggattggtct   3720
aatactatga gagacaatgc ccagagcata atggaagcag atccgctgcg caatttggta   3780
ttttcgattc atatgtacgg tgtatacaat acagcgagca aggtagaaga atatatcaag   3840
```

```
tcatttgtgg agaaagggct gccattagtt attggggagt ttgggcatca gcatacagat   3900

ggtgaccctg acgaggaagc tattgtcagg tatgcaaaac aatacaagat aggacttttt   3960

agctggtctt ggtgtggcaa ttcgagctat gtagggtact tggacatggt aaacaattgg   4020

gaccccaata atccaactcc atgggggcaa tggtataaaa ctaatgcgat tggtgctgaa   4080

taa                                                                 4083


<210> SEQ ID NO 46
<211> LENGTH: 1060
<212> TYPE: PRT
<213> ORGANISM: Caldicellulosiruptor bescii

<400> SEQUENCE: 46

Met Ala Thr Thr Phe Asn Tyr Gly Glu Ala Leu Gln Lys Ala Ile Met
 1               5                  10                  15

Phe Tyr Glu Phe Gln Met Ser Gly Lys Leu Pro Ser Trp Ile Arg Asn
            20                  25                  30

Asn Trp Arg Gly Asp Ser Gly Leu Asn Asp Gly Lys Asp Val Gly Leu
        35                  40                  45

Asp Leu Thr Gly Gly Trp His Asp Ala Gly Asp His Val Lys Phe Asn
    50                  55                  60

Leu Pro Met Ser Tyr Ser Ala Ser Met Leu Ser Trp Ala Val Tyr Glu
65                  70                  75                  80

Tyr Lys Ala Ala Phe Glu Lys Ser Gly Gln Leu Glu His Ile Leu Asn
                85                  90                  95

Gln Ile Glu Trp Val Asn Asp Tyr Phe Val Lys Cys His Pro Ser Lys
            100                 105                 110

Tyr Val Tyr Tyr Tyr Gln Val Gly Asp Pro Ile Glu Asp His Asn Phe
        115                 120                 125

Trp Gly Pro Ala Glu Val Met Gln Met Lys Arg Pro Ala Tyr Lys Cys
    130                 135                 140

Asp Leu Asn Asn Pro Ala Ser Ser Val Val Ala Glu Thr Ala Ala Ser
145                 150                 155                 160

Leu Ala Ala Ala Ser Ile Val Ile Arg Glu Arg Asn Ser Gln Lys Ala
                165                 170                 175

Asp Thr Tyr Leu Gln His Ala Met Val Leu Phe Asp Phe Ala Asp Arg
            180                 185                 190

Thr Arg Ser Asp Ala Gly Tyr Thr Ala Ala Thr Gly Phe Tyr Thr Ser
        195                 200                 205

Gly Gly Phe Ile Asp Asp Leu Gly Trp Ala Ala Val Trp Leu Tyr Leu
    210                 215                 220

Ala Thr Asn Asp Lys Ser Tyr Leu Asp Lys Ala Glu Ala Leu Met Ala
225                 230                 235                 240

Glu Tyr Ala Gly Gly Thr Asn Thr Trp Thr Gln Cys Trp Asp Asp Val
                245                 250                 255

Arg Tyr Gly Ala Ile Leu Leu Leu Ala Lys Ile Thr Asn Lys Asp Ile
            260                 265                 270

Tyr Lys Gly Ala Val Glu Arg Asn Leu Asp His Trp Thr Tyr Asn Ile
        275                 280                 285

Thr Tyr Thr Pro Lys Gly Leu Ala Trp Ile Thr Gly Trp Gly Ser Leu
    290                 295                 300

Arg Tyr Ala Thr Thr Ala Ala Phe Leu Ala Phe Val Tyr Ala Asp Trp
305                 310                 315                 320

Ser Gly Cys Pro Glu Asn Lys Arg Thr Ala Tyr Leu Lys Phe Gly Glu
```

-continued

```
                325                 330                 335

Ser Gln Ile Asn Tyr Ala Leu Gly Ser Thr Gly Arg Ser Phe Leu Val
            340                 345                 350

Gly Phe Gly Gln Asn Tyr Pro Gln His Pro His His Arg Asn Ala His
        355                 360                 365

Ser Ser Trp Ala Asn Ser Met Arg Ile Pro Glu Tyr His Arg His Ile
    370                 375                 380

Leu Tyr Gly Ala Leu Val Gly Gly Pro Gly Ser Asp Asp Ser Tyr Asn
385                 390                 395                 400

Asp Asp Ile Thr Asp Tyr Val Gln Asn Glu Val Ala Cys Asp Tyr Asn
                405                 410                 415

Ala Gly Ile Val Gly Ala Leu Ala Lys Met Tyr Leu Met Tyr Gly Gly
            420                 425                 430

Asp Pro Ile Pro Asn Phe Lys Ala Ile Glu Lys Pro Thr Asn Asp Glu
        435                 440                 445

Ile Phe Val Glu Ser Lys Phe Gly Asn Ser Gln Gly Thr Asn Tyr Thr
    450                 455                 460

Glu Ile Ile Ser Tyr Ile Tyr Asn Arg Thr Gly Trp Pro Pro Arg Val
465                 470                 475                 480

Thr Asp Asn Leu Asn Phe Lys Tyr Phe Ile Asp Leu Ser Glu Leu Ile
                485                 490                 495

Lys Ala Gly Tyr Gly Pro Asp Val Val Lys Val Glu Thr Tyr Tyr Ser
            500                 505                 510

Glu Gly Gly Lys Ile Ser Gly Pro Tyr Val Trp Asn Ala Ser Lys Asn
        515                 520                 525

Leu Tyr Tyr Ile Leu Val Asp Phe Thr Gly Thr Lys Ile Tyr Pro Gly
    530                 535                 540

Gly Glu Val Glu His Lys Lys Gln Ala Gln Phe Lys Ile Ser Val Pro
545                 550                 555                 560

Gln Gly Val Pro Trp Asp Pro Thr Asn Asp Pro Ser Tyr Ala Gly Leu
                565                 570                 575

Thr Lys Glu Leu Ser Lys Asn Lys Phe Ile Ala Ala Tyr Glu Gly Asn
            580                 585                 590

Val Leu Val Trp Gly Gln Glu Pro Glu Gly Ser Ser Ser Ser Thr Pro
        595                 600                 605

Thr Pro Thr Pro Thr Pro Thr Pro Thr Leu Thr Pro Thr Pro Thr Ser
    610                 615                 620

Thr Ala Thr Pro Thr Pro Thr Pro Thr Pro Thr Pro Thr Ser Thr Pro
625                 630                 635                 640

Thr Ala Thr Pro Thr Ala Thr Pro Thr Pro Thr Pro Thr Pro Ser Ser
                645                 650                 655

Thr Pro Val Ala Gly Gly Gln Ile Lys Val Leu Tyr Ala Asn Lys Glu
            660                 665                 670

Thr Asn Ser Thr Thr Asn Thr Ile Arg Pro Trp Leu Lys Val Val Asn
        675                 680                 685

Thr Gly Ser Ser Ser Ile Asp Leu Ser Arg Val Thr Ile Arg Tyr Trp
    690                 695                 700

Tyr Thr Val Asp Gly Asp Lys Ala Gln Ser Ala Ile Ser Asp Trp Ala
705                 710                 715                 720

Gln Ile Gly Ala Ser Asn Val Thr Phe Lys Phe Val Lys Leu Ser Ser
                725                 730                 735

Ser Val Ser Gly Ala Asp Tyr Tyr Leu Glu Ile Gly Phe Lys Ser Gly
            740                 745                 750
```

```
Ala Gly Gln Leu Gln Ala Gly Lys Asp Thr Gly Glu Ile Gln Ile Arg
        755                 760                 765

Phe Asn Lys Ser Asp Trp Ser Asn Tyr Asn Gln Gly Asn Asp Trp Ser
    770                 775                 780

Trp Met Gln Ser Met Thr Ser Tyr Gly Glu Asn Val Lys Val Thr Ala
785                 790                 795                 800

Tyr Ile Asp Gly Val Leu Val Trp Gly Gln Glu Pro Ser Gly Ala Thr
                805                 810                 815

Pro Thr Pro Thr Ala Thr Pro Ala Pro Thr Val Thr Pro Thr Pro Thr
            820                 825                 830

Pro Ala Pro Thr Pro Thr Pro Thr Pro Thr Pro Thr Ala Thr Pro Thr
        835                 840                 845

Pro Thr Pro Thr Pro Thr Pro Thr Pro Thr Ala Thr Pro Thr Pro Thr
    850                 855                 860

Pro Ser Ser Thr Pro Val Ala Gly Gly Gln Ile Lys Val Leu Tyr Ala
865                 870                 875                 880

Asn Lys Glu Thr Asn Ser Thr Thr Asn Thr Ile Arg Pro Trp Leu Lys
                885                 890                 895

Val Val Asn Thr Gly Ser Ser Ser Ile Asp Leu Ser Arg Val Thr Ile
            900                 905                 910

Arg Tyr Trp Tyr Thr Val Asp Gly Asp Lys Ala Gln Ser Ala Ile Ser
        915                 920                 925

Asp Trp Ala Gln Ile Gly Ala Ser Asn Val Thr Phe Lys Phe Val Lys
    930                 935                 940

Leu Ser Ser Ser Val Ser Gly Ala Asp Tyr Tyr Leu Glu Ile Gly Phe
945                 950                 955                 960

Lys Ser Gly Ala Gly Gln Leu Gln Ala Gly Lys Asp Thr Gly Glu Ile
                965                 970                 975

Gln Ile Arg Phe Asn Lys Ser Asp Trp Ser Asn Tyr Asn Gln Gly Asn
            980                 985                 990

Asp Trp Ser Trp Met Gln Ser Met Thr Ser Tyr Gly Glu Asn Val Lys
        995                 1000                1005

Val Thr Ala Tyr Ile Asp Gly Val Leu Val Trp Gly Gln Glu Pro Ser
    1010                1015                1020

Gly Ala Thr Pro Thr Pro Thr Ala Thr Pro Ala Pro Thr Val Thr Pro
1025                1030                1035                1040

Thr Pro Thr Pro Thr Pro Thr Pro Thr Pro Ser Ser Gly Ile Val Lys
                1045                1050                1055

Ile Asp Thr Ser
            1060


<210> SEQ ID NO 47
<211> LENGTH: 3183
<212> TYPE: DNA
<213> ORGANISM: Caldicellulosiruptor bescii

<400> SEQUENCE: 47

atggcaacaa cctttaacta tggtgaagct cttcaaaaag cgatcatgtt ttatgaattt      60

cagatgtcag gtaaactacc atcatggatc cgtaacaact ggcgcgggga ttctggtcta     120

aatgatggca aagatgtagg tttagatctt actggtggct ggcatgatgc gggcgaccat     180

gtaaagttta atctaccaat gtcatacagt gcatcaatgc tttcgtgggc agtttatgag     240

tacaaagcag catttgagaa aagtggtcag cttgaacata tacttaacca gattgaatgg     300
```

-continued

```
gtaaacgact actttgtaaa atgccatcca tcaaagtatg tatactacta tcaagttggt    360
gacccaattg aagatcataa cttctggggt ccagcagaag ttatgcaaat gaaacgacca    420
gcatacaagt gtgacttaaa taatccagca agttcggttg ttgcagaaac agcagcatcc    480
ttagctgcag cttcaatcgt catacgtgaa agaaatagtc aaaaggcaga cacatatttg    540
cagcatgcga tggtactctt tgattttgcc gatagaactc gtagtgatgc agggtatacc    600
gcagcaacag gcttttacac atcaggtggt tttattgatg atcttggttg ggcagcagtg    660
tggttatatc ttgcgacaaa tgacaaatca tatttagata aagctgaggc acttatggca    720
gaatatgccg gtggcacaaa tacatggaca cagtgctggg acgatgtaag atacggagca    780
atattgcttt tagcaaaaat tactaataaa gacatatata aaggtgctgt tgaaagaaat    840
cttgatcatt ggacatataa cataacctat acacctaaag gtcttgcatg gataacaggg    900
tggggctcac ttaggtatgc cacaactgca gctttcttag cgtttgttta tgcagattgg    960
tcaggatgtc cagaaaataa gcgaacagct tatctaaaat ttggtgagag tcagattaac   1020
tatgcattag gttcaacagg aagaagcttt ttggtaggat ttgggcaaaa ttatccacaa   1080
catccacatc acagaaatgc acacagttca tgggcgaaca gtatgcgaat acctgaatat   1140
catcgacaca tactttatgg tgcattagta ggcggaccag gctctgatga tagttacaat   1200
gatgatatta ctgactatgt tcaaaacgag gtggcttgtg actacaatgc tggtattgta   1260
ggtgctctgg caaaaatgta ccttatgtat ggaggagacc caatacctaa tttcaaagct   1320
atcgaaaagc caactaatga tgaaattttt gttgaatcca agtttggtaa ttcacagggt   1380
acaaactata ccgaaataat ttcatacatt tataacagaa cgggatggcc gcctcgagtc   1440
acagataatc taaactttaa gtattttatt gacctaagtg agttaatcaa ggctgggtat   1500
ggtcctgatg ttgttaaagt agagacatat tattcagaag gtggaaaaat atctggacca   1560
tacgtatgga atgcatcaaa gaacctttac tatatattag ttgattttac aggaacaaaa   1620
atatatccag gtggggaagt agaacacaaa aaacaagctc aatttaagat atctgtgcca   1680
caaggtgttc catgggatcc aactaatgac ccatcttatg caggattaac aaaagaactt   1740
agtaaaaata agttcatagc agcttatgaa ggtaacgtgc tggtatgggg acaagaacca   1800
gagggttcgt caagttcaac cccaacccca acaccaacac caacaccaac actgactcca   1860
acaccgacat caactgctac accaacaccg acacctacac caacaccaac gtcaacacca   1920
actgctacac caacagcaac gccaacacca acaccgacgc cgagcagcac acctgtagca   1980
ggcgggcaga taaaggtatt gtatgctaac aaggagacaa atagcacaac aaacacgata   2040
aggccatggt tgaaggtagt gaacactgga agcagcagca tagatttaag cagggtaacg   2100
ataaggtact ggtacacggt agatggggac aaggcacaga gtgcgatatc agactgggca   2160
cagataggag caagcaatgt gacattcaag tttgtgaagc tgagcagtag cgtaagtgga   2220
gcggactatt atttagagat aggatttaag agtggagctg ggcagttgca ggctggtaaa   2280
gacacagggg agatacagat aaggtttaac aagagtgact ggagcaatta caatcagggg   2340
aatgactggt catggatgca gagcatgacg agttatggag agaatgtgaa ggtaacagcg   2400
tatatagatg gtgtattggt atggggacag gagccgagtg gagcgacacc aacaccgaca   2460
gcaacaccag caccgacagt gacaccgaca ccaacaccag caccaacacc aaccccgact   2520
ccaacaccaa ctgctacacc aacgccaaca ccgactccaa caccaacacc aactgctacc   2580
ccaacaccga cgccgagcag cacacctgta gcaggtggac agataaaggt attgtatgct   2640
aacaaggaga caaatagcac aacaaacacg ataaggccat ggttgaaggt agtgaacact   2700
```

```
ggaagcagca gcatagattt aagcagggta acgataaggt actggtacac ggtagatggg   2760

gacaaggcac agagtgcgat atcagactgg gcacagatag gagcaagcaa tgtgacattc   2820

aagtttgtga agctgagcag tagcgtaagt ggagcggact attatttaga gataggattt   2880

aagagtggag ctgggcagtt gcaggctggt aaagacacag gggagataca gataaggttt   2940

aacaagagtg actggagcaa ttacaatcag gggaatgact ggtcatggat gcagagcatg   3000

acgagttatg gagagaatgt gaaggtaaca gcgtatatag atggtgtatt ggtatgggga   3060

caggagccga gtggagcgac accaacaccg acagcaacac cagcaccgac agtgacacct   3120

acacctacac caactccaac tccaacgccg agcagtggaa tagtgaagat agatactagc   3180

taa                                                                 3183
```

```
<210> SEQ ID NO 48
<211> LENGTH: 898
<212> TYPE: PRT
<213> ORGANISM: Caldicellulosiruptor bescii

<400> SEQUENCE: 48

Met Asn Phe Lys Ala Ile Glu Lys Pro Thr Asn Asp Glu Ile Phe Val
 1               5                  10                  15

Glu Ser Lys Phe Gly Asn Ser Gln Gly Thr Asn Tyr Thr Glu Ile Ile
            20                  25                  30

Ser Tyr Ile Tyr Asn Arg Thr Gly Trp Pro Pro Arg Val Thr Asp Asn
        35                  40                  45

Leu Asn Phe Lys Tyr Phe Ile Asp Leu Ser Glu Leu Ile Lys Ala Gly
    50                  55                  60

Tyr Gly Pro Asp Val Val Lys Val Glu Thr Tyr Tyr Ser Glu Gly Gly
65                  70                  75                  80

Lys Ile Ser Gly Pro Tyr Val Trp Asn Ala Ser Lys Asn Leu Tyr Tyr
                85                  90                  95

Ile Leu Val Asp Phe Thr Gly Thr Lys Ile Tyr Pro Gly Gly Glu Val
            100                 105                 110

Glu His Lys Lys Gln Ala Gln Phe Lys Ile Ser Val Pro Gln Gly Val
        115                 120                 125

Pro Trp Asp Pro Thr Asn Asp Pro Ser Tyr Ala Gly Leu Thr Lys Glu
    130                 135                 140

Leu Ser Lys Asn Lys Phe Ile Ala Ala Tyr Glu Gly Asn Val Leu Val
145                 150                 155                 160

Trp Gly Gln Glu Pro Glu Gly Ser Ser Ser Ser Thr Pro Thr Pro Thr
                165                 170                 175

Pro Thr Pro Thr Pro Thr Leu Thr Pro Thr Pro Thr Ser Thr Ala Thr
            180                 185                 190

Pro Thr Pro Thr Pro Thr Pro Thr Pro Thr Ser Thr Pro Thr Ala Thr
        195                 200                 205

Pro Thr Ala Thr Pro Thr Pro Thr Pro Thr Pro Ser Ser Thr Pro Val
    210                 215                 220

Ala Gly Gly Gln Ile Lys Val Leu Tyr Ala Asn Lys Glu Thr Asn Ser
225                 230                 235                 240

Thr Thr Asn Thr Ile Arg Pro Trp Leu Lys Val Val Asn Thr Gly Ser
                245                 250                 255

Ser Ser Ile Asp Leu Ser Arg Val Thr Ile Arg Tyr Trp Tyr Thr Val
            260                 265                 270

Asp Gly Asp Lys Ala Gln Ser Ala Ile Ser Asp Trp Ala Gln Ile Gly
```

```
        275                 280                 285

Ala Ser Asn Val Thr Phe Lys Phe Val Lys Leu Ser Ser Ser Val Ser
    290                 295                 300

Gly Ala Asp Tyr Tyr Leu Glu Ile Gly Phe Lys Ser Gly Ala Gly Gln
305                 310                 315                 320

Leu Gln Ala Gly Lys Asp Thr Gly Glu Ile Gln Ile Arg Phe Asn Lys
                325                 330                 335

Ser Asp Trp Ser Asn Tyr Asn Gln Gly Asn Asp Trp Ser Trp Met Gln
            340                 345                 350

Ser Met Thr Ser Tyr Gly Glu Asn Val Lys Val Thr Ala Tyr Ile Asp
        355                 360                 365

Gly Val Leu Val Trp Gly Gln Glu Pro Ser Gly Ala Thr Pro Thr Pro
    370                 375                 380

Thr Ala Thr Pro Ala Pro Thr Val Thr Pro Thr Pro Thr Pro Ala Pro
385                 390                 395                 400

Thr Pro Thr Pro Thr Pro Thr Pro Thr Ala Thr Pro Thr Pro Thr Pro
                405                 410                 415

Thr Pro Thr Pro Thr Pro Thr Ala Thr Pro Thr Pro Thr Pro Ser Ser
            420                 425                 430

Thr Pro Val Ala Gly Gly Gln Ile Lys Val Leu Tyr Ala Asn Lys Glu
        435                 440                 445

Thr Asn Ser Thr Thr Asn Thr Ile Arg Pro Trp Leu Lys Val Val Asn
    450                 455                 460

Thr Gly Ser Ser Ser Ile Asp Leu Ser Arg Val Thr Ile Arg Tyr Trp
465                 470                 475                 480

Tyr Thr Val Asp Gly Asp Lys Ala Gln Ser Ala Ile Ser Asp Trp Ala
                485                 490                 495

Gln Ile Gly Ala Ser Asn Val Thr Phe Lys Phe Val Lys Leu Ser Ser
            500                 505                 510

Ser Val Ser Gly Ala Asp Tyr Tyr Leu Glu Ile Gly Phe Lys Ser Gly
        515                 520                 525

Ala Gly Gln Leu Gln Ala Gly Lys Asp Thr Gly Glu Ile Gln Ile Arg
    530                 535                 540

Phe Asn Lys Ser Asp Trp Ser Asn Tyr Asn Gln Gly Asn Asp Trp Ser
545                 550                 555                 560

Trp Met Gln Ser Met Thr Ser Tyr Gly Glu Asn Val Lys Val Thr Ala
                565                 570                 575

Tyr Ile Asp Gly Val Leu Val Trp Gly Gln Glu Pro Ser Gly Ala Thr
            580                 585                 590

Pro Thr Pro Thr Ala Thr Pro Ala Pro Thr Val Thr Pro Thr Pro Thr
        595                 600                 605

Pro Thr Pro Thr Pro Thr Pro Ser Ser Gly Ile Val Lys Ile Asp Thr
    610                 615                 620

Ser Thr Leu Ile Gly Thr Asn His Ala His Cys Trp Tyr Arg Asp Lys
625                 630                 635                 640

Leu Glu Thr Ala Leu Arg Gly Ile Arg Ser Trp Gly Met Asn Ser Val
                645                 650                 655

Arg Val Val Leu Ser Asn Gly Tyr Arg Trp Thr Lys Ile Pro Ala Ser
            660                 665                 670

Glu Val Ala Asn Ile Ile Ser Leu Ser Arg Ser Leu Gly Phe Arg Ala
        675                 680                 685

Ile Val Leu Glu Val His Asp Thr Thr Gly Tyr Gly Glu Asp Gly Ala
    690                 695                 700
```

```
Ala Cys Ser Leu Ala Gln Ala Val Glu Tyr Trp Lys Glu Ile Lys Ser
705                 710                 715                 720

Val Leu Glu Gly Asn Glu Asp Phe Val Ile Ile Asn Ile Gly Asn Glu
                725                 730                 735

Pro Tyr Gly Asn Asn Asn Tyr Gln Asn Trp Ile Asn Asp Thr Lys Asn
            740                 745                 750

Ala Ile Lys Ala Leu Arg Asp Ala Gly Phe Lys His Thr Ile Met Val
        755                 760                 765

Asp Ala Pro Asn Trp Gly Gln Asp Trp Ser Asn Thr Met Arg Asp Asn
    770                 775                 780

Ala Gln Ser Ile Met Glu Ala Asp Pro Leu Arg Asn Leu Val Phe Ser
785                 790                 795                 800

Ile His Met Tyr Gly Val Tyr Asn Thr Ala Ser Lys Val Glu Glu Tyr
                805                 810                 815

Ile Lys Ser Phe Val Glu Lys Gly Leu Pro Leu Val Ile Gly Glu Phe
            820                 825                 830

Gly His Gln His Thr Asp Gly Asp Pro Asp Glu Glu Ala Ile Val Arg
        835                 840                 845

Tyr Ala Lys Gln Tyr Lys Ile Gly Leu Phe Ser Trp Ser Trp Cys Gly
    850                 855                 860

Asn Ser Ser Tyr Val Gly Tyr Leu Asp Met Val Asn Asn Trp Asp Pro
865                 870                 875                 880

Asn Asn Pro Thr Pro Trp Gly Gln Trp Tyr Lys Thr Asn Ala Ile Gly
                885                 890                 895

Ala Glu
```

<210> SEQ ID NO 49
<211> LENGTH: 2697
<212> TYPE: DNA
<213> ORGANISM: Caldicellulosiruptor bescii

<400> SEQUENCE: 49

```
atgaatttca aagctatcga aaagccaact aatgatgaaa tttttgttga atccaagttt     60

ggtaattcac agggtacaaa ctataccgaa ataatttcat acatttataa cagaacggga    120

tggccgcctc gagtcacaga taatctaaac tttaagtatt ttattgacct aagtgagtta    180

atcaaggctg ggtatggtcc tgatgttgtt aaagtagaga catattattc agaaggtgga    240

aaaatatctg gaccatacgt atggaatgca tcaaagaacc tttactatat attagttgat    300

tttacaggaa caaaaatata tccaggtggg gaagtagaac acaaaaaaca agctcaattt    360

aagatatctg tgccacaagg tgttccatgg gatccaacta atgacccatc ttatgcagga    420

ttaacaaaag aacttagtaa aaataagttc atagcagctt atgaaggtaa cgtgctggta    480

tggggacaag aaccagaggg ttcgtcaagt tcaaccccaa ccccaacacc aacaccaaca    540

ccaacactga ctccaacacc gacatcaact gctacaccaa caccgacacc tacaccaaca    600

ccaacgtcaa caccaactgc tacaccaaca gcaacgccaa caccaacacc gacgccgagc    660

agcacacctg tagcaggcgg gcagataaag gtattgtatg ctaacaagga gacaaatagc    720

acaacaaaca cgataaggcc atggttgaag gtagtgaaca ctggaagcag cagcatagat    780

ttaagcaggg taacgataag gtactggtac acggtagatg gggacaaggc acagagtgcg    840

atatcagact gggcacagat aggagcaagc aatgtgacat tcaagtttgt gaagctgagc    900

agtagcgtaa gtggagcgga ctattattta gagataggat ttaagagtgg agctgggcag    960
```

-continued

```
ttgcaggctg gtaaagacac aggggagata cagataaggt ttaacaagag tgactggagc   1020

aattacaatc aggggaatga ctggtcatgg atgcagagca tgacgagtta tggagagaat   1080

gtgaaggtaa cagcgtatat agatggtgta ttggtatggg gacaggagcc gagtggagcg   1140

acaccaacac cgacagcaac accagcaccg acagtgacac cgacaccaac accagcacca   1200

acaccaaccc cgactccaac accaactgct acaccaacgc caacaccgac tccaacacca   1260

acaccaactg ctaccccaac accgacgccg agcagcacac ctgtagcagg tggacagata   1320

aaggtattgt atgctaacaa ggagacaaat agcacaacaa acacgataag gccatggttg   1380

aaggtagtga acactggaag cagcagcata gatttaagca gggtaacgat aaggtactgg   1440

tacacggtag atggggacaa ggcacagagt gcgatatcag actgggcaca gataggagca   1500

agcaatgtga cattcaagtt tgtgaagctg agcagtagcg taagtggagc ggactattat   1560

ttagagatag gatttaagag tggagctggg cagttgcagg ctggtaaaga cacaggggag   1620

atacagataa ggtttaacaa gagtgactgg agcaattaca atcaggggaa tgactggtca   1680

tggatgcaga gcatgacgag ttatggagag aatgtgaagg taacagcgta tatagatggt   1740

gtattggtat ggggacagga gccgagtgga gcgacaccaa caccgacagc aacaccagca   1800

ccgacagtga cacctacacc tacaccaact ccaactccaa cgccgagcag tggaatagtg   1860

aagatagata ctagcacatt aataggaaca aatcacgcac attgctggta cagagataaa   1920

cttgagacgg cattgcgagg aataaggtca tggggtatga actctgtgag ggtagtgttg   1980

agtaatggct atcgatggac gaagatacca gcaagtgaag tagcaaatat tatatcattg   2040

tcaagaagtc ttggattcag agccattgta ttagaagttc acgacacgac aggatatggt   2100

gaggacggtg cagcatgttc attggcgcaa gcagtagaat attggaaaga gataaagagt   2160

gtgttagaag gcaatgagga ttttgttata ataaacattg gtaatgagcc gtatgggaac   2220

aataactatc aaaactggat taatgacacg aagaatgcta taaaagcgct aagggatgca   2280

gggttcaagc acacgataat ggttgatgca ccgaactggg ggcaggattg gtctaatact   2340

atgagagaca atgcccagag cataatggaa gcagatccgc tgcgcaattt ggtattttcg   2400

attcatatgt acggtgtata caatacagcg agcaaggtag aagaatatat caagtcattt   2460

gtggagaaag ggctgccatt agttattggg gagtttgggc atcagcatac agatggtgac   2520

cctgacgagg aagctattgt caggtatgca aaacaataca agataggact ttttagctgg   2580

tcttggtgtg gcaattcgag ctatgtaggg tacttggaca tggtaaacaa ttgggacccc   2640

aataatccaa ctccatgggg gcaatggtat aaaactaatg cgattggtgc tgaataa      2697
```

<210> SEQ ID NO 50
<211> LENGTH: 4044
<212> TYPE: DNA
<213> ORGANISM: Caldicellulosiruptor bescii

<400> SEQUENCE: 50

```
atggcacatc accaccacca tcacgtggat gacgacgaca agatggcaac aacctttaac     60

tatggtgaag ctcttcaaaa agcgatcatg ttttatgaat ttcagatgtc aggtaaacta    120

ccatcatgga tccgtaacaa ctggcgcggg gattctggtc taaatgatgg caaagatgta    180

ggtttagatc ttactggtgg ctggcatgat gcgggcgacc atgtaaagtt taatctacca    240

atgtcataca gtgcatcaat gctttcgtgg gcagtttatg agtacaaagc agcatttgag    300

aaaagtggtc agcttgaaca tatacttaac cagattgaat gggtaaacga ctactttgta    360

aaatgccatc catcaaagta tgtatactac tatcaagttg gtgacccaat tgaagatcat    420
```

-continued

```
aacttctggg gtccagcaga agttatgcaa atgaaacgac cagcatacaa gtgtgactta    480
aataatccag caagttcggt tgttgcagaa acagcagcat ccttagctgc agcttcaatc    540
gtcatacgtg aaagaaatag tcaaaaggca gacacatatt tgcagcatgc gatggtactc    600
tttgattttg ccgatagaac tcgtagtgat gcagggtata ccgcagcaac aggcttttac    660
acatcaggtg gttttattga tgatcttggt tgggcagcag tgtggttata tcttgcgaca    720
aatgacaaat catatttaga taaagctgag gcacttatgg cagaatatgc cggtggcaca    780
aatacatgga cacagtgctg ggacgatgta agatacggag caatattgct tttagcaaaa    840
attactaata aagacatata taaaggtgct gttgaaagaa atcttgatca ttggacatat    900
aacataacct atacacctaa aggtcttgca tggataacag ggtggggctc acttaggtat    960
gccacaactg cagctttctt agcgtttgtt tatgcagatt ggtcaggatg tccagaaaat   1020
aagcgaacag cttatctaaa atttggtgag agtcagatta actatgcatt aggttcaaca   1080
ggaagaagct tttggtagg atttgggcaa aattatccac aacatccaca tcacagaaat    1140
gcacacagtt catgggcgaa cagtatgcga atacctgaat atcatcgaca catactttat   1200
ggtgcattag taggcggacc aggctctgat gatagttaca atgatgatat tactgactat   1260
gttcaaaacg aggtggcttg tgactacaat gctggtattg taggtgctct ggcaaaaatg   1320
taccttatgt atggaggaga cccaatacct aatttcaaag ctatcgaaaa gccaactaat   1380
gatgaaattt ttgttgaatc caagtttggt aattcacagg gtacaaacta taccgaaata   1440
atttcataca tttataacag aacgggatgg ccgcctcgag tcacagataa tctaaacttt   1500
aagtatttta ttgacctaag tgagttaatc aaggctgggt atggtcctga tgttgttaaa   1560
gtagagacat attattcaga aggtggaaaa atatctggac catacgtatg gaatgcatca   1620
aagaaccttt actatatatt agttgatttt acaggaacaa aaatatatcc aggtggggaa   1680
gtagaacaca aaaaacaagc tcaatttaag atatctgtgc cacaaggtgt tccatgggat   1740
ccaactaatg acccatctta tgcaggatta acaaaagaac ttagtaaaaa taagttcata   1800
gcagcttatg aaggtaacgt gctggtatgg ggacaagaac cagagggttc gtcaagttca   1860
accccaaccc caacaccaac accaacacca acactgactc caacaccgac atcaactgct   1920
acaccaacac cgacacctac accaacacca acgtcaacac caactgctac accaacagca   1980
acgccaacac caacaccgac gccgagcagc acacctgtag caggcgggca gataaaggta   2040
ttgtatgcta acaaggagac aaatagcaca acaaacacga taaggccatg gttgaaggta   2100
gtgaacactg gaagcagcag catagattta agcagggtaa cgataaggta ctggtacacg   2160
gtagatgggg acaaggcaca gagtgcgata tcagactggg cacagatagg agcaagcaat   2220
gtgacattca agtttgtgaa gctgagcagt agcgtaagtg gagcggacta ttatttagag   2280
ataggattta agagtggagc tgggcagttg caggctggta aagacacagg ggagatacag   2340
ataaggttta acaagagtga ctggagcaat tacaatcagg ggaatgactg gtcatggatg   2400
cagagcatga cgagttatgg agagaatgtg aaggtaacag cgtatataga tggtgtattg   2460
gtatggggac aggagccgag tggagcgaca ccaacaccga cagcaacacc agcaccgaca   2520
gtgacaccga caccaacacc agcaccaaca ccaaccccga ctccaacacc aactgctaca   2580
ccaacgccaa caccgactcc aacaccaaca ccaactgcta ccccaacacc gacgccgagc   2640
agcacacctg tagcaggtgg acagataaag gtattgtatg ctaacaagga gacaaatagc   2700
acaacaaaca cgataaggcc atggttgaag gtagtgaaca ctggaagcag cagcatagat   2760
```

-continued

```
ttaagcaggg taacgataag gtactggtac acggtagatg gggacaaggc acagagtgcg   2820

atatcagact gggcacagat aggagcaagc aatgtgacat tcaagtttgt gaagctgagc   2880

agtagcgtaa gtggagcgga ctattattta gagataggat ttaagagtgg agctgggcag   2940

ttgcaggctg gtaaagacac aggggagata cagataaggt ttaacaagag tgactggagc   3000

aattacaatc aggggaatga ctggtcatgg atgcagagca tgacgagtta tggagagaat   3060

gtgaaggtaa cagcgtatat agatggtgta ttggtatggg gacaggagcc gagtggagcg   3120

acaccaacac cgacagcaac accagcaccg acagtgacac ctacacctac accaactcca   3180

actccaacgc cgagcagtgg aatagtgaag atagatacta gcacattaat aggaacaaat   3240

cacgcacatt gctggtacag agataaactt gagacggcat tgcgaggaat aaggtcatgg   3300

ggtatgaact ctgtgagggt agtgttgagt aatggctatc gatggacgaa gataccagca   3360

agtgaagtag caaatattat atcattgtca agaagtcttg gattcagagc cattgtatta   3420

gaagttcacg acacgacagg atatggtgag gacggtgcag catgttcatt ggcgcaagca   3480

gtagaatatt ggaaagagat aaagagtgtg ttagaaggca atgaggattt tgttataata   3540

aacattggta atgagccgta tgggaacaat aactatcaaa actggattaa tgacacgaag   3600

aatgctataa aagcgctaag ggatgcaggg ttcaagcaca cgataatggt tgatgcaccg   3660

aactgggggc aggattggtc taatactatg agagacaatg cccagagcat aatggaagca   3720

gatccgctgc gcaatttggt attttcgatt catatgtacg gtgtatacaa tacagcgagc   3780

aaggtagaag aatatatcaa gtcatttgtg gagaaagggc tgccattagt tattggggag   3840

tttgggcatc agcatacaga tggtgaccct gacgaggaag ctattgtcag gtatgcaaaa   3900

caatacaaga taggactttt tagctggtct tggtgtggca attcgagcta tgtagggtac   3960

ttggacatgg taaacaattg ggaccccaat aatccaactc catgggggca atggtataaa   4020

actaatgcga ttggtgctga ataa                                           4044
```

<210> SEQ ID NO 51
<211> LENGTH: 1347
<212> TYPE: PRT
<213> ORGANISM: Caldicellulosiruptor bescii

<400> SEQUENCE: 51

```
Met Ala His His His His His His Val Asp Asp Asp Asp Lys Met Ala
1               5                   10                  15

Thr Thr Phe Asn Tyr Gly Glu Ala Leu Gln Lys Ala Ile Met Phe Tyr
            20                  25                  30

Glu Phe Gln Met Ser Gly Lys Leu Pro Ser Trp Ile Arg Asn Asn Trp
        35                  40                  45

Arg Gly Asp Ser Gly Leu Asn Asp Gly Lys Asp Val Gly Leu Asp Leu
    50                  55                  60

Thr Gly Gly Trp His Asp Ala Gly Asp His Val Lys Phe Asn Leu Pro
65                  70                  75                  80

Met Ser Tyr Ser Ala Ser Met Leu Ser Trp Ala Val Tyr Glu Tyr Lys
                85                  90                  95

Ala Ala Phe Glu Lys Ser Gly Gln Leu Glu His Ile Leu Asn Gln Ile
            100                 105                 110

Glu Trp Val Asn Asp Tyr Phe Val Lys Cys His Pro Ser Lys Tyr Val
        115                 120                 125

Tyr Tyr Tyr Gln Val Gly Asp Pro Ile Glu Asp His Asn Phe Trp Gly
    130                 135                 140
```

-continued

```
Pro Ala Glu Val Met Gln Met Lys Arg Pro Ala Tyr Lys Cys Asp Leu
145                 150                 155                 160

Asn Asn Pro Ala Ser Ser Val Val Ala Glu Thr Ala Ala Ser Leu Ala
                165                 170                 175

Ala Ala Ser Ile Val Ile Arg Glu Arg Asn Ser Gln Lys Ala Asp Thr
            180                 185                 190

Tyr Leu Gln His Ala Met Val Leu Phe Asp Phe Ala Asp Arg Thr Arg
        195                 200                 205

Ser Asp Ala Gly Tyr Thr Ala Ala Thr Gly Phe Tyr Thr Ser Gly Gly
    210                 215                 220

Phe Ile Asp Asp Leu Gly Trp Ala Ala Val Trp Leu Tyr Leu Ala Thr
225                 230                 235                 240

Asn Asp Lys Ser Tyr Leu Asp Lys Ala Glu Ala Leu Met Ala Glu Tyr
                245                 250                 255

Ala Gly Gly Thr Asn Thr Trp Thr Gln Cys Trp Asp Asp Val Arg Tyr
            260                 265                 270

Gly Ala Ile Leu Leu Leu Ala Lys Ile Thr Asn Lys Asp Ile Tyr Lys
        275                 280                 285

Gly Ala Val Glu Arg Asn Leu Asp His Trp Thr Tyr Asn Ile Thr Tyr
    290                 295                 300

Thr Pro Lys Gly Leu Ala Trp Ile Thr Gly Trp Gly Ser Leu Arg Tyr
305                 310                 315                 320

Ala Thr Thr Ala Ala Phe Leu Ala Phe Val Tyr Ala Asp Trp Ser Gly
                325                 330                 335

Cys Pro Glu Asn Lys Arg Thr Ala Tyr Leu Lys Phe Gly Glu Ser Gln
            340                 345                 350

Ile Asn Tyr Ala Leu Gly Ser Thr Gly Arg Ser Phe Leu Val Gly Phe
        355                 360                 365

Gly Gln Asn Tyr Pro Gln His Pro His His Arg Asn Ala His Ser Ser
    370                 375                 380

Trp Ala Asn Ser Met Arg Ile Pro Glu Tyr His Arg His Ile Leu Tyr
385                 390                 395                 400

Gly Ala Leu Val Gly Gly Pro Gly Ser Asp Asp Ser Tyr Asn Asp Asp
                405                 410                 415

Ile Thr Asp Tyr Val Gln Asn Glu Val Ala Cys Asp Tyr Asn Ala Gly
            420                 425                 430

Ile Val Gly Ala Leu Ala Lys Met Tyr Leu Met Tyr Gly Gly Asp Pro
        435                 440                 445

Ile Pro Asn Phe Lys Ala Ile Glu Lys Pro Thr Asn Asp Glu Ile Phe
    450                 455                 460

Val Glu Ser Lys Phe Gly Asn Ser Gln Gly Thr Asn Tyr Thr Glu Ile
465                 470                 475                 480

Ile Ser Tyr Ile Tyr Asn Arg Thr Gly Trp Pro Pro Arg Val Thr Asp
                485                 490                 495

Asn Leu Asn Phe Lys Tyr Phe Ile Asp Leu Ser Glu Leu Ile Lys Ala
            500                 505                 510

Gly Tyr Gly Pro Asp Val Val Lys Val Glu Thr Tyr Tyr Ser Glu Gly
        515                 520                 525

Gly Lys Ile Ser Gly Pro Tyr Val Trp Asn Ala Ser Lys Asn Leu Tyr
    530                 535                 540

Tyr Ile Leu Val Asp Phe Thr Gly Thr Lys Ile Tyr Pro Gly Gly Glu
545                 550                 555                 560

Val Glu His Lys Lys Gln Ala Gln Phe Lys Ile Ser Val Pro Gln Gly
```

```
                565                 570                 575

Val Pro Trp Asp Pro Thr Asn Asp Pro Ser Tyr Ala Gly Leu Thr Lys
            580                 585                 590

Glu Leu Ser Lys Asn Lys Phe Ile Ala Ala Tyr Glu Gly Asn Val Leu
        595                 600                 605

Val Trp Gly Gln Glu Pro Glu Gly Ser Ser Ser Ser Thr Pro Thr Pro
    610                 615                 620

Thr Pro Thr Pro Thr Pro Thr Leu Thr Pro Thr Pro Thr Ser Thr Ala
625                 630                 635                 640

Thr Pro Thr Pro Thr Pro Thr Pro Thr Pro Thr Ser Thr Pro Thr Ala
                645                 650                 655

Thr Pro Thr Ala Thr Pro Thr Pro Thr Pro Thr Pro Ser Ser Thr Pro
            660                 665                 670

Val Ala Gly Gly Gln Ile Lys Val Leu Tyr Ala Asn Lys Glu Thr Asn
        675                 680                 685

Ser Thr Thr Asn Thr Ile Arg Pro Trp Leu Lys Val Val Asn Thr Gly
    690                 695                 700

Ser Ser Ser Ile Asp Leu Ser Arg Val Thr Ile Arg Tyr Trp Tyr Thr
705                 710                 715                 720

Val Asp Gly Asp Lys Ala Gln Ser Ala Ile Ser Asp Trp Ala Gln Ile
                725                 730                 735

Gly Ala Ser Asn Val Thr Phe Lys Phe Val Lys Leu Ser Ser Ser Val
            740                 745                 750

Ser Gly Ala Asp Tyr Tyr Leu Glu Ile Gly Phe Lys Ser Gly Ala Gly
        755                 760                 765

Gln Leu Gln Ala Gly Lys Asp Thr Gly Glu Ile Gln Ile Arg Phe Asn
    770                 775                 780

Lys Ser Asp Trp Ser Asn Tyr Asn Gln Gly Asn Asp Trp Ser Trp Met
785                 790                 795                 800

Gln Ser Met Thr Ser Tyr Gly Glu Asn Val Lys Val Thr Ala Tyr Ile
                805                 810                 815

Asp Gly Val Leu Val Trp Gly Gln Glu Pro Ser Gly Ala Thr Pro Thr
            820                 825                 830

Pro Thr Ala Thr Pro Ala Pro Thr Val Thr Pro Thr Pro Thr Pro Ala
        835                 840                 845

Pro Thr Pro Thr Pro Thr Pro Thr Pro Thr Ala Thr Pro Thr Pro Thr
    850                 855                 860

Pro Thr Pro Thr Pro Thr Pro Thr Ala Thr Pro Thr Pro Thr Pro Ser
865                 870                 875                 880

Ser Thr Pro Val Ala Gly Gly Gln Ile Lys Val Leu Tyr Ala Asn Lys
                885                 890                 895

Glu Thr Asn Ser Thr Thr Asn Thr Ile Arg Pro Trp Leu Lys Val Val
            900                 905                 910

Asn Thr Gly Ser Ser Ser Ile Asp Leu Ser Arg Val Thr Ile Arg Tyr
        915                 920                 925

Trp Tyr Thr Val Asp Gly Asp Lys Ala Gln Ser Ala Ile Ser Asp Trp
    930                 935                 940

Ala Gln Ile Gly Ala Ser Asn Val Thr Phe Lys Phe Val Lys Leu Ser
945                 950                 955                 960

Ser Ser Val Ser Gly Ala Asp Tyr Tyr Leu Glu Ile Gly Phe Lys Ser
                965                 970                 975

Gly Ala Gly Gln Leu Gln Ala Gly Lys Asp Thr Gly Glu Ile Gln Ile
            980                 985                 990
```

```
Arg Phe Asn Lys Ser Asp Trp Ser Asn Tyr Asn Gln Gly Asn Asp Trp
        995                 1000                1005

Ser Trp Met Gln Ser Met Thr Ser Tyr Gly Glu Asn Val Lys Val Thr
    1010                1015                1020

Ala Tyr Ile Asp Gly Val Leu Val Trp Gly Gln Glu Pro Ser Gly Ala
1025                1030                1035                1040

Thr Pro Thr Pro Thr Ala Thr Pro Ala Pro Thr Val Thr Pro Thr Pro
                1045                1050                1055

Thr Pro Thr Pro Thr Pro Thr Pro Ser Ser Gly Ile Val Lys Ile Asp
            1060                1065                1070

Thr Ser Thr Leu Ile Gly Thr Asn His Ala His Cys Trp Tyr Arg Asp
        1075                1080                1085

Lys Leu Glu Thr Ala Leu Arg Gly Ile Arg Ser Trp Gly Met Asn Ser
    1090                1095                1100

Val Arg Val Val Leu Ser Asn Gly Tyr Arg Trp Thr Lys Ile Pro Ala
1105                1110                1115                1120

Ser Glu Val Ala Asn Ile Ile Ser Leu Ser Arg Ser Leu Gly Phe Arg
                1125                1130                1135

Ala Ile Val Leu Glu Val His Asp Thr Thr Gly Tyr Gly Glu Asp Gly
            1140                1145                1150

Ala Ala Cys Ser Leu Ala Gln Ala Val Glu Tyr Trp Lys Glu Ile Lys
        1155                1160                1165

Ser Val Leu Glu Gly Asn Glu Asp Phe Val Ile Ile Asn Ile Gly Asn
    1170                1175                1180

Glu Pro Tyr Gly Asn Asn Asn Tyr Gln Asn Trp Ile Asn Asp Thr Lys
1185                1190                1195                1200

Asn Ala Ile Lys Ala Leu Arg Asp Ala Gly Phe Lys His Thr Ile Met
                1205                1210                1215

Val Asp Ala Pro Asn Trp Gly Gln Asp Trp Ser Asn Thr Met Arg Asp
            1220                1225                1230

Asn Ala Gln Ser Ile Met Glu Ala Asp Pro Leu Arg Asn Leu Val Phe
        1235                1240                1245

Ser Ile His Met Tyr Gly Val Tyr Asn Thr Ala Ser Lys Val Glu Glu
    1250                1255                1260

Tyr Ile Lys Ser Phe Val Glu Lys Gly Leu Pro Leu Val Ile Gly Glu
1265                1270                1275                1280

Phe Gly His Gln His Thr Asp Gly Asp Pro Asp Glu Glu Ala Ile Val
                1285                1290                1295

Arg Tyr Ala Lys Gln Tyr Lys Ile Gly Leu Phe Ser Trp Ser Trp Cys
            1300                1305                1310

Gly Asn Ser Ser Tyr Val Gly Tyr Leu Asp Met Val Asn Asn Trp Asp
        1315                1320                1325

Pro Asn Asn Pro Thr Pro Trp Gly Gln Trp Tyr Lys Thr Asn Ala Ile
    1330                1335                1340

Gly Ala Glu
1345


<210> SEQ ID NO 52
<211> LENGTH: 3225
<212> TYPE: DNA
<213> ORGANISM: Caldicellulosiruptor bescii

<400> SEQUENCE: 52

atggcacatc accaccacca tcacgtggat gacgacgaca agatggcaac aacctttaac      60
```

-continued

```
tatggtgaag ctcttcaaaa agcgatcatg ttttatgaat ttcagatgtc aggtaaacta    120
ccatcatgga tccgtaacaa ctggcgcggg gattctggtc taaatgatgg caaagatgta    180
ggtttagatc ttactggtgg ctggcatgat gcgggcgacc atgtaaagtt taatctacca    240
atgtcataca gtgcatcaat gctttcgtgg gcagtttatg agtacaaagc agcatttgag    300
aaaagtggtc agcttgaaca tatacttaac cagattgaat gggtaaacga ctactttgta    360
aaatgccatc catcaaagta tgtatactac tatcaagttg gtgacccaat tgaagatcat    420
aacttctggg gtccagcaga agttatgcaa atgaaacgac cagcatacaa gtgtgactta    480
aataatccag caagttcggt tgttgcagaa acagcagcat ccttagctgc agcttcaatc    540
gtcatacgtg aaagaaatag tcaaaaggca gacacatatt tgcagcatgc gatggtactc    600
tttgattttg ccgatagaac tcgtagtgat gcagggtata ccgcagcaac aggcttttac    660
acatcaggtg gttttattga tgatcttggt tgggcagcag tgtggttata tcttgcgaca    720
aatgacaaat catatttaga taaagctgag gcacttatgg cagaatatgc cggtggcaca    780
aatacatgga cacagtgctg ggacgatgta agatacggag caatattgct tttagcaaaa    840
attactaata aagacatata taaaggtgct gttgaaagaa atcttgatca ttggacatat    900
aacataacct atacacctaa aggtcttgca tggataacag ggtggggctc acttaggtat    960
gccacaactg cagctttctt agcgtttgtt tatgcagatt ggtcaggatg tccagaaaat   1020
aagcgaacag cttatctaaa atttggtgag agtcagatta actatgcatt aggttcaaca   1080
ggaagaagct tttggtagg atttgggcaa aattatccac aacatccaca tcacagaaat   1140
gcacacagtt catgggcgaa cagtatgcga atacctgaat atcatcgaca catactttat   1200
ggtgcattag taggcggacc aggctctgat gatagttaca atgatgatat tactgactat   1260
gttcaaaacg aggtggcttg tgactacaat gctggtattg taggtgctct ggcaaaaatg   1320
taccttatgt atggaggaga cccaatacct aatttcaaag ctatcgaaaa gccaactaat   1380
gatgaaattt ttgttgaatc caagtttggt aattcacagg gtacaaacta taccgaaata   1440
atttcataca tttataacag aacgggatgg ccgcctcgag tcacagataa tctaaacttt   1500
aagtatttta ttgacctaag tgagttaatc aaggctgggt atggtcctga tgttgttaaa   1560
gtagagacat attattcaga aggtggaaaa atatctggac catacgtatg gaatgcatca   1620
aagaaccttt actatatatt agttgatttt acaggaacaa aaatatatcc aggtggggaa   1680
gtagaacaca aaaaacaagc tcaatttaag atatctgtgc cacaaggtgt tccatgggat   1740
ccaactaatg acccatctta tgcaggatta acaaaaagaac ttagtaaaaa taagttcata   1800
gcagcttatg aaggtaacgt gctggtatgg ggacaagaac cagagggttc gtcaagttca   1860
accccaaccc caacaccaac accaacacca acactgactc caacaccgac atcaactgct   1920
acaccaacac cgacacctac accaacacca acgtcaacac caactgctac accaacagca   1980
acgccaacac caacaccgac gccgagcagc acacctgtag caggcgggca gataaaggta   2040
ttgtatgcta acaaggagac aaatagcaca acaaacacga taaggccatg gttgaaggta   2100
gtgaacactg gaagcagcag catagattta agcagggtaa cgataaggta ctggtacacg   2160
gtagatgggg acaaggcaca gagtgcgata tcagactggg cacagatagg agcaagcaat   2220
gtgacattca agtttgtgaa gctgagcagt agcgtaagtg gagcggacta ttatttagag   2280
ataggattta agagtggagc tgggcagttg caggctggta aagacacagg ggagatacag   2340
ataaggttta acaagagtga ctggagcaat tacaatcagg ggaatgactg gtcatggatg   2400
```

cagagcatga cgagttatgg agagaatgtg aaggtaacag cgtatataga tggtgtattg 2460
gtatggggac aggagccgag tggagcgaca ccaacaccga cagcaacacc agcaccgaca 2520
gtgacaccga caccaacacc agcaccaaca ccaaccccga ctccaacacc aactgctaca 2580
ccaacgccaa caccgactcc aacaccaaca ccaactgcta ccccaacacc gacgccgagc 2640
agcacacctg tagcaggtgg acagataaag gtattgtatg ctaacaagga gacaaatagc 2700
acaacaaaca cgataaggcc atggttgaag gtagtgaaca ctggaagcag cagcatagat 2760
ttaagcaggg taacgataag gtactggtac acggtagatg gggacaaggc acagagtgcg 2820
atatcagact gggcacagat aggagcaagc aatgtgacat tcaagtttgt gaagctgagc 2880
agtagcgtaa gtggagcgga ctattattta gagataggat ttaagagtgg agctgggcag 2940
ttgcaggctg gtaaagacac aggggagata cagataaggt ttaacaagag tgactggagc 3000
aattacaatc aggggaatga ctggtcatgg atgcagagca tgacgagtta tggagagaat 3060
gtgaaggtaa cagcgtatat agatggtgta ttggtatggg gacaggagcc gagtggagcg 3120
acaccaacac cgacagcaac accagcaccg acagtgacac ctacacctac accaactcca 3180
actccaacgc cgagcagtgg aatagtgaag atagatacta gctaa 3225

<210> SEQ ID NO 53
<211> LENGTH: 1074
<212> TYPE: PRT
<213> ORGANISM: Caldicellulosiruptor bescii

<400> SEQUENCE: 53

Met Ala His His His His His His Val Asp Asp Asp Asp Lys Met Ala
1 5 10 15

Thr Thr Phe Asn Tyr Gly Glu Ala Leu Gln Lys Ala Ile Met Phe Tyr
20 25 30

Glu Phe Gln Met Ser Gly Lys Leu Pro Ser Trp Ile Arg Asn Asn Trp
35 40 45

Arg Gly Asp Ser Gly Leu Asn Asp Gly Lys Asp Val Gly Leu Asp Leu
50 55 60

Thr Gly Gly Trp His Asp Ala Gly Asp His Val Lys Phe Asn Leu Pro
65 70 75 80

Met Ser Tyr Ser Ala Ser Met Leu Ser Trp Ala Val Tyr Glu Tyr Lys
85 90 95

Ala Ala Phe Glu Lys Ser Gly Gln Leu Glu His Ile Leu Asn Gln Ile
100 105 110

Glu Trp Val Asn Asp Tyr Phe Val Lys Cys His Pro Ser Lys Tyr Val
115 120 125

Tyr Tyr Tyr Gln Val Gly Asp Pro Ile Glu Asp His Asn Phe Trp Gly
130 135 140

Pro Ala Glu Val Met Gln Met Lys Arg Pro Ala Tyr Lys Cys Asp Leu
145 150 155 160

Asn Asn Pro Ala Ser Ser Val Val Ala Glu Thr Ala Ala Ser Leu Ala
165 170 175

Ala Ala Ser Ile Val Ile Arg Glu Arg Asn Ser Gln Lys Ala Asp Thr
180 185 190

Tyr Leu Gln His Ala Met Val Leu Phe Asp Phe Ala Asp Arg Thr Arg
195 200 205

Ser Asp Ala Gly Tyr Thr Ala Ala Thr Gly Phe Tyr Thr Ser Gly Gly
210 215 220

Phe Ile Asp Asp Leu Gly Trp Ala Ala Val Trp Leu Tyr Leu Ala Thr

```
225                 230                 235                 240

Asn Asp Lys Ser Tyr Leu Asp Lys Ala Glu Ala Leu Met Ala Glu Tyr
                245                 250                 255

Ala Gly Gly Thr Asn Thr Trp Thr Gln Cys Trp Asp Asp Val Arg Tyr
            260                 265                 270

Gly Ala Ile Leu Leu Leu Ala Lys Ile Thr Asn Lys Asp Ile Tyr Lys
        275                 280                 285

Gly Ala Val Glu Arg Asn Leu Asp His Trp Thr Tyr Asn Ile Thr Tyr
    290                 295                 300

Thr Pro Lys Gly Leu Ala Trp Ile Thr Gly Trp Gly Ser Leu Arg Tyr
305                 310                 315                 320

Ala Thr Thr Ala Ala Phe Leu Ala Phe Val Tyr Ala Asp Trp Ser Gly
                325                 330                 335

Cys Pro Glu Asn Lys Arg Thr Ala Tyr Leu Lys Phe Gly Glu Ser Gln
            340                 345                 350

Ile Asn Tyr Ala Leu Gly Ser Thr Gly Arg Ser Phe Leu Val Gly Phe
        355                 360                 365

Gly Gln Asn Tyr Pro Gln His Pro His His Arg Asn Ala His Ser Ser
    370                 375                 380

Trp Ala Asn Ser Met Arg Ile Pro Glu Tyr His Arg His Ile Leu Tyr
385                 390                 395                 400

Gly Ala Leu Val Gly Gly Pro Gly Ser Asp Asp Ser Tyr Asn Asp Asp
                405                 410                 415

Ile Thr Asp Tyr Val Gln Asn Glu Val Ala Cys Asp Tyr Asn Ala Gly
            420                 425                 430

Ile Val Gly Ala Leu Ala Lys Met Tyr Leu Met Tyr Gly Gly Asp Pro
        435                 440                 445

Ile Pro Asn Phe Lys Ala Ile Glu Lys Pro Thr Asn Asp Glu Ile Phe
    450                 455                 460

Val Glu Ser Lys Phe Gly Asn Ser Gln Gly Thr Asn Tyr Thr Glu Ile
465                 470                 475                 480

Ile Ser Tyr Ile Tyr Asn Arg Thr Gly Trp Pro Pro Arg Val Thr Asp
                485                 490                 495

Asn Leu Asn Phe Lys Tyr Phe Ile Asp Leu Ser Glu Leu Ile Lys Ala
            500                 505                 510

Gly Tyr Gly Pro Asp Val Val Lys Val Glu Thr Tyr Tyr Ser Glu Gly
        515                 520                 525

Gly Lys Ile Ser Gly Pro Tyr Val Trp Asn Ala Ser Lys Asn Leu Tyr
    530                 535                 540

Tyr Ile Leu Val Asp Phe Thr Gly Thr Lys Ile Tyr Pro Gly Gly Glu
545                 550                 555                 560

Val Glu His Lys Lys Gln Ala Gln Phe Lys Ile Ser Val Pro Gln Gly
                565                 570                 575

Val Pro Trp Asp Pro Thr Asn Asp Pro Ser Tyr Ala Gly Leu Thr Lys
            580                 585                 590

Glu Leu Ser Lys Asn Lys Phe Ile Ala Ala Tyr Glu Gly Asn Val Leu
        595                 600                 605

Val Trp Gly Gln Glu Pro Glu Gly Ser Ser Ser Ser Thr Pro Thr Pro
    610                 615                 620

Thr Pro Thr Pro Thr Pro Thr Leu Thr Pro Thr Pro Thr Ser Thr Ala
625                 630                 635                 640

Thr Pro Thr Pro Thr Pro Thr Pro Thr Pro Thr Ser Thr Pro Thr Ala
                645                 650                 655
```

-continued

```
Thr Pro Thr Ala Thr Pro Thr Pro Thr Pro Thr Pro Ser Ser Thr Pro
            660                 665                 670

Val Ala Gly Gly Gln Ile Lys Val Leu Tyr Ala Asn Lys Glu Thr Asn
        675                 680                 685

Ser Thr Thr Asn Thr Ile Arg Pro Trp Leu Lys Val Val Asn Thr Gly
    690                 695                 700

Ser Ser Ser Ile Asp Leu Ser Arg Val Thr Ile Arg Tyr Trp Tyr Thr
705                 710                 715                 720

Val Asp Gly Asp Lys Ala Gln Ser Ala Ile Ser Asp Trp Ala Gln Ile
                725                 730                 735

Gly Ala Ser Asn Val Thr Phe Lys Phe Val Lys Leu Ser Ser Ser Val
            740                 745                 750

Ser Gly Ala Asp Tyr Tyr Leu Glu Ile Gly Phe Lys Ser Gly Ala Gly
        755                 760                 765

Gln Leu Gln Ala Gly Lys Asp Thr Gly Glu Ile Gln Ile Arg Phe Asn
    770                 775                 780

Lys Ser Asp Trp Ser Asn Tyr Asn Gln Gly Asn Asp Trp Ser Trp Met
785                 790                 795                 800

Gln Ser Met Thr Ser Tyr Gly Glu Asn Val Lys Val Thr Ala Tyr Ile
                805                 810                 815

Asp Gly Val Leu Val Trp Gly Gln Glu Pro Ser Gly Ala Thr Pro Thr
            820                 825                 830

Pro Thr Ala Thr Pro Ala Pro Thr Val Thr Pro Thr Pro Thr Pro Ala
        835                 840                 845

Pro Thr Pro Thr Pro Thr Pro Thr Pro Thr Ala Thr Pro Thr Pro Thr
    850                 855                 860

Pro Thr Pro Thr Pro Thr Pro Thr Ala Thr Pro Thr Pro Thr Pro Ser
865                 870                 875                 880

Ser Thr Pro Val Ala Gly Gly Gln Ile Lys Val Leu Tyr Ala Asn Lys
                885                 890                 895

Glu Thr Asn Ser Thr Thr Asn Thr Ile Arg Pro Trp Leu Lys Val Val
            900                 905                 910

Asn Thr Gly Ser Ser Ser Ile Asp Leu Ser Arg Val Thr Ile Arg Tyr
        915                 920                 925

Trp Tyr Thr Val Asp Gly Asp Lys Ala Gln Ser Ala Ile Ser Asp Trp
    930                 935                 940

Ala Gln Ile Gly Ala Ser Asn Val Thr Phe Lys Phe Val Lys Leu Ser
945                 950                 955                 960

Ser Ser Val Ser Gly Ala Asp Tyr Tyr Leu Glu Ile Gly Phe Lys Ser
                965                 970                 975

Gly Ala Gly Gln Leu Gln Ala Gly Lys Asp Thr Gly Glu Ile Gln Ile
            980                 985                 990

Arg Phe Asn Lys Ser Asp Trp Ser Asn Tyr Asn Gln Gly Asn Asp Trp
        995                 1000                1005

Ser Trp Met Gln Ser Met Thr Ser Tyr Gly Glu Asn Val Lys Val Thr
    1010                1015                1020

Ala Tyr Ile Asp Gly Val Leu Val Trp Gly Gln Glu Pro Ser Gly Ala
1025                1030                1035                1040

Thr Pro Thr Pro Thr Ala Thr Pro Ala Pro Thr Val Thr Pro Thr Pro
                1045                1050                1055

Thr Pro Thr Pro Thr Pro Thr Pro Ser Ser Gly Ile Val Lys Ile Asp
            1060                1065                1070
```

Thr Ser

<210> SEQ ID NO 54
<211> LENGTH: 2739
<212> TYPE: DNA
<213> ORGANISM: Caldicellulosiruptor bescii

<400> SEQUENCE: 54
atggcacatc accaccacca tcacgtggat gacgacgaca agatgaattt caaagctatc 60
gaaaagccaa ctaatgatga aatttttgtt gaatccaagt ttggtaattc acagggtaca 120
aactataccg aaataatttc atacatttat aacagaacgg gatggccgcc tcgagtcaca 180
gataatctaa actttaagta ttttattgac ctaagtgagt taatcaaggc tgggtatggt 240
cctgatgttg ttaaagtaga gacatattat tcagaaggtg gaaaaatatc tggaccatac 300
gtatggaatg catcaaagaa cctttactat atattagttg attttacagg aacaaaaata 360
tatccaggtg gggaagtaga acacaaaaaa caagctcaat ttaagatatc tgtgccacaa 420
ggtgttccat gggatccaac taatgaccca tcttatgcag gattaacaaa agaacttagt 480
aaaaataagt tcatagcagc ttatgaaggt aacgtgctgg tatggggaca agaaccagag 540
ggttcgtcaa gttcaacccc aaccccaaca ccaacaccaa caccaacact gactccaaca 600
ccgacatcaa ctgctacacc aacaccgaca cctacaccaa caccaacgtc aacaccaact 660
gctacaccaa cagcaacgcc aacaccaaca ccgacgccga gcagcacacc tgtagcaggc 720
gggcagataa aggtattgta tgctaacaag gagacaaata gcacaacaaa cacgataagg 780
ccatggttga aggtagtgaa cactggaagc agcagcatag atttaagcag ggtaacgata 840
aggtactggt acacggtaga tggggacaag gcacagagtg cgatatcaga ctgggcacag 900
ataggagcaa gcaatgtgac attcaagttt gtgaagctga gcagtagcgt aagtggagcg 960
gactattatt tagagatagg atttaagagt ggagctgggc agttgcaggc tggtaaagac 1020
acaggggaga tacagataag gtttaacaag agtgactgga gcaattacaa tcaggggaat 1080
gactggtcat ggatgcagag catgacgagt tatggagaga atgtgaaggt aacagcgtat 1140
atagatggtg tattggtatg gggacaggag ccgagtggag cgacaccaac accgacagca 1200
acaccagcac cgacagtgac accgacacca acaccagcac caacaccaac cccgactcca 1260
acaccaactg ctacaccaac gccaacaccg actccaacac caacaccaac tgctacccca 1320
acaccgacgc cgagcagcac acctgtagca ggtggacaga taaaggtatt gtatgctaac 1380
aaggagacaa atagcacaac aaacacgata aggccatggt tgaaggtagt gaacactgga 1440
agcagcagca tagatttaag cagggtaacg ataaggtact ggtacacggt agatggggac 1500
aaggcacaga gtgcgatatc agactgggca cagataggag caagcaatgt gacattcaag 1560
tttgtgaagc tgagcagtag cgtaagtgga gcggactatt atttagagat aggatttaag 1620
agtggagctg ggcagttgca ggctggtaaa gacacagggg agatacagat aaggtttaac 1680
aagagtgact ggagcaatta caatcagggg aatgactggt catggatgca gagcatgacg 1740
agttatggag agaatgtgaa ggtaacagcg tatatagatg gtgtattggt atggggacag 1800
gagccgagtg gagcgacacc aacaccgaca gcaacaccag caccgacagt gacacctaca 1860
cctacaccaa ctccaactcc aacgccgagc agtggaatag tgaagataga tactagcaca 1920
ttaataggaa caaatcacgc acattgctgg tacagagata aacttgagac ggcattgcga 1980
ggaataaggt catggggtat gaactctgtg agggtagtgt tgagtaatgg ctatcgatgg 2040
acgaagatac cagcaagtga agtagcaaat attatatcat tgtcaagaag tcttggattc 2100

```
agagccattg tattagaagt tcacgacacg acaggatatg gtgaggacgg tgcagcatgt   2160

tcattggcgc aagcagtaga atattggaaa gagataaaga gtgtgttaga aggcaatgag   2220

gattttgtta taataaacat tggtaatgag ccgtatggga acaataacta tcaaaactgg   2280

attaatgaca cgaagaatgc tataaaagcg ctaagggatg cagggttcaa gcacacgata   2340

atggttgatg caccgaactg gggcaggat tggtctaata ctatgagaga caatgcccag   2400

agcataatgg aagcagatcc gctgcgcaat ttggtatttt cgattcatat gtacggtgta   2460

tacaatacag cgagcaaggt agaagaatat atcaagtcat ttgtggagaa agggctgcca   2520

ttagttattg gggagtttgg gcatcagcat acagatggtg accctgacga ggaagctatt   2580

gtcaggtatg caaaacaata caagatagga ctttttagct ggtcttggtg tggcaattcg   2640

agctatgtag ggtacttgga catggtaaac aattgggacc ccaataatcc aactccatgg   2700

gggcaatggt ataaaactaa tgcgattggt gctgaataa                          2739
```

```
<210> SEQ ID NO 55
<211> LENGTH: 912
<212> TYPE: PRT
<213> ORGANISM: Caldicellulosiruptor bescii

<400> SEQUENCE: 55

Met Ala His His His His His His Val Asp Asp Asp Asp Lys Met Asn
1               5                   10                  15

Phe Lys Ala Ile Glu Lys Pro Thr Asn Asp Glu Ile Phe Val Glu Ser
            20                  25                  30

Lys Phe Gly Asn Ser Gln Gly Thr Asn Tyr Thr Glu Ile Ile Ser Tyr
        35                  40                  45

Ile Tyr Asn Arg Thr Gly Trp Pro Pro Arg Val Thr Asp Asn Leu Asn
    50                  55                  60

Phe Lys Tyr Phe Ile Asp Leu Ser Glu Leu Ile Lys Ala Gly Tyr Gly
65                  70                  75                  80

Pro Asp Val Val Lys Val Glu Thr Tyr Tyr Ser Glu Gly Gly Lys Ile
                85                  90                  95

Ser Gly Pro Tyr Val Trp Asn Ala Ser Lys Asn Leu Tyr Tyr Ile Leu
            100                 105                 110

Val Asp Phe Thr Gly Thr Lys Ile Tyr Pro Gly Gly Glu Val Glu His
        115                 120                 125

Lys Lys Gln Ala Gln Phe Lys Ile Ser Val Pro Gln Gly Val Pro Trp
    130                 135                 140

Asp Pro Thr Asn Asp Pro Ser Tyr Ala Gly Leu Thr Lys Glu Leu Ser
145                 150                 155                 160

Lys Asn Lys Phe Ile Ala Ala Tyr Glu Gly Asn Val Leu Val Trp Gly
                165                 170                 175

Gln Glu Pro Glu Gly Ser Ser Ser Ser Thr Pro Thr Pro Thr Pro Thr
            180                 185                 190

Pro Thr Pro Thr Leu Thr Pro Thr Pro Thr Ser Thr Ala Thr Pro Thr
        195                 200                 205

Pro Thr Pro Thr Pro Thr Pro Thr Ser Thr Pro Thr Ala Thr Pro Thr
    210                 215                 220

Ala Thr Pro Thr Pro Thr Pro Thr Pro Ser Ser Thr Pro Val Ala Gly
225                 230                 235                 240

Gly Gln Ile Lys Val Leu Tyr Ala Asn Lys Glu Thr Asn Ser Thr Thr
                245                 250                 255
```

```
Asn Thr Ile Arg Pro Trp Leu Lys Val Val Asn Thr Gly Ser Ser Ser
            260                 265                 270

Ile Asp Leu Ser Arg Val Thr Ile Arg Tyr Trp Tyr Thr Val Asp Gly
        275                 280                 285

Asp Lys Ala Gln Ser Ala Ile Ser Asp Trp Ala Gln Ile Gly Ala Ser
    290                 295                 300

Asn Val Thr Phe Lys Phe Val Lys Leu Ser Ser Ser Val Ser Gly Ala
305                 310                 315                 320

Asp Tyr Tyr Leu Glu Ile Gly Phe Lys Ser Gly Ala Gly Gln Leu Gln
                325                 330                 335

Ala Gly Lys Asp Thr Gly Glu Ile Gln Ile Arg Phe Asn Lys Ser Asp
            340                 345                 350

Trp Ser Asn Tyr Asn Gln Gly Asn Asp Trp Ser Trp Met Gln Ser Met
        355                 360                 365

Thr Ser Tyr Gly Glu Asn Val Lys Val Thr Ala Tyr Ile Asp Gly Val
    370                 375                 380

Leu Val Trp Gly Gln Glu Pro Ser Gly Ala Thr Pro Thr Pro Thr Ala
385                 390                 395                 400

Thr Pro Ala Pro Thr Val Thr Pro Thr Pro Thr Pro Ala Pro Thr Pro
                405                 410                 415

Thr Pro Thr Pro Thr Pro Thr Ala Thr Pro Thr Pro Thr Pro Thr Pro
            420                 425                 430

Thr Pro Thr Pro Thr Ala Thr Pro Thr Pro Thr Pro Ser Ser Thr Pro
        435                 440                 445

Val Ala Gly Gly Gln Ile Lys Val Leu Tyr Ala Asn Lys Glu Thr Asn
    450                 455                 460

Ser Thr Thr Asn Thr Ile Arg Pro Trp Leu Lys Val Val Asn Thr Gly
465                 470                 475                 480

Ser Ser Ser Ile Asp Leu Ser Arg Val Thr Ile Arg Tyr Trp Tyr Thr
                485                 490                 495

Val Asp Gly Asp Lys Ala Gln Ser Ala Ile Ser Asp Trp Ala Gln Ile
            500                 505                 510

Gly Ala Ser Asn Val Thr Phe Lys Phe Val Lys Leu Ser Ser Ser Val
        515                 520                 525

Ser Gly Ala Asp Tyr Tyr Leu Glu Ile Gly Phe Lys Ser Gly Ala Gly
    530                 535                 540

Gln Leu Gln Ala Gly Lys Asp Thr Gly Glu Ile Gln Ile Arg Phe Asn
545                 550                 555                 560

Lys Ser Asp Trp Ser Asn Tyr Asn Gln Gly Asn Asp Trp Ser Trp Met
                565                 570                 575

Gln Ser Met Thr Ser Tyr Gly Glu Asn Val Lys Val Thr Ala Tyr Ile
            580                 585                 590

Asp Gly Val Leu Val Trp Gly Gln Glu Pro Ser Gly Ala Thr Pro Thr
        595                 600                 605

Pro Thr Ala Thr Pro Ala Pro Thr Val Thr Pro Thr Pro Thr Pro Thr
    610                 615                 620

Pro Thr Pro Thr Pro Ser Ser Gly Ile Val Lys Ile Asp Thr Ser Thr
625                 630                 635                 640

Leu Ile Gly Thr Asn His Ala His Cys Trp Tyr Arg Asp Lys Leu Glu
                645                 650                 655

Thr Ala Leu Arg Gly Ile Arg Ser Trp Gly Met Asn Ser Val Arg Val
            660                 665                 670

Val Leu Ser Asn Gly Tyr Arg Trp Thr Lys Ile Pro Ala Ser Glu Val
```

-continued

```
        675                 680                 685

Ala Asn Ile Ile Ser Leu Ser Arg Ser Leu Gly Phe Arg Ala Ile Val
    690                 695                 700

Leu Glu Val His Asp Thr Thr Gly Tyr Gly Glu Asp Gly Ala Ala Cys
705                 710                 715                 720

Ser Leu Ala Gln Ala Val Glu Tyr Trp Lys Glu Ile Lys Ser Val Leu
                725                 730                 735

Glu Gly Asn Glu Asp Phe Val Ile Ile Asn Ile Gly Asn Glu Pro Tyr
            740                 745                 750

Gly Asn Asn Asn Tyr Gln Asn Trp Ile Asn Asp Thr Lys Asn Ala Ile
        755                 760                 765

Lys Ala Leu Arg Asp Ala Gly Phe Lys His Thr Ile Met Val Asp Ala
    770                 775                 780

Pro Asn Trp Gly Gln Asp Trp Ser Asn Thr Met Arg Asp Asn Ala Gln
785                 790                 795                 800

Ser Ile Met Glu Ala Asp Pro Leu Arg Asn Leu Val Phe Ser Ile His
                805                 810                 815

Met Tyr Gly Val Tyr Asn Thr Ala Ser Lys Val Glu Glu Tyr Ile Lys
            820                 825                 830

Ser Phe Val Glu Lys Gly Leu Pro Leu Val Ile Gly Glu Phe Gly His
        835                 840                 845

Gln His Thr Asp Gly Asp Pro Asp Glu Glu Ala Ile Val Arg Tyr Ala
    850                 855                 860

Lys Gln Tyr Lys Ile Gly Leu Phe Ser Trp Ser Trp Cys Gly Asn Ser
865                 870                 875                 880

Ser Tyr Val Gly Tyr Leu Asp Met Val Asn Asn Trp Asp Pro Asn Asn
                885                 890                 895

Pro Thr Pro Trp Gly Gln Trp Tyr Lys Thr Asn Ala Ile Gly Ala Glu
            900                 905                 910
```

<210> SEQ ID NO 56
<211> LENGTH: 42
<212> TYPE: DNA
<213> ORGANISM: Artificial Sequence
<220> FEATURE:
<223> OTHER INFORMATION: Synthesized Construct

<400> SEQUENCE: 56
gacgacgaca agatggctac atctaatgat ggagtagtga ag 42

<210> SEQ ID NO 57
<211> LENGTH: 45
<212> TYPE: DNA
<213> ORGANISM: Artificial Sequence
<220> FEATURE:
<223> OTHER INFORMATION: Synthesized Construct

<400> SEQUENCE: 57
gaggagaagc ccggttaatt ttgcggctgg aactggcgct ggttc 45

<210> SEQ ID NO 58
<211> LENGTH: 44
<212> TYPE: DNA
<213> ORGANISM: Artificial Sequence
<220> FEATURE:
<223> OTHER INFORMATION: Synthesized Construct

<400> SEQUENCE: 58
gaggagaagc ccggttatgg cattggtatt actgtctgca ccgg 44

<210> SEQ ID NO 59
<211> LENGTH: 44
<212> TYPE: DNA
<213> ORGANISM: Artificial Sequence
<220> FEATURE:
<223> OTHER INFORMATION: Synthesized Construct

<400> SEQUENCE: 59
gacgacgaca agatgggtgc ctcttcagta cctacttcaa cacc 44

<210> SEQ ID NO 60
<211> LENGTH: 1414
<212> TYPE: PRT
<213> ORGANISM: Caldicellulosiruptor bescii

<400> SEQUENCE: 60

Met Arg Val Lys Thr Lys Met Gly Lys Lys Trp Leu Ser Ile Leu Cys
1 5 10 15

Thr Val Val Phe Leu Leu Asn Ile Leu Phe Ile Ala Asn Val Thr Asn
20 25 30

Leu Pro Lys Val Gly Ala Ala Thr Ser Asn Asp Gly Val Val Lys Ile
35 40 45

Asp Thr Ser Thr Leu Ile Gly Thr Asn His Ala His Cys Trp Tyr Arg
50 55 60

Asp Lys Leu Glu Thr Ala Leu Arg Gly Ile Arg Ser Trp Gly Met Asn
65 70 75 80

Ser Val Arg Val Val Leu Ser Asn Gly Tyr Arg Trp Thr Lys Ile Pro
85 90 95

Ala Ser Glu Val Ala Asn Ile Ile Ser Leu Ser Arg Ser Leu Gly Phe
100 105 110

Arg Ala Ile Val Leu Glu Val His Asp Thr Thr Gly Tyr Gly Glu Asp
115 120 125

Gly Ala Ala Cys Ser Leu Ala Gln Ala Val Glu Tyr Trp Lys Glu Ile
130 135 140

Lys Ser Val Leu Glu Gly Asn Glu Asp Phe Val Ile Ile Asn Ile Gly
145 150 155 160

Asn Glu Pro Tyr Gly Asn Asn Asn Tyr Gln Asn Trp Ile Asn Asp Thr
165 170 175

Lys Asn Ala Ile Lys Ala Leu Arg Asp Ala Gly Phe Lys His Thr Ile
180 185 190

Met Val Asp Ala Pro Asn Trp Gly Gln Asp Trp Ser Asn Thr Met Arg
195 200 205

Asp Asn Ala Gln Ser Ile Met Glu Ala Asp Pro Leu Arg Asn Leu Val
210 215 220

Phe Ser Ile His Met Tyr Gly Val Tyr Asn Thr Ala Ser Lys Val Glu
225 230 235 240

Glu Tyr Ile Lys Ser Phe Val Glu Lys Gly Leu Pro Leu Val Ile Gly
245 250 255

Glu Phe Gly His Gln His Thr Asp Gly Asp Pro Asp Glu Glu Ala Ile
260 265 270

Val Arg Tyr Ala Lys Gln Tyr Lys Ile Gly Leu Phe Ser Trp Ser Trp
275 280 285

Cys Gly Asn Ser Ser Tyr Val Gly Tyr Leu Asp Met Val Asn Asn Trp
290 295 300

Asp Pro Asn Asn Pro Thr Pro Trp Gly Gln Trp Tyr Lys Thr Asn Ala

```
305                 310                 315                 320

Ile Gly Ala Ser Ser Val Pro Thr Ser Thr Pro Thr Pro Thr Pro Thr
                325                 330                 335

Ala Thr Pro Thr Ala Thr Pro Thr Pro Thr Leu Thr Pro Thr Pro Thr
            340                 345                 350

Pro Thr Pro Thr Pro Thr Ser Thr Pro Thr Ala Thr Pro Thr Ala Thr
        355                 360                 365

Pro Thr Pro Thr Pro Thr Pro Ser Ser Thr Pro Val Ala Gly Gly Gln
    370                 375                 380

Ile Lys Val Leu Tyr Ala Asn Lys Glu Thr Asn Ser Thr Thr Asn Thr
385                 390                 395                 400

Ile Arg Pro Trp Leu Lys Val Val Asn Thr Gly Ser Ser Ser Ile Asp
                405                 410                 415

Leu Ser Arg Val Thr Ile Arg Tyr Trp Tyr Thr Val Asp Gly Asp Lys
            420                 425                 430

Ala Gln Ser Ala Ile Ser Asp Trp Ala Gln Ile Gly Ala Ser Asn Val
        435                 440                 445

Thr Phe Lys Phe Val Lys Leu Ser Ser Ser Val Ser Gly Ala Asp Tyr
    450                 455                 460

Tyr Leu Glu Ile Gly Phe Lys Ser Gly Ala Gly Gln Leu Gln Ala Gly
465                 470                 475                 480

Lys Asp Thr Gly Glu Ile Gln Ile Arg Phe Asn Lys Ser Asp Trp Ser
                485                 490                 495

Asn Tyr Asn Gln Gly Asn Asp Trp Ser Trp Met Gln Ser Met Thr Ser
            500                 505                 510

Tyr Gly Glu Asn Val Lys Val Thr Ala Tyr Ile Asp Gly Val Leu Val
        515                 520                 525

Trp Gly Gln Glu Pro Ser Gly Ala Thr Pro Thr Pro Thr Ala Thr Pro
    530                 535                 540

Ala Pro Thr Pro Thr Pro Thr Pro Thr Pro Thr Ala Thr Pro Thr Pro
545                 550                 555                 560

Thr Pro Thr Pro Thr Pro Thr Pro Thr Ala Thr Pro Thr Pro Thr Pro
                565                 570                 575

Ser Ser Thr Pro Val Ala Gly Gly Gln Ile Lys Val Leu Tyr Ala Asn
            580                 585                 590

Lys Glu Thr Asn Ser Thr Thr Asn Thr Ile Arg Pro Trp Leu Lys Val
        595                 600                 605

Val Asn Thr Gly Ser Ser Ser Ile Asp Leu Ser Arg Val Thr Ile Arg
    610                 615                 620

Tyr Trp Tyr Thr Val Asp Gly Asp Lys Ala Gln Ser Ala Ile Ser Asp
625                 630                 635                 640

Trp Ala Gln Ile Gly Ala Ser Asn Val Thr Phe Lys Phe Val Lys Leu
                645                 650                 655

Ser Ser Ser Val Ser Gly Ala Asp Tyr Tyr Leu Glu Ile Gly Phe Lys
            660                 665                 670

Ser Gly Ala Gly Gln Leu Gln Ala Gly Lys Asp Thr Gly Glu Ile Gln
        675                 680                 685

Ile Arg Phe Asn Lys Ser Asp Trp Ser Asn Tyr Asn Gln Gly Asn Asp
    690                 695                 700

Trp Ser Trp Met Gln Ser Met Thr Ser Tyr Gly Glu Asn Val Lys Val
705                 710                 715                 720

Thr Ala Tyr Ile Asp Gly Val Leu Val Trp Gly Gln Glu Pro Ser Gly
                725                 730                 735
```

```
Ala Thr Pro Thr Pro Thr Ala Thr Pro Ala Pro Thr Pro Thr Pro Thr
            740                 745                 750

Pro Thr Pro Thr Ala Thr Pro Thr Pro Thr Pro Thr Pro Thr Pro Thr
        755                 760                 765

Pro Thr Ala Thr Pro Thr Pro Thr Pro Ser Ser Thr Pro Val Ala Gly
    770                 775                 780

Gly Gln Ile Lys Val Leu Tyr Ala Asn Lys Glu Thr Asn Ser Thr Thr
785                 790                 795                 800

Asn Thr Ile Arg Pro Trp Leu Lys Val Val Asn Thr Gly Ser Ser Ser
                805                 810                 815

Ile Asp Leu Ser Arg Val Thr Ile Arg Tyr Trp Tyr Thr Val Asp Gly
            820                 825                 830

Asp Lys Ala Gln Ser Ala Ile Ser Asp Trp Ala Gln Ile Gly Ala Ser
        835                 840                 845

Asn Val Thr Phe Lys Phe Val Lys Leu Ser Ser Ser Val Ser Gly Ala
    850                 855                 860

Asp Tyr Tyr Leu Glu Ile Gly Phe Lys Ser Gly Ala Gly Gln Leu Gln
865                 870                 875                 880

Ala Gly Lys Asp Thr Gly Glu Ile Gln Ile Arg Phe Asn Lys Ser Asp
                885                 890                 895

Trp Ser Asn Tyr Asn Gln Gly Asn Asp Trp Ser Trp Met Gln Ser Met
            900                 905                 910

Thr Ser Tyr Gly Glu Asn Val Lys Val Thr Ala Tyr Ile Asp Gly Val
        915                 920                 925

Leu Val Trp Gly Gln Glu Pro Ser Gly Ala Thr Pro Thr Pro Thr Ala
    930                 935                 940

Thr Pro Ala Pro Thr Val Thr Pro Thr Ala Thr Pro Ala Pro Thr Pro
945                 950                 955                 960

Thr Pro Thr Pro Thr Val Thr Ala Thr Pro Thr Pro Thr Pro Thr Pro
                965                 970                 975

Val Gln Thr Val Ile Pro Met Pro Thr Val Thr Pro Asn Pro Thr Ser
            980                 985                 990

Thr Pro Ser Ile Leu Asp Asp Thr Asn Asp Asp Trp Leu Tyr Val Ser
        995                 1000                1005

Gly Asn Lys Ile Val Asp Lys Asp Gly Lys Pro Val Trp Leu Thr Gly
    1010                1015                1020

Ile Asn Trp Phe Gly Tyr Asn Thr Gly Thr Asn Val Phe Asp Gly Val
1025                1030                1035                1040

Trp Ser Cys Asn Leu Lys Asp Thr Leu Ala Glu Ile Ala Asn Arg Gly
                1045                1050                1055

Phe Asn Leu Leu Arg Ile Pro Ile Ser Ala Glu Ile Ile Leu Asn Trp
            1060                1065                1070

Ser Gln Gly Ile Tyr Pro Lys Pro Asn Ile Asn Tyr Tyr Val Asn Pro
        1075                1080                1085

Glu Leu Glu Gly Lys Asn Ser Leu Glu Val Phe Asp Ile Val Val Gln
    1090                1095                1100

Ile Cys Lys Glu Val Gly Leu Lys Ile Met Leu Asp Ile His Ser Ile
1105                1110                1115                1120

Lys Thr Asp Ala Met Gly His Ile Tyr Pro Val Trp Tyr Asp Asp Lys
                1125                1130                1135

Phe Thr Pro Glu Asp Phe Tyr Lys Ala Cys Glu Trp Ile Thr Asn Arg
            1140                1145                1150
```

-continued

```
Tyr Lys Asn Asp Asp Thr Ile Ile Ala Phe Asp Leu Lys Asn Glu Pro
        1155                1160                1165

His Gly Lys Pro Trp Gln Asp Thr Thr Phe Ala Lys Trp Asp Asn Ser
    1170                1175                1180

Thr Asp Ile Asn Asn Trp Lys Tyr Ala Ala Glu Thr Cys Ala Lys Arg
1185                1190                1195                1200

Ile Leu Asn Ile Asn Pro Asn Leu Leu Ile Val Ile Glu Gly Ile Glu
                1205                1210                1215

Ala Tyr Pro Lys Asp Asp Val Thr Trp Thr Ser Lys Ser Tyr Ser Asp
            1220                1225                1230

Tyr Tyr Ser Thr Trp Trp Gly Gly Asn Leu Arg Gly Val Lys Lys Tyr
        1235                1240                1245

Pro Ile Asn Leu Gly Lys Tyr Gln Asn Lys Val Val Tyr Ser Pro His
    1250                1255                1260

Asp Tyr Gly Pro Ser Val Tyr Gln Gln Pro Trp Phe Tyr Pro Gly Phe
1265                1270                1275                1280

Thr Lys Glu Ser Leu Leu Gln Asp Cys Trp Arg Pro Asn Trp Ala Tyr
                1285                1290                1295

Ile Met Glu Glu Asn Ile Ala Pro Leu Leu Ile Gly Glu Trp Gly Gly
            1300                1305                1310

Tyr Leu Asp Gly Ala Asp Asn Glu Lys Trp Met Arg Tyr Leu Arg Asp
        1315                1320                1325

Tyr Ile Ile Glu Asn His Ile His His Thr Phe Trp Cys Phe Asn Ala
    1330                1335                1340

Asn Ser Gly Asp Thr Gly Gly Met Val Gly Tyr Asp Phe Thr Thr Trp
1345                1350                1355                1360

Asp Glu Lys Lys Tyr Ser Phe Leu Lys Pro Ala Leu Trp Gln Asp Ser
                1365                1370                1375

Gln Gly Arg Phe Val Gly Leu Asp His Lys Arg Pro Leu Gly Thr Asn
            1380                1385                1390

Gly Lys Asn Ile Asn Ile Thr Ile Tyr Tyr Asn Asn Asn Glu Pro Ala
        1395                1400                1405

Pro Val Pro Ala Ala Lys
    1410


<210> SEQ ID NO 61
<211> LENGTH: 1376
<212> TYPE: PRT
<213> ORGANISM: Caldicellulosiruptor bescii

<400> SEQUENCE: 61

Ala Thr Ser Asn Asp Gly Val Val Lys Ile Asp Thr Ser Thr Leu Ile
 1               5                  10                  15

Gly Thr Asn His Ala His Cys Trp Tyr Arg Asp Lys Leu Glu Thr Ala
            20                  25                  30

Leu Arg Gly Ile Arg Ser Trp Gly Met Asn Ser Val Arg Val Val Leu
        35                  40                  45

Ser Asn Gly Tyr Arg Trp Thr Lys Ile Pro Ala Ser Glu Val Ala Asn
    50                  55                  60

Ile Ile Ser Leu Ser Arg Ser Leu Gly Phe Arg Ala Ile Val Leu Glu
65                  70                  75                  80

Val His Asp Thr Thr Gly Tyr Gly Glu Asp Gly Ala Ala Cys Ser Leu
                85                  90                  95

Ala Gln Ala Val Glu Tyr Trp Lys Glu Ile Lys Ser Val Leu Glu Gly
            100                 105                 110
```

```
Asn Glu Asp Phe Val Ile Ile Asn Ile Gly Asn Glu Pro Tyr Gly Asn
        115                 120                 125

Asn Asn Tyr Gln Asn Trp Ile Asn Asp Thr Lys Asn Ala Ile Lys Ala
    130                 135                 140

Leu Arg Asp Ala Gly Phe Lys His Thr Ile Met Val Asp Ala Pro Asn
145                 150                 155                 160

Trp Gly Gln Asp Trp Ser Asn Thr Met Arg Asp Asn Ala Gln Ser Ile
                165                 170                 175

Met Glu Ala Asp Pro Leu Arg Asn Leu Val Phe Ser Ile His Met Tyr
            180                 185                 190

Gly Val Tyr Asn Thr Ala Ser Lys Val Glu Glu Tyr Ile Lys Ser Phe
        195                 200                 205

Val Glu Lys Gly Leu Pro Leu Val Ile Gly Glu Phe Gly His Gln His
    210                 215                 220

Thr Asp Gly Asp Pro Asp Glu Glu Ala Ile Val Arg Tyr Ala Lys Gln
225                 230                 235                 240

Tyr Lys Ile Gly Leu Phe Ser Trp Ser Trp Cys Gly Asn Ser Ser Tyr
                245                 250                 255

Val Gly Tyr Leu Asp Met Val Asn Asn Trp Asp Pro Asn Asn Pro Thr
            260                 265                 270

Pro Trp Gly Gln Trp Tyr Lys Thr Asn Ala Ile Gly Ala Ser Ser Val
        275                 280                 285

Pro Thr Ser Thr Pro Thr Pro Thr Pro Thr Ala Thr Pro Thr Ala Thr
    290                 295                 300

Pro Thr Pro Thr Leu Thr Pro Thr Pro Thr Pro Thr Pro Thr Pro Thr
305                 310                 315                 320

Ser Thr Pro Thr Ala Thr Pro Thr Ala Thr Pro Thr Pro Thr Pro Thr
                325                 330                 335

Pro Ser Ser Thr Pro Val Ala Gly Gly Gln Ile Lys Val Leu Tyr Ala
            340                 345                 350

Asn Lys Glu Thr Asn Ser Thr Thr Asn Thr Ile Arg Pro Trp Leu Lys
        355                 360                 365

Val Val Asn Thr Gly Ser Ser Ser Ile Asp Leu Ser Arg Val Thr Ile
    370                 375                 380

Arg Tyr Trp Tyr Thr Val Asp Gly Asp Lys Ala Gln Ser Ala Ile Ser
385                 390                 395                 400

Asp Trp Ala Gln Ile Gly Ala Ser Asn Val Thr Phe Lys Phe Val Lys
                405                 410                 415

Leu Ser Ser Ser Val Ser Gly Ala Asp Tyr Tyr Leu Glu Ile Gly Phe
            420                 425                 430

Lys Ser Gly Ala Gly Gln Leu Gln Ala Gly Lys Asp Thr Gly Glu Ile
        435                 440                 445

Gln Ile Arg Phe Asn Lys Ser Asp Trp Ser Asn Tyr Asn Gln Gly Asn
    450                 455                 460

Asp Trp Ser Trp Met Gln Ser Met Thr Ser Tyr Gly Glu Asn Val Lys
465                 470                 475                 480

Val Thr Ala Tyr Ile Asp Gly Val Leu Val Trp Gly Gln Glu Pro Ser
                485                 490                 495

Gly Ala Thr Pro Thr Pro Thr Ala Thr Pro Ala Pro Thr Pro Thr Pro
            500                 505                 510

Thr Pro Thr Pro Thr Ala Thr Pro Thr Pro Thr Pro Thr Pro Thr Pro
        515                 520                 525
```

```
Thr Pro Thr Ala Thr Pro Thr Pro Thr Pro Ser Ser Thr Pro Val Ala
    530                 535                 540

Gly Gly Gln Ile Lys Val Leu Tyr Ala Asn Lys Glu Thr Asn Ser Thr
545                 550                 555                 560

Thr Asn Thr Ile Arg Pro Trp Leu Lys Val Val Asn Thr Gly Ser Ser
                565                 570                 575

Ser Ile Asp Leu Ser Arg Val Thr Ile Arg Tyr Trp Tyr Thr Val Asp
            580                 585                 590

Gly Asp Lys Ala Gln Ser Ala Ile Ser Asp Trp Ala Gln Ile Gly Ala
        595                 600                 605

Ser Asn Val Thr Phe Lys Phe Val Lys Leu Ser Ser Ser Val Ser Gly
    610                 615                 620

Ala Asp Tyr Tyr Leu Glu Ile Gly Phe Lys Ser Gly Ala Gly Gln Leu
625                 630                 635                 640

Gln Ala Gly Lys Asp Thr Gly Glu Ile Gln Ile Arg Phe Asn Lys Ser
                645                 650                 655

Asp Trp Ser Asn Tyr Asn Gln Gly Asn Asp Trp Ser Trp Met Gln Ser
            660                 665                 670

Met Thr Ser Tyr Gly Glu Asn Val Lys Val Thr Ala Tyr Ile Asp Gly
        675                 680                 685

Val Leu Val Trp Gly Gln Glu Pro Ser Gly Ala Thr Pro Thr Pro Thr
    690                 695                 700

Ala Thr Pro Ala Pro Thr Pro Thr Pro Thr Pro Thr Pro Thr Ala Thr
705                 710                 715                 720

Pro Thr Pro Thr Pro Thr Pro Thr Pro Thr Pro Thr Ala Thr Pro Thr
                725                 730                 735

Pro Thr Pro Ser Ser Thr Pro Val Ala Gly Gly Gln Ile Lys Val Leu
            740                 745                 750

Tyr Ala Asn Lys Glu Thr Asn Ser Thr Thr Asn Thr Ile Arg Pro Trp
        755                 760                 765

Leu Lys Val Val Asn Thr Gly Ser Ser Ser Ile Asp Leu Ser Arg Val
    770                 775                 780

Thr Ile Arg Tyr Trp Tyr Thr Val Asp Gly Asp Lys Ala Gln Ser Ala
785                 790                 795                 800

Ile Ser Asp Trp Ala Gln Ile Gly Ala Ser Asn Val Thr Phe Lys Phe
                805                 810                 815

Val Lys Leu Ser Ser Ser Val Ser Gly Ala Asp Tyr Tyr Leu Glu Ile
            820                 825                 830

Gly Phe Lys Ser Gly Ala Gly Gln Leu Gln Ala Gly Lys Asp Thr Gly
        835                 840                 845

Glu Ile Gln Ile Arg Phe Asn Lys Ser Asp Trp Ser Asn Tyr Asn Gln
    850                 855                 860

Gly Asn Asp Trp Ser Trp Met Gln Ser Met Thr Ser Tyr Gly Glu Asn
865                 870                 875                 880

Val Lys Val Thr Ala Tyr Ile Asp Gly Val Leu Val Trp Gly Gln Glu
                885                 890                 895

Pro Ser Gly Ala Thr Pro Thr Pro Thr Ala Thr Pro Ala Pro Thr Val
            900                 905                 910

Thr Pro Thr Ala Thr Pro Ala Pro Thr Pro Thr Pro Thr Pro Thr Val
        915                 920                 925

Thr Ala Thr Pro Thr Pro Thr Pro Thr Pro Val Gln Thr Val Ile Pro
    930                 935                 940

Met Pro Thr Val Thr Pro Asn Pro Thr Ser Thr Pro Ser Ile Leu Asp
```

-continued 945 950 955 960

Asp Thr Asn Asp Asp Trp Leu Tyr Val Ser Gly Asn Lys Ile Val Asp
965 970 975

Lys Asp Gly Lys Pro Val Trp Leu Thr Gly Ile Asn Trp Phe Gly Tyr
980 985 990

Asn Thr Gly Thr Asn Val Phe Asp Gly Val Trp Ser Cys Asn Leu Lys
995 1000 1005

Asp Thr Leu Ala Glu Ile Ala Asn Arg Gly Phe Asn Leu Leu Arg Ile
1010 1015 1020

Pro Ile Ser Ala Glu Ile Ile Leu Asn Trp Ser Gln Gly Ile Tyr Pro
1025 1030 1035 1040

Lys Pro Asn Ile Asn Tyr Tyr Val Asn Pro Glu Leu Glu Gly Lys Asn
1045 1050 1055

Ser Leu Glu Val Phe Asp Ile Val Val Gln Ile Cys Lys Glu Val Gly
1060 1065 1070

Leu Lys Ile Met Leu Asp Ile His Ser Ile Lys Thr Asp Ala Met Gly
1075 1080 1085

His Ile Tyr Pro Val Trp Tyr Asp Asp Lys Phe Thr Pro Glu Asp Phe
1090 1095 1100

Tyr Lys Ala Cys Glu Trp Ile Thr Asn Arg Tyr Lys Asn Asp Asp Thr
1105 1110 1115 1120

Ile Ile Ala Phe Asp Leu Lys Asn Glu Pro His Gly Lys Pro Trp Gln
1125 1130 1135

Asp Thr Thr Phe Ala Lys Trp Asp Asn Ser Thr Asp Ile Asn Asn Trp
1140 1145 1150

Lys Tyr Ala Ala Glu Thr Cys Ala Lys Arg Ile Leu Asn Ile Asn Pro
1155 1160 1165

Asn Leu Leu Ile Val Ile Glu Gly Ile Glu Ala Tyr Pro Lys Asp Asp
1170 1175 1180

Val Thr Trp Thr Ser Lys Ser Tyr Ser Asp Tyr Tyr Ser Thr Trp Trp
1185 1190 1195 1200

Gly Gly Asn Leu Arg Gly Val Lys Lys Tyr Pro Ile Asn Leu Gly Lys
1205 1210 1215

Tyr Gln Asn Lys Val Val Tyr Ser Pro His Asp Tyr Gly Pro Ser Val
1220 1225 1230

Tyr Gln Gln Pro Trp Phe Tyr Pro Gly Phe Thr Lys Glu Ser Leu Leu
1235 1240 1245

Gln Asp Cys Trp Arg Pro Asn Trp Ala Tyr Ile Met Glu Glu Asn Ile
1250 1255 1260

Ala Pro Leu Leu Ile Gly Glu Trp Gly Gly Tyr Leu Asp Gly Ala Asp
1265 1270 1275 1280

Asn Glu Lys Trp Met Arg Tyr Leu Arg Asp Tyr Ile Ile Glu Asn His
1285 1290 1295

Ile His His Thr Phe Trp Cys Phe Asn Ala Asn Ser Gly Asp Thr Gly
1300 1305 1310

Gly Met Val Gly Tyr Asp Phe Thr Thr Trp Asp Glu Lys Lys Tyr Ser
1315 1320 1325

Phe Leu Lys Pro Ala Leu Trp Gln Asp Ser Gln Gly Arg Phe Val Gly
1330 1335 1340

Leu Asp His Lys Arg Pro Leu Gly Thr Asn Gly Lys Asn Ile Asn Ile
1345 1350 1355 1360

Thr Ile Tyr Tyr Asn Asn Asn Glu Pro Ala Pro Val Pro Ala Ala Lys
1365 1370 1375

<210> SEQ ID NO 62
<211> LENGTH: 4245
<212> TYPE: DNA
<213> ORGANISM: Caldicellulosiruptor bescii

<400> SEQUENCE: 62
atgagagtaa aaacaaaaat ggggaagaaa tggttgagta tactatgtac agttgttttt 60
ttattgaaca ttttgtttat agcaaatgta acgaatttac ccaaagttgg tgcggctaca 120
tctaatgatg gagtagtgaa gatagatact agcacattaa taggaacaaa tcacgcacat 180
tgctggtaca gagataaact tgagacggca ttgcgaggaa taaggtcatg ggtatgaac 240 tctgtgaggg tagtgttgag taatggctat cgatggacga agataccagc aagtgaagta 300
gcaaatatta tatcattgtc aagaagtctt ggattcagag ccattgtatt agaagttcac 360
gacacgacag gatatggtga ggacggtgca gcatgttcat tggcgcaagc agtagaatat 420
tggaaagaga taaagagtgt gttagaaggc aatgaggatt ttgttataat aaacattggt 480
aatgagccgt atgggaacaa taactatcaa aactggatta atgacacgaa gaatgctata 540
aaagcgctaa gggatgcagg gttcaagcac acgataatgg ttgatgcacc gaactggggg 600
caggattggt ctaatactat gagagacaat gcccagagca taatggaagc agatccgctg 660
cgcaatttgg tattttcgat tcatatgtac ggtgtataca atacagcgag caaggtagaa 720
gaatatatca agtcatttgt ggagaaaggg ctgccattag ttattgggga gtttgggcat 780
cagcatacag atggtgaccc tgacgaggaa gctattgtca ggtatgcaaa acaatacaag 840
ataggacttt ttagctggtc ttggtgtggc aattcgagct atgtagggta cttggacatg 900
gtaaacaatt gggaccccaa taatccaact ccatgggggc aatggtataa aactaatgcg 960
attggtgcct cttcagtacc tacttcaaca ccaacaccga caccaactgc tacaccaaca 1020
gcaacaccaa caccaacact gactccaaca ccgacaccta caccaacacc aacgtcaaca 1080
ccaactgcta caccaacagc aacgccaaca ccaacaccga cgccgagcag cacacctgta 1140
gcaggtggac agataaaggt attgtatgct aacaaggaga caaatagcac aacaaatacg 1200
ataaggccat ggttgaaggt agtgaacact ggaagcagca gcatagattt gagcagggta 1260
acgataaggt actggtacac ggtagatggg gacaaggcac agagtgcgat atcagactgg 1320
gcacagatag gagcaagcaa tgtgacattc aagtttgtga agctgagcag tagcgtaagt 1380
ggagcggact attatttaga gataggattt aagagtggag ctgggcagtt gcaggctggt 1440
aaagacacag gggagataca gataaggttt aacaagagtg actggagcaa ttacaatcag 1500
gggaatgact ggtcatggat gcagagcatg acgagttatg gagagaatgt gaaggtaaca 1560
gcgtatatag atggtgtatt ggtatgggga caggagccga gtggagcgac accaacaccg 1620
acagcaacac cagcaccaac accaaccccg accccaacac caactgctac accaacgcca 1680
acaccgactc caacaccaac accaactgct accccaacac cgacgccgag cagtacacct 1740
gtagcaggtg gacagataaa ggtattgtat gctaacaagg agacaaatag cacaacaaac 1800
acgataaggc catggttgaa ggtagtgaac actggaagca gcagcataga tttgagcagg 1860
gtaacgataa ggtactggta cacggtagat ggggacaagg cacagagtgc gatatcagac 1920
tgggcacaga taggagcaag caatgtgaca ttcaagtttg tgaagctgag cagtagcgta 1980
agtggagcgg actattattt agagatagga tttaagagtg gagctgggca gttgcaggct 2040
ggtaaagaca caggggagat acagataagg tttaacaaga gtgactggag caattacaat 2100

-continued

```
caggggaatg actggtcatg gatgcagagc atgacgagtt atggagagaa tgtgaaggta   2160
acagcgtata tagatggtgt attggtatgg ggacaggagc cgagtggagc gacaccaaca   2220
ccgacagcaa caccagcacc aacaccaacc ccgaccccaa caccaactgc tacaccaacg   2280
ccaacaccga ctccaacacc aacaccaact gctaccccaa caccgacgcc gagcagtaca   2340
cctgtagcag gtggacagat aaaggtattg tatgctaaca aggagacaaa tagcacaaca   2400
aacacgataa ggccatggtt gaaggtagtg aacactggaa gcagcagcat agatttgagc   2460
agggtaacga taaggtactg gtacacggta gatggggaca aggcacagag tgcgatatca   2520
gactgggcac agataggagc aagcaatgtg acattcaagt ttgtgaagct gagcagtagc   2580
gtaagtggag cggactatta tttagagata ggatttaaga gtggagctgg gcagttgcag   2640
gctggtaaag acacagggga gatacagata aggtttaaca agagtgactg gagcaattac   2700
aatcagggga atgactggtc atggatgcag agcatgacga gttatggaga gaatgtgaag   2760
gtaacagcgt atatagatgg tgtattggta tggggacagg agccgagtgg agcgacacca   2820
acaccgacag caacaccagc accgacagtg acaccgacag caacaccagc accaacacca   2880
accccgaccc caacagtaac ggcaaccccg acaccgacac caacaccggt gcagacagta   2940
ataccaatgc caacagtaac tccaaatcca acatcaacac cgagtattct tgatgataca   3000
aatgatgatt ggctttatgt aagtggtaat aaaatagttg ataaagatgg taaaccggta   3060
tggttaacag gtattaactg gtttggatac aatacaggta caaatgtttt tgatggtgta   3120
tggagttgca atctaaaaga tactctagct gaaatagcca atagaggctt taatttgcta   3180
agaattccaa tatcagccga gattatactg aactggtcgc aaggtattta tccaaaacca   3240
aatataaact actacgttaa tccagagctt gagggcaaaa acagtcttga agtatttgac   3300
atagttgtac aaatatgtaa agaagttggt ttgaaaatta tgttggatat tcacagcata   3360
aaaacagacg caatgggaca tatctatcca gtatggtatg atgataaatt tactccagag   3420
gatttttata aggcgtgtga gtggattaca aatagatata aaaatgatga tactattata   3480
gcttttgacc taaaaaatga gccacatgga aaaccatggc aagacacaac atttgcaaaa   3540
tgggataatt caacagatat taataattgg aaatatgcgg ctgaaacatg tgcgaaacgt   3600
atactaaata taaatccaaa ccttcttatt gtaatagaag gaattgaagc gtatccaaaa   3660
gatgacgtta catggacatc aaaatcctat agcgattact attcaacatg gtggggcggt   3720
aacttgcgag gtgttaaaaa gtatcctatt aatctgggta aatatcaaaa taaagtagta   3780
tattcacctc atgattacgg accctctgtt taccagcagc cgtggtttta tccaggcttc   3840
acaaaagaat ctttactaca agattgttgg cgtccgaatt gggcttacat catggaagaa   3900
aacattgcgc cgctgctgat aggtgaatgg ggtggttatc ttgatggagc tgataacgaa   3960
aagtggatga gatatctacg agattatatt atagagaatc atattcatca cacattttgg   4020
tgctttaatg ctaactcagg tgacactgga ggtatggttg gatacgattt tacgacatgg   4080
gatgaaaaaa aatactcatt tttaaagccg gctctttggc aagacagtca aggtaggttt   4140
gttggattag atcacaagcg acccttaggt acaaatggga aaaacattaa tattacaata   4200
tactacaaca ataatgaacc agcgccagtt ccagccgcaa aatga                   4245
```

<210> SEQ ID NO 63
<211> LENGTH: 4131
<212> TYPE: DNA
<213> ORGANISM: Caldicellulosiruptor bescii

<400> SEQUENCE: 63

-continued

```
gctacatcta atgatggagt agtgaagata gatactagca cattaatagg aacaaatcac     60
gcacattgct ggtacagaga taaacttgag acggcattgc gaggaataag gtcatggggt    120
atgaactctg tgagggtagt gttgagtaat ggctatcgat ggacgaagat accagcaagt    180
gaagtagcaa atattatatc attgtcaaga agtcttggat tcagagccat tgtattagaa    240
gttcacgaca cgacaggata tggtgaggac ggtgcagcat gttcattggc gcaagcagta    300
gaatattgga aagagataaa gagtgtgtta gaaggcaatg aggattttgt tataataaac    360
attggtaatg agccgtatgg gaacaataac tatcaaaact ggattaatga cacgaagaat    420
gctataaaag cgctaaggga tgcagggttc aagcacacga taatggttga tgcaccgaac    480
tgggggcagg attggtctaa tactatgaga gacaatgccc agagcataat ggaagcagat    540
ccgctgcgca atttggtatt ttcgattcat atgtacggtg tatacaatac agcgagcaag    600
gtagaagaat atatcaagtc atttgtggag aaagggctgc cattagttat tggggagttt    660
gggcatcagc atacagatgg tgaccctgac gaggaagcta ttgtcaggta tgcaaaacaa    720
tacaagatag gactttttag ctggtcttgg tgtggcaatt cgagctatgt agggtacttg    780
gacatggtaa acaattggga ccccaataat ccaactccat gggggcaatg gtataaaact    840
aatgcgattg gtgcctcttc agtacctact tcaacaccaa caccgacacc aactgctaca    900
ccaacagcaa caccaacacc aacactgact ccaacaccga cacctacacc aacaccaacg    960
tcaacaccaa ctgctacacc aacagcaacg ccaacaccaa caccgacgcc gagcagcaca   1020
cctgtagcag gtggacagat aaaggtattg tatgctaaca aggagacaaa tagcacaaca   1080
aatacgataa ggccatggtt gaaggtagtg aacactggaa gcagcagcat agatttgagc   1140
agggtaacga taaggtactg gtacacggta gatggggaca aggcacagag tgcgatatca   1200
gactgggcac agataggagc aagcaatgtg acattcaagt ttgtgaagct gagcagtagc   1260
gtaagtggag cggactatta tttagagata ggatttaaga gtggagctgg gcagttgcag   1320
gctggtaaag acacagggga gatacagata aggtttaaca agagtgactg gagcaattac   1380
aatcagggga atgactggtc atggatgcag agcatgacga gttatggaga gaatgtgaag   1440
gtaacagcgt atatagatgg tgtattggta tggggacagg agccgagtgg agcgacacca   1500
acaccgacag caacaccagc accaacacca accccgaccc caacaccaac tgctacacca   1560
acgccaacac cgactccaac accaacacca actgctaccc caacaccgac gccgagcagt   1620
acacctgtag caggtggaca gataaaggta ttgtatgcta acaaggagac aaatagcaca   1680
acaaacacga taaggccatg gttgaaggta gtgaacactg gaagcagcag catagatttg   1740
agcagggtaa cgataaggta ctggtacacg gtagatgggg acaaggcaca gagtgcgata   1800
tcagactggg cacagatagg agcaagcaat gtgacattca agtttgtgaa gctgagcagt   1860
agcgtaagtg gagcggacta ttatttagag ataggattta agagtggagc tgggcagttg   1920
caggctggta aagacacagg ggagatacag ataaggttta acaagagtga ctggagcaat   1980
tacaatcagg ggaatgactg gtcatggatg cagagcatga cgagttatgg agagaatgtg   2040
aaggtaacag cgtatataga tggtgtattg gtatggggac aggagccgag tggagcgaca   2100
ccaacaccga cagcaacacc agcaccaaca ccaaccccga ccccaacacc aactgctaca   2160
ccaacgccaa caccgactcc aacaccaaca ccaactgcta ccccaacacc gacgccgagc   2220
agtacacctg tagcaggtgg acagataaag gtattgtatg ctaacaagga gacaaatagc   2280
acaacaaaca cgataaggcc atggttgaag gtagtgaaca ctggaagcag cagcatagat   2340
```

-continued ttgagcaggg taacgataag gtactggtac acggtagatg gggacaaggc acagagtgcg 2400
atatcagact gggcacagat aggagcaagc aatgtgacat tcaagtttgt gaagctgagc 2460
agtagcgtaa gtggagcgga ctattattta gagataggat ttaagagtgg agctgggcag 2520
ttgcaggctg gtaaagacac aggggagata cagataaggt ttaacaagag tgactggagc 2580
aattacaatc aggggaatga ctggtcatgg atgcagagca tgacgagtta tggagagaat 2640
gtgaaggtaa cagcgtatat agatggtgta ttggtatggg gacaggagcc gagtggagcg 2700
acaccaacac cgacagcaac accagcaccg acagtgacac cgacagcaac accagcacca 2760
acaccaaccc cgaccccaac agtaacggca accccgacac cgacaccaac accggtgcag 2820
acagtaatac caatgccaac agtaactcca aatccaacat caacaccgag tattcttgat 2880
gatacaaatg atgattggct ttatgtaagt ggtaataaaa tagttgataa agatggtaaa 2940
ccggtatggt taacaggtat taactggttt ggatacaata caggtacaaa tgtttttgat 3000
ggtgtatgga gttgcaatct aaaagatact ctagctgaaa tagccaatag aggctttaat 3060
ttgctaagaa ttccaatatc agccgagatt atactgaact ggtcgcaagg tatttatcca 3120
aaaccaaata taaactacta cgttaatcca gagcttgagg gcaaaaacag tcttgaagta 3180
tttgacatag ttgtacaaat atgtaaagaa gttggtttga aaattatgtt ggatattcac 3240
agcataaaaa cagacgcaat gggacatatc tatccagtat ggtatgatga taaatttact 3300
ccagaggatt tttataaggc gtgtgagtgg attacaaata gatataaaaa tgatgatact 3360
attatagctt ttgacctaaa aaatgagcca catggaaaac catggcaaga cacaacattt 3420
gcaaaatggg ataattcaac agatattaat aattggaaat atgcggctga aacatgtgcg 3480
aaacgtatac taaatataaa tccaaacctt cttattgtaa tagaaggaat tgaagcgtat 3540
ccaaaagatg acgttacatg gacatcaaaa tcctatagcg attactattc aacatggtgg 3600
ggcggtaact tgcgaggtgt taaaaagtat cctattaatc tgggtaaata tcaaaataaa 3660
gtagtatatt cacctcatga ttacggaccc tctgtttacc agcagccgtg gttttatcca 3720
ggcttcacaa aagaatcttt actacaagat tgttggcgtc cgaattgggc ttacatcatg 3780
gaagaaaaca ttgcgccgct gctgataggt gaatggggtg gttatcttga tggagctgat 3840
aacgaaaagt ggatgagata tctacgagat tatattatag agaatcatat tcatcacaca 3900
ttttggtgct ttaatgctaa ctcaggtgac actggaggta tggttggata cgattttacg 3960
acatgggatg aaaaaaaata ctcatttttta aagccggctc tttggcaaga cagtcaaggt 4020
aggtttgttg gattagatca caagcgaccc ttaggtacaa atgggaaaaa cattaatatt 4080
acaatatact acaacaataa tgaaccagcg ccagttccag ccgcaaaatg a 4131

<210> SEQ ID NO 64
<211> LENGTH: 4176
<212> TYPE: DNA
<213> ORGANISM: Caldicellulosiruptor bescii

<400> SEQUENCE: 64
atggcacatc accaccacca tcacgtggat gacgacgaca agatggctac atctaatgat 60
ggagtagtga agatagatac tagcacatta ataggaacaa atcacgcaca ttgctggtac 120
agagataaac ttgagacggc attgcgagga ataaggtcat ggggtatgaa ctctgtgagg 180
gtagtgttga gtaatggcta tcgatggacg aagataccag caagtgaagt agcaaatatt 240
atatcattgt caagaagtct tggattcaga gccattgtat tagaagttca cgacacgaca 300
ggatatggtg aggacggtgc agcatgttca ttggcgcaag cagtagaata ttggaaagag 360

-continued

```
ataaagagtg tgttagaagg caatgaggat tttgttataa taaacattgg taatgagccg    420
tatgggaaca ataactatca aaactggatt aatgacacga agaatgctat aaaagcgcta    480
agggatgcag ggttcaagca cacgataatg gttgatgcac cgaactgggg gcaggattgg    540
tctaatacta tgagagacaa tgcccagagc ataatggaag cagatccgct gcgcaatttg    600
gtattttcga ttcatatgta cggtgtatac aatacagcga gcaaggtaga agaatatatc    660
aagtcatttg tggagaaagg gctgccatta gttattgggg agtttgggca tcagcataca    720
gatggtgacc ctgacgagga agctattgtc aggtatgcaa aacaatacaa gataggactt    780
tttagctggt cttggtgtgg caattcgagc tatgtagggt acttggacat ggtaaacaat    840
tgggacccca ataatccaac tccatggggg caatggtata aaactaatgc gattggtgcc    900
tcttcagtac ctacttcaac accaacaccg acaccaactg ctacaccaac agcaacacca    960
acaccaacac tgactccaac accgacacct acaccaacac caacgtcaac accaactgct   1020
acaccaacag caacgccaac accaacaccg acgccgagca gcacacctgt agcaggtgga   1080
cagataaagg tattgtatgc taacaaggag acaaatagca caacaaatac gataaggcca   1140
tggttgaagg tagtgaacac tggaagcagc agcatagatt tgagcagggt aacgataagg   1200
tactggtaca cggtagatgg ggacaaggca cagagtgcga tatcagactg gcacagata   1260
ggagcaagca atgtgacatt caagtttgtg aagctgagca gtagcgtaag tggagcggac   1320
tattatttag agataggatt taagagtgga gctgggcagt tgcaggctgg taaagacaca   1380
ggggagatac agataaggtt taacaagagt gactggagca attacaatca ggggaatgac   1440
tggtcatgga tgcagagcat gacgagttat ggagagaatg tgaaggtaac agcgtatata   1500
gatggtgtat tggtatgggg acaggagccg agtggagcga caccaacacc gacagcaaca   1560
ccagcaccaa caccaacccc gaccccaaca ccaactgcta caccaacgcc aacaccgact   1620
ccaacaccaa caccaactgc taccccaaca ccgacgccga gcagtacacc tgtagcaggt   1680
ggacagataa aggtattgta tgctaacaag gagacaaata gcacaacaaa cacgataagg   1740
ccatggttga aggtagtgaa cactggaagc agcagcatag atttgagcag ggtaacgata   1800
aggtactggt acacggtaga tggggacaag gcacagagtg cgatatcaga ctgggcacag   1860
ataggagcaa gcaatgtgac attcaagttt gtgaagctga gcagtagcgt aagtggagcg   1920
gactattatt tagagatagg atttaagagt ggagctgggc agttgcaggc tggtaaagac   1980
acaggggaga tacagataag gtttaacaag agtgactgga gcaattacaa tcaggggaat   2040
gactggtcat ggatgcagag catgacgagt tatggagaga atgtgaaggt aacagcgtat   2100
atagatggtg tattggtatg gggacaggag ccgagtggag cgacaccaac accgacagca   2160
acaccagcac caacaccaac cccgacccca acaccaactg ctacaccaac gccaacaccg   2220
actccaacac caacaccaac tgctacccca acaccgacgc cgagcagtac acctgtagca   2280
ggtggacaga taaaggtatt gtatgctaac aaggagacaa atagcacaac aaacacgata   2340
aggccatggt tgaaggtagt gaacactgga agcagcagca tagatttgag cagggtaacg   2400
ataaggtact ggtacacggt agatggggac aaggcacaga gtgcgatatc agactgggca   2460
cagataggag caagcaatgt gacattcaag tttgtgaagc tgagcagtag cgtaagtgga   2520
gcggactatt atttagagat aggatttaag agtggagctg ggcagttgca ggctggtaaa   2580
gacacagggg agatacagat aaggtttaac aagagtgact ggagcaatta caatcagggg   2640
aatgactggt catggatgca gagcatgacg agttatggag agaatgtgaa ggtaacagcg   2700
```

-continued

```
tatatagatg gtgtattggt atggggacag gagccgagtg gagcgacacc aacaccgaca   2760
gcaacaccag caccgacagt gacaccgaca gcaacaccag caccaacacc aaccccgacc   2820
ccaacagtaa cggcaacccc gacaccgaca ccaacaccgg tgcagacagt aataccaatg   2880
ccaacagtaa ctccaaatcc aacatcaaca ccgagtattc ttgatgatac aaatgatgat   2940
tggctttatg taagtggtaa taaaatagtt gataaagatg gtaaaccggt atggttaaca   3000
ggtattaact ggtttggata caatacaggt acaaatgttt ttgatggtgt atggagttgc   3060
aatctaaaag atactctagc tgaaatagcc aatagaggct ttaatttgct aagaattcca   3120
atatcagccg agattatact gaactggtcg caaggtattt atccaaaacc aaatataaac   3180
tactacgtta atccagagct tgagggcaaa aacagtcttg aagtatttga catagttgta   3240
caaatatgta aagaagttgg tttgaaaatt atgttggata ttcacagcat aaaaacagac   3300
gcaatgggac atatctatcc agtatggtat gatgataaat ttactccaga ggatttttat   3360
aaggcgtgtg agtggattac aaatagatat aaaaatgatg atactattat agcttttgac   3420
ctaaaaaatg agccacatgg aaaaccatgg caagacacaa catttgcaaa atgggataat   3480
tcaacagata ttaataattg gaaatatgcg gctgaaacat gtgcgaaacg tatactaaat   3540
ataaatccaa accttcttat tgtaatagaa ggaattgaag cgtatccaaa agatgacgtt   3600
acatggacat caaaatccta tagcgattac tattcaacat ggtggggcgg taacttgcga   3660
ggtgttaaaa agtatcctat taatctgggt aaatatcaaa ataaagtagt atattcacct   3720
catgattacg gaccctctgt ttaccagcag ccgtggtttt atccaggctt cacaaaagaa   3780
tctttactac aagattgttg gcgtccgaat tgggcttaca tcatggaaga aaacattgcg   3840
ccgctgctga taggtgaatg gggtggttat cttgatggag ctgataacga aaagtggatg   3900
agatatctac gagattatat tatagagaat catattcatc acacattttg gtgctttaat   3960
gctaactcag gtgacactgg aggtatggtt ggatacgatt ttacgacatg ggatgaaaaa   4020
aaatactcat ttttaaagcc ggctctttgg caagacagtc aaggtaggtt tgttggatta   4080
gatcacaagc gacccttagg tacaaatggg aaaaacatta atattacaat atactacaac   4140
aataatgaac cagcgccagt tccagccgca aaataa                             4176
```

<210> SEQ ID NO 65
<211> LENGTH: 1391
<212> TYPE: PRT
<213> ORGANISM: Caldicellulosiruptor bescii

<400> SEQUENCE: 65

```
Met Ala His His His His His His Val Asp Asp Asp Asp Lys Met Ala
1               5                   10                  15

Thr Ser Asn Asp Gly Val Val Lys Ile Asp Thr Ser Thr Leu Ile Gly
            20                  25                  30

Thr Asn His Ala His Cys Trp Tyr Arg Asp Lys Leu Glu Thr Ala Leu
        35                  40                  45

Arg Gly Ile Arg Ser Trp Gly Met Asn Ser Val Arg Val Val Leu Ser
    50                  55                  60

Asn Gly Tyr Arg Trp Thr Lys Ile Pro Ala Ser Glu Val Ala Asn Ile
65                  70                  75                  80

Ile Ser Leu Ser Arg Ser Leu Gly Phe Arg Ala Ile Val Leu Glu Val
                85                  90                  95

His Asp Thr Thr Gly Tyr Gly Glu Asp Gly Ala Ala Cys Ser Leu Ala
            100                 105                 110
```

```
Gln Ala Val Glu Tyr Trp Lys Glu Ile Lys Ser Val Leu Glu Gly Asn
        115                 120                 125

Glu Asp Phe Val Ile Ile Asn Ile Gly Asn Glu Pro Tyr Gly Asn Asn
    130                 135                 140

Asn Tyr Gln Asn Trp Ile Asn Asp Thr Lys Asn Ala Ile Lys Ala Leu
145                 150                 155                 160

Arg Asp Ala Gly Phe Lys His Thr Ile Met Val Asp Ala Pro Asn Trp
                165                 170                 175

Gly Gln Asp Trp Ser Asn Thr Met Arg Asp Asn Ala Gln Ser Ile Met
            180                 185                 190

Glu Ala Asp Pro Leu Arg Asn Leu Val Phe Ser Ile His Met Tyr Gly
        195                 200                 205

Val Tyr Asn Thr Ala Ser Lys Val Glu Glu Tyr Ile Lys Ser Phe Val
    210                 215                 220

Glu Lys Gly Leu Pro Leu Val Ile Gly Glu Phe Gly His Gln His Thr
225                 230                 235                 240

Asp Gly Asp Pro Asp Glu Glu Ala Ile Val Arg Tyr Ala Lys Gln Tyr
                245                 250                 255

Lys Ile Gly Leu Phe Ser Trp Ser Trp Cys Gly Asn Ser Ser Tyr Val
            260                 265                 270

Gly Tyr Leu Asp Met Val Asn Asn Trp Asp Pro Asn Asn Pro Thr Pro
        275                 280                 285

Trp Gly Gln Trp Tyr Lys Thr Asn Ala Ile Gly Ala Ser Ser Val Pro
    290                 295                 300

Thr Ser Thr Pro Thr Pro Thr Pro Thr Ala Thr Pro Thr Ala Thr Pro
305                 310                 315                 320

Thr Pro Thr Leu Thr Pro Thr Pro Thr Pro Thr Pro Thr Pro Thr Ser
                325                 330                 335

Thr Pro Thr Ala Thr Pro Thr Ala Thr Pro Thr Pro Thr Pro Thr Pro
            340                 345                 350

Ser Ser Thr Pro Val Ala Gly Gly Gln Ile Lys Val Leu Tyr Ala Asn
        355                 360                 365

Lys Glu Thr Asn Ser Thr Thr Asn Thr Ile Arg Pro Trp Leu Lys Val
    370                 375                 380

Val Asn Thr Gly Ser Ser Ser Ile Asp Leu Ser Arg Val Thr Ile Arg
385                 390                 395                 400

Tyr Trp Tyr Thr Val Asp Gly Asp Lys Ala Gln Ser Ala Ile Ser Asp
                405                 410                 415

Trp Ala Gln Ile Gly Ala Ser Asn Val Thr Phe Lys Phe Val Lys Leu
            420                 425                 430

Ser Ser Ser Val Ser Gly Ala Asp Tyr Tyr Leu Glu Ile Gly Phe Lys
        435                 440                 445

Ser Gly Ala Gly Gln Leu Gln Ala Gly Lys Asp Thr Gly Glu Ile Gln
    450                 455                 460

Ile Arg Phe Asn Lys Ser Asp Trp Ser Asn Tyr Asn Gln Gly Asn Asp
465                 470                 475                 480

Trp Ser Trp Met Gln Ser Met Thr Ser Tyr Gly Glu Asn Val Lys Val
                485                 490                 495

Thr Ala Tyr Ile Asp Gly Val Leu Val Trp Gly Gln Glu Pro Ser Gly
            500                 505                 510

Ala Thr Pro Thr Pro Thr Ala Thr Pro Ala Pro Thr Pro Thr Pro Thr
        515                 520                 525

Pro Thr Pro Thr Ala Thr Pro Thr Pro Thr Pro Thr Pro Thr Pro Thr
```

```
    530                 535                 540

Pro Thr Ala Thr Pro Thr Pro Thr Pro Ser Ser Thr Pro Val Ala Gly
545                 550                 555                 560

Gly Gln Ile Lys Val Leu Tyr Ala Asn Lys Glu Thr Asn Ser Thr Thr
                565                 570                 575

Asn Thr Ile Arg Pro Trp Leu Lys Val Val Asn Thr Gly Ser Ser Ser
            580                 585                 590

Ile Asp Leu Ser Arg Val Thr Ile Arg Tyr Trp Tyr Thr Val Asp Gly
        595                 600                 605

Asp Lys Ala Gln Ser Ala Ile Ser Asp Trp Ala Gln Ile Gly Ala Ser
    610                 615                 620

Asn Val Thr Phe Lys Phe Val Lys Leu Ser Ser Ser Val Ser Gly Ala
625                 630                 635                 640

Asp Tyr Tyr Leu Glu Ile Gly Phe Lys Ser Gly Ala Gly Gln Leu Gln
                645                 650                 655

Ala Gly Lys Asp Thr Gly Glu Ile Gln Ile Arg Phe Asn Lys Ser Asp
            660                 665                 670

Trp Ser Asn Tyr Asn Gln Gly Asn Asp Trp Ser Trp Met Gln Ser Met
        675                 680                 685

Thr Ser Tyr Gly Glu Asn Val Lys Val Thr Ala Tyr Ile Asp Gly Val
    690                 695                 700

Leu Val Trp Gly Gln Glu Pro Ser Gly Ala Thr Pro Thr Pro Thr Ala
705                 710                 715                 720

Thr Pro Ala Pro Thr Pro Thr Pro Thr Pro Thr Pro Thr Ala Thr Pro
                725                 730                 735

Thr Pro Thr Pro Thr Pro Thr Pro Thr Pro Thr Ala Thr Pro Thr Pro
            740                 745                 750

Thr Pro Ser Ser Thr Pro Val Ala Gly Gly Gln Ile Lys Val Leu Tyr
        755                 760                 765

Ala Asn Lys Glu Thr Asn Ser Thr Thr Asn Thr Ile Arg Pro Trp Leu
    770                 775                 780

Lys Val Val Asn Thr Gly Ser Ser Ser Ile Asp Leu Ser Arg Val Thr
785                 790                 795                 800

Ile Arg Tyr Trp Tyr Thr Val Asp Gly Asp Lys Ala Gln Ser Ala Ile
                805                 810                 815

Ser Asp Trp Ala Gln Ile Gly Ala Ser Asn Val Thr Phe Lys Phe Val
            820                 825                 830

Lys Leu Ser Ser Ser Val Ser Gly Ala Asp Tyr Tyr Leu Glu Ile Gly
        835                 840                 845

Phe Lys Ser Gly Ala Gly Gln Leu Gln Ala Gly Lys Asp Thr Gly Glu
    850                 855                 860

Ile Gln Ile Arg Phe Asn Lys Ser Asp Trp Ser Asn Tyr Asn Gln Gly
865                 870                 875                 880

Asn Asp Trp Ser Trp Met Gln Ser Met Thr Ser Tyr Gly Glu Asn Val
                885                 890                 895

Lys Val Thr Ala Tyr Ile Asp Gly Val Leu Val Trp Gly Gln Glu Pro
            900                 905                 910

Ser Gly Ala Thr Pro Thr Pro Thr Ala Thr Pro Ala Pro Thr Val Thr
        915                 920                 925

Pro Thr Ala Thr Pro Ala Pro Thr Pro Thr Pro Thr Pro Thr Val Thr
    930                 935                 940

Ala Thr Pro Thr Pro Thr Pro Thr Pro Val Gln Thr Val Ile Pro Met
945                 950                 955                 960
```

-continued

```
Pro Thr Val Thr Pro Asn Pro Thr Ser Thr Pro Ser Ile Leu Asp Asp
                965                 970                 975

Thr Asn Asp Asp Trp Leu Tyr Val Ser Gly Asn Lys Ile Val Asp Lys
            980                 985                 990

Asp Gly Lys Pro Val Trp Leu Thr Gly Ile Asn Trp Phe Gly Tyr Asn
        995                 1000                1005

Thr Gly Thr Asn Val Phe Asp Gly Val Trp Ser Cys Asn Leu Lys Asp
    1010                1015                1020

Thr Leu Ala Glu Ile Ala Asn Arg Gly Phe Asn Leu Leu Arg Ile Pro
1025                1030                1035                1040

Ile Ser Ala Glu Ile Ile Leu Asn Trp Ser Gln Gly Ile Tyr Pro Lys
                1045                1050                1055

Pro Asn Ile Asn Tyr Tyr Val Asn Pro Glu Leu Glu Gly Lys Asn Ser
            1060                1065                1070

Leu Glu Val Phe Asp Ile Val Val Gln Ile Cys Lys Glu Val Gly Leu
        1075                1080                1085

Lys Ile Met Leu Asp Ile His Ser Ile Lys Thr Asp Ala Met Gly His
    1090                1095                1100

Ile Tyr Pro Val Trp Tyr Asp Asp Lys Phe Thr Pro Glu Asp Phe Tyr
1105                1110                1115                1120

Lys Ala Cys Glu Trp Ile Thr Asn Arg Tyr Lys Asn Asp Asp Thr Ile
                1125                1130                1135

Ile Ala Phe Asp Leu Lys Asn Glu Pro His Gly Lys Pro Trp Gln Asp
            1140                1145                1150

Thr Thr Phe Ala Lys Trp Asp Asn Ser Thr Asp Ile Asn Asn Trp Lys
        1155                1160                1165

Tyr Ala Ala Glu Thr Cys Ala Lys Arg Ile Leu Asn Ile Asn Pro Asn
    1170                1175                1180

Leu Leu Ile Val Ile Glu Gly Ile Glu Ala Tyr Pro Lys Asp Asp Val
1185                1190                1195                1200

Thr Trp Thr Ser Lys Ser Tyr Ser Asp Tyr Tyr Ser Thr Trp Trp Gly
                1205                1210                1215

Gly Asn Leu Arg Gly Val Lys Lys Tyr Pro Ile Asn Leu Gly Lys Tyr
            1220                1225                1230

Gln Asn Lys Val Val Tyr Ser Pro His Asp Tyr Gly Pro Ser Val Tyr
        1235                1240                1245

Gln Gln Pro Trp Phe Tyr Pro Gly Phe Thr Lys Glu Ser Leu Leu Gln
    1250                1255                1260

Asp Cys Trp Arg Pro Asn Trp Ala Tyr Ile Met Glu Glu Asn Ile Ala
1265                1270                1275                1280

Pro Leu Leu Ile Gly Glu Trp Gly Gly Tyr Leu Asp Gly Ala Asp Asn
                1285                1290                1295

Glu Lys Trp Met Arg Tyr Leu Arg Asp Tyr Ile Ile Glu Asn His Ile
            1300                1305                1310

His His Thr Phe Trp Cys Phe Asn Ala Asn Ser Gly Asp Thr Gly Gly
        1315                1320                1325

Met Val Gly Tyr Asp Phe Thr Thr Trp Asp Glu Lys Lys Tyr Ser Phe
    1330                1335                1340

Leu Lys Pro Ala Leu Trp Gln Asp Ser Gln Gly Arg Phe Val Gly Leu
1345                1350                1355                1360

Asp His Lys Arg Pro Leu Gly Thr Asn Gly Lys Asn Ile Asn Ile Thr
                1365                1370                1375
```

-continued

```
Ile Tyr Tyr Asn Asn Asn Glu Pro Ala Pro Val Pro Ala Ala Lys
            1380                1385                1390


<210> SEQ ID NO 66
<211> LENGTH: 2886
<212> TYPE: DNA
<213> ORGANISM: Caldicellulosiruptor bescii

<400> SEQUENCE: 66

atggcacatc accaccacca tcacgtggat gacgacgaca agatggctac atctaatgat     60

ggagtagtga agatagatac tagcacatta ataggaacaa atcacgcaca ttgctggtac    120

agagataaac ttgagacggc attgcgagga ataaggtcat ggggtatgaa ctctgtgagg    180

gtagtgttga gtaatggcta tcgatggacg aagataccag caagtgaagt agcaaatatt    240

atatcattgt caagaagtct tggattcaga gccattgtat tagaagttca cgacacgaca    300

ggatatggtg aggacggtgc agcatgttca ttggcgcaag cagtagaata ttggaaagag    360

ataaagagtg tgttagaagg caatgaggat tttgttataa taaacattgg taatgagccg    420

tatgggaaca ataactatca aaactggatt aatgacacga agaatgctat aaaagcgcta    480

agggatgcag ggttcaagca cacgataatg gttgatgcac cgaactgggg gcaggattgg    540

tctaatacta tgagagacaa tgcccagagc ataatggaag cagatccgct gcgcaatttg    600

gtattttcga ttcatatgta cggtgtatac aatacagcga gcaaggtaga agaatatatc    660

aagtcatttg tggagaaagg gctgccatta gttattgggg agtttgggca tcagcataca    720

gatggtgacc ctgacgagga agctattgtc aggtatgcaa aacaatacaa gataggactt    780

tttagctggt cttggtgtgg caattcgagc tatgtagggt acttggacat ggtaaacaat    840

tgggacccca ataatccaac tccatggggg caatggtata aaactaatgc gattggtgcc    900

tcttcagtac ctacttcaac accaacaccg acaccaactg ctacaccaac agcaacacca    960

acaccaacac tgactccaac accgacacct acaccaacac caacgtcaac accaactgct   1020

acaccaacag caacgccaac accaacaccg acgccgagca gcacacctgt agcaggtgga   1080

cagataaagg tattgtatgc taacaaggag acaaatagca caacaaatac gataaggcca   1140

tggttgaagg tagtgaacac tggaagcagc agcatagatt tgagcagggt aacgataagg   1200

tactggtaca cggtagatgg ggacaaggca cagagtgcga tatcagactg ggcacagata   1260

ggagcaagca atgtgacatt caagtttgtg aagctgagca gtagcgtaag tggagcggac   1320

tattatttag agataggatt taagagtgga gctgggcagt tgcaggctgg taaagacaca   1380

ggggagatac agataaggtt taacaagagt gactggagca attacaatca ggggaatgac   1440

tggtcatgga tgcagagcat gacgagttat ggagagaatg tgaaggtaac agcgtatata   1500

gatggtgtat tggtatgggg acaggagccg agtggagcga caccaacacc gacagcaaca   1560

ccagcaccaa caccaacccc gaccccaaca ccaactgcta caccaacgcc aacaccgact   1620

ccaacaccaa caccaactgc taccccaaca ccgacgccga gcagtacacc tgtagcaggt   1680

ggacagataa aggtattgta tgctaacaag gagacaaata gcacaacaaa cacgataagg   1740

ccatggttga aggtagtgaa cactggaagc agcagcatag atttgagcag ggtaacgata   1800

aggtactggt acacggtaga tggggacaag gcacagagtg cgatatcaga ctgggcacag   1860

ataggagcaa gcaatgtgac attcaagttt gtgaagctga gcagtagcgt aagtggagcg   1920

gactattatt tagagatagg atttaagagt ggagctgggc agttgcaggc tggtaaagac   1980

acaggggaga tacagataag gtttaacaag agtgactgga gcaattacaa tcaggggaat   2040
```

-continued gactggtcat ggatgcagag catgacgagt tatggagaga atgtgaaggt aacagcgtat 2100
atagatggtg tattggtatg gggacaggag ccgagtggag cgacaccaac accgacagca 2160
acaccagcac caacaccaac cccgacccca acaccaactg ctacaccaac gccaacaccg 2220
actccaacac caacaccaac tgctacccca acaccgacgc cgagcagtac acctgtagca 2280
ggtggacaga taaaggtatt gtatgctaac aaggagacaa atagcacaac aaacacgata 2340
aggccatggt tgaaggtagt gaacactgga agcagcagca tagatttgag cagggtaacg 2400
ataaggtact ggtacacggt agatggggac aaggcacaga gtgcgatatc agactgggca 2460
cagataggag caagcaatgt gacattcaag tttgtgaagc tgagcagtag cgtaagtgga 2520
gcggactatt atttagagat aggatttaag agtggagctg ggcagttgca ggctggtaaa 2580
gacacagggg agatacagat aaggtttaac aagagtgact ggagcaatta caatcagggg 2640
aatgactggt catggatgca gagcatgacg agttatggag agaatgtgaa ggtaacagcg 2700
tatatagatg gtgtattggt atggggacag gagccgagtg gagcgacacc aacaccgaca 2760
gcaacaccag caccgacagt gacaccgaca gcaacaccag caccaacacc aaccccgacc 2820
ccaacagtaa cggcaacccc gacaccgaca ccaacaccgg tgcagacagt aataccaatg 2880
ccataa 2886

<210> SEQ ID NO 67
<211> LENGTH: 961
<212> TYPE: PRT
<213> ORGANISM: Caldicellulosiruptor bescii

<400> SEQUENCE: 67

Met Ala His His His His His His Val Asp Asp Asp Asp Lys Met Ala
1 5 10 15

Thr Ser Asn Asp Gly Val Val Lys Ile Asp Thr Ser Thr Leu Ile Gly
20 25 30

Thr Asn His Ala His Cys Trp Tyr Arg Asp Lys Leu Glu Thr Ala Leu
35 40 45

Arg Gly Ile Arg Ser Trp Gly Met Asn Ser Val Arg Val Val Leu Ser
50 55 60

Asn Gly Tyr Arg Trp Thr Lys Ile Pro Ala Ser Glu Val Ala Asn Ile
65 70 75 80

Ile Ser Leu Ser Arg Ser Leu Gly Phe Arg Ala Ile Val Leu Glu Val
85 90 95

His Asp Thr Thr Gly Tyr Gly Glu Asp Gly Ala Ala Cys Ser Leu Ala
100 105 110

Gln Ala Val Glu Tyr Trp Lys Glu Ile Lys Ser Val Leu Glu Gly Asn
115 120 125

Glu Asp Phe Val Ile Ile Asn Ile Gly Asn Glu Pro Tyr Gly Asn Asn
130 135 140

Asn Tyr Gln Asn Trp Ile Asn Asp Thr Lys Asn Ala Ile Lys Ala Leu
145 150 155 160

Arg Asp Ala Gly Phe Lys His Thr Ile Met Val Asp Ala Pro Asn Trp
165 170 175

Gly Gln Asp Trp Ser Asn Thr Met Arg Asp Asn Ala Gln Ser Ile Met
180 185 190

Glu Ala Asp Pro Leu Arg Asn Leu Val Phe Ser Ile His Met Tyr Gly
195 200 205

Val Tyr Asn Thr Ala Ser Lys Val Glu Glu Tyr Ile Lys Ser Phe Val
210 215 220

```
Glu Lys Gly Leu Pro Leu Val Ile Gly Glu Phe Gly His Gln His Thr
225                 230                 235                 240

Asp Gly Asp Pro Asp Glu Glu Ala Ile Val Arg Tyr Ala Lys Gln Tyr
                245                 250                 255

Lys Ile Gly Leu Phe Ser Trp Ser Trp Cys Gly Asn Ser Ser Tyr Val
            260                 265                 270

Gly Tyr Leu Asp Met Val Asn Asn Trp Asp Pro Asn Asn Pro Thr Pro
        275                 280                 285

Trp Gly Gln Trp Tyr Lys Thr Asn Ala Ile Gly Ala Ser Ser Val Pro
    290                 295                 300

Thr Ser Thr Pro Thr Pro Thr Pro Thr Ala Thr Pro Thr Ala Thr Pro
305                 310                 315                 320

Thr Pro Thr Leu Thr Pro Thr Pro Thr Pro Thr Pro Thr Pro Thr Ser
                325                 330                 335

Thr Pro Thr Ala Thr Pro Thr Ala Thr Pro Thr Pro Thr Pro Thr Pro
            340                 345                 350

Ser Ser Thr Pro Val Ala Gly Gly Gln Ile Lys Val Leu Tyr Ala Asn
        355                 360                 365

Lys Glu Thr Asn Ser Thr Thr Asn Thr Ile Arg Pro Trp Leu Lys Val
    370                 375                 380

Val Asn Thr Gly Ser Ser Ser Ile Asp Leu Ser Arg Val Thr Ile Arg
385                 390                 395                 400

Tyr Trp Tyr Thr Val Asp Gly Asp Lys Ala Gln Ser Ala Ile Ser Asp
                405                 410                 415

Trp Ala Gln Ile Gly Ala Ser Asn Val Thr Phe Lys Phe Val Lys Leu
            420                 425                 430

Ser Ser Ser Val Ser Gly Ala Asp Tyr Tyr Leu Glu Ile Gly Phe Lys
        435                 440                 445

Ser Gly Ala Gly Gln Leu Gln Ala Gly Lys Asp Thr Gly Glu Ile Gln
    450                 455                 460

Ile Arg Phe Asn Lys Ser Asp Trp Ser Asn Tyr Asn Gln Gly Asn Asp
465                 470                 475                 480

Trp Ser Trp Met Gln Ser Met Thr Ser Tyr Gly Glu Asn Val Lys Val
                485                 490                 495

Thr Ala Tyr Ile Asp Gly Val Leu Val Trp Gly Gln Glu Pro Ser Gly
            500                 505                 510

Ala Thr Pro Thr Pro Thr Ala Thr Pro Ala Pro Thr Pro Thr Pro Thr
        515                 520                 525

Pro Thr Pro Thr Ala Thr Pro Thr Pro Thr Pro Thr Pro Thr Pro Thr
    530                 535                 540

Pro Thr Ala Thr Pro Thr Pro Thr Pro Ser Ser Thr Pro Val Ala Gly
545                 550                 555                 560

Gly Gln Ile Lys Val Leu Tyr Ala Asn Lys Glu Thr Asn Ser Thr Thr
                565                 570                 575

Asn Thr Ile Arg Pro Trp Leu Lys Val Val Asn Thr Gly Ser Ser Ser
            580                 585                 590

Ile Asp Leu Ser Arg Val Thr Ile Arg Tyr Trp Tyr Thr Val Asp Gly
        595                 600                 605

Asp Lys Ala Gln Ser Ala Ile Ser Asp Trp Ala Gln Ile Gly Ala Ser
    610                 615                 620

Asn Val Thr Phe Lys Phe Val Lys Leu Ser Ser Ser Val Ser Gly Ala
625                 630                 635                 640
```

-continued

```
Asp Tyr Tyr Leu Glu Ile Gly Phe Lys Ser Gly Ala Gly Gln Leu Gln
                645                 650                 655

Ala Gly Lys Asp Thr Gly Glu Ile Gln Ile Arg Phe Asn Lys Ser Asp
            660                 665                 670

Trp Ser Asn Tyr Asn Gln Gly Asn Asp Trp Ser Trp Met Gln Ser Met
        675                 680                 685

Thr Ser Tyr Gly Glu Asn Val Lys Val Thr Ala Tyr Ile Asp Gly Val
    690                 695                 700

Leu Val Trp Gly Gln Glu Pro Ser Gly Ala Thr Pro Thr Pro Thr Ala
705                 710                 715                 720

Thr Pro Ala Pro Thr Pro Thr Pro Thr Pro Thr Pro Thr Ala Thr Pro
                725                 730                 735

Thr Pro Thr Pro Thr Pro Thr Pro Thr Pro Thr Ala Thr Pro Thr Pro
            740                 745                 750

Thr Pro Ser Ser Thr Pro Val Ala Gly Gly Gln Ile Lys Val Leu Tyr
        755                 760                 765

Ala Asn Lys Glu Thr Asn Ser Thr Thr Asn Thr Ile Arg Pro Trp Leu
    770                 775                 780

Lys Val Val Asn Thr Gly Ser Ser Ser Ile Asp Leu Ser Arg Val Thr
785                 790                 795                 800

Ile Arg Tyr Trp Tyr Thr Val Asp Gly Asp Lys Ala Gln Ser Ala Ile
                805                 810                 815

Ser Asp Trp Ala Gln Ile Gly Ala Ser Asn Val Thr Phe Lys Phe Val
            820                 825                 830

Lys Leu Ser Ser Ser Val Ser Gly Ala Asp Tyr Tyr Leu Glu Ile Gly
        835                 840                 845

Phe Lys Ser Gly Ala Gly Gln Leu Gln Ala Gly Lys Asp Thr Gly Glu
    850                 855                 860

Ile Gln Ile Arg Phe Asn Lys Ser Asp Trp Ser Asn Tyr Asn Gln Gly
865                 870                 875                 880

Asn Asp Trp Ser Trp Met Gln Ser Met Thr Ser Tyr Gly Glu Asn Val
                885                 890                 895

Lys Val Thr Ala Tyr Ile Asp Gly Val Leu Val Trp Gly Gln Glu Pro
            900                 905                 910

Ser Gly Ala Thr Pro Thr Pro Thr Ala Thr Pro Ala Pro Thr Val Thr
        915                 920                 925

Pro Thr Ala Thr Pro Ala Pro Thr Pro Thr Pro Thr Pro Thr Val Thr
    930                 935                 940

Ala Thr Pro Thr Pro Thr Pro Thr Pro Val Gln Thr Val Ile Pro Met
945                 950                 955                 960

Pro


<210> SEQ ID NO 68
<211> LENGTH: 3327
<212> TYPE: DNA
<213> ORGANISM: Caldicellulosiruptor bescii

<400> SEQUENCE: 68

atggcacatc accaccacca tcacgtggat gacgacgaca agatgggtgc ctcttcagta      60

cctacttcaa caccaacacc gacaccaact gctacaccaa cagcaacacc aacaccaaca     120

ctgactccaa caccgacacc tacaccaaca ccaacgtcaa caccaactgc tacaccaaca     180

gcaacgccaa caccaacacc gacgccgagc agcacacctg tagcaggtgg acagataaag     240

gtattgtatg ctaacaagga gacaaatagc acaacaaata cgataaggcc atggttgaag     300
```

```
gtagtgaaca ctggaagcag cagcatagat ttgagcaggg taacgataag gtactggtac    360
acggtagatg gggacaaggc acagagtgcg atatcagact gggcacagat aggagcaagc    420
aatgtgacat tcaagtttgt gaagctgagc agtagcgtaa gtggagcgga ctattattta    480
gagataggat ttaagagtgg agctgggcag ttgcaggctg gtaaagacac aggggagata    540
cagataaggt ttaacaagag tgactggagc aattacaatc aggggaatga ctggtcatgg    600
atgcagagca tgacgagtta tggagagaat gtgaaggtaa cagcgtatat agatggtgta    660
ttggtatggg gacaggagcc gagtggagcg acaccaacac cgacagcaac accagcacca    720
acaccaaccc cgaccccaac accaactgct acaccaacgc caacaccgac tccaacacca    780
acaccaactg ctaccccaac accgacgccg agcagtacac ctgtagcagg tggacagata    840
aaggtattgt atgctaacaa ggagacaaat agcacaacaa acacgataag gccatggttg    900
aaggtagtga acactggaag cagcagcata gatttgagca gggtaacgat aaggtactgg    960
tacacggtag atggggacaa ggcacagagt gcgatatcag actgggcaca gataggagca   1020
agcaatgtga cattcaagtt tgtgaagctg agcagtagcg taagtggagc ggactattat   1080
ttagagatag gatttaagag tggagctggg cagttgcagg ctggtaaaga cacaggggag   1140
atacagataa ggtttaacaa gagtgactgg agcaattaca atcaggggaa tgactggtca   1200
tggatgcaga gcatgacgag ttatggagag aatgtgaagg taacagcgta tatagatggt   1260
gtattggtat ggggacagga gccgagtgga gcgacaccaa caccgacagc aacaccagca   1320
ccaacaccaa ccccgacccc aacaccaact gctacaccaa cgccaacacc gactccaaca   1380
ccaacaccaa ctgctacccc aacaccgacg ccgagcagta cacctgtagc aggtggacag   1440
ataaaggtat tgtatgctaa caaggagaca aatagcacaa caaacacgat aaggccatgg   1500
ttgaaggtag tgaacactgg aagcagcagc atagatttga gcagggtaac gataaggtac   1560
tggtacacgg tagatgggga caaggcacag agtgcgatat cagactgggc acagatagga   1620
gcaagcaatg tgacattcaa gtttgtgaag ctgagcagta gcgtaagtgg agcggactat   1680
tatttagaga taggatttaa gagtggagct gggcagttgc aggctggtaa agacacaggg   1740
gagatacaga taaggtttaa caagagtgac tggagcaatt acaatcaggg gaatgactgg   1800
tcatggatgc agagcatgac gagttatgga gagaatgtga aggtaacagc gtatatagat   1860
ggtgtattgg tatggggaca ggagccgagt ggagcgacac caacaccgac agcaacacca   1920
gcaccgacag tgacaccgac agcaacacca gcaccaacac caaccccgac cccaacagta   1980
acggcaaccc cgacaccgac accaacaccg gtgcagacag taataccaat gccaacagta   2040
actccaaatc caacatcaac accgagtatt cttgatgata caaatgatga ttggctttat   2100
gtaagtggta ataaaatagt tgataaagat ggtaaaccgg tatggttaac aggtattaac   2160
tggtttggat acaatacagg tacaaatgtt tttgatggtg tatggagttg caatctaaaa   2220
gatactctag ctgaaatagc caatagaggc tttaatttgc taagaattcc aatatcagcc   2280
gagattatac tgaactggtc gcaaggtatt tatccaaaac caaatataaa ctactacgtt   2340
aatccagagc ttgagggcaa aaacagtctt gaagtatttg acatagttgt acaaatatgt   2400
aaagaagttg gtttgaaaat tatgttggat attcacagca taaaaacaga cgcaatggga   2460
catatctatc cagtatggta tgatgataaa tttactccag aggattttta taaggcgtgt   2520
gagtggatta caaatagata taaaaatgat gatactatta tagcttttga cctaaaaaat   2580
gagccacatg gaaaaccatg gcaagacaca acatttgcaa aatgggataa ttcaacagat   2640
```

-continued

```
attaataatt ggaaatatgc ggctgaaaca tgtgcgaaac gtatactaaa tataaatcca   2700

aaccttctta ttgtaataga aggaattgaa gcgtatccaa aagatgacgt tacatggaca   2760

tcaaaatcct atagcgatta ctattcaaca tggtggggcg gtaacttgcg aggtgttaaa   2820

aagtatccta ttaatctggg taaatatcaa aataaagtag tatattcacc tcatgattac   2880

ggaccctctg tttaccagca gccgtggttt tatccaggct tcacaaaaga atctttacta   2940

caagattgtt ggcgtccgaa ttgggcttac atcatggaag aaaacattgc gccgctgctg   3000

ataggtgaat ggggtggtta tcttgatgga gctgataacg aaaagtggat gagatatcta   3060

cgagattata ttatagagaa tcatattcat cacacatttt ggtgctttaa tgctaactca   3120

ggtgacactg gaggtatggt tggatacgat tttacgacat gggatgaaaa aaaatactca   3180

tttttaaagc cggctctttg gcaagacagt caaggtaggt ttgttggatt agatcacaag   3240

cgacccttag gtacaaatgg gaaaaacatt aatattacaa tatactacaa caataatgaa   3300

ccagcgccag ttccagccgc aaaataa                                        3327
```

<210> SEQ ID NO 69
<211> LENGTH: 1108
<212> TYPE: PRT
<213> ORGANISM: Caldicellulosiruptor bescii

<400> SEQUENCE: 69

```
Met Ala His His His His His His Val Asp Asp Asp Asp Lys Met Gly
1               5                   10                  15

Ala Ser Ser Val Pro Thr Ser Thr Pro Thr Pro Thr Pro Thr Ala Thr
            20                  25                  30

Pro Thr Ala Thr Pro Thr Pro Thr Leu Thr Pro Thr Pro Thr Pro Thr
        35                  40                  45

Pro Thr Pro Thr Ser Thr Pro Thr Ala Thr Pro Thr Ala Thr Pro Thr
    50                  55                  60

Pro Thr Pro Thr Pro Ser Ser Thr Pro Val Ala Gly Gly Gln Ile Lys
65                  70                  75                  80

Val Leu Tyr Ala Asn Lys Glu Thr Asn Ser Thr Thr Asn Thr Ile Arg
                85                  90                  95

Pro Trp Leu Lys Val Val Asn Thr Gly Ser Ser Ser Ile Asp Leu Ser
            100                 105                 110

Arg Val Thr Ile Arg Tyr Trp Tyr Thr Val Asp Gly Asp Lys Ala Gln
        115                 120                 125

Ser Ala Ile Ser Asp Trp Ala Gln Ile Gly Ala Ser Asn Val Thr Phe
    130                 135                 140

Lys Phe Val Lys Leu Ser Ser Ser Val Ser Gly Ala Asp Tyr Tyr Leu
145                 150                 155                 160

Glu Ile Gly Phe Lys Ser Gly Ala Gly Gln Leu Gln Ala Gly Lys Asp
                165                 170                 175

Thr Gly Glu Ile Gln Ile Arg Phe Asn Lys Ser Asp Trp Ser Asn Tyr
            180                 185                 190

Asn Gln Gly Asn Asp Trp Ser Trp Met Gln Ser Met Thr Ser Tyr Gly
        195                 200                 205

Glu Asn Val Lys Val Thr Ala Tyr Ile Asp Gly Val Leu Val Trp Gly
    210                 215                 220

Gln Glu Pro Ser Gly Ala Thr Pro Thr Pro Thr Ala Thr Pro Ala Pro
225                 230                 235                 240

Thr Pro Thr Pro Thr Pro Thr Pro Thr Ala Thr Pro Thr Pro Thr Pro
                245                 250                 255
```

-continued

```
Thr Pro Thr Pro Thr Pro Thr Ala Thr Pro Thr Pro Thr Pro Ser Ser
            260                 265                 270

Thr Pro Val Ala Gly Gly Gln Ile Lys Val Leu Tyr Ala Asn Lys Glu
        275                 280                 285

Thr Asn Ser Thr Thr Asn Thr Ile Arg Pro Trp Leu Lys Val Val Asn
    290                 295                 300

Thr Gly Ser Ser Ser Ile Asp Leu Ser Arg Val Thr Ile Arg Tyr Trp
305                 310                 315                 320

Tyr Thr Val Asp Gly Asp Lys Ala Gln Ser Ala Ile Ser Asp Trp Ala
                325                 330                 335

Gln Ile Gly Ala Ser Asn Val Thr Phe Lys Phe Val Lys Leu Ser Ser
            340                 345                 350

Ser Val Ser Gly Ala Asp Tyr Tyr Leu Glu Ile Gly Phe Lys Ser Gly
        355                 360                 365

Ala Gly Gln Leu Gln Ala Gly Lys Asp Thr Gly Glu Ile Gln Ile Arg
    370                 375                 380

Phe Asn Lys Ser Asp Trp Ser Asn Tyr Asn Gln Gly Asn Asp Trp Ser
385                 390                 395                 400

Trp Met Gln Ser Met Thr Ser Tyr Gly Glu Asn Val Lys Val Thr Ala
                405                 410                 415

Tyr Ile Asp Gly Val Leu Val Trp Gly Gln Glu Pro Ser Gly Ala Thr
            420                 425                 430

Pro Thr Pro Thr Ala Thr Pro Ala Pro Thr Pro Thr Pro Thr Pro Thr
        435                 440                 445

Pro Thr Ala Thr Pro Thr Pro Thr Pro Thr Pro Thr Pro Thr Pro Thr
    450                 455                 460

Ala Thr Pro Thr Pro Thr Pro Ser Ser Thr Pro Val Ala Gly Gly Gln
465                 470                 475                 480

Ile Lys Val Leu Tyr Ala Asn Lys Glu Thr Asn Ser Thr Thr Asn Thr
                485                 490                 495

Ile Arg Pro Trp Leu Lys Val Val Asn Thr Gly Ser Ser Ser Ile Asp
            500                 505                 510

Leu Ser Arg Val Thr Ile Arg Tyr Trp Tyr Thr Val Asp Gly Asp Lys
        515                 520                 525

Ala Gln Ser Ala Ile Ser Asp Trp Ala Gln Ile Gly Ala Ser Asn Val
    530                 535                 540

Thr Phe Lys Phe Val Lys Leu Ser Ser Ser Val Ser Gly Ala Asp Tyr
545                 550                 555                 560

Tyr Leu Glu Ile Gly Phe Lys Ser Gly Ala Gly Gln Leu Gln Ala Gly
                565                 570                 575

Lys Asp Thr Gly Glu Ile Gln Ile Arg Phe Asn Lys Ser Asp Trp Ser
            580                 585                 590

Asn Tyr Asn Gln Gly Asn Asp Trp Ser Trp Met Gln Ser Met Thr Ser
        595                 600                 605

Tyr Gly Glu Asn Val Lys Val Thr Ala Tyr Ile Asp Gly Val Leu Val
    610                 615                 620

Trp Gly Gln Glu Pro Ser Gly Ala Thr Pro Thr Pro Thr Ala Thr Pro
625                 630                 635                 640

Ala Pro Thr Val Thr Pro Thr Ala Thr Pro Ala Pro Thr Pro Thr Pro
                645                 650                 655

Thr Pro Thr Val Thr Ala Thr Pro Thr Pro Thr Pro Thr Pro Val Gln
            660                 665                 670
```

```
Thr Val Ile Pro Met Pro Thr Val Thr Pro Asn Pro Thr Ser Thr Pro
        675                 680                 685

Ser Ile Leu Asp Asp Thr Asn Asp Asp Trp Leu Tyr Val Ser Gly Asn
    690                 695                 700

Lys Ile Val Asp Lys Asp Gly Lys Pro Val Trp Leu Thr Gly Ile Asn
705                 710                 715                 720

Trp Phe Gly Tyr Asn Thr Gly Thr Asn Val Phe Asp Gly Val Trp Ser
                725                 730                 735

Cys Asn Leu Lys Asp Thr Leu Ala Glu Ile Ala Asn Arg Gly Phe Asn
            740                 745                 750

Leu Leu Arg Ile Pro Ile Ser Ala Glu Ile Ile Leu Asn Trp Ser Gln
        755                 760                 765

Gly Ile Tyr Pro Lys Pro Asn Ile Asn Tyr Tyr Val Asn Pro Glu Leu
    770                 775                 780

Glu Gly Lys Asn Ser Leu Glu Val Phe Asp Ile Val Val Gln Ile Cys
785                 790                 795                 800

Lys Glu Val Gly Leu Lys Ile Met Leu Asp Ile His Ser Ile Lys Thr
                805                 810                 815

Asp Ala Met Gly His Ile Tyr Pro Val Trp Tyr Asp Asp Lys Phe Thr
            820                 825                 830

Pro Glu Asp Phe Tyr Lys Ala Cys Glu Trp Ile Thr Asn Arg Tyr Lys
        835                 840                 845

Asn Asp Asp Thr Ile Ile Ala Phe Asp Leu Lys Asn Glu Pro His Gly
    850                 855                 860

Lys Pro Trp Gln Asp Thr Thr Phe Ala Lys Trp Asp Asn Ser Thr Asp
865                 870                 875                 880

Ile Asn Asn Trp Lys Tyr Ala Ala Glu Thr Cys Ala Lys Arg Ile Leu
                885                 890                 895

Asn Ile Asn Pro Asn Leu Leu Ile Val Ile Glu Gly Ile Glu Ala Tyr
            900                 905                 910

Pro Lys Asp Asp Val Thr Trp Thr Ser Lys Ser Tyr Ser Asp Tyr Tyr
        915                 920                 925

Ser Thr Trp Trp Gly Gly Asn Leu Arg Gly Val Lys Lys Tyr Pro Ile
    930                 935                 940

Asn Leu Gly Lys Tyr Gln Asn Lys Val Val Tyr Ser Pro His Asp Tyr
945                 950                 955                 960

Gly Pro Ser Val Tyr Gln Gln Pro Trp Phe Tyr Pro Gly Phe Thr Lys
                965                 970                 975

Glu Ser Leu Leu Gln Asp Cys Trp Arg Pro Asn Trp Ala Tyr Ile Met
            980                 985                 990

Glu Glu Asn Ile Ala Pro Leu Leu Ile Gly Glu Trp Gly Gly Tyr Leu
        995                 1000                1005

Asp Gly Ala Asp Asn Glu Lys Trp Met Arg Tyr Leu Arg Asp Tyr Ile
    1010                1015                1020

Ile Glu Asn His Ile His His Thr Phe Trp Cys Phe Asn Ala Asn Ser
1025                1030                1035                1040

Gly Asp Thr Gly Gly Met Val Gly Tyr Asp Phe Thr Thr Trp Asp Glu
                1045                1050                1055

Lys Lys Tyr Ser Phe Leu Lys Pro Ala Leu Trp Gln Asp Ser Gln Gly
            1060                1065                1070

Arg Phe Val Gly Leu Asp His Lys Arg Pro Leu Gly Thr Asn Gly Lys
        1075                1080                1085

Asn Ile Asn Ile Thr Ile Tyr Tyr Asn Asn Asn Glu Pro Ala Pro Val
```

1090 1095 1100

Pro Ala Ala Lys
1105

<210> SEQ ID NO 70
<211> LENGTH: 42
<212> TYPE: DNA
<213> ORGANISM: Artificial Sequence
<220> FEATURE:
<223> OTHER INFORMATION: Synthesized Construct

<400> SEQUENCE: 70
gacgacgaca agatgcaaga ggttagggct ggttcgttta ac 42

<210> SEQ ID NO 71
<211> LENGTH: 43
<212> TYPE: DNA
<213> ORGANISM: Artificial Sequence
<220> FEATURE:
<223> OTHER INFORMATION: Synthesized Construct

<400> SEQUENCE: 71
gaggagaagc ccggttattg attgccaaac agtatttcat atg 43

<210> SEQ ID NO 72
<211> LENGTH: 41
<212> TYPE: DNA
<213> ORGANISM: Artificial Sequence
<220> FEATURE:
<223> OTHER INFORMATION: Synthesized Construct

<400> SEQUENCE: 72
gaggagaagc ccggttatac ctttatctgt ccacctgcta c 41

<210> SEQ ID NO 73
<211> LENGTH: 42
<212> TYPE: DNA
<213> ORGANISM: Artificial Sequence
<220> FEATURE:
<223> OTHER INFORMATION: Synthesized Construct

<400> SEQUENCE: 73
gacgacgaca agatgttcaa agctattgaa actccaacaa ac 42

<210> SEQ ID NO 74
<211> LENGTH: 1759
<212> TYPE: PRT
<213> ORGANISM: Caldicellulosiruptor bescii

<400> SEQUENCE: 74

Met Lys Arg Tyr Arg Arg Ile Ile Ala Met Val Val Thr Phe Ile Phe
1 5 10 15

Ile Leu Gly Val Val Tyr Gly Val Lys Pro Trp Gln Glu Val Arg Ala
20 25 30

Gly Ser Phe Asn Tyr Gly Glu Ala Leu Gln Lys Ala Ile Met Phe Tyr
35 40 45

Glu Phe Gln Met Ser Gly Lys Leu Pro Asn Trp Val Arg Asn Asn Trp
50 55 60

Arg Gly Asp Ser Ala Leu Lys Asp Gly Gln Asp Asn Gly Leu Asp Leu
65 70 75 80

Thr Gly Gly Trp Phe Asp Ala Gly Asp His Val Lys Phe Asn Leu Pro
85 90 95

-continued

```
Met Ser Tyr Thr Gly Thr Met Leu Ser Trp Ala Val Tyr Glu Tyr Lys
            100                 105                 110

Asp Ala Phe Val Lys Ser Gly Gln Leu Glu His Ile Leu Asn Gln Ile
        115                 120                 125

Glu Trp Val Asn Asp Tyr Phe Val Lys Cys His Pro Ser Lys Tyr Val
    130                 135                 140

Tyr Tyr Tyr Gln Val Gly Asp Gly Ser Lys Asp His Ala Trp Trp Gly
145                 150                 155                 160

Pro Ala Glu Val Met Gln Met Glu Arg Pro Ser Phe Lys Val Thr Gln
                165                 170                 175

Ser Ser Pro Gly Ser Thr Val Val Ala Glu Thr Ala Ala Ser Leu Ala
            180                 185                 190

Ala Ala Ser Ile Val Leu Lys Asp Arg Asn Pro Thr Lys Ala Ala Thr
        195                 200                 205

Tyr Leu Gln His Ala Lys Glu Leu Tyr Glu Phe Ala Glu Val Thr Lys
    210                 215                 220

Ser Asp Ala Gly Tyr Thr Ala Ala Asn Gly Tyr Tyr Asn Ser Trp Ser
225                 230                 235                 240

Gly Phe Tyr Asp Glu Leu Ser Trp Ala Ala Val Trp Leu Tyr Leu Ala
                245                 250                 255

Thr Asn Asp Ser Thr Tyr Leu Thr Lys Ala Glu Ser Tyr Val Gln Asn
            260                 265                 270

Trp Pro Lys Ile Ser Gly Ser Asn Thr Ile Asp Tyr Lys Trp Ala His
        275                 280                 285

Cys Trp Asp Asp Val His Asn Gly Ala Ala Leu Leu Leu Ala Lys Ile
    290                 295                 300

Thr Gly Lys Asp Ile Tyr Lys Gln Ile Ile Glu Ser His Leu Asp Tyr
305                 310                 315                 320

Trp Thr Thr Gly Tyr Asn Gly Glu Arg Ile Lys Tyr Thr Pro Lys Gly
                325                 330                 335

Leu Ala Trp Leu Asp Gln Trp Gly Ser Leu Arg Tyr Ala Thr Thr Thr
            340                 345                 350

Ala Phe Leu Ala Phe Val Tyr Ser Asp Trp Val Gly Cys Pro Ser Thr
        355                 360                 365

Lys Lys Glu Ile Tyr Arg Lys Phe Gly Glu Ser Gln Ile Asp Tyr Ala
    370                 375                 380

Leu Gly Ser Ala Gly Arg Ser Phe Val Val Gly Phe Gly Thr Asn Pro
385                 390                 395                 400

Pro Lys Arg Pro His His Arg Thr Ala His Ser Ser Trp Ala Asp Ser
                405                 410                 415

Gln Ser Ile Pro Ser Tyr His Arg His Thr Leu Tyr Gly Ala Leu Val
            420                 425                 430

Gly Gly Pro Gly Ser Asp Asp Ser Tyr Thr Asp Asp Ile Ser Asn Tyr
        435                 440                 445

Val Asn Asn Glu Val Ala Cys Asp Tyr Asn Ala Gly Phe Val Gly Ala
    450                 455                 460

Leu Ala Lys Met Tyr Gln Leu Tyr Gly Gly Asn Pro Ile Pro Asp Phe
465                 470                 475                 480

Lys Ala Ile Glu Thr Pro Thr Asn Asp Glu Phe Phe Val Glu Ala Gly
                485                 490                 495

Ile Asn Ala Ser Gly Thr Asn Phe Ile Glu Ile Lys Ala Ile Val Asn
            500                 505                 510

Asn Gln Ser Gly Trp Pro Ala Arg Ala Thr Asp Lys Leu Lys Phe Arg
```

-continued

```
        515                 520                 525

Tyr Phe Val Asp Leu Ser Glu Leu Ile Lys Ala Gly Tyr Ser Pro Asn
    530                 535                 540

Gln Leu Thr Leu Ser Thr Asn Tyr Asn Gln Gly Ala Lys Val Ser Gly
545                 550                 555                 560

Pro Tyr Val Trp Asp Ala Ser Lys Asn Ile Tyr Tyr Ile Leu Val Asp
                565                 570                 575

Phe Thr Gly Thr Leu Ile Tyr Pro Gly Gly Gln Asp Lys Tyr Lys Lys
            580                 585                 590

Glu Val Gln Phe Arg Ile Ala Ala Pro Gln Asn Val Gln Trp Asp Asn
        595                 600                 605

Ser Asn Asp Tyr Ser Phe Gln Asp Ile Lys Gly Val Ser Ser Gly Ser
    610                 615                 620

Val Val Lys Thr Lys Tyr Ile Pro Leu Tyr Asp Gly Asp Val Lys Val
625                 630                 635                 640

Trp Gly Glu Glu Pro Gly Thr Ser Gly Ala Thr Pro Thr Pro Thr Ala
                645                 650                 655

Thr Ala Thr Pro Thr Pro Thr Pro Thr Val Thr Pro Thr Pro Thr Pro
            660                 665                 670

Thr Pro Thr Ser Thr Ala Thr Pro Thr Pro Thr Pro Thr Pro Thr Val
        675                 680                 685

Thr Pro Thr Pro Thr Pro Thr Pro Thr Ala Thr Pro Thr Ala Thr Pro
    690                 695                 700

Thr Pro Thr Ser Thr Pro Ser Ser Thr Pro Val Ala Gly Gly Gln Ile
705                 710                 715                 720

Lys Val Leu Tyr Ala Asn Lys Glu Thr Asn Ser Thr Thr Asn Thr Ile
                725                 730                 735

Arg Pro Trp Leu Lys Val Val Asn Thr Gly Ser Ser Ser Ile Asp Leu
            740                 745                 750

Ser Arg Val Thr Ile Arg Tyr Trp Tyr Thr Val Asp Gly Asp Lys Ala
        755                 760                 765

Gln Ser Ala Ile Ser Asp Trp Ala Gln Ile Gly Ala Ser Asn Val Thr
    770                 775                 780

Phe Lys Phe Val Lys Leu Ser Ser Ser Val Ser Gly Ala Asp Tyr Tyr
785                 790                 795                 800

Leu Glu Ile Gly Phe Lys Ser Gly Ala Gly Gln Leu Gln Ala Gly Lys
                805                 810                 815

Asp Thr Gly Glu Ile Gln Ile Arg Phe Asn Lys Ser Asp Trp Ser Asn
            820                 825                 830

Tyr Asn Gln Gly Asn Asp Trp Ser Trp Met Gln Ser Met Thr Asn Tyr
        835                 840                 845

Gly Glu Asn Val Lys Val Thr Ala Tyr Ile Asp Gly Val Leu Val Trp
    850                 855                 860

Gly Gln Glu Pro Ser Gly Ala Thr Pro Thr Pro Thr Ala Thr Pro Ala
865                 870                 875                 880

Pro Thr Val Thr Pro Thr Pro Thr Pro Thr Pro Thr Ser Thr Pro Thr
                885                 890                 895

Ala Thr Pro Thr Ala Thr Pro Thr Pro Thr Pro Thr Pro Ser Ser Thr
            900                 905                 910

Pro Val Ala Gly Gly Gln Ile Lys Val Leu Tyr Ala Asn Lys Glu Thr
        915                 920                 925

Asn Ser Thr Thr Asn Thr Ile Arg Pro Trp Leu Lys Val Val Asn Thr
    930                 935                 940
```

```
Gly Ser Ser Ser Ile Asp Leu Ser Arg Val Thr Ile Arg Tyr Trp Tyr
945                 950                 955                 960

Thr Val Asp Gly Asp Lys Ala Gln Ser Ala Ile Ser Asp Trp Ala Gln
                965                 970                 975

Ile Gly Ala Ser Asn Val Thr Phe Lys Phe Val Lys Leu Ser Ser Ser
            980                 985                 990

Val Ser Gly Ala Asp Tyr Tyr Leu Glu Ile Gly Phe Lys Ser Gly Ala
        995                 1000                1005

Gly Gln Leu Gln Ala Gly Lys Asp Thr Gly Glu Ile Gln Ile Arg Phe
    1010                1015                1020

Asn Lys Ser Asp Trp Ser Asn Tyr Asn Gln Gly Asn Asp Trp Ser Trp
1025                1030                1035                1040

Met Gln Ser Met Thr Asn Tyr Gly Glu Asn Val Lys Val Thr Ala Tyr
                1045                1050                1055

Ile Asp Gly Val Leu Val Trp Gly Gln Glu Pro Ser Gly Ala Thr Pro
            1060                1065                1070

Thr Pro Thr Ala Thr Pro Ala Pro Thr Val Thr Pro Thr Pro Thr Pro
        1075                1080                1085

Ala Pro Thr Pro Thr Pro Thr Pro Thr Pro Thr Ala Thr Pro Thr Pro
    1090                1095                1100

Thr Pro Thr Pro Thr Pro Thr Ala Thr Pro Thr Val Thr Ala Thr Pro
1105                1110                1115                1120

Thr Pro Thr Pro Ser Ser Thr Pro Ser Val Leu Gly Glu Tyr Gly Gln
                1125                1130                1135

Arg Phe Met Trp Leu Trp Asn Lys Ile His Asp Pro Ala Asn Gly Tyr
            1140                1145                1150

Phe Asn Gln Asp Gly Ile Pro Tyr His Ser Val Glu Thr Leu Ile Cys
        1155                1160                1165

Glu Ala Pro Asp Tyr Gly His Leu Thr Thr Ser Glu Ala Phe Ser Tyr
    1170                1175                1180

Tyr Val Trp Leu Glu Ala Val Tyr Gly Lys Leu Thr Gly Asp Trp Ser
1185                1190                1195                1200

Lys Phe Lys Thr Ala Trp Asp Thr Leu Glu Lys Tyr Met Ile Pro Ser
                1205                1210                1215

Ala Glu Asp Gln Pro Met Arg Ser Tyr Asp Pro Asn Lys Pro Ala Thr
            1220                1225                1230

Tyr Ala Gly Glu Trp Glu Thr Pro Asp Lys Tyr Pro Ser Pro Leu Glu
        1235                1240                1245

Phe Asn Val Pro Val Gly Lys Asp Pro Leu His Asn Glu Leu Val Ser
    1250                1255                1260

Thr Tyr Gly Ser Thr Leu Met Tyr Gly Met His Trp Leu Met Asp Val
1265                1270                1275                1280

Asp Asn Trp Tyr Gly Tyr Gly Lys Arg Gly Asp Gly Val Ser Arg Ala
                1285                1290                1295

Ser Phe Ile Asn Thr Phe Gln Arg Gly Pro Glu Glu Ser Val Trp Glu
            1300                1305                1310

Thr Val Pro His Pro Ser Trp Glu Glu Phe Lys Trp Gly Gly Pro Asn
        1315                1320                1325

Gly Phe Leu Asp Leu Phe Ile Lys Asp Gln Asn Tyr Ser Lys Gln Trp
    1330                1335                1340

Arg Tyr Thr Asp Ala Pro Asp Ala Asp Ala Arg Ala Ile Gln Ala Thr
1345                1350                1355                1360
```

```
Tyr Trp Ala Lys Val Trp Ala Lys Glu Gln Gly Lys Phe Asn Glu Ile
                1365                1370                1375

Ser Ser Tyr Val Ala Lys Ala Ala Lys Met Gly Asp Tyr Leu Arg Tyr
            1380                1385                1390

Ala Met Phe Asp Lys Tyr Phe Lys Pro Leu Gly Cys Gln Asp Lys Asn
        1395                1400                1405

Ala Ala Gly Gly Thr Gly Tyr Asp Ser Ala His Tyr Leu Leu Ser Trp
    1410                1415                1420

Tyr Tyr Ala Trp Gly Gly Ala Leu Asp Gly Ala Trp Ser Trp Lys Ile
1425                1430                1435                1440

Gly Ser Ser His Val His Phe Gly Tyr Gln Asn Pro Met Ala Ala Trp
                1445                1450                1455

Ala Leu Ala Asn Asp Ser Asp Met Lys Pro Lys Ser Pro Asn Gly Ala
            1460                1465                1470

Ser Asp Trp Ala Lys Ser Leu Lys Arg Gln Ile Glu Phe Tyr Arg Trp
        1475                1480                1485

Leu Gln Ser Ala Glu Gly Ala Ile Ala Gly Gly Ala Thr Asn Ser Trp
    1490                1495                1500

Asn Gly Arg Tyr Glu Lys Tyr Pro Ala Gly Thr Ala Thr Phe Tyr Gly
1505                1510                1515                1520

Met Ala Tyr Glu Pro Asn Pro Val Tyr His Asp Pro Gly Ser Asn Thr
                1525                1530                1535

Trp Phe Gly Phe Gln Ala Trp Ser Met Gln Arg Val Ala Glu Tyr Tyr
            1540                1545                1550

Tyr Val Thr Gly Asp Lys Asp Ala Gly Ala Leu Leu Glu Lys Trp Val
        1555                1560                1565

Ser Trp Val Lys Ser Val Val Lys Leu Asn Ser Asp Gly Thr Phe Ala
    1570                1575                1580

Ile Pro Ser Thr Leu Asp Trp Ser Gly Gln Pro Asp Thr Trp Asn Gly
1585                1590                1595                1600

Ala Tyr Thr Gly Asn Ser Asn Leu His Val Lys Val Val Asp Tyr Gly
                1605                1610                1615

Thr Asp Leu Gly Ile Thr Ala Ser Leu Ala Asn Ala Leu Leu Tyr Tyr
            1620                1625                1630

Ser Ala Gly Thr Lys Lys Tyr Gly Val Phe Asp Glu Gly Ala Lys Asn
        1635                1640                1645

Leu Ala Lys Glu Leu Leu Asp Arg Met Trp Lys Leu Tyr Arg Asp Glu
    1650                1655                1660

Lys Gly Leu Ser Ala Pro Glu Lys Arg Ala Asp Tyr Lys Arg Phe Phe
1665                1670                1675                1680

Glu Gln Glu Val Tyr Ile Pro Ala Gly Trp Ile Gly Lys Met Pro Asn
                1685                1690                1695

Gly Asp Val Ile Lys Ser Gly Val Lys Phe Ile Asp Ile Arg Ser Lys
            1700                1705                1710

Tyr Lys Gln Asp Pro Asp Trp Pro Lys Leu Glu Ala Ala Tyr Lys Ser
        1715                1720                1725

Gly Gln Ala Pro Glu Phe Arg Tyr His Arg Phe Trp Ala Gln Cys Asp
    1730                1735                1740

Ile Ala Ile Ala Asn Ala Thr Tyr Glu Ile Leu Phe Gly Asn Gln
1745                1750                1755
```

<210> SEQ ID NO 75
<211> LENGTH: 5196
<212> TYPE: DNA

<213> ORGANISM: Caldicellulosiruptor bescii

<400> SEQUENCE: 75

```
caagaggtta gggctggttc gtttaactat ggggaagctt tacaaaaagc tatcatgttt     60
tacgaatttc aaatgtctgg taaacttccg aattgggtac gcaacaactg gcgtggcgac    120
tcagcattaa aggatggtca agacaatggg cttgatttga caggtggttg gtttgacgca    180
ggtgatcacg tcaagtttaa ccttccaatg tcatacactg gtacaatgtt gtcatgggca    240
gtgtatgagt acaaagatgc atttgtcaag agtggtcaat tggaacatat cttaaatcaa    300
atcgaatggg ttaatgacta ttttgtaaaa tgtcatccaa gcaaatatgt atactattac    360
caggttgggg atggaagtaa agatcatgca tggtggggac ctgctgaggt tatgcaaatg    420
gagagacctt catttaaggt cacccaaagc agtcctggat ctacagtagt agcagagaca    480
gcagcttcct tagcagcagc ttcaattgtt ttgaaagaca gaaatcccac taaagcagca    540
acatatctgc aacatgcaaa agaattatat gagtttgcag aagtaacaaa aagcgatgca    600
ggttacactg ctgcaaatgg atattacaat tcatggagcg gtttctatga tgagctttct    660
tgggcagcag tttggttgta tttggcaaca aatgattcaa catatctcac aaaagctgag    720
tcatatgtcc aaaattggcc caaaatttct ggcagtaaca caattgacta caagtgggct    780
cattgctggg atgatgttca caatggagcg gcattattgt tagcaaaaat taccggtaag    840
gatatttata aacaaattat tgaaagtcac ttagattact ggactacagg atacaatggc    900
gaaaggatta agtatacacc aaaaggatta gcatggcttg atcaatgggg ttcgttgaga    960
tatgcaacaa ctacagcatt tttggcattt gtttatagcg attgggttgg ctgtccaagc   1020
acaaaaaaag aaatatatag aaaatttgga gaaagccaga ttgattatgc gttaggctca   1080
gctggaagaa gctttgttgt tggatttggt acaaatccac caaagagacc gcatcacaga   1140
actgctcata gctcatgggc agacagtcag agtatacctt catatcacag acatacatta   1200
tatggagcgc ttgttggtgg tccaggctct gatgatagct acacagatga tataagtaac   1260
tatgtgaaca atgaggttgc atgtgattat aatgcagggt ttgtgggtgc attagcaaag   1320
atgtatcaat tgtacggtgg gaatccaata ccagatttca aagctattga aactccaaca   1380
aacgacgaat tctttgttga agctggtata aatgcatccg gaactaactt tattgaaatt   1440
aaagcgatag ttaataacca aagtggttgg cctgccagag caacagataa gcttaaattt   1500
agatattttg ttgacctgag tgaattaatt aaagcaggat attcaccaaa tcaattaacc   1560
ttgagcacca attataatca aggtgcaaaa gtaagtggac cttatgtatg ggatgcaagc   1620
aaaaatatat actacatttt agtagacttt actggcacat tgatttatcc aggtggtcaa   1680
gacaaatata agaaagaagt ccaattcaga attgcagcac cacagaatgt acagtgggat   1740
aattctaacg actattcttt ccaggatata aagggagttt caagtggttc agttgttaaa   1800
actaaatata ttccacttta tgatggagat gtgaaagtat ggggtgaaga accaggaact   1860
tctggagcaa caccgacacc aacagcaaca gcaacaccaa caccaacgcc gacagtaaca   1920
ccaacaccga ctccaacacc aacatcaact gctacaccaa caccgacacc aacaccgaca   1980
gtaacaccaa ccccgactcc gacaccgact gctacaccaa cagcaacgcc aacaccaaca   2040
tcgacgccga gcagcacacc tgtagcaggt ggacagataa aggtattgta tgctaacaag   2100
gagacaaata gcacaactaa tacgataagg ccatggttga aggtagtgaa cactggaagc   2160
agcagcatag atttgagcag ggtaacgata aggtactggt acacggtaga tggggacaag   2220
gcacagagtg cgatatcaga ctgggcacag ataggagcaa gcaatgtgac attcaagttt   2280
```

```
gtgaagctga gcagtagcgt aagtggagcg gactattatt tagagatagg atttaagagt   2340
ggagctgggc agttgcaggc tggcaaagac acaggggaga tacagataag gtttaacaag   2400
agtgattgga gcaattacaa tcaggggaat gactggtcat ggatgcagag catgacgaat   2460
tatggagaga atgtgaaggt aacagcgtat atagatggtg tattggtatg gggacaggag   2520
ccgagtggag cgacaccaac accgacagcg acaccagcac cgacagtgac accgacacct   2580
acaccaacac caacgtcaac accaactgct acaccaacag caacgccaac accaacaccg   2640
acgccgagca gcacacctgt agcaggcggg cagataaagg tattgtatgc taacaaggag   2700
acaaatagca caacaaacac gataaggcca tggttgaagg tagtgaacac tggaagcagc   2760
agcatagatt tgagcagggt aacgataagg tactggtaca cggtagatgg ggacaaggca   2820
cagagtgcga tatcagactg ggcacagata ggagcaagca atgtgacatt caagtttgtg   2880
aagctgagca gtagcgtaag tggagcggac tattatttag agataggatt taagagtgga   2940
gctgggcagt tgcaggctgg taaagacaca ggggagatac agataaggtt taacaagagt   3000
gactggagca attacaatca ggggaatgac tggtcatgga tgcagagcat gacgaattat   3060
ggagagaatg tgaaggtaac agcgtatata gatggtgtat tggtatgggg acaggagccg   3120
agtggagcga caccaacacc gacagcgaca ccagcaccga cagtgacacc gacacctaca   3180
ccagcaccaa ctccaacccc gacaccaaca ccaactgcta caccaacacc aacgccaaca   3240
ccaaccccaa ccgcgacacc aacagtaaca gcaacaccaa caccgacgcc gagcagcaca   3300
ccgagtgtgc ttggcgaata tgggcagagg tttatgtggt tatggaacaa gatacatgat   3360
cctgcgaacg ggtattttaa ccaggatggg ataccatatc attcggtaga gacattgata   3420
tgcgaagcac ctgattatgg tcatttgacc acgagtgagg cattttcgta ctatgtatgg   3480
ttagaggcag tgtatggtaa gttaacgggt gactggagca aatttaagac agcatgggac   3540
acattagaga agtatatgat accatcagcg gaagatcagc cgatgaggtc atatgatcct   3600
aacaagccag cgacatacgc aggggagtgg gagacaccgg acaagtatcc atcgccgttg   3660
gagtttaatg tacctgttgg caaagacccg ttgcataatg aacttgtgag cacatatggt   3720
agcacattaa tgtatggtat gcactggttg atggacgtag acaactggta tggatatggc   3780
aagagagggg acggagtaag tcgggcatca tttatcaaca cgttccagag agggcctgag   3840
gagtctgtat gggagacggt gccgcatccg agctgggagg aattcaagtg gggcggaccg   3900
aatggatttt tagatttgtt tattaaggat cagaactatt cgaagcagtg gagatatacg   3960
gatgcaccag atgctgatgc gagagctatt caggctactt attgggcgaa agtatgggcg   4020
aaggagcaag gtaagtttaa tgagataagc agctatgtag cgaaggcagc gaagatggga   4080
gactatttaa ggtatgcgat gtttgacaag tatttcaagc cattaggatg tcaggataag   4140
aatgcggctg gaggaacggg gtatgacagt gcacattatc tgctatcatg gtattatgca   4200
tggggtggag cattggatgg agcatggtca tggaagatag ggagcagcca tgtgcacttt   4260
ggatatcaga atccgatggc ggcatgggca ttagcgaatg atagtgatat gaagccgaag   4320
tcgccgaatg gagcgagtga ctgggcaaag agtttgaaga ggcagataga attttacagg   4380
tggttacagt cagcggaggg agcgatagca ggaggcgcga caaattcatg gaatggcaga   4440
tatgagaagt atccagcagg gacagcaaca ttttatggaa tggcatatga accgaatccg   4500
gtatatcatg atcctgggag caacacatgg tttggattcc aggcatggtc gatgcagagg   4560
gtagcggagt attactatgt gacaggagat aaggacgcag gagcactgct tgagaagtgg   4620
```

```
gtaagctggg ttaagagtgt agtgaagttg aatagtgatg gtacgtttgc gataccgtcg   4680

acgcttgatt ggagcggaca acctgataca tggaacgggg cgtatacagg gaatagcaac   4740

ttacatgtta aggtagtgga ctatggtact gacttaggaa taacagcgtc attggcgaat   4800

gcgttgttgt actatagtgc agggacgaag aagtatgggg tatttgatga gggagcgaag   4860

aatttagcga aggaattgct ggacaggatg tggaagttgt acagggatga gaagggattg   4920

tcagcgccag agaagagagc ggactacaag aggttctttg agcaagaggt atatataccg   4980

gcaggatgga tagggaagat gccgaatgga gatgtaataa agagtggagt taagtttata   5040

gacataagga gcaagtataa acaagatcct gattggccga agttagaggc ggcatacaag   5100

tcagggcagg cacctgagtt cagatatcac aggttctggg cacagtgcga catagcaata   5160

gctaatgcaa catatgaaat actgtttggc aatcaa                            5196


<210> SEQ ID NO 76
<211> LENGTH: 695
<212> TYPE: PRT
<213> ORGANISM: Caldicellulosiruptor bescii

<400> SEQUENCE: 76

Gln Glu Val Arg Ala Gly Ser Phe Asn Tyr Gly Glu Ala Leu Gln Lys
 1               5                  10                  15

Ala Ile Met Phe Tyr Glu Phe Gln Met Ser Gly Lys Leu Pro Asn Trp
            20                  25                  30

Val Arg Asn Asn Trp Arg Gly Asp Ser Ala Leu Lys Asp Gly Gln Asp
        35                  40                  45

Asn Gly Leu Asp Leu Thr Gly Gly Trp Phe Asp Ala Gly Asp His Val
    50                  55                  60

Lys Phe Asn Leu Pro Met Ser Tyr Thr Gly Thr Met Leu Ser Trp Ala
65                  70                  75                  80

Val Tyr Glu Tyr Lys Asp Ala Phe Val Lys Ser Gly Gln Leu Glu His
                85                  90                  95

Ile Leu Asn Gln Ile Glu Trp Val Asn Asp Tyr Phe Val Lys Cys His
            100                 105                 110

Pro Ser Lys Tyr Val Tyr Tyr Tyr Gln Val Gly Asp Gly Ser Lys Asp
        115                 120                 125

His Ala Trp Trp Gly Pro Ala Glu Val Met Gln Met Glu Arg Pro Ser
    130                 135                 140

Phe Lys Val Thr Gln Ser Ser Pro Gly Ser Thr Val Val Ala Glu Thr
145                 150                 155                 160

Ala Ala Ser Leu Ala Ala Ala Ser Ile Val Leu Lys Asp Arg Asn Pro
                165                 170                 175

Thr Lys Ala Ala Thr Tyr Leu Gln His Ala Lys Glu Leu Tyr Glu Phe
            180                 185                 190

Ala Glu Val Thr Lys Ser Asp Ala Gly Tyr Thr Ala Ala Asn Gly Tyr
        195                 200                 205

Tyr Asn Ser Trp Ser Gly Phe Tyr Asp Glu Leu Ser Trp Ala Ala Val
    210                 215                 220

Trp Leu Tyr Leu Ala Thr Asn Asp Ser Thr Tyr Leu Thr Lys Ala Glu
225                 230                 235                 240

Ser Tyr Val Gln Asn Trp Pro Lys Ile Ser Gly Ser Asn Thr Ile Asp
                245                 250                 255

Tyr Lys Trp Ala His Cys Trp Asp Asp Val His Asn Gly Ala Ala Leu
            260                 265                 270
```

-continued

```
Leu Leu Ala Lys Ile Thr Gly Lys Asp Ile Tyr Lys Gln Ile Ile Glu
        275                 280                 285

Ser His Leu Asp Tyr Trp Thr Thr Gly Tyr Asn Gly Glu Arg Ile Lys
    290                 295                 300

Tyr Thr Pro Lys Gly Leu Ala Trp Leu Asp Gln Trp Gly Ser Leu Arg
305                 310                 315                 320

Tyr Ala Thr Thr Thr Ala Phe Leu Ala Phe Val Tyr Ser Asp Trp Val
                325                 330                 335

Gly Cys Pro Ser Thr Lys Lys Glu Ile Tyr Arg Lys Phe Gly Glu Ser
            340                 345                 350

Gln Ile Asp Tyr Ala Leu Gly Ser Ala Gly Arg Ser Phe Val Val Gly
        355                 360                 365

Phe Gly Thr Asn Pro Pro Lys Arg Pro His His Arg Thr Ala His Ser
    370                 375                 380

Ser Trp Ala Asp Ser Gln Ser Ile Pro Ser Tyr His Arg His Thr Leu
385                 390                 395                 400

Tyr Gly Ala Leu Val Gly Gly Pro Gly Ser Asp Asp Ser Tyr Thr Asp
                405                 410                 415

Asp Ile Ser Asn Tyr Val Asn Asn Glu Val Ala Cys Asp Tyr Asn Ala
            420                 425                 430

Gly Phe Val Gly Ala Leu Ala Lys Met Tyr Gln Leu Tyr Gly Gly Asn
        435                 440                 445

Pro Ile Pro Asp Phe Lys Ala Ile Glu Thr Pro Thr Asn Asp Glu Phe
    450                 455                 460

Phe Val Glu Ala Gly Ile Asn Ala Ser Gly Thr Asn Phe Ile Glu Ile
465                 470                 475                 480

Lys Ala Ile Val Asn Asn Gln Ser Gly Trp Pro Ala Arg Ala Thr Asp
                485                 490                 495

Lys Leu Lys Phe Arg Tyr Phe Val Asp Leu Ser Glu Leu Ile Lys Ala
            500                 505                 510

Gly Tyr Ser Pro Asn Gln Leu Thr Leu Ser Thr Asn Tyr Asn Gln Gly
        515                 520                 525

Ala Lys Val Ser Gly Pro Tyr Val Trp Asp Ala Ser Lys Asn Ile Tyr
    530                 535                 540

Tyr Ile Leu Val Asp Phe Thr Gly Thr Leu Ile Tyr Pro Gly Gly Gln
545                 550                 555                 560

Asp Lys Tyr Lys Lys Glu Val Gln Phe Arg Ile Ala Ala Pro Gln Asn
                565                 570                 575

Val Gln Trp Asp Asn Ser Asn Asp Tyr Ser Phe Gln Asp Ile Lys Gly
            580                 585                 590

Val Ser Ser Gly Ser Val Val Lys Thr Lys Tyr Ile Pro Leu Tyr Asp
        595                 600                 605

Gly Asp Val Lys Val Trp Gly Glu Glu Pro Gly Thr Ser Gly Ala Thr
    610                 615                 620

Pro Thr Pro Thr Ala Thr Ala Thr Pro Thr Pro Thr Pro Thr Val Thr
625                 630                 635                 640

Pro Thr Pro Thr Pro Thr Pro Thr Ser Thr Ala Thr Pro Thr Pro Thr
                645                 650                 655

Pro Thr Pro Thr Val Thr Pro Thr Pro Thr Pro Thr Pro Thr Ala Thr
            660                 665                 670

Pro Thr Ala Thr Pro Thr Pro Thr Ser Thr Pro Ser Ser Thr Pro Val
        675                 680                 685

Ala Gly Gly Gln Ile Lys Val
```

-continued 690 695

<210> SEQ ID NO 77
<211> LENGTH: 2085
<212> TYPE: DNA
<213> ORGANISM: Caldicellulosiruptor bescii

<400> SEQUENCE: 77
caagaggtta gggctggttc gtttaactat ggggaagctt tacaaaaagc tatcatgttt 60
tacgaatttc aaatgtctgg taaacttccg aattgggtac gcaacaactg gcgtggcgac 120
tcagcattaa aggatggtca agacaatggg cttgatttga caggtggttg gtttgacgca 180
ggtgatcacg tcaagtttaa ccttccaatg tcatacactg gtacaatgtt gtcatgggca 240
gtgtatgagt acaaagatgc atttgtcaag agtggtcaat tggaacatat cttaaatcaa 300
atcgaatggg ttaatgacta ttttgtaaaa tgtcatccaa gcaaatatgt atactattac 360
caggttgggg atggaagtaa agatcatgca tggtggggac ctgctgaggt tatgcaaatg 420
gagagacctt catttaaggt cacccaaagc agtcctggat ctacagtagt agcagagaca 480
gcagcttcct tagcagcagc ttcaattgtt ttgaaagaca gaaatcccac taaagcagca 540
acatatctgc aacatgcaaa agaattatat gagtttgcag aagtaacaaa aagcgatgca 600
ggttacactg ctgcaaatgg atattacaat tcatggagcg gtttctatga tgagcttttct 660 tgggcagcag tttggttgta tttggcaaca aatgattcaa catatctcac aaaagctgag 720
tcatatgtcc aaaattggcc caaaatttct ggcagtaaca caattgacta caagtgggct 780
cattgctggg atgatgttca caatggagcg gcattattgt tagcaaaaat taccggtaag 840
gatatttata aacaaattat tgaaagtcac ttagattact ggactacagg atacaatggc 900
gaaaggatta agtatacacc aaaaggatta gcatggcttg atcaatgggg ttcgttgaga 960
tatgcaacaa ctacagcatt tttggcattt gtttatagcg attgggttgg ctgtccaagc 1020
acaaaaaaag aaatatatag aaaatttgga gaaagccaga ttgattatgc gttaggctca 1080
gctggaagaa gctttgttgt tggatttggt acaaatccac caaagagacc gcatcacaga 1140
actgctcata gctcatgggc agacagtcag agtatacctt catatcacag acatacatta 1200
tatggagcgc ttgttggtgg tccaggctct gatgatagct acacagatga tataagtaac 1260
tatgtgaaca atgaggttgc atgtgattat aatgcagggt ttgtgggtgc attagcaaag 1320
atgtatcaat tgtacggtgg gaatccaata ccagatttca aagctattga aactccaaca 1380
aacgacgaat tctttgttga agctggtata aatgcatccg gaactaactt tattgaaatt 1440
aaagcgatag ttaataacca aagtggttgg cctgccagag caacagataa gcttaaattt 1500
agatattttg ttgacctgag tgaattaatt aaagcaggat attcaccaaa tcaattaacc 1560
ttgagcacca attataatca aggtgcaaaa gtaagtggac cttatgtatg ggatgcaagc 1620
aaaaatatat actacatttt agtagacttt actggcacat tgatttatcc aggtggtcaa 1680
gacaaatata agaaagaagt ccaattcaga attgcagcac cacagaatgt acagtgggat 1740
aattctaacg actattcttt ccaggatata aagggagttt caagtggttc agttgttaaa 1800
actaaatata ttccacttta tgatggagat gtgaaagtat ggggtgaaga accaggaact 1860
tctggagcaa caccgacacc aacagcaaca gcaacaccaa caccaacgcc gacagtaaca 1920
ccaacaccga ctccaacacc aacatcaact gctacaccaa caccgacacc aacaccgaca 1980
gtaacaccaa ccccgactcc gacaccgact gctacaccaa cagcaacgcc aacaccaaca 2040
tcgacgccga gcagcacacc tgtagcaggt ggacagataa aggta 2085

<210> SEQ ID NO 78
<211> LENGTH: 1280
<212> TYPE: PRT
<213> ORGANISM: Caldicellulosiruptor bescii

<400> SEQUENCE: 78

```
Phe Lys Ala Ile Glu Thr Pro Thr Asn Asp Glu Phe Phe Val Glu Ala
 1               5                  10                  15

Gly Ile Asn Ala Ser Gly Thr Asn Phe Ile Glu Ile Lys Ala Ile Val
            20                  25                  30

Asn Asn Gln Ser Gly Trp Pro Ala Arg Ala Thr Asp Lys Leu Lys Phe
        35                  40                  45

Arg Tyr Phe Val Asp Leu Ser Glu Leu Ile Lys Ala Gly Tyr Ser Pro
    50                  55                  60

Asn Gln Leu Thr Leu Ser Thr Asn Tyr Asn Gln Gly Ala Lys Val Ser
65                  70                  75                  80

Gly Pro Tyr Val Trp Asp Ala Ser Lys Asn Ile Tyr Tyr Ile Leu Val
                85                  90                  95

Asp Phe Thr Gly Thr Leu Ile Tyr Pro Gly Gly Gln Asp Lys Tyr Lys
            100                 105                 110

Lys Glu Val Gln Phe Arg Ile Ala Ala Pro Gln Asn Val Gln Trp Asp
        115                 120                 125

Asn Ser Asn Asp Tyr Ser Phe Gln Asp Ile Lys Gly Val Ser Ser Gly
    130                 135                 140

Ser Val Val Lys Thr Lys Tyr Ile Pro Leu Tyr Asp Gly Asp Val Lys
145                 150                 155                 160

Val Trp Gly Glu Glu Pro Gly Thr Ser Gly Ala Thr Pro Thr Pro Thr
                165                 170                 175

Ala Thr Ala Thr Pro Thr Pro Thr Pro Thr Val Thr Pro Thr Pro Thr
            180                 185                 190

Pro Thr Pro Thr Ser Thr Ala Thr Pro Thr Pro Thr Pro Thr Pro Thr
        195                 200                 205

Val Thr Pro Thr Pro Thr Pro Thr Pro Thr Ala Thr Pro Thr Ala Thr
    210                 215                 220

Pro Thr Pro Thr Ser Thr Pro Ser Ser Thr Pro Val Ala Gly Gly Gln
225                 230                 235                 240

Ile Lys Val Leu Tyr Ala Asn Lys Glu Thr Asn Ser Thr Thr Asn Thr
                245                 250                 255

Ile Arg Pro Trp Leu Lys Val Val Asn Thr Gly Ser Ser Ser Ile Asp
            260                 265                 270

Leu Ser Arg Val Thr Ile Arg Tyr Trp Tyr Thr Val Asp Gly Asp Lys
        275                 280                 285

Ala Gln Ser Ala Ile Ser Asp Trp Ala Gln Ile Gly Ala Ser Asn Val
    290                 295                 300

Thr Phe Lys Phe Val Lys Leu Ser Ser Ser Val Ser Gly Ala Asp Tyr
305                 310                 315                 320

Tyr Leu Glu Ile Gly Phe Lys Ser Gly Ala Gly Gln Leu Gln Ala Gly
                325                 330                 335

Lys Asp Thr Gly Glu Ile Gln Ile Arg Phe Asn Lys Ser Asp Trp Ser
            340                 345                 350

Asn Tyr Asn Gln Gly Asn Asp Trp Ser Trp Met Gln Ser Met Thr Asn
        355                 360                 365

Tyr Gly Glu Asn Val Lys Val Thr Ala Tyr Ile Asp Gly Val Leu Val
```

-continued

```
    370                 375                 380

Trp Gly Gln Glu Pro Ser Gly Ala Thr Pro Thr Pro Thr Ala Thr Pro
385                 390                 395                 400

Ala Pro Thr Val Thr Pro Thr Pro Thr Pro Thr Pro Thr Ser Thr Pro
                405                 410                 415

Thr Ala Thr Pro Thr Ala Thr Pro Thr Pro Thr Pro Thr Pro Ser Ser
            420                 425                 430

Thr Pro Val Ala Gly Gly Gln Ile Lys Val Leu Tyr Ala Asn Lys Glu
        435                 440                 445

Thr Asn Ser Thr Thr Asn Thr Ile Arg Pro Trp Leu Lys Val Val Asn
    450                 455                 460

Thr Gly Ser Ser Ser Ile Asp Leu Ser Arg Val Thr Ile Arg Tyr Trp
465                 470                 475                 480

Tyr Thr Val Asp Gly Asp Lys Ala Gln Ser Ala Ile Ser Asp Trp Ala
                485                 490                 495

Gln Ile Gly Ala Ser Asn Val Thr Phe Lys Phe Val Lys Leu Ser Ser
            500                 505                 510

Ser Val Ser Gly Ala Asp Tyr Tyr Leu Glu Ile Gly Phe Lys Ser Gly
        515                 520                 525

Ala Gly Gln Leu Gln Ala Gly Lys Asp Thr Gly Glu Ile Gln Ile Arg
    530                 535                 540

Phe Asn Lys Ser Asp Trp Ser Asn Tyr Asn Gln Gly Asn Asp Trp Ser
545                 550                 555                 560

Trp Met Gln Ser Met Thr Asn Tyr Gly Glu Asn Val Lys Val Thr Ala
                565                 570                 575

Tyr Ile Asp Gly Val Leu Val Trp Gly Gln Glu Pro Ser Gly Ala Thr
            580                 585                 590

Pro Thr Pro Thr Ala Thr Pro Ala Pro Thr Val Thr Pro Thr Pro Thr
        595                 600                 605

Pro Ala Pro Thr Pro Thr Pro Thr Pro Thr Pro Thr Ala Thr Pro Thr
    610                 615                 620

Pro Thr Pro Thr Pro Thr Pro Thr Ala Thr Pro Thr Val Thr Ala Thr
625                 630                 635                 640

Pro Thr Pro Thr Pro Ser Ser Thr Pro Ser Val Leu Gly Glu Tyr Gly
                645                 650                 655

Gln Arg Phe Met Trp Leu Trp Asn Lys Ile His Asp Pro Ala Asn Gly
            660                 665                 670

Tyr Phe Asn Gln Asp Gly Ile Pro Tyr His Ser Val Glu Thr Leu Ile
        675                 680                 685

Cys Glu Ala Pro Asp Tyr Gly His Leu Thr Thr Ser Glu Ala Phe Ser
    690                 695                 700

Tyr Tyr Val Trp Leu Glu Ala Val Tyr Gly Lys Leu Thr Gly Asp Trp
705                 710                 715                 720

Ser Lys Phe Lys Thr Ala Trp Asp Thr Leu Glu Lys Tyr Met Ile Pro
                725                 730                 735

Ser Ala Glu Asp Gln Pro Met Arg Ser Tyr Asp Pro Asn Lys Pro Ala
            740                 745                 750

Thr Tyr Ala Gly Glu Trp Glu Thr Pro Asp Lys Tyr Pro Ser Pro Leu
        755                 760                 765

Glu Phe Asn Val Pro Val Gly Lys Asp Pro Leu His Asn Glu Leu Val
    770                 775                 780

Ser Thr Tyr Gly Ser Thr Leu Met Tyr Gly Met His Trp Leu Met Asp
785                 790                 795                 800
```

```
Val Asp Asn Trp Tyr Gly Tyr Gly Lys Arg Gly Asp Gly Val Ser Arg
                805                 810                 815

Ala Ser Phe Ile Asn Thr Phe Gln Arg Gly Pro Glu Glu Ser Val Trp
            820                 825                 830

Glu Thr Val Pro His Pro Ser Trp Glu Glu Phe Lys Trp Gly Gly Pro
        835                 840                 845

Asn Gly Phe Leu Asp Leu Phe Ile Lys Asp Gln Asn Tyr Ser Lys Gln
    850                 855                 860

Trp Arg Tyr Thr Asp Ala Pro Asp Ala Asp Ala Arg Ala Ile Gln Ala
865                 870                 875                 880

Thr Tyr Trp Ala Lys Val Trp Ala Lys Glu Gln Gly Lys Phe Asn Glu
                885                 890                 895

Ile Ser Ser Tyr Val Ala Lys Ala Ala Lys Met Gly Asp Tyr Leu Arg
            900                 905                 910

Tyr Ala Met Phe Asp Lys Tyr Phe Lys Pro Leu Gly Cys Gln Asp Lys
        915                 920                 925

Asn Ala Ala Gly Gly Thr Gly Tyr Asp Ser Ala His Tyr Leu Leu Ser
    930                 935                 940

Trp Tyr Tyr Ala Trp Gly Gly Ala Leu Asp Gly Ala Trp Ser Trp Lys
945                 950                 955                 960

Ile Gly Ser Ser His Val His Phe Gly Tyr Gln Asn Pro Met Ala Ala
                965                 970                 975

Trp Ala Leu Ala Asn Asp Ser Asp Met Lys Pro Lys Ser Pro Asn Gly
            980                 985                 990

Ala Ser Asp Trp Ala Lys Ser Leu Lys Arg Gln Ile Glu Phe Tyr Arg
        995                 1000                1005

Trp Leu Gln Ser Ala Glu Gly Ala Ile Ala Gly Gly Ala Thr Asn Ser
    1010                1015                1020

Trp Asn Gly Arg Tyr Glu Lys Tyr Pro Ala Gly Thr Ala Thr Phe Tyr
1025                1030                1035                1040

Gly Met Ala Tyr Glu Pro Asn Pro Val Tyr His Asp Pro Gly Ser Asn
                1045                1050                1055

Thr Trp Phe Gly Phe Gln Ala Trp Ser Met Gln Arg Val Ala Glu Tyr
            1060                1065                1070

Tyr Tyr Val Thr Gly Asp Lys Asp Ala Gly Ala Leu Leu Glu Lys Trp
        1075                1080                1085

Val Ser Trp Val Lys Ser Val Val Lys Leu Asn Ser Asp Gly Thr Phe
    1090                1095                1100

Ala Ile Pro Ser Thr Leu Asp Trp Ser Gly Gln Pro Asp Thr Trp Asn
1105                1110                1115                1120

Gly Ala Tyr Thr Gly Asn Ser Asn Leu His Val Lys Val Val Asp Tyr
                1125                1130                1135

Gly Thr Asp Leu Gly Ile Thr Ala Ser Leu Ala Asn Ala Leu Leu Tyr
            1140                1145                1150

Tyr Ser Ala Gly Thr Lys Lys Tyr Gly Val Phe Asp Glu Gly Ala Lys
        1155                1160                1165

Asn Leu Ala Lys Glu Leu Leu Asp Arg Met Trp Lys Leu Tyr Arg Asp
    1170                1175                1180

Glu Lys Gly Leu Ser Ala Pro Glu Lys Arg Ala Asp Tyr Lys Arg Phe
1185                1190                1195                1200

Phe Glu Gln Glu Val Tyr Ile Pro Ala Gly Trp Ile Gly Lys Met Pro
                1205                1210                1215
```

-continued

```
Asn Gly Asp Val Ile Lys Ser Gly Val Lys Phe Ile Asp Ile Arg Ser
            1220                1225                1230

Lys Tyr Lys Gln Asp Pro Asp Trp Pro Lys Leu Glu Ala Ala Tyr Lys
        1235                1240                1245

Ser Gly Gln Ala Pro Glu Phe Arg Tyr His Arg Phe Trp Ala Gln Cys
    1250                1255                1260

Asp Ile Ala Ile Ala Asn Ala Thr Tyr Glu Ile Leu Phe Gly Asn Gln
1265                1270                1275                1280


<210> SEQ ID NO 79
<211> LENGTH: 3840
<212> TYPE: DNA
<213> ORGANISM: Caldicellulosiruptor bescii

<400> SEQUENCE: 79

ttcaaagcta ttgaaactcc aacaaacgac gaattctttg ttgaagctgg tataaatgca     60

tccggaacta actttattga aattaaagcg atagttaata accaaagtgg ttggcctgcc    120

agagcaacag ataagcttaa atttagatat tttgttgacc tgagtgaatt aattaaagca    180

ggatattcac caaatcaatt aaccttgagc accaattata atcaaggtgc aaaagtaagt    240

ggaccttatg tatgggatgc aagcaaaaat atatactaca ttttagtaga ctttactggc    300

acattgattt atccaggtgg tcaagacaaa tataagaaag aagtccaatt cagaattgca    360

gcaccacaga atgtacagtg ggataattct aacgactatt ctttccagga tataaaggga    420

gtttcaagtg gttcagttgt taaaactaaa tatattccac tttatgatgg agatgtgaaa    480

gtatggggtg aagaaccagg aacttctgga gcaacaccga caccaacagc aacagcaaca    540

ccaacaccaa cgccgacagt aacaccaaca ccgactccaa caccaacatc aactgctaca    600

ccaacaccga caccaacacc gacagtaaca ccaaccccga ctccgacacc gactgctaca    660

ccaacagcaa cgccaacacc aacatcgacg ccgagcagca cacctgtagc aggtggacag    720

ataaaggtat tgtatgctaa caaggagaca aatagcacaa ctaatacgat aaggccatgg    780

ttgaaggtag tgaacactgg aagcagcagc atagatttga gcagggtaac gataaggtac    840

tggtacacgg tagatgggga caaggcacag agtgcgatat cagactgggc acagatagga    900

gcaagcaatg tgacattcaa gtttgtgaag ctgagcagta gcgtaagtgg agcggactat    960

tatttagaga taggatttaa gagtggagct gggcagttgc aggctggcaa agacacaggg   1020

gagatacaga taaggtttaa caagagtgat tggagcaatt acaatcaggg gaatgactgg   1080

tcatggatgc agagcatgac gaattatgga gagaatgtga aggtaacagc gtatatagat   1140

ggtgtattgg tatggggaca ggagccgagt ggagcgacac caacaccgac agcgacacca   1200

gcaccgacag tgacaccgac acctacacca acaccaacgt caacaccaac tgctacacca   1260

acagcaacgc caacaccaac accgacgccg agcagcacac ctgtagcagg cgggcagata   1320

aaggtattgt atgctaacaa ggagacaaat agcacaacaa acacgataag gccatggttg   1380

aaggtagtga acactggaag cagcagcata gatttgagca gggtaacgat aaggtactgg   1440

tacacggtag atggggacaa ggcacagagt gcgatatcag actgggcaca gataggagca   1500

agcaatgtga cattcaagtt tgtgaagctg agcagtagcg taagtggagc ggactattat   1560

ttagagatag gatttaagag tggagctggg cagttgcagg ctggtaaaga cacaggggag   1620

atacagataa ggtttaacaa gagtgactgg agcaattaca atcaggggaa tgactggtca   1680

tggatgcaga gcatgacgaa ttatggagag aatgtgaagg taacagcgta tatagatggt   1740

gtattggtat ggggacagga gccgagtgga gcgacaccaa caccgacagc gacaccagca   1800
```

```
ccgacagtga caccgacacc tacaccagca ccaactccaa ccccgacacc aacaccaact   1860
gctacaccaa caccaacgcc aacaccaacc ccaaccgcga caccaacagt aacagcaaca   1920
ccaacaccga cgccgagcag cacaccgagt gtgcttggcg aatatgggca gaggtttatg   1980
tggttatgga acaagataca tgatcctgcg aacgggtatt ttaaccagga tgggatacca   2040
tatcattcgg tagagacatt gatatgcgaa gcacctgatt atggtcattt gaccacgagt   2100
gaggcatttt cgtactatgt atggttagag gcagtgtatg gtaagttaac gggtgactgg   2160
agcaaattta agacagcatg ggacacatta gagaagtata tgataccatc agcggaagat   2220
cagccgatga ggtcatatga tcctaacaag ccagcgacat acgcagggga gtgggagaca   2280
ccggacaagt atccatcgcc gttggagttt aatgtacctg ttggcaaaga cccgttgcat   2340
aatgaacttg tgagcacata tggtagcaca ttaatgtatg gtatgcactg gttgatggac   2400
gtagacaact ggtatggata tggcaagaga ggggacggag taagtcgggc atcatttatc   2460
aacacgttcc agagagggcc tgaggagtct gtatgggaga cggtgccgca tccgagctgg   2520
gaggaattca agtggggcgg accgaatgga tttttagatt tgtttattaa ggatcagaac   2580
tattcgaagc agtggagata tacggatgca ccagatgctg atgcgagagc tattcaggct   2640
acttattggg cgaaagtatg ggcgaaggag caaggtaagt ttaatgagat aagcagctat   2700
gtagcgaagg cagcgaagat gggagactat ttaaggtatg cgatgtttga caagtatttc   2760
aagccattag gatgtcagga taagaatgcg gctggaggaa cggggtatga cagtgcacat   2820
tatctgctat catggtatta tgcatggggt ggagcattgg atggagcatg gtcatggaag   2880
atagggagca gccatgtgca ctttggatat cagaatccga tggcggcatg ggcattagcg   2940
aatgatagtg atatgaagcc gaagtcgccg aatggagcga gtgactgggc aaagagtttg   3000
aagaggcaga tagaatttta caggtggtta cagtcagcgg agggagcgat agcaggaggc   3060
gcgacaaatt catggaatgg cagatatgag aagtatccag cagggacagc aacattttat   3120
ggaatggcat atgaaccgaa tccggtatat catgatcctg ggagcaacac atggtttgga   3180
ttccaggcat ggtcgatgca gagggtagcg gagtattact atgtgacagg agataaggac   3240
gcaggagcac tgcttgagaa gtgggtaagc tgggttaaga gtgtagtgaa gttgaatagt   3300
gatggtacgt ttgcgatacc gtcgacgctt gattggagcg gacaacctga tacatggaac   3360
ggggcgtata cagggaatag caacttacat gttaaggtag tggactatgg tactgactta   3420
ggaataacag cgtcattggc gaatgcgttg ttgtactata gtgcagggac gaagaagtat   3480
ggggtatttg atgagggagc gaagaattta gcgaaggaat tgctggacag gatgtggaag   3540
ttgtacaggg atgagaaggg attgtcagcg ccagagaaga gagcggacta caagaggttc   3600
tttgagcaag aggtatatat accggcagga tggataggga agatgccgaa tggagatgta   3660
ataaagagtg gagttaagtt tatagacata aggagcaagt ataaacaaga tcctgattgg   3720
ccgaagttag aggcggcata caagtcaggg caggcacctg agttcagata tcacaggttc   3780
tgggcacagt gcgacatagc aatagctaat gcaacatatg aaatactgtt tggcaatcaa   3840
```

<210> SEQ ID NO 80
<211> LENGTH: 2127
<212> TYPE: DNA
<213> ORGANISM: Caldicellulosiruptor bescii

<400> SEQUENCE: 80

```
atggcacatc accaccacca tcacgtggat gacgacgaca agcaagaggt tagggctggt     60
```

```
tcgtttaact atggggaagc tttacaaaaa gctatcatgt tttacgaatt tcaaatgtct    120
ggtaaacttc cgaattgggt acgcaacaac tggcgtggcg actcagcatt aaaggatggt    180
caagacaatg ggcttgattt gacaggtggt tggtttgacg caggtgatca cgtcaagttt    240
aaccttccaa tgtcatacac tggtacaatg ttgtcatggg cagtgtatga gtacaaagat    300
gcatttgtca agagtggtca attggaacat atcttaaatc aaatcgaatg ggttaatgac    360
tattttgtaa aatgtcatcc aagcaaatat gtatactatt accaggttgg ggatggaagt    420
aaagatcatg catggtgggg acctgctgag gttatgcaaa tggagagacc ttcatttaag    480
gtcacccaaa gcagtcctgg atctacagta gtagcagaga cagcagcttc cttagcagca    540
gcttcaattg ttttgaaaga cagaaatccc actaaagcag caacatatct gcaacatgca    600
aaagaattat atgagtttgc agaagtaaca aaaagcgatg caggttacac tgctgcaaat    660
ggatattaca attcatggag cggtttctat gatgagcttt cttgggcagc agtttggttg    720
tatttggcaa caaatgattc aacatatctc acaaaagctg agtcatatgt ccaaaattgg    780
cccaaaattt ctggcagtaa cacaattgac tacaagtggg ctcattgctg ggatgatgtt    840
cacaatggag cggcattatt gttagcaaaa attaccggta aggatattta taaacaaatt    900
attgaaagtc acttagatta ctggactaca ggatacaatg gcgaaaggat taagtataca    960
ccaaaaggat tagcatggct tgatcaatgg ggttcgttga gatatgcaac aactacagca   1020
tttttggcat ttgtttatag cgattgggtt ggctgtccaa gcacaaaaaa agaaatatat   1080
agaaaatttg gagaaagcca gattgattat gcgttaggct cagctggaag aagctttgtt   1140
gttggatttg gtacaaatcc accaaagaga ccgcatcaca gaactgctca tagctcatgg   1200
gcagacagtc agagtatacc ttcatatcac agacatacat tatatggagc gcttgttggt   1260
ggtccaggct ctgatgatag ctacacagat gatataagta actatgtgaa caatgaggtt   1320
gcatgtgatt ataatgcagg gtttgtgggt gcattagcaa agatgtatca attgtacggt   1380
gggaatccaa taccagattt caaagctatt gaaactccaa caaacgacga attctttgtt   1440
gaagctggta taaatgcatc cggaactaac tttattgaaa ttaaagcgat agttaataac   1500
caaagtggtt ggcctgccag agcaacagat aagcttaaat ttagatattt tgttgacctg   1560
agtgaattaa ttaaagcagg atattcacca aatcaattaa ccttgagcac caattataat   1620
caaggtgcaa aagtaagtgg accttatgta tgggatgcaa gcaaaaatat atactacatt   1680
ttagtagact ttactggcac attgatttat ccaggtggtc aagacaaata taagaaagaa   1740
gtccaattca gaattgcagc accacagaat gtacagtggg ataattctaa cgactattct   1800
ttccaggata taaagggagt ttcaagtggt tcagttgtta aaactaaata tattccactt   1860
tatgatggag atgtgaaagt atggggtgaa gaaccaggaa cttctggagc aacaccgaca   1920
ccaacagcaa cagcaacacc aacaccaacg ccgacagtaa caccaacacc gactccaaca   1980
ccaacatcaa ctgctacacc aacaccgaca ccaacaccga cagtaacacc aaccccgact   2040
ccgacaccga ctgctacacc aacagcaacg ccaacaccaa catcgacgcc gagcagcaca   2100
cctgtagcag gtggacagat aaaggta                                        2127
```

<210> SEQ ID NO 81
<211> LENGTH: 709
<212> TYPE: PRT
<213> ORGANISM: Caldicellulosiruptor bescii

<400> SEQUENCE: 81

Met Ala His His His His His His Val Asp Asp Asp Asp Lys Gln Glu

-continued

```
1               5                   10                  15

Val Arg Ala Gly Ser Phe Asn Tyr Gly Glu Ala Leu Gln Lys Ala Ile
            20                  25                  30

Met Phe Tyr Glu Phe Gln Met Ser Gly Lys Leu Pro Asn Trp Val Arg
        35                  40                  45

Asn Asn Trp Arg Gly Asp Ser Ala Leu Lys Asp Gly Gln Asp Asn Gly
    50                  55                  60

Leu Asp Leu Thr Gly Gly Trp Phe Asp Ala Gly Asp His Val Lys Phe
65                  70                  75                  80

Asn Leu Pro Met Ser Tyr Thr Gly Thr Met Leu Ser Trp Ala Val Tyr
                85                  90                  95

Glu Tyr Lys Asp Ala Phe Val Lys Ser Gly Gln Leu Glu His Ile Leu
            100                 105                 110

Asn Gln Ile Glu Trp Val Asn Asp Tyr Phe Val Lys Cys His Pro Ser
        115                 120                 125

Lys Tyr Val Tyr Tyr Tyr Gln Val Gly Asp Gly Ser Lys Asp His Ala
    130                 135                 140

Trp Trp Gly Pro Ala Glu Val Met Gln Met Glu Arg Pro Ser Phe Lys
145                 150                 155                 160

Val Thr Gln Ser Ser Pro Gly Ser Thr Val Val Ala Glu Thr Ala Ala
                165                 170                 175

Ser Leu Ala Ala Ala Ser Ile Val Leu Lys Asp Arg Asn Pro Thr Lys
            180                 185                 190

Ala Ala Thr Tyr Leu Gln His Ala Lys Glu Leu Tyr Glu Phe Ala Glu
        195                 200                 205

Val Thr Lys Ser Asp Ala Gly Tyr Thr Ala Ala Asn Gly Tyr Tyr Asn
    210                 215                 220

Ser Trp Ser Gly Phe Tyr Asp Glu Leu Ser Trp Ala Ala Val Trp Leu
225                 230                 235                 240

Tyr Leu Ala Thr Asn Asp Ser Thr Tyr Leu Thr Lys Ala Glu Ser Tyr
                245                 250                 255

Val Gln Asn Trp Pro Lys Ile Ser Gly Ser Asn Thr Ile Asp Tyr Lys
            260                 265                 270

Trp Ala His Cys Trp Asp Asp Val His Asn Gly Ala Ala Leu Leu Leu
        275                 280                 285

Ala Lys Ile Thr Gly Lys Asp Ile Tyr Lys Gln Ile Ile Glu Ser His
    290                 295                 300

Leu Asp Tyr Trp Thr Thr Gly Tyr Asn Gly Glu Arg Ile Lys Tyr Thr
305                 310                 315                 320

Pro Lys Gly Leu Ala Trp Leu Asp Gln Trp Gly Ser Leu Arg Tyr Ala
                325                 330                 335

Thr Thr Thr Ala Phe Leu Ala Phe Val Tyr Ser Asp Trp Val Gly Cys
            340                 345                 350

Pro Ser Thr Lys Lys Glu Ile Tyr Arg Lys Phe Gly Glu Ser Gln Ile
        355                 360                 365

Asp Tyr Ala Leu Gly Ser Ala Gly Arg Ser Phe Val Val Gly Phe Gly
    370                 375                 380

Thr Asn Pro Pro Lys Arg Pro His His Arg Thr Ala His Ser Ser Trp
385                 390                 395                 400

Ala Asp Ser Gln Ser Ile Pro Ser Tyr His Arg His Thr Leu Tyr Gly
                405                 410                 415

Ala Leu Val Gly Gly Pro Gly Ser Asp Asp Ser Tyr Thr Asp Asp Ile
            420                 425                 430
```

```
Ser Asn Tyr Val Asn Asn Glu Val Ala Cys Asp Tyr Asn Ala Gly Phe
        435                 440                 445

Val Gly Ala Leu Ala Lys Met Tyr Gln Leu Tyr Gly Gly Asn Pro Ile
    450                 455                 460

Pro Asp Phe Lys Ala Ile Glu Thr Pro Thr Asn Asp Glu Phe Phe Val
465                 470                 475                 480

Glu Ala Gly Ile Asn Ala Ser Gly Thr Asn Phe Ile Glu Ile Lys Ala
                485                 490                 495

Ile Val Asn Asn Gln Ser Gly Trp Pro Ala Arg Ala Thr Asp Lys Leu
            500                 505                 510

Lys Phe Arg Tyr Phe Val Asp Leu Ser Glu Leu Ile Lys Ala Gly Tyr
        515                 520                 525

Ser Pro Asn Gln Leu Thr Leu Ser Thr Asn Tyr Asn Gln Gly Ala Lys
    530                 535                 540

Val Ser Gly Pro Tyr Val Trp Asp Ala Ser Lys Asn Ile Tyr Tyr Ile
545                 550                 555                 560

Leu Val Asp Phe Thr Gly Thr Leu Ile Tyr Pro Gly Gly Gln Asp Lys
                565                 570                 575

Tyr Lys Lys Glu Val Gln Phe Arg Ile Ala Ala Pro Gln Asn Val Gln
            580                 585                 590

Trp Asp Asn Ser Asn Asp Tyr Ser Phe Gln Asp Ile Lys Gly Val Ser
        595                 600                 605

Ser Gly Ser Val Val Lys Thr Lys Tyr Ile Pro Leu Tyr Asp Gly Asp
    610                 615                 620

Val Lys Val Trp Gly Glu Glu Pro Gly Thr Ser Gly Ala Thr Pro Thr
625                 630                 635                 640

Pro Thr Ala Thr Ala Thr Pro Thr Pro Thr Pro Thr Val Thr Pro Thr
                645                 650                 655

Pro Thr Pro Thr Pro Thr Ser Thr Ala Thr Pro Thr Pro Thr Pro Thr
            660                 665                 670

Pro Thr Val Thr Pro Thr Pro Thr Pro Thr Pro Thr Ala Thr Pro Thr
        675                 680                 685

Ala Thr Pro Thr Pro Thr Ser Thr Pro Ser Ser Thr Pro Val Ala Gly
    690                 695                 700

Gly Gln Ile Lys Val
705
```

<210> SEQ ID NO 82
<211> LENGTH: 42
<212> TYPE: DNA
<213> ORGANISM: Artificial Sequence
<220> FEATURE:
<223> OTHER INFORMATION: Synthesized Construct

<400> SEQUENCE: 82
gacgacgaca agatggctac atctaatgat ggagtagtga ag 42

<210> SEQ ID NO 83
<211> LENGTH: 55
<212> TYPE: DNA
<213> ORGANISM: Artificial Sequence
<220> FEATURE:
<223> OTHER INFORMATION: Synthesized Construct

<400> SEQUENCE: 83
gaggagaagc ccggttaatt tagtttgtac tgaggttgaa tataaaacga tatgg 55

<210> SEQ ID NO 84
<211> LENGTH: 47
<212> TYPE: DNA
<213> ORGANISM: Artificial Sequence
<220> FEATURE:
<223> OTHER INFORMATION: Synthesized Construct

<400> SEQUENCE: 84
gaggagaagc ccggttagtt aaaccttatc tgtatctccc ctgtgtc 47

<210> SEQ ID NO 85
<211> LENGTH: 47
<212> TYPE: DNA
<213> ORGANISM: Artificial Sequence
<220> FEATURE:
<223> OTHER INFORMATION: Synthesized Construct

<400> SEQUENCE: 85
gacgacgaca agatggtagg gtacttggac atggtaaaca attggga 47

<210> SEQ ID NO 86
<211> LENGTH: 1294
<212> TYPE: PRT
<213> ORGANISM: Caldicellulosiruptor bescii

<400> SEQUENCE: 86

Met Arg Val Lys Thr Lys Met Gly Lys Lys Trp Leu Ser Ile Leu Cys
1 5 10 15

Thr Val Val Phe Leu Leu Asn Ile Leu Phe Ile Ala Asn Val Thr Asn
20 25 30

Leu Pro Lys Val Gly Ala Ala Thr Ser Asn Asp Gly Val Val Lys Ile
35 40 45

Asp Thr Ser Thr Leu Ile Gly Thr Asn His Ala His Cys Trp Tyr Arg
50 55 60

Asp Lys Leu Glu Thr Ala Leu Arg Gly Ile Arg Ser Trp Gly Met Asn
65 70 75 80

Ser Val Arg Val Val Leu Ser Asn Gly Tyr Arg Trp Thr Lys Ile Pro
85 90 95

Ala Ser Glu Val Ala Asn Ile Ile Ser Leu Ser Arg Ser Leu Gly Phe
100 105 110

Arg Ala Ile Val Leu Glu Val His Asp Thr Thr Gly Tyr Gly Glu Asp
115 120 125

Gly Ala Ala Cys Ser Leu Ala Gln Ala Val Glu Tyr Trp Lys Glu Ile
130 135 140

Lys Ser Val Leu Glu Gly Asn Glu Asp Phe Val Ile Ile Asn Ile Gly
145 150 155 160

Asn Glu Pro Tyr Gly Asn Asn Asn Tyr Gln Asn Trp Ile Asn Asp Thr
165 170 175

Lys Asn Ala Ile Lys Ala Leu Arg Asp Ala Gly Phe Lys His Thr Ile
180 185 190

Met Val Asp Ala Pro Asn Trp Gly Gln Asp Trp Ser Asn Thr Met Arg
195 200 205

Asp Asn Ala Gln Ser Ile Met Glu Ala Asp Pro Leu Arg Asn Leu Val
210 215 220

Phe Ser Ile His Met Tyr Gly Val Tyr Asn Thr Ala Ser Lys Val Glu
225 230 235 240

Glu Tyr Ile Lys Ser Phe Val Glu Lys Gly Leu Pro Leu Val Ile Gly
245 250 255

```
Glu Phe Gly His Gln His Thr Asp Gly Asp Pro Asp Glu Glu Ala Ile
            260                 265                 270

Val Arg Tyr Ala Lys Gln Tyr Lys Ile Gly Leu Phe Ser Trp Ser Trp
        275                 280                 285

Cys Gly Asn Ser Ser Tyr Val Gly Tyr Leu Asp Met Val Asn Asn Trp
    290                 295                 300

Asp Pro Asn Asn Pro Thr Pro Trp Gly Gln Trp Tyr Lys Thr Asn Ala
305                 310                 315                 320

Ile Gly Ala Ser Ser Val Pro Thr Ser Thr Pro Thr Pro Thr Pro Thr
                325                 330                 335

Ala Thr Pro Thr Ala Thr Pro Thr Pro Thr Pro Thr Pro Ser Ser Thr
            340                 345                 350

Pro Val Ala Gly Gly Gln Ile Lys Val Leu Tyr Ala Asn Lys Glu Thr
        355                 360                 365

Asn Ser Thr Thr Asn Thr Ile Arg Pro Trp Leu Lys Val Val Asn Thr
    370                 375                 380

Gly Ser Ser Ser Ile Asp Leu Ser Arg Val Thr Ile Arg Tyr Trp Tyr
385                 390                 395                 400

Thr Val Asp Gly Asp Lys Ala Gln Ser Ala Ile Ser Asp Trp Ala Gln
                405                 410                 415

Ile Gly Ala Ser Asn Val Thr Phe Lys Phe Val Lys Leu Ser Ser Ser
            420                 425                 430

Val Ser Gly Ala Asp Tyr Tyr Leu Glu Ile Gly Phe Lys Ser Gly Ala
        435                 440                 445

Gly Gln Leu Gln Ala Gly Lys Asp Thr Gly Glu Ile Gln Ile Arg Phe
    450                 455                 460

Asn Lys Ser Asp Trp Ser Asn Tyr Asn Gln Gly Asn Asp Trp Ser Trp
465                 470                 475                 480

Met Gln Ser Met Thr Ser Tyr Gly Glu Asn Val Lys Val Thr Ala Tyr
                485                 490                 495

Ile Asp Gly Val Leu Val Trp Gly Gln Glu Pro Ser Gly Ala Thr Pro
            500                 505                 510

Thr Pro Thr Ala Thr Pro Ala Pro Thr Val Thr Pro Thr Ala Thr Pro
        515                 520                 525

Ala Pro Thr Pro Thr Pro Thr Pro Thr Pro Thr Ala Thr Pro Thr Pro
    530                 535                 540

Thr Pro Thr Pro Thr Pro Thr Pro Thr Ala Thr Pro Thr Pro Thr Pro
545                 550                 555                 560

Ser Ser Thr Pro Val Ala Gly Gly Gln Ile Lys Val Leu Tyr Ala Asn
                565                 570                 575

Lys Glu Thr Asn Ser Thr Thr Asn Thr Ile Arg Pro Trp Leu Lys Val
            580                 585                 590

Val Asn Thr Gly Ser Ser Ser Ile Asp Leu Ser Arg Val Thr Ile Arg
        595                 600                 605

Tyr Trp Tyr Thr Val Asp Gly Asp Lys Ala Gln Ser Ala Ile Ser Asp
    610                 615                 620

Trp Ala Gln Ile Gly Ala Ser Asn Val Thr Phe Lys Phe Val Lys Leu
625                 630                 635                 640

Ser Ser Ser Val Ser Gly Ala Asp Tyr Tyr Leu Glu Ile Gly Phe Lys
                645                 650                 655

Ser Gly Ala Gly Gln Leu Gln Ala Gly Lys Asp Thr Gly Glu Ile Gln
            660                 665                 670
```

```
Ile Arg Phe Asn Lys Ser Asp Trp Ser Asn Tyr Asn Gln Gly Asn Asp
        675                 680                 685

Trp Ser Trp Met Gln Ser Met Thr Ser Tyr Gly Glu Asn Val Lys Val
    690                 695                 700

Thr Ala Tyr Ile Asp Gly Val Leu Val Trp Gly Gln Glu Pro Ser Gly
705                 710                 715                 720

Ala Thr Pro Thr Pro Thr Ala Thr Pro Ala Pro Thr Ser Thr Ser Thr
                725                 730                 735

Pro Thr Pro Thr Val Thr Pro Thr Pro Thr Pro Thr Pro Thr Ala Thr
            740                 745                 750

Pro Thr Pro Thr Ala Thr Ser Ile Pro Leu Pro Thr Val Ser Pro Ser
        755                 760                 765

Ser Ala Val Ile Glu Ile Ala Ile Asn Thr Asn Lys Asp Arg Ser Pro
    770                 775                 780

Ile Ser Pro Tyr Ile Tyr Gly Ala Asn Gln Asp Ile Gly Gly Val Val
785                 790                 795                 800

His Pro Ala Arg Arg Leu Gly Gly Asn Arg Leu Thr Gly Tyr Asn Trp
                805                 810                 815

Glu Asn Asn Phe Ser Asn Ala Gly Asn Asp Trp Tyr His Ser Ser Asp
            820                 825                 830

Asp Tyr Leu Cys Trp Ser Met Gly Ile Ser Gly Glu Asp Ala Lys Val
        835                 840                 845

Pro Ala Ala Val Val Ser Lys Phe His Glu Tyr Ser Leu Lys Asn Asn
    850                 855                 860

Ala Tyr Ser Ala Ile Thr Leu Gln Met Ala Gly Tyr Val Ser Lys Asp
865                 870                 875                 880

Asn Tyr Gly Thr Val Ser Glu Asn Glu Thr Ala Pro Ser Asn Arg Trp
                885                 890                 895

Ala Glu Val Lys Phe Lys Lys Asp Ala Pro Leu Ser Leu Asn Pro Asp
            900                 905                 910

Leu Asn Asp Asn Phe Val Tyr Met Asp Glu Phe Ile Asn Tyr Leu Ile
        915                 920                 925

Asn Lys Tyr Gly Met Ala Ser Ser Pro Thr Gly Ile Lys Gly Tyr Ile
    930                 935                 940

Leu Asp Asn Glu Pro Asp Leu Trp Val Ser Thr His Pro Arg Ile His
945                 950                 955                 960

Pro Asn Lys Val Thr Cys Lys Glu Leu Ile Asp Lys Ser Val Glu Leu
                965                 970                 975

Ala Lys Val Ile Lys Thr Leu Asp Pro Ser Ala Glu Val Phe Gly Tyr
            980                 985                 990

Ala Ser Tyr Gly Phe Met Gly Tyr Tyr Ser Leu Gln Asp Ala Pro Asp
        995                 1000                1005

Trp Asn Gln Val Lys Gly Asp His Arg Trp Phe Ile Ser Trp Tyr Leu
    1010                1015                1020

Glu Gln Met Lys Lys Ala Ser Asp Ser Tyr Gly Lys Arg Leu Leu Asp
1025                1030                1035                1040

Val Leu Asp Leu His Trp Tyr Pro Glu Ala Arg Gly Gly Asn Ile Arg
                1045                1050                1055

Val Cys Phe Asp Gly Glu Asn Asp Thr Ser Lys Glu Val Ala Ile Ala
            1060                1065                1070

Arg Met Gln Ala Pro Arg Thr Leu Trp Asp Pro Thr Tyr Lys Thr Ser
        1075                1080                1085

Val Lys Gly Gln Ile Thr Ala Gly Glu Asn Ser Trp Ile Asn Gln Trp
```

```
    1090                1095                1100

Phe Ser Asp Tyr Leu Pro Ile Ile Pro Asn Ile Lys Ala Asp Ile Glu
1105                1110                1115                1120

Lys Tyr Tyr Pro Gly Thr Lys Leu Ala Ile Ser Glu Phe Asp Tyr Gly
                1125                1130                1135

Gly Arg Asn His Ile Ser Gly Gly Ile Ala Leu Ala Asp Val Leu Gly
            1140                1145                1150

Ile Phe Gly Lys Tyr Gly Val Tyr Phe Ala Ala Arg Trp Gly Asp Ser
        1155                1160                1165

Gly Ser Tyr Ala Ala Ala Ala Tyr Asn Ile Tyr Leu Asn Tyr Asp Gly
    1170                1175                1180

Lys Gly Ser Lys Tyr Gly Asn Thr Asn Val Gly Ala Asn Thr Asn Asp
1185                1190                1195                1200

Val Glu Asn Met Pro Val Tyr Ala Ser Ile Asn Gly Gln Asp Asp Ser
                1205                1210                1215

Glu Leu His Ile Ile Leu Ile Asn Arg Asn Tyr Asp Arg Lys Leu Pro
            1220                1225                1230

Ala Lys Ile Ser Ile Thr Ser Ser Lys Asn Tyr Thr Lys Ala Glu Ile
        1235                1240                1245

Tyr Gly Phe Asp Ser Asn Ser Pro Thr Val Arg Lys Met Gly Ser Val
    1250                1255                1260

Asp Asn Ile Glu Asn Asn Val Leu Thr Leu Glu Val Pro Asn Leu Thr
1265                1270                1275                1280

Val Phe His Ile Val Leu Tyr Ser Thr Ser Val Gln Thr Lys
                1285                1290


<210> SEQ ID NO 87
<211> LENGTH: 1256
<212> TYPE: PRT
<213> ORGANISM: Caldicellulosiruptor bescii

<400> SEQUENCE: 87

Ala Thr Ser Asn Asp Gly Val Val Lys Ile Asp Thr Ser Thr Leu Ile
 1               5                  10                  15

Gly Thr Asn His Ala His Cys Trp Tyr Arg Asp Lys Leu Glu Thr Ala
            20                  25                  30

Leu Arg Gly Ile Arg Ser Trp Gly Met Asn Ser Val Arg Val Val Leu
        35                  40                  45

Ser Asn Gly Tyr Arg Trp Thr Lys Ile Pro Ala Ser Glu Val Ala Asn
    50                  55                  60

Ile Ile Ser Leu Ser Arg Ser Leu Gly Phe Arg Ala Ile Val Leu Glu
65                  70                  75                  80

Val His Asp Thr Thr Gly Tyr Gly Glu Asp Gly Ala Ala Cys Ser Leu
                85                  90                  95

Ala Gln Ala Val Glu Tyr Trp Lys Glu Ile Lys Ser Val Leu Glu Gly
            100                 105                 110

Asn Glu Asp Phe Val Ile Ile Asn Ile Gly Asn Glu Pro Tyr Gly Asn
        115                 120                 125

Asn Asn Tyr Gln Asn Trp Ile Asn Asp Thr Lys Asn Ala Ile Lys Ala
    130                 135                 140

Leu Arg Asp Ala Gly Phe Lys His Thr Ile Met Val Asp Ala Pro Asn
145                 150                 155                 160

Trp Gly Gln Asp Trp Ser Asn Thr Met Arg Asp Asn Ala Gln Ser Ile
                165                 170                 175
```

```
Met Glu Ala Asp Pro Leu Arg Asn Leu Val Phe Ser Ile His Met Tyr
            180                 185                 190

Gly Val Tyr Asn Thr Ala Ser Lys Val Glu Glu Tyr Ile Lys Ser Phe
        195                 200                 205

Val Glu Lys Gly Leu Pro Leu Val Ile Gly Glu Phe Gly His Gln His
    210                 215                 220

Thr Asp Gly Asp Pro Asp Glu Glu Ala Ile Val Arg Tyr Ala Lys Gln
225                 230                 235                 240

Tyr Lys Ile Gly Leu Phe Ser Trp Ser Trp Cys Gly Asn Ser Ser Tyr
                245                 250                 255

Val Gly Tyr Leu Asp Met Val Asn Asn Trp Asp Pro Asn Asn Pro Thr
            260                 265                 270

Pro Trp Gly Gln Trp Tyr Lys Thr Asn Ala Ile Gly Ala Ser Ser Val
        275                 280                 285

Pro Thr Ser Thr Pro Thr Pro Thr Pro Thr Ala Thr Pro Thr Ala Thr
    290                 295                 300

Pro Thr Pro Thr Pro Thr Pro Ser Ser Thr Pro Val Ala Gly Gly Gln
305                 310                 315                 320

Ile Lys Val Leu Tyr Ala Asn Lys Glu Thr Asn Ser Thr Thr Asn Thr
                325                 330                 335

Ile Arg Pro Trp Leu Lys Val Val Asn Thr Gly Ser Ser Ser Ile Asp
            340                 345                 350

Leu Ser Arg Val Thr Ile Arg Tyr Trp Tyr Thr Val Asp Gly Asp Lys
        355                 360                 365

Ala Gln Ser Ala Ile Ser Asp Trp Ala Gln Ile Gly Ala Ser Asn Val
    370                 375                 380

Thr Phe Lys Phe Val Lys Leu Ser Ser Ser Val Ser Gly Ala Asp Tyr
385                 390                 395                 400

Tyr Leu Glu Ile Gly Phe Lys Ser Gly Ala Gly Gln Leu Gln Ala Gly
                405                 410                 415

Lys Asp Thr Gly Glu Ile Gln Ile Arg Phe Asn Lys Ser Asp Trp Ser
            420                 425                 430

Asn Tyr Asn Gln Gly Asn Asp Trp Ser Trp Met Gln Ser Met Thr Ser
        435                 440                 445

Tyr Gly Glu Asn Val Lys Val Thr Ala Tyr Ile Asp Gly Val Leu Val
    450                 455                 460

Trp Gly Gln Glu Pro Ser Gly Ala Thr Pro Thr Pro Thr Ala Thr Pro
465                 470                 475                 480

Ala Pro Thr Val Thr Pro Thr Ala Thr Pro Ala Pro Thr Pro Thr Pro
                485                 490                 495

Thr Pro Thr Pro Thr Ala Thr Pro Thr Pro Thr Pro Thr Pro Thr Pro
            500                 505                 510

Thr Pro Thr Ala Thr Pro Thr Pro Thr Pro Ser Ser Thr Pro Val Ala
        515                 520                 525

Gly Gly Gln Ile Lys Val Leu Tyr Ala Asn Lys Glu Thr Asn Ser Thr
    530                 535                 540

Thr Asn Thr Ile Arg Pro Trp Leu Lys Val Val Asn Thr Gly Ser Ser
545                 550                 555                 560

Ser Ile Asp Leu Ser Arg Val Thr Ile Arg Tyr Trp Tyr Thr Val Asp
                565                 570                 575

Gly Asp Lys Ala Gln Ser Ala Ile Ser Asp Trp Ala Gln Ile Gly Ala
            580                 585                 590

Ser Asn Val Thr Phe Lys Phe Val Lys Leu Ser Ser Ser Val Ser Gly
```

```
        595                 600                 605

Ala Asp Tyr Tyr Leu Glu Ile Gly Phe Lys Ser Gly Ala Gly Gln Leu
    610                 615                 620

Gln Ala Gly Lys Asp Thr Gly Glu Ile Gln Ile Arg Phe Asn Lys Ser
625                 630                 635                 640

Asp Trp Ser Asn Tyr Asn Gln Gly Asn Asp Trp Ser Trp Met Gln Ser
                645                 650                 655

Met Thr Ser Tyr Gly Glu Asn Val Lys Val Thr Ala Tyr Ile Asp Gly
            660                 665                 670

Val Leu Val Trp Gly Gln Glu Pro Ser Gly Ala Thr Pro Thr Pro Thr
        675                 680                 685

Ala Thr Pro Ala Pro Thr Ser Thr Ser Thr Pro Thr Pro Thr Val Thr
    690                 695                 700

Pro Thr Pro Thr Pro Thr Pro Thr Ala Thr Pro Thr Pro Thr Ala Thr
705                 710                 715                 720

Ser Ile Pro Leu Pro Thr Val Ser Pro Ser Ser Ala Val Ile Glu Ile
                725                 730                 735

Ala Ile Asn Thr Asn Lys Asp Arg Ser Pro Ile Ser Pro Tyr Ile Tyr
            740                 745                 750

Gly Ala Asn Gln Asp Ile Gly Gly Val Val His Pro Ala Arg Arg Leu
        755                 760                 765

Gly Gly Asn Arg Leu Thr Gly Tyr Asn Trp Glu Asn Asn Phe Ser Asn
    770                 775                 780

Ala Gly Asn Asp Trp Tyr His Ser Ser Asp Asp Tyr Leu Cys Trp Ser
785                 790                 795                 800

Met Gly Ile Ser Gly Glu Asp Ala Lys Val Pro Ala Ala Val Val Ser
                805                 810                 815

Lys Phe His Glu Tyr Ser Leu Lys Asn Asn Ala Tyr Ser Ala Ile Thr
            820                 825                 830

Leu Gln Met Ala Gly Tyr Val Ser Lys Asp Asn Tyr Gly Thr Val Ser
        835                 840                 845

Glu Asn Glu Thr Ala Pro Ser Asn Arg Trp Ala Glu Val Lys Phe Lys
    850                 855                 860

Lys Asp Ala Pro Leu Ser Leu Asn Pro Asp Leu Asn Asp Asn Phe Val
865                 870                 875                 880

Tyr Met Asp Glu Phe Ile Asn Tyr Leu Ile Asn Lys Tyr Gly Met Ala
                885                 890                 895

Ser Ser Pro Thr Gly Ile Lys Gly Tyr Ile Leu Asp Asn Glu Pro Asp
            900                 905                 910

Leu Trp Val Ser Thr His Pro Arg Ile His Pro Asn Lys Val Thr Cys
        915                 920                 925

Lys Glu Leu Ile Asp Lys Ser Val Glu Leu Ala Lys Val Ile Lys Thr
    930                 935                 940

Leu Asp Pro Ser Ala Glu Val Phe Gly Tyr Ala Ser Tyr Gly Phe Met
945                 950                 955                 960

Gly Tyr Tyr Ser Leu Gln Asp Ala Pro Asp Trp Asn Gln Val Lys Gly
                965                 970                 975

Asp His Arg Trp Phe Ile Ser Trp Tyr Leu Glu Gln Met Lys Lys Ala
            980                 985                 990

Ser Asp Ser Tyr Gly Lys Arg Leu Leu Asp Val Leu Asp Leu His Trp
        995                 1000                1005

Tyr Pro Glu Ala Arg Gly Gly Asn Ile Arg Val Cys Phe Asp Gly Glu
    1010                1015                1020
```

```
Asn Asp Thr Ser Lys Glu Val Ala Ile Ala Arg Met Gln Ala Pro Arg
1025                1030                1035                1040

Thr Leu Trp Asp Pro Thr Tyr Lys Thr Ser Val Lys Gly Gln Ile Thr
                1045                1050                1055

Ala Gly Glu Asn Ser Trp Ile Asn Gln Trp Phe Ser Asp Tyr Leu Pro
            1060                1065                1070

Ile Ile Pro Asn Ile Lys Ala Asp Ile Glu Lys Tyr Tyr Pro Gly Thr
        1075                1080                1085

Lys Leu Ala Ile Ser Glu Phe Asp Tyr Gly Gly Arg Asn His Ile Ser
    1090                1095                1100

Gly Gly Ile Ala Leu Ala Asp Val Leu Gly Ile Phe Gly Lys Tyr Gly
1105                1110                1115                1120

Val Tyr Phe Ala Ala Arg Trp Gly Asp Ser Gly Ser Tyr Ala Ala Ala
                1125                1130                1135

Ala Tyr Asn Ile Tyr Leu Asn Tyr Asp Gly Lys Gly Ser Lys Tyr Gly
            1140                1145                1150

Asn Thr Asn Val Gly Ala Asn Thr Asn Asp Val Glu Asn Met Pro Val
        1155                1160                1165

Tyr Ala Ser Ile Asn Gly Gln Asp Asp Ser Glu Leu His Ile Ile Leu
    1170                1175                1180

Ile Asn Arg Asn Tyr Asp Arg Lys Leu Pro Ala Lys Ile Ser Ile Thr
1185                1190                1195                1200

Ser Ser Lys Asn Tyr Thr Lys Ala Glu Ile Tyr Gly Phe Asp Ser Asn
                1205                1210                1215

Ser Pro Thr Val Arg Lys Met Gly Ser Val Asp Asn Ile Glu Asn Asn
            1220                1225                1230

Val Leu Thr Leu Glu Val Pro Asn Leu Thr Val Phe His Ile Val Leu
        1235                1240                1245

Tyr Ser Thr Ser Val Gln Thr Lys
    1250                1255
```

<210> SEQ ID NO 88
<211> LENGTH: 3885
<212> TYPE: DNA
<213> ORGANISM: Caldicellulosiruptor bescii

<400> SEQUENCE: 88

```
atgagagtaa aaacaaaaat ggggaagaaa tggttgagta tactatgtac agttgttttt      60

ttattgaaca ttttgtttat agcaaatgta acgaatttac ccaaagttgg tgcggctaca     120

tctaatgatg gagtagtgaa gatagatact agcacattaa taggaacaaa tcacgcacat     180

tgctggtaca gagataaact tgagacggca ttgcgaggaa taaggtcatg gggtatgaac     240

tctgtgaggg tagtgttgag taatggctat cgatggacga agataccagc aagtgaagta     300

gcaaatatta tatcattgtc aagaagtctt ggattcagag ccattgtatt agaagttcac     360

gacacgacag gatatggtga ggacggtgca gcatgttcat tggcgcaagc agtagaatat     420

tggaaagaga taaagagtgt gttagaaggc aatgaggatt ttgttataat aaacattggt     480

aatgagccgt atgggaacaa taactatcaa aactggatta atgacacgaa gaatgctata     540

aaagcgctaa gggatgcagg gttcaagcac acgataatgg ttgatgcacc gaactggggg     600

caggattggt ctaatactat gagagacaat gcccagagca taatggaagc agatccgctg     660

cgcaatttgg tattttcgat tcatatgtac ggtgtataca atacagcgag caaggtagaa     720

gaatatatca agtcatttgt ggagaaaggg ctgccattag ttattgggga gtttgggcat     780
```

cagcatacag atggtgaccc tgacgaggaa gctattgtca ggtatgcaaa acaatacaag 840
ataggacttt ttagctggtc ttggtgtggc aattcgagct atgtagggta cttggacatg 900
gtaaacaatt gggaccccaa taatccaact ccatgggggc aatggtataa aactaatgcg 960
attggtgcct cttcagtacc tacttcaaca ccaacaccga caccaactgc tacaccaaca 1020
gcaacgccaa caccaacacc gacgccgagc agcacacctg tagcaggtgg acagataaag 1080
gtattgtatg ctaacaagga gacaaatagc acaacaaata cgataaggcc atggttgaag 1140
gtagtgaaca ctggaagcag cagcatagat ttgagcaggg taacgataag gtactggtac 1200
acggtagatg gggacaaggc acagagtgcg atatcagact gggcacagat aggagcaagc 1260
aatgtgacat tcaagtttgt gaagctgagc agtagcgtaa gtggagcgga ctattattta 1320
gagataggat ttaagagtgg agctgggcag ttgcaggctg gtaaagacac aggggagata 1380
cagataaggt ttaacaagag tgactggagc aattacaatc aggggaatga ctggtcatgg 1440
atgcagagca tgacgagtta tggagagaat gtgaaggtaa cagcgtatat agatggtgta 1500
ttggtatggg gacaggagcc gagtggagcg acaccaacac cgacagcaac accagcaccg 1560
acagtgacac cgacagcaac accagcacca acaccaaccc cgaccccaac accaactgct 1620
acaccaacgc caacaccgac tccaacacca acaccaactg ctaccccaac accgacgccg 1680
agcagtacac ctgtagcagg tggacagata aaggtactgt atgctaacaa ggagacaaat 1740
agcacaacaa acacgataag gccatggttg aaggtagtga acactggaag cagcagcata 1800
gatttgagca gggtaacgat aaggtactgg tacacggtag atggggacaa ggcacagagt 1860
gcgatatcag actgggcaca gataggagca agcaatgtga cattcaagtt tgtgaagctg 1920
agcagtagcg taagtggagc ggactattat ttagagatag gatttaagag tggagctggg 1980
cagttgcagg ctggtaaaga cacaggggag atacagataa ggtttaacaa gagtgactgg 2040
agcaattaca atcaggggaa tgactggtca tggatgcaga gcatgacgag ttatggagag 2100
aatgtgaagg taacagcgta tatagatggt gtattggtat ggggacagga gccgagtgga 2160
gcgacaccaa caccgacagc aacaccagca ccaacatcga catcgacgcc aacaccgaca 2220
gtaacaccaa ccccgacccc aacaccaact gctacaccaa cacccacggc aacgtcaatt 2280
ccattaccaa cagtatcacc atcgtcggct gttattgaaa tagcaataaa tacaaataaa 2340
gataggtcac caattagccc gtacatttat ggtgcaaacc aggatattgg aggtgtagtt 2400
catcctgcaa gaaggttagg tggaaacaga ctaacaggat acaattggga aaacaacttt 2460
tcaaatgcgg ggaacgattg gtatcattca agtgacgatt atttgtgctg gagcatggga 2520
atttctggtg aagatgcgaa ggttccagca gcagtggtat ctaaatttca tgagtattcc 2580
cttaaaaata atgcttattc tgctataact ttgcaaatgg caggatatgt gtcaaaagat 2640
aattatggta ctgttagtga aaatgaaaca gctccatcta acaggtgggc agaggtaaaa 2700
tttaagaagg atgctccttt atctttgaat ccagacttga atgataactt tgtttatatg 2760
gatgaattca taaattattt gataaacaaa tacggaatgg cttcttcacc taccgggata 2820
aaagggtata tacttgataa tgagcctgat ttgtgggtct caacacatcc ccgtatacat 2880
cctaataagg tcacatgcaa agagttgatt gataaatctg ttgaactggc aaaagttata 2940
aaaacccttg atccatcagc tgaagttttt ggatatgcat catatgggtt tatgggttat 3000
tatagtctcc aagatgcgcc tgattggaac caagttaaag gagatcatag atggtttata 3060
agctggtatc tggaacagat gaaaaaagca tcagacagtt atggaaaaag attattagat 3120
gtgcttgatt tacactggta tccagaagca cgaggtggaa atattcgcgt gtgctttgat 3180
ggcgaaaatg acacatcaaa agaagttgct atagctagga tgcaagctcc aagaacacta 3240
tgggacccga cctacaaaac atcagtgaaa gggcaaatta cagctggtga gaacagctgg 3300
ataaaccagt ggttttcaga ttatttgcct ataattccaa acataaaagc ggacatagag 3360
aaatattatc ctggtacaaa acttgctatt agcgaattcg attatggcgg tcgaaatcat 3420
atttcagggg gaattgcttt agctgatgtg ctcggtatat ttggtaaata tggagtgtac 3480
tttgcagcaa gatggggcga ttctggtagt tatgcagcag ctgcatataa catttatctt 3540
aattatgatg gaaaaggctc aaaatatggc aatacaaatg taggtgctaa tacaaatgat 3600
gttgaaaata tgccagttta tgcttcaata aatggacagg atgattctga acttcatatt 3660
atactaataa acagaaacta tgacagaaaa ttgcctgcga agatcagcat tacaagttca 3720
aaaaactata caaaagcaga aatttatggt tttgatagca atagtcctac tgttagaaaa 3780
atgggaagtg tggataatat cgaaaacaat gttttaactc ttgaggtacc taatttaaca 3840
gttttccata tcgttttata ttcaacctca gtacaaacta aataa 3885

<210> SEQ ID NO 89
<211> LENGTH: 3771
<212> TYPE: DNA
<213> ORGANISM: Caldicellulosiruptor bescii

<400> SEQUENCE: 89
gctacatcta atgatggagt agtgaagata gatactagca cattaatagg aacaaatcac 60
gcacattgct ggtacagaga taaacttgag acggcattgc gaggaataag gtcatggggt 120
atgaactctg tgagggtagt gttgagtaat ggctatcgat ggacgaagat accagcaagt 180
gaagtagcaa atattatatc attgtcaaga agtcttggat tcagagccat tgtattagaa 240
gttcacgaca cgacaggata tggtgaggac ggtgcagcat gttcattggc gcaagcagta 300
gaatattgga aagagataaa gagtgtgtta gaaggcaatg aggattttgt tataataaac 360
attggtaatg agccgtatgg gaacaataac tatcaaaact ggattaatga cacgaagaat 420
gctataaaag cgctaaggga tgcagggttc aagcacacga taatggttga tgcaccgaac 480
tgggggcagg attggtctaa tactatgaga gacaatgccc agagcataat ggaagcagat 540
ccgctgcgca atttggtatt ttcgattcat atgtacggtg tatacaatac agcgagcaag 600
gtagaagaat atatcaagtc atttgtggag aaagggctgc cattagttat tggggagttt 660
gggcatcagc atacagatgg tgaccctgac gaggaagcta ttgtcaggta tgcaaaacaa 720
tacaagatag gactttttag ctggtcttgg tgtggcaatt cgagctatgt agggtacttg 780
gacatggtaa acaattggga ccccaataat ccaactccat gggggcaatg gtataaaact 840
aatgcgattg gtgcctcttc agtacctact tcaacaccaa caccgacacc aactgctaca 900
ccaacagcaa cgccaacacc aacaccgacg ccgagcagca cacctgtagc aggtggacag 960
ataaaggtat tgtatgctaa caaggagaca aatagcacaa caaatacgat aaggccatgg 1020
ttgaaggtag tgaacactgg aagcagcagc atagatttga gcagggtaac gataaggtac 1080
tggtacacgg tagatgggga caaggcacag agtgcgatat cagactgggc acagatagga 1140
gcaagcaatg tgacattcaa gtttgtgaag ctgagcagta gcgtaagtgg agcggactat 1200
tatttagaga taggatttaa gagtggagct gggcagttgc aggctggtaa agacacaggg 1260
gagatacaga taaggtttaa caagagtgac tggagcaatt acaatcaggg gaatgactgg 1320
tcatggatgc agagcatgac gagttatgga gagaatgtga aggtaacagc gtatatagat 1380

-continued ggtgtattgg tatggggaca ggagccgagt ggagcgacac caacaccgac agcaacacca 1440
gcaccgacag tgacaccgac agcaacacca gcaccaacac caaccccgac cccaacacca 1500
actgctacac caacgccaac accgactcca acaccaacac caactgctac cccaacaccg 1560
acgccgagca gtacacctgt agcaggtgga cagataaagg tactgtatgc taacaaggag 1620
acaaatagca caacaaacac gataaggcca tggttgaagg tagtgaacac tggaagcagc 1680
agcatagatt tgagcagggt aacgataagg tactggtaca cggtagatgg ggacaaggca 1740
cagagtgcga tatcagactg ggcacagata ggagcaagca atgtgacatt caagtttgtg 1800
aagctgagca gtagcgtaag tggagcggac tattatttag agataggatt taagagtgga 1860
gctgggcagt tgcaggctgg taaagacaca ggggagatac agataaggtt taacaagagt 1920
gactggagca attacaatca ggggaatgac tggtcatgga tgcagagcat gacgagttat 1980
ggagagaatg tgaaggtaac agcgtatata gatggtgtat tggtatgggg acaggagccg 2040
agtggagcga caccaacacc gacagcaaca ccagcaccaa catcgacatc gacgccaaca 2100
ccgacagtaa caccaacccc gaccccaaca ccaactgcta caccaacacc cacggcaacg 2160
tcaattccat taccaacagt atcaccatcg tcggctgtta ttgaaatagc aataaataca 2220
aataaagata ggtcaccaat tagcccgtac atttatggtg caaaccagga tattggaggt 2280
gtagttcatc ctgcaagaag gttaggtgga aacagactaa caggatacaa ttgggaaaac 2340
aacttttcaa atgcggggaa cgattggtat cattcaagtg acgattattt gtgctggagc 2400
atgggaattt ctggtgaaga tgcgaaggtt ccagcagcag tggtatctaa atttcatgag 2460
tattccctta aaaataatgc ttattctgct ataactttgc aaatggcagg atatgtgtca 2520
aaagataatt atggtactgt tagtgaaaat gaaacagctc catctaacag gtgggcagag 2580
gtaaaattta agaaggatgc tcctttatct ttgaatccag acttgaatga taactttgtt 2640
tatatggatg aattcataaa ttatttgata aacaaatacg gaatggcttc ttcacctacc 2700
gggataaaag ggtatatact tgataatgag cctgatttgt gggtctcaac acatccccgt 2760
atacatccta ataaggtcac atgcaaagag ttgattgata aatctgttga actggcaaaa 2820
gttataaaaa cccttgatcc atcagctgaa gtttttggat atgcatcata tgggtttatg 2880
ggttattata gtctccaaga tgcgcctgat tggaaccaag ttaaaggaga tcatagatgg 2940
tttataagct ggtatctgga acagatgaaa aaagcatcag acagttatgg aaaaagatta 3000
ttagatgtgc ttgatttaca ctggtatcca gaagcacgag gtggaaatat tcgcgtgtgc 3060
tttgatggcg aaaatgacac atcaaaagaa gttgctatag ctaggatgca agctccaaga 3120
acactatggg acccgaccta caaaacatca gtgaaagggc aaattacagc tggtgagaac 3180
agctggataa accagtggtt ttcagattat ttgcctataa ttccaaacat aaaagcggac 3240
atagagaaat attatcctgg tacaaaactt gctattagcg aattcgatta tggcggtcga 3300
aatcatattt caggggggaat tgctttagct gatgtgctcg gtatatttgg taaatatgga 3360
gtgtactttg cagcaagatg gggcgattct ggtagttatg cagcagctgc atataacatt 3420
tatcttaatt atgatggaaa aggctcaaaa tatggcaata caaatgtagg tgctaataca 3480
aatgatgttg aaaatatgcc agtttatgct tcaataaatg gacaggatga ttctgaactt 3540
catattatac taataaacag aaactatgac agaaaattgc ctgcgaagat cagcattaca 3600
agttcaaaaa actatacaaa agcagaaatt tatggttttg atagcaatag tcctactgtt 3660
agaaaaatgg gaagtgtgga taatatcgaa aacaatgttt taactcttga ggtacctaat 3720
ttaacagttt tccatatcgt tttatattca acctcagtac aaactaaata a 3771

<210> SEQ ID NO 90
<211> LENGTH: 3816
<212> TYPE: DNA
<213> ORGANISM: Caldicellulosiruptor bescii

<400> SEQUENCE: 90
atggcacatc accaccacca tcacgtggat gacgacgaca agatggctac atctaatgat 60
ggagtagtga agatagatac tagcacatta ataggaacaa atcacgcaca ttgctggtac 120
agagataaac ttgagacggc attgcgagga ataaggtcat ggggtatgaa ctctgtgagg 180
gtagtgttga gtaatggcta tcgatggacg aagataccag caagtgaagt agcaaatatt 240
atatcattgt caagaagtct tggattcaga gccattgtat tagaagttca cgacacgaca 300
ggatatggtg aggacggtgc agcatgttca ttggcgcaag cagtagaata ttggaaagag 360
ataaagagtg tgttagaagg caatgaggat tttgttataa taaacattgg taatgagccg 420
tatgggaaca ataactatca aaactggatt aatgacacga agaatgctat aaaagcgcta 480
agggatgcag ggttcaagca cacgataatg gttgatgcac cgaactgggg gcaggattgg 540
tctaatacta tgagagacaa tgcccagagc ataatggaag cagatccgct gcgcaatttg 600
gtattttcga ttcatatgta cggtgtatac aatacagcga gcaaggtaga agaatatatc 660
aagtcatttg tggagaaagg gctgccatta gttattgggg agtttgggca tcagcataca 720
gatggtgacc ctgacgagga agctattgtc aggtatgcaa aacaatacaa gataggactt 780
tttagctggt cttggtgtgg caattcgagc tatgtagggt acttggacat ggtaaacaat 840 tgggaccccca ataatccaac tccatggggg caatggtata aaactaatgc gattggtgcc 900
tcttcagtac ctacttcaac accaacaccg acaccaactg ctacaccaac agcaacgcca 960
acaccaacac cgacgccgag cagcacacct gtagcaggtg gacagataaa ggtattgtat 1020
gctaacaagg agacaaatag cacaacaaat acgataaggc catggttgaa ggtagtgaac 1080
actggaagca gcagcataga tttgagcagg gtaacgataa ggtactggta cacggtagat 1140
ggggacaagg cacagagtgc gatatcagac tgggcacaga taggagcaag caatgtgaca 1200
ttcaagtttg tgaagctgag cagtagcgta agtggagcgg actattattt agagatagga 1260
tttaagagtg gagctgggca gttgcaggct ggtaaagaca caggggagat acagataagg 1320
tttaacaaga gtgactggag caattacaat caggggaatg actggtcatg gatgcagagc 1380
atgacgagtt atggagagaa tgtgaaggta acagcgtata tagatggtgt attggtatgg 1440
ggacaggagc cgagtggagc gacaccaaca ccgacagcaa caccagcacc gacagtgaca 1500
ccgacagcaa caccagcacc aacaccaacc ccgaccccaa caccaactgc tacaccaacg 1560
ccaacaccga ctccaacacc aacaccaact gctaccccaa caccgacgcc gagcagtaca 1620
cctgtagcag gtggacagat aaaggtactg tatgctaaca aggagacaaa tagcacaaca 1680
aacacgataa ggccatggtt gaaggtagtg aacactggaa gcagcagcat agatttgagc 1740
agggtaacga taaggtactg gtacacggta gatggggaca aggcacagag tgcgatatca 1800
gactgggcac agataggagc aagcaatgtg acattcaagt ttgtgaagct gagcagtagc 1860
gtaagtggag cggactatta tttagagata ggatttaaga gtggagctgg gcagttgcag 1920
gctggtaaag acacagggga gatacagata aggtttaaca agagtgactg gagcaattac 1980
aatcagggga atgactggtc atggatgcag agcatgacga gttatggaga gaatgtgaag 2040
gtaacagcgt atatagatgg tgtattggta tggggacagg agccgagtgg agcgacacca 2100

```
acaccgacag caacaccagc accaacatcg acatcgacgc caacaccgac agtaacacca   2160

accccgaccc caacaccaac tgctacacca acacccacgg caacgtcaat tccattacca   2220

acagtatcac catcgtcggc tgttattgaa atagcaataa atacaaataa agataggtca   2280

ccaattagcc cgtacattta tggtgcaaac caggatattg gaggtgtagt tcatcctgca   2340

agaaggttag gtggaaacag actaacagga tacaattggg aaaacaactt ttcaaatgcg   2400

gggaacgatt ggtatcattc aagtgacgat tatttgtgct ggagcatggg aatttctggt   2460

gaagatgcga aggttccagc agcagtggta tctaaatttc atgagtattc ccttaaaaat   2520

aatgcttatt ctgctataac tttgcaaatg gcaggatatg tgtcaaaaga taattatggt   2580

actgttagtg aaaatgaaac agctccatct aacaggtggg cagaggtaaa atttaagaag   2640

gatgctcctt tatctttgaa tccagacttg aatgataact ttgtttatat ggatgaattc   2700

ataaattatt tgataaacaa atacggaatg gcttcttcac ctaccgggat aaaagggtat   2760

atacttgata atgagcctga tttgtgggtc tcaacacatc cccgtataca tcctaataag   2820

gtcacatgca aagagttgat tgataaatct gttgaactgg caaaagttat aaaaaccctt   2880

gatccatcag ctgaagtttt tggatatgca tcatatgggt ttatgggtta ttatagtctc   2940

caagatgcgc ctgattggaa ccaagttaaa ggagatcata gatggtttat aagctggtat   3000

ctggaacaga tgaaaaaagc atcagacagt tatggaaaaa gattattaga tgtgcttgat   3060

ttacactggt atccagaagc acgaggtgga aatattcgcg tgtgctttga tggcgaaaat   3120

gacacatcaa aagaagttgc tatagctagg atgcaagctc caagaacact atgggacccg   3180

acctacaaaa catcagtgaa agggcaaatt acagctggtg agaacagctg gataaaccag   3240

tggttttcag attatttgcc tataattcca aacataaaag cggacataga gaaatattat   3300

cctggtacaa aacttgctat tagcgaattc gattatggcg gtcgaaatca tatttcaggg   3360

ggaattgctt tagctgatgt gctcggtata tttggtaaat atggagtgta ctttgcagca   3420

agatggggcg attctggtag ttatgcagca gctgcatata acatttatct taattatgat   3480

ggaaaaggct caaaatatgg caatacaaat gtaggtgcta atacaaatga tgttgaaaat   3540

atgccagttt atgcttcaat aaatggacag gatgattctg aacttcatat tatactaata   3600

aacagaaact atgacagaaa attgcctgcg aagatcagca ttacaagttc aaaaaactat   3660

acaaaagcag aaatttatgg ttttgatagc aatagtccta ctgttagaaa aatgggaagt   3720

gtggataata tcgaaaacaa tgttttaact cttgaggtac ctaatttaac agttttccat   3780

atcgttttat attcaacctc agtacaaact aaataa                             3816
```

<210> SEQ ID NO 91
<211> LENGTH: 1271
<212> TYPE: PRT
<213> ORGANISM: Caldicellulosiruptor bescii

<400> SEQUENCE: 91

```
Met Ala His His His His His His Val Asp Asp Asp Asp Lys Met Ala
 1               5                  10                  15

Thr Ser Asn Asp Gly Val Val Lys Ile Asp Thr Ser Thr Leu Ile Gly
            20                  25                  30

Thr Asn His Ala His Cys Trp Tyr Arg Asp Lys Leu Glu Thr Ala Leu
        35                  40                  45

Arg Gly Ile Arg Ser Trp Gly Met Asn Ser Val Arg Val Val Leu Ser
    50                  55                  60
```

-continued

```
Asn Gly Tyr Arg Trp Thr Lys Ile Pro Ala Ser Glu Val Ala Asn Ile
65                  70                  75                  80

Ile Ser Leu Ser Arg Ser Leu Gly Phe Arg Ala Ile Val Leu Glu Val
                85                  90                  95

His Asp Thr Thr Gly Tyr Gly Glu Asp Gly Ala Ala Cys Ser Leu Ala
            100                 105                 110

Gln Ala Val Glu Tyr Trp Lys Glu Ile Lys Ser Val Leu Glu Gly Asn
        115                 120                 125

Glu Asp Phe Val Ile Ile Asn Ile Gly Asn Glu Pro Tyr Gly Asn Asn
    130                 135                 140

Asn Tyr Gln Asn Trp Ile Asn Asp Thr Lys Asn Ala Ile Lys Ala Leu
145                 150                 155                 160

Arg Asp Ala Gly Phe Lys His Thr Ile Met Val Asp Ala Pro Asn Trp
                165                 170                 175

Gly Gln Asp Trp Ser Asn Thr Met Arg Asp Asn Ala Gln Ser Ile Met
            180                 185                 190

Glu Ala Asp Pro Leu Arg Asn Leu Val Phe Ser Ile His Met Tyr Gly
        195                 200                 205

Val Tyr Asn Thr Ala Ser Lys Val Glu Glu Tyr Ile Lys Ser Phe Val
    210                 215                 220

Glu Lys Gly Leu Pro Leu Val Ile Gly Glu Phe Gly His Gln His Thr
225                 230                 235                 240

Asp Gly Asp Pro Asp Glu Glu Ala Ile Val Arg Tyr Ala Lys Gln Tyr
                245                 250                 255

Lys Ile Gly Leu Phe Ser Trp Ser Trp Cys Gly Asn Ser Ser Tyr Val
            260                 265                 270

Gly Tyr Leu Asp Met Val Asn Asn Trp Asp Pro Asn Asn Pro Thr Pro
        275                 280                 285

Trp Gly Gln Trp Tyr Lys Thr Asn Ala Ile Gly Ala Ser Ser Val Pro
    290                 295                 300

Thr Ser Thr Pro Thr Pro Thr Pro Thr Ala Thr Pro Thr Ala Thr Pro
305                 310                 315                 320

Thr Pro Thr Pro Thr Pro Ser Ser Thr Pro Val Ala Gly Gly Gln Ile
                325                 330                 335

Lys Val Leu Tyr Ala Asn Lys Glu Thr Asn Ser Thr Thr Asn Thr Ile
            340                 345                 350

Arg Pro Trp Leu Lys Val Val Asn Thr Gly Ser Ser Ser Ile Asp Leu
        355                 360                 365

Ser Arg Val Thr Ile Arg Tyr Trp Tyr Thr Val Asp Gly Asp Lys Ala
    370                 375                 380

Gln Ser Ala Ile Ser Asp Trp Ala Gln Ile Gly Ala Ser Asn Val Thr
385                 390                 395                 400

Phe Lys Phe Val Lys Leu Ser Ser Ser Val Ser Gly Ala Asp Tyr Tyr
                405                 410                 415

Leu Glu Ile Gly Phe Lys Ser Gly Ala Gly Gln Leu Gln Ala Gly Lys
            420                 425                 430

Asp Thr Gly Glu Ile Gln Ile Arg Phe Asn Lys Ser Asp Trp Ser Asn
        435                 440                 445

Tyr Asn Gln Gly Asn Asp Trp Ser Trp Met Gln Ser Met Thr Ser Tyr
    450                 455                 460

Gly Glu Asn Val Lys Val Thr Ala Tyr Ile Asp Gly Val Leu Val Trp
465                 470                 475                 480

Gly Gln Glu Pro Ser Gly Ala Thr Pro Thr Pro Thr Ala Thr Pro Ala
```

```
                485                 490                 495

Pro Thr Val Thr Pro Thr Ala Thr Pro Ala Pro Thr Pro Thr Pro Thr
            500                 505                 510

Pro Thr Pro Thr Ala Thr Pro Thr Pro Thr Pro Thr Pro Thr Pro Thr
        515                 520                 525

Pro Thr Ala Thr Pro Thr Pro Thr Pro Ser Ser Thr Pro Val Ala Gly
    530                 535                 540

Gly Gln Ile Lys Val Leu Tyr Ala Asn Lys Glu Thr Asn Ser Thr Thr
545                 550                 555                 560

Asn Thr Ile Arg Pro Trp Leu Lys Val Val Asn Thr Gly Ser Ser Ser
                565                 570                 575

Ile Asp Leu Ser Arg Val Thr Ile Arg Tyr Trp Tyr Thr Val Asp Gly
            580                 585                 590

Asp Lys Ala Gln Ser Ala Ile Ser Asp Trp Ala Gln Ile Gly Ala Ser
        595                 600                 605

Asn Val Thr Phe Lys Phe Val Lys Leu Ser Ser Ser Val Ser Gly Ala
    610                 615                 620

Asp Tyr Tyr Leu Glu Ile Gly Phe Lys Ser Gly Ala Gly Gln Leu Gln
625                 630                 635                 640

Ala Gly Lys Asp Thr Gly Glu Ile Gln Ile Arg Phe Asn Lys Ser Asp
                645                 650                 655

Trp Ser Asn Tyr Asn Gln Gly Asn Asp Trp Ser Trp Met Gln Ser Met
            660                 665                 670

Thr Ser Tyr Gly Glu Asn Val Lys Val Thr Ala Tyr Ile Asp Gly Val
        675                 680                 685

Leu Val Trp Gly Gln Glu Pro Ser Gly Ala Thr Pro Thr Pro Thr Ala
    690                 695                 700

Thr Pro Ala Pro Thr Ser Thr Ser Thr Pro Thr Pro Thr Val Thr Pro
705                 710                 715                 720

Thr Pro Thr Pro Thr Pro Thr Ala Thr Pro Thr Pro Thr Ala Thr Ser
                725                 730                 735

Ile Pro Leu Pro Thr Val Ser Pro Ser Ser Ala Val Ile Glu Ile Ala
            740                 745                 750

Ile Asn Thr Asn Lys Asp Arg Ser Pro Ile Ser Pro Tyr Ile Tyr Gly
        755                 760                 765

Ala Asn Gln Asp Ile Gly Gly Val Val His Pro Ala Arg Arg Leu Gly
    770                 775                 780

Gly Asn Arg Leu Thr Gly Tyr Asn Trp Glu Asn Asn Phe Ser Asn Ala
785                 790                 795                 800

Gly Asn Asp Trp Tyr His Ser Ser Asp Asp Tyr Leu Cys Trp Ser Met
                805                 810                 815

Gly Ile Ser Gly Glu Asp Ala Lys Val Pro Ala Ala Val Val Ser Lys
            820                 825                 830

Phe His Glu Tyr Ser Leu Lys Asn Asn Ala Tyr Ser Ala Ile Thr Leu
        835                 840                 845

Gln Met Ala Gly Tyr Val Ser Lys Asp Asn Tyr Gly Thr Val Ser Glu
    850                 855                 860

Asn Glu Thr Ala Pro Ser Asn Arg Trp Ala Glu Val Lys Phe Lys Lys
865                 870                 875                 880

Asp Ala Pro Leu Ser Leu Asn Pro Asp Leu Asn Asp Asn Phe Val Tyr
                885                 890                 895

Met Asp Glu Phe Ile Asn Tyr Leu Ile Asn Lys Tyr Gly Met Ala Ser
            900                 905                 910
```

Ser Pro Thr Gly Ile Lys Gly Tyr Ile Leu Asp Asn Glu Pro Asp Leu
915 920 925

Trp Val Ser Thr His Pro Arg Ile His Pro Asn Lys Val Thr Cys Lys
930 935 940

Glu Leu Ile Asp Lys Ser Val Glu Leu Ala Lys Val Ile Lys Thr Leu
945 950 955 960

Asp Pro Ser Ala Glu Val Phe Gly Tyr Ala Ser Tyr Gly Phe Met Gly
965 970 975

Tyr Tyr Ser Leu Gln Asp Ala Pro Asp Trp Asn Gln Val Lys Gly Asp
980 985 990

His Arg Trp Phe Ile Ser Trp Tyr Leu Glu Gln Met Lys Lys Ala Ser
995 1000 1005

Asp Ser Tyr Gly Lys Arg Leu Leu Asp Val Leu Asp Leu His Trp Tyr
1010 1015 1020

Pro Glu Ala Arg Gly Gly Asn Ile Arg Val Cys Phe Asp Gly Glu Asn
1025 1030 1035 1040

Asp Thr Ser Lys Glu Val Ala Ile Ala Arg Met Gln Ala Pro Arg Thr
1045 1050 1055

Leu Trp Asp Pro Thr Tyr Lys Thr Ser Val Lys Gly Gln Ile Thr Ala
1060 1065 1070

Gly Glu Asn Ser Trp Ile Asn Gln Trp Phe Ser Asp Tyr Leu Pro Ile
1075 1080 1085

Ile Pro Asn Ile Lys Ala Asp Ile Glu Lys Tyr Tyr Pro Gly Thr Lys
1090 1095 1100

Leu Ala Ile Ser Glu Phe Asp Tyr Gly Gly Arg Asn His Ile Ser Gly
1105 1110 1115 1120

Gly Ile Ala Leu Ala Asp Val Leu Gly Ile Phe Gly Lys Tyr Gly Val
1125 1130 1135

Tyr Phe Ala Ala Arg Trp Gly Asp Ser Gly Ser Tyr Ala Ala Ala Ala
1140 1145 1150

Tyr Asn Ile Tyr Leu Asn Tyr Asp Gly Lys Gly Ser Lys Tyr Gly Asn
1155 1160 1165

Thr Asn Val Gly Ala Asn Thr Asn Asp Val Glu Asn Met Pro Val Tyr
1170 1175 1180

Ala Ser Ile Asn Gly Gln Asp Asp Ser Glu Leu His Ile Ile Leu Ile
1185 1190 1195 1200

Asn Arg Asn Tyr Asp Arg Lys Leu Pro Ala Lys Ile Ser Ile Thr Ser
1205 1210 1215

Ser Lys Asn Tyr Thr Lys Ala Glu Ile Tyr Gly Phe Asp Ser Asn Ser
1220 1225 1230

Pro Thr Val Arg Lys Met Gly Ser Val Asp Asn Ile Glu Asn Asn Val
1235 1240 1245

Leu Thr Leu Glu Val Pro Asn Leu Thr Val Phe His Ile Val Leu Tyr
1250 1255 1260

Ser Thr Ser Val Gln Thr Lys
1265 1270

<210> SEQ ID NO 92
<211> LENGTH: 1962
<212> TYPE: DNA
<213> ORGANISM: Caldicellulosiruptor bescii

<400> SEQUENCE: 92
atggcacatc accaccacca tcacgtggat gacgacgaca agatggctac atctaatgat 60

```
ggagtagtga agatagatac tagcacatta ataggaacaa atcacgcaca ttgctggtac    120

agagataaac ttgagacggc attgcgagga ataaggtcat ggggtatgaa ctctgtgagg    180

gtagtgttga gtaatggcta tcgatggacg aagataccag caagtgaagt agcaaatatt    240

atatcattgt caagaagtct tggattcaga gccattgtat tagaagttca cgacacgaca    300

ggatatggtg aggacggtgc agcatgttca ttggcgcaag cagtagaata ttggaaagag    360

ataaagagtg tgttagaagg caatgaggat tttgttataa taaacattgg taatgagccg    420

tatgggaaca ataactatca aaactggatt aatgacacga agaatgctat aaaagcgcta    480

agggatgcag ggttcaagca cacgataatg gttgatgcac cgaactgggg gcaggattgg    540

tctaatacta tgagagacaa tgcccagagc ataatggaag cagatccgct gcgcaatttg    600

gtattttcga ttcatatgta cggtgtatac aatacagcga gcaaggtaga agaatatatc    660

aagtcatttg tggagaaagg gctgccatta gttattgggg agtttgggca tcagcataca    720

gatggtgacc ctgacgagga agctattgtc aggtatgcaa aacaatacaa gataggactt    780

tttagctggt cttggtgtgg caattcgagc tatgtagggt acttggacat ggtaaacaat    840

tgggacccca ataatccaac tccatggggg caatggtata aactaatgc gattggtgcc    900

tcttcagtac ctacttcaac accaacaccg acaccaactg ctacaccaac agcaacgcca    960

acaccaacac cgacgccgag cagcacacct gtagcaggtg gacagataaa ggtattgtat   1020

gctaacaagg agacaaatag cacaacaaat acgataaggc catggttgaa ggtagtgaac   1080

actggaagca gcagcataga tttgagcagg gtaacgataa ggtactggta cacggtagat   1140

ggggacaagg cacagagtgc gatatcagac tgggcacaga taggagcaag caatgtgaca   1200

ttcaagtttg tgaagctgag cagtagcgta agtggagcgg actattattt agagatagga   1260

tttaagagtg gagctgggca gttgcaggct ggtaaagaca caggggagat acagataagg   1320

tttaacaaga gtgactggag caattacaat caggggaatg actggtcatg gatgcagagc   1380

atgacgagtt atggagagaa tgtgaaggta acagcgtata tagatggtgt attggtatgg   1440

ggacaggagc cgagtggagc gacaccaaca ccgacagcaa caccagcacc gacagtgaca   1500

ccgacagcaa caccagcacc aacaccaacc ccgaccccaa caccaactgc tacaccaacg   1560

ccaacaccga ctccaacacc aacaccaact gctaccccaa caccgacgcc gagcagtaca   1620

cctgtagcag gtggacagat aaaggtactg tatgctaaca aggagacaaa tagcacaaca   1680

aacacgataa ggccatggtt gaaggtagtg aacactggaa gcagcagcat agatttgagc   1740

agggtaacga taaggtactg gtacacggta gatggggaca aggcacagag tgcgatatca   1800

gactgggcac agataggagc aagcaatgtg acattcaagt ttgtgaagct gagcagtagc   1860

gtaagtggag cggactatta tttagagata ggatttaaga gtggagctgg gcagttgcag   1920

gctggtaaag acacagggga gatacagata aggtttaact aa                       1962
```

<210> SEQ ID NO 93
<211> LENGTH: 653
<212> TYPE: PRT
<213> ORGANISM: Caldicellulosiruptor bescii

<400> SEQUENCE: 93

```
Met Ala His His His His His His Val Asp Asp Asp Asp Lys Met Ala
 1               5                  10                  15

Thr Ser Asn Asp Gly Val Val Lys Ile Asp Thr Ser Thr Leu Ile Gly
            20                  25                  30
```

-continued

```
Thr Asn His Ala His Cys Trp Tyr Arg Asp Lys Leu Glu Thr Ala Leu
        35                  40                  45

Arg Gly Ile Arg Ser Trp Gly Met Asn Ser Val Arg Val Val Leu Ser
    50                  55                  60

Asn Gly Tyr Arg Trp Thr Lys Ile Pro Ala Ser Glu Val Ala Asn Ile
65                  70                  75                  80

Ile Ser Leu Ser Arg Ser Leu Gly Phe Arg Ala Ile Val Leu Glu Val
                85                  90                  95

His Asp Thr Thr Gly Tyr Gly Glu Asp Gly Ala Ala Cys Ser Leu Ala
            100                 105                 110

Gln Ala Val Glu Tyr Trp Lys Glu Ile Lys Ser Val Leu Glu Gly Asn
        115                 120                 125

Glu Asp Phe Val Ile Ile Asn Ile Gly Asn Glu Pro Tyr Gly Asn Asn
    130                 135                 140

Asn Tyr Gln Asn Trp Ile Asn Asp Thr Lys Asn Ala Ile Lys Ala Leu
145                 150                 155                 160

Arg Asp Ala Gly Phe Lys His Thr Ile Met Val Asp Ala Pro Asn Trp
                165                 170                 175

Gly Gln Asp Trp Ser Asn Thr Met Arg Asp Asn Ala Gln Ser Ile Met
            180                 185                 190

Glu Ala Asp Pro Leu Arg Asn Leu Val Phe Ser Ile His Met Tyr Gly
        195                 200                 205

Val Tyr Asn Thr Ala Ser Lys Val Glu Glu Tyr Ile Lys Ser Phe Val
    210                 215                 220

Glu Lys Gly Leu Pro Leu Val Ile Gly Glu Phe Gly His Gln His Thr
225                 230                 235                 240

Asp Gly Asp Pro Asp Glu Glu Ala Ile Val Arg Tyr Ala Lys Gln Tyr
                245                 250                 255

Lys Ile Gly Leu Phe Ser Trp Ser Trp Cys Gly Asn Ser Ser Tyr Val
            260                 265                 270

Gly Tyr Leu Asp Met Val Asn Asn Trp Asp Pro Asn Asn Pro Thr Pro
        275                 280                 285

Trp Gly Gln Trp Tyr Lys Thr Asn Ala Ile Gly Ala Ser Ser Val Pro
    290                 295                 300

Thr Ser Thr Pro Thr Pro Thr Pro Thr Ala Thr Pro Thr Ala Thr Pro
305                 310                 315                 320

Thr Pro Thr Pro Thr Pro Ser Ser Thr Pro Val Ala Gly Gly Gln Ile
                325                 330                 335

Lys Val Leu Tyr Ala Asn Lys Glu Thr Asn Ser Thr Thr Asn Thr Ile
            340                 345                 350

Arg Pro Trp Leu Lys Val Val Asn Thr Gly Ser Ser Ser Ile Asp Leu
        355                 360                 365

Ser Arg Val Thr Ile Arg Tyr Trp Tyr Thr Val Asp Gly Asp Lys Ala
    370                 375                 380

Gln Ser Ala Ile Ser Asp Trp Ala Gln Ile Gly Ala Ser Asn Val Thr
385                 390                 395                 400

Phe Lys Phe Val Lys Leu Ser Ser Ser Val Ser Gly Ala Asp Tyr Tyr
                405                 410                 415

Leu Glu Ile Gly Phe Lys Ser Gly Ala Gly Gln Leu Gln Ala Gly Lys
            420                 425                 430

Asp Thr Gly Glu Ile Gln Ile Arg Phe Asn Lys Ser Asp Trp Ser Asn
        435                 440                 445

Tyr Asn Gln Gly Asn Asp Trp Ser Trp Met Gln Ser Met Thr Ser Tyr
```

-continued

```
    450                 455                 460

Gly Glu Asn Val Lys Val Thr Ala Tyr Ile Asp Gly Val Leu Val Trp
465                 470                 475                 480

Gly Gln Glu Pro Ser Gly Ala Thr Pro Thr Pro Thr Ala Thr Pro Ala
                485                 490                 495

Pro Thr Val Thr Pro Thr Ala Thr Pro Ala Pro Thr Pro Thr Pro Thr
            500                 505                 510

Pro Thr Pro Thr Ala Thr Pro Thr Pro Thr Pro Thr Pro Thr Pro Thr
        515                 520                 525

Pro Thr Ala Thr Pro Thr Pro Thr Pro Ser Ser Thr Pro Val Ala Gly
    530                 535                 540

Gly Gln Ile Lys Val Leu Tyr Ala Asn Lys Glu Thr Asn Ser Thr Thr
545                 550                 555                 560

Asn Thr Ile Arg Pro Trp Leu Lys Val Val Asn Thr Gly Ser Ser Ser
                565                 570                 575

Ile Asp Leu Ser Arg Val Thr Ile Arg Tyr Trp Tyr Thr Val Asp Gly
            580                 585                 590

Asp Lys Ala Gln Ser Ala Ile Ser Asp Trp Ala Gln Ile Gly Ala Ser
        595                 600                 605

Asn Val Thr Phe Lys Phe Val Lys Leu Ser Ser Ser Val Ser Gly Ala
    610                 615                 620

Asp Tyr Tyr Leu Glu Ile Gly Phe Lys Ser Gly Ala Gly Gln Leu Gln
625                 630                 635                 640

Ala Gly Lys Asp Thr Gly Glu Ile Gln Ile Arg Phe Asn
                645                 650
```

<210> SEQ ID NO 94
<211> LENGTH: 3048
<212> TYPE: DNA
<213> ORGANISM: Caldicellulosiruptor bescii

<400> SEQUENCE: 94

```
atggcacatc accaccacca tcacgtggat gacgacgaca agatggtagg gtacttggac      60

atggtaaaca attgggaccc caataatcca actccatggg ggcaatggta taaaactaat     120

gcgattggtg cctcttcagt acctacttca acaccaacac cgacaccaac tgctacacca     180

acagcaacgc caacaccaac accgacgccg agcagcacac ctgtagcagg tggacagata     240

aaggtattgt atgctaacaa ggagacaaat agcacaacaa atacgataag gccatggttg     300

aaggtagtga acactggaag cagcagcata gatttgagca gggtaacgat aaggtactgg     360

tacacggtag atggggacaa ggcacagagt gcgatatcag actgggcaca gataggagca     420

agcaatgtga cattcaagtt tgtgaagctg agcagtagcg taagtggagc ggactattat     480

ttagagatag gatttaagag tggagctggg cagttgcagg ctggtaaaga cacaggggag     540

atacagataa ggtttaacaa gagtgactgg agcaattaca atcaggggaa tgactggtca     600

tggatgcaga gcatgacgag ttatggagag aatgtgaagg taacagcgta tatagatggt     660

gtattggtat ggggacagga gccgagtgga gcgacaccaa caccgacagc aacaccagca     720

ccgacagtga caccgacagc aacaccagca ccaacaccaa ccccgacccc aacaccaact     780

gctacaccaa cgccaacacc gactccaaca ccaacaccaa ctgctacccc aacaccgacg     840

ccgagcagta cacctgtagc aggtggacag ataaaggtac tgtatgctaa caaggagaca     900

aatagcacaa caaacacgat aaggccatgg ttgaaggtag tgaacactgg aagcagcagc     960

atagatttga gcagggtaac gataaggtac tggtacacgg tagatgggga caaggcacag    1020
```

```
agtgcgatat cagactgggc acagatagga gcaagcaatg tgacattcaa gtttgtgaag   1080

ctgagcagta gcgtaagtgg agcggactat tatttagaga taggatttaa gagtggagct   1140

gggcagttgc aggctggtaa agacacaggg gagatacaga taaggtttaa caagagtgac   1200

tggagcaatt acaatcaggg gaatgactgg tcatggatgc agagcatgac gagttatgga   1260

gagaatgtga aggtaacagc gtatatagat ggtgtattgg tatggggaca ggagccgagt   1320

ggagcgacac caacaccgac agcaacacca gcaccaacat cgacatcgac gccaacaccg   1380

acagtaacac caaccccgac cccaacacca actgctacac caacacccac ggcaacgtca   1440

attccattac caacagtatc accatcgtcg gctgttattg aaatagcaat aaatacaaat   1500

aaagataggt caccaattag cccgtacatt tatggtgcaa accaggatat tggaggtgta   1560

gttcatcctg caagaaggtt aggtggaaac agactaacag gatacaattg ggaaaacaac   1620

ttttcaaatg cggggaacga ttggtatcat tcaagtgacg attatttgtg ctggagcatg   1680

ggaatttctg gtgaagatgc gaaggttcca gcagcagtgg tatctaaatt tcatgagtat   1740

tcccttaaaa ataatgctta ttctgctata actttgcaaa tggcaggata tgtgtcaaaa   1800

gataattatg gtactgttag tgaaaatgaa acagctccat ctaacaggtg ggcagaggta   1860

aaatttaaga aggatgctcc tttatctttg aatccagact tgaatgataa ctttgtttat   1920

atggatgaat tcataaatta tttgataaac aaatacggaa tggcttcttc acctaccggg   1980

ataaaagggt atatacttga taatgagcct gatttgtggg tctcaacaca tccccgtata   2040

catcctaata aggtcacatg caaagagttg attgataaat ctgttgaact ggcaaaagtt   2100

ataaaaaccc ttgatccatc agctgaagtt tttggatatg catcatatgg gtttatgggt   2160

tattatagtc tccaagatgc gcctgattgg aaccaagtta aaggagatca tagatggttt   2220

ataagctggt atctggaaca gatgaaaaaa gcatcagaca gttatggaaa aagattatta   2280

gatgtgcttg atttacactg gtatccagaa gcacgaggtg gaaatattcg cgtgtgcttt   2340

gatggcgaaa atgacacatc aaaagaagtt gctatagcta ggatgcaagc tccaagaaca   2400

ctatgggacc cgacctacaa aacatcagtg aaagggcaaa ttacagctgg tgagaacagc   2460

tggataaacc agtggttttc agattatttg cctataattc caaacataaa agcggacata   2520

gagaaatatt atcctggtac aaaacttgct attagcgaat tcgattatgg cggtcgaaat   2580

catatttcag ggggaattgc tttagctgat gtgctcggta tatttggtaa atatggagtg   2640

tactttgcag caagatgggg cgattctggt agttatgcag cagctgcata taacatttat   2700

cttaattatg atggaaaagg ctcaaaatat ggcaatacaa atgtaggtgc taatacaaat   2760

gatgttgaaa atatgccagt ttatgcttca ataaatggac aggatgattc tgaacttcat   2820

attatactaa taaacagaaa ctatgacaga aaattgcctg cgaagatcag cattacaagt   2880

tcaaaaaact atacaaaagc agaaatttat ggttttgata gcaatagtcc tactgttaga   2940

aaaatgggaa gtgtggataa tatcgaaaac aatgttttaa ctcttgaggt acctaattta   3000

acagttttcc atatcgtttt atattcaacc tcagtacaaa ctaaataa             3048
```

<210> SEQ ID NO 95
<211> LENGTH: 1015
<212> TYPE: PRT
<213> ORGANISM: Caldicellulosiruptor bescii

<400> SEQUENCE: 95

```
Met Ala His His His His His His Val Asp Asp Asp Asp Lys Met Val
1               5                   10                  15
```

```
Gly Tyr Leu Asp Met Val Asn Asn Trp Asp Pro Asn Asn Pro Thr Pro
            20                  25                  30

Trp Gly Gln Trp Tyr Lys Thr Asn Ala Ile Gly Ala Ser Ser Val Pro
        35                  40                  45

Thr Ser Thr Pro Thr Pro Thr Pro Thr Ala Thr Pro Thr Ala Thr Pro
    50                  55                  60

Thr Pro Thr Pro Thr Pro Ser Ser Thr Pro Val Ala Gly Gly Gln Ile
65                  70                  75                  80

Lys Val Leu Tyr Ala Asn Lys Glu Thr Asn Ser Thr Thr Asn Thr Ile
                85                  90                  95

Arg Pro Trp Leu Lys Val Val Asn Thr Gly Ser Ser Ser Ile Asp Leu
            100                 105                 110

Ser Arg Val Thr Ile Arg Tyr Trp Tyr Thr Val Asp Gly Asp Lys Ala
        115                 120                 125

Gln Ser Ala Ile Ser Asp Trp Ala Gln Ile Gly Ala Ser Asn Val Thr
    130                 135                 140

Phe Lys Phe Val Lys Leu Ser Ser Ser Val Ser Gly Ala Asp Tyr Tyr
145                 150                 155                 160

Leu Glu Ile Gly Phe Lys Ser Gly Ala Gly Gln Leu Gln Ala Gly Lys
                165                 170                 175

Asp Thr Gly Glu Ile Gln Ile Arg Phe Asn Lys Ser Asp Trp Ser Asn
            180                 185                 190

Tyr Asn Gln Gly Asn Asp Trp Ser Trp Met Gln Ser Met Thr Ser Tyr
        195                 200                 205

Gly Glu Asn Val Lys Val Thr Ala Tyr Ile Asp Gly Val Leu Val Trp
    210                 215                 220

Gly Gln Glu Pro Ser Gly Ala Thr Pro Thr Pro Thr Ala Thr Pro Ala
225                 230                 235                 240

Pro Thr Val Thr Pro Thr Ala Thr Pro Ala Pro Thr Pro Thr Pro Thr
                245                 250                 255

Pro Thr Pro Thr Ala Thr Pro Thr Pro Thr Pro Thr Pro Thr Pro Thr
            260                 265                 270

Pro Thr Ala Thr Pro Thr Pro Thr Pro Ser Ser Thr Pro Val Ala Gly
        275                 280                 285

Gly Gln Ile Lys Val Leu Tyr Ala Asn Lys Glu Thr Asn Ser Thr Thr
    290                 295                 300

Asn Thr Ile Arg Pro Trp Leu Lys Val Val Asn Thr Gly Ser Ser Ser
305                 310                 315                 320

Ile Asp Leu Ser Arg Val Thr Ile Arg Tyr Trp Tyr Thr Val Asp Gly
                325                 330                 335

Asp Lys Ala Gln Ser Ala Ile Ser Asp Trp Ala Gln Ile Gly Ala Ser
            340                 345                 350

Asn Val Thr Phe Lys Phe Val Lys Leu Ser Ser Ser Val Ser Gly Ala
        355                 360                 365

Asp Tyr Tyr Leu Glu Ile Gly Phe Lys Ser Gly Ala Gly Gln Leu Gln
    370                 375                 380

Ala Gly Lys Asp Thr Gly Glu Ile Gln Ile Arg Phe Asn Lys Ser Asp
385                 390                 395                 400

Trp Ser Asn Tyr Asn Gln Gly Asn Asp Trp Ser Trp Met Gln Ser Met
                405                 410                 415

Thr Ser Tyr Gly Glu Asn Val Lys Val Thr Ala Tyr Ile Asp Gly Val
            420                 425                 430
```

```
Leu Val Trp Gly Gln Glu Pro Ser Gly Ala Thr Pro Thr Pro Thr Ala
        435                 440                 445

Thr Pro Ala Pro Thr Ser Thr Ser Thr Pro Thr Pro Thr Val Thr Pro
    450                 455                 460

Thr Pro Thr Pro Thr Pro Thr Ala Thr Pro Thr Pro Thr Ala Thr Ser
465                 470                 475                 480

Ile Pro Leu Pro Thr Val Ser Pro Ser Ser Ala Val Ile Glu Ile Ala
                485                 490                 495

Ile Asn Thr Asn Lys Asp Arg Ser Pro Ile Ser Pro Tyr Ile Tyr Gly
            500                 505                 510

Ala Asn Gln Asp Ile Gly Gly Val Val His Pro Ala Arg Arg Leu Gly
        515                 520                 525

Gly Asn Arg Leu Thr Gly Tyr Asn Trp Glu Asn Asn Phe Ser Asn Ala
    530                 535                 540

Gly Asn Asp Trp Tyr His Ser Ser Asp Asp Tyr Leu Cys Trp Ser Met
545                 550                 555                 560

Gly Ile Ser Gly Glu Asp Ala Lys Val Pro Ala Ala Val Val Ser Lys
                565                 570                 575

Phe His Glu Tyr Ser Leu Lys Asn Asn Ala Tyr Ser Ala Ile Thr Leu
            580                 585                 590

Gln Met Ala Gly Tyr Val Ser Lys Asp Asn Tyr Gly Thr Val Ser Glu
        595                 600                 605

Asn Glu Thr Ala Pro Ser Asn Arg Trp Ala Glu Val Lys Phe Lys Lys
    610                 615                 620

Asp Ala Pro Leu Ser Leu Asn Pro Asp Leu Asn Asp Asn Phe Val Tyr
625                 630                 635                 640

Met Asp Glu Phe Ile Asn Tyr Leu Ile Asn Lys Tyr Gly Met Ala Ser
                645                 650                 655

Ser Pro Thr Gly Ile Lys Gly Tyr Ile Leu Asp Asn Glu Pro Asp Leu
            660                 665                 670

Trp Val Ser Thr His Pro Arg Ile His Pro Asn Lys Val Thr Cys Lys
        675                 680                 685

Glu Leu Ile Asp Lys Ser Val Glu Leu Ala Lys Val Ile Lys Thr Leu
    690                 695                 700

Asp Pro Ser Ala Glu Val Phe Gly Tyr Ala Ser Tyr Gly Phe Met Gly
705                 710                 715                 720

Tyr Tyr Ser Leu Gln Asp Ala Pro Asp Trp Asn Gln Val Lys Gly Asp
                725                 730                 735

His Arg Trp Phe Ile Ser Trp Tyr Leu Glu Gln Met Lys Lys Ala Ser
            740                 745                 750

Asp Ser Tyr Gly Lys Arg Leu Leu Asp Val Leu Asp Leu His Trp Tyr
        755                 760                 765

Pro Glu Ala Arg Gly Gly Asn Ile Arg Val Cys Phe Asp Gly Glu Asn
    770                 775                 780

Asp Thr Ser Lys Glu Val Ala Ile Ala Arg Met Gln Ala Pro Arg Thr
785                 790                 795                 800

Leu Trp Asp Pro Thr Tyr Lys Thr Ser Val Lys Gly Gln Ile Thr Ala
                805                 810                 815

Gly Glu Asn Ser Trp Ile Asn Gln Trp Phe Ser Asp Tyr Leu Pro Ile
            820                 825                 830

Ile Pro Asn Ile Lys Ala Asp Ile Glu Lys Tyr Tyr Pro Gly Thr Lys
        835                 840                 845

Leu Ala Ile Ser Glu Phe Asp Tyr Gly Gly Arg Asn His Ile Ser Gly
```

```
    850                 855                 860

Gly Ile Ala Leu Ala Asp Val Leu Gly Ile Phe Gly Lys Tyr Gly Val
865                 870                 875                 880

Tyr Phe Ala Ala Arg Trp Gly Asp Ser Gly Ser Tyr Ala Ala Ala Ala
                885                 890                 895

Tyr Asn Ile Tyr Leu Asn Tyr Asp Gly Lys Gly Ser Lys Tyr Gly Asn
            900                 905                 910

Thr Asn Val Gly Ala Asn Thr Asn Asp Val Glu Asn Met Pro Val Tyr
        915                 920                 925

Ala Ser Ile Asn Gly Gln Asp Asp Ser Glu Leu His Ile Ile Leu Ile
    930                 935                 940

Asn Arg Asn Tyr Asp Arg Lys Leu Pro Ala Lys Ile Ser Ile Thr Ser
945                 950                 955                 960

Ser Lys Asn Tyr Thr Lys Ala Glu Ile Tyr Gly Phe Asp Ser Asn Ser
                965                 970                 975

Pro Thr Val Arg Lys Met Gly Ser Val Asp Asn Ile Glu Asn Asn Val
            980                 985                 990

Leu Thr Leu Glu Val Pro Asn Leu Thr Val Phe His Ile Val Leu Tyr
        995                 1000                1005

Ser Thr Ser Val Gln Thr Lys
    1010                1015


<210> SEQ ID NO 96
<211> LENGTH: 37
<212> TYPE: DNA
<213> ORGANISM: Artificial Sequence
<220> FEATURE:
<223> OTHER INFORMATION: Synthesized Construct

<400> SEQUENCE: 96

gacgacgaca agatgcagag catactgtat gaaaagg                          37


<210> SEQ ID NO 97
<211> LENGTH: 40
<212> TYPE: DNA
<213> ORGANISM: Artificial Sequence
<220> FEATURE:
<223> OTHER INFORMATION: Synthesized Construct

<400> SEQUENCE: 97

gaggagaagc ccggttactc aaaaaggata ttggtaaatc                       40


<210> SEQ ID NO 98
<211> LENGTH: 755
<212> TYPE: PRT
<213> ORGANISM: Caldicellulosiruptor bescii

<400> SEQUENCE: 98

Met Arg Lys Ile Ile Leu Lys Phe Cys Ala Leu Met Met Val Val Ile
 1               5                  10                  15

Leu Ile Val Ser Ile Leu Gln Ile Leu Pro Val Phe Ala Gln Ser Ile
            20                  25                  30

Leu Tyr Glu Lys Glu Lys Tyr Pro His Leu Leu Gly Asn Gln Val Val
        35                  40                  45

Lys Lys Pro Ser Val Ala Gly Arg Leu Gln Ile Ile Glu Lys Asp Gly
    50                  55                  60

Lys Lys Tyr Leu Ala Asp Gln Lys Gly Glu Ile Ile Gln Leu Arg Gly
65                  70                  75                  80
```

-continued

```
Met Ser Thr His Gly Leu Gln Trp Tyr Gly Asp Ile Ile Asn Lys Asn
                85                  90                  95

Ala Phe Lys Ala Leu Ser Lys Asp Trp Glu Cys Asn Val Ile Arg Leu
            100                 105                 110

Ala Met Tyr Val Gly Glu Gly Gly Tyr Ala Ser Asn Pro Ser Ile Lys
        115                 120                 125

Glu Lys Val Ile Glu Gly Ile Lys Leu Ala Ile Glu Asn Asp Met Tyr
    130                 135                 140

Val Ile Val Asp Trp His Val Leu Asn Pro Gly Asp Pro Asn Ala Glu
145                 150                 155                 160

Ile Tyr Lys Gly Ala Lys Asp Phe Phe Lys Glu Ile Ala Thr Ser Phe
                165                 170                 175

Pro Asn Asp Tyr His Ile Ile Tyr Glu Leu Cys Asn Glu Pro Asn Pro
            180                 185                 190

Asn Glu Pro Gly Val Glu Asn Ser Leu Asp Gly Trp Lys Lys Val Lys
        195                 200                 205

Ala Tyr Ala Gln Pro Ile Ile Lys Met Leu Arg Ser Leu Gly Asn Gln
    210                 215                 220

Asn Ile Ile Ile Val Gly Ser Pro Asn Trp Ser Gln Arg Pro Asp Phe
225                 230                 235                 240

Ala Ile Gln Asp Pro Ile Asn Asp Lys Asn Val Met Tyr Ser Val His
                245                 250                 255

Phe Tyr Ser Gly Thr His Lys Val Asp Gly Tyr Val Phe Glu Asn Met
            260                 265                 270

Lys Asn Ala Phe Glu Asn Gly Val Pro Ile Phe Val Ser Glu Trp Gly
        275                 280                 285

Thr Ser Leu Ala Ser Gly Asp Gly Gly Pro Tyr Leu Asp Glu Ala Asp
    290                 295                 300

Lys Trp Leu Glu Tyr Leu Asn Ser Asn Tyr Ile Ser Trp Val Asn Trp
305                 310                 315                 320

Ser Leu Ser Asn Lys Asn Glu Thr Ser Ala Ala Phe Val Pro Tyr Ile
                325                 330                 335

Asn Gly Met His Asp Ala Thr Pro Leu Asp Pro Gly Asp Asp Lys Val
            340                 345                 350

Trp Asp Ile Glu Glu Leu Ser Ile Ser Gly Glu Tyr Val Arg Ala Arg
        355                 360                 365

Ile Lys Gly Ile Ala Tyr Gln Pro Ile Lys Arg Asp Asn Lys Ile Lys
    370                 375                 380

Glu Gly Glu Asn Ala Pro Leu Gly Glu Lys Val Leu Pro Ser Thr Phe
385                 390                 395                 400

Glu Asp Asp Thr Arg Gln Gly Trp Asp Trp Asp Gly Pro Ser Gly Val
                405                 410                 415

Lys Gly Pro Ile Thr Ile Glu Ser Ala Asn Gly Ser Lys Ala Leu Ser
            420                 425                 430

Phe Asn Val Glu Tyr Pro Glu Lys Lys Pro Gln Asp Gly Trp Ala Thr
        435                 440                 445

Ala Ala Arg Leu Ile Leu Lys Asp Ile Asn Val Glu Arg Gly Asn Asn
    450                 455                 460

Lys Tyr Leu Ala Phe Asp Phe Tyr Leu Lys Pro Asp Arg Ala Ser Lys
465                 470                 475                 480

Gly Met Ile Gln Ile Phe Leu Ala Phe Ser Pro Pro Ser Leu Gly Tyr
                485                 490                 495

Trp Ala Gln Val Gln Asp Ser Phe Asn Ile Asp Leu Ala Lys Leu Ser
```

```
            500                 505                 510

Ser Ala Lys Lys Ile Glu Asp Arg Ile Tyr Lys Phe Asn Val Phe Phe
        515                 520                 525

Asp Leu Asp Lys Ile Gln Asp Asn Lys Val Leu Ser Pro Asp Thr Leu
    530                 535                 540

Leu Arg Asp Ile Ile Val Val Ile Ala Asp Gly Asn Ser Asp Phe Lys
545                 550                 555                 560

Gly Lys Met Tyr Ile Asp Asn Val Arg Phe Thr Asn Ile Leu Phe Glu
                565                 570                 575

Asp Ile Asn Phe Glu Asn Ser Leu Tyr Asp Val Ile Asp Lys Leu Tyr
            580                 585                 590

Ser Lys Gly Ile Ile Lys Gly Ile Ser Val Phe Lys Tyr Leu Pro Asp
        595                 600                 605

Lys Asn Ile Thr Arg Ala Glu Phe Ala Ala Leu Cys Val Arg Ala Leu
    610                 615                 620

Asn Leu Lys Ile Glu Lys Tyr Asp Gly Arg Phe Ser Asp Val Lys Ser
625                 630                 635                 640

Gly Asn Trp Tyr Ser Asp Val Val Tyr Thr Ala Tyr Lys Asn Lys Leu
                645                 650                 655

Phe Glu Ile Lys Glu Asn Lys Phe Phe Pro Glu Asn Ile Leu Lys Arg
            660                 665                 670

Glu Glu Ala Val Ala Leu Ala Ile Glu Val Tyr Lys Arg Leu Thr Gly
        675                 680                 685

Lys Ile Glu Val Asn Thr Asp Asp Val Pro Ile Ala Asp Glu Lys Leu
    690                 695                 700

Ile Asn Pro Gln Tyr Arg Glu Ser Val Lys Leu Ala Ile Lys Leu Gly
705                 710                 715                 720

Ile Val Asp Leu Tyr Ser Asp Gly Thr Phe Glu Pro Asn Lys Ser Val
                725                 730                 735

Ser Arg Gly Glu Val Ala Thr Ile Leu Tyr Asn Leu Leu Asn Leu Ala
            740                 745                 750

Gly Lys Leu
        755
```

<210> SEQ ID NO 99
<211> LENGTH: 2268
<212> TYPE: DNA
<213> ORGANISM: Caldicellulosiruptor bescii

<400> SEQUENCE: 99

```
atgaggaaaa ttattttaaa gttttgtgca ctcatgatgg tagtgatttt gattgtttcc      60

attttacaaa tattacctgt atttgcccag agcatactgt atgaaaagga aaaatatcca     120

catcttcttg gcaatcaggt agttaaaaaa ccatcggttg ccggcagact gcagattatt     180

gaaaaggacg gaaaaaagta tttagctgac cagaaaggag aaataattca gcttcgtggt     240

atgagtacac atggacttca gtggtatggt gatattataa acaaaaatgc atttaaagct     300

ctttcaaaag attgggagtg caacgttata aggcttgcga tgtatgtggg tgaaggcgga     360

tatgcttcaa acccaagtat taaagaaaaa gttatagaag ggattaagct tgctattgag     420

aatgacatgt atgtaattgt tgactggcat gtattaaatc ccggtgaccc gaacgcagaa     480

atttataaag ggcaaaaaga ctttttcaaa gagatagcta caagttttcc caatgactat     540

cacataatat atgaactttg caatgaacca aatccaaatg aaccgggagt agaaaatagc     600

ttggatggct ggaaaaaagt aaaggcttat gcacagccca tcataaaaat gctcagaagt     660
```

```
ttggggaatc agaacattat aattgtaggt tcgccaaact ggagtcagag acctgacttt    720

gcaattcaag accctataaa tgataagaat gttatgtatt cagttcattt ttactctgga    780

actcacaaag ttgatggata tgtttttgaa aacatgaaaa atgcgtttga aaatggcgtg    840

ccaattttcg tgagtgaatg gggaacaagt ttggcaagcg gtgatggtgg accgtatctt    900

gatgaagcag ataagtggct tgaatattta aattcaaact atattagctg ggtgaactgg    960

tcgctgtcaa acaaaaatga gacatcagct gcttttgttc catatataaa tggtatgcat   1020

gatgccacac cacttgaccc tggtgatgat aaggtgtggg acatagaaga gcttagtatt   1080

tctggagagt atgtgagggc aaggataaaa ggaattgctt atcagccaat taagagagat   1140

aacaaaataa aagaaggaga aaatgcacct ttaggcgaaa aagtcttacc atccacgttt   1200

gaagatgaca ctcgtcaggg ctgggattgg gatggaccat ctggtgtgaa aggtcctatt   1260

actatcgaaa gtgcgaatgg ttcaaaagcg ctatctttta atgttgagta tccagagaaa   1320

aaaccacaag atggctgggc aacagctgca aggcttatac ttaaagacat aaatgtagaa   1380

aggggaaata ataaatattt ggcttttgat ttttatttga aaccagatag ggcttcaaaa   1440

ggtatgattc agatattttt agctttttca ccaccttcct taggttactg ggctcaggta   1500

caagacagtt ttaatattga ccttgcaaaa ctgtcaagtg caaaaaagat agaagacaga   1560

atttataagt tcaatgtatt ttttgactta gacaagatac aagataataa agtactgagt   1620

ccagacacac tcttgagaga tataatagta gtcatagcag atggcaatag cgattttaag   1680

gggaaaatgt atatagataa tgttagattt accaatatcc tttttgagga tatcaatttt   1740

gaaaatagcc tttatgatgt tatagacaag ctttattcta aaggaatcat aaaaggaatt   1800

tcagtattta agtacttgcc agataaaaac attacaaggg ctgaatttgc tgcactttgt   1860

gtcagggcac tgaacctgaa aattgaaaaa tacgatggta gattttctga tgtgaaaagc   1920

ggcaactggt attcagatgt agtttatacg gcgtataaaa acaaattgtt tgaaataaaa   1980

gagaataaat tctttcctga aaatatttta aaaagagaag aagcagtagc tttggcaatt   2040

gaagtgtata aaagattgac tggtaagata gaagttaata cagacgatgt tccaattgct   2100

gatgaaaaac ttataaatcc tcaatacaga gaaagcgtga agttagcaat taagctcggt   2160

attgttgacc tgtattcaga cggaacattt gaaccaaata agagcgtttc aagaggggag   2220

gtggcaacaa ttctctataa tctcttgaac ttagcaggca agctatga                2268
```

<210> SEQ ID NO 100
<211> LENGTH: 547
<212> TYPE: PRT
<213> ORGANISM: Caldicellulosiruptor bescii

<400> SEQUENCE: 100

```
Gln Ser Ile Leu Tyr Glu Lys Glu Lys Tyr Pro His Leu Leu Gly Asn
 1               5                  10                  15

Gln Val Val Lys Lys Pro Ser Val Ala Gly Arg Leu Gln Ile Ile Glu
            20                  25                  30

Lys Asp Gly Lys Lys Tyr Leu Ala Asp Gln Lys Gly Glu Ile Ile Gln
        35                  40                  45

Leu Arg Gly Met Ser Thr His Gly Leu Gln Trp Tyr Gly Asp Ile Ile
    50                  55                  60

Asn Lys Asn Ala Phe Lys Ala Leu Ser Lys Asp Trp Glu Cys Asn Val
65                  70                  75                  80

Ile Arg Leu Ala Met Tyr Val Gly Glu Gly Gly Tyr Ala Ser Asn Pro
```

-continued

```
                85                  90                  95

Ser Ile Lys Glu Lys Val Ile Glu Gly Ile Lys Leu Ala Ile Glu Asn
            100                 105                 110

Asp Met Tyr Val Ile Val Asp Trp His Val Leu Asn Pro Gly Asp Pro
        115                 120                 125

Asn Ala Glu Ile Tyr Lys Gly Ala Lys Asp Phe Phe Lys Glu Ile Ala
    130                 135                 140

Thr Ser Phe Pro Asn Asp Tyr His Ile Ile Tyr Glu Leu Cys Asn Glu
145                 150                 155                 160

Pro Asn Pro Asn Glu Pro Gly Val Glu Asn Ser Leu Asp Gly Trp Lys
                165                 170                 175

Lys Val Lys Ala Tyr Ala Gln Pro Ile Ile Lys Met Leu Arg Ser Leu
            180                 185                 190

Gly Asn Gln Asn Ile Ile Ile Val Gly Ser Pro Asn Trp Ser Gln Arg
        195                 200                 205

Pro Asp Phe Ala Ile Gln Asp Pro Ile Asn Asp Lys Asn Val Met Tyr
    210                 215                 220

Ser Val His Phe Tyr Ser Gly Thr His Lys Val Asp Gly Tyr Val Phe
225                 230                 235                 240

Glu Asn Met Lys Asn Ala Phe Glu Asn Gly Val Pro Ile Phe Val Ser
                245                 250                 255

Glu Trp Gly Thr Ser Leu Ala Ser Gly Asp Gly Gly Pro Tyr Leu Asp
            260                 265                 270

Glu Ala Asp Lys Trp Leu Glu Tyr Leu Asn Ser Asn Tyr Ile Ser Trp
        275                 280                 285

Val Asn Trp Ser Leu Ser Asn Lys Asn Glu Thr Ser Ala Ala Phe Val
    290                 295                 300

Pro Tyr Ile Asn Gly Met His Asp Ala Thr Pro Leu Asp Pro Gly Asp
305                 310                 315                 320

Asp Lys Val Trp Asp Ile Glu Glu Leu Ser Ile Ser Gly Glu Tyr Val
                325                 330                 335

Arg Ala Arg Ile Lys Gly Ile Ala Tyr Gln Pro Ile Lys Arg Asp Asn
            340                 345                 350

Lys Ile Lys Glu Gly Glu Asn Ala Pro Leu Gly Glu Lys Val Leu Pro
        355                 360                 365

Ser Thr Phe Glu Asp Asp Thr Arg Gln Gly Trp Asp Trp Asp Gly Pro
    370                 375                 380

Ser Gly Val Lys Gly Pro Ile Thr Ile Glu Ser Ala Asn Gly Ser Lys
385                 390                 395                 400

Ala Leu Ser Phe Asn Val Glu Tyr Pro Glu Lys Lys Pro Gln Asp Gly
                405                 410                 415

Trp Ala Thr Ala Ala Arg Leu Ile Leu Lys Asp Ile Asn Val Glu Arg
            420                 425                 430

Gly Asn Asn Lys Tyr Leu Ala Phe Asp Phe Tyr Leu Lys Pro Asp Arg
        435                 440                 445

Ala Ser Lys Gly Met Ile Gln Ile Phe Leu Ala Phe Ser Pro Pro Ser
    450                 455                 460

Leu Gly Tyr Trp Ala Gln Val Gln Asp Ser Phe Asn Ile Asp Leu Ala
465                 470                 475                 480

Lys Leu Ser Ser Ala Lys Lys Ile Glu Asp Arg Ile Tyr Lys Phe Asn
                485                 490                 495

Val Phe Phe Asp Leu Asp Lys Ile Gln Asp Asn Lys Val Leu Ser Pro
            500                 505                 510
```

Asp Thr Leu Leu Arg Asp Ile Ile Val Val Ile Ala Asp Gly Asn Ser
        515                 520                 525

Asp Phe Lys Gly Lys Met Tyr Ile Asp Asn Val Arg Phe Thr Asn Ile
    530                 535                 540

Leu Phe Glu
545

<210> SEQ ID NO 101
<211> LENGTH: 1641
<212> TYPE: DNA
<213> ORGANISM: Caldicellulosiruptor bescii

<400> SEQUENCE: 101
cagagcatac tgtatgaaaa ggaaaaatat ccacatcttc ttggcaatca ggtagttaaa 60
aaaccatcgg ttgccggcag actgcagatt attgaaaagg acggaaaaaa gtatttagct 120
gaccagaaag gagaaataat tcagcttcgt ggtatgagta cacatggact tcagtggtat 180
ggtgatatta taaacaaaaa tgcatttaaa gctctttcaa aagattggga gtgcaacgtt 240
ataaggcttg cgatgtatgt gggtgaaggc ggatatgctt caaacccaag tattaaagaa 300
aaagttatag aagggattaa gcttgctatt gagaatgaca tgtatgtaat tgttgactgg 360
catgtattaa atcccggtga cccgaacgca gaaatttata aaggggcaaa agactttttc 420
aaagagatag ctacaagttt tcccaatgac tatcacataa tatatgaact ttgcaatgaa 480
ccaaatccaa atgaaccggg agtagaaaat agcttggatg gctggaaaaa agtaaaggct 540
tatgcacagc ccatcataaa aatgctcaga agtttgggga atcagaacat tataattgta 600
ggttcgccaa actggagtca gagacctgac tttgcaattc aagaccctat aaatgataag 660
aatgttatgt attcagttca tttttactct ggaactcaca aagttgatgg atatgttttt 720
gaaaacatga aaaatgcgtt tgaaaatggc gtgccaattt tcgtgagtga atggggaaca 780
agtttggcaa gcggtgatgg tggaccgtat cttgatgaag cagataagtg gcttgaatat 840
ttaaattcaa actatattag ctgggtgaac tggtcgctgt caaacaaaaa tgagacatca 900
gctgcttttg ttccatatat aaatggtatg catgatgcca caccacttga ccctggtgat 960
gataaggtgt gggacataga agagcttagt atttctggag agtatgtgag ggcaaggata 1020
aaaggaattg cttatcagcc aattaagaga gataacaaaa taaaagaagg agaaaatgca 1080
cctttaggcg aaaaagtctt accatccacg tttgaagatg acactcgtca gggctgggat 1140
tgggatggac catctggtgt gaaaggtcct attactatcg aaagtgcgaa tggttcaaaa 1200
gcgctatctt ttaatgttga gtatccagag aaaaaaccac aagatggctg ggcaacagct 1260
gcaaggctta tacttaaaga cataaatgta gaaaggggaa ataataaata tttggctttt 1320
gatttttatt tgaaaccaga tagggcttca aaaggtatga ttcagatatt tttagctttt 1380
tcaccacctt ccttaggtta ctgggctcag gtacaagaca gttttaatat tgaccttgca 1440
aaactgtcaa gtgcaaaaaa gatagaagac agaatttata agttcaatgt atttttttgac 1500 ttagacaaga tacaagataa taaagtactg agtccagaca cactcttgag agatataata 1560
gtagtcatag cagatggcaa tagcgatttt aaggggaaaa tgtatataga taatgttaga 1620
tttaccaata tcctttttga g 1641

<210> SEQ ID NO 102
<211> LENGTH: 1674
<212> TYPE: DNA
<213> ORGANISM: Caldicellulosiruptor bescii

<400> SEQUENCE: 102
atggcacatc accaccacca tcacgtggat atgcagagca tactgtatga aaaggaaaaa 60
tatccacatc ttcttggcaa tcaggtagtt aaaaaaccat cggttgccgg cagactgcag 120
attattgaaa aggacggaaa aaagtattta gctgaccaga aaggagaaat aattcagctt 180
cgtggtatga gtacacatgg acttcagtgg tatggtgata ttataaacaa aaatgcattt 240
aaagctcttt caaaagattg ggagtgcaac gttataaggc ttgcgatgta tgtgggtgaa 300
ggcggatatg cttcaaaccc aagtattaaa gaaaaagtta tagaagggat taagcttgct 360
attgagaatg acatgtatgt aattgttgac tggcatgtat taaatcccgg tgacccgaac 420
gcagaaattt ataaaggggc aaaagacttt ttcaaagaga tagctacaag ttttcccaat 480
gactatcaca taatatatga actttgcaat gaaccaaatc caaatgaacc gggagtagaa 540
aatagcttgg atggctggaa aaaagtaaag gcttatgcac agcccatcat aaaaatgctc 600
agaagtttgg ggaatcagaa cattataatt gtaggttcgc caaactggag tcagagacct 660
gactttgcaa ttcaagaccc tataaatgat aagaatgtta tgtattcagt tcatttttac 720
tctggaactc acaaagttga tggatatgtt tttgaaaaca tgaaaaatgc gtttgaaaat 780
ggcgtgccaa ttttcgtgag tgaatgggga acaagtttgg caagcggtga tggtggaccg 840
tatcttgatg aagcagataa gtggcttgaa tatttaaatt caaactatat tagctgggtg 900
aactggtcgc tgtcaaacaa aaatgagaca tcagctgctt ttgttccata tataaatggt 960
atgcatgatg ccacaccact tgaccctggt gatgataagg tgtgggacat agaagagctt 1020
agtatttctg gagagtatgt gagggcaagg ataaaaggaa ttgcttatca gccaattaag 1080
agagataaca aaataaaaga aggagaaaat gcacctttag gcgaaaaagt cttaccatcc 1140
acgtttgaag atgacactcg tcagggctgg gattgggatg gaccatctgg tgtgaaaggt 1200
cctattacta tcgaaagtgc gaatggttca aaagcgctat cttttaatgt tgagtatcca 1260
gagaaaaaac cacaagatgg ctgggcaaca gctgcaaggc ttatacttaa agacataaat 1320
gtagaaaggg gaaataataa atatttggct tttgattttt atttgaaacc agatagggct 1380
tcaaaaggta tgattcagat atttttagct tttcaccac cttccttagg ttactgggct 1440
caggtacaag acagttttaa tattgacctt gcaaaactgt caagtgcaaa aaagatagaa 1500
gacagaattt ataagttcaa tgtatttttt gacttagaca agatacaaga taataaagta 1560
ctgagtccag acacactctt gagagatata atagtagtca tagcagatgg caatagcgat 1620
tttaagggga aaatgtatat agataatgtt agatttacca atatcctttt tgag 1674

<210> SEQ ID NO 103
<211> LENGTH: 562
<212> TYPE: PRT
<213> ORGANISM: Caldicellulosiruptor bescii

<400> SEQUENCE: 103

Met Ala His His His His His His Val Asp Asp Asp Asp Lys Met Gln
1 5 10 15

Ser Ile Leu Tyr Glu Lys Glu Lys Tyr Pro His Leu Leu Gly Asn Gln
20 25 30

Val Val Lys Lys Pro Ser Val Ala Gly Arg Leu Gln Ile Ile Glu Lys
35 40 45

Asp Gly Lys Lys Tyr Leu Ala Asp Gln Lys Gly Glu Ile Ile Gln Leu
50 55 60

-continued

```
Arg Gly Met Ser Thr His Gly Leu Gln Trp Tyr Gly Asp Ile Ile Asn
65                  70                  75                  80

Lys Asn Ala Phe Lys Ala Leu Ser Lys Asp Trp Glu Cys Asn Val Ile
                85                  90                  95

Arg Leu Ala Met Tyr Val Gly Glu Gly Gly Tyr Ala Ser Asn Pro Ser
            100                 105                 110

Ile Lys Glu Lys Val Ile Glu Gly Ile Lys Leu Ala Ile Glu Asn Asp
        115                 120                 125

Met Tyr Val Ile Val Asp Trp His Val Leu Asn Pro Gly Asp Pro Asn
    130                 135                 140

Ala Glu Ile Tyr Lys Gly Ala Lys Asp Phe Phe Lys Glu Ile Ala Thr
145                 150                 155                 160

Ser Phe Pro Asn Asp Tyr His Ile Ile Tyr Glu Leu Cys Asn Glu Pro
                165                 170                 175

Asn Pro Asn Glu Pro Gly Val Glu Asn Ser Leu Asp Gly Trp Lys Lys
            180                 185                 190

Val Lys Ala Tyr Ala Gln Pro Ile Ile Lys Met Leu Arg Ser Leu Gly
        195                 200                 205

Asn Gln Asn Ile Ile Ile Val Gly Ser Pro Asn Trp Ser Gln Arg Pro
    210                 215                 220

Asp Phe Ala Ile Gln Asp Pro Ile Asn Asp Lys Asn Val Met Tyr Ser
225                 230                 235                 240

Val His Phe Tyr Ser Gly Thr His Lys Val Asp Gly Tyr Val Phe Glu
                245                 250                 255

Asn Met Lys Asn Ala Phe Glu Asn Gly Val Pro Ile Phe Val Ser Glu
            260                 265                 270

Trp Gly Thr Ser Leu Ala Ser Gly Asp Gly Gly Pro Tyr Leu Asp Glu
        275                 280                 285

Ala Asp Lys Trp Leu Glu Tyr Leu Asn Ser Asn Tyr Ile Ser Trp Val
    290                 295                 300

Asn Trp Ser Leu Ser Asn Lys Asn Glu Thr Ser Ala Ala Phe Val Pro
305                 310                 315                 320

Tyr Ile Asn Gly Met His Asp Ala Thr Pro Leu Asp Pro Gly Asp Asp
                325                 330                 335

Lys Val Trp Asp Ile Glu Glu Leu Ser Ile Ser Gly Glu Tyr Val Arg
            340                 345                 350

Ala Arg Ile Lys Gly Ile Ala Tyr Gln Pro Ile Lys Arg Asp Asn Lys
        355                 360                 365

Ile Lys Glu Gly Glu Asn Ala Pro Leu Gly Glu Lys Val Leu Pro Ser
    370                 375                 380

Thr Phe Glu Asp Asp Thr Arg Gln Gly Trp Asp Trp Asp Gly Pro Ser
385                 390                 395                 400

Gly Val Lys Gly Pro Ile Thr Ile Glu Ser Ala Asn Gly Ser Lys Ala
                405                 410                 415

Leu Ser Phe Asn Val Glu Tyr Pro Glu Lys Lys Pro Gln Asp Gly Trp
            420                 425                 430

Ala Thr Ala Ala Arg Leu Ile Leu Lys Asp Ile Asn Val Glu Arg Gly
        435                 440                 445

Asn Asn Lys Tyr Leu Ala Phe Asp Phe Tyr Leu Lys Pro Asp Arg Ala
    450                 455                 460

Ser Lys Gly Met Ile Gln Ile Phe Leu Ala Phe Ser Pro Pro Ser Leu
465                 470                 475                 480

Gly Tyr Trp Ala Gln Val Gln Asp Ser Phe Asn Ile Asp Leu Ala Lys
```

```
                485                 490                 495

Leu Ser Ser Ala Lys Lys Ile Glu Asp Arg Ile Tyr Lys Phe Asn Val
            500                 505                 510

Phe Phe Asp Leu Asp Lys Ile Gln Asp Asn Lys Val Leu Ser Pro Asp
        515                 520                 525

Thr Leu Leu Arg Asp Ile Ile Val Val Ile Ala Asp Gly Asn Ser Asp
    530                 535                 540

Phe Lys Gly Lys Met Tyr Ile Asp Asn Val Arg Phe Thr Asn Ile Leu
545                 550                 555                 560

Phe Glu


<210> SEQ ID NO 104
<211> LENGTH: 44
<212> TYPE: DNA
<213> ORGANISM: Artificial Sequence
<220> FEATURE:
<223> OTHER INFORMATION: Synthesized Construct

<400> SEQUENCE: 104

gacgacgaca agatgagttt accaaaagga tttctgtggg gtgc                      44


<210> SEQ ID NO 105
<211> LENGTH: 41
<212> TYPE: DNA
<213> ORGANISM: Artificial Sequence
<220> FEATURE:
<223> OTHER INFORMATION: Synthesized Construct

<400> SEQUENCE: 105

gaggagaagc ccggttatga gttttccttt atatactgct g                         41


<210> SEQ ID NO 106
<211> LENGTH: 452
<212> TYPE: PRT
<213> ORGANISM: Caldicellulosiruptor bescii

<400> SEQUENCE: 106

Met Ser Leu Pro Lys Gly Phe Leu Trp Gly Ala Ala Thr Ala Ser Tyr
 1               5                  10                  15

Gln Ile Glu Gly Ala Trp Asn Glu Asp Gly Lys Gly Glu Ser Ile Trp
            20                  25                  30

Asp Arg Phe Thr His Gln Lys Gly Asn Ile Leu Tyr Gly His Asn Gly
        35                  40                  45

Asp Val Ala Cys Asp His Tyr His Arg Phe Glu Glu Asp Val Ser Leu
    50                  55                  60

Met Lys Glu Leu Gly Leu Lys Ala Tyr Arg Phe Ser Ile Ala Trp Ala
65                  70                  75                  80

Arg Ile Phe Pro Asp Gly Phe Gly Thr Val Asn Gln Lys Gly Leu Glu
                85                  90                  95

Phe Tyr Asp Arg Leu Ile Asn Lys Leu Val Glu Asn Gly Ile Glu Pro
            100                 105                 110

Val Val Thr Ile Tyr His Trp Asp Leu Pro Gln Lys Leu Gln Asp Ile
        115                 120                 125

Gly Gly Trp Ala Asn Pro Glu Ile Val Asn Tyr Tyr Phe Glu Tyr Ala
    130                 135                 140

Met Leu Ile Val Asn Arg Tyr Lys Asp Lys Val Lys Lys Trp Ile Thr
145                 150                 155                 160

Phe Asn Glu Pro Tyr Cys Ile Ala Phe Leu Gly His Phe Tyr Gly Val
```

```
                165                 170                 175

His Ala Pro Gly Ile Lys Asp Phe Lys Val Ala Met Asp Val Val His
            180                 185                 190

Asn Ile Met Leu Ser His Phe Lys Val Val Lys Ala Val Lys Glu Asn
        195                 200                 205

Asn Ile Asp Val Glu Val Gly Ile Thr Leu Asn Leu Thr Pro Val Tyr
    210                 215                 220

Phe Gln Thr Glu Arg Leu Gly Tyr Lys Val Ser Glu Ile Glu Arg Glu
225                 230                 235                 240

Met Val Asn Leu Ser Ser Gln Leu Asp Asn Glu Leu Phe Leu Asp Pro
                245                 250                 255

Val Leu Lys Gly Ser Tyr Pro Gln Lys Leu Phe Asp Tyr Leu Val Gln
            260                 265                 270

Lys Asp Leu Leu Glu Thr Gln Lys Val Leu Ser Met Gln Gln Glu Val
        275                 280                 285

Lys Glu Asn Phe Val Phe Pro Asp Phe Leu Gly Ile Asn Tyr Tyr Thr
    290                 295                 300

Arg Ala Val Arg Leu Tyr Asp Glu Asn Ser Asn Trp Ile Phe Pro Ile
305                 310                 315                 320

Arg Trp Glu His Pro Ala Gly Glu Tyr Thr Glu Met Gly Trp Glu Val
                325                 330                 335

Phe Pro Gln Gly Leu Tyr Asp Leu Leu Ile Trp Ile Lys Glu Ser Tyr
            340                 345                 350

Pro Gln Ile Pro Ile Tyr Ile Thr Glu Asn Gly Ala Ala Tyr Asn Asp
        355                 360                 365

Lys Val Glu Asp Gly Arg Val His Asp Gln Lys Arg Val Glu Tyr Leu
    370                 375                 380

Lys Gln His Phe Glu Ala Ala Arg Lys Ala Ile Glu Asn Gly Val Asp
385                 390                 395                 400

Leu Arg Gly Tyr Phe Val Trp Ser Leu Leu Asp Asn Leu Glu Trp Ala
                405                 410                 415

Met Gly Tyr Thr Lys Arg Phe Gly Val Ile Tyr Val Asp Tyr Glu Thr
            420                 425                 430

Gln Lys Arg Ile Lys Lys Asp Ser Phe Tyr Phe Tyr Gln Gln Tyr Ile
        435                 440                 445

Lys Glu Asn Ser
    450


<210> SEQ ID NO 107
<211> LENGTH: 1359
<212> TYPE: DNA
<213> ORGANISM: Caldicellulosiruptor bescii

<400> SEQUENCE: 107

atgagtttac caaaaggatt tctgtggggt gctgcaactg catcatatca gattgagggt      60

gcttggaatg aagatggaaa aggtgaatct atatgggaca ggtttacaca tcaaaaagga     120

aatattttat atggtcataa tggcgacgtt gcctgtgacc actatcatag gttcgaagaa     180

gatgtctctc ttatgaaaga acttggacta aaagcctaca ggttttctat tgcatgggcg     240

agaatttttc cagatggttt cggtactgtg aatcaaaaag gtcttgagtt ttatgataga     300

ctcatcaaca agcttgttga aaacggtatt gaaccggttg tcaccattta tcactgggat     360

cttcctcaaa agctacaaga cattggcggt tgggcaaacc cagaaattgt aaattattat     420

tttgaatatg caatgcttat cgtaaaccgt tataaagaca aagtaaaaaa atggataaca     480
```

-continued

```
tttaatgaac cttattgtat tgccttttttg ggacactttt atggagttca tgcaccagga    540

ataaaagact ttaaagttgc aatggatgtt gtgcacaaca ttatgctttc tcattttaag    600

gttgtaaaag ctgtaaagga aaacaatatt gatgttgagg taggaattac actaaattta    660

actccagttt actttcaaac agagcgtctt ggatataagg taagcgaaat tgaaagagaa    720

atggtaaacc tcagcagcca gcttgacaat gaacttttcc ttgatccagt actcaaagga    780

agctatccac aaaagctgtt tgattacctt gttcaaaaag atttgttgga aactcaaaaa    840

gtattgagta tgcagcagga agtaaaagaa aatttcgttt ttcctgattt tcttggtatc    900

aactactata cacgtgctgt caggctttac gatgaaaatt ctaactggat atttccaata    960

agatgggaac atcctgcagg agagtacacc gagatgggct gggaagtgtt cccacaagga   1020

ctttatgatc ttttgatttg gattaaagaa agttacccac aaattccaat ttatataaca   1080

gaaaacggtg ctgcttataa cgacaaggta gaagatggaa gagttcatga ccaaaagaga   1140

gtggagtatt taaaacagca ctttgaagca gcaagaaagg caattgaaaa tggagtggat   1200

ttgcgaggtt attttgtgtg gtctttgttg gacaatcttg aatgggcaat gggttataca   1260

aaaaggtttg gagttatata tgtggactat gaaacccaaa aaggattaa aaaagacagc   1320

ttctattttt atcagcagta tataaaggaa aactcataa                        1359
```

```
<210> SEQ ID NO 108
<211> LENGTH: 1401
<212> TYPE: DNA
<213> ORGANISM: Caldicellulosiruptor bescii

<400> SEQUENCE: 108
```

```
atggcacatc accaccacca tcacgtggat gacgacgaca agatgagttt accaaaagga     60

tttctgtggg gtgctgcaac tgcatcatat cagattgagg gtgcttggaa tgaagatgga    120

aaaggtgaat ctatatggga caggtttaca catcaaaaag gaaatatttt atatggtcat    180

aatggcgacg ttgcctgtga ccactatcat aggttcgaag aagatgtctc tcttatgaaa    240

gaacttggac taaaagccta caggttttct attgcatggg cgagaatttt tccagatggt    300

ttcggtactg tgaatcaaaa aggtcttgag ttttatgata gactcatcaa caagcttgtt    360

gaaaacggta ttgaaccggt tgtcaccatt tatcactggg atcttcctca aaagctacaa    420

gacattggcg gttgggcaaa cccagaaatt gtaaattatt attttgaata tgcaatgctt    480

atcgtaaacc gttataaaga caaagtaaaa aaatggataa catttaatga accttattgt    540

attgcctttt tgggacactt ttatggagtt catgcaccag gaataaaaga ctttaaagtt    600

gcaatggatg ttgtgcacaa cattatgctt tctcatttta aggttgtaaa agctgtaaag    660

gaaaacaata ttgatgttga ggtaggaatt acactaaatt taactccagt ttactttcaa    720

acagagcgtc ttggatataa ggtaagcgaa attgaaagag aaatggtaaa cctcagcagc    780

cagcttgaca atgaactttt ccttgatcca gtactcaaag gaagctatcc acaaaagctg    840

tttgattacc ttgttcaaaa agatttgttg gaaactcaaa aagtattgag tatgcagcag    900

gaagtaaaag aaaatttcgt tttcctgat tttcttggta tcaactacta tacacgtgct    960

gtcaggcttt acgatgaaaa ttctaactgg atatttccaa taagatggga acatcctgca   1020

ggagagtaca ccgagatggg ctgggaagtg ttcccacaag gactttatga tcttttgatt   1080

tggattaaag aaagttaccc acaaattcca atttatataa cagaaaacgg tgctgcttat   1140

aacgacaagg tagaagatgg aagagttcat gaccaaaaga gagtggagta tttaaaacag   1200
```

cactttgaag cagcaagaaa ggcaattgaa aatggagtgg atttgcgagg ttattttgtg 1260
tggtctttgt tggacaatct tgaatgggca atgggttata caaaaaggtt tggagttata 1320
tatgtggact atgaaaccca aaaaaggatt aaaaaagaca gcttctattt ttatcagcag 1380
tatataaagg aaaactcata a 1401

<210> SEQ ID NO 109
<211> LENGTH: 466
<212> TYPE: PRT
<213> ORGANISM: Caldicellulosiruptor bescii

<400> SEQUENCE: 109

Met Ala His His His His His His Val Asp Asp Asp Asp Lys Met Ser
1 5 10 15

Leu Pro Lys Gly Phe Leu Trp Gly Ala Ala Thr Ala Ser Tyr Gln Ile
20 25 30

Glu Gly Ala Trp Asn Glu Asp Gly Lys Gly Glu Ser Ile Trp Asp Arg
35 40 45

Phe Thr His Gln Lys Gly Asn Ile Leu Tyr Gly His Asn Gly Asp Val
50 55 60

Ala Cys Asp His Tyr His Arg Phe Glu Glu Asp Val Ser Leu Met Lys
65 70 75 80

Glu Leu Gly Leu Lys Ala Tyr Arg Phe Ser Ile Ala Trp Ala Arg Ile
85 90 95

Phe Pro Asp Gly Phe Gly Thr Val Asn Gln Lys Gly Leu Glu Phe Tyr
100 105 110

Asp Arg Leu Ile Asn Lys Leu Val Glu Asn Gly Ile Glu Pro Val Val
115 120 125

Thr Ile Tyr His Trp Asp Leu Pro Gln Lys Leu Gln Asp Ile Gly Gly
130 135 140

Trp Ala Asn Pro Glu Ile Val Asn Tyr Tyr Phe Glu Tyr Ala Met Leu
145 150 155 160

Ile Val Asn Arg Tyr Lys Asp Lys Val Lys Lys Trp Ile Thr Phe Asn
165 170 175

Glu Pro Tyr Cys Ile Ala Phe Leu Gly His Phe Tyr Gly Val His Ala
180 185 190

Pro Gly Ile Lys Asp Phe Lys Val Ala Met Asp Val Val His Asn Ile
195 200 205

Met Leu Ser His Phe Lys Val Val Lys Ala Val Lys Glu Asn Asn Ile
210 215 220

Asp Val Glu Val Gly Ile Thr Leu Asn Leu Thr Pro Val Tyr Phe Gln
225 230 235 240

Thr Glu Arg Leu Gly Tyr Lys Val Ser Glu Ile Glu Arg Glu Met Val
245 250 255

Asn Leu Ser Ser Gln Leu Asp Asn Glu Leu Phe Leu Asp Pro Val Leu
260 265 270

Lys Gly Ser Tyr Pro Gln Lys Leu Phe Asp Tyr Leu Val Gln Lys Asp
275 280 285

Leu Leu Glu Thr Gln Lys Val Leu Ser Met Gln Gln Glu Val Lys Glu
290 295 300

Asn Phe Val Phe Pro Asp Phe Leu Gly Ile Asn Tyr Tyr Thr Arg Ala
305 310 315 320

Val Arg Leu Tyr Asp Glu Asn Ser Asn Trp Ile Phe Pro Ile Arg Trp
325 330 335

```
Glu His Pro Ala Gly Glu Tyr Thr Glu Met Gly Trp Glu Val Phe Pro
            340                 345                 350

Gln Gly Leu Tyr Asp Leu Leu Ile Trp Ile Lys Glu Ser Tyr Pro Gln
        355                 360                 365

Ile Pro Ile Tyr Ile Thr Glu Asn Gly Ala Ala Tyr Asn Asp Lys Val
    370                 375                 380

Glu Asp Gly Arg Val His Asp Gln Lys Arg Val Glu Tyr Leu Lys Gln
385                 390                 395                 400

His Phe Glu Ala Ala Arg Lys Ala Ile Glu Asn Gly Val Asp Leu Arg
                405                 410                 415

Gly Tyr Phe Val Trp Ser Leu Leu Asp Asn Leu Glu Trp Ala Met Gly
            420                 425                 430

Tyr Thr Lys Arg Phe Gly Val Ile Tyr Val Asp Tyr Glu Thr Gln Lys
        435                 440                 445

Arg Ile Lys Lys Asp Ser Phe Tyr Phe Tyr Gln Gln Tyr Ile Lys Glu
    450                 455                 460

Asn Ser
465
```

<210> SEQ ID NO 110
<211> LENGTH: 3282
<212> TYPE: DNA
<213> ORGANISM: Caldicellulosiruptor bescii

<400> SEQUENCE: 110

```
ggtgcctctt cagtacctac ttcaacacca acaccgacac caactgctac accaacagca     60

acaccaacac caacactgac tccaacaccg acacctacac caacaccaac gtcaacacca    120

actgctacac caacagcaac gccaacacca acaccgacgc cgagcagcac acctgtagca    180

ggtggacaga taaaggtatt gtatgctaac aaggagacaa atagcacaac aaatacgata    240

aggccatggt tgaaggtagt gaacactgga agcagcagca tagatttgag cagggtaacg    300

ataaggtact ggtacacggt agatggggac aaggcacaga gtgcgatatc agactgggca    360

cagataggag caagcaatgt gacattcaag tttgtgaagc tgagcagtag cgtaagtgga    420

gcggactatt atttagagat aggatttaag agtggagctg ggcagttgca ggctggtaaa    480

gacacagggg agatacagat aaggtttaac aagagtgact ggagcaatta caatcagggg    540

aatgactggt catggatgca gagcatgacg agttatggag agaatgtgaa ggtaacagcg    600

tatatagatg gtgtattggt atggggacag gagccgagtg gagcgacacc aacaccgaca    660

gcaacaccag caccaacacc aaccccgacc ccaacaccaa ctgctacacc aacgccaaca    720

ccgactccaa caccaacacc aactgctacc ccaacaccga cgccgagcag tacacctgta    780

gcaggtggac agataaaggt attgtatgct aacaaggaga caaatagcac aacaaacacg    840

ataaggccat ggttgaaggt agtgaacact ggaagcagca gcatagattt gagcagggta    900

acgataaggt actggtacac ggtagatggg gacaaggcac agagtgcgat atcagactgg    960

gcacagatag gagcaagcaa tgtgacattc aagtttgtga agctgagcag tagcgtaagt   1020

ggagcggact attatttaga gataggattt aagagtggag ctgggcagtt gcaggctggt   1080

aaagacacag gggagataca gataaggttt aacaagagtg actggagcaa ttacaatcag   1140

gggaatgact ggtcatggat gcagagcatg acgagttatg gagagaatgt gaaggtaaca   1200

gcgtatatag atggtgtatt ggtatgggga caggagccga gtggagcgac accaacaccg   1260

acagcaacac cagcaccaac accaaccccg accccaacac caactgctac accaacgcca   1320
```

acaccgactc caacaccaac accaactgct accccaacac cgacgccgag cagtacacct 1380
gtagcaggtg gacagataaa ggtattgtat gctaacaagg agacaaatag cacaacaaac 1440
acgataaggc catggttgaa ggtagtgaac actggaagca gcagcataga tttgagcagg 1500
gtaacgataa ggtactggta cacggtagat ggggacaagg cacagagtgc gatatcagac 1560
tgggcacaga taggagcaag caatgtgaca ttcaagtttg tgaagctgag cagtagcgta 1620
agtggagcgg actattattt agagatagga tttaagagtg gagctgggca gttgcaggct 1680
ggtaaagaca caggggagat acagataagg tttaacaaga gtgactggag caattacaat 1740
caggggaatg actggtcatg gatgcagagc atgacgagtt atggagagaa tgtgaaggta 1800
acagcgtata tagatggtgt attggtatgg ggacaggagc cgagtggagc gacaccaaca 1860
ccgacagcaa caccagcacc gacagtgaca ccgacagcaa caccagcacc aacaccaacc 1920
ccgaccccaa cagtaacggc aaccccgaca ccgacaccaa caccggtgca gacagtaata 1980
ccaatgccaa cagtaactcc aaatccaaca tcaacaccga gtattcttga tgatacaaat 2040
gatgattggc tttatgtaag tggtaataaa atagttgata aagatggtaa accggtatgg 2100
ttaacaggta ttaactggtt tggatacaat acaggtacaa atgtttttga tggtgtatgg 2160
agttgcaatc taaaagatac tctagctgaa atagccaata gaggctttaa tttgctaaga 2220
attccaatat cagccgagat tatactgaac tggtcgcaag gtatttatcc aaaaccaaat 2280
ataaactact acgttaatcc agagcttgag ggcaaaaaca gtcttgaagt atttgacata 2340
gttgtacaaa tatgtaaaga agttggtttg aaaattatgt tggatattca cagcataaaa 2400
acagacgcaa tgggacatat ctatccagta tggtatgatg ataaatttac tccagaggat 2460
ttttataagg cgtgtgagtg gattacaaat agatataaaa atgatgatac tattatagct 2520
tttgacctaa aaaatgagcc acatggaaaa ccatggcaag acacaacatt tgcaaaatgg 2580
gataattcaa cagatattaa taattggaaa tatgcggctg aaacatgtgc gaaacgtata 2640
ctaaatataa atccaaacct tcttattgta atagaaggaa ttgaagcgta tccaaaagat 2700
gacgttacat ggacatcaaa atcctatagc gattactatt caacatggtg ggcggtaac 2760 ttgcgaggtg ttaaaaagta tcctattaat ctgggtaaat atcaaaataa agtagtatat 2820
tcacctcatg attacggacc ctctgtttac cagcagccgt ggttttatcc aggcttcaca 2880
aaagaatctt tactacaaga ttgttggcgt ccgaattggg cttacatcat ggaagaaaac 2940
attgcgccgc tgctgatagg tgaatggggt ggttatcttg atggagctga taacgaaaag 3000
tggatgagat atctacgaga ttatattata gagaatcata ttcatcacac attttggtgc 3060
tttaatgcta actcaggtga cactggaggt atggttggat acgattttac gacatgggat 3120
gaaaaaaaat actcattttt aaagccggct ctttggcaag acagtcaagg taggtttgtt 3180
ggattagatc acaagcgacc cttaggtaca aatgggaaaa acattaatat tacaatatac 3240
tacaacaata atgaaccagc gccagttcca gccgcaaaat aa 3282

<210> SEQ ID NO 111
<211> LENGTH: 1093
<212> TYPE: PRT
<213> ORGANISM: Caldicellulosiruptor bescii

<400> SEQUENCE: 111

Gly Ala Ser Ser Val Pro Thr Ser Thr Pro Thr Pro Thr Pro Thr Ala
1 5 10 15

Thr Pro Thr Ala Thr Pro Thr Pro Thr Leu Thr Pro Thr Pro Thr Pro
20 25 30

```
Thr Pro Thr Pro Thr Ser Thr Pro Thr Ala Thr Pro Thr Ala Thr Pro
        35                  40                  45

Thr Pro Thr Pro Thr Pro Ser Ser Thr Pro Val Ala Gly Gly Gln Ile
    50                  55                  60

Lys Val Leu Tyr Ala Asn Lys Glu Thr Asn Ser Thr Thr Asn Thr Ile
65                  70                  75                  80

Arg Pro Trp Leu Lys Val Val Asn Thr Gly Ser Ser Ser Ile Asp Leu
                85                  90                  95

Ser Arg Val Thr Ile Arg Tyr Trp Tyr Thr Val Asp Gly Asp Lys Ala
            100                 105                 110

Gln Ser Ala Ile Ser Asp Trp Ala Gln Ile Gly Ala Ser Asn Val Thr
        115                 120                 125

Phe Lys Phe Val Lys Leu Ser Ser Ser Val Ser Gly Ala Asp Tyr Tyr
    130                 135                 140

Leu Glu Ile Gly Phe Lys Ser Gly Ala Gly Gln Leu Gln Ala Gly Lys
145                 150                 155                 160

Asp Thr Gly Glu Ile Gln Ile Arg Phe Asn Lys Ser Asp Trp Ser Asn
                165                 170                 175

Tyr Asn Gln Gly Asn Asp Trp Ser Trp Met Gln Ser Met Thr Ser Tyr
            180                 185                 190

Gly Glu Asn Val Lys Val Thr Ala Tyr Ile Asp Gly Val Leu Val Trp
        195                 200                 205

Gly Gln Glu Pro Ser Gly Ala Thr Pro Thr Pro Thr Ala Thr Pro Ala
    210                 215                 220

Pro Thr Pro Thr Pro Thr Pro Thr Pro Thr Ala Thr Pro Thr Pro Thr
225                 230                 235                 240

Pro Thr Pro Thr Pro Thr Pro Thr Ala Thr Pro Thr Pro Thr Pro Ser
                245                 250                 255

Ser Thr Pro Val Ala Gly Gly Gln Ile Lys Val Leu Tyr Ala Asn Lys
            260                 265                 270

Glu Thr Asn Ser Thr Thr Asn Thr Ile Arg Pro Trp Leu Lys Val Val
        275                 280                 285

Asn Thr Gly Ser Ser Ser Ile Asp Leu Ser Arg Val Thr Ile Arg Tyr
    290                 295                 300

Trp Tyr Thr Val Asp Gly Asp Lys Ala Gln Ser Ala Ile Ser Asp Trp
305                 310                 315                 320

Ala Gln Ile Gly Ala Ser Asn Val Thr Phe Lys Phe Val Lys Leu Ser
                325                 330                 335

Ser Ser Val Ser Gly Ala Asp Tyr Tyr Leu Glu Ile Gly Phe Lys Ser
            340                 345                 350

Gly Ala Gly Gln Leu Gln Ala Gly Lys Asp Thr Gly Glu Ile Gln Ile
        355                 360                 365

Arg Phe Asn Lys Ser Asp Trp Ser Asn Tyr Asn Gln Gly Asn Asp Trp
    370                 375                 380

Ser Trp Met Gln Ser Met Thr Ser Tyr Gly Glu Asn Val Lys Val Thr
385                 390                 395                 400

Ala Tyr Ile Asp Gly Val Leu Val Trp Gly Gln Glu Pro Ser Gly Ala
                405                 410                 415

Thr Pro Thr Pro Thr Ala Thr Pro Ala Pro Thr Pro Thr Pro Thr Pro
            420                 425                 430

Thr Pro Thr Ala Thr Pro Thr Pro Thr Pro Thr Pro Thr Pro Thr Pro
        435                 440                 445
```

```
Thr Ala Thr Pro Thr Pro Thr Pro Ser Ser Thr Pro Val Ala Gly Gly
    450                 455                 460

Gln Ile Lys Val Leu Tyr Ala Asn Lys Glu Thr Asn Ser Thr Thr Asn
465                 470                 475                 480

Thr Ile Arg Pro Trp Leu Lys Val Val Asn Thr Gly Ser Ser Ser Ile
                485                 490                 495

Asp Leu Ser Arg Val Thr Ile Arg Tyr Trp Tyr Thr Val Asp Gly Asp
            500                 505                 510

Lys Ala Gln Ser Ala Ile Ser Asp Trp Ala Gln Ile Gly Ala Ser Asn
        515                 520                 525

Val Thr Phe Lys Phe Val Lys Leu Ser Ser Ser Val Ser Gly Ala Asp
    530                 535                 540

Tyr Tyr Leu Glu Ile Gly Phe Lys Ser Gly Ala Gly Gln Leu Gln Ala
545                 550                 555                 560

Gly Lys Asp Thr Gly Glu Ile Gln Ile Arg Phe Asn Lys Ser Asp Trp
                565                 570                 575

Ser Asn Tyr Asn Gln Gly Asn Asp Trp Ser Trp Met Gln Ser Met Thr
            580                 585                 590

Ser Tyr Gly Glu Asn Val Lys Val Thr Ala Tyr Ile Asp Gly Val Leu
        595                 600                 605

Val Trp Gly Gln Glu Pro Ser Gly Ala Thr Pro Thr Pro Thr Ala Thr
    610                 615                 620

Pro Ala Pro Thr Val Thr Pro Thr Ala Thr Pro Ala Pro Thr Pro Thr
625                 630                 635                 640

Pro Thr Pro Thr Val Thr Ala Thr Pro Thr Pro Thr Pro Thr Pro Val
                645                 650                 655

Gln Thr Val Ile Pro Met Pro Thr Val Thr Pro Asn Pro Thr Ser Thr
            660                 665                 670

Pro Ser Ile Leu Asp Asp Thr Asn Asp Asp Trp Leu Tyr Val Ser Gly
        675                 680                 685

Asn Lys Ile Val Asp Lys Asp Gly Lys Pro Val Trp Leu Thr Gly Ile
    690                 695                 700

Asn Trp Phe Gly Tyr Asn Thr Gly Thr Asn Val Phe Asp Gly Val Trp
705                 710                 715                 720

Ser Cys Asn Leu Lys Asp Thr Leu Ala Glu Ile Ala Asn Arg Gly Phe
                725                 730                 735

Asn Leu Leu Arg Ile Pro Ile Ser Ala Glu Ile Ile Leu Asn Trp Ser
            740                 745                 750

Gln Gly Ile Tyr Pro Lys Pro Asn Ile Asn Tyr Tyr Val Asn Pro Glu
        755                 760                 765

Leu Glu Gly Lys Asn Ser Leu Glu Val Phe Asp Ile Val Val Gln Ile
    770                 775                 780

Cys Lys Glu Val Gly Leu Lys Ile Met Leu Asp Ile His Ser Ile Lys
785                 790                 795                 800

Thr Asp Ala Met Gly His Ile Tyr Pro Val Trp Tyr Asp Asp Lys Phe
                805                 810                 815

Thr Pro Glu Asp Phe Tyr Lys Ala Cys Glu Trp Ile Thr Asn Arg Tyr
            820                 825                 830

Lys Asn Asp Asp Thr Ile Ile Ala Phe Asp Leu Lys Asn Glu Pro His
        835                 840                 845

Gly Lys Pro Trp Gln Asp Thr Thr Phe Ala Lys Trp Asp Asn Ser Thr
    850                 855                 860

Asp Ile Asn Asn Trp Lys Tyr Ala Ala Glu Thr Cys Ala Lys Arg Ile
```

-continued

```
865                 870                 875                 880

Leu Asn Ile Asn Pro Asn Leu Leu Ile Val Ile Glu Gly Ile Glu Ala
                885                 890                 895

Tyr Pro Lys Asp Asp Val Thr Trp Thr Ser Lys Ser Tyr Ser Asp Tyr
            900                 905                 910

Tyr Ser Thr Trp Trp Gly Gly Asn Leu Arg Gly Val Lys Lys Tyr Pro
        915                 920                 925

Ile Asn Leu Gly Lys Tyr Gln Asn Lys Val Val Tyr Ser Pro His Asp
    930                 935                 940

Tyr Gly Pro Ser Val Tyr Gln Gln Pro Trp Phe Tyr Pro Gly Phe Thr
945                 950                 955                 960

Lys Glu Ser Leu Leu Gln Asp Cys Trp Arg Pro Asn Trp Ala Tyr Ile
                965                 970                 975

Met Glu Glu Asn Ile Ala Pro Leu Leu Ile Gly Glu Trp Gly Gly Tyr
            980                 985                 990

Leu Asp Gly Ala Asp Asn Glu Lys Trp Met Arg Tyr Leu Arg Asp Tyr
        995                 1000                1005

Ile Ile Glu Asn His Ile His His Thr Phe Trp Cys Phe Asn Ala Asn
    1010                1015                1020

Ser Gly Asp Thr Gly Gly Met Val Gly Tyr Asp Phe Thr Thr Trp Asp
1025                1030                1035                1040

Glu Lys Lys Tyr Ser Phe Leu Lys Pro Ala Leu Trp Gln Asp Ser Gln
                1045                1050                1055

Gly Arg Phe Val Gly Leu Asp His Lys Arg Pro Leu Gly Thr Asn Gly
            1060                1065                1070

Lys Asn Ile Asn Ile Thr Ile Tyr Tyr Asn Asn Asn Glu Pro Ala Pro
        1075                1080                1085

Val Pro Ala Ala Lys
    1090


<210> SEQ ID NO 112
<211> LENGTH: 3003
<212> TYPE: DNA
<213> ORGANISM: Caldicellulosiruptor bescii

<400> SEQUENCE: 112

gtagggtact tggacatggt aaacaattgg gaccccaata atccaactcc atgggggcaa      60

tggtataaaa ctaatgcgat tggtgcctct tcagtaccta cttcaacacc aacaccgaca     120

ccaactgcta caccaacagc aacgccaaca ccaacaccga cgccgagcag cacacctgta     180

gcaggtggac agataaaggt attgtatgct aacaaggaga caaatagcac aacaaatacg     240

ataaggccat ggttgaaggt agtgaacact ggaagcagca gcatagattt gagcagggta     300

acgataaggt actggtacac ggtagatggg gacaaggcac agagtgcgat atcagactgg     360

gcacagatag gagcaagcaa tgtgacattc aagtttgtga agctgagcag tagcgtaagt     420

ggagcggact attatttaga gataggattt aagagtggag ctgggcagtt gcaggctggt     480

aaagacacag gggagataca gataaggttt aacaagagtg actggagcaa ttacaatcag     540

gggaatgact ggtcatggat gcagagcatg acgagttatg gagagaatgt gaaggtaaca     600

gcgtatatag atggtgtatt ggtatgggga caggagccga gtggagcgac accaacaccg     660

acagcaacac cagcaccgac agtgacaccg acagcaacac cagcaccaac accaaccccg     720

accccaacac caactgctac accaacgcca acaccgactc caacaccaac accaactgct     780

accccaacac cgacgccgag cagtacacct gtagcaggtg gacagataaa ggtactgtat     840
```

```
gctaacaagg agacaaatag cacaacaaac acgataaggc catggttgaa ggtagtgaac    900
actggaagca gcagcataga tttgagcagg gtaacgataa ggtactggta cacggtagat    960
ggggacaagg cacagagtgc gatatcagac tgggcacaga taggagcaag caatgtgaca   1020
ttcaagtttg tgaagctgag cagtagcgta agtggagcgg actattattt agagatagga   1080
tttaagagtg gagctgggca gttgcaggct ggtaaagaca caggggagat acagataagg   1140
tttaacaaga gtgactggag caattacaat caggggaatg actggtcatg gatgcagagc   1200
atgacgagtt atggagagaa tgtgaaggta acagcgtata tagatggtgt attggtatgg   1260
ggacaggagc cgagtggagc gacaccaaca ccgacagcaa caccagcacc aacatcgaca   1320
tcgacgccaa caccgacagt aacaccaacc ccgaccccaa caccaactgc tacaccaaca   1380
cccacggcaa cgtcaattcc attaccaaca gtatcaccat cgtcggctgt tattgaaata   1440
gcaataaata caaataaaga taggtcacca attagcccgt acatttatgg tgcaaaccag   1500
gatattggag gtgtagttca tcctgcaaga aggttaggtg gaaacagact aacaggatac   1560
aattgggaaa acaacttttc aaatgcgggg aacgattggt atcattcaag tgacgattat   1620
ttgtgctgga gcatgggaat ttctggtgaa gatgcgaagg ttccagcagc agtggtatct   1680
aaatttcatg agtattccct taaaaataat gcttattctg ctataacttt gcaaatggca   1740
ggatatgtgt caaaagataa ttatggtact gttagtgaaa atgaaacagc tccatctaac   1800
aggtgggcag aggtaaaatt taagaaggat gctcctttat ctttgaatcc agacttgaat   1860
gataactttg tttatatgga tgaattcata aattatttga taaacaaata cggaatggct   1920
tcttcaccta ccgggataaa agggtatata cttgataatg agcctgattt gtgggtctca   1980
acacatcccc gtatacatcc taataaggtc acatgcaaag agttgattga taaatctgtt   2040
gaactggcaa aagttataaa aacccttgat ccatcagctg aagtttttgg atatgcatca   2100
tatgggttta tgggttatta tagtctccaa gatgcgcctg attggaacca agttaaagga   2160
gatcatagat ggtttataag ctggtatctg gaacagatga aaaaagcatc agacagttat   2220
ggaaaaagat tattagatgt gcttgattta cactggtatc cagaagcacg aggtggaaat   2280
attcgcgtgt gctttgatgg cgaaaatgac acatcaaaag aagttgctat agctaggatg   2340
caagctccaa gaacactatg ggacccgacc tacaaaacat cagtgaaagg gcaaattaca   2400
gctggtgaga acagctggat aaaccagtgg ttttcagatt atttgcctat aattccaaac   2460
ataaaagcgg acatagagaa atattatcct ggtacaaaac ttgctattag cgaattcgat   2520
tatggcggtc gaaatcatat ttcaggggga attgctttag ctgatgtgct cggtatattt   2580
ggtaaatatg gagtgtactt tgcagcaaga tggggcgatt ctggtagtta tgcagcagct   2640
gcatataaca tttatcttaa ttatgatgga aaaggctcaa aatatggcaa tacaaatgta   2700
ggtgctaata caaatgatgt tgaaaatatg ccagtttatg cttcaataaa tggacaggat   2760
gattctgaac ttcatattat actaataaac agaaactatg acagaaaatt gcctgcgaag   2820
atcagcatta caagttcaaa aaactataca aaagcagaaa tttatggttt tgatagcaat   2880
agtcctactg ttagaaaaat gggaagtgtg gataatatcg aaaacaatgt tttaactctt   2940
gaggtaccta atttaacagt tttccatatc gttttatatt caacctcagt acaaactaaa   3000
taa                                                                 3003
```

<210> SEQ ID NO 113
<211> LENGTH: 1000
<212> TYPE: PRT

<213> ORGANISM: Caldicellulosiruptor bescii

<400> SEQUENCE: 113

Val Gly Tyr Leu Asp Met Val Asn Asn Trp Asp Pro Asn Asn Pro Thr
1 5 10 15

Pro Trp Gly Gln Trp Tyr Lys Thr Asn Ala Ile Gly Ala Ser Ser Val
20 25 30

Pro Thr Ser Thr Pro Thr Pro Thr Pro Thr Ala Thr Pro Thr Ala Thr
35 40 45

Pro Thr Pro Thr Pro Thr Pro Ser Ser Thr Pro Val Ala Gly Gly Gln
50 55 60

Ile Lys Val Leu Tyr Ala Asn Lys Glu Thr Asn Ser Thr Thr Asn Thr
65 70 75 80

Ile Arg Pro Trp Leu Lys Val Val Asn Thr Gly Ser Ser Ser Ile Asp
85 90 95

Leu Ser Arg Val Thr Ile Arg Tyr Trp Tyr Thr Val Asp Gly Asp Lys
100 105 110

Ala Gln Ser Ala Ile Ser Asp Trp Ala Gln Ile Gly Ala Ser Asn Val
115 120 125

Thr Phe Lys Phe Val Lys Leu Ser Ser Ser Val Ser Gly Ala Asp Tyr
130 135 140

Tyr Leu Glu Ile Gly Phe Lys Ser Gly Ala Gly Gln Leu Gln Ala Gly
145 150 155 160

Lys Asp Thr Gly Glu Ile Gln Ile Arg Phe Asn Lys Ser Asp Trp Ser
165 170 175

Asn Tyr Asn Gln Gly Asn Asp Trp Ser Trp Met Gln Ser Met Thr Ser
180 185 190

Tyr Gly Glu Asn Val Lys Val Thr Ala Tyr Ile Asp Gly Val Leu Val
195 200 205

Trp Gly Gln Glu Pro Ser Gly Ala Thr Pro Thr Pro Thr Ala Thr Pro
210 215 220

Ala Pro Thr Val Thr Pro Thr Ala Thr Pro Ala Pro Thr Pro Thr Pro
225 230 235 240

Thr Pro Thr Pro Thr Ala Thr Pro Thr Pro Thr Pro Thr Pro Thr Pro
245 250 255

Thr Pro Thr Ala Thr Pro Thr Pro Thr Pro Ser Ser Thr Pro Val Ala
260 265 270

Gly Gly Gln Ile Lys Val Leu Tyr Ala Asn Lys Glu Thr Asn Ser Thr
275 280 285

Thr Asn Thr Ile Arg Pro Trp Leu Lys Val Val Asn Thr Gly Ser Ser
290 295 300

Ser Ile Asp Leu Ser Arg Val Thr Ile Arg Tyr Trp Tyr Thr Val Asp
305 310 315 320

Gly Asp Lys Ala Gln Ser Ala Ile Ser Asp Trp Ala Gln Ile Gly Ala
325 330 335

Ser Asn Val Thr Phe Lys Phe Val Lys Leu Ser Ser Ser Val Ser Gly
340 345 350

Ala Asp Tyr Tyr Leu Glu Ile Gly Phe Lys Ser Gly Ala Gly Gln Leu
355 360 365

Gln Ala Gly Lys Asp Thr Gly Glu Ile Gln Ile Arg Phe Asn Lys Ser
370 375 380

Asp Trp Ser Asn Tyr Asn Gln Gly Asn Asp Trp Ser Trp Met Gln Ser
385 390 395 400

-continued

```
Met Thr Ser Tyr Gly Glu Asn Val Lys Val Thr Ala Tyr Ile Asp Gly
                405                 410                 415

Val Leu Val Trp Gly Gln Glu Pro Ser Gly Ala Thr Pro Thr Pro Thr
            420                 425                 430

Ala Thr Pro Ala Pro Thr Ser Thr Ser Thr Pro Thr Pro Thr Val Thr
        435                 440                 445

Pro Thr Pro Thr Pro Thr Pro Thr Ala Thr Pro Thr Pro Thr Ala Thr
    450                 455                 460

Ser Ile Pro Leu Pro Thr Val Ser Pro Ser Ser Ala Val Ile Glu Ile
465                 470                 475                 480

Ala Ile Asn Thr Asn Lys Asp Arg Ser Pro Ile Ser Pro Tyr Ile Tyr
                485                 490                 495

Gly Ala Asn Gln Asp Ile Gly Gly Val Val His Pro Ala Arg Arg Leu
            500                 505                 510

Gly Gly Asn Arg Leu Thr Gly Tyr Asn Trp Glu Asn Asn Phe Ser Asn
        515                 520                 525

Ala Gly Asn Asp Trp Tyr His Ser Ser Asp Asp Tyr Leu Cys Trp Ser
    530                 535                 540

Met Gly Ile Ser Gly Glu Asp Ala Lys Val Pro Ala Ala Val Val Ser
545                 550                 555                 560

Lys Phe His Glu Tyr Ser Leu Lys Asn Asn Ala Tyr Ser Ala Ile Thr
                565                 570                 575

Leu Gln Met Ala Gly Tyr Val Ser Lys Asp Asn Tyr Gly Thr Val Ser
            580                 585                 590

Glu Asn Glu Thr Ala Pro Ser Asn Arg Trp Ala Glu Val Lys Phe Lys
        595                 600                 605

Lys Asp Ala Pro Leu Ser Leu Asn Pro Asp Leu Asn Asp Asn Phe Val
    610                 615                 620

Tyr Met Asp Glu Phe Ile Asn Tyr Leu Ile Asn Lys Tyr Gly Met Ala
625                 630                 635                 640

Ser Ser Pro Thr Gly Ile Lys Gly Tyr Ile Leu Asp Asn Glu Pro Asp
                645                 650                 655

Leu Trp Val Ser Thr His Pro Arg Ile His Pro Asn Lys Val Thr Cys
            660                 665                 670

Lys Glu Leu Ile Asp Lys Ser Val Glu Leu Ala Lys Val Ile Lys Thr
        675                 680                 685

Leu Asp Pro Ser Ala Glu Val Phe Gly Tyr Ala Ser Tyr Gly Phe Met
    690                 695                 700

Gly Tyr Tyr Ser Leu Gln Asp Ala Pro Asp Trp Asn Gln Val Lys Gly
705                 710                 715                 720

Asp His Arg Trp Phe Ile Ser Trp Tyr Leu Glu Gln Met Lys Lys Ala
                725                 730                 735

Ser Asp Ser Tyr Gly Lys Arg Leu Leu Asp Val Leu Asp Leu His Trp
            740                 745                 750

Tyr Pro Glu Ala Arg Gly Gly Asn Ile Arg Val Cys Phe Asp Gly Glu
        755                 760                 765

Asn Asp Thr Ser Lys Glu Val Ala Ile Ala Arg Met Gln Ala Pro Arg
    770                 775                 780

Thr Leu Trp Asp Pro Thr Tyr Lys Thr Ser Val Lys Gly Gln Ile Thr
785                 790                 795                 800

Ala Gly Glu Asn Ser Trp Ile Asn Gln Trp Phe Ser Asp Tyr Leu Pro
                805                 810                 815

Ile Ile Pro Asn Ile Lys Ala Asp Ile Glu Lys Tyr Tyr Pro Gly Thr
```

820 825 830

Lys Leu Ala Ile Ser Glu Phe Asp Tyr Gly Gly Arg Asn His Ile Ser
835 840 845

Gly Gly Ile Ala Leu Ala Asp Val Leu Gly Ile Phe Gly Lys Tyr Gly
850 855 860

Val Tyr Phe Ala Ala Arg Trp Gly Asp Ser Gly Ser Tyr Ala Ala Ala
865 870 875 880

Ala Tyr Asn Ile Tyr Leu Asn Tyr Asp Gly Lys Gly Ser Lys Tyr Gly
885 890 895

Asn Thr Asn Val Gly Ala Asn Thr Asn Asp Val Glu Asn Met Pro Val
900 905 910

Tyr Ala Ser Ile Asn Gly Gln Asp Asp Ser Glu Leu His Ile Ile Leu
915 920 925

Ile Asn Arg Asn Tyr Asp Arg Lys Leu Pro Ala Lys Ile Ser Ile Thr
930 935 940

Ser Ser Lys Asn Tyr Thr Lys Ala Glu Ile Tyr Gly Phe Asp Ser Asn
945 950 955 960

Ser Pro Thr Val Arg Lys Met Gly Ser Val Asp Asn Ile Glu Asn Asn
965 970 975

Val Leu Thr Leu Glu Val Pro Asn Leu Thr Val Phe His Ile Val Leu
980 985 990

Tyr Ser Thr Ser Val Gln Thr Lys
995 1000

<210> SEQ ID NO 114
<211> LENGTH: 1332
<212> TYPE: PRT
<213> ORGANISM: Caldicellulosiruptor bescii

<400> SEQUENCE: 114

Ala Thr Thr Phe Asn Tyr Gly Glu Ala Leu Gln Lys Ala Ile Met Phe
1 5 10 15

Tyr Glu Phe Gln Met Ser Gly Lys Leu Pro Ser Trp Ile Arg Asn Asn
20 25 30

Trp Arg Gly Asp Ser Gly Leu Asn Asp Gly Lys Asp Val Gly Leu Asp
35 40 45

Leu Thr Gly Gly Trp His Asp Ala Gly Asp His Val Lys Phe Asn Leu
50 55 60

Pro Met Ser Tyr Ser Ala Ser Met Leu Ser Trp Ala Val Tyr Glu Tyr
65 70 75 80

Lys Ala Ala Phe Glu Lys Ser Gly Gln Leu Glu His Ile Leu Asn Gln
85 90 95

Ile Glu Trp Val Asn Asp Tyr Phe Val Lys Cys His Pro Ser Lys Tyr
100 105 110

Val Tyr Tyr Tyr Gln Val Gly Asp Pro Ile Glu Asp His Asn Phe Trp
115 120 125

Gly Pro Ala Glu Val Met Gln Met Lys Arg Pro Ala Tyr Lys Cys Asp
130 135 140

Leu Asn Asn Pro Ala Ser Ser Val Val Ala Glu Thr Ala Ala Ser Leu
145 150 155 160

Ala Ala Ala Ser Ile Val Ile Arg Glu Arg Asn Ser Gln Lys Ala Asp
165 170 175

Thr Tyr Leu Gln His Ala Met Val Leu Phe Asp Phe Ala Asp Arg Thr
180 185 190

```
Arg Ser Asp Ala Gly Tyr Thr Ala Ala Thr Gly Phe Tyr Thr Ser Gly
        195                 200                 205

Gly Phe Ile Asp Asp Leu Gly Trp Ala Ala Val Trp Leu Tyr Leu Ala
    210                 215                 220

Thr Asn Asp Lys Ser Tyr Leu Asp Lys Ala Glu Ala Leu Met Ala Glu
225                 230                 235                 240

Tyr Ala Gly Gly Thr Asn Thr Trp Thr Gln Cys Trp Asp Asp Val Arg
                245                 250                 255

Tyr Gly Ala Ile Leu Leu Leu Ala Lys Ile Thr Asn Lys Asp Ile Tyr
            260                 265                 270

Lys Gly Ala Val Glu Arg Asn Leu Asp His Trp Thr Tyr Asn Ile Thr
        275                 280                 285

Tyr Thr Pro Lys Gly Leu Ala Trp Ile Thr Gly Trp Gly Ser Leu Arg
    290                 295                 300

Tyr Ala Thr Thr Ala Ala Phe Leu Ala Phe Val Tyr Ala Asp Trp Ser
305                 310                 315                 320

Gly Cys Pro Glu Asn Lys Arg Thr Ala Tyr Leu Lys Phe Gly Glu Ser
                325                 330                 335

Gln Ile Asn Tyr Ala Leu Gly Ser Thr Gly Arg Ser Phe Leu Val Gly
            340                 345                 350

Phe Gly Gln Asn Tyr Pro Gln His Pro His His Arg Asn Ala His Ser
        355                 360                 365

Ser Trp Ala Asn Ser Met Arg Ile Pro Glu Tyr His Arg His Ile Leu
    370                 375                 380

Tyr Gly Ala Leu Val Gly Gly Pro Gly Ser Asp Asp Ser Tyr Asn Asp
385                 390                 395                 400

Asp Ile Thr Asp Tyr Val Gln Asn Glu Val Ala Cys Asp Tyr Asn Ala
                405                 410                 415

Gly Ile Val Gly Ala Leu Ala Lys Met Tyr Leu Met Tyr Gly Gly Asp
            420                 425                 430

Pro Ile Pro Asn Phe Lys Ala Ile Glu Lys Pro Thr Asn Asp Glu Ile
        435                 440                 445

Phe Val Glu Ser Lys Phe Gly Asn Ser Gln Gly Thr Asn Tyr Thr Glu
    450                 455                 460

Ile Ile Ser Tyr Ile Tyr Asn Arg Thr Gly Trp Pro Pro Arg Val Thr
465                 470                 475                 480

Asp Asn Leu Asn Phe Lys Tyr Phe Ile Asp Leu Ser Glu Leu Ile Lys
                485                 490                 495

Ala Gly Tyr Gly Pro Asp Val Val Lys Val Glu Thr Tyr Tyr Ser Glu
            500                 505                 510

Gly Gly Lys Ile Ser Gly Pro Tyr Val Trp Asn Ala Ser Lys Asn Leu
        515                 520                 525

Tyr Tyr Ile Leu Val Asp Phe Thr Gly Thr Lys Ile Tyr Pro Gly Gly
    530                 535                 540

Glu Val Glu His Lys Lys Gln Ala Gln Phe Lys Ile Ser Val Pro Gln
545                 550                 555                 560

Gly Val Pro Trp Asp Pro Thr Asn Asp Pro Ser Tyr Ala Gly Leu Thr
                565                 570                 575

Lys Glu Leu Ser Lys Asn Lys Phe Ile Ala Ala Tyr Glu Gly Asn Val
            580                 585                 590

Leu Val Trp Gly Gln Glu Pro Glu Gly Ser Ser Ser Ser Thr Pro Thr
        595                 600                 605

Pro Thr Pro Thr Pro Thr Pro Thr Leu Thr Pro Thr Pro Thr Ser Thr
```

-continued

```
    610                 615                 620

Ala Thr Pro Thr Pro Thr Pro Thr Pro Thr Pro Thr Ser Thr Pro Thr
625                 630                 635                 640

Ala Thr Pro Thr Ala Thr Pro Thr Pro Thr Pro Thr Pro Ser Ser Thr
                645                 650                 655

Pro Val Ala Gly Gly Gln Ile Lys Val Leu Tyr Ala Asn Lys Glu Thr
                660                 665                 670

Asn Ser Thr Thr Asn Thr Ile Arg Pro Trp Leu Lys Val Val Asn Thr
        675                 680                 685

Gly Ser Ser Ser Ile Asp Leu Ser Arg Val Thr Ile Arg Tyr Trp Tyr
    690                 695                 700

Thr Val Asp Gly Asp Lys Ala Gln Ser Ala Ile Ser Asp Trp Ala Gln
705                 710                 715                 720

Ile Gly Ala Ser Asn Val Thr Phe Lys Phe Val Lys Leu Ser Ser Ser
                725                 730                 735

Val Ser Gly Ala Asp Tyr Tyr Leu Glu Ile Gly Phe Lys Ser Gly Ala
                740                 745                 750

Gly Gln Leu Gln Ala Gly Lys Asp Thr Gly Glu Ile Gln Ile Arg Phe
        755                 760                 765

Asn Lys Ser Asp Trp Ser Asn Tyr Asn Gln Gly Asn Asp Trp Ser Trp
    770                 775                 780

Met Gln Ser Met Thr Ser Tyr Gly Glu Asn Val Lys Val Thr Ala Tyr
785                 790                 795                 800

Ile Asp Gly Val Leu Val Trp Gly Gln Glu Pro Ser Gly Ala Thr Pro
                805                 810                 815

Thr Pro Thr Ala Thr Pro Ala Pro Thr Val Thr Pro Thr Pro Thr Pro
                820                 825                 830

Ala Pro Thr Pro Thr Pro Thr Pro Thr Pro Thr Ala Thr Pro Thr Pro
        835                 840                 845

Thr Pro Thr Pro Thr Pro Thr Pro Thr Ala Thr Pro Thr Pro Thr Pro
    850                 855                 860

Ser Ser Thr Pro Val Ala Gly Gly Gln Ile Lys Val Leu Tyr Ala Asn
865                 870                 875                 880

Lys Glu Thr Asn Ser Thr Thr Asn Thr Ile Arg Pro Trp Leu Lys Val
                885                 890                 895

Val Asn Thr Gly Ser Ser Ser Ile Asp Leu Ser Arg Val Thr Ile Arg
            900                 905                 910

Tyr Trp Tyr Thr Val Asp Gly Asp Lys Ala Gln Ser Ala Ile Ser Asp
        915                 920                 925

Trp Ala Gln Ile Gly Ala Ser Asn Val Thr Phe Lys Phe Val Lys Leu
    930                 935                 940

Ser Ser Ser Val Ser Gly Ala Asp Tyr Tyr Leu Glu Ile Gly Phe Lys
945                 950                 955                 960

Ser Gly Ala Gly Gln Leu Gln Ala Gly Lys Asp Thr Gly Glu Ile Gln
                965                 970                 975

Ile Arg Phe Asn Lys Ser Asp Trp Ser Asn Tyr Asn Gln Gly Asn Asp
            980                 985                 990

Trp Ser Trp Met Gln Ser Met Thr Ser Tyr Gly Glu Asn Val Lys Val
        995                 1000                1005

Thr Ala Tyr Ile Asp Gly Val Leu Val Trp Gly Gln Glu Pro Ser Gly
    1010                1015                1020

Ala Thr Pro Thr Pro Thr Ala Thr Pro Ala Pro Thr Val Thr Pro Thr
1025                1030                1035                1040
```

```
Pro Thr Pro Thr Pro Thr Pro Thr Pro Ser Ser Gly Ile Val Lys Ile
                1045                1050                1055

Asp Thr Ser Thr Leu Ile Gly Thr Asn His Ala His Cys Trp Tyr Arg
            1060                1065                1070

Asp Lys Leu Glu Thr Ala Leu Arg Gly Ile Arg Ser Trp Gly Met Asn
        1075                1080                1085

Ser Val Arg Val Val Leu Ser Asn Gly Tyr Arg Trp Thr Lys Ile Pro
    1090                1095                1100

Ala Ser Glu Val Ala Asn Ile Ile Ser Leu Ser Arg Ser Leu Gly Phe
1105                1110                1115                1120

Arg Ala Ile Val Leu Glu Val His Asp Thr Thr Gly Tyr Gly Glu Asp
                1125                1130                1135

Gly Ala Ala Cys Ser Leu Ala Gln Ala Val Glu Tyr Trp Lys Glu Ile
            1140                1145                1150

Lys Ser Val Leu Glu Gly Asn Glu Asp Phe Val Ile Ile Asn Ile Gly
        1155                1160                1165

Asn Glu Pro Tyr Gly Asn Asn Asn Tyr Gln Asn Trp Ile Asn Asp Thr
    1170                1175                1180

Lys Asn Ala Ile Lys Ala Leu Arg Asp Ala Gly Phe Lys His Thr Ile
1185                1190                1195                1200

Met Val Asp Ala Pro Asn Trp Gly Gln Asp Trp Ser Asn Thr Met Arg
                1205                1210                1215

Asp Asn Ala Gln Ser Ile Met Glu Ala Asp Pro Leu Arg Asn Leu Val
            1220                1225                1230

Phe Ser Ile His Met Tyr Gly Val Tyr Asn Thr Ala Ser Lys Val Glu
        1235                1240                1245

Glu Tyr Ile Lys Ser Phe Val Glu Lys Gly Leu Pro Leu Val Ile Gly
    1250                1255                1260

Glu Phe Gly His Gln His Thr Asp Gly Asp Pro Asp Glu Glu Ala Ile
1265                1270                1275                1280

Val Arg Tyr Ala Lys Gln Tyr Lys Ile Gly Leu Phe Ser Trp Ser Trp
                1285                1290                1295

Cys Gly Asn Ser Ser Tyr Val Gly Tyr Leu Asp Met Val Asn Asn Trp
            1300                1305                1310

Asp Pro Asn Asn Pro Thr Pro Trp Gly Gln Trp Tyr Lys Thr Asn Ala
        1315                1320                1325

Ile Gly Ala Glu
    1330
```

<210> SEQ ID NO 115
<211> LENGTH: 3999
<212> TYPE: DNA
<213> ORGANISM: Caldicellulosiruptor bescii

<400> SEQUENCE: 115

```
gcaacaacct ttaactatgg tgaagctctt caaaaagcga tcatgtttta tgaatttcag      60

atgtcaggta aactaccatc atggatccgt aacaactggc gcggggattc tggtctaaat     120

gatggcaaag atgtaggttt agatcttact ggtggctggc atgatgcggg cgaccatgta     180

aagtttaatc taccaatgtc atacagtgca tcaatgcttt cgtgggcagt ttatgagtac     240

aaagcagcat ttgagaaaag tggtcagctt gaacatatac ttaaccagat tgaatgggta     300

aacgactact ttgtaaaatg ccatccatca aagtatgtat actactatca agttggtgac     360

ccaattgaag atcataactt ctggggtcca gcagaagtta tgcaaatgaa acgaccagca     420
```

```
tacaagtgtg acttaaataa tccagcaagt tcggttgttg cagaaacagc agcatcctta    480
gctgcagctt caatcgtcat acgtgaaaga aatagtcaaa aggcagacac atatttgcag    540
catgcgatgg tactctttga ttttgccgat agaactcgta gtgatgcagg gtataccgca    600
gcaacaggct tttacacatc aggtggtttt attgatgatc ttggttgggc agcagtgtgg    660
ttatatcttg cgacaaatga caaatcatat ttagataaag ctgaggcact tatggcagaa    720
tatgccggtg gcacaaatac atggacacag tgctgggacg atgtaagata cggagcaata    780
ttgcttttag caaaaattac taataaagac atatataaag gtgctgttga aagaaatctt    840
gatcattgga catataacat aacctataca cctaaaggtc ttgcatggat aacagggtgg    900
ggctcactta ggtatgccac aactgcagct ttcttagcgt ttgtttatgc agattggtca    960
ggatgtccag aaaataagcg aacagcttat ctaaaatttg gtgagagtca gattaactat   1020
gcattaggtt caacaggaag aagctttttg gtaggatttg ggcaaaatta tccacaacat   1080
ccacatcaca gaaatgcaca cagttcatgg gcgaacagta tgcgaatacc tgaatatcat   1140
cgacacatac tttatggtgc attagtaggc ggaccaggct ctgatgatag ttacaatgat   1200
gatattactg actatgttca aaacgaggtg gcttgtgact acaatgctgg tattgtaggt   1260
gctctggcaa aaatgtacct tatgtatgga ggagacccaa tacctaattt caaagctatc   1320
gaaaagccaa ctaatgatga aatttttgtt gaatccaagt ttggtaattc acagggtaca   1380
aactataccg aaataatttc atacatttat aacagaacgg gatggccgcc tcgagtcaca   1440
gataatctaa actttaagta ttttattgac ctaagtgagt taatcaaggc tgggtatggt   1500
cctgatgttg ttaaagtaga gacatattat tcagaaggtg gaaaaatatc tggaccatac   1560
gtatggaatg catcaaagaa cctttactat atattagttg attttacagg aacaaaaata   1620
tatccaggtg gggaagtaga acacaaaaaa caagctcaat ttaagatatc tgtgccacaa   1680
ggtgttccat gggatccaac taatgaccca tcttatgcag gattaacaaa agaacttagt   1740
aaaaataagt tcatagcagc ttatgaaggt aacgtgctgg tatggggaca agaaccagag   1800
ggttcgtcaa gttcaacccc aaccccaaca ccaacaccaa caccaacact gactccaaca   1860
ccgacatcaa ctgctacacc aacaccgaca cctacaccaa caccaacgtc aacaccaact   1920
gctacaccaa cagcaacgcc aacaccaaca ccgacgccga gcagcacacc tgtagcaggc   1980
gggcagataa aggtattgta tgctaacaag gagacaaata gcacaacaaa cacgataagg   2040
ccatggttga aggtagtgaa cactggaagc agcagcatag atttaagcag ggtaacgata   2100
aggtactggt acacggtaga tggggacaag gcacagagtg cgatatcaga ctgggcacag   2160
ataggagcaa gcaatgtgac attcaagttt gtgaagctga gcagtagcgt aagtggagcg   2220
gactattatt tagagatagg atttaagagt ggagctgggc agttgcaggc tggtaaagac   2280
acaggggaga tacagataag gtttaacaag agtgactgga gcaattacaa tcaggggaat   2340
gactggtcat ggatgcagag catgacgagt tatggagaga atgtgaaggt aacagcgtat   2400
atagatggtg tattggtatg gggacaggag ccgagtggag cgacaccaac accgacagca   2460
acaccagcac cgacagtgac accgacacca acaccagcac caacaccaac cccgactcca   2520
acaccaactg ctacaccaac gccaacaccg actccaacac caacaccaac tgctacccca   2580
acaccgacgc cgagcagcac acctgtagca ggtggacaga taaaggtatt gtatgctaac   2640
aaggagacaa atagcacaac aaacacgata aggccatggt tgaaggtagt gaacactgga   2700
agcagcagca tagatttaag cagggtaacg ataaggtact ggtacacggt agatggggac   2760
```

aaggcacaga gtgcgatatc agactgggca cagataggag caagcaatgt gacattcaag 2820
tttgtgaagc tgagcagtag cgtaagtgga gcggactatt atttagagat aggatttaag 2880
agtggagctg ggcagttgca ggctggtaaa gacacagggg agatacagat aaggtttaac 2940
aagagtgact ggagcaatta caatcagggg aatgactggt catggatgca gagcatgacg 3000
agttatggag agaatgtgaa ggtaacagcg tatatagatg gtgtattggt atggggacag 3060
gagccgagtg gagcgacacc aacaccgaca gcaacaccag caccgacagt gacacctaca 3120
cctacaccaa ctccaactcc aacgccgagc agtggaatag tgaagataga tactagcaca 3180
ttaataggaa caaatcacgc acattgctgg tacagagata aacttgagac ggcattgcga 3240
ggaataaggt catggggtat gaactctgtg agggtagtgt tgagtaatgg ctatcgatgg 3300
acgaagatac cagcaagtga agtagcaaat attatatcat tgtcaagaag tcttggattc 3360
agagccattg tattagaagt tcacgacacg acaggatatg gtgaggacgg tgcagcatgt 3420
tcattggcgc aagcagtaga atattggaaa gagataaaga gtgtgttaga aggcaatgag 3480
gattttgtta taataaacat tggtaatgag ccgtatggga acaataacta tcaaaactgg 3540
attaatgaca cgaagaatgc tataaaagcg ctaagggatg cagggttcaa gcacacgata 3600
atggttgatg caccgaactg gggcaggat tggtctaata ctatgagaga caatgcccag 3660
agcataatgg aagcagatcc gctgcgcaat ttggtatttt cgattcatat gtacggtgta 3720
tacaatacag cgagcaaggt agaagaatat atcaagtcat ttgtggagaa agggctgcca 3780
ttagttattg gggagtttgg gcatcagcat acagatggtg accctgacga ggaagctatt 3840
gtcaggtatg caaaacaata caagatagga ctttttagct ggtcttggtg tggcaattcg 3900
agctatgtag ggtacttgga catggtaaac aattgggacc ccaataatcc aactccatgg 3960
gggcaatggt ataaaactaa tgcgattggt gctgaataa 3999

<210> SEQ ID NO 116
<211> LENGTH: 5280
<212> TYPE: DNA
<213> ORGANISM: Caldicellulosiruptor bescii

<400> SEQUENCE: 116
atgaagcgtt acagaagaat tattgccatg gttgtaacct tcatatttat tttaggagtg 60
gtatatggag ttaaaccatg gcaagaggtt agggctggtt cgtttaacta tggggaagct 120
ttacaaaaag ctatcatgtt ttacgaattt caaatgtctg gtaaacttcc gaattgggta 180
cgcaacaact ggcgtggcga ctcagcatta aaggatggtc aagacaatgg gcttgatttg 240
acaggtggtt ggtttgacgc aggtgatcac gtcaagttta accttccaat gtcatacact 300
ggtacaatgt tgtcatgggc agtgtatgag tacaaagatg catttgtcaa gagtggtcaa 360
ttggaacata tcttaaatca aatcgaatgg gttaatgact attttgtaaa atgtcatcca 420
agcaaatatg tatactatta ccaggttggg gatggaagta aagatcatgc atggtgggga 480
cctgctgagg ttatgcaaat ggagagacct tcatttaagg tcacccaaag cagtcctgga 540
tctacagtag tagcagagac agcagcttcc ttagcagcag cttcaattgt tttgaaagac 600
agaaatccca ctaaagcagc aacatatctg caacatgcaa aagaattata tgagtttgca 660
gaagtaacaa aaagcgatgc aggttacact gctgcaaatg gatattacaa ttcatggagc 720
ggtttctatg atgagctttc ttgggcagca gtttggttgt atttggcaac aaatgattca 780
acatatctca caaaagctga gtcatatgtc caaaattggc ccaaaatttc tggcagtaac 840
acaattgact acaagtgggc tcattgctgg gatgatgttc acaatggagc ggcattattg 900

-continued

```
ttagcaaaaa ttaccggtaa ggatatttat aaacaaatta ttgaaagtca cttagattac    960
tggactacag gatacaatgg cgaaaggatt aagtatacac caaaaggatt agcatggctt   1020
gatcaatggg gttcgttgag atatgcaaca actacagcat ttttggcatt tgtttatagc   1080
gattgggttg gctgtccaag cacaaaaaaa gaaatatata gaaaatttgg agaaagccag   1140
attgattatg cgttaggctc agctggaaga agctttgttg ttggatttgg tacaaatcca   1200
ccaaagagac cgcatcacag aactgctcat agctcatggg cagacagtca gagtatacct   1260
tcatatcaca gacatacatt atatggagcg cttgttggtg gtccaggctc tgatgatagc   1320
tacacagatg atataagtaa ctatgtgaac aatgaggttg catgtgatta taatgcaggg   1380
tttgtgggtg cattagcaaa gatgtatcaa ttgtacggtg ggaatccaat accagatttc   1440
aaagctattg aaactccaac aaacgacgaa ttctttgttg aagctggtat aaatgcatcc   1500
ggaactaact ttattgaaat taaagcgata gttaataacc aaagtggttg gcctgccaga   1560
gcaacagata agcttaaatt tagatatttt gttgacctga gtgaattaat taaagcagga   1620
tattcaccaa atcaattaac cttgagcacc aattataatc aaggtgcaaa agtaagtgga   1680
ccttatgtat gggatgcaag caaaaatata tactacattt tagtagactt tactggcaca   1740
ttgatttatc caggtggtca agacaaatat aagaaagaag tccaattcag aattgcagca   1800
ccacagaatg tacagtggga taattctaac gactattctt tccaggatat aaagggagtt   1860
tcaagtggtt cagttgttaa aactaaatat attccacttt atgatggaga tgtgaaagta   1920
tggggtgaag aaccaggaac ttctggagca acaccgacac caacagcaac agcaacacca   1980
acaccaacgc cgacagtaac accaacaccg actccaacac caacatcaac tgctacacca   2040
acaccgacac caacaccgac agtaacacca accccgactc cgacaccgac tgctacacca   2100
acagcaacgc caacaccaac atcgacgccg agcagcacac ctgtagcagg tggacagata   2160
aaggtattgt atgctaacaa ggagacaaat agcacaacta atacgataag gccatggttg   2220
aaggtagtga acactggaag cagcagcata gatttgagca gggtaacgat aaggtactgg   2280
tacacggtag atggggacaa ggcacagagt gcgatatcag actgggcaca gataggagca   2340
agcaatgtga cattcaagtt tgtgaagctg agcagtagcg taagtggagc ggactattat   2400
ttagagatag gatttaagag tggagctggg cagttgcagg ctggcaaaga cacaggggag   2460
atacagataa ggtttaacaa gagtgattgg agcaattaca atcaggggaa tgactggtca   2520
tggatgcaga gcatgacgaa ttatggagag aatgtgaagg taacagcgta tatagatggt   2580
gtattggtat ggggacagga gccgagtgga gcgacaccaa caccgacagc gacaccagca   2640
ccgacagtga caccgacacc tacaccaaca ccaacgtcaa caccaactgc tacaccaaca   2700
gcaacgccaa caccaacacc gacgccgagc agcacacctg tagcaggcgg gcagataaag   2760
gtattgtatg ctaacaagga gacaaatagc acaacaaaca cgataaggcc atggttgaag   2820
gtagtgaaca ctggaagcag cagcatagat ttgagcaggg taacgataag gtactggtac   2880
acggtagatg gggacaaggc acagagtgcg atatcagact gggcacagat aggagcaagc   2940
aatgtgacat tcaagtttgt gaagctgagc agtagcgtaa gtggagcgga ctattattta   3000
gagataggat ttaagagtgg agctgggcag ttgcaggctg gtaaagacac aggggagata   3060
cagataaggt ttaacaagag tgactggagc aattacaatc aggggaatga ctggtcatgg   3120
atgcagagca tgacgaatta tggagagaat gtgaaggtaa cagcgtatat agatggtgta   3180
ttggtatggg gacaggagcc gagtggagcg acaccaacac cgacagcgac accagcaccg   3240
```

```
acagtgacac cgacacctac accagcacca actccaaccc cgacaccaac accaactgct   3300

acaccaacac caacgccaac accaacccca accgcgacac caacagtaac agcaacacca   3360

acaccgacgc cgagcagcac accgagtgtg cttggcgaat atgggcagag gtttatgtgg   3420

ttatggaaca agatacatga tcctgcgaac gggtatttta accaggatgg gataccatat   3480

cattcggtag agacattgat atgcgaagca cctgattatg gtcatttgac cacgagtgag   3540

gcattttcgt actatgtatg gttagaggca gtgtatggta agttaacggg tgactggagc   3600

aaatttaaga cagcatggga cacattagag aagtatatga taccatcagc ggaagatcag   3660

ccgatgaggt catatgatcc taacaagcca gcgacatacg caggggagtg ggagacaccg   3720

gacaagtatc catcgccgtt ggagtttaat gtacctgttg gcaaagaccc gttgcataat   3780

gaacttgtga gcacatatgg tagcacatta atgtatggta tgcactggtt gatggacgta   3840

gacaactggt atggatatgg caagagaggg gacggagtaa gtcgggcatc atttatcaac   3900

acgttccaga gagggcctga ggagtctgta tgggagacgg tgccgcatcc gagctgggag   3960

gaattcaagt ggggcggacc gaatggattt ttagatttgt ttattaagga tcagaactat   4020

tcgaagcagt ggagatatac ggatgcacca gatgctgatg cgagagctat tcaggctact   4080

tattgggcga aagtatgggc gaaggagcaa ggtaagttta atgagataag cagctatgta   4140

gcgaaggcag cgaagatggg agactattta aggtatgcga tgtttgacaa gtatttcaag   4200

ccattaggat gtcaggataa gaatgcggct ggaggaacgg ggtatgacag tgcacattat   4260

ctgctatcat ggtattatgc atggggtgga gcattggatg gagcatggtc atggaagata   4320

gggagcagcc atgtgcactt tggatatcag aatccgatgg cggcatgggc attagcgaat   4380

gatagtgata tgaagccgaa gtcgccgaat ggagcgagtg actgggcaaa gagtttgaag   4440

aggcagatag aattttacag gtggttacag tcagcggagg gagcgatagc aggaggcgcg   4500

acaaattcat ggaatggcag atatgagaag tatccagcag ggacagcaac attttatgga   4560

atggcatatg aaccgaatcc ggtatatcat gatcctggga gcaacacatg gtttggattc   4620

caggcatggt cgatgcagag ggtagcggag tattactatg tgacaggaga taaggacgca   4680

ggagcactgc ttgagaagtg ggtaagctgg gttaagagtg tagtgaagtt gaatagtgat   4740

ggtacgtttg cgataccgtc gacgcttgat tggagcggac aacctgatac atggaacggg   4800

gcgtatacag ggaatagcaa cttacatgtt aaggtagtgg actatggtac tgacttagga   4860

ataacagcgt cattggcgaa tgcgttgttg tactatagtg cagggacgaa gaagtatggg   4920

gtatttgatg agggagcgaa gaatttagcg aaggaattgc tggacaggat gtggaagttg   4980

tacagggatg agaagggatt gtcagcgcca gagaagagag cggactacaa gaggttcttt   5040

gagcaagagg tatatatacc ggcaggatgg atagggaaga tgccgaatgg agatgtaata   5100

aagagtggag ttaagtttat agacataagg agcaagtata aacaagatcc tgattggccg   5160

aagttagagg cggcatacaa gtcagggcag gcacctgagt tcagatatca caggttctgg   5220

gcacagtgcg acatagcaat agctaatgca acatatgaaa tactgtttgg caatcaataa   5280
```

```
<210> SEQ ID NO 117
<211> LENGTH: 638
<212> TYPE: PRT
<213> ORGANISM: Caldicellulosiruptor bescii

<400> SEQUENCE: 117

Ala Thr Ser Asn Asp Gly Val Val Lys Ile Asp Thr Ser Thr Leu Ile
 1               5                  10                  15
```

-continued

```
Gly Thr Asn His Ala His Cys Trp Tyr Arg Asp Lys Leu Glu Thr Ala
            20                  25                  30

Leu Arg Gly Ile Arg Ser Trp Gly Met Asn Ser Val Arg Val Val Leu
        35                  40                  45

Ser Asn Gly Tyr Arg Trp Thr Lys Ile Pro Ala Ser Glu Val Ala Asn
    50                  55                  60

Ile Ile Ser Leu Ser Arg Ser Leu Gly Phe Arg Ala Ile Val Leu Glu
65                  70                  75                  80

Val His Asp Thr Thr Gly Tyr Gly Glu Asp Gly Ala Ala Cys Ser Leu
                85                  90                  95

Ala Gln Ala Val Glu Tyr Trp Lys Glu Ile Lys Ser Val Leu Glu Gly
            100                 105                 110

Asn Glu Asp Phe Val Ile Ile Asn Ile Gly Asn Glu Pro Tyr Gly Asn
        115                 120                 125

Asn Asn Tyr Gln Asn Trp Ile Asn Asp Thr Lys Asn Ala Ile Lys Ala
    130                 135                 140

Leu Arg Asp Ala Gly Phe Lys His Thr Ile Met Val Asp Ala Pro Asn
145                 150                 155                 160

Trp Gly Gln Asp Trp Ser Asn Thr Met Arg Asp Asn Ala Gln Ser Ile
                165                 170                 175

Met Glu Ala Asp Pro Leu Arg Asn Leu Val Phe Ser Ile His Met Tyr
            180                 185                 190

Gly Val Tyr Asn Thr Ala Ser Lys Val Glu Glu Tyr Ile Lys Ser Phe
        195                 200                 205

Val Glu Lys Gly Leu Pro Leu Val Ile Gly Glu Phe Gly His Gln His
    210                 215                 220

Thr Asp Gly Asp Pro Asp Glu Glu Ala Ile Val Arg Tyr Ala Lys Gln
225                 230                 235                 240

Tyr Lys Ile Gly Leu Phe Ser Trp Ser Trp Cys Gly Asn Ser Ser Tyr
                245                 250                 255

Val Gly Tyr Leu Asp Met Val Asn Asn Trp Asp Pro Asn Asn Pro Thr
            260                 265                 270

Pro Trp Gly Gln Trp Tyr Lys Thr Asn Ala Ile Gly Ala Ser Ser Val
        275                 280                 285

Pro Thr Ser Thr Pro Thr Pro Thr Pro Thr Ala Thr Pro Thr Ala Thr
    290                 295                 300

Pro Thr Pro Thr Pro Thr Pro Ser Ser Thr Pro Val Ala Gly Gly Gln
305                 310                 315                 320

Ile Lys Val Leu Tyr Ala Asn Lys Glu Thr Asn Ser Thr Thr Asn Thr
                325                 330                 335

Ile Arg Pro Trp Leu Lys Val Val Asn Thr Gly Ser Ser Ser Ile Asp
            340                 345                 350

Leu Ser Arg Val Thr Ile Arg Tyr Trp Tyr Thr Val Asp Gly Asp Lys
        355                 360                 365

Ala Gln Ser Ala Ile Ser Asp Trp Ala Gln Ile Gly Ala Ser Asn Val
    370                 375                 380

Thr Phe Lys Phe Val Lys Leu Ser Ser Ser Val Ser Gly Ala Asp Tyr
385                 390                 395                 400

Tyr Leu Glu Ile Gly Phe Lys Ser Gly Ala Gly Gln Leu Gln Ala Gly
                405                 410                 415

Lys Asp Thr Gly Glu Ile Gln Ile Arg Phe Asn Lys Ser Asp Trp Ser
            420                 425                 430

Asn Tyr Asn Gln Gly Asn Asp Trp Ser Trp Met Gln Ser Met Thr Ser
```

```
        435                 440                 445

Tyr Gly Glu Asn Val Lys Val Thr Ala Tyr Ile Asp Gly Val Leu Val
    450                 455                 460

Trp Gly Gln Glu Pro Ser Gly Ala Thr Pro Thr Pro Thr Ala Thr Pro
465                 470                 475                 480

Ala Pro Thr Val Thr Pro Thr Ala Thr Pro Ala Pro Thr Pro Thr Pro
                485                 490                 495

Thr Pro Thr Pro Thr Ala Thr Pro Thr Pro Thr Pro Thr Pro Thr Pro
            500                 505                 510

Thr Pro Thr Ala Thr Pro Thr Pro Thr Pro Ser Ser Thr Pro Val Ala
        515                 520                 525

Gly Gly Gln Ile Lys Val Leu Tyr Ala Asn Lys Glu Thr Asn Ser Thr
    530                 535                 540

Thr Asn Thr Ile Arg Pro Trp Leu Lys Val Val Asn Thr Gly Ser Ser
545                 550                 555                 560

Ser Ile Asp Leu Ser Arg Val Thr Ile Arg Tyr Trp Tyr Thr Val Asp
                565                 570                 575

Gly Asp Lys Ala Gln Ser Ala Ile Ser Asp Trp Ala Gln Ile Gly Ala
            580                 585                 590

Ser Asn Val Thr Phe Lys Phe Val Lys Leu Ser Ser Ser Val Ser Gly
        595                 600                 605

Ala Asp Tyr Tyr Leu Glu Ile Gly Phe Lys Ser Gly Ala Gly Gln Leu
    610                 615                 620

Gln Ala Gly Lys Asp Thr Gly Glu Ile Gln Ile Arg Phe Asn
625                 630                 635


<210> SEQ ID NO 118
<211> LENGTH: 1917
<212> TYPE: DNA
<213> ORGANISM: Caldicellulosiruptor bescii

<400> SEQUENCE: 118

gctacatcta atgatggagt agtgaagata gatactagca cattaatagg aacaaatcac      60

gcacattgct ggtacagaga taaacttgag acggcattgc gaggaataag gtcatggggt     120

atgaactctg tgagggtagt gttgagtaat ggctatcgat ggacgaagat accagcaagt     180

gaagtagcaa atattatatc attgtcaaga agtcttggat tcagagccat tgtattagaa     240

gttcacgaca cgacaggata tggtgaggac ggtgcagcat gttcattggc gcaagcagta     300

gaatattgga aagagataaa gagtgtgtta gaaggcaatg aggattttgt tataataaac     360

attggtaatg agccgtatgg gaacaataac tatcaaaact ggattaatga cacgaagaat     420

gctataaaag cgctaaggga tgcagggttc aagcacacga taatggttga tgcaccgaac     480

tgggggcagg attggtctaa tactatgaga gacaatgccc agagcataat ggaagcagat     540

ccgctgcgca atttggtatt ttcgattcat atgtacggtg tatacaatac agcgagcaag     600

gtagaagaat atatcaagtc atttgtggag aaagggctgc cattagttat tggggagttt     660

gggcatcagc atacagatgg tgaccctgac gaggaagcta ttgtcaggta tgcaaaacaa     720

tacaagatag gactttttag ctggtcttgg tgtggcaatt cgagctatgt agggtacttg     780

gacatggtaa acaattggga ccccaataat ccaactccat gggggcaatg gtataaaact     840

aatgcgattg gtgcctcttc agtacctact tcaacaccaa caccgacacc aactgctaca     900

ccaacagcaa cgccaacacc aacaccgacg ccgagcagca cacctgtagc aggtggacag     960

ataaaggtat tgtatgctaa caaggagaca aatagcacaa caaatacgat aaggccatgg    1020
```

-continued

```
ttgaaggtag tgaacactgg aagcagcagc atagatttga gcagggtaac gataaggtac   1080

tggtacacgg tagatgggga caaggcacag agtgcgatat cagactgggc acagatagga   1140

gcaagcaatg tgacattcaa gtttgtgaag ctgagcagta gcgtaagtgg agcggactat   1200

tatttagaga taggatttaa gagtggagct gggcagttgc aggctggtaa agacacaggg   1260

gagatacaga taaggtttaa caagagtgac tggagcaatt acaatcaggg gaatgactgg   1320

tcatggatgc agagcatgac gagttatgga gagaatgtga aggtaacagc gtatatagat   1380

ggtgtattgg tatggggaca ggagccgagt ggagcgacac caacaccgac agcaacacca   1440

gcaccgacag tgacaccgac agcaacacca gcaccaacac caaccccgac cccaacacca   1500

actgctacac caacgccaac accgactcca acaccaacac caactgctac cccaacaccg   1560

acgccgagca gtacacctgt agcaggtgga cagataaagg tactgtatgc taacaaggag   1620

acaaatagca caacaaacac gataaggcca tggttgaagg tagtgaacac tggaagcagc   1680

agcatagatt tgagcagggt aacgataagg tactggtaca cggtagatgg ggacaaggca   1740

cagagtgcga tatcagactg ggcacagata ggagcaagca atgtgacatt caagtttgtg   1800

aagctgagca gtagcgtaag tggagcggac tattatttag agataggatt taagagtgga   1860

gctgggcagt tgcaggctgg taaagacaca ggggagatac agataaggtt taactaa      1917
```

<210> SEQ ID NO 119
<211> LENGTH: 726
<212> TYPE: PRT
<213> ORGANISM: Caldicellulosiruptor bescii

<400> SEQUENCE: 119

```
Gln Ser Ile Leu Tyr Glu Lys Glu Lys Tyr Pro His Leu Leu Gly Asn
1               5                   10                  15

Gln Val Val Lys Lys Pro Ser Val Ala Gly Arg Leu Gln Ile Ile Glu
            20                  25                  30

Lys Asp Gly Lys Lys Tyr Leu Ala Asp Gln Lys Gly Glu Ile Ile Gln
        35                  40                  45

Leu Arg Gly Met Ser Thr His Gly Leu Gln Trp Tyr Gly Asp Ile Ile
    50                  55                  60

Asn Lys Asn Ala Phe Lys Ala Leu Ser Lys Asp Trp Glu Cys Asn Val
65                  70                  75                  80

Ile Arg Leu Ala Met Tyr Val Gly Glu Gly Gly Tyr Ala Ser Asn Pro
                85                  90                  95

Ser Ile Lys Glu Lys Val Ile Glu Gly Ile Lys Leu Ala Ile Glu Asn
            100                 105                 110

Asp Met Tyr Val Ile Val Asp Trp His Val Leu Asn Pro Gly Asp Pro
        115                 120                 125

Asn Ala Glu Ile Tyr Lys Gly Ala Lys Asp Phe Phe Lys Glu Ile Ala
    130                 135                 140

Thr Ser Phe Pro Asn Asp Tyr His Ile Ile Tyr Glu Leu Cys Asn Glu
145                 150                 155                 160

Pro Asn Pro Asn Glu Pro Gly Val Glu Asn Ser Leu Asp Gly Trp Lys
                165                 170                 175

Lys Val Lys Ala Tyr Ala Gln Pro Ile Ile Lys Met Leu Arg Ser Leu
            180                 185                 190

Gly Asn Gln Asn Ile Ile Ile Val Gly Ser Pro Asn Trp Ser Gln Arg
        195                 200                 205

Pro Asp Phe Ala Ile Gln Asp Pro Ile Asn Asp Lys Asn Val Met Tyr
```

```
    210                 215                 220

Ser Val His Phe Tyr Ser Gly Thr His Lys Val Asp Gly Tyr Val Phe
225                 230                 235                 240

Glu Asn Met Lys Asn Ala Phe Glu Asn Gly Val Pro Ile Phe Val Ser
                245                 250                 255

Glu Trp Gly Thr Ser Leu Ala Ser Gly Asp Gly Gly Pro Tyr Leu Asp
            260                 265                 270

Glu Ala Asp Lys Trp Leu Glu Tyr Leu Asn Ser Asn Tyr Ile Ser Trp
        275                 280                 285

Val Asn Trp Ser Leu Ser Asn Lys Asn Glu Thr Ser Ala Ala Phe Val
    290                 295                 300

Pro Tyr Ile Asn Gly Met His Asp Ala Thr Pro Leu Asp Pro Gly Asp
305                 310                 315                 320

Asp Lys Val Trp Asp Ile Glu Glu Leu Ser Ile Ser Gly Glu Tyr Val
                325                 330                 335

Arg Ala Arg Ile Lys Gly Ile Ala Tyr Gln Pro Ile Lys Arg Asp Asn
            340                 345                 350

Lys Ile Lys Glu Gly Glu Asn Ala Pro Leu Gly Glu Lys Val Leu Pro
        355                 360                 365

Ser Thr Phe Glu Asp Asp Thr Arg Gln Gly Trp Asp Trp Asp Gly Pro
    370                 375                 380

Ser Gly Val Lys Gly Pro Ile Thr Ile Glu Ser Ala Asn Gly Ser Lys
385                 390                 395                 400

Ala Leu Ser Phe Asn Val Glu Tyr Pro Glu Lys Lys Pro Gln Asp Gly
                405                 410                 415

Trp Ala Thr Ala Ala Arg Leu Ile Leu Lys Asp Ile Asn Val Glu Arg
            420                 425                 430

Gly Asn Asn Lys Tyr Leu Ala Phe Asp Phe Tyr Leu Lys Pro Asp Arg
        435                 440                 445

Ala Ser Lys Gly Met Ile Gln Ile Phe Leu Ala Phe Ser Pro Pro Ser
    450                 455                 460

Leu Gly Tyr Trp Ala Gln Val Gln Asp Ser Phe Asn Ile Asp Leu Ala
465                 470                 475                 480

Lys Leu Ser Ser Ala Lys Lys Ile Glu Asp Arg Ile Tyr Lys Phe Asn
                485                 490                 495

Val Phe Phe Asp Leu Asp Lys Ile Gln Asp Asn Lys Val Leu Ser Pro
            500                 505                 510

Asp Thr Leu Leu Arg Asp Ile Ile Val Val Ile Ala Asp Gly Asn Ser
        515                 520                 525

Asp Phe Lys Gly Lys Met Tyr Ile Asp Asn Val Arg Phe Thr Asn Ile
    530                 535                 540

Leu Phe Glu Asp Ile Asn Phe Glu Asn Ser Leu Tyr Asp Val Ile Asp
545                 550                 555                 560

Lys Leu Tyr Ser Lys Gly Ile Ile Lys Gly Ile Ser Val Phe Lys Tyr
                565                 570                 575

Leu Pro Asp Lys Asn Ile Thr Arg Ala Glu Phe Ala Ala Leu Cys Val
            580                 585                 590

Arg Ala Leu Asn Leu Lys Ile Glu Lys Tyr Asp Gly Arg Phe Ser Asp
        595                 600                 605

Val Lys Ser Gly Asn Trp Tyr Ser Asp Val Val Tyr Thr Ala Tyr Lys
    610                 615                 620

Asn Lys Leu Phe Glu Ile Lys Glu Asn Lys Phe Phe Pro Glu Asn Ile
625                 630                 635                 640
```

```
Leu Lys Arg Glu Glu Ala Val Ala Leu Ala Ile Glu Val Tyr Lys Arg
                645                 650                 655

Leu Thr Gly Lys Ile Glu Val Asn Thr Asp Asp Val Pro Ile Ala Asp
            660                 665                 670

Glu Lys Leu Ile Asn Pro Gln Tyr Arg Glu Ser Val Lys Leu Ala Ile
        675                 680                 685

Lys Leu Gly Ile Val Asp Leu Tyr Ser Asp Gly Thr Phe Glu Pro Asn
    690                 695                 700

Lys Ser Val Ser Arg Gly Glu Val Ala Thr Ile Leu Tyr Asn Leu Leu
705                 710                 715                 720

Asn Leu Ala Gly Lys Leu
                725


<210> SEQ ID NO 120
<211> LENGTH: 2181
<212> TYPE: DNA
<213> ORGANISM: Caldicellulosiruptor bescii

<400> SEQUENCE: 120

cagagcatac tgtatgaaaa ggaaaaatat ccacatcttc ttggcaatca ggtagttaaa     60

aaaccatcgg ttgccggcag actgcagatt attgaaaagg acggaaaaaa gtatttagct    120

gaccagaaag gagaaataat tcagcttcgt ggtatgagta cacatggact tcagtggtat    180

ggtgatatta taaacaaaaa tgcatttaaa gctctttcaa aagattggga gtgcaacgtt    240

ataaggcttg cgatgtatgt gggtgaaggc ggatatgctt caaacccaag tattaaagaa    300

aaagttatag aagggattaa gcttgctatt gagaatgaca tgtatgtaat tgttgactgg    360

catgtattaa atcccggtga cccgaacgca gaaatttata aaggggcaaa agactttttc    420

aaagagatag ctacaagttt tcccaatgac tatcacataa tatatgaact ttgcaatgaa    480

ccaaatccaa atgaaccggg agtagaaaat agcttggatg gctggaaaaa agtaaaggct    540

tatgcacagc ccatcataaa aatgctcaga agtttgggga atcagaacat tataattgta    600

ggttcgccaa actggagtca gagacctgac tttgcaattc aagaccctat aaatgataag    660

aatgttatgt attcagttca tttttactct ggaactcaca aagttgatgg atatgttttt    720

gaaaacatga aaaatgcgtt tgaaaatggc gtgccaattt tcgtgagtga atggggaaca    780

agtttggcaa gcggtgatgg tggaccgtat cttgatgaag cagataagtg gcttgaatat    840

ttaaattcaa actatattag ctgggtgaac tggtcgctgt caaacaaaaa tgagacatca    900

gctgcttttg ttccatatat aaatggtatg catgatgcca caccacttga ccctggtgat    960

gataaggtgt gggacataga agagcttagt atttctggag agtatgtgag ggcaaggata   1020

aaaggaattg cttatcagcc aattaagaga gataacaaaa taaaagaagg agaaaatgca   1080

cctttaggcg aaaaagtctt accatccacg tttgaagatg acactcgtca gggctgggat   1140

tgggatggac catctggtgt gaaaggtcct attactatcg aaagtgcgaa tggttcaaaa   1200

gcgctatctt ttaatgttga gtatccagag aaaaaaccac aagatggctg ggcaacagct   1260

gcaaggctta tacttaaaga cataaatgta gaaaggggaa ataataaata tttggctttt   1320

gatttttatt tgaaaccaga tagggcttca aaaggtatga ttcagatatt tttagctttt   1380

tcaccacctt ccttaggtta ctgggctcag gtacaagaca gttttaatat tgaccttgca   1440

aaactgtcaa gtgcaaaaaa gatagaagac agaatttata agttcaatgt attttttgac   1500

ttagacaaga tacaagataa taaagtactg agtccagaca cactcttgag agatataata   1560
```

gtagtcatag cagatggcaa tagcgatttt aaggggaaaa tgtatataga taatgttaga 1620
tttaccaata tcctttttga ggatatcaat tttgaaaata gcctttatga tgttatagac 1680
aagctttatt ctaaaggaat cataaaagga atttcagtat ttaagtactt gccagataaa 1740
aacattacaa gggctgaatt tgctgcactt tgtgtcaggg cactgaacct gaaaattgaa 1800
aaatacgatg gtagattttc tgatgtgaaa agcggcaact ggtattcaga tgtagtttat 1860
acggcgtata aaaacaaatt gtttgaaata aaagagaata aattctttcc tgaaaatatt 1920
ttaaaaagag aagaagcagt agctttggca attgaagtgt ataaaagatt gactggtaag 1980
atagaagtta atacagacga tgttccaatt gctgatgaaa aacttataaa tcctcaatac 2040
agagaaagcg tgaagttagc aattaagctc ggtattgttg acctgtattc agacggaaca 2100
tttgaaccaa ataagagcgt ttcaagaggg gaggtggcaa caattctcta taatctcttg 2160
aacttagcag gcaagctatg a 2181

<210> SEQ ID NO 121
<211> LENGTH: 1732
<212> TYPE: PRT
<213> ORGANISM: Caldicellulosiruptor bescii

<400> SEQUENCE: 121

Gln Glu Val Arg Ala Gly Ser Phe Asn Tyr Gly Glu Ala Leu Gln Lys
1 5 10 15

Ala Ile Met Phe Tyr Glu Phe Gln Met Ser Gly Lys Leu Pro Asn Trp
20 25 30

Val Arg Asn Asn Trp Arg Gly Asp Ser Ala Leu Lys Asp Gly Gln Asp
35 40 45

Asn Gly Leu Asp Leu Thr Gly Gly Trp Phe Asp Ala Gly Asp His Val
50 55 60

Lys Phe Asn Leu Pro Met Ser Tyr Thr Gly Thr Met Leu Ser Trp Ala
65 70 75 80

Val Tyr Glu Tyr Lys Asp Ala Phe Val Lys Ser Gly Gln Leu Glu His
85 90 95

Ile Leu Asn Gln Ile Glu Trp Val Asn Asp Tyr Phe Val Lys Cys His
100 105 110

Pro Ser Lys Tyr Val Tyr Tyr Tyr Gln Val Gly Asp Gly Ser Lys Asp
115 120 125

His Ala Trp Trp Gly Pro Ala Glu Val Met Gln Met Glu Arg Pro Ser
130 135 140

Phe Lys Val Thr Gln Ser Ser Pro Gly Ser Thr Val Val Ala Glu Thr
145 150 155 160

Ala Ala Ser Leu Ala Ala Ala Ser Ile Val Leu Lys Asp Arg Asn Pro
165 170 175

Thr Lys Ala Ala Thr Tyr Leu Gln His Ala Lys Glu Leu Tyr Glu Phe
180 185 190

Ala Glu Val Thr Lys Ser Asp Ala Gly Tyr Thr Ala Ala Asn Gly Tyr
195 200 205

Tyr Asn Ser Trp Ser Gly Phe Tyr Asp Glu Leu Ser Trp Ala Ala Val
210 215 220

Trp Leu Tyr Leu Ala Thr Asn Asp Ser Thr Tyr Leu Thr Lys Ala Glu
225 230 235 240

Ser Tyr Val Gln Asn Trp Pro Lys Ile Ser Gly Ser Asn Thr Ile Asp
245 250 255

Tyr Lys Trp Ala His Cys Trp Asp Asp Val His Asn Gly Ala Ala Leu

-continued

```
            260                 265                 270

Leu Leu Ala Lys Ile Thr Gly Lys Asp Ile Tyr Lys Gln Ile Ile Glu
        275                 280                 285

Ser His Leu Asp Tyr Trp Thr Thr Gly Tyr Asn Gly Glu Arg Ile Lys
    290                 295                 300

Tyr Thr Pro Lys Gly Leu Ala Trp Leu Asp Gln Trp Gly Ser Leu Arg
305                 310                 315                 320

Tyr Ala Thr Thr Thr Ala Phe Leu Ala Phe Val Tyr Ser Asp Trp Val
                325                 330                 335

Gly Cys Pro Ser Thr Lys Lys Glu Ile Tyr Arg Lys Phe Gly Glu Ser
            340                 345                 350

Gln Ile Asp Tyr Ala Leu Gly Ser Ala Gly Arg Ser Phe Val Val Gly
        355                 360                 365

Phe Gly Thr Asn Pro Pro Lys Arg Pro His His Arg Thr Ala His Ser
    370                 375                 380

Ser Trp Ala Asp Ser Gln Ser Ile Pro Ser Tyr His Arg His Thr Leu
385                 390                 395                 400

Tyr Gly Ala Leu Val Gly Gly Pro Gly Ser Asp Asp Ser Tyr Thr Asp
                405                 410                 415

Asp Ile Ser Asn Tyr Val Asn Asn Glu Val Ala Cys Asp Tyr Asn Ala
            420                 425                 430

Gly Phe Val Gly Ala Leu Ala Lys Met Tyr Gln Leu Tyr Gly Gly Asn
        435                 440                 445

Pro Ile Pro Asp Phe Lys Ala Ile Glu Thr Pro Thr Asn Asp Glu Phe
    450                 455                 460

Phe Val Glu Ala Gly Ile Asn Ala Ser Gly Thr Asn Phe Ile Glu Ile
465                 470                 475                 480

Lys Ala Ile Val Asn Asn Gln Ser Gly Trp Pro Ala Arg Ala Thr Asp
                485                 490                 495

Lys Leu Lys Phe Arg Tyr Phe Val Asp Leu Ser Glu Leu Ile Lys Ala
            500                 505                 510

Gly Tyr Ser Pro Asn Gln Leu Thr Leu Ser Thr Asn Tyr Asn Gln Gly
        515                 520                 525

Ala Lys Val Ser Gly Pro Tyr Val Trp Asp Ala Ser Lys Asn Ile Tyr
    530                 535                 540

Tyr Ile Leu Val Asp Phe Thr Gly Thr Leu Ile Tyr Pro Gly Gly Gln
545                 550                 555                 560

Asp Lys Tyr Lys Lys Glu Val Gln Phe Arg Ile Ala Ala Pro Gln Asn
                565                 570                 575

Val Gln Trp Asp Asn Ser Asn Asp Tyr Ser Phe Gln Asp Ile Lys Gly
            580                 585                 590

Val Ser Ser Gly Ser Val Val Lys Thr Lys Tyr Ile Pro Leu Tyr Asp
        595                 600                 605

Gly Asp Val Lys Val Trp Gly Glu Glu Pro Gly Thr Ser Gly Ala Thr
    610                 615                 620

Pro Thr Pro Thr Ala Thr Ala Thr Pro Thr Pro Thr Pro Thr Val Thr
625                 630                 635                 640

Pro Thr Pro Thr Pro Thr Pro Thr Ser Thr Ala Thr Pro Thr Pro Thr
                645                 650                 655

Pro Thr Pro Thr Val Thr Pro Thr Pro Thr Pro Thr Pro Thr Ala Thr
            660                 665                 670

Pro Thr Ala Thr Pro Thr Pro Thr Ser Thr Pro Ser Ser Thr Pro Val
        675                 680                 685
```

-continued

```
Ala Gly Gly Gln Ile Lys Val Leu Tyr Ala Asn Lys Glu Thr Asn Ser
    690                 695                 700

Thr Thr Asn Thr Ile Arg Pro Trp Leu Lys Val Val Asn Thr Gly Ser
705                 710                 715                 720

Ser Ser Ile Asp Leu Ser Arg Val Thr Ile Arg Tyr Trp Tyr Thr Val
                725                 730                 735

Asp Gly Asp Lys Ala Gln Ser Ala Ile Ser Asp Trp Ala Gln Ile Gly
            740                 745                 750

Ala Ser Asn Val Thr Phe Lys Phe Val Lys Leu Ser Ser Ser Val Ser
        755                 760                 765

Gly Ala Asp Tyr Tyr Leu Glu Ile Gly Phe Lys Ser Gly Ala Gly Gln
    770                 775                 780

Leu Gln Ala Gly Lys Asp Thr Gly Glu Ile Gln Ile Arg Phe Asn Lys
785                 790                 795                 800

Ser Asp Trp Ser Asn Tyr Asn Gln Gly Asn Asp Trp Ser Trp Met Gln
                805                 810                 815

Ser Met Thr Asn Tyr Gly Glu Asn Val Lys Val Thr Ala Tyr Ile Asp
            820                 825                 830

Gly Val Leu Val Trp Gly Gln Glu Pro Ser Gly Ala Thr Pro Thr Pro
        835                 840                 845

Thr Ala Thr Pro Ala Pro Thr Val Thr Pro Thr Pro Thr Pro Thr Pro
    850                 855                 860

Thr Ser Thr Pro Thr Ala Thr Pro Thr Ala Thr Pro Thr Pro Thr Pro
865                 870                 875                 880

Thr Pro Ser Ser Thr Pro Val Ala Gly Gly Gln Ile Lys Val Leu Tyr
                885                 890                 895

Ala Asn Lys Glu Thr Asn Ser Thr Thr Asn Thr Ile Arg Pro Trp Leu
            900                 905                 910

Lys Val Val Asn Thr Gly Ser Ser Ser Ile Asp Leu Ser Arg Val Thr
        915                 920                 925

Ile Arg Tyr Trp Tyr Thr Val Asp Gly Asp Lys Ala Gln Ser Ala Ile
    930                 935                 940

Ser Asp Trp Ala Gln Ile Gly Ala Ser Asn Val Thr Phe Lys Phe Val
945                 950                 955                 960

Lys Leu Ser Ser Ser Val Ser Gly Ala Asp Tyr Tyr Leu Glu Ile Gly
                965                 970                 975

Phe Lys Ser Gly Ala Gly Gln Leu Gln Ala Gly Lys Asp Thr Gly Glu
            980                 985                 990

Ile Gln Ile Arg Phe Asn Lys Ser Asp Trp Ser Asn Tyr Asn Gln Gly
        995                 1000                1005

Asn Asp Trp Ser Trp Met Gln Ser Met Thr Asn Tyr Gly Glu Asn Val
    1010                1015                1020

Lys Val Thr Ala Tyr Ile Asp Gly Val Leu Val Trp Gly Gln Glu Pro
1025                1030                1035                1040

Ser Gly Ala Thr Pro Thr Pro Thr Ala Thr Pro Ala Pro Thr Val Thr
                1045                1050                1055

Pro Thr Pro Thr Pro Ala Pro Thr Pro Thr Pro Thr Pro Thr Pro Thr
            1060                1065                1070

Ala Thr Pro Thr Pro Thr Pro Thr Pro Thr Pro Thr Ala Thr Pro Thr
        1075                1080                1085

Val Thr Ala Thr Pro Thr Pro Thr Pro Ser Ser Thr Pro Ser Val Leu
    1090                1095                1100
```

```
Gly Glu Tyr Gly Gln Arg Phe Met Trp Leu Trp Asn Lys Ile His Asp
1105                1110                1115                1120

Pro Ala Asn Gly Tyr Phe Asn Gln Asp Gly Ile Pro Tyr His Ser Val
                1125                1130                1135

Glu Thr Leu Ile Cys Glu Ala Pro Asp Tyr Gly His Leu Thr Thr Ser
            1140                1145                1150

Glu Ala Phe Ser Tyr Tyr Val Trp Leu Glu Ala Val Tyr Gly Lys Leu
        1155                1160                1165

Thr Gly Asp Trp Ser Lys Phe Lys Thr Ala Trp Asp Thr Leu Glu Lys
    1170                1175                1180

Tyr Met Ile Pro Ser Ala Glu Asp Gln Pro Met Arg Ser Tyr Asp Pro
1185                1190                1195                1200

Asn Lys Pro Ala Thr Tyr Ala Gly Glu Trp Glu Thr Pro Asp Lys Tyr
               1205                1210                1215

Pro Ser Pro Leu Glu Phe Asn Val Pro Val Gly Lys Asp Pro Leu His
           1220                1225                1230

Asn Glu Leu Val Ser Thr Tyr Gly Ser Thr Leu Met Tyr Gly Met His
       1235                1240                1245

Trp Leu Met Asp Val Asp Asn Trp Tyr Gly Tyr Gly Lys Arg Gly Asp
   1250                1255                1260

Gly Val Ser Arg Ala Ser Phe Ile Asn Thr Phe Gln Arg Gly Pro Glu
1265                1270                1275                1280

Glu Ser Val Trp Glu Thr Val Pro His Pro Ser Trp Glu Glu Phe Lys
                1285                1290                1295

Trp Gly Gly Pro Asn Gly Phe Leu Asp Leu Phe Ile Lys Asp Gln Asn
            1300                1305                1310

Tyr Ser Lys Gln Trp Arg Tyr Thr Asp Ala Pro Asp Ala Asp Ala Arg
        1315                1320                1325

Ala Ile Gln Ala Thr Tyr Trp Ala Lys Val Trp Ala Lys Glu Gln Gly
    1330                1335                1340

Lys Phe Asn Glu Ile Ser Ser Tyr Val Ala Lys Ala Ala Lys Met Gly
1345                1350                1355                1360

Asp Tyr Leu Arg Tyr Ala Met Phe Asp Lys Tyr Phe Lys Pro Leu Gly
                1365                1370                1375

Cys Gln Asp Lys Asn Ala Ala Gly Gly Thr Gly Tyr Asp Ser Ala His
            1380                1385                1390

Tyr Leu Leu Ser Trp Tyr Tyr Ala Trp Gly Gly Ala Leu Asp Gly Ala
        1395                1400                1405

Trp Ser Trp Lys Ile Gly Ser Ser His Val His Phe Gly Tyr Gln Asn
    1410                1415                1420

Pro Met Ala Ala Trp Ala Leu Ala Asn Asp Ser Asp Met Lys Pro Lys
1425                1430                1435                1440

Ser Pro Asn Gly Ala Ser Asp Trp Ala Lys Ser Leu Lys Arg Gln Ile
                1445                1450                1455

Glu Phe Tyr Arg Trp Leu Gln Ser Ala Glu Gly Ala Ile Ala Gly Gly
            1460                1465                1470

Ala Thr Asn Ser Trp Asn Gly Arg Tyr Glu Lys Tyr Pro Ala Gly Thr
        1475                1480                1485

Ala Thr Phe Tyr Gly Met Ala Tyr Glu Pro Asn Pro Val Tyr His Asp
    1490                1495                1500

Pro Gly Ser Asn Thr Trp Phe Gly Phe Gln Ala Trp Ser Met Gln Arg
1505                1510                1515                1520

Val Ala Glu Tyr Tyr Tyr Val Thr Gly Asp Lys Asp Ala Gly Ala Leu
```

```
                1525                1530                1535

Leu Glu Lys Trp Val Ser Trp Val Lys Ser Val Val Lys Leu Asn Ser
            1540                1545                1550

Asp Gly Thr Phe Ala Ile Pro Ser Thr Leu Asp Trp Ser Gly Gln Pro
        1555                1560                1565

Asp Thr Trp Asn Gly Ala Tyr Thr Gly Asn Ser Asn Leu His Val Lys
    1570                1575                1580

Val Val Asp Tyr Gly Thr Asp Leu Gly Ile Thr Ala Ser Leu Ala Asn
1585                1590                1595                1600

Ala Leu Leu Tyr Tyr Ser Ala Gly Thr Lys Lys Tyr Gly Val Phe Asp
                1605                1610                1615

Glu Gly Ala Lys Asn Leu Ala Lys Glu Leu Leu Asp Arg Met Trp Lys
            1620                1625                1630

Leu Tyr Arg Asp Glu Lys Gly Leu Ser Ala Pro Glu Lys Arg Ala Asp
        1635                1640                1645

Tyr Lys Arg Phe Phe Glu Gln Glu Val Tyr Ile Pro Ala Gly Trp Ile
    1650                1655                1660

Gly Lys Met Pro Asn Gly Asp Val Ile Lys Ser Gly Val Lys Phe Ile
1665                1670                1675                1680

Asp Ile Arg Ser Lys Tyr Lys Gln Asp Pro Asp Trp Pro Lys Leu Glu
                1685                1690                1695

Ala Ala Tyr Lys Ser Gly Gln Ala Pro Glu Phe Arg Tyr His Arg Phe
            1700                1705                1710

Trp Ala Gln Cys Asp Ile Ala Ile Ala Asn Ala Thr Tyr Glu Ile Leu
        1715                1720                1725

Phe Gly Asn Gln
    1730


<210> SEQ ID NO 122
<211> LENGTH: 946
<212> TYPE: PRT
<213> ORGANISM: Caldicellulosiruptor bescii

<400> SEQUENCE: 122

Ala Thr Ser Asn Asp Gly Val Val Lys Ile Asp Thr Ser Thr Leu Ile
 1               5                  10                  15

Gly Thr Asn His Ala His Cys Trp Tyr Arg Asp Lys Leu Glu Thr Ala
            20                  25                  30

Leu Arg Gly Ile Arg Ser Trp Gly Met Asn Ser Val Arg Val Val Leu
        35                  40                  45

Ser Asn Gly Tyr Arg Trp Thr Lys Ile Pro Ala Ser Glu Val Ala Asn
    50                  55                  60

Ile Ile Ser Leu Ser Arg Ser Leu Gly Phe Arg Ala Ile Val Leu Glu
65                  70                  75                  80

Val His Asp Thr Thr Gly Tyr Gly Glu Asp Gly Ala Ala Cys Ser Leu
                85                  90                  95

Ala Gln Ala Val Glu Tyr Trp Lys Glu Ile Lys Ser Val Leu Glu Gly
            100                 105                 110

Asn Glu Asp Phe Val Ile Ile Asn Ile Gly Asn Glu Pro Tyr Gly Asn
        115                 120                 125

Asn Asn Tyr Gln Asn Trp Ile Asn Asp Thr Lys Asn Ala Ile Lys Ala
    130                 135                 140

Leu Arg Asp Ala Gly Phe Lys His Thr Ile Met Val Asp Ala Pro Asn
145                 150                 155                 160
```

```
Trp Gly Gln Asp Trp Ser Asn Thr Met Arg Asp Asn Ala Gln Ser Ile
                165                 170                 175

Met Glu Ala Asp Pro Leu Arg Asn Leu Val Phe Ser Ile His Met Tyr
            180                 185                 190

Gly Val Tyr Asn Thr Ala Ser Lys Val Glu Glu Tyr Ile Lys Ser Phe
        195                 200                 205

Val Glu Lys Gly Leu Pro Leu Val Ile Gly Glu Phe Gly His Gln His
    210                 215                 220

Thr Asp Gly Asp Pro Asp Glu Glu Ala Ile Val Arg Tyr Ala Lys Gln
225                 230                 235                 240

Tyr Lys Ile Gly Leu Phe Ser Trp Ser Trp Cys Gly Asn Ser Ser Tyr
                245                 250                 255

Val Gly Tyr Leu Asp Met Val Asn Asn Trp Asp Pro Asn Asn Pro Thr
            260                 265                 270

Pro Trp Gly Gln Trp Tyr Lys Thr Asn Ala Ile Gly Ala Ser Ser Val
        275                 280                 285

Pro Thr Ser Thr Pro Thr Pro Thr Pro Thr Ala Thr Pro Thr Ala Thr
    290                 295                 300

Pro Thr Pro Thr Leu Thr Pro Thr Pro Thr Pro Thr Pro Thr Pro Thr
305                 310                 315                 320

Ser Thr Pro Thr Ala Thr Pro Thr Ala Thr Pro Thr Pro Thr Pro Thr
                325                 330                 335

Pro Ser Ser Thr Pro Val Ala Gly Gly Gln Ile Lys Val Leu Tyr Ala
            340                 345                 350

Asn Lys Glu Thr Asn Ser Thr Thr Asn Thr Ile Arg Pro Trp Leu Lys
        355                 360                 365

Val Val Asn Thr Gly Ser Ser Ser Ile Asp Leu Ser Arg Val Thr Ile
    370                 375                 380

Arg Tyr Trp Tyr Thr Val Asp Gly Asp Lys Ala Gln Ser Ala Ile Ser
385                 390                 395                 400

Asp Trp Ala Gln Ile Gly Ala Ser Asn Val Thr Phe Lys Phe Val Lys
                405                 410                 415

Leu Ser Ser Ser Val Ser Gly Ala Asp Tyr Tyr Leu Glu Ile Gly Phe
            420                 425                 430

Lys Ser Gly Ala Gly Gln Leu Gln Ala Gly Lys Asp Thr Gly Glu Ile
        435                 440                 445

Gln Ile Arg Phe Asn Lys Ser Asp Trp Ser Asn Tyr Asn Gln Gly Asn
    450                 455                 460

Asp Trp Ser Trp Met Gln Ser Met Thr Ser Tyr Gly Glu Asn Val Lys
465                 470                 475                 480

Val Thr Ala Tyr Ile Asp Gly Val Leu Val Trp Gly Gln Glu Pro Ser
                485                 490                 495

Gly Ala Thr Pro Thr Pro Thr Ala Thr Pro Ala Pro Thr Pro Thr Pro
            500                 505                 510

Thr Pro Thr Pro Thr Ala Thr Pro Thr Pro Thr Pro Thr Pro Thr Pro
        515                 520                 525

Thr Pro Thr Ala Thr Pro Thr Pro Thr Pro Ser Ser Thr Pro Val Ala
    530                 535                 540

Gly Gly Gln Ile Lys Val Leu Tyr Ala Asn Lys Glu Thr Asn Ser Thr
545                 550                 555                 560

Thr Asn Thr Ile Arg Pro Trp Leu Lys Val Val Asn Thr Gly Ser Ser
                565                 570                 575

Ser Ile Asp Leu Ser Arg Val Thr Ile Arg Tyr Trp Tyr Thr Val Asp
```

```
            580                 585                 590

Gly Asp Lys Ala Gln Ser Ala Ile Ser Asp Trp Ala Gln Ile Gly Ala
        595                 600                 605

Ser Asn Val Thr Phe Lys Phe Val Lys Leu Ser Ser Ser Val Ser Gly
    610                 615                 620

Ala Asp Tyr Tyr Leu Glu Ile Gly Phe Lys Ser Gly Ala Gly Gln Leu
625                 630                 635                 640

Gln Ala Gly Lys Asp Thr Gly Glu Ile Gln Ile Arg Phe Asn Lys Ser
                645                 650                 655

Asp Trp Ser Asn Tyr Asn Gln Gly Asn Asp Trp Ser Trp Met Gln Ser
            660                 665                 670

Met Thr Ser Tyr Gly Glu Asn Val Lys Val Thr Ala Tyr Ile Asp Gly
        675                 680                 685

Val Leu Val Trp Gly Gln Glu Pro Ser Gly Ala Thr Pro Thr Pro Thr
    690                 695                 700

Ala Thr Pro Ala Pro Thr Pro Thr Pro Thr Pro Thr Pro Thr Ala Thr
705                 710                 715                 720

Pro Thr Pro Thr Pro Thr Pro Thr Pro Thr Pro Thr Ala Thr Pro Thr
                725                 730                 735

Pro Thr Pro Ser Ser Thr Pro Val Ala Gly Gly Gln Ile Lys Val Leu
            740                 745                 750

Tyr Ala Asn Lys Glu Thr Asn Ser Thr Thr Asn Thr Ile Arg Pro Trp
        755                 760                 765

Leu Lys Val Val Asn Thr Gly Ser Ser Ser Ile Asp Leu Ser Arg Val
    770                 775                 780

Thr Ile Arg Tyr Trp Tyr Thr Val Asp Gly Asp Lys Ala Gln Ser Ala
785                 790                 795                 800

Ile Ser Asp Trp Ala Gln Ile Gly Ala Ser Asn Val Thr Phe Lys Phe
                805                 810                 815

Val Lys Leu Ser Ser Ser Val Ser Gly Ala Asp Tyr Tyr Leu Glu Ile
            820                 825                 830

Gly Phe Lys Ser Gly Ala Gly Gln Leu Gln Ala Gly Lys Asp Thr Gly
        835                 840                 845

Glu Ile Gln Ile Arg Phe Asn Lys Ser Asp Trp Ser Asn Tyr Asn Gln
    850                 855                 860

Gly Asn Asp Trp Ser Trp Met Gln Ser Met Thr Ser Tyr Gly Glu Asn
865                 870                 875                 880

Val Lys Val Thr Ala Tyr Ile Asp Gly Val Leu Val Trp Gly Gln Glu
                885                 890                 895

Pro Ser Gly Ala Thr Pro Thr Pro Thr Ala Thr Pro Ala Pro Thr Val
            900                 905                 910

Thr Pro Thr Ala Thr Pro Ala Pro Thr Pro Thr Pro Thr Pro Thr Val
        915                 920                 925

Thr Ala Thr Pro Thr Pro Thr Pro Thr Pro Val Gln Thr Val Ile Pro
    930                 935                 940

Met Pro
945
```

<210> SEQ ID NO 123
<211> LENGTH: 2841
<212> TYPE: DNA
<213> ORGANISM: Caldicellulosiruptor bescii

<400> SEQUENCE: 123

-continued

```
gctacatcta atgatggagt agtgaagata gatactagca cattaatagg aacaaatcac     60
gcacattgct ggtacagaga taaacttgag acggcattgc gaggaataag gtcatggggt    120
atgaactctg tgagggtagt gttgagtaat ggctatcgat ggacgaagat accagcaagt    180
gaagtagcaa atattatatc attgtcaaga agtcttggat tcagagccat tgtattagaa    240
gttcacgaca cgacaggata tggtgaggac ggtgcagcat gttcattggc gcaagcagta    300
gaatattgga aagagataaa gagtgtgtta gaaggcaatg aggattttgt tataataaac    360
attggtaatg agccgtatgg gaacaataac tatcaaaact ggattaatga cacgaagaat    420
gctataaaag cgctaaggga tgcagggttc aagcacacga taatggttga tgcaccgaac    480
tgggggcagg attggtctaa tactatgaga gacaatgccc agagcataat ggaagcagat    540
ccgctgcgca atttggtatt ttcgattcat atgtacggtg tatacaatac agcgagcaag    600
gtagaagaat atatcaagtc atttgtggag aaagggctgc cattagttat tggggagttt    660
gggcatcagc atacagatgg tgaccctgac gaggaagcta ttgtcaggta tgcaaaacaa    720
tacaagatag gactttttag ctggtcttgg tgtggcaatt cgagctatgt agggtacttg    780
gacatggtaa acaattggga ccccaataat ccaactccat gggggcaatg gtataaaact    840
aatgcgattg gtgcctcttc agtacctact tcaacaccaa caccgacacc aactgctaca    900
ccaacagcaa caccaacacc aacactgact ccaacaccga cacctacacc aacaccaacg    960
tcaacaccaa ctgctacacc aacagcaacg ccaacaccaa caccgacgcc gagcagcaca   1020
cctgtagcag gtggacagat aaaggtattg tatgctaaca aggagacaaa tagcacaaca   1080
aatacgataa ggccatggtt gaaggtagtg aacactggaa gcagcagcat agatttgagc   1140
agggtaacga taaggtactg gtacacggta gatggggaca aggcacagag tgcgatatca   1200
gactgggcac agataggagc aagcaatgtg acattcaagt ttgtgaagct gagcagtagc   1260
gtaagtggag cggactatta tttagagata ggatttaaga gtggagctgg gcagttgcag   1320
gctggtaaag acacagggga gatacagata aggtttaaca agagtgactg gagcaattac   1380
aatcagggga atgactggtc atggatgcag agcatgacga gttatggaga gaatgtgaag   1440
gtaacagcgt atatagatgg tgtattggta tggggacagg agccgagtgg agcgacacca   1500
acaccgacag caacaccagc accaacacca accccgaccc caacaccaac tgctacacca   1560
acgccaacac cgactccaac accaacacca actgctaccc caacaccgac gccgagcagt   1620
acacctgtag caggtggaca gataaaggta ttgtatgcta acaaggagac aaatagcaca   1680
acaaacacga taaggccatg gttgaaggta gtgaacactg gaagcagcag catagatttg   1740
agcagggtaa cgataaggta ctggtacacg gtagatgggg acaaggcaca gagtgcgata   1800
tcagactggg cacagatagg agcaagcaat gtgacattca agtttgtgaa gctgagcagt   1860
agcgtaagtg gagcggacta ttatttagag ataggattta agagtggagc tgggcagttg   1920
caggctggta aagacacagg ggagatacag ataaggttta acaagagtga ctggagcaat   1980
tacaatcagg ggaatgactg gtcatggatg cagagcatga cgagttatgg agagaatgtg   2040
aaggtaacag cgtatataga tggtgtattg gtatggggac aggagccgag tggagcgaca   2100
ccaacaccga cagcaacacc agcaccaaca ccaaccccga ccccaacacc aactgctaca   2160
ccaacgccaa caccgactcc aacaccaaca ccaactgcta ccccaacacc gacgccgagc   2220
agtacacctg tagcaggtgg acagataaag gtattgtatg ctaacaagga gacaaatagc   2280
acaacaaaca cgataaggcc atggttgaag gtagtgaaca ctggaagcag cagcatagat   2340
ttgagcaggg taacgataag gtactggtac acggtagatg ggacaaggc acagagtgcg   2400
```

```
atatcagact gggcacagat aggagcaagc aatgtgacat tcaagtttgt gaagctgagc   2460

agtagcgtaa gtggagcgga ctattattta gagataggat ttaagagtgg agctgggcag   2520

ttgcaggctg gtaaagacac aggggagata cagataaggt ttaacaagag tgactggagc   2580

aattacaatc aggggaatga ctggtcatgg atgcagagca tgacgagtta tggagagaat   2640

gtgaaggtaa cagcgtatat agatggtgta ttggtatggg gacaggagcc gagtggagcg   2700

acaccaacac cgacagcaac accagcaccg acagtgacac cgacagcaac accagcacca   2760

acaccaaccc cgaccccaac agtaacggca accccgacac cgacaccaac accggtgcag   2820

acagtaatac caatgccata a                                             2841
```

<210> SEQ ID NO 124
<211> LENGTH: 817
<212> TYPE: PRT
<213> ORGANISM: Caldicellulosiruptor bescii

<400> SEQUENCE: 124

```
Ala Thr Thr Phe Asn Tyr Gly Glu Ala Leu Gln Lys Ala Ile Met Phe
 1               5                  10                  15

Tyr Glu Phe Gln Met Ser Gly Lys Leu Pro Ser Trp Ile Arg Asn Asn
            20                  25                  30

Trp Arg Gly Asp Ser Gly Leu Asn Asp Gly Lys Asp Val Gly Leu Asp
        35                  40                  45

Leu Thr Gly Gly Trp His Asp Ala Gly Asp His Val Lys Phe Asn Leu
    50                  55                  60

Pro Met Ser Tyr Ser Ala Ser Met Leu Ser Trp Ala Val Tyr Glu Tyr
65                  70                  75                  80

Lys Ala Ala Phe Glu Lys Ser Gly Gln Leu Glu His Ile Leu Asn Gln
                85                  90                  95

Ile Glu Trp Val Asn Asp Tyr Phe Val Lys Cys His Pro Ser Lys Tyr
            100                 105                 110

Val Tyr Tyr Tyr Gln Val Gly Asp Pro Ile Glu Asp His Asn Phe Trp
        115                 120                 125

Gly Pro Ala Glu Val Met Gln Met Lys Arg Pro Ala Tyr Lys Cys Asp
    130                 135                 140

Leu Asn Asn Pro Ala Ser Ser Val Val Ala Glu Thr Ala Ala Ser Leu
145                 150                 155                 160

Ala Ala Ala Ser Ile Val Ile Arg Glu Arg Asn Ser Gln Lys Ala Asp
                165                 170                 175

Thr Tyr Leu Gln His Ala Met Val Leu Phe Asp Phe Ala Asp Arg Thr
            180                 185                 190

Arg Ser Asp Ala Gly Tyr Thr Ala Ala Thr Gly Phe Tyr Thr Ser Gly
        195                 200                 205

Gly Phe Ile Asp Asp Leu Gly Trp Ala Ala Val Trp Leu Tyr Leu Ala
    210                 215                 220

Thr Asn Asp Lys Ser Tyr Leu Asp Lys Ala Glu Ala Leu Met Ala Glu
225                 230                 235                 240

Tyr Ala Gly Gly Thr Asn Thr Trp Thr Gln Cys Trp Asp Asp Val Arg
                245                 250                 255

Tyr Gly Ala Ile Leu Leu Leu Ala Lys Ile Thr Asn Lys Asp Ile Tyr
            260                 265                 270

Lys Gly Ala Val Glu Arg Asn Leu Asp His Trp Thr Tyr Asn Ile Thr
        275                 280                 285
```

-continued

```
Tyr Thr Pro Lys Gly Leu Ala Trp Ile Thr Gly Trp Gly Ser Leu Arg
    290                 295                 300

Tyr Ala Thr Thr Ala Ala Phe Leu Ala Phe Val Tyr Ala Asp Trp Ser
305                 310                 315                 320

Gly Cys Pro Glu Asn Lys Arg Thr Ala Tyr Leu Lys Phe Gly Glu Ser
                325                 330                 335

Gln Ile Asn Tyr Ala Leu Gly Ser Thr Gly Arg Ser Phe Leu Val Gly
            340                 345                 350

Phe Gly Gln Asn Tyr Pro Gln His Pro His His Arg Asn Ala His Ser
        355                 360                 365

Ser Trp Ala Asn Ser Met Arg Ile Pro Glu Tyr His Arg His Ile Leu
    370                 375                 380

Tyr Gly Ala Leu Val Gly Gly Pro Gly Ser Asp Asp Ser Tyr Asn Asp
385                 390                 395                 400

Asp Ile Thr Asp Tyr Val Gln Asn Glu Val Ala Cys Asp Tyr Asn Ala
                405                 410                 415

Gly Ile Val Gly Ala Leu Ala Lys Met Tyr Leu Met Tyr Gly Gly Asp
            420                 425                 430

Pro Ile Pro Asn Phe Lys Ala Ile Glu Lys Pro Thr Asn Asp Glu Ile
        435                 440                 445

Phe Val Glu Ser Lys Phe Gly Asn Ser Gln Gly Thr Asn Tyr Thr Glu
    450                 455                 460

Ile Ile Ser Tyr Ile Tyr Asn Arg Thr Gly Trp Pro Pro Arg Val Thr
465                 470                 475                 480

Asp Asn Leu Asn Phe Lys Tyr Phe Ile Asp Leu Ser Glu Leu Ile Lys
                485                 490                 495

Ala Gly Tyr Gly Pro Asp Val Val Lys Val Glu Thr Tyr Tyr Ser Glu
            500                 505                 510

Gly Gly Lys Ile Ser Gly Pro Tyr Val Trp Asn Ala Ser Lys Asn Leu
        515                 520                 525

Tyr Tyr Ile Leu Val Asp Phe Thr Gly Thr Lys Ile Tyr Pro Gly Gly
    530                 535                 540

Glu Val Glu His Lys Lys Gln Ala Gln Phe Lys Ile Ser Val Pro Gln
545                 550                 555                 560

Gly Val Pro Trp Asp Pro Thr Asn Asp Pro Ser Tyr Ala Gly Leu Thr
                565                 570                 575

Lys Glu Leu Ser Lys Asn Lys Phe Ile Ala Ala Tyr Glu Gly Asn Val
            580                 585                 590

Leu Val Trp Gly Gln Glu Pro Glu Gly Ser Ser Ser Ser Thr Pro Thr
        595                 600                 605

Pro Thr Pro Thr Pro Thr Pro Thr Leu Thr Pro Thr Pro Thr Ser Thr
    610                 615                 620

Ala Thr Pro Thr Pro Thr Pro Thr Pro Thr Pro Thr Ser Thr Pro Thr
625                 630                 635                 640

Ala Thr Pro Thr Ala Thr Pro Thr Pro Thr Pro Thr Pro Ser Ser Thr
                645                 650                 655

Pro Val Ala Gly Gly Gln Ile Lys Val Leu Tyr Ala Asn Lys Glu Thr
            660                 665                 670

Asn Ser Thr Thr Asn Thr Ile Arg Pro Trp Leu Lys Val Val Asn Thr
        675                 680                 685

Gly Ser Ser Ser Ile Asp Leu Ser Arg Val Thr Ile Arg Tyr Trp Tyr
    690                 695                 700

Thr Val Asp Gly Asp Lys Ala Gln Ser Ala Ile Ser Asp Trp Ala Gln
```

-continued 705 710 715 720

Ile Gly Ala Ser Asn Val Thr Phe Lys Phe Val Lys Leu Ser Ser Ser
725 730 735

Val Ser Gly Ala Asp Tyr Tyr Leu Glu Ile Gly Phe Lys Ser Gly Ala
740 745 750

Gly Gln Leu Gln Ala Gly Lys Asp Thr Gly Glu Ile Gln Ile Arg Phe
755 760 765

Asn Lys Ser Asp Trp Ser Asn Tyr Asn Gln Gly Asn Asp Trp Ser Trp
770 775 780

Met Gln Ser Met Thr Ser Tyr Gly Glu Asn Val Lys Val Thr Ala Tyr
785 790 795 800

Ile Asp Gly Val Leu Val Trp Gly Gln Glu Pro Ser Gly Ala Thr Pro
805 810 815

Thr

<210> SEQ ID NO 125
<211> LENGTH: 2451
<212> TYPE: DNA
<213> ORGANISM: Caldicellulosiruptor bescii

<400> SEQUENCE: 125
gcaacaacct ttaactatgg tgaagctctt caaaaagcga tcatgtttta tgaatttcag 60
atgtcaggta aactaccatc atggatccgt aacaactggc gcggggattc tggtctaaat 120
gatggcaaag atgtaggttt agatcttact ggtggctggc atgatgcggg cgaccatgta 180
aagtttaatc taccaatgtc atacagtgca tcaatgcttt cgtgggcagt ttatgagtac 240
aaagcagcat ttgagaaaag tggtcagctt gaacatatac ttaaccagat tgaatgggta 300
aacgactact ttgtaaaatg ccatccatca aagtatgtat actactatca agttggtgac 360
ccaattgaag atcataactt ctggggtcca gcagaagtta tgcaaatgaa acgaccagca 420
tacaagtgtg acttaaataa tccagcaagt tcggttgttg cagaaacagc agcatcctta 480
gctgcagctt caatcgtcat acgtgaaaga aatagtcaaa aggcagacac atatttgcag 540
catgcgatgg tactctttga ttttgccgat agaactcgta gtgatgcagg gtataccgca 600
gcaacaggct tttacacatc aggtggtttt attgatgatc ttggttgggc agcagtgtgg 660
ttatatcttg cgacaaatga caaatcatat ttagataaag ctgaggcact tatggcagaa 720
tatgccggtg gcacaaatac atggacacag tgctgggacg atgtaagata cggagcaata 780
ttgcttttag caaaaattac taataaagac atatataaag gtgctgttga aagaaatctt 840
gatcattgga catataacat aacctataca cctaaaggtc ttgcatggat aacagggtgg 900
ggctcactta ggtatgccac aactgcagct ttcttagcgt ttgtttatgc agattggtca 960
ggatgtccag aaaataagcg aacagcttat ctaaaatttg gtgagagtca gattaactat 1020
gcattaggtt caacaggaag aagcttttttg gtaggatttg ggcaaaatta tccacaacat 1080
ccacatcaca gaaatgcaca cagttcatgg gcgaacagta tgcgaatacc tgaatatcat 1140
cgacacatac tttatggtgc attagtaggc ggaccaggct ctgatgatag ttacaatgat 1200
gatattactg actatgttca aaacgaggtg gcttgtgact acaatgctgg tattgtaggt 1260
gctctggcaa aaatgtacct tatgtatgga ggagacccaa tacctaattt caaagctatc 1320
gaaaagccaa ctaatgatga aatttttgtt gaatccaagt ttggtaattc acagggtaca 1380
aactataccg aaataatttc atacatttat aacagaacgg gatggccgcc tcgagtcaca 1440
gataatctaa actttaagta ttttattgac ctaagtgagt taatcaaggc tgggtatggt 1500

```
cctgatgttg ttaaagtaga gacatattat tcagaaggtg gaaaaatatc tggaccatac   1560

gtatggaatg catcaaagaa cctttactat atattagttg attttacagg aacaaaaata   1620

tatccaggtg ggaagtaga acacaaaaaa caagctcaat ttaagatatc tgtgccacaa   1680

ggtgttccat gggatccaac taatgaccca tcttatgcag gattaacaaa agaacttagt   1740

aaaaataagt tcatagcagc ttatgaaggt aacgtgctgg tatggggaca agaaccagag   1800

ggttcgtcaa gttcaacccc aaccccaaca ccaacaccaa caccaacact gactccaaca   1860

ccgacatcaa ctgctacacc aacaccgaca cctacaccaa caccaacgtc aacaccaact   1920

gctacaccaa cagcaacgcc aacaccaaca ccgacgccga gcagcacacc tgtagcaggc   1980

gggcagataa aggtattgta tgctaacaag gagacaaata gcacaacaaa cacgataagg   2040

ccatggttga aggtagtgaa cactggaagc agcagcatag atttaagcag ggtaacgata   2100

aggtactggt acacggtaga tggggacaag gcacagagtg cgatatcaga ctgggcacag   2160

ataggagcaa gcaatgtgac attcaagttt gtgaagctga gcagtagcgt aagtggagcg   2220

gactattatt tagagatagg atttaagagt ggagctgggc agttgcaggc tggtaaagac   2280

acaggggaga tacagataag gtttaacaag agtgactgga gcaattacaa tcaggggaat   2340

gactggtcat ggatgcagag catgacgagt tatggagaga atgtgaaggt aacagcgtat   2400

atagatggtg tattggtatg gggacaggag ccgagtggag cgacaccaac a            2451
```

```
<210> SEQ ID NO 126
<211> LENGTH: 665
<212> TYPE: PRT
<213> ORGANISM: Caldicellulosiruptor bescii

<400> SEQUENCE: 126

Ala Thr Thr Phe Asn Tyr Gly Glu Ala Leu Gln Lys Ala Ile Met Phe
 1               5                  10                  15

Tyr Glu Phe Gln Met Ser Gly Lys Leu Pro Ser Trp Ile Arg Asn Asn
            20                  25                  30

Trp Arg Gly Asp Ser Gly Leu Asn Asp Gly Lys Asp Val Gly Leu Asp
        35                  40                  45

Leu Thr Gly Gly Trp His Asp Ala Gly Asp His Val Lys Phe Asn Leu
    50                  55                  60

Pro Met Ser Tyr Ser Ala Ser Met Leu Ser Trp Ala Val Tyr Glu Tyr
65                  70                  75                  80

Lys Ala Ala Phe Glu Lys Ser Gly Gln Leu Glu His Ile Leu Asn Gln
                85                  90                  95

Ile Glu Trp Val Asn Asp Tyr Phe Val Lys Cys His Pro Ser Lys Tyr
            100                 105                 110

Val Tyr Tyr Tyr Gln Val Gly Asp Pro Ile Glu Asp His Asn Phe Trp
        115                 120                 125

Gly Pro Ala Glu Val Met Gln Met Lys Arg Pro Ala Tyr Lys Cys Asp
    130                 135                 140

Leu Asn Asn Pro Ala Ser Ser Val Val Ala Glu Thr Ala Ala Ser Leu
145                 150                 155                 160

Ala Ala Ala Ser Ile Val Ile Arg Glu Arg Asn Ser Gln Lys Ala Asp
                165                 170                 175

Thr Tyr Leu Gln His Ala Met Val Leu Phe Asp Phe Ala Asp Arg Thr
            180                 185                 190

Arg Ser Asp Ala Gly Tyr Thr Ala Ala Thr Gly Phe Tyr Thr Ser Gly
        195                 200                 205
```

-continued

```
Gly Phe Ile Asp Asp Leu Gly Trp Ala Ala Val Trp Leu Tyr Leu Ala
    210                 215                 220

Thr Asn Asp Lys Ser Tyr Leu Asp Lys Ala Glu Ala Leu Met Ala Glu
225                 230                 235                 240

Tyr Ala Gly Gly Thr Asn Thr Trp Thr Gln Cys Trp Asp Asp Val Arg
                245                 250                 255

Tyr Gly Ala Ile Leu Leu Leu Ala Lys Ile Thr Asn Lys Asp Ile Tyr
            260                 265                 270

Lys Gly Ala Val Glu Arg Asn Leu Asp His Trp Thr Tyr Asn Ile Thr
        275                 280                 285

Tyr Thr Pro Lys Gly Leu Ala Trp Ile Thr Gly Trp Gly Ser Leu Arg
    290                 295                 300

Tyr Ala Thr Thr Ala Ala Phe Leu Ala Phe Val Tyr Ala Asp Trp Ser
305                 310                 315                 320

Gly Cys Pro Glu Asn Lys Arg Thr Ala Tyr Leu Lys Phe Gly Glu Ser
                325                 330                 335

Gln Ile Asn Tyr Ala Leu Gly Ser Thr Gly Arg Ser Phe Leu Val Gly
            340                 345                 350

Phe Gly Gln Asn Tyr Pro Gln His Pro His His Arg Asn Ala His Ser
        355                 360                 365

Ser Trp Ala Asn Ser Met Arg Ile Pro Glu Tyr His Arg His Ile Leu
    370                 375                 380

Tyr Gly Ala Leu Val Gly Gly Pro Gly Ser Asp Asp Ser Tyr Asn Asp
385                 390                 395                 400

Asp Ile Thr Asp Tyr Val Gln Asn Glu Val Ala Cys Asp Tyr Asn Ala
                405                 410                 415

Gly Ile Val Gly Ala Leu Ala Lys Met Tyr Leu Met Tyr Gly Gly Asp
            420                 425                 430

Pro Ile Pro Asn Phe Lys Ala Ile Glu Lys Pro Thr Asn Asp Glu Ile
        435                 440                 445

Phe Val Glu Ser Lys Phe Gly Asn Ser Gln Gly Thr Asn Tyr Thr Glu
    450                 455                 460

Ile Ile Ser Tyr Ile Tyr Asn Arg Thr Gly Trp Pro Pro Arg Val Thr
465                 470                 475                 480

Asp Asn Leu Asn Phe Lys Tyr Phe Ile Asp Leu Ser Glu Leu Ile Lys
                485                 490                 495

Ala Gly Tyr Gly Pro Asp Val Val Lys Val Glu Thr Tyr Tyr Ser Glu
            500                 505                 510

Gly Gly Lys Ile Ser Gly Pro Tyr Val Trp Asn Ala Ser Lys Asn Leu
        515                 520                 525

Tyr Tyr Ile Leu Val Asp Phe Thr Gly Thr Lys Ile Tyr Pro Gly Gly
    530                 535                 540

Glu Val Glu His Lys Lys Gln Ala Gln Phe Lys Ile Ser Val Pro Gln
545                 550                 555                 560

Gly Val Pro Trp Asp Pro Thr Asn Asp Pro Ser Tyr Ala Gly Leu Thr
                565                 570                 575

Lys Glu Leu Ser Lys Asn Lys Phe Ile Ala Ala Tyr Glu Gly Asn Val
            580                 585                 590

Leu Val Trp Gly Gln Glu Pro Glu Gly Ser Ser Ser Ser Thr Pro Thr
        595                 600                 605

Pro Thr Pro Thr Pro Thr Pro Thr Leu Thr Pro Thr Pro Thr Ser Thr
    610                 615                 620
```

-continued

```
Ala Thr Pro Thr Pro Thr Pro Thr Pro Thr Pro Thr Ser Thr Pro Thr
625                 630                 635                 640

Ala Thr Pro Thr Ala Thr Pro Thr Pro Thr Pro Thr Pro Ser Ser Thr
                645                 650                 655

Pro Val Ala Gly Gly Gln Ile Lys Val
            660                 665


<210> SEQ ID NO 127
<211> LENGTH: 1995
<212> TYPE: DNA
<213> ORGANISM: Caldicellulosiruptor bescii

<400> SEQUENCE: 127

gcaacaacct ttaactatgg tgaagctctt caaaaagcga tcatgtttta tgaatttcag     60

atgtcaggta aactaccatc atggatccgt aacaactggc gcggggattc tggtctaaat    120

gatggcaaag atgtaggttt agatcttact ggtggctggc atgatgcggg cgaccatgta    180

aagtttaatc taccaatgtc atacagtgca tcaatgcttt cgtgggcagt ttatgagtac    240

aaagcagcat ttgagaaaag tggtcagctt gaacatatac ttaaccagat tgaatgggta    300

aacgactact ttgtaaaatg ccatccatca aagtatgtat actactatca agttggtgac    360

ccaattgaag atcataactt ctggggtcca gcagaagtta tgcaaatgaa acgaccagca    420

tacaagtgtg acttaaataa tccagcaagt tcggttgttg cagaaacagc agcatcctta    480

gctgcagctt caatcgtcat acgtgaaaga aatagtcaaa aggcagacac atatttgcag    540

catgcgatgg tactctttga ttttgccgat agaactcgta gtgatgcagg gtataccgca    600

gcaacaggct tttacacatc aggtggtttt attgatgatc ttggttgggc agcagtgtgg    660

ttatatcttg cgacaaatga caaatcatat ttagataaag ctgaggcact tatggcagaa    720

tatgccggtg gcacaaatac atggacacag tgctgggacg atgtaagata cggagcaata    780

ttgcttttag caaaaattac taataaagac atatataaag gtgctgttga aagaaatctt    840

gatcattgga catataacat aacctataca cctaaaggtc ttgcatggat aacagggtgg    900

ggctcactta ggtatgccac aactgcagct ttcttagcgt ttgtttatgc agattggtca    960

ggatgtccag aaaataagcg aacagcttat ctaaaatttg gtgagagtca gattaactat   1020

gcattaggtt caacaggaag aagctttttg gtaggatttg ggcaaaatta tccacaacat   1080

ccacatcaca gaaatgcaca cagttcatgg gcgaacagta tgcgaatacc tgaatatcat   1140

cgacacatac tttatggtgc attagtaggc ggaccaggct ctgatgatag ttacaatgat   1200

gatattactg actatgttca aaacgaggtg gcttgtgact acaatgctgg tattgtaggt   1260

gctctggcaa aaatgtacct tatgtatgga ggagacccaa tacctaattt caaagctatc   1320

gaaaagccaa ctaatgatga aatttttgtt gaatccaagt ttggtaattc acagggtaca   1380

aactataccg aaataatttc atacatttat aacagaacgg gatggccgcc tcgagtcaca   1440

gataatctaa actttaagta ttttattgac ctaagtgagt taatcaaggc tgggtatggt   1500

cctgatgttg ttaaagtaga gacatattat tcagaaggtg gaaaaatatc tggaccatac   1560

gtatggaatg catcaaagaa cctttactat atattagttg attttacagg aacaaaaata   1620

tatccaggtg gggaagtaga acacaaaaaa caagctcaat ttaagatatc tgtgccacaa   1680

ggtgttccat gggatccaac taatgaccca tcttatgcag gattaacaaa agaacttagt   1740

aaaaataagt tcatagcagc ttatgaaggt aacgtgctgg tatggggaca agaaccagag   1800

ggttcgtcaa gttcaacccc aaccccaaca ccaacaccaa caccaacact gactccaaca   1860
```

-continued ccgacatcaa ctgctacacc aacaccgaca cctacaccaa caccaacgtc aacaccaact 1920
gctacaccaa cagcaacgcc aacaccaaca ccgacgccga gcagcacacc tgtagcaggc 1980
gggcagataa aggta 1995

<210> SEQ ID NO 128
<211> LENGTH: 440
<212> TYPE: PRT
<213> ORGANISM: Caldicellulosiruptor bescii

<400> SEQUENCE: 128

Ala Thr Thr Phe Asn Tyr Gly Glu Ala Leu Gln Lys Ala Ile Met Phe
1 5 10 15

Tyr Glu Phe Gln Met Ser Gly Lys Leu Pro Ser Trp Ile Arg Asn Asn
20 25 30

Trp Arg Gly Asp Ser Gly Leu Asn Asp Gly Lys Asp Val Gly Leu Asp
35 40 45

Leu Thr Gly Gly Trp His Asp Ala Gly Asp His Val Lys Phe Asn Leu
50 55 60

Pro Met Ser Tyr Ser Ala Ser Met Leu Ser Trp Ala Val Tyr Glu Tyr
65 70 75 80

Lys Ala Ala Phe Glu Lys Ser Gly Gln Leu Glu His Ile Leu Asn Gln
85 90 95

Ile Glu Trp Val Asn Asp Tyr Phe Val Lys Cys His Pro Ser Lys Tyr
100 105 110

Val Tyr Tyr Tyr Gln Val Gly Asp Pro Ile Glu Asp His Asn Phe Trp
115 120 125

Gly Pro Ala Glu Val Met Gln Met Lys Arg Pro Ala Tyr Lys Cys Asp
130 135 140

Leu Asn Asn Pro Ala Ser Ser Val Val Ala Glu Thr Ala Ala Ser Leu
145 150 155 160

Ala Ala Ala Ser Ile Val Ile Arg Glu Arg Asn Ser Gln Lys Ala Asp
165 170 175

Thr Tyr Leu Gln His Ala Met Val Leu Phe Asp Phe Ala Asp Arg Thr
180 185 190

Arg Ser Asp Ala Gly Tyr Thr Ala Ala Thr Gly Phe Tyr Thr Ser Gly
195 200 205

Gly Phe Ile Asp Asp Leu Gly Trp Ala Ala Val Trp Leu Tyr Leu Ala
210 215 220

Thr Asn Asp Lys Ser Tyr Leu Asp Lys Ala Glu Ala Leu Met Ala Glu
225 230 235 240

Tyr Ala Gly Gly Thr Asn Thr Trp Thr Gln Cys Trp Asp Asp Val Arg
245 250 255

Tyr Gly Ala Ile Leu Leu Leu Ala Lys Ile Thr Asn Lys Asp Ile Tyr
260 265 270

Lys Gly Ala Val Glu Arg Asn Leu Asp His Trp Thr Tyr Asn Ile Thr
275 280 285

Tyr Thr Pro Lys Gly Leu Ala Trp Ile Thr Gly Trp Gly Ser Leu Arg
290 295 300

Tyr Ala Thr Thr Ala Ala Phe Leu Ala Phe Val Tyr Ala Asp Trp Ser
305 310 315 320

Gly Cys Pro Glu Asn Lys Arg Thr Ala Tyr Leu Lys Phe Gly Glu Ser
325 330 335

Gln Ile Asn Tyr Ala Leu Gly Ser Thr Gly Arg Ser Phe Leu Val Gly
340 345 350

```
Phe Gly Gln Asn Tyr Pro Gln His Pro His His Arg Asn Ala His Ser
        355                 360                 365

Ser Trp Ala Asn Ser Met Arg Ile Pro Glu Tyr His Arg His Ile Leu
    370                 375                 380

Tyr Gly Ala Leu Val Gly Gly Pro Gly Ser Asp Asp Ser Tyr Asn Asp
385                 390                 395                 400

Asp Ile Thr Asp Tyr Val Gln Asn Glu Val Ala Cys Asp Tyr Asn Ala
                405                 410                 415

Gly Ile Val Gly Ala Leu Ala Lys Met Tyr Leu Met Tyr Gly Gly Asp
            420                 425                 430

Pro Ile Pro Asn Phe Lys Ala Ile
        435                 440


<210> SEQ ID NO 129
<211> LENGTH: 1320
<212> TYPE: DNA
<213> ORGANISM: Caldicellulosiruptor bescii

<400> SEQUENCE: 129

gcaacaacct ttaactatgg tgaagctctt caaaaagcga tcatgtttta tgaatttcag     60

atgtcaggta aactaccatc atggatccgt aacaactggc gcggggattc tggtctaaat    120

gatggcaaag atgtaggttt agatcttact ggtggctggc atgatgcggg cgaccatgta    180

aagtttaatc taccaatgtc atacagtgca tcaatgcttt cgtgggcagt ttatgagtac    240

aaagcagcat ttgagaaaag tggtcagctt gaacatatac ttaaccagat tgaatgggta    300

aacgactact ttgtaaaatg ccatccatca aagtatgtat actactatca agttggtgac    360

ccaattgaag atcataactt ctggggtcca gcagaagtta tgcaaatgaa acgaccagca    420

tacaagtgtg acttaaataa tccagcaagt tcggttgttg cagaaacagc agcatcctta    480

gctgcagctt caatcgtcat acgtgaaaga aatagtcaaa aggcagacac atatttgcag    540

catgcgatgg tactctttga ttttgccgat agaactcgta gtgatgcagg gtataccgca    600

gcaacaggct tttacacatc aggtggtttt attgatgatc ttggttgggc agcagtgtgg    660

ttatatcttg cgacaaatga caaatcatat ttagataaag ctgaggcact tatggcagaa    720

tatgccggtg gcacaaatac atggacacag tgctgggacg atgtaagata cggagcaata    780

ttgcttttag caaaaattac taataaagac atatataaag gtgctgttga aagaaatctt    840

gatcattgga catataacat aacctataca cctaaaggtc ttgcatggat aacagggtgg    900

ggctcactta ggtatgccac aactgcagct ttcttagcgt ttgtttatgc agattggtca    960

ggatgtccag aaaataagcg aacagcttat ctaaaatttg gtgagagtca gattaactat   1020

gcattaggtt caacaggaag aagcttttttg gtaggatttg ggcaaaatta tccacaacat   1080

ccacatcaca gaaatgcaca cagttcatgg gcgaacagta tgcgaatacc tgaatatcat   1140

cgacacatac tttatggtgc attagtaggc ggaccaggct ctgatgatag ttacaatgat   1200

gatattactg actatgttca aaacgaggtg gcttgtgact acaatgctgg tattgtaggt   1260

gctctggcaa aaatgtacct tatgtatgga ggagacccaa tacctaattt caaagctatc   1320


<210> SEQ ID NO 130
<211> LENGTH: 160
<212> TYPE: PRT
<213> ORGANISM: Caldicellulosiruptor bescii

<400> SEQUENCE: 130
```

-continued

```
Ile Glu Lys Pro Thr Asn Asp Glu Ile Phe Val Glu Ser Lys Phe Gly
 1               5                  10                  15

Asn Ser Gln Gly Thr Asn Tyr Thr Glu Ile Ile Ser Tyr Ile Tyr Asn
            20                  25                  30

Arg Thr Gly Trp Pro Pro Arg Val Thr Asp Asn Leu Asn Phe Lys Tyr
        35                  40                  45

Phe Ile Asp Leu Ser Glu Leu Ile Lys Ala Gly Tyr Gly Pro Asp Val
    50                  55                  60

Val Lys Val Glu Thr Tyr Tyr Ser Glu Gly Gly Lys Ile Ser Gly Pro
65                  70                  75                  80

Tyr Val Trp Asn Ala Ser Lys Asn Leu Tyr Tyr Ile Leu Val Asp Phe
                85                  90                  95

Thr Gly Thr Lys Ile Tyr Pro Gly Gly Glu Val Glu His Lys Lys Gln
            100                 105                 110

Ala Gln Phe Lys Ile Ser Val Pro Gln Gly Val Pro Trp Asp Pro Thr
        115                 120                 125

Asn Asp Pro Ser Tyr Ala Gly Leu Thr Lys Glu Leu Ser Lys Asn Lys
    130                 135                 140

Phe Ile Ala Ala Tyr Glu Gly Asn Val Leu Val Trp Gly Gln Glu Pro
145                 150                 155                 160


<210> SEQ ID NO 131
<211> LENGTH: 480
<212> TYPE: DNA
<213> ORGANISM: Caldicellulosiruptor bescii

<400> SEQUENCE: 131

atcgaaaagc caactaatga tgaaattttt gttgaatcca agtttggtaa ttcacagggt      60

acaaactata ccgaaataat ttcatacatt tataacagaa cgggatggcc gcctcgagtc     120

acagataatc taaactttaa gtattttatt gacctaagtg agttaatcaa ggctgggtat     180

ggtcctgatg ttgttaaagt agagacatat tattcagaag gtggaaaaat atctggacca     240

tacgtatgga atgcatcaaa gaacctttac tatatattag ttgattttac aggaacaaaa     300

atatatccag gtggggaagt agaacacaaa aaacaagctc aatttaagat atctgtgcca     360

caaggtgttc catgggatcc aactaatgac ccatcttatg caggattaac aaaagaactt     420

agtaaaaata agttcatagc agcttatgaa ggtaacgtgc tggtatgggg acaagaacca     480


<210> SEQ ID NO 132
<211> LENGTH: 161
<212> TYPE: PRT
<213> ORGANISM: Caldicellulosiruptor bescii

<400> SEQUENCE: 132

Pro Val Ala Gly Gly Gln Ile Lys Val Leu Tyr Ala Asn Lys Glu Thr
 1               5                  10                  15

Asn Ser Thr Thr Asn Thr Ile Arg Pro Trp Leu Lys Val Val Asn Thr
            20                  25                  30

Gly Ser Ser Ser Ile Asp Leu Ser Arg Val Thr Ile Arg Tyr Trp Tyr
        35                  40                  45

Thr Val Asp Gly Asp Lys Ala Gln Ser Ala Ile Ser Asp Trp Ala Gln
    50                  55                  60

Ile Gly Ala Ser Asn Val Thr Phe Lys Phe Val Lys Leu Ser Ser Ser
65                  70                  75                  80

Val Ser Gly Ala Asp Tyr Tyr Leu Glu Ile Gly Phe Lys Ser Gly Ala
                85                  90                  95
```

```
Gly Gln Leu Gln Ala Gly Lys Asp Thr Gly Glu Ile Gln Ile Arg Phe
            100                 105                 110

Asn Lys Ser Asp Trp Ser Asn Tyr Asn Gln Gly Asn Asp Trp Ser Trp
        115                 120                 125

Met Gln Ser Met Thr Ser Tyr Gly Glu Asn Val Lys Val Thr Ala Tyr
    130                 135                 140

Ile Asp Gly Val Leu Val Trp Gly Gln Glu Pro Ser Gly Ala Thr Pro
145                 150                 155                 160

Thr


<210> SEQ ID NO 133
<211> LENGTH: 483
<212> TYPE: DNA
<213> ORGANISM: Caldicellulosiruptor bescii

<400> SEQUENCE: 133

cctgtagcag gcgggcagat aaaggtattg tatgctaaca aggagacaaa tagcacaaca      60

aacacgataa ggccatggtt gaaggtagtg aacactggaa gcagcagcat agatttaagc     120

agggtaacga taaggtactg gtacacggta gatggggaca aggcacagag tgcgatatca     180

gactgggcac agataggagc aagcaatgtg acattcaagt ttgtgaagct gagcagtagc     240

gtaagtggag cggactatta tttagagata ggatttaaga gtggagctgg gcagttgcag     300

gctggtaaag acacagggga gatacagata aggtttaaca agagtgactg gagcaattac     360

aatcagggga atgactggtc atggatgcag agcatgacga gttatggaga gaatgtgaag     420

gtaacagcgt atatagatgg tgtattggta tggggacagg agccgagtgg agcgacacca     480

aca                                                                   483


<210> SEQ ID NO 134
<211> LENGTH: 33
<212> TYPE: DNA
<213> ORGANISM: Artificial Sequence
<220> FEATURE:
<223> OTHER INFORMATION: Synthesized Construct

<400> SEQUENCE: 134

gacgacgaca agatgaactt tgaaggaaga gac                                   33


<210> SEQ ID NO 135
<211> LENGTH: 32
<212> TYPE: DNA
<213> ORGANISM: Artificial Sequence
<220> FEATURE:
<223> OTHER INFORMATION: Synthesized Construct

<400> SEQUENCE: 135

gaggagaagc ccggttattt tttagccttt ac                                    32


<210> SEQ ID NO 136
<211> LENGTH: 36
<212> TYPE: DNA
<213> ORGANISM: Artificial Sequence
<220> FEATURE:
<223> OTHER INFORMATION: Synthesized Construct

<400> SEQUENCE: 136

gacgacgaca agatgaaaaa agcaaaagtc atctac                                36


<210> SEQ ID NO 137
```

<211> LENGTH: 39
<212> TYPE: DNA
<213> ORGANISM: Artificial Sequence
<220> FEATURE:
<223> OTHER INFORMATION: Synthesized Construct

<400> SEQUENCE: 137
gaggagaagc ccggttaatt ttctttcttc tttaacctg 39

<210> SEQ ID NO 138
<211> LENGTH: 36
<212> TYPE: DNA
<213> ORGANISM: Artificial Sequence
<220> FEATURE:
<223> OTHER INFORMATION: Synthesized Construct

<400> SEQUENCE: 138
gacgacgaca agatgatttt atcaaggagc agtaac 36

<210> SEQ ID NO 139
<211> LENGTH: 34
<212> TYPE: DNA
<213> ORGANISM: Artificial Sequence
<220> FEATURE:
<223> OTHER INFORMATION: Synthesized Construct

<400> SEQUENCE: 139
gaggagaagc ccggttacgg atatattagt cttc 34

<210> SEQ ID NO 140
<211> LENGTH: 36
<212> TYPE: DNA
<213> ORGANISM: Artificial Sequence
<220> FEATURE:
<223> OTHER INFORMATION: Synthesized Construct

<400> SEQUENCE: 140
gacgacgaca agatgtcaat tgaaaaaagg gtaaac 36

<210> SEQ ID NO 141
<211> LENGTH: 30
<212> TYPE: DNA
<213> ORGANISM: Artificial Sequence
<220> FEATURE:
<223> OTHER INFORMATION: Synthesized Construct

<400> SEQUENCE: 141
gaggagaagc ccggttattc acaccatgca 30

<210> SEQ ID NO 142
<211> LENGTH: 39
<212> TYPE: DNA
<213> ORGANISM: Artificial Sequence
<220> FEATURE:
<223> OTHER INFORMATION: Synthesized Construct

<400> SEQUENCE: 142
gacgacgaca agatggtttt tgaaatgcca cttgaaaag 39

<210> SEQ ID NO 143
<211> LENGTH: 53
<212> TYPE: DNA
<213> ORGANISM: Artificial Sequence
<220> FEATURE:
<223> OTHER INFORMATION: Synthesized Construct

<400> SEQUENCE: 143
gaggagaagc ccggttattt tatcatctcc ataagataca taaatatctt gtc 53

<210> SEQ ID NO 144
<211> LENGTH: 39
<212> TYPE: DNA
<213> ORGANISM: Artificial Sequence
<220> FEATURE:
<223> OTHER INFORMATION: Synthesized Construct

<400> SEQUENCE: 144
gacgacgaca agatgctcag agacatagtt ccatttggc 39

<210> SEQ ID NO 145
<211> LENGTH: 41
<212> TYPE: DNA
<213> ORGANISM: Artificial Sequence
<220> FEATURE:
<223> OTHER INFORMATION: Synthesized Construct

<400> SEQUENCE: 145
gaggagaagc ccggttattc tatatcaatt gttcttacat c 41

<210> SEQ ID NO 146
<211> LENGTH: 148
<212> TYPE: PRT
<213> ORGANISM: Caldicellulosiruptor bescii

<400> SEQUENCE: 146

Met Leu Arg Asp Ile Val Pro Phe Gly Lys Arg Pro Phe Asp Ile Met
1 5 10 15

Arg Lys Ile Glu Arg Glu Phe Phe Asp Ile Asp Asp Trp Phe Glu Asp
20 25 30

Phe Phe Ala Pro Phe Glu Lys Gly Thr Arg Phe Met Arg Thr Asp Ile
35 40 45

Lys Glu Thr Glu Asn Glu Tyr Ile Ile Glu Ala Glu Leu Pro Gly Val
50 55 60

Lys Lys Glu Asp Ile Lys Ile Glu Leu Tyr Asp Asn Lys Leu Thr Ile
65 70 75 80

Lys Ala Glu Thr Lys Lys Glu Glu Lys Glu Glu Arg Glu Asn Phe Ile
85 90 95

Arg Arg Glu Arg Arg Tyr Gly Ala Phe Ser Arg Thr Phe Tyr Leu Asp
100 105 110

Asn Val Lys Glu Asp Gly Ile Lys Ala Lys Tyr Glu Asp Gly Ile Leu
115 120 125

Arg Ile Val Leu Pro Lys Glu Arg Pro Ser Lys Pro Asp Val Arg Thr
130 135 140

Ile Asp Ile Glu
145

<210> SEQ ID NO 147
<211> LENGTH: 447
<212> TYPE: DNA
<213> ORGANISM: Caldicellulosiruptor bescii

<400> SEQUENCE: 147
atgctcagag acatagttcc atttggcaaa agaccatttg acattatgag aaagattgaa 60
agagagtttt ttgacattga tgactggttt gaagatttct ttgcaccatt tgaaaaaggt 120
acaagattca tgagaactga cattaaggag actgaaaatg agtatattat tgaagcagaa 180
cttccggggg tcaaaaaaga ggatatcaag atagagcttt atgataacaa acttacaata 240
aaggcagaga caaagaaaga ggaaaaagaa gagagagaaa actttataag acgagaaaga 300
agatatggtg cattttcccg aacattctat cttgacaatg taaaagagga tggtatcaaa 360
gcaaaatacg aggacggaat cttgagaata gtacttccaa aagaaagacc ttcaaaacca 420
gatgtaagaa caattgatat agaataa 447

<210> SEQ ID NO 148
<211> LENGTH: 489
<212> TYPE: DNA
<213> ORGANISM: Caldicellulosiruptor bescii

<400> SEQUENCE: 148
atggcacatc accaccacca tcacgtggat gacgacgaca agatgctcag agacatagtt 60
ccatttggca aaagaccatt tgacattatg agaaagattg aaagagagtt ttttgacatt 120
gatgactggt ttgaagattt ctttgcacca tttgaaaaag gtacaagatt catgagaact 180
gacattaagg agactgaaaa tgagtatatt attgaagcag aacttccggg ggtcaaaaaa 240
gaggatatca agatagagct ttatgataac aaacttacaa taaaggcaga gacaaagaaa 300
gaggaaaaag aagagagaga aaactttata agacgagaaa gaagatatgg tgcattttcc 360
cgaacattct atcttgacaa tgtaaaagag gatggtatca aagcaaaata cgaggacgga 420
atcttgagaa tagtacttcc aaaagaaaga ccttcaaaac cagatgtaag aacaattgat 480
atagaataa 489

<210> SEQ ID NO 149
<211> LENGTH: 162
<212> TYPE: PRT
<213> ORGANISM: Caldicellulosiruptor bescii

<400> SEQUENCE: 149

Met Ala His His His His His His Val Asp Asp Asp Asp Lys Met Leu
1 5 10 15

Arg Asp Ile Val Pro Phe Gly Lys Arg Pro Phe Asp Ile Met Arg Lys
20 25 30

Ile Glu Arg Glu Phe Phe Asp Ile Asp Asp Trp Phe Glu Asp Phe Phe
35 40 45

Ala Pro Phe Glu Lys Gly Thr Arg Phe Met Arg Thr Asp Ile Lys Glu
50 55 60

Thr Glu Asn Glu Tyr Ile Ile Glu Ala Glu Leu Pro Gly Val Lys Lys
65 70 75 80

Glu Asp Ile Lys Ile Glu Leu Tyr Asp Asn Lys Leu Thr Ile Lys Ala
85 90 95

Glu Thr Lys Lys Glu Glu Lys Glu Glu Arg Glu Asn Phe Ile Arg Arg
100 105 110

Glu Arg Arg Tyr Gly Ala Phe Ser Arg Thr Phe Tyr Leu Asp Asn Val
115 120 125

Lys Glu Asp Gly Ile Lys Ala Lys Tyr Glu Asp Gly Ile Leu Arg Ile
130 135 140

Val Leu Pro Lys Glu Arg Pro Ser Lys Pro Asp Val Arg Thr Ile Asp
145 150 155 160

Ile Glu

<210> SEQ ID NO 150
<211> LENGTH: 113

<212> TYPE: PRT
<213> ORGANISM: Caldicellulosiruptor bescii

<400> SEQUENCE: 150

Tyr Val Tyr Tyr Tyr Gln Val Gly Asp Pro Ile Glu Asp His Asn Phe
1 5 10 15

Trp Gly Pro Ala Glu Val Met Gln Ala Ala Thr Gly Phe Tyr Thr Ser
20 25 30

Gly Gly Phe Ile Asp Asp Leu Gly Tyr Ala Gly Gly Thr Asn Thr Trp
35 40 45

Thr Gln Cys Trp Asp Asp Val Arg Tyr Gly Ala Asn Ile Thr Tyr Thr
50 55 60

Pro Lys Gly Leu Ala Trp Ile Thr Gly Trp Gly Ser Leu Arg Tyr Ala
65 70 75 80

Thr Thr Ser Phe Leu Val Gly Phe Gly Gln Asn Tyr Pro Gln His Pro
85 90 95

His His Arg Asn Ala His Ser Ser Trp Ala Asn Ser Met Arg Ile Pro
100 105 110

Glu

<210> SEQ ID NO 151
<211> LENGTH: 119
<212> TYPE: PRT
<213> ORGANISM: Clostridium cellulolyticum

<400> SEQUENCE: 151

Gly Val Tyr Tyr Tyr Gln Val Gly Asp Gly Gly Lys Asp His Ser Trp
1 5 10 15

Trp Gly Pro Ala Glu Val Met Gln Ala Ala Ser Gly Tyr Tyr Ser Ser
20 25 30

Ser Ser Phe Tyr Asp Asp Leu Ser Trp Gly Lys Glu Gln Gln Thr Asp
35 40 45

Ile Ile Ala Tyr Lys Trp Gly Gln Cys Trp Asp Asp Val His Tyr Gly
50 55 60

Ala Arg Val Ser Tyr Thr Pro Lys Gly Leu Ala Trp Leu Phe Gln Trp
65 70 75 80

Gly Ser Leu Arg His Ala Thr Thr Ser Phe Val Val Gly Tyr Gly Val
85 90 95

Asn Pro Pro Gln His Pro His His Arg Thr Ala His Gly Ser Trp Thr
100 105 110

Asp Gln Met Thr Ser Pro Thr
115

<210> SEQ ID NO 152
<211> LENGTH: 121
<212> TYPE: PRT
<213> ORGANISM: Thermobifida fusca

<400> SEQUENCE: 152

Asn Val Leu Tyr Val Gln Val Gly Asp Gly Asp Ala Asp His Lys Trp
1 5 10 15

Trp Gly Pro Ala Glu Val Met Pro Pro Ala Gly Ala Phe Tyr Asn Ser
20 25 30

Trp Ser Gly Tyr Gln Asp Glu Leu Val Leu Ser Thr Glu Gln Gln Thr
35 40 45

Asp Leu Arg Ser Tyr Arg Trp Thr Ile Ala Trp Asp Asp Lys Ser Tyr
50 55 60

```
Gly Thr Arg Val Pro Tyr Ser Pro Gly Gly Met Ala Val Leu Asp Thr
65                  70                  75                  80

Trp Gly Ala Leu Arg Tyr Ala Ala Asn Ser Ser Tyr Val Val Gly Phe
                85                  90                  95

Gly Asn Asn Pro Pro Arg Asn Pro His His Arg Thr Ala His Gly Ser
            100                 105                 110

Trp Thr Asp Ser Ile Ala Ser Pro Ala
        115                 120


<210> SEQ ID NO 153
<211> LENGTH: 52
<212> TYPE: PRT
<213> ORGANISM: Caldicellulosiruptor bescii

<400> SEQUENCE: 153

Glu Ile Phe Val Glu Ser Lys Phe Gly Asn Ser Gln Gly Thr Asn Tyr
 1               5                  10                  15

Thr Glu Ile Ile Ser Tyr Ile Gly Pro Asp Val Val Lys Val Glu Thr
            20                  25                  30

Tyr Tyr Ser Glu Gly Pro Gly Gly Glu Val Glu His Lys Lys Gln Ala
        35                  40                  45

Gln Phe Lys Ile
    50


<210> SEQ ID NO 154
<211> LENGTH: 52
<212> TYPE: PRT
<213> ORGANISM: Caldicellulosiruptor kronotskyensis

<400> SEQUENCE: 154

Glu Ile Phe Val Glu Ser Lys Phe Gly Asn Ser Gln Gly Thr Asn Tyr
 1               5                  10                  15

Thr Glu Ile Ile Ser Tyr Ile Gly Pro Asp Val Val Lys Val Glu Thr
            20                  25                  30

Tyr Tyr Ser Glu Gly Pro Gly Gly Glu Val Glu His Lys Lys Gln Ala
        35                  40                  45

Gln Phe Lys Ile
    50


<210> SEQ ID NO 155
<211> LENGTH: 52
<212> TYPE: PRT
<213> ORGANISM: Caldicellulosiruptor saccharolyticus

<400> SEQUENCE: 155

Glu Ile Phe Val Glu Ser Lys Phe Gly Asn Ser Gln Gly Ala Asn Tyr
 1               5                  10                  15

Thr Glu Ile Ile Ser Tyr Ile Gly Pro Asp Ile Val Lys Val Glu Thr
            20                  25                  30

Tyr Tyr Ser Glu Gly Pro Gly Gly Glu Val Glu His Lys Lys Gln Ala
        35                  40                  45

Gln Phe Lys Ile
    50


<210> SEQ ID NO 156
<211> LENGTH: 52
<212> TYPE: PRT
<213> ORGANISM: Caldicellulosiruptor obsidiansis
```

<400> SEQUENCE: 156

Glu Ile Phe Val Glu Ser Lys Phe Gly Asn Ser Gln Gly Ala Asn Tyr
1 5 10 15

Thr Glu Ile Ile Ser Tyr Ile Ser Ala Asp Val Val Lys Val Asp Thr
20 25 30

Tyr Tyr Ala Glu Gly Pro Gly Gly Glu Val Glu His Lys Lys Gln Ala
35 40 45

Gln Phe Lys Ile
50

<210> SEQ ID NO 157
<211> LENGTH: 52
<212> TYPE: PRT
<213> ORGANISM: Caldicellulosiruptor sp. Tok7B.1

<400> SEQUENCE: 157

Glu Ile Phe Val Glu Ser Lys Phe Gly Asn Ser Gln Gly Pro Asn Tyr
1 5 10 15

Thr Glu Val Ile Ser Tyr Ile Ser Pro Asp Val Val Lys Val Asp Thr
20 25 30

Tyr Tyr Ile Glu Gly Pro Gly Gly Glu Val Glu His Lys Lys Gln Ala
35 40 45

Gln Phe Lys Ile
50

<210> SEQ ID NO 158
<211> LENGTH: 51
<212> TYPE: PRT
<213> ORGANISM: Clostridium cellulolyticum

<400> SEQUENCE: 158

Glu Val Ile Ile Lys Ala Gly Leu Asn Ser Thr Gly Pro Asn Tyr Thr
1 5 10 15

Glu Ile Lys Ala Val Val Asp Pro Leu Ser Leu Val Thr Ser Ser Asn
20 25 30

Tyr Ser Glu Gly Pro Gly Gly Gln Ser Ala Cys Arg Arg Glu Val Gln
35 40 45

Phe Arg Ile
50

<210> SEQ ID NO 159
<211> LENGTH: 51
<212> TYPE: PRT
<213> ORGANISM: Clostridium cellulovorans

<400> SEQUENCE: 159

Glu Phe Phe Val Glu Ala Gly Val Asn Cys Thr Gly Pro Asn Phe Val
1 5 10 15

Glu Ile Lys Ala Leu Val Ser Ala Asp Asp Leu Lys Val Thr Val Gly
20 25 30

Tyr Asn Thr Gly Pro Gly Gly Gln Ser Asp Tyr Lys Lys Glu Ile Gln
35 40 45

Phe Arg Ile
50

<210> SEQ ID NO 160
<211> LENGTH: 51
<212> TYPE: PRT
<213> ORGANISM: Clostridium stercorarium

<400> SEQUENCE: 160

Glu Phe Phe Val Met Ala Gly Ile Asn Ala Ser Gly Gln Asn Phe Ile
1 5 10 15

Glu Ile Lys Ala Leu Leu Ser Ala Ser Asp Val Thr Ile Thr Thr Asn
20 25 30

Tyr Asn Ala Gly Pro Gly Gly Gln Ser Ala Tyr Arg Lys Glu Val Gln
35 40 45

Phe Arg Ile
50

<210> SEQ ID NO 161
<211> LENGTH: 51
<212> TYPE: PRT
<213> ORGANISM: Clostridium phytofermentans

<400> SEQUENCE: 161

Glu Leu Phe Ile Gln Ala Gly Ile Asn Ala Ser Gly Pro Ser Phe Ile
1 5 10 15

Glu Val Lys Ala Leu Val Thr Lys Asn Asp Phe Thr Val Ser Thr Asn
20 25 30

Tyr Asn Asn Gly Pro Gly Gly Gln Ser Ala Tyr Lys Lys Glu Val Gln
35 40 45

Phe Arg Ile
50

<210> SEQ ID NO 162
<211> LENGTH: 51
<212> TYPE: PRT
<213> ORGANISM: Clostridium thermocellum

<400> SEQUENCE: 162

Asp Glu Ile Phe Val Glu Ala Gly Val Asn Ala Ser Gly Asn Asn Phe
1 5 10 15

Ile Glu Ile Lys Ala Ile Ser Ala Ser Asp Leu Gln Val Ser Ser Ser
20 25 30

Tyr Asn Gln Gly Pro Gly Gly Gln Ser Ala Tyr Lys Lys Glu Val Gln
35 40 45

Phe Arg Ile
50

<210> SEQ ID NO 163
<211> LENGTH: 51
<212> TYPE: PRT
<213> ORGANISM: Paenibacillus barcinonensis

<400> SEQUENCE: 163

Asp Glu Tyr Phe Val Glu Ala Ala Val Arg Ser Ser Gly Ser Asn Tyr
1 5 10 15

Thr Glu Ile Arg Ala Leu Thr Val Ser Asp Val Gln Val Thr Val Ser
20 25 30

Ser Ser Glu Gly Pro Gly Gly Glu Gly Asn Tyr Arg Lys Glu Val Gln
35 40 45

Phe Arg Ile
50

<210> SEQ ID NO 164
<211> LENGTH: 51
<212> TYPE: PRT

<213> ORGANISM: Clostridium thermocellum

<400> SEQUENCE: 164

```
Asp Glu Phe Phe Val Glu Ala Ala Ile Asn Gln Ala Ser Asp His Phe
 1               5                  10                  15

Thr Glu Ile Lys Ala Leu Ser Val Asp Asp Ile Lys Val Thr Ile Gly
            20                  25                  30

Tyr Cys Glu Ser Pro Ile Gly Gln Glu Gln Tyr Ala Ala Glu Leu Gln
        35                  40                  45

Phe Arg Ile
    50
```

<210> SEQ ID NO 165
<211> LENGTH: 52
<212> TYPE: PRT
<213> ORGANISM: Cellulomonas fimi

<400> SEQUENCE: 165

```
Asp Gln Leu Phe Val Glu Ala Met Leu Asn Gln Pro Pro Ser Gly Thr
 1               5                  10                  15

Phe Thr Glu Val Lys Ala Met Ala Ala Ser Asp Val Thr Leu Ser Ala
            20                  25                  30

Asn Tyr Ser Glu Cys Pro Gly Gly Gln Ser Gln His Arg Arg Glu Ile
        35                  40                  45

Gln Phe Arg Leu
    50
```

<210> SEQ ID NO 166
<211> LENGTH: 52
<212> TYPE: PRT
<213> ORGANISM: Cellulomonas flavigena

<400> SEQUENCE: 166

```
Asp Glu Ile Phe Val Glu Ala Gln Leu Asn Gln Ala Pro Gly Ser Thr
 1               5                  10                  15

Phe Thr Glu Val Lys Ala Met Ala Ala Ser Asp Val Thr Leu Ala Ala
            20                  25                  30

Asn Tyr Ser Glu Cys Pro Gly Gly Gln Ser Gln His Arg Arg Glu Ile
        35                  40                  45

Gln Phe Arg Leu
    50
```

<210> SEQ ID NO 167
<211> LENGTH: 51
<212> TYPE: PRT
<213> ORGANISM: Thermobifida fusca

<400> SEQUENCE: 167

```
Glu Ile Phe Val Glu Ala Gln Ile Asn Thr Pro Gly Thr Thr Phe Thr
 1               5                  10                  15

Glu Ile Lys Ala Met Ile Asp Pro Ala Asp Ile Thr Val Ser Ser Ala
            20                  25                  30

Tyr Asn Gln Cys Pro Gly Gly Gln Ser Glu His Arg Arg Glu Val Gln
        35                  40                  45

Phe Arg Ile
    50
```